US012042534B2

(12) United States Patent
Palese et al.

(10) Patent No.: US 12,042,534 B2
(45) Date of Patent: Jul. 23, 2024

(54) NEWCASTLE DISEASE VIRUSES AND USES THEREOF

(71) Applicants: Icahn School of Medicine at Mount Sinai, New York, NY (US); Memorial Sloan Kettering Cancer Center, New York, NY (US)

(72) Inventors: Peter Palese, New York, NY (US); Adolfo Garcia-Sastre, New York, NY (US); Dmitriy Zamarin, New York, NY (US); Jedd D. Wolchok, New York, NY (US)

(73) Assignees: ICAHN SCHOOL OF MEDICINE AT MOUNT SINAI, New York, NY (US); MEMORIAL SLOAN KETTERING CANCER CENTER, New York, NY (US)

( * ) Notice: Subject to any disclaimer, the term of this patent is extended or adjusted under 35 U.S.C. 154(b) by 938 days.

(21) Appl. No.: 16/611,813

(22) PCT Filed: May 11, 2018

(86) PCT No.: PCT/US2018/032255
§ 371 (c)(1),
(2) Date: Nov. 7, 2019

(87) PCT Pub. No.: WO2018/209194
PCT Pub. Date: Nov. 15, 2018

(65) Prior Publication Data

US 2020/0061184 A1 Feb. 27, 2020

Related U.S. Application Data

(60) Provisional application No. 62/507,690, filed on May 17, 2017, provisional application No. 62/505,759, filed on May 12, 2017.

(51) Int. Cl.

| | |
|---|---|
| ***A61K 39/17*** | (2006.01) |
| ***A61K 35/768*** | (2015.01) |
| ***A61K 39/00*** | (2006.01) |
| ***A61K 39/395*** | (2006.01) |
| ***A61P 35/00*** | (2006.01) |
| ***C07K 14/54*** | (2006.01) |
| ***C07K 16/28*** | (2006.01) |
| ***C12N 15/86*** | (2006.01) |

(52) U.S. Cl.
CPC ............ *A61K 39/17* (2013.01); *A61K 35/768* (2013.01); *A61K 39/0005* (2013.01); *A61K 39/3955* (2013.01); *A61P 35/00* (2018.01); *C07K 14/5434* (2013.01); *C07K 16/28* (2013.01); *C12N 15/86* (2013.01)

(58) Field of Classification Search
CPC ..... C07K 14/5434; A61K 39/17; C12N 15/86
See application file for complete search history.

(56) References Cited

U.S. PATENT DOCUMENTS

| | | | |
|---|---|---|---|
| 4,444,887 | A | 4/1984 | Hoffman |
| 4,474,893 | A | 10/1984 | Reading |
| 4,676,980 | A | 6/1987 | Segal et al. |
| 4,714,681 | A | 12/1987 | Reading |
| 4,716,111 | A | 12/1987 | Osband et al. |
| 4,816,397 | A | 3/1989 | Boss et al. |
| 4,816,567 | A | 3/1989 | Cabilly et al. |
| 4,925,648 | A | 5/1990 | Hansen et al. |
| 5,122,464 | A | 6/1992 | Wilson et al. |
| 5,166,057 | A | 11/1992 | Palese et al. |
| 5,223,409 | A | 6/1993 | Ladner et al. |
| 5,225,539 | A | 7/1993 | Winter |
| 5,273,745 | A | 12/1993 | Schirrmacher |
| 5,403,484 | A | 4/1995 | Ladner et al. |
| 5,413,923 | A | 5/1995 | Kucherlapati et al. |
| 5,427,908 | A | 6/1995 | Dower et al. |
| 5,516,637 | A | 5/1996 | Huang et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |

(Continued)

FOREIGN PATENT DOCUMENTS

| | | | |
|---|---|---|---|
| AU | 2002307971 | | 10/2002 |
| AU | 2008202252 | A1 | 6/2008 |
| CN | 101787373 | | 7/2010 |
| CN | 102740887 | | 10/2012 |

(Continued)

OTHER PUBLICATIONS

Aigner et al., "An effective tumor vaccine optimized for costimulation via bispecific and trispecific fusion proteins," *Int. J. Oncol.*, 32(4): 777-789 (2008).

(Continued)

*Primary Examiner* — Vanessa L. Ford
*Assistant Examiner* — Sandra Dillahunt
(74) *Attorney, Agent, or Firm* — JONES DAY

(57) ABSTRACT

Described herein are chimeric Newcastle disease viruses comprising a packaged genome comprising a transgene encoding interleukin-12. The chimeric Newcastle disease viruses and compositions thereof are useful in combination with an antagonist of programmed cell death protein 1 ("PD-1") or a ligand thereof in the treatment of cancer. In particular, described herein are methods for treating cancer comprising administering the chimeric Newcastle disease viruses in combination with an antagonist of PD-1 or a ligand thereof, wherein the chimeric Newcastle disease virus comprises a packaged genome comprising a transgene encoding interleukin-12.

9 Claims, 62 Drawing Sheets

Figure 1:
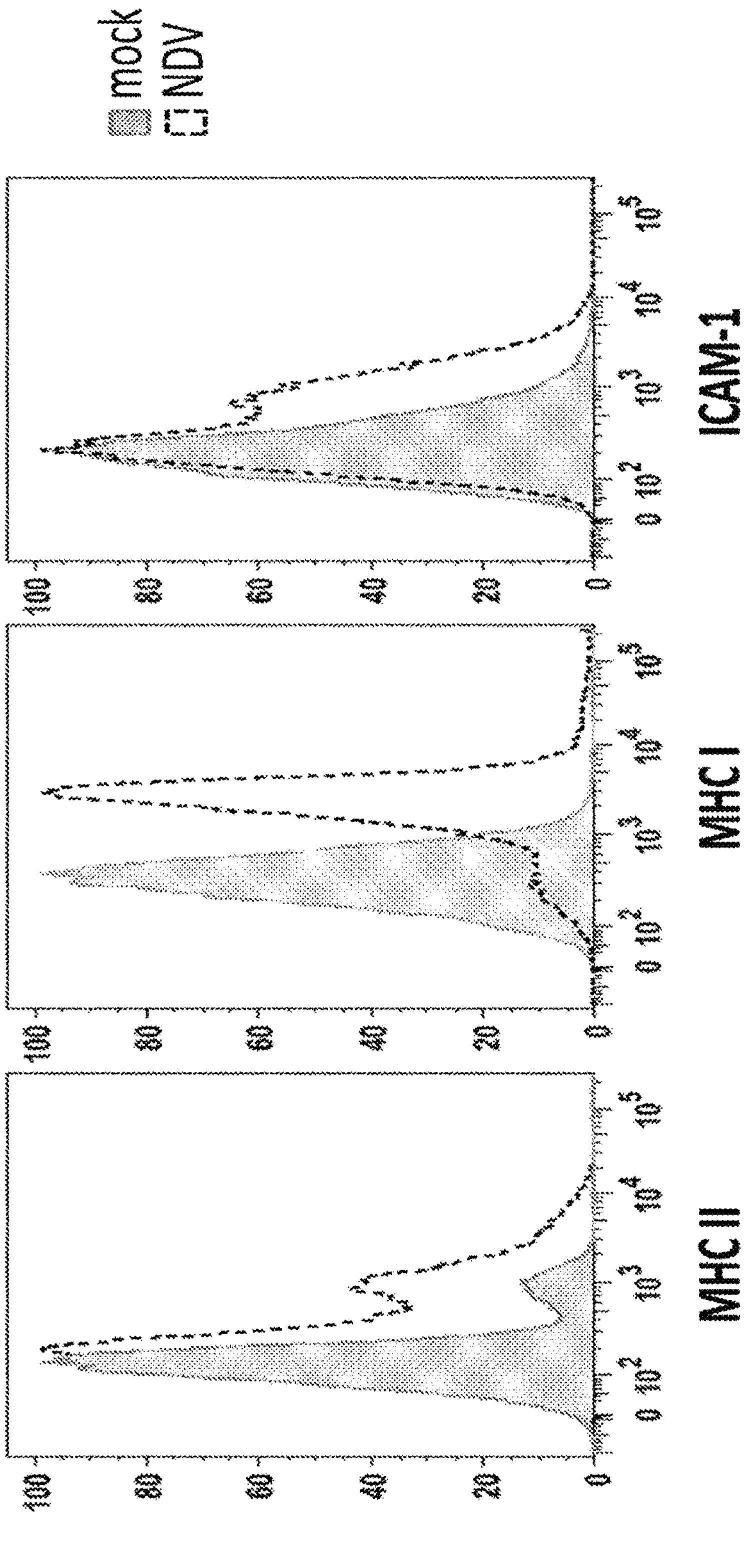

Specification includes a Sequence Listing.

(56) References Cited

U.S. PATENT DOCUMENTS

| | | | |
|---|---|---|---|
| 5,571,698 | A | 11/1996 | Ladner et al. |
| 5,573,920 | A | 11/1996 | Randle |
| 5,580,717 | A | 12/1996 | Dower et al. |
| 5,585,089 | A | 12/1996 | Queen et al. |
| 5,601,819 | A | 2/1997 | Wong et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,698,426 | A | 12/1997 | Huse |
| 5,731,168 | A | 3/1998 | Carter et al. |
| 5,733,743 | A | 3/1998 | Stuart et al. |
| 5,750,753 | A | 5/1998 | Kimae et al. |
| 5,766,886 | A | 6/1998 | Studnicka et al. |
| 5,780,225 | A | 7/1998 | Wigler et al. |
| 5,786,199 | A | 7/1998 | Palese |
| 5,807,715 | A | 9/1998 | Morrison et al. |
| 5,814,318 | A | 9/1998 | Lonberg et al. |
| 5,820,871 | A | 10/1998 | Palese et al. |
| 5,821,047 | A | 10/1998 | Garrard et al. |
| 5,854,037 | A | 12/1998 | Palese et al. |
| 5,891,680 | A | 4/1999 | Lieschke et al. |
| 5,939,598 | A | 8/1999 | Kucherlapati et al. |
| 5,969,108 | A | 10/1999 | McCafferty et al. |
| 6,005,079 | A | 12/1999 | Casterman et al. |
| 6,146,642 | A | 11/2000 | Garcia-Sastre et al. |
| 6,190,901 | B1 | 2/2001 | Sundick et al. |
| 6,287,554 | B1 | 9/2001 | Sundick et al. |
| 6,329,511 | B1 | 12/2001 | Vasquez et al. |
| 6,331,415 | B1 | 12/2001 | Cabilly et al. |
| 6,407,213 | B1 | 6/2002 | Carter et al. |
| 6,451,323 | B1 | 9/2002 | Garcia-Sastre et al. |
| 6,544,785 | B1 | 4/2003 | Palese et al. |
| 6,635,416 | B2 | 10/2003 | Palese et al. |
| 6,649,372 | B1 | 11/2003 | Palese et al. |
| 6,669,943 | B1 | 12/2003 | Palese et al. |
| 6,719,979 | B2 | 4/2004 | Peeters et al. |
| 6,737,522 | B2 | 5/2004 | Sundick et al. |
| 6,811,784 | B2 | 11/2004 | Haller et al. |
| 6,852,522 | B1 | 2/2005 | Palese et al. |
| 6,896,881 | B1 | 5/2005 | Russell et al. |
| 7,052,685 | B1 | 5/2006 | Rook |
| 7,056,689 | B1 | 6/2006 | Lorence et al. |
| 7,060,430 | B2 | 6/2006 | Palese et al. |
| 7,141,550 | B2 | 11/2006 | Molling et al. |
| 7,223,389 | B2 | 5/2007 | Zakay-Rones et al. |
| 7,244,558 | B1 | 7/2007 | Samal et al. |
| 7,332,169 | B2 | 2/2008 | Peeters et al. |
| 7,384,774 | B2 | 6/2008 | Palese et al. |
| 7,442,379 | B2 | 10/2008 | Garcia-sastre et al. |
| 7,442,527 | B2 | 10/2008 | Palese et al. |
| 7,470,426 | B1 | 12/2008 | Roberts et al. |
| 7,488,802 | B2 | 2/2009 | Collins et al. |
| 7,494,808 | B2 | 2/2009 | Palese et al. |
| 7,547,442 | B2 | 6/2009 | Peeters et al. |
| 7,709,226 | B2 | 5/2010 | Foote |
| 7,736,640 | B2 | 6/2010 | Lorence et al. |
| 7,780,962 | B2 | 8/2010 | Roberts et al. |
| 7,833,774 | B2 | 11/2010 | Palese et al. |
| 7,858,081 | B2 | 12/2010 | Bernard et al. |
| 8,043,612 | B2 | 10/2011 | Roberts et al. |
| 8,105,578 | B2 | 1/2012 | Roberts et al. |
| 8,124,084 | B2 | 2/2012 | Lefrancois et al. |
| 8,163,879 | B2 | 4/2012 | Wong et al. |
| 8,168,757 | B2 | 5/2012 | Finnefrock et al. |
| 8,326,547 | B2 | 12/2012 | Liu et al. |
| 8,354,509 | B2 | 1/2013 | Craven et al. |
| 8,475,790 | B2 | 7/2013 | Jure-kunkel |
| 8,486,418 | B2 | 7/2013 | Bublot et al. |
| 8,490,289 | B2 | 7/2013 | Nystrom et al. |
| 8,492,118 | B2 | 7/2013 | Wong et al. |
| 8,507,222 | B2 | 8/2013 | Wong et al. |
| 8,591,881 | B2 | 11/2013 | Palese et al. |
| 8,709,417 | B2 | 4/2014 | Allison et al. |
| 8,765,462 | B2 | 7/2014 | Medin et al. |
| 8,871,191 | B2 | 10/2014 | Pavlakis et al. |
| 8,900,587 | B2 | 12/2014 | Craven et al. |
| 8,940,288 | B2 | 1/2015 | Lefrancois et al. |
| 8,952,136 | B2 | 2/2015 | Carven et al. |
| 9,217,136 | B2 | 12/2015 | Palese et al. |
| 9,370,563 | B2 | 6/2016 | Garzón Morales et al. |
| 9,375,475 | B2 | 6/2016 | Allison et al. |
| 9,387,242 | B2 | 7/2016 | Palese et al. |
| 9,476,033 | B2 | 10/2016 | Samal et al. |
| 9,616,118 | B2 | 4/2017 | Bublot et al. |
| 9,642,298 | B1 | 5/2017 | Martin |
| 9,821,016 | B2 | 11/2017 | Lauer et al. |
| 9,937,196 | B2 | 4/2018 | Samal et al. |
| 10,023,637 | B2 | 7/2018 | Allison et al. |
| 10,035,984 | B2 | 7/2018 | Palese et al. |
| 10,251,922 | B2 | 4/2019 | Palese et al. |
| 10,308,913 | B2 | 6/2019 | Palese et al. |
| 10,383,936 | B2 | 8/2019 | Samal et al. |
| 10,519,426 | B2 | 12/2019 | Cheng et al. |
| 2002/0052030 | A1 | 5/2002 | Wonderling et al. |
| 2002/0150554 | A1 | 10/2002 | Sundick et al. |
| 2003/0044384 | A1 | 3/2003 | Roberts et al. |
| 2003/0078410 | A1 | 4/2003 | Garcia-sastre et al. |
| 2003/0224017 | A1 | 12/2003 | Samal et al. |
| 2004/0005545 | A1 | 1/2004 | Fouchier et al. |
| 2004/0234552 | A1 | 11/2004 | Peeters et al. |
| 2005/0042664 | A1 | 2/2005 | Wu et al. |
| 2005/0048549 | A1 | 3/2005 | Cao et al. |
| 2005/0191617 | A1 | 9/2005 | Inoue et al. |
| 2005/0235134 | A1 | 10/2005 | O'Sullivan |
| 2005/0238622 | A1 | 10/2005 | Axelrod et al. |
| 2006/0159695 | A1 | 7/2006 | Delvecchio et al. |
| 2006/0216310 | A1 | 9/2006 | Lorence et al. |
| 2007/0082848 | A1 | 4/2007 | Alitalo et al. |
| 2008/0057037 | A1 | 3/2008 | Roberts et al. |
| 2008/0206201 | A1 | 8/2008 | Beier et al. |
| 2009/0061521 | A1 | 3/2009 | Palese et al. |
| 2009/0081161 | A1 | 3/2009 | Roberts et al. |
| 2009/0082299 | A1 | 3/2009 | Felber et al. |
| 2009/0175826 | A1 | 7/2009 | Subbiah et al. |
| 2009/0208495 | A1 | 8/2009 | Beier et al. |
| 2009/0214590 | A1 | 8/2009 | Sundick et al. |
| 2009/0238791 | A1 | 9/2009 | Jacques et al. |
| 2009/0280144 | A1 | 11/2009 | Garcia-sastre et al. |
| 2010/0092430 | A1 | 4/2010 | Beier et al. |
| 2010/0297072 | A1 | 11/2010 | DePinho et al. |
| 2011/0020282 | A1 | 1/2011 | Beier et al. |
| 2011/0044937 | A1 | 2/2011 | Bell et al. |
| 2011/0081311 | A1 | 4/2011 | Pavlakis et al. |
| 2011/0081374 | A1 | 4/2011 | Bublot et al. |
| 2011/0158938 | A1 | 6/2011 | Bernard et al. |
| 2011/0189189 | A1 | 8/2011 | Jure-kunkel |
| 2012/0034242 | A1 | 2/2012 | Jooss et al. |
| 2012/0058141 | A1 | 3/2012 | Palese et al. |
| 2012/0058538 | A1 | 3/2012 | Palese et al. |
| 2012/0064112 | A1 | 3/2012 | Samal et al. |
| 2012/0071859 | A1 | 3/2012 | Morgan et al. |
| 2012/0114648 | A1 | 5/2012 | Langermann et al. |
| 2012/0122185 | A1 | 5/2012 | Palese et al. |
| 2013/0084264 | A1 | 4/2013 | Schrier et al. |
| 2013/0108665 | A1 | 5/2013 | Liang |
| 2014/0044678 | A1 | 2/2014 | Palese et al. |
| 2014/0271677 | A1 | 3/2014 | Palese et al. |
| 2014/0134128 | A1 | 5/2014 | Wong et al. |
| 2014/0159960 | A1 | 6/2014 | Mueller |
| 2014/0186303 | A1 | 7/2014 | Subbiah et al. |
| 2014/0205560 | A1 | 7/2014 | Wong et al. |
| 2014/0219955 | A1 | 8/2014 | Wong et al. |
| 2014/0242025 | A1 | 8/2014 | Wong et al. |
| 2014/0377221 | A1 | 12/2014 | Tufaro et al. |
| 2015/0017121 | A1 | 1/2015 | Becher et al. |
| 2015/0093357 | A1 | 4/2015 | Lefrancois et al. |
| 2015/0132257 | A1 | 5/2015 | Wong et al. |
| 2015/0133531 | A1 | 5/2015 | Wiegand |
| 2015/0139945 | A1 | 5/2015 | Lefrancois et al. |
| 2015/0152188 | A1 | 6/2015 | Morisseau et al. |
| 2015/0250837 | A1 | 9/2015 | Nolin et al. |
| 2016/0015760 | A1 | 1/2016 | Palese et al. |
| 2016/0068823 | A1 | 3/2016 | Palese et al. |

(56) References Cited

U.S. PATENT DOCUMENTS

| | | | | |
|---|---|---|---|---|
| 2016/0137721 | A1 | 5/2016 | Palese et al. | |
| 2016/0208222 | A1 | 7/2016 | Cheng et al. | |
| 2017/0037379 | A1 | 2/2017 | Palese et al. | |
| 2017/0247425 | A1 | 8/2017 | Ungerechts et al. | |
| 2017/0285037 | A1 | 10/2017 | Kulangara et al. | |
| 2018/0078592 | A1 | 3/2018 | Palese et al. | |
| 2018/0251555 | A1 | 9/2018 | Allison et al. | |
| 2018/0256655 | A1 | 9/2018 | Palese et al. | |
| 2018/0280455 | A1 * | 10/2018 | Palese ................ | A61K 39/3955 |
| 2020/0297787 | A1 | 9/2020 | Garcia-Sastre et al. | |
| 2021/0198323 | A1 | 7/2021 | Durbin et al. | |
| 2022/0241358 | A1 | 8/2022 | Garcia-Sastre et al. | |

FOREIGN PATENT DOCUMENTS

| | | | | |
|---|---|---|---|---|
| CN | 105188746 | A | 12/2015 | |
| CN | 105734023 | | 7/2016 | |
| CN | 106166294 | | 11/2016 | |
| DE | 3922-444 | A | 1/1991 | |
| EP | 0239400 | | 8/1994 | |
| EP | 0702085 | | 3/1996 | |
| EP | 0780475 | | 6/1997 | |
| EP | 0974660 | | 1/2000 | |
| EP | 0592106 | | 11/2004 | |
| EP | 0519596 | | 2/2005 | |
| EP | 1248654 | | 10/2005 | |
| EP | 1032269 | | 8/2007 | |
| EP | 1486211 | | 10/2008 | |
| EP | 2085092 | | 8/2009 | |
| EP | 0702085 | B2 | 1/2010 | |
| EP | 2669381 | | 12/2013 | |
| EP | 2579884 | B1 | 6/2014 | |
| EP | 2393921 | | 7/2015 | |
| EP | 2987856 | | 2/2016 | |
| EP | 2766035 | | 3/2018 | |
| JP | 2012-527465 | A | 11/2012 | |
| JP | 2016-517269 | A | 6/2016 | |
| JP | 2016-533749 | A | 11/2016 | |
| TW | 201606079 | A | 2/2016 | |
| WO | WO 1986/005807 | | 10/1986 | |
| WO | WO 1989/001036 | | 2/1989 | |
| WO | WO 1990/002809 | | 3/1990 | |
| WO | WO 1991/000360 | | 1/1991 | |
| WO | WO 1991/009967 | | 7/1991 | |
| WO | WO 1991/010737 | | 7/1991 | |
| WO | WO 1991/010741 | | 7/1991 | |
| WO | WO 1992/000373 | | 1/1992 | |
| WO | WO 1992/001047 | | 1/1992 | |
| WO | WO 1992/008802 | | 5/1992 | |
| WO | WO 1992/018619 | | 10/1992 | |
| WO | WO 1992/022324 | | 12/1992 | |
| WO | WO 1993/011236 | | 6/1993 | |
| WO | WO 1993/017105 | | 9/1993 | |
| WO | WO 1993/017715 | | 9/1993 | |
| WO | WO 1994/004678 | | 3/1994 | |
| WO | WO 1994/004690 | | 3/1994 | |
| WO | WO 1994/025591 | | 11/1994 | |
| WO | WO 1994/025627 | | 11/1994 | |
| WO | WO 1995/015982 | | 6/1995 | |
| WO | WO 1995/020401 | | 8/1995 | |
| WO | WO 1996/033735 | | 10/1996 | |
| WO | WO 1996/034096 | | 10/1996 | |
| WO | WO 1996/034625 | | 11/1996 | |
| WO | WO 1997/006270 | | 2/1997 | |
| WO | WO 1997/012032 | | 4/1997 | |
| WO | WO 1997/013844 | | 4/1997 | |
| WO | WO 1997/014433 | | 4/1997 | |
| WO | WO 1998/002530 | | 1/1998 | |
| WO | WO 1998/013501 | | 4/1998 | |
| WO | WO 1998/016654 | | 4/1998 | |
| WO | WO 1998/024893 | | 6/1998 | |
| WO | WO 1998/046645 | | 10/1998 | |
| WO | WO 1998/050433 | | 11/1998 | |
| WO | WO 1998/053078 | | 11/1998 | |
| WO | WO 1999/002657 | | 1/1999 | |
| WO | WO 1999/015672 | | 4/1999 | |
| WO | WO 1999/018799 | | 4/1999 | |
| WO | WO 1999/066045 | | 12/1999 | |
| WO | WO 2000/062735 | | 10/2000 | |
| WO | WO 2000/067786 | | 11/2000 | |
| WO | WO 2001/004333 | | 1/2001 | |
| WO | WO 2001/020989 | | 3/2001 | |
| WO | WO 2001/044301 | | 6/2001 | |
| WO | WO 2002/081621 | | 10/2002 | |
| WO | WO 2002/102404 | | 12/2002 | |
| WO | WO 2003/092579 | | 11/2003 | |
| WO | WO 2006/050984 | | 5/2006 | |
| WO | WO 2007/008918 | | 1/2007 | |
| WO | WO 2007001677 | A2 | 1/2007 | |
| WO | WO 2007001677 | A3 | 1/2007 | |
| WO | WO 2007/064802 | | 6/2007 | |
| WO | WO 2007/084342 | | 7/2007 | |
| WO | WO 2007/113648 | | 10/2007 | |
| WO | WO 2008/011726 | | 1/2008 | |
| WO | WO 2008/156712 | | 12/2008 | |
| WO | WO 2009/002562 | | 12/2008 | |
| WO | WO 2009/095167 | | 8/2009 | |
| WO | WO 2009101149 | A2 | 8/2009 | |
| WO | WO 2009101149 | A3 | 8/2009 | |
| WO | WO 2010/091262 | | 8/2010 | |
| WO | WO 2010/135242 | | 11/2010 | |
| WO | WO 2010126766 | A1 | 11/2010 | |
| WO | WO 2011/022656 | | 2/2011 | |
| WO | WO 2011/041613 | | 4/2011 | |
| WO | WO 2011/119628 | | 9/2011 | |
| WO | WO 2011154476 | A1 | 12/2011 | |
| WO | WO 2012/000188 | | 1/2012 | |
| WO | WO 2012/000443 | | 1/2012 | |
| WO | WO 2012/142529 | | 10/2012 | |
| WO | WO 2013/053775 | | 4/2013 | |
| WO | WO 2013/112942 | | 8/2013 | |
| WO | WO 2013/178344 | | 12/2013 | |
| WO | WO 2014/047350 | | 3/2014 | |
| WO | WO 2014/066527 | | 5/2014 | |
| WO | WO 2014/158811 | | 10/2014 | |
| WO | WO 2014/170032 | | 10/2014 | |
| WO | WO 2015/018528 | | 2/2015 | |
| WO | WO 2015/018529 | | 2/2015 | |
| WO | WO 2015/032755 | | 3/2015 | |
| WO | WO-2015032755 | A1 * | 3/2015 | ........... A61K 35/768 |
| WO | WO 2015/127501 | | 9/2015 | |
| WO | WO 2015/131994 | | 9/2015 | |
| WO | WO 2016/018920 | | 2/2016 | |
| WO | WO 2016/048903 | | 3/2016 | |
| WO | WO 2016/094377 | | 6/2016 | |
| WO | WO 2017/019894 | | 2/2017 | |
| WO | WO 2017/019896 | | 2/2017 | |
| WO | WO 2017/019897 | | 2/2017 | |
| WO | WO 2017/062953 | | 4/2017 | |
| WO | WO-2017062953 | A1 * | 4/2017 | ............. A61P 35/00 |
| WO | WO 2017/083291 | | 5/2017 | |
| WO | WO 2017/118867 | | 7/2017 | |
| WO | WO 2017/123981 | | 7/2017 | |
| WO | WO 2017/190112 | | 11/2017 | |
| WO | WO 2018/027316 | | 2/2018 | |
| WO | WO 2018104540 | A1 | 6/2018 | |
| WO | WO 2018104540 | A4 | 6/2018 | |
| WO | WO 2018/209194 | | 11/2018 | |
| WO | WO 2018218151 | A1 | 11/2018 | |
| WO | WO 2019197275 | A1 | 10/2019 | |
| WO | WO 2019209859 | A1 | 10/2019 | |
| WO | WO 2020014591 | A1 | 1/2020 | |
| WO | WO 2020037215 | A1 | 2/2020 | |
| WO | WO 2020043835 | A1 | 3/2020 | |
| WO | WO 2020079427 | A1 | 4/2020 | |
| WO | WO 2021174121 | A1 | 9/2021 | |

OTHER PUBLICATIONS

Alexander, "Newcastle disease, Newcastle disease virus—an avian paramyxovirus," Kluwer Academic Publishers, Dordrecht, The Netherlands, pp. 1-22 (1988).

(56) References Cited

OTHER PUBLICATIONS

Al-Lazikani et al., "Standard conformations for the canonical structures of immunoglobulins," *J. Mol. Biol.*, 273(4):927-948 (1997).
Altomonte et al., "Engineered newcastle disease virus as an improved oncolytic agent against hepatocellular carcinoma," *Mol. Ther.*, 18: 275-284 (2010).
Annels et al., "Oncolytic Immunotherapy for Bladder Cancer Using Coxsackie A21 Virus," *Mol. Ther. Oncolytics*, 9:1-12 (2018).
Assudani et al., "Immunotherapeutic potential of DISC-HSV and OX40L in cancer," *Cancer Immunol. Immunother.*, 55:104-111 (2006).
Ayers et al., "IFN-γ-related mRNA profile predicts clinical response to PD-1 blockade," *J. Clin. Invest.*, 127(8):2930-2940 (2017).
Ayllon et al., "Rescue of Recombinant Newcastle Disease Virus from cDNA," *J. Vis. Exp.*, 80:e50830 (2013).
Baca et al., "Antibody humanization using monovalent phage display," *J. Biol. Chem.*, 272(16):10678-10684 (1997).
Barber et al. "Restoring function in exhausted CD8 T cells during chronic viral infection," *Nature* 439:682-687, with Supplemental Material attached (2006).
Bart et al., "Role of interferon in the anti-melanoma effects of poly (I).poly (C) and Newcastle disease virus," *Nat. New. Biol.*, 245:229-230 (1973).
Bauzon et al., "Armed therapeutic viruses—a disruptive therapy on the horizon of cancer immunotherapy," *Front. Immunol.*, 5(74):doi: 10.3389/fimmu.2014.00074 (2014).
Blackburn et al., "Tissue-specific differences in PD-1 and PD-L1 expression during chronic viral infection: implications for CD8 T-cell exhaustion," *J. Virol.*, 84(4):2078-2089 (2010) (Epub Dec. 2, 2009).
Blake et al., "Automated kinetic exclusion assays to quantify protein binding interactions in homogeneous solution," *Anal. Biochem.*, 272(2):123-134 (1999).
Bohnsack et al., "Adaptation of the Immune-Related Response Criteria: irRECIST," ESMO, Abstract 4958, pp. 1-8 (2014).
Brahmer et al., "Phase I study of single-agent anti-programmed death-1 (MDX-1106) in refractory solid tumors: safety, clinical activity, pharmacodynamics, and immunologic correlates," *J. Clin. Oncol.*, 28(19):3167-3175 (2010).
Brahmer et al., "Safety and activity of anti-PD-L1 antibody in patients with advanced cancer," *N. Engl. J. Med.*, 366(26):2455-2465 (2012).
Brinkmann et al., "Phage display of disulfide-stabilized Fv fragments," *J. Immunol. Methods*, 182(1):41-50 (1995).
Brown et al., "Role of PD-1 in regulating acute infections," *Curr. Opin. Immunol.*, 22(3):397-401 (2010).
Bryant et al., "Development of intermediate-grade (mantle cell) and low-grade (small lymphocytic and marginal zone) human non-Hodgkin's lymphomas xenotransplanted in severe combined immunodeficiency mouse models," *Lab. Invest.*, 80:557-573 (2000).
Buijs et al., "Recombinant Immunomodulating Lentogenic or Mesogenic Oncolytic Newcastle Disease Virus for Treatment of Pancreatic Adenocarcinoma," *Viruses*, 7:2980-2998 (2015).
Burton et al., "Human antibodies from combinatorial libraries," *Adv. Immunol.*, 57:191-280 (1994).
Calain et al., "The Rule of Six, a Basic Feature for Efficient Replication of Sendai Virus Defective Interfering RNA," *J. Virol.*, 67(8):4822-4830 (1993).
Caldas et al., "Design and synthesis of germline-based hemi-humanized single-chain Fv against the CD18 surface antigen," *Protein Eng.*, 13(5):353-360 (2000).
Car et al., "The Toxicology of Interleukin-12: A Review," *Toxicol. Pathol.*, 27(1):58-63 (1999).
Carpenter et al., "Non-Fc receptor-binding humanized anti-CD3 antibodies induce apoptosis of activated human T cells," *J. Immunol.*, 165(11):6205-6213 (2000).
Carthon et al., "Preoperative CTLA-4 blockade: tolerability and immune monitoring in the setting of a presurgical clinical trial," *Clin. Canc. Res.*, 16(10):2861-2871 (2010).
Caruso et al., "Adenovirus-mediated interleukin-12 gene therapy for metastatic colon carcinoma," *Proc. Natl. Acad. Sci. USA*, 93:11302-11306 (1996).
Chen et al., "CD4 T Cells Require ICOS-Mediated P13K Signaling to Increase T-Bet Expression in the Setting of Anti-CTLA-4 Therapy," *Cancer Immunol. Res.*, 2(2):167-176 (2013).
Cheng et al., "Genetic Modification of Oncolytic Newcastle Disease Virus for Cancer Therapy." *J. Virol.*, 90(1):5343-5352 (2016).
Chothia et al., "Canonical structures for the hypervariable regions of immunoglobulins," *J. Mol. Biol.*, 196(4):901-917 (1987).
Chothia et al., "Conformations of immunoglobulin hypervariable regions," *Nature*, 342:877-883 (1989).
Chothia et al., "Structural repertoire of the human VH segments," *J. Mol. Biol.*, 227(3):799-817 (1992).
Chumakov et al., "Oncolytic Enteroviruses," *Mol. Biol. (Mosk)*, 46(5):639-650 (2012).
Clinical Trial NCT01295827, "Study of Pembrolizumab (MK-3475) in Participants With Progressive Locally Advanced or Metastatic Carcinoma, Melanoma, or Non-small Cell Lung Carcinoma (P07990/MK-3475-001/KEYNOTE-001) (KEYNOTE-001)," Merck Sharp & Dohme Corp., updated Sep. 13, 2018 (13 pages).
Colbère-Garapin et al., "A new dominant hybrid selective marker for higher eukaryotic cells," *J. Mol. Biol.*, 150(1):1-14 (1981).
Crouse et al., "Expression and amplification of engineered mouse dihydrofolate reductase minigenes," *Mol. Cell Biol.*, 3(2):257-266 (1983).
Csatary et al., "MTH-68/H oncolytic viral treatment in human high-grade gliomas," *J. Neurooncol.*, 67:83-93 (2004).
Cull et al., "Screening for receptor ligands using large libraries of peptides linked to the C terminus of the lac repressor," *Proc. Natl. Acad. Sci. USA*, 89(5):1865-1869 (1992).
Cuoto et al., "Anti-BA46 monoclonal antibody Mc3: humanization using a novel positional consensus and in vivo and in vitro characterization," *Cancer Res.*, 55(8): 1717-1722 (1995).
Cuoto et al., "Designing human consensus antibodies with minimal positional templates," *Cancer Res.*, 55(23 Suppl):5973s-5977s (1995).
Curran et al., "Combination CTLA-4 blockade and 4-1BB activation enhances tumor rejection by increasing T-cell infiltration, proliferation, and cytokine production," *PLoS One*, 6(4):e19499 (2011).
Curran et al., "PD-1 and CTLA-4 combination blockade expands infiltrating T cells and reduces regulatory T and myeloid cells within B16 melanoma tumors," *Proc. Natl. Acad. Sci. USA*, 107(9):4275-4280 (2010).
Cwirla et al., "Peptides on phage: a vast library of peptides for identifying ligands," *Proc. Natl. Acad. Sci. USA*, 87(16):6378-6382 (1990).
De Leeuw et al., "Virulence of Newcastle disease virus is determined by the cleavage site of the fusion protein and by both the stem region and globular head of the haemagglutinin-neuraminidase protein," *J. Gen. Virol.*, 86(5): 1759-1769 (2005).
De Sousa Linhares et al., "Not All Immune Checkpoints Are Created Equal," *Front. Immunol.*, 9:1909 (2018).
Dezfouli et al., "Enhancing CTL responses to melanoma cell vaccines in vivo: synergistic increases obtained using IFNgamma primed and IFNbeta treated B7-1+ B16-F10 melanoma cells," *Immunol. Cell. Biol.*, 81(6):459-471 (2003).
Diamond et al., "Type I interferon is selectively required by dendritic cells for immune rejection of tumors," *J. Exp. Med.*, 208(10):1989-2003 (2011).
Dias et al., "Targeted cancer immunotherapy with oncolytic adenovirus coding for a fully human monoclonal antibody specific for CTLA-4," *Gen Ther.*, 19(10):988-998 (2012).
Dortmans et al., "Virulence of Newcastle disease virus: what is known so far?" *Vet. Res.*, 42:122 (2011).
Douin-Echinard et al., "Enhancement of anti-tumor immunity by injection of fibroblasts genetically engineered to produce IL-12 and to express CD70," *Gene Therapy of Cancer*, edited by Walden et al., Plenum Press, New York, 353-357 (1998).
Dupraz et al., "Dominant negative MyD88 proteins inhibit interleukin-1β/interferon-γ-mediated induction of nuclear factor κB-dependent nitrite production and apoptosis in β cells," *J. Biol. Chem.*, 275:37672-37678 (2000).

(56) References Cited

OTHER PUBLICATIONS

Eisenhauer et al., "New response evaluation criteria in solid tumours: revised RECIST guideline (version 1.1)," *Eur. J. Cancer*, 45:228-247 (2009).
Elankumaran et al., "Type I interferon-sensitive recombinant newcastle disease virus for oncolytic virotherapy," *J. Virol.*, 84:3835-3844 (2010).
Fan et al., "Engagement of the ICOS pathway markedly enhances efficacy of CTLA-4 blockade in cancer immunotherapy," *J. Exp. Med.*, 211(4):715-725 (2014).
Fecci et al., "Systemic CTLA-4 blockade ameliorates glioma-induced changes to the CD4+ T cell compartment without affecting regulatory T-cell function," *Clin. Cancer Res.*, 13: 2158-2167 (2007).
Felici et al., "Selection of antibody ligands from a large library of oligopeptides expressed on a multivalent exposition vector," *J. Mol. Biol.*, 222(2):301-310 (1991).
Fields et al., "Adenoviridae and Their Replication," *Fundamental Virology*, 2nd Edition, Raven Press, Chapter 31, pp. 771-813 (1991).
Fiola et al., "Tumor selective replication of Newcastle disease virus: association with defects of tumor cells in antiviral defence," *Int. J. Cancer*, 119(2): 328-338 (2006).
Fisher et al., "IL-6 trans-signaling licenses mouse and human tumor microvascular gateways for trafficking of cytotoxic T cells," *J. Clin. Invest.*, 121(10):3846-3859 (2011).
Fodde et al., "Disease model: familial adenomatous polyposis," *Trends Mol. Med.*, 7:369-373 (2001).
Fodor et al., "Multiplexed biochemical assays with biological chips," *Nature*, 364(6437):555-556 (1993).
Foecking et al., "Powerful and versatile enhancer-promoter unit for mammalian expression vectors," *Gene*, 45(1):101-105 (1986).
Foote et al., "Antibody framework residues affecting the conformation of the hypervariable loops," *J. Mol. Biol.*, 224(2):487-499 (1992).
Fournier et al., "Oncolytic Newcastle Disease Virus as Cutting Edge between Tumor and Host," *Biology*, 2:936-975 (2013).
Foy et al., "Regulation of interferon regulatory factor-3 by the hepatitis C virus serine protease," *Science*, 300(5622):1145-1148 (2003).
Franciszkiewicz et al., "Role of chemokines and chemokine receptors in shaping the effector phase of the antitumor immune response," *Cancer Res.*, 72(24):6325-6332 (2012).
Fransen et al., "Controlled Local Delivery of CTLA-4 Blocking Antibody Induces $CD8^+$ T-Cell-Dependent Tumor Eradication and Decreases Risk of Toxic Side Effects," *Clin. Cancer Res.*, 19(19):5381-5389 (2013).
Freeman et al., "Phase I/II trial of intravenous NDV-HUJ oncolytic virus in recurrent glioblastoma multiforme," *Mol. Ther.*, 13:221-228 (2006).
Fu et al., "The ICOS/ICOSL Pathway is Required for Optimal Antitumor Responses Mediated by Anti-CTLA-4 Therapy," *Cancer Res.*, 71:5445-5454 (2011).
Fuertes et al., "Host type I IFN signals are required for antitumor CD8+ T cell responses through CD8 {alpha}+ dendritic cells," *J. Exp. Med.*, 208(10):2005-2016 (2011).
Galivo et al., "Interference of CD40L-Mediated Tumor Immunotherapy by Oncolytic Vesicular Stomatitis Virus," *Human Gene Therapy*, 21:439-450 (2010).
Gambotto et al., "Induction of antitumor immunity by direct intratumoral injection of a recombinant adenovirus vector expressing interleukin-12," *Cancer Gene Ther.*, 6(1):45-53 (1999).
Gao et al., "Expression of transgenes from newcastle disease virus with a segmented genome," *J. Virol.*, 82(6): 2692-2698 (2008).
Garcia-Sastre et al., "Introduction of foreign sequences into the genome of influenza A virus," *Dev. Biol. Stand.*, 82:237-246 (1994).
Garcia-Sastre et al., "Use of a mammalian internal ribosomal entry site element for expression of a foreign protein by a transfectant influenza virus," *J. Virol.*, 68:6254-6261 (1994).
Gardiner et al., "A Randomized, Double-Blind, Placebo-Controlled Assessment of BMS-936558, a Fully Human Monoclonal Antibody to Programmed Death-1 (PD-1), in Patients with Chronic Hepatitis C Virus Infection," *PLoS One*, 8(5):e63818 (2013).
GenBank Accession No. AAD00274.1, "CD70 [Mus musculus]," Jan. 5, 1999.
GenBank Accession No. AAS67141.1, "fusion protein [Avian avulavirus 1]," Mar. 22, 2004.
GenBank Accession No. AAS67147.1, "fusion protein [Avian avulavirus 1]," Mar. 22, 2004.
GenBank Accession No. AAS67153.1, "fusion protein [Avian avulavirus 1]," Mar. 22, 2004.
GenBank Accession No. AAS67159.1, "fusion protein [Avian avulavirus 1]," Mar. 22, 2004.
GenBank Accession No. AAS67165.1, "fusion protein [Avian avulavirus 1]," Mar. 22, 2004.
GenBank Accession No. ACJ53752.1, "fusion protein [Avian avulavirus 1]," Nov. 25, 2008.
GenBank Accession No. ACJ53758.1, "fusion protein [Avian avulavirus 1]," Nov. 25, 2008.
GenBank Accession No. ACK57498.1, "fusion protein [Avian avulavirus 1]," Apr. 19, 2011.
GenBank Accession No. ADF59234.1, "fusion protein [Avian avulavirus 1]," Aug. 16, 2011.
GenBank Accession No. AF124443.1, "Newcastle disease virus isolate Roakin matrix protein mRNA, complete cds," Mar. 6, 2000.
GenBank Accession No. AF163440.1, "Newcastle disease virus fusion glycoprotein precursor, gene, complete cds," Jul. 6, 1999.
GenBank Accession No. AF309418.1, "Newcastle disease virus B1, complete genome," Dec. 2, 2000.
GenBank Accession No. AIA66858.1, "NBS-LRR resistance protein, partial [Solanum viarum]," Jun. 4, 2014.
GenBank Accession No. AIA66951.1, "fusion protein [Avian avulavirus 1]," Jun. 4, 2014.
GenBank Accession No. AY143159.1, "Newcastle disease virus strain MET95 hemagglutinin-neuraminidase protein HN gene, complete cds," Jul. 25, 2003.
GenBank Accession No. AY351959.1, "Newcastle disease virus hemagglutinin-neuraminidase gene, complete cds," Aug. 25, 2003.
GenBank Accession No. AY390310.1, "Newcastle disease virus strain YG97 from goose fusion protein gene, partial cds," Jul. 26, 2016.
GenBank Accession No. AY845400.2, "Newcastle disease virus strain LaSota, complete genome," Mar. 17, 2005.
GenBank Accession No. CAG46642.1, "CD86, partial [*Homo sapiens*]," Jul. 26, 2016.
GenBank Accession No. EU293914.1, "Newcastle disease virus strain Italien, complete genome," Jun. 24, 2008.
GenBank Accession No. JF950510.1, Newcastle disease virus strain LaSota, complete genome, Aug. 10, 2011.
GenBank Accession No. M11220.1, "Human granulocyte-macrophage colony stimulating factor (GM-CSF) mRNA," Nov. 8, 1994.
GenBank Accession No. NC_002617.1, "Newcastle disease virus B1, complete genome," Nov. 30, 2009.
GenBank Accession No. NM_000402.2, "*Homo sapiens* glucose-6-phosphate dehydrogenase (G6PD), nuclear gene encoding mitochondrial protein, mRNA," May 7, 2006.
GenBank Accession No. NM_000585.4, "*Homo sapiens* interleukin 15 (IL15), transcript variant 3, mRNA," May 6, 2017.
GenBank Accession No. NM_000586.3, "*Homo sapiens* interleukin 2 (IL2), mRNA," Apr. 30, 2017.
GenBank Accession No. NM_000590.1, "*Homo sapiens* interleukin 9 (IL9), mRNA," May 6, 2017.
GenBank Accession No. NM_000594.3, "*Homo sapiens* tumor necrosis factor (TNF), mRNA," May 7, 2017.
GenBank Accession No. NM_000619.2, "*Homo sapiens* interferon gamma (IFNG), mRNA," May 13, 2017.
GenBank Accession No. NM_000880.3, "*Homo sapiens* interleukin 7 (IL7), transcript variant 1, mRNA," May 10, 2017.
GenBank Accession No. NM_000882.3, "*Homo sapiens* interleukin 12A (IL12A), mRNA," Apr. 30, 2017.
GenBank Accession No. NM_000937.2, *Homo sapiens* polymerase (RNA) II (DNA directed) polypeptide A, 220kDa (POLR2A), mRNA.

(56) References Cited

OTHER PUBLICATIONS

GenBank Accession No. NM_001024736.1, "*Homo sapiens* CD276 molecule (CD276), transcript variant 1, mRNA," May 7, 2017.
GenBank Accession No. NM_001090.2, "*Homo sapiens* ATP binding cassette subfamily F member 1 (ABCF1), transcript variant 2, mRNA," Apr. 27, 2017.
GenBank Accession No. NM_001099270.1, "*Homo sapiens* zinc finger and BTB domain containing 34 (ZBTB34), mRNA," Apr. 30, 2017.
GenBank Accession No. NM_001172085.1, "*Homo sapiens* TATA-box binding protein (TBP), transcript variant 2, mRNA," Apr. 17, 2017.
GenBank Accession No. NM_001199886.1, "*Homo sapiens* interleukin 7 (IL7), transcript variant 2, mRNA," May 10, 2017.
GenBank Accession No. NM_001199887.1, "*Homo sapiens* interleukin 7 (IL7), transcript variant 3, mRNA," May 10, 2017.
GenBank Accession No. NM_001199888.1, "*Homo sapiens* interleukin 7 (IL7), transcript variant 4, mRNA," May 10, 2017.
GenBank Accession No. NM_001207006.2, "*Homo sapiens* interleukin 21 (IL21), transcript variant 2, mRNA," May 7, 2017.
GenBank Accession No. NM_001242.4, "*Homo sapiens* CD27 molecule (CD27), mRNA," Apr. 28, 2017.
GenBank Accession No. NM_001252.3, "*Homo sapiens* CD70 molecule (CD70), mRNA," Jan. 11, 2014.
GenBank Accession No. NM_001267706.1, "*Homo sapiens* CD274 molecule (CD274), transcript variant 2, mRNA," Apr. 23, 2017.
GenBank Accession No. NM_001314029.1, "*Homo sapiens* CD274 molecule (CD274), transcript variant 4, mRNA," Apr. 23, 2017.
GenBank Accession No. NM_001768.5, "*Homo sapiens* CD8a molecule (CD8A), transcript variant 1, mRNA," Sep. 28, 2008.
GenBank Accession No. NM_002122.3, "*Homo sapiens* major histocompatibility complex, class II, DQ alpha 1 (HLA-DQA1), mRNA," May 7, 2017.
GenBank Accession No. NM_002124.1, "*Homo sapiens* major histocompatibility complex, class II, DR beta 1 (HLA-DRB1), mRNA," Jul. 31, 2007.
GenBank Accession No. NM_002164.3, "*Homo sapiens* indoleamine-pyrrole 2,3 dioxygenase (INDO), mRNA," Aug. 6, 2007.
GenBank Accession No. NM_002187.2, "*Homo sapiens* interleukin 12B (IL12B), mRNA," May 6, 2017.
GenBank Accession No. NM_002190.2, "*Homo sapiens* interleukin 17A (IL17A), mRNA," May 7, 2017.
GenBank Accession No. NM_002286.5, "*Homo sapiens* lymphocyte activating 3 (LAG3), mRNA," May 7, 2017.
GenBank Accession No. NM_002416.1, "*Homo sapiens* chemokine (C-X-C motif) ligand 9 (CXCL9), mRNA," Sep. 25, 2014.
GenBank Accession No. NM_002801.2, "*Homo sapiens* proteasome (prosome, macropain) subunit, beta type, 10 (PSMB10), mRNA," Feb. 10, 2011.
GenBank Accession No. NM_002985.2, "*Homo sapiens* C—C motif chemokine ligand 5 (CCL5), transcript variant 1, mRNA," May 6, 2017.
GenBank Accession No. NM_003326.3, "*Homo sapiens* tumor necrosis factor (ligand) superfamily, member 4 (TNFSF4), mRNA," May 4, 2014.
GenBank Accession No. NM_003811.3, "*Homo sapiens* TNF superfamily member 9 (TNFSF9), mRNA," Mar. 4, 2017.
GenBank Accession No. NM_004072.1, "*Homo sapiens* chemokine-like receptor 1 (CMKLR1), mRNA," Jul. 13, 2008.
GenBank Accession No. NM_004152.2, "*Homo sapiens* ornithine decarboxylase antizyme 1 (OAZ1), mRNA," Jul. 4, 2014.
GenBank Accession No. NM_004168.1, "*Homo sapiens* succinate dehydrogenase complex, subunit A, flavoprotein (Fp) (SDHA), nuclear gene encoding mitochondrial protein, mRNA," Jun. 3, 2007.
GenBank Accession No. NM_005018.2, "*Homo sapiens* programmed cell death 1 (PDCD1), mRNA," May 6, 2017.
GenBank Accession No. NM_005191.3, "*Homo sapiens* CD80 molecule (CD80), mRNA," May 6, 2017.
GenBank Accession No. NM_005516.4, "*Homo sapiens* major histocompatibility complex, class I, E (HLA-E), mRNA," Jul. 5, 2010.
GenBank Accession No. NM_005601.3, "*Homo sapiens* natural killer cell granule protein 7 (NKG7), mRNA," Apr. 26, 2017.
GenBank Accession No. NM_006564.1, "*Homo sapiens* C-X-C motif chemokine receptor 6 (CXCR6), mRNA," Apr. 25, 2017.
GenBank Accession No. NM_007315.2, "*Homo sapiens* signal transducer and activator of transcription 1, 91kDa (STAT1), transcript variant alpha, mRNA," Apr. 29, 2008.
GenBank Accession No. NM_009404.3, "Mus musculus tumor necrosis factor (ligand) superfamily, member 9 (Tnfsf9), mRNA," Apr. 29, 2017.
GenBank Accession No. NM 009452.2, "Mus musculus tumor necrosis factor (ligand) superfamily, member 4 (Tnfsf4), mRNA," May 12, 2017.
GenBank Accession No. NM_009855.2, "Mus musculus CD80 antigen (Cd80), mRNA," Apr. 28, 2017.
GenBank Accession No. NM_011617.2, "Mus musculus CD70 antigen (Cd70), mRNA," Sep. 1, 2016.
GenBank Accession No. NM_014143.3, "*Homo sapiens* CD274 molecule (CD274), transcript variant 1, mRNA," Apr. 30, 2017.
GenBank Accession No. NM_015259.4, "*Homo sapiens* inducible T-cell co-stimulator ligand (ICOSLG), mRNA," Sep. 2, 2013.
GenBank Accession No. NM_015527.3, "*Homo sapiens* TBC1 domain family member 10B (TBC1D10B), mRNA," May 2, 2017.
GenBank Accession No. NM_015790.3, "Mus musculus icos ligand (Icosl), mRNA," Feb. 15, 2015.
GenBank Accession No. NM_017970.3, "*Homo sapiens* NRDE-2, necessary for RNA interference, domain containing (NRDE2), mRNA," May 10, 2017.
GenBank Accession No. NM_018955.2, "*Homo sapiens* ubiquitin B (Ubb), mRNA," Apr. 17, 2013.
GenBank Accession No. NM_019388.3, "Mus musculus CD86 antigen (Cd86), mRNA," May 2, 2017.
GenBank Accession No. NM_020525.4, "*Homo sapiens* interleukin 22 (IL22), mRNA," Apr. 26, 2017.
GenBank Accession No. NM_021803.3, "*Homo sapiens* interleukin 21 (IL21), transcript variant 1, mRNA," May 7, 2017.
GenBank Accession No. NM_025239.3, "*Homo sapiens* programmed cell death 1 ligand 2 (PDCDILG2), mRNA," May 3, 2017.
GenBank Accession No. NM_052902.2, "*Homo sapiens* serine/threonine kinase 11 interacting protein (STK11IP), mRNA," Mar. 22, 2015.
GenBank Accession No. NM_172175.2, "*Homo sapiens* interleukin 15 (IL15), transcript variant 2, mRNA," May 6, 2017.
GenBank Accession No. NM_173799.2, "*Homo sapiens* T cell immunoreceptor with Ig and ITIM domains (TIGIT), mRNA," Jun. 18, 2009.
GenBank Accession No. NP_001243.1, "CD70 antigen isoform 1 [*Homo sapiens*]," Oct. 8, 2016.
GenBank Accession No. NP_001254635.1, "programmed cell death 1 ligand 1 isoform b precursor [*Homo sapiens*]," Apr. 23, 2017.
GenBank Accession No. NP_001300958.1, "programmed cell death 1 ligand 1 isoform c precursor [*Homo sapiens*]," Apr. 23, 2017.
GenBank Accession No. NP_002178.2, "interleukin-12 subunit beta precursor [*Homo sapiens*]," May 6, 2017.
GenBank Accession No. NP_003317.1, "tumor necrosis factor ligand superfamily member 4 isoform 1 [*Homo sapiens*]," Apr. 23, 2017.
GenBank Accession No. NP_003802.1, "tumor necrosis factor ligand superfamily member 9 [*Homo sapiens*]," Mar. 4, 2017.
GenBank Accession No. NP_005009.2, "programmed cell death protein 1 precursor [*Homo sapiens*]," May 6, 2017.
GenBank Accession No. NP_005182.1, "T-lymphocyte activation antigen CD80 precursor [*Homo sapiens*]," Apr. 30, 2017.
GenBank Accession No. NP_033430.1, "tumor necrosis factor ligand superfamily member 9 [Mus musculus ]," Apr. 29, 2017.
GenBank Accession No. NP_033478.1, "tumor necrosis factor ligand superfamily member 4 [Mus musculus]," May 12, 2017.
GenBank Accession No. NP_033985.3, "T-lymphocyte activation antigen CD80 precursor [Mus musculus]," Apr. 28, 2017.

(56) References Cited

OTHER PUBLICATIONS

GenBank Accession No. NP_054862.1, "programmed cell death 1 ligand 1 isoform a precursor [*Homo sapiens*]," Apr. 30, 2017.
GenBank Accession No. NP_056074.1, "ICOS ligand isoform a precursor [*Homo sapiens*]," Apr. 23, 2017.
GenBank Accession No. NP_056605.1, "ICOS ligand precursor [Mus musculus]," Feb. 15, 2015.
GenBank Accession No. NP_056606.1, "F-box only protein 8 [Mus musculus]," Apr. 8, 2003.
GenBank Accession No. NP_062261.3, "T-lymphocyte activation antigen CD86 precursor [Mus musculus]," May 2, 2017.
GenBank Accession No. NP_079515.2, "programmed cell death 1 ligand 2 precursor [*Homo sapiens*]," May 3, 2017.
GenBank Accession No. U25837.1, "Newcastle disease virus isolate Ulster matrix protein mRNA, complete cds," Jul. 12, 1996.
GenBank Accession No. NP_000873.2, "interleukin-12 subunit alpha precursor [*Homo sapiens*]," Apr. 30, 2017.
Ghaneh et al., "Adenovirus-mediated transfer of p53 and p16(INK4a) results in pancreatic cancer regression in vitro and in vivo," *Gene Ther.*, 8:199-208 (2001).
Gillies et al., "High-level expression of chimeric antibodies using adapted cDNA variable region cassettes," *J. Immunol. Methods*, 125(1-2):191-202 (1989).
Goff et al., "A Majority of Infectious Newcastle Disease Virus Particles Contain a Single Genome, while a Minority Contain Multiple Genomes," *J. Virol.*, 86(19):10852-10856 (2012).
Gruber et al., "Efficient tumor cell lysis mediated by a bispecific single chain antibody expressed in *Escherichia coli*," *J. Immunol.*, 152(11):5368-5374 (1994).
Guo et al., "Oncolytic immunotherapy: dying the right way is a key to eliciting potent antitumor immunity," *Front. Oncol.*, 4(74):1-11 (2014).
Haas et al., "Bispecific antibodies increase T-cell stimulatory capacity in vitro of human autologous virus-modified tumor vaccine," *Clin. Cancer Res.*, 4(3):721-730 (1998).
Haas et al., "A tumor vaccine containing ant-CD# and anti-CD28 bispecific antibodies triggers strong and durable antitumor activity in human lymphocytes," *Int. J. Cancer*, 188(3):658-667 (2006).
Haas et al., "An effective strategy of human tumor vaccine modification by coupling bispecific costimulatory molecules," *Cancer Gene Therapy*, 6(3):254-262 (1999).
Hamid et al., "Safety and Tumor Responses with Lambrolizumab (Anti-PD-1) in Melanoma," *N. Engl. J. Med.*, 369(2):134-144 (2013).
Hamid et al., "Combination of MEDI0680, an anti-PD-1 antibody, with durvalumab, an anti-PD-L1 antibody: A phase 1, open-label study in advanced malignancies," *Ann. Oncol.*, 27(suppl. 6):1050PD (2016).
He et al., "Humanization and pharmacokinetics of a monoclonal antibody with specificity for both E- and P-selectin," *J. Immunol.*, 160(2):1029-1035 (1998).
Heery et al., "Phase I open-label, multiple ascending dose trial of MSB0010718C, an anti-PD-L1 monoclonal antibody, in advanced solid malignancies," *J. Clin. Oncol.*, 32(suppl. 5S):abstract 3064 (2014).
Hemminki et al., "Oncolytic Immunotherapy: Where Are We Clinically? ," *Scientifica*, 2014, Article ID 862925 (2014).
Herber et al., "Squamous epithelial hyperplasia and carcinoma in mice transgenic for the human papillomavirus type 16 E7 oncogene," *J. Virol.*, 70:1873-1881 (1996).
Herbst et al., "Predictive correlates of response to the anti-PD-L1 antibody MPDL3280A in cancer patients," *Nature*, 515(7528):563-567 (2014).
Herbst et al., "A study of MPDL3280A, an engineered PD-L1 antibody in patients with locally advanced or metastatic tumors," *J. Clin. Oncol.*, 31(suppl):abstact 3000 (2013).
Hirano et al., "Blockade of B7—H1 and PD-1 by Monoclonal Antibodies Potentiates Cancer Therapeutic Immunity," *Cancer Res.*, 65(3):1089-1096 (2005).
Hirschhorn-Cymerman et al., "Induction of tumoricidal function in CD4+ T cells is associated with concomitant memory and terminally differentiated phenotype," *J. Exp. Med.*, 209(11):2113-2126 (2012).
Hofmeyer et al., "The PD-1/PD-L1 (B7-H1) Pathway in Chronic Infection-Induced Cytotoxic T Lymphocyte Exhaustion," *J. Biomed. Biotechnol.*, 2011:451694 (2011).
Holliger et al., ""Diabodies": small bivalent and bispecific antibody fragments," *Proc. Natl. Acad. Sci. USA*, 90(14):6444-6448 (1993).
Hollinger et al., "Engineered antibody fragments and the rise of single domains," *Nature Biotech.*, 23(9):1126-1136 (2005).
Hosokawa et al., "In vivo analysis of mammary and non-mammary tumorigenesis in MMTV-cyclin D1 transgenic mice deficient in p53," *Transgenic Res.*, 10:471-478 (2001).
Hotte et al., "An optimized clinical regimen for the oncolytic virus PV701," *Clin. Cancer Res.*, 13:977-985 (2007).
Hou et al., "Study on the effect of Newcastle disease virus vaccine and interleukin-12 to the tranjsplantable nude mice model of human ovarian cancer," *Chin. J. Cancer Prev. Treat.*, 16(18):1375-1378 (2009).
Houdebine, "Production of Pharmaceutical Proteins by Transgenic Animals." *Comp. Immunol. Microbiol. Infect. Dis.*, 32(2):107-121 (2009).
Hough et al., "A model for spontaneous B-lineage lymphomas in IgHmu-HOX11 transgenic mice," *Proc. Natl. Acad. Sci USA*, 95:13853-13858 (1998).
Houghten et al. "The use of synthetic peptide combinatorial libraries for the identification of bioactive peptides," *Biotechniques*, 13(3):412-421 (1992).
Huang et al., "Newcastle disease virus V protein is associated with viral pathogenesis and functions as an alpha interferon antagonist," *J. Virol.*, 77:8676-8685 (2003).
Huang et al., "Preclinical validation: LV/IL-12 transduction of patient leukemia cells for immunotherapy of AML," *Mol. Ther.*, 3:16074 (2016).
Huard et al., "CD4/major histocompatibility complex class II interaction analyzed with CD4- and lymphocyte activation gene-3 (LAG-3)-Ig fusion proteins," *Eur. J. Immunol.*, 25:2718-2721 (1995).
Infante et al., "Clinical and pharmacodynamic (PD) results of a phase I trial with AMP-224 (B7-DC Fc) that binds to the PD-1 receptor," *J. Clin. Oncol.*, 31(suppl): abstract 3044 (2013).
Inouye et al., "Up-promoter mutations in the lpp gene of *Escherichia coli*," *Nucleic Acids Res.*, 13(9):3101-3110 (1985).
International Nonproprietary Names for Pharmaceutical Substances (INN), WHO Drug Information, vol. 27, No. 2, 2013, List 109.
Ishida et al., "Induced expression of PD-1, a novel member of the immunoglobulin gene superfamily, upon programmed cell death," *Embo. J.*, 11:3887-3895 (1992).
Iwai et al., "PD-1 Inhibits Antiviral Immunity at the Effector Phase in the Liver," *J. Exp. Med.*, 198(1):39-50 (2003).
Iwai et al., "Involvement of PD-L1 on tumor cells in the escape from host immune system and tumor immunotherapy by PD-L1 blockade," *Proc. Natl. Acad. Sci USA*, 99:12293-12297 (2002).
Jones et al., "Molecular interactions within the IL-6/IL-12 cytokine/receptor superfamily," *Immunol. Res.*, 51(1):5-14 (2011).
Kabat et al., "Attempts to locate complementarity-determining residues in the variable positions of light and heavy chains," *Ann. NY Acad. Sci.*, 190:382-391 (1971).
Kado et al., "Intestinal Microflora Are Necessary for Development of Spontaneous Adenocarcinoma of the Large Intestine in T-Cell Receptor β Chain and p53 Double-Knockout Mice," *Cancer Res.*, 61:2395-2398 (2001).
Kamphorst et al., "Rescue of exhausted CD8 T cells by PD-1-targeted therapies is CD28-dependent," *Science*, 355(6332):1423-1427 (2017).
Kato et al., "Cell type-specific involvement of RIG-I in antiviral response," *Immunity*, 23(1):19-28 (2005).
Kettleborough et al., "Isolation of tumor cell-specific single-chain Fv from immunized mice using phage-antibody libraries and the re-construction of whole antibodies from these antibody fragments," *Eur. J. Immunol.*, 24:952-958 (1994).
Keytruda Highlights of Prescribing Information, revised Aug. 2018.
Keytruda Highlights of Prescribing Information, revised Oct. 2016.

(56) References Cited

OTHER PUBLICATIONS

Keytruda Highlights of Prescribing Information, Reference ID: 3862712, Dec. 2015.
Khattar et al., "A Y526Q mutation in the Newcastle disease virus HN protein reduces its functional activities and attenuates virus replication and pathogenicity," *J. Virol.*, 83:7779-7782 (2009).
Kilpatrick et al., "Rapid development of affinity matured monoclonal antibodies using RIMMS," *Hybridoma*, 16(4):381-389 (1997).
Kim et al., "Evaluation of fusion protein cleavage site sequences of Newcastle disease virus in genotype matched vaccines," *PLoS One*, 12(3):e0173965 (2017).
Kim et al., "Expression and characterization of a recombinant Fab fragment derived from an anti-human alpha-fetoprotein monoclonal antibody," *Mol. Cells.*, 11:158-163 (2001).
Kim et al., "LaSota fusion (F) cleavage motif-mediated fusion activity is affected by other regions of the F protein from different genotype Newcastle disease virus in a chimeric virus: implication for virulence attenuation," *J. Gen. Virol.*, 97(6):1297-1303 (2016).
Kohler, "Immunoglobulin chain loss in hybridoma lines," *Proc. Natl. Acad. Sci. USA*, 77(4):2197-2199 (1980).
Kostelny et al., "Formation of a bispecific antibody by the use of leucine zippers," *J. Immunol.*, 148(5):1547-1553 (1992).
Kozbor et al., "A human hybrid myeloma for production of human monoclonal antibodies," *J. Immunol.*, 133(6):3001-3005 (1984).
Krishnamurthy et al., "Differentially regulated interferon response determines the outcome of Newcastle disease virus infection in normal and tumor cell lines," *J. Virology*, 80:5145-5155 (2006).
Kulangara et al., "Development of the combined positive score (CPS) for the evaluation of PD-L1 in solid tumors with the immunohistochemistry assay PD-L1 IHC 22C3 pharmDx," *J. Clin. Oncol.*, 35(15_suppl):e14589 (2017).
Kuraguchi et al., "Tumor-associated Apc mutations in Mlh1-/- Apc1638N mice reveal a mutational signature of Mlh1 deficiency," *Oncogene*, 19(50):5755-5763 (2001).
Lam et al., "A new type of synthetic peptide library for identifying ligand-binding activity," *Nature*, 354(6348):82-84 (1991).
Lamb et al., Paramyxoviridae: The Viruses and Their Replication. In B.N. Fields, D.M. Knipe, & P.M. Howley (Eds.), *Fundamental Virology*, pp. 577-605, Philadelphia, PA (1996).
Leach et al., "Enhancement of antitumor immunity by CTLA-4 blockade," *Science*, 271:1734-1736 (1996).
Lee et al., "Isolation of cDNA for a human granulocyte-macrophage colony-stimulating factor by functional expression in mammalian cells," *Proc. Natl. Acad. Sci. USA*, 82(13):4360-4364 (1985).
Lefranc et al., "IMGT, the international ImMunoGene Tics database," *Nucl. Acids Res.*, 27(1):209-212 (1999).
Lefranc, "The IMGT unique numbering for immunoglobulins, T-cell receptors, and Ig-like domains," *Immunologist*, 7:132-136 (1999).
Lei et al., "An oncolytic adenovirus expressing granulocyte macrophage colony-stimulating factor shows improved specificity and efficacy for treating human solid tumors," *Cancer Gene Therapy*, 16:33-43 (2009).
Leonard et al., "Effects of single-dose interleukin-12 exposure on interleukin-12-associated toxicity and interferon-gamma production," *Blood*, 90(7):2541-2548 (1997).
Li et al., "Therapeutic effects of a fusogenic Newcastle disease virus in treating head and neck cancer," *Head Neck*, 33(10):1394-1399 (2011).
Li et al., "Decreased dependence on receptor recognition for the fusion promotion activity of L289A-mutated newcastle disease virus fusion protein correlates with a monoclonal antibody-detected conformational change," *J. Virol.*, 79(2):1180-1190 (2005).
Lieschke et al., "Bioactive murine and human interleukin-12 fusion proteins which retain antitumor activity in vivo," *Nature*, 15: 35-40 (1997).
Lipson et al., "Durable Cancer Regression Off-treatment and Effective Re-induction Therapy with an Anti-PD-1 Antibody," *Clin. Cancer Res.*, 19(2):462-468 (2013).
Liu et al., "Adenovirus-mediated intratumoral expression of immunostimulatory proteins in combination with systemic Treg inactivation induces tumor-destructive immune responses in mouse models," *Cancer Gene Ther.*, 18(6):407-418 (2011).
Liu et al., "ICP34.5 deleted herpes simplex virus with enhanced oncolytic, immune stimulating, and anti-tumour properties," *Gene Therapy*, 10:292-303 (2003).
Logan et al., "Adenovirus tripartite leader sequence enhances translation of mRNAs late after infection," *Proc. Natl. Acad. Sci. USA*, 81:3655-3659 (1984).
Lorence et al., "Phase 1 clinical experience using intravenous administration of PV701, an oncolytic Newcastle disease virus," *Curr. Cancer Drug Targets*, 7:157-167 (2007).
Lotze et al., "Cytokine Gene Therapy of Cancer Using Interleukin-12: Murine and Clinical Trials," *Ann. N.Y. Acad. Sci.*, 795:440-454 (1995).
Lowy et al., "Isolation of Transforming DNA: Cloning the Hamster aprt Gene," *Cell* 22:817-823 (1980).
Lutzky, "A phase 1 study of MEDI4736, an anti-PD-L1 antibody, in patients with advanced solid tumors," *J. Clin. Oncol.*, 32(suppl 5S):abstract 3001 (2014).
MacCallum et al., "Antibody-antigen interactions: contact analysis and binding site topography," *J. Mol. Biol.*, 262(5):732-745 (1996).
Maeda et al., "Live bivalent vaccine for parainfluenza and influenza virus infections," *J. Viral.*, 79(11):6674-6679 (2005).
Mansour et al., "Oncolytic specificity of newcastle disease virus is mediated by selectivity for apoptosis-resistant cells," *J. Virol.*, 85(12):6015-6023 (2011).
Martin, "Protein Sequence and Structure Analysis of Antibody Variable Domains," *Antibody Engineering*, Kontermann et al. eds., Springer-Verlag, Berlin, Chapter 31, pp. 33-51 (2001).
Mazzolini et al., "Adenoviral Gene Transfer of Interleukin 12 into Tumors Synergizes with Adoptive T Cell Therapy Both at the Induction and Effector Level," *Human Gene Ther.*, 11:113-125 (2000).
Mazzolini et al., "Regression of colon cancer and induction of antitumor immunity by intratumoral injection of adenovirus expressing interleukin-12," *Cancer Gene Ther.*, 6(6):514-522 (1999).
McDermott et al., "Atezolizumab, an Anti-Programmed Death-Ligand 1 Antibody, in Metastatic Renal Cell Carcinoma: Long-Term Safety, Clinical Activity, and Immune Correlates From a Phase Ia Study," *J. Clin. Oncol.*, 34(8):833-842 (2016).
Menne et al., "A comparison of signal sequence prediction methods using a test set of signal peptides," *Bioinfomratics*, 16(8):741-742 (2000).
Meseck et al., "A Functional Recombinant Human 4-1BB Ligand for Immune Costimulatory Therapy of Cancer," *J. Immunother.*, 34(2):175-182 (2011).
Milstein et al., "Hybrid hybridomas and their use in immunohistochemistry," *Nature*, 305:537-539 (1983).
Morea et al., "Antibody modeling: implications for engineering and design," *Methods*, 20(3):267-279 (2000).
Morgan et al., "Human gene therapy," *Annu. Rev. Biochem.*, 62:191-217 (1993).
Morris et al., "Lung-specific expression in mice of a dominant negative mutant form of the p53 tumor suppressor protein," *J. La. State Med. Soc.*, 150(4):179-185 (1998).
Morrison, "Transfectomas provide novel chimeric antibodies," *Science*, 229(4719):1202-1207 (1985).
Mulligan et al., "Selection for animal cells that express the Escherichia coli gene coding for xanthine-guanine phosphoribosyltransferase," *Proc. Natl. Acad. Sci. USA*, 78:2072-2076 (1981).
Mulligan, "The basic science of gene therapy," *Science*, 260:926-932 (1993).
Muranski et al., "Tumor-specific Th17-polarized cells eradicate large established melanoma," *Blood*, 112(2):362-373 (2008).
Murawski et al., "Newcastle disease virus-like particles containing respiratory syncytial virus G protein induced protection in BALB/c mice, with no evidence of immunopathology", *J. Virol.*, 84(2):1110-1123 (2010).
Muyldermans, "Single domain camel antibodies: current status," *J. Biotechnol.*, 74(4):277-302 (2001).

(56) References Cited

OTHER PUBLICATIONS

Naganawa et al., "Generation of mouse-human hybridomas secreting human monoclonal antibodies to Japanese cedar pollen allergen Cry j1," *Hum. Antibodies*, 14:27-31 (2005).
Nakaya et al., "Recombinant Newcastle disease virus as a vaccine vector," *J. Virol*., 75:11868-11873 (2001).
Narvaiza et al., "Intratumoral Coinjection of Two Adenoviruses, One Encoding the Chemokine IFN-γ-Inducible Protein-10 and Another Encoding IL-12, Results in Marked Antitumoral Synergy," *J. Immunol*., 164(6):3112-3122 (2000).
Niu et al., "Recombinant Newcastle Disease virus Expressing IL15 Demonstrates Promising Antitumor Efficiency in Melanoma Model," *Technol. Cancer Res. Treatment*, 14(5):607-615 (2015).
Nuttall et al., "Immunoglobulin VH domains and beyond: design and selection of single-domain binding and targeting reagents," *Curr. Pharm. Biotechnol*., 1(3):253-263 (2000).
O'Hare et al., "Transformation of mouse fibroblasts to methotrexate resistance by a recombinant plasmid expressing a prokaryotic dihydrofolate reductase," *Proc. Natl. Acad. Sci. USA* 78:1527-1531 (1981).
Opdivo (nivolumab), Highlights of Prescribing Information, Reference ID: 3677021, Dec. 2014.
Oseledchyk et al., "Lysis-independent potentiation of immune checkpoint blockade by oncolytic virus," *Oncotarget* 9(47):28702-28716 with Supplementary Materials (2 pages) (2018).
Overwijk et al., "Tumor regression and autoimmunity after reversal of a functionally tolerant state of self-reactive CD8+ T cells," *J. Exp. Med*., 198(4):569-580 (2003).
Padlan, "A possible procedure for reducing the immunogenicity of antibody variable domains while preserving their ligand-binding properties," *Mol. Immunol*., 28:489-498 (1991).
Pardoll, "The blockade of immune checkpoints in cancer immunotherapy," *Nat. Rev. Cancer*, 12(4):252-264 (2012).
Park et al., "Engineered viral vaccine constructs with dual specificity: avian influenza and Newcastle disease," *Proc. Natl. Acad. Sci*. (*USA*), 103:8203-8208 (2006).
Park et al., "Newcastle disease virus V protein is a determinant of host range restriction," *J. Virol*., 77(17):9522-9532 (2003).
Patent Cooperation Treaty, International Search Report for PCT/US2014/020299, dated Aug. 15, 2014.
Patent Cooperation Treaty, International Search Report for PCT/US2006/045859, dated Mar. 28, 2007.
Patent Cooperation Treaty, International Search Report for PCT/US2010/023335, dated Jun. 7, 2010.
Patent Cooperation Treaty, International Search Report for PCT/US2018/032255, dated Nov. 19, 2018.
Patent Cooperation Treaty, Written Opinion for PCT/US2006/045859, dated Mar. 28, 2007.
Patent Cooperation Treaty, Written Opinion for PCT/US2010/023335, dated Jun. 7, 2010.
Patent Cooperation Treaty, Written Opinion for PCT/US2014/020299, dated Jul. 19, 2014.
Patent Cooperation Treaty, Written Opinion for PCT/US2018/032255, dated Nov. 19, 2018.
Pecora et al., "Phase I trial of intravenous administration of PV701, an oncolytic virus, in patients with advanced solid cancers," *J. Clon. Oncol*., 20:2251-2266 (2002).
Pedersen et al., "Comparison of surface accessible residues in human and murine immunoglobulin Fv domains. Implication for humanization of murine antibodies," *J. Mol. Biol*., 235(3):959-973 (1994).
Peeters et al., "Generation of a recombinant chimeric Newcastle disease virus vaccine that allows serological differentiation between vaccinated and infected animals," *Vaccine*, 19:1616-1627 (2001).
Peeters et al., "Rescue of Newcastle disease virus from cloned cDNA: evidence that cleavability of the fusion protein is a major determinant for virulence," *J. Virol*., 73(6):5001-5009 (1999).
Peggs et al., "Cancer immunotherapy: co-stimulatory agonists and co-inhibitory antagonists," *Clin. Immunol*., 157(1):9-19 (2009).
Persic et al., "An integrated vector system for the eukaryotic expression of antibodies or their fragments after selection from phage display libraries," *Gene*, 187:9-18 (1997).
Phuangsab et al., "Newcastle disease virus therapy of human tumor xenografts: antitumor effects of local or systemic administration," *Cancer Lett*., 172:27-36 (2001).
Plitt et al., "Cancer therapy with Newcastle disease virus: rationale for new immunotherapeutic combinations," *Clinical Investigation*, 5(1):75-87 (2015).
Proudfoot, "Transcriptional interference and termination between duplicated α-globin gene constructs suggests a novel mechanism for gene regulation," *Nature*, 322(7):562-565 (1986).
Puhler et al., "Generation of a recombinant oncolytic Newcastle disease virus and expression of a full IgG antibody from two transgenes," *Gene Ther*., 15:371-383 (2008).
Puzanov et al., "Phase 1 results of a phase 1b/2, multicenter, open-label trial to evaluate safety and efficacy of talimogene laherparepvec (T-VEC) and ipilimumab (ipi) vs ipi alone in previously untreated, unresected stage IIIB-IV melanoma," *J. Immunother. Cancer*, 1(Suppl 1):P84 (2013).
Quetglas et al., "Virotherapy with a Semliki Forest Virus-Based Vector Encoding IL12 Synergizes with PD-1/PD-L1 Blockade," *Cancer Immunol. Res*., 3(5):449-454 (2015).
Quezada et al., "CTLA4 blockade and GM-CSF combination immunotherapy alters the intratumor balance of effector and regulatory T cells," *J. Clin. Invest*., 116(7): 1935-1945 (2006).
Quinn et al., "Rapid quantitation of recombinant retrovirus produced by packaging cell clones," *Biotechniques*, 23(6):1038-1044 (1997).
Ravindra et al., "Newcastle disease virus as an oncolytic agent," *Indian J. Med. Rres*., 130(5):507-513 (2009).
Ren et al., "Recombinant Newcastle Disease Virus Encoding IL-12 and/or IL-2 as Potential Candidate for Hepatoma Carcinoma Therapy," *Technol. Cancer Res. Treat*., 15(5):doi: 10.1177/1533034615601521 (2016).
Ribas et al., "Oncolytic Virotherapy Promotes Intratumoral T Cell Infiltration and Improves Anti-PD-1 Immunotherapy," *Cell*, 170(6):1109-1119 (2017).
Riechmann et al., "Single domain antibodies: comparison of camel VH and camelised human VH domains," *J. Immunol. Methods*, 231:25-38 (1999).
Robbins et al., "Human tumor antigens recognized by T cells," *Curr. Opin. Immunol*., 8(5):628-636 (1996).
Robert et al., "Ipilimumab plus dacarbazine for previously untreated metastatic melanoma," *N. Engl. J. Med*., 364(26):2517-2526 (2011).
Roguska et al., "A comparison of two murine monoclonal antibodies humanized by CDR-grafting and variable domain resurfacing," *Protein Eng*., 9(10):895-904 (1996).
Roguska et al., "Humanization of murine monoclonal antibodies through variable domain resurfacing," *Proc. Natl. Acad. Sci USA*, 91(3):969-973 (1994).
Ruther et al., "Easy identification of cDNA clones," *EMBO J*., 2(10):1791-1794 (1983).
Santerre et al., "Expression of prokaryotic genes for hygromycin B and G418 resistance as dominant-selection markers in mouse L cells," *Gene*, 30:147-156 (1984).
Sapoznik et al. "Novel anti-melanoma immunotherapies: disarming tumor escape mechanisms," *Clin Dev Immunol*., 2012: 818214. doi: 10.1155/2012/818214. Epub Apr. 23, 2012 (2012).
Sawai et al., "Direct production of the Fab fragment derived from the sperm immobilizing antibody using polymerase chain reaction and cDNA expression vectors," *A. J. Reprod. Immunol*., 34(1):26-34 (1995).
Scapin et al., "Structure of full-length human anti-PD1 therapeutic IgG4 antibody pembrolizumab," *Nat. Struct. Mol. Biol*., 22(12):953-958 (2015).
Schickli et al., "Plasmid-only rescue of influenza A virus vaccine candidates," *Phil. Trans. R. Soc. Lond*., 356:1965-1973 (2001).
Schirrmacher et al., "Antitumor effects of Newcastle Disease Virus in vivo: Local versus systemic effects," *Int. J. Oncol*., 18:945-952 (2001).

(56) References Cited

OTHER PUBLICATIONS

Schirrmacher et al., "Newcastle disease virus: a promising vector for viral therapy, immune therapy, and gene therapy of cancer," *Methods Mol. Biol.*, 542: 565-605 (2009).
Scott et al., "Searching for peptide ligands with an epitope library," *Science*, 249(4967):386-390 (1990).
Seliger et al., "Characterization of the major histocompatibility complex class I deficiencies in B16 melanoma cells," *Cancer Res.*, 61(3):1095-1099 (2001).
Seppi et al., "Direct determination of oxygen by HPLC. 2. Chamber and sample application system for determination of o(2) at trace levels," *Anal. Chem.*, 69(21):4476-4481 (1997).
Sergel et al., "A Single Amino Acid Change in the Newcastle Disease Virus Fusion Protein Alters the Requirement for HN Protein in Fusion," *J. Virol.*, 74(11):5101-5107 (2000).
Sharma et al., "Triggering the interferon antiviral response through an ikk-related pathway," *Science*, 300(5622):1148-1151 (2003).
Shenk, "Adenoviridae: The Viruses and Their Replication," *Fundamental Virology*, Fields et al. eds., Lippincott-Raven, Philadelphia, PA, pp. 979-1016 (1996).
Shim et al., "Inhibitory Receptors Induced by VSV Viroimmunotherapy Are Not Necessarily Targets for Improving Treatment Efficacy," *Mol. Ther.*, 25(4):962-975 (2017).
Shinmoto et al., "Generation of mouse-human hybridomas secreting antibodies against peanut allergen Ara h1," *Cytotechnology*, 46(1):19-23 (2004).
Shinohara et al., "Structure and chromosomal localization of the human PD-1 gene (PDCD1)," *Genomics*, 23:704-706 (1994).
Silberhumer et al., "Genetically engineered oncolytic Newcastle disease virus effectively induces sustained remission of malignant pleural mesothelioma," *Mol. Cancer Ther.*, 9(10):2761-2769 (2010).
Simpson et al., "Regulation of CD4 T cell activation and effector function by inducible costimulator (ICOS)," *Curr. Opin. Immunol.*, 22(3):326-332 (2010).
Sinkovics et al., "Newcastle disease virus (NDV): brief history of its oncolytic strains," *J. Clin. Virol,*. 16:1-15 (2000).
Song et al., "Antitumor efficacy of viral therapy using genetically engineered Newcastle disease virus [NDV(F3aa)-GFP] for peritoneally disseminated gastric cancer," *J. Mol. Med. (Berl)*., 88(6):589-596 (2010).
Spranger et al., "Up-regulation of PD-L1, IDO, and T(regs) in the melanoma tumor microenvironment is driven by CD8(+) T cells," *Sci. Transl. Med.*, 5(200):200ra116 (2013).
Studnicka et al., "Human-engineered monoclonal antibodies retain full specific binding activity by preserving non-CDR complementarity-modulating residues," *Protein Eng.*, 7(6):805-814 (1994).
Su et al., "Immunoadjuvant activities of a recombinant chicken IL-12 in chickens vaccinated with Newcastle disease virus recombinant HN protein," *Veterinary Microbiology*, 151:220-228 (2011).
Suresh et al., "Bispecific monoclonal antibodies from hybrid hybridomas," *Methods Enzymol.*, 121:210-228 (1986).
Swann et al., "Type I IFN contributes to NK cell homeostasis, activation, and antitumor function," *J. Immunol.*, 178(12):7540-7549 (2007).
Swayne et al., "Recombinant paramyxovirus type 1-avian influenza-H7 virus as a vaccine for protection of chickens against influenza and Newcastle disease," *Avian Dis.*, 47:1047-1050 (2003).
Szybalska et al., "Genetics of human cess line. IV. DNA-mediated heritable transformation of a biochemical trait," *Proc. Natl. Acad. Sci. USA*48:2026-2034 (1992).
Tan et al., ""Superhumanized" antibodies: reduction of immunogenic potential by complementarity-determining region grafting with human germline sequences: application to an anti-CD28," *J. Immunol.*, 169(2):1119-1125 (2002).
Tang et al., "Use of a peptide mimotope to guide the humanization of MRK-16, an anti-P-glycoprotein monoclonal antibody," *J. Biol. Chem.*, 274(39):27371-27378 (1999).
Tecentriq, Highlights of Prescribing Information, Reference ID: 3933242, May 2016.
Tecentriq, Highlights of Prescribing Information, Reference ID: 4000525, Oct. 2016.
Therasse et al., "New guidelines to evaluate the response to treatment in solid tumors. European Organization for Research and Treatment of Cancer, National Cancer Institute of the United States, National Cancer Institute of Canada," *J. Natl. Cancer Inst.*, 92(3):205-216 (2000).
Tolstoshev, "Gene therapy, concepts, current trials and future directions," *Ann. Rev. Pharmacol. Toxicol.*, 32:573-596 (1993).
Topalian et al., "Safety, activity, and immune correlates of anti-PD-1 antibody in cancer," *New Eng. J. Med.*, 366:2443-2454 (2012).
Tramontano et al., "Framework residue 71 is a major determinant of the position and conformation of the second hypervariable region in the VH domains of immunoglobulins," *J. Mol. Biol.*, 215(1):175-182 (1990).
Traunecker et al., "Bispecific single chain molecules (Janusins) target cytotoxic lymphocytes on HIV infected cells," *EMBO J.*, 10(12):3655-3659 (1991).
Tumeh et al., "PD-1 blockade induces responses by inhibiting adaptive immune resistance," *Nature*, 515(7528):568-571 (2014). (Extended Data Figures 1-6 and Extended Data Tables 1-4 attached).
Turk et al., "Concomitant tumor immunity to a poorly immunogenic melanoma is prevented by regulatory T cells," *J. Exp. Med.*, 200(6):771-782 (2004).
Tuve et al., "In situ adenovirus vaccination engages T effector cells against cancer," *Vaccine*, 27:4225-4239 (2009).
U.S. Appl. No. 14/774,962, Non-Final Office Action mailed Nov. 9, 2016.
U.S. Appl. No. 14/205,776, Non-Final Office Action dated Jan. 28, 2015.
U.S. Appl. No. 14/205,776, Amendment under 37 C.F.R. 1.111 dated Jun. 9, 2015.
U.S. Appl. No. 14/205,776, Final Office Action dated Aug. 10, 2015.
U.S. Appl. No. 14/205,776, Amendment and Response dated Jan. 8, 2016.
U.S. Appl. No. 14/205,776, Non-Final Office Action dated Mar. 4, 2016.
U.S. Appl. No. 14/205,776, Final Office Action dated Sep. 23, 2016.
U.S. Appl. No. 15/789,340, Non-Final Office Action date Feb. 19, 2019.
U.S. Appl. No. 15/789,340, Amendment and Response dated May 17, 2019.
U.S. Appl. No. 15/789,340, Final Office Action dated Jun. 14, 2019.
U.S. Appl. No. 15/789,539, Non-Final Office Action mailed Jul. 30, 2018.
U.S. Appl. No. 15/789,539, Amendment and Response dated Oct. 30, 2018.
U.S. Appl. No. 15/789,539, Notice of Allowance mailed Dec. 11, 2018.
U.S. Appl. No. 15/588,251, Non-Final Office Action dated Jul. 16, 2018.
Vail et al., "Spontaneously occurring tumors of companion animals as models for human cancer," *Cancer Invest.*, 18:781-792 (2000).
Van Heeke et al., "Expression of human asparagine synthetase in *Escherichia coli,*" *J. Biol. Chem.*, 264(10):5503-5509 (1989).
Velu et al., "Role of PD-1 co-inhibitory pathway in HIV infection and potential therapeutic options," *Retrovirology*, 12:14 (2015).
Verma et al., "Gene therapy—promises, problems and prospects," *Nature*, 389:239-242 (1997).
Vigil et al., "Recombinant Newcastle disease virus as a vaccine vector for cancer therapy," *Molecular Therapy*, 16(11):1883-1890 (2008).
Vigil et al., "Use of reverse genetics to enhance the oncolytic properties of Newcastle disease virus," *Cancer Research*, 67(17):8285-8292 (2007).
Vlasak et al., "Use of flow cytometry for characterization of human cytomegalovirus vaccine particles," *Vaccine*, 34:2321-2328 (2016).
Von Heijne, "A new method for predicting signal sequence cleavage sites," *Nucleic Acids Res.*, 14(11):4683-4690 (1986).
Von Heijne, "Patterns of amino acids near signal-sequence cleavage sites," *Eur. J. Biochem.*, 133(1):17-21 (1983).

(56) References Cited

OTHER PUBLICATIONS

Waitz et al., "Potent induction of tumor immunity by combining tumor cryoablation with anti-CTLA-4 therapy," *Cancer Res.*,72(2):430-439 (2012).
Wakamatsu et al., "Convergent and divergent effects of costimulatory molecules in conventional and regulatory CD4+ T cells," *Proc. Natl. Acad. Sci. USA*, 110(3):1023-1028 (2013).
Wakamatsu et al., "The effect on pathogenesis of Newcastle disease virus LaSota strain from a mutation of the fusion cleavage site to a virulent sequence," *Avian Dis.*, 50(4):483-488 (2006).
Walter et al., "Targeted inhibition of interferon—dependent intercellular adhesion molecule-1 (ICAM-1) expression using dominant-negative stat1," *J. Biol. Chem.*, 272(45):28582-28589 (1997).
Walter et al., "Two avirulent, lentogenic strains of Newcastle disease virus are cytotoxic for some human pancreatic tumor lines in vitro," *J. Pancreas*, 13(5):502-513 (2012).
Wang et al., "A Novel, Clinically Relevant Animal Model of Metastatic Pancreatic Adenocarcinoma Biology and Therapy," *Int. J. Pancreatol.*, 29(1):37-46 (2001).
Wang et al., "Impact of modification of cleavage site of fusion protein and foreign gene insertion on the virulence of Newcastle Disease Virus LaSota vaccine strain," *Wei Sheng Wu Xue Bao*, 48(3):362-368 (2008). (English abstract attached).
Weber et al., "Viral suppression of the interferon system," *Biochimie*, 89(6-7):836-842 (2007).
Wigler et al., "Transformation of mammalian cells with an amplifiable dominant-acting gene," *Proc Natl. Acad. Sci. USA*, 77:3567-3570 (1980).
Wigler et al., "Transfer of purified herpes virus thymidine kinase gene to cultured mouse cells," *Cell*, 11(1):223-232 (1977).
Wilden et al., "Expression of RIG-I, IRF3, IFN-beta and IRF7 determines resistance or susceptibility of cells to infection by Newcastle Disease Virus," *Int. J. Oncol.*, 34(4):971-982 (2009).
Wold et al., "Adenovirus vectors for gene therapy, vaccination and cancer gene therapy," *Curr. Gene Ther.*, 13(6):421-433 (2013).
Woller et al., "Oncolytic viruses as anticancer vaccines," *Front. Oncol.*, 4(188):1-13 (2014).
Wren et al., "SIGNAL-Sequence Information and GeNomic AnaLysis," *Comput. Methods Programs Biomed.*, 68(2):177-181 (2002).
Wu et al., "Delivery systems for gene therapy," *Biotherapy*, 3(1):87-95 (1991).
Yamaki et al., "The potential of recombinant vesicular stomatitis virus-mediated virotherapy against metastatic colon cancer," *Int. J. Mol. Med.*, 31:299-306 (2013).
Yao et al., "Reviving exhausted T lymphocytes during chronic virus infection by B7—H1 blockade," *Trends Mol. Med.*, 12(6):244-246 (2006).
Ying et al., "Adenovirus-mediated intratumoral expression of immunostimulatory proteins in combination with systemic Treg inactivation induces tumor-destructive immune responses in mouse models," *Cancer Gene Ther.*, 18(6):407-418 (2011).
Yoneyama et al., "The RNA helicase RIG-I has an essential function in double-stranded RNA-induced innate antiviral responses," *Nature Immunol.*, 5:730-737 (2004).
Zamarin et al., "Potentiation of immunomodulatory antibody therapy with oncolytic viruses for treatment of cancer," *Mol. Therapy—Oncolytics*, 1:14004; doi:10.1038/mto.2014.4. (2014).
Zamarin et al., "Upregulation of PD-L1 in tumor microenvironment is a resistance mechanism for onolytic virus immunotherapy," *J. Immunother. Cancer*, 5(Suppl 2):87 (2017).
Zamarin et al., "Enhancement of Oncolytic Properties of Genetically-Engineered Fusogenic Newcastle Disease Virus through Antagonism of Cellular Innate Immune Responses," *Mol. Ther.*, 16(Suppl. 1), Abstract #43 (2008).
Zamarin et al., "Enhancement of oncolytic properties of recombinant Newcastle disease virus through antagonism of cellular innate immune responses," *Mol. Ther.*, 17(4):697-706 (2009).
Zamarin et al., "Genetically engineered Newcastle disease virus for malignant melanoma therapy," *Gene Ther.*, 16(6):796-804 (2009).
Zamarin et al., "Intratumoral modulation of the inducible co-stimulator ICOS by recombinant oncolytic virus promotes systemic anti-tumour immunity," *Nat. Commun.*, 8:14340 (2017).
Zamarin et al., "Localized oncolytic virotherapy inflames distant tumors and synergizes with immune checkpoint blockade leading to systemic tumor rejection," *J. Immunother. Cancer*, 1(Suppl 1):O9 (2013).
Zamarin et al., "Localized oncolytic virotherapy overcomes systemic tumor resistance to immune checkpoint blockade immunotherapy," *Sci. Transl. Med.*, 6(226):226ra32 (2014).
Zamarin et al., "Oncolytic Newcastle disease virus for cancer therapy: old challenges and new directions," *Future Microbiol.*, 7:347-367 (2012).
Zamarin et al., "PD-L1 in tumor microenvironment mediates resistance to oncolytic immunotherapy," *J. Clin. Invest.*, 128(4):1413-1428, with Supplemental Information (2018).
Zhang et al., "Anti-Oncogene and Tumor Suppressor Gene Therapy—Examples from a Lung Cancer Animal Model," In-Vivo, 8:755-769 (1994).
Zhao et al., "P and M gene junction is the optimal insertion site in Newcastle disease virus vaccine vector for foreign gene expression," *J. Gen. Virol.*, 96(Pt 1):40-45 (2015) (Epub Oct. 1, 2014).
Zimmer et al., "A chimeric respiratory syncytial virus fusion protein functionally replaces the F and HN glycoproteins in recombinant sendai virus," *J Virol.*, 79(16):10467-10477 (2005).
Zitvogel et al., "Type I interferons in anticancer immunity," *Nature Rev. Innumol.*, 15:405-414 (2015).
Afonso et al., 2016, "Taxonomy of the order Mononegavirales: update 2016," Arch Virol., 161(8):2351-2360.
Alexander et al., 1978, "Relationship of parakeet/Netherlands/449/75 virus to other avian paramyxoviruses," Res. Vet. Sci., 25(1):105-106.
Alexander et al., 1981, "Characterization of viruses from doves representing a new serotype of avian paramyxoviruses," Arch. Virol., 68(3-4):265-269.
Alper et al., 2009, "Rate of concurrent otitis media in upper respiratory tract infections with specific viruses," Arch. Otolaryngol. Head Neck Surg., 135(1):17-21.
Bai et al., 2002, "Dendritic cells pulsed with viral oncolysates potently stimulate autologous T cells from cancer patients," Int. J. Oncol., 21(4):685-694.
Bankowski et al., 1981, "Effect of paramyxovirus yucaipa on fertility, hatchability, and poult yield of turkeys," Avian. Dis., 25(2):517-520.
Belladonna et al., 2013, "Bioengineering heterodimeric cytokines: turning promiscuous proteins into therapeutic agents," Biotechnol. Genet. Eng. Rev., 29:149-174.
Bohle et al., 1990, "Postoperative active specific immunization in colorectal cancer patients with virus-modified autologous tumor-cell vaccine. First clinical results with tumor-cell vaccines modified with live but avirulent Newcastle disease virus," Cancer, 66(7):1517-1523.
Boisseau, 1993, "Basis for the evaluation of the microbiological risks due to veterinary drug residues in food," Vet. Microbiol., 35(3-4):187-192.
Briand et al., 2012, "Complete genome sequence of a novel avian paramyxovirus," J Virol., 86(14):7710.
Carnero et al., 2009, "Optimization of human immunodeficiency virus gag expression by newcastle disease virus vectors for the induction of potent immune responses," J Virol., 83(2):584-597 (Epub Nov. 12, 2008).
Cassel et al., 1965, "Newcastle Disease Virus as an Antineoplastic Agent," Cancer, 18:863-868.
Cho et al., 2018, "Co-expression of the Hemagglutinin and Neuraminidase by Heterologous Newcastle Disease Virus Vectors Protected Chickens against H5 Clade 2.3.4.4 HPAI Viruses," Sci. Rep., 8(1):16854 (9 pages).
Cloud et al., 1980, "Characterization of Nine Avian Paramyxoviruses," Avian Dis., 24(1):139-152.
Cuadrado-Castano et al., 2015, "Enhancement of the proapoptotic properties of newcastle disease virus promotes tumor remission in syngeneic murine cancer models," Mol Cancer Ther., 14(5):1247-1258.

(56) References Cited

OTHER PUBLICATIONS

Cuadrado-Castano et al., 2015, "The therapeutic effect of death: Newcastle disease virus and its antitumor potential," Virus Res., 209:56-66.
Dortmans et al., 2012, "Newcastle disease virus outbreaks: vaccine mismatch or inadequate application?," Vet. Microbiol., 160(1-2):17-22.
Doyle et al., 1927, "A Hitherto Unrecorded Disease Of Fowls Due To A Filter-passing Virus," J. Comp. Pathol. Ther., 40:144-169.
Dulos et al., 2012, "PD-1 blockade augments Th1 and Th17 and suppresses Th2 responses in peripheral blood from patients with prostate and advanced melanoma cancer," J Immunother, 35(2):169-178.
Durbin et al., 1996, "Targeted disruption of the mouse Stat1 gene results in compromised innate immunity to viral disease," Cell, 84(3):443-450.
Elmberg et al., 2017, "Potential disease transmission from wild geese and swans to livestock, poultry and humans: a review of the scientific literature from a One Health perspective," Infect Ecol Epidemiol., 7(1):1300450 (21 pages).
Fournier et al., 2009, "Polarization of human monocyte-derived dendritic cells to DC1 by in vitro stimulation with Newcastle Disease Virus," J. Buon., 14 Suppl 1:S111-S122.
Fournier et al., 2012, "Analysis of three properties of Newcastle disease virus for fighting cancer: tumor-selective replication, antitumor cytotoxicity, and immunostimulation," Methods Mol Biol., 797:177-204.
Ganar et al., 2014, "Newcastle disease virus: current status and our understanding," Virus Res., 184:71-81.
Ginting et al., 2017, "Proinflammatory response induced by Newcastle disease virus in tumor and normal cells," Oncolytic Virother, 6:21-30.
Gogoi et al., 2017, "Avian Paramyxovirus: A Brief Review," Transbound. Emerg. Dis., 64(1):53-67 (Epub 2015).
Grund et al., 2014, "Avian paramyoxvirus-8 immunization reduces viral shedding after homologous APMV-8 challenge but fails to protect against Newcastle disease," Virol. J., 11:179 (6 pages).
Heicappell et al., 1986, "Prevention of metastatic spread by postoperative immunotherapy with virally modified autologous tumor cells. I. Parameters for optimal therapeutic effects," Int. J. Cancer, 37(4):569-577.
Hines et al., 2012, "Avian paramyxovirus serotype-1: a review of disease distribution, clinical symptoms, and laboratory diagnostics," Vet Med Int., 2012:708216 (17 pages).
Jarahian et al., 2009, "Activation of natural killer cells by newcastle disease virus hemagglutinin-neuraminidase," J Virol., 83(16):8108-8121.
Kapczynski et al., 2013, "Immune responses of poultry to Newcastle disease virus," Dev Comp Immunol., 41(3):447-453.
Karcher et al., 2004, "Antitumor vaccination in patients with head and neck squamous cell carcinomas with autologous virus-modified tumor cells," Cancer Res., 64(21):8057-8061.
KEYTRUDA® (pembrolizumab) Prescribing Information, revised Jan. 2020 (85 pages).
KEYTRUDA® (pembrolizumab) Prescribing Information, revised Jun. 2018 (53 pages).
Kim et al., 1969, "Respiratory syncytial virus disease in infants despite prior administration of antigenic inactivated vaccine," Am. J. Epidemiol., 89(4):422-434.
Kim et al., 2012, "Replication, neurotropism, and pathogenicity of avian paramyxovirus serotypes 1-9 in chickens and ducks, " PLoS One. 2012;7(4):e34927 (13 pages).
Kim et al., 2013, "Mutations in the fusion protein cleavage site of avian paramyxovirus serotype 4 confer increased replication and syncytium formation in vitro but not increased replication and pathogenicity in chickens and ducks," PLoS One, 8(1):e50598 (15 pages).
Kim et al., 2017, "A novel chimeric Newcastle disease virus vectored vaccine against highly pathogenic avian influenza virus," Virology, 503:31-36.
Kumar et al., 2011, "Evaluation of the Newcastle disease virus F and HN proteins in protective immunity by using a recombinant avian paramyxovirus type 3 vector in chickens," J. Virol., 85(13):6521-6534 (retracted).
Kumar et al., 2020, "Retraction for Kumar et al., "Evaluation of the Newcastle Disease Virus F and HN Proteins in Protective Immunity by Using a Recombinant Avian Paramyxovirus Type 3 Vector in Chickens"," J. Virol., 94(6):e01867-19 (1 page).
Lam et al., 2011, "Safety and clinical usage of newcastle disease virus in cancer therapy," J Biomed Biotechnol, 2011:718710 (13 pages).
Li et al., 2016, "A Mini-Review for Cancer Immunotherapy: Molecular Understanding of PD-1/PD-L1 Pathway & Translational Blockade of Immune Checkpoints," Int. J. Mol. Sci., 17(7):1151 (22 pages).
Liang et al., 2003, "Application of autologous tumor cell vaccine and NDV vaccine in treatment of tumors of digestive tract," World J Gastroenterol., 9(3):495-498.
Lipkind et al., 1986, "Antigenic relationships between avian paramyxoviruses. I. Quantitative characteristics based on hemagglutination and neuraminidase inhibition tests," Arch. Virol., 89(1-4):89-111.
Liu et al., 2018, "Chimeric Newcastle disease virus-vectored vaccine protects chickens against H9N2 avian influenza virus in the presence of pre-existing NDV immunity," Arch. Virol., 163(12):3365-3371.
Lorence et al., 1988, "Newcastle disease virus as an antineoplastic agent: induction of tumor necrosis factor-alpha and augmentation of its cytotoxicity," J. Natl. Cancer Inst., 80(16):1305-1312.
Maamary et al., 2011, "Newcastle disease virus expressing a dendritic cell-targeted HIV gag protein induces a potent gag-specific immune response in mice," J Virol., 85(5):2235-2246.
Martinez-Sobrido et al., 2006, "Protection against respiratory syncytial virus by a recombinant Newcastle disease virus vector," J Virol., 80(3):1130-1139.
Mustaffa-Babjee et al., 1974, "A pathogenic paramyxovirus from a budgerigar (*Melopsittacus undulatus*)," Avian Dis., 18(2):226-230.
Nayak et al., 2009, "Immunization of chickens with Newcastle disease virus expressing H5 hemagglutinin protects against highly pathogenic H5N1 avian influenza viruses," PLoS One, 4(8):e6509 (10 pages).
Nguyen et al., 2020, "Oncolytic Virus Encoding a Master Pro-Inflammatory Cytokine Interleukin 12 in Cancer Immunotherapy," Cells, 9(2), 400.
Nolden et al., 2016, "Reverse genetics in high throughput: rapid generation of complete negative strand RNA virus cDNA clones and recombinant viruses thereof," Sci Rep., 6:23887 (15 pages).
OPDIVO® (nivolumab) Prescribing Information, revised Apr. 2018 (83 pages).
OPDIVO® (nivolumab) Prescribing Information, revised Sep. 2019 (31 pages).
Park et al., 2003, "Newcastle disease virus (NDV)-based assay demonstrates interferon-antagonist activity for the Ndv V protein and the Nipah virus V, W, and C proteins," J Virol., 77(2):1501-1511.
Pelaia et al., 2006, "Respiratory infections and asthma," Respir. Med., 100(5):775-784 (Epub 2005).
Pomer et al., 1995, "Tumor response and 4 year survival-data of patients with advanced renal-cell carcinoma treated with autologous tumor vaccine and subcutaneous R-IL-2 and IFN-alpha(2b)," Int. J. Oncol., 6(5):947-954.
Romer-Oberdorfer et al., 1999, "Generation of recombinant lentogenic Newcastle disease virus from cDNA" J Gen Virol., 80(Pt 11):2987-2995.
Schirrmacher et al., 1998, "Immunization with virus-modified tumor cells" Semin. Oncol., 25(6):677-696.
Schirrmacher et al., 1999, "Human tumor cell modification by virus infection: an efficient and safe way to produce cancer vaccine with pleiotropic immune stimulatory properties when using Newcastle disease virus," Gene Ther., 6(1):63-73.
Schirrmacher et al., 2014, "Long-term remission of prostate cancer with extensive bone metastases upon immuno- and virotherapy: A case report," Oncol Lett., 8(6):2403-2406.

(56) References Cited

OTHER PUBLICATIONS

Schirrmacher et al., 2014, "Multimodal cancer therapy involving oncolytic newcastle disease virus, autologous immune cells, and bi-specific antibodies," Front Oncol., 4:224 (5 pages).
Schirrmacher, 2016, "Fifty Years of Clinical Application of Newcastle Disease Virus: Time to Celebrate!" Biomedicines, 4(3), 14 pages.
Senne et al., 2004, "Control of Newcastle disease by vaccination," Dev. Biol. (Basel), 119:165-170.
Shnyrova et al., 2007, "Vesicle formation by self-assembly of membrane-bound matrix proteins into a fluidlike budding domain," J Cell Biol., 179(4):627-633.
Shortridge et al., 1980, "Isolation and properties of viruses from poultry in Hong Kong which represent a new (sixth) distinct group of avian paramyxoviruses," J Gen Virol., 49(2):255-262.
Stanislawek et al., 2002, "Avian paramyxoviruses and influenza viruses isolated from mallard ducks (*Anas platyrhynchos*) in New Zealand," Arch. Virol., 147(7):1287-1302.
Steglich et al., 2013, "Chimeric newcastle disease virus protects chickens against avian influenza in the presence of maternally derived NDV immunity," PLoS One, 8(9):e72530 (14 pages).
Steiner et al., 2004, "Antitumor vaccination of patients with glioblastoma multiforme: a pilot study to assess feasibility, safety, and clinical benefit," J Clin Oncol., 22(21):4272-4281.
Swayne, 2003, "Vaccines for List A poultry diseases: emphasis on avian influenza," Dev. Biol. (Basel), 114:201-212.
Tumova et al., 1979, "A hitherto unreported paramyxovirus of turkeys," Res. Vet. Sci., 27(2):135-140.
Van Den Hoogen et al., 2001, "A newly discovered human pneumovirus isolated from young children with respiratory tract disease," Nat. Med., 7(6):719-724.
Washburn et al., 2002, "Human tumor cell infection by Newcastle Disease Virus leads to upregulation of HLA and cell adhesion molecules and to induction of interferons, chemokines and finally apoptosis," Int. J. Oncol., 21(1):85-93.
Webster et al., 1976, "Ortho- and paramyxoviruses from migrating feral ducks: characterization of a new group of influenza A viruses," J Gen Virol., 32(2):217-225.
Wheelock et al., 1964, "Observations on the repeated administration of viruses to a patient with acute leukemia. A preliminary report," N. Engl. J. Med., 271:645-651.
Yamane et al., 1982, "Characterization of avian paramyxoviruses isolated from feral ducks in northern Japan: the presence of three distinct viruses in nature," Microbiol Immunol., 26(7):557-568.
Yoshida et al., 2017, "Avian Paramyxovirus Type-3 as a Vaccine Vector: Identification of a Genome Location for High Level Expression of a Foreign Gene," Front Microbiol., 8:693 (8 pages).
Yoshida et al., 2019, "Novel avian paramyxovirus-based vaccine vectors expressing the Ebola virus glycoprotein elicit mucosal and humoral immune responses in guinea pigs," Sci. Rep., 9(1):5520 (10 pages).
Zamarin et al., 2014, "Localized oncolytic virotherapy overcomes systemic tumor resistance to immune checkpoint blockade immunotherapy," Sci. Transl. Med., 6(226):226ra32, with Supplemental Materials (109 pages).
Zamarin et al., 2017, "P415: Upregulation of PD-L1 in tumor microenvironment is a resistance mechanism for onolytic virus immunotherapy," J. Immunother. Cancer, 5(Suppl 2):87, p. 202.
Zhang et al., 2017, "Targeting Melanoma with Cancer-Killing Viruses," Open Virol. J., 11:28-47.
Zhao et al., 2008, "Recombinant Newcastle disease virus expressing human interleukin-2 serves as a potential candidate for tumor therapy," Virus Res., 136(1-2):75-80.
Choi, 2017, "Newcastle disease virus vectored vaccines as bivalent or antigen delivery vaccines," Clin. Exp. Vaccine Res., 6(2):72-82.
Huang et al., 2020, "A recombinant oncolytic Newcastle virus expressing MIP-3α promotes systemic antitumor immunity," J. Immunother Cancer, 8(2):e000330 (14 pages).
International Search Report and Written Opinion for International Patent Application No. PCT/US2021/020085 (Pub. No. WO 2021174121) mailed Jul. 27, 2021 (13 pages).
Javaheri et al., 2022, "Avian Paramyxovirus 4 Antitumor Activity Leads to Complete Remissions and Long-term Protective Memory in Preclinical Melanoma and Colon Carcinoma Models," Cancer Res. Commun., 2(7):602-615.
Kim et al., 2011, "Roles of the fusion and hemagglutinin-neuraminidase proteins in replication, tropism, and pathogenicity of avian paramyxoviruses," J. Virol., 85(17):8582-8596.
Lipkind et al., 1988, "Antigenic relationships between avian paramyxoviruses. III. A mathematical model of antigenic drift and a computer-assisted approach for construction of a phylogenetic tree," Arch. Virol., 103(1-2):83-98.
Liu et al., 2005, "Effects of chicken newcastle disease virus vaccine to the human ovarian carcinoma cell strain in vitro," J. Shandong University Health Sci., 43(11):1058-1068 (in Chinese with English abstract).
McGinnes et al., 2011, "Assembly and immunological properties of Newcastle disease virus-like particles containing the respiratory syncytial virus F and G proteins," J. Virol., 85(1):366-377 (Epub 2010).
Ramamurthy et al., 2021, "Evaluation of the oncolytic property of recombinant Newcastle disease virus strain R2B in 4T1 and B16-F10 cells in-vitro," Res. Vet. Sci., 139:159-165.

* cited by examiner

G

| | | Day 14 Tumor Volume ($mm^3$) | | | | |
|---|---|---|---|---|---|---|
| Group | Treatment | Median | 68% CI, lower | 68% CI, Upper | CRs | PRs |
| 1 | mIgG1 control + PBS | 1031 | 920 | 1093 | 0/10 | 0/10 |
| 2 | mIgG1 control + NDV-WT | 344 | 161 | 383 | 0/10 | 0/10 |
| 3 | muDX400 + NDV-WT | 32 | 21 | 152 | 2/10 | 4/10 |
| **4** | **muDX400 + NDV-muIL-12** | **24** | **16** | **38** | **2/10** | **8/10** |
| 5 | muDX400 + NDV-muIL-23 | 45 | 37 | 66 | 0/10 | 9/10 |
| 6 | muDX400 + NDV-muIL-27 | 31 | 21 | 78 | 0/10 | 8/10 |

CI = confidence interval; CR = complete regression; PR = partial regression.

Non-injected Tumors

N

| | | Day 14 Tumor Volume ($mm^3$) | | | | |
|---|---|---|---|---|---|---|
| Group | Treatment | Median | 68% CI, lower | 68% CI, Upper | CRs | PRs |
| 1 | mIgG1 control + PBS | 1031 | 920 | 1093 | 0/10 | 0/10 |
| 2 | mIgG1 control + NDV-WT | 344 | 161 | 383 | 0/10 | 0/10 |
| 3 | muDX400 + NDV-WT | 32 | 21 | 152 | 1/10 | 3/10 |
| **4** | **muDX400 + NDV-muIL-12** | **24** | **16** | **38** | **5/10** | **2/10** |
| 5 | muDX400 + NDV-muIL-23 | 45 | 37 | 66 | 3/10 | 2/10 |
| 6 | muDX400 + NDV-muIL-27 | 31 | 21 | 78 | 2/10 | 0/10 |

CI = confidence interval; CR = complete regression; PR = partial regression.

FIG. 38I - FIG. 38J

FIG. 38I

| Injected Tumors | | | | | | |
|---|---|---|---|---|---|---|
| | | Day 18 Tumor Volume ($mm^3$) | | | | |
| Group | Treatment | Median | 68% CI, lower | 68% CI, Upper | CRs | PRs |
| 1* | mIgG1 control + PBS | 552 | 394 | 1033 | 0/12 | 0/12 |
| 2 | muDX400 + NDV-WT | 319 | 99 | 596 | 2/12 | 1/12 |
| **3** | **muDX400 + NDV-muIL-12** | **18** | **15** | **29** | **4/12** | **7/12** |
| 4 | muDX400 + NDV-muIL-2 | 0 | 0 | 32 | 6/12 | 4/12 |

CI = confidence interval; CR = complete regression; PR = partial regression.
*Values for Day 11 are presented since animals in this group were euthanized prior to tumor measurement on Day 14 because total tumor volume reached 2000 $mm^3$ or poor health in majority of animals.

FIG. 38J

| Non-injected Tumors | | | | | | |
|---|---|---|---|---|---|---|
| | | Day 18 Tumor Volume ($mm^3$) | | | | |
| Group | Treatment | Median | 68% CI, lower | 68% CI, Upper | CRs | PRs |
| 1* | mIgG1 control + PBS | 540 | 468 | 654 | 0/12 | 0/12 |
| 2 | muDX400 + NDV-WT | 512 | 448 | 679 | 1/12 | 0/12 |
| **3** | **muDX400 + NDV-muIL-12** | **130** | **102** | **244** | **2/12** | **0/12** |
| 4 | muDX400 + NDV-muIL-2 | 253 | 207 | 1036 | 0/12 | 0/12 |

CI = confidence interval; CR = complete regression; PR = partial regression.
*Values for Day 11 are presented since animals in this group were euthanized prior to tumor measurement on Day 14 because total tumor volume reached 2000 $mm^3$ or poor health in majority of animals.

ANOVA (Friedman Test) followed by Dunn's multiple comparisons test

**** P < 0.0001

NEWCASTLE DISEASE VIRUSES AND USES THEREOF

This application is a U.S. national stage of International Patent Application No. PCT/US2018/032255, filed May 11, 2018, which claims the benefit of priority of U.S. provisional patent application No. 62/505,759, filed May 12, 2017, and U.S. provisional patent application No. 62/507,690, filed May 17, 2017, each of which is incorporated by reference herein in its entirety.

This invention was made with government support under T32 CA009207 and HHSN26620070010C awarded by the National Institutes of Health. The government has certain rights in the invention.

The instant application contains a Sequence Listing which has been submitted electronically in ASCII format and is hereby incorporated by reference in its entirety. Said ASCII copy, created on May 11, 2018, is named 6923-272-228 SL.txt and is 263,022 bytes in size.

1. INTRODUCTION

Described herein are methods for treating cancer, comprising administering to a subject chimeric Newcastle disease virus ("NDV") (or a composition comprising such a chimeric NDV) and an antagonist of programmed cell death protein 1 ("PD-1") or a ligand thereof (or a composition comprising such an antagonist), wherein the chimeric NDV comprises a packaged genome comprising a transgene encoding interleukin-12 ("IL-12"). In a specific aspect, described herein are methods for treating cancer comprising administering a chimeric Newcastle disease virus (or a composition comprising such a chimeric NDV) and an anti-PD-1 antibody that blocks the interaction between PD-1 and a ligand thereof (e.g., PD-L1, PD-L2 or both PD-L1 and PD-L2) antibody (or a composition comprising such an antagonist), wherein the chimeric NDV comprises a packaged genome comprising a transgene encoding IL-12. In another aspect, described herein are a chimeric Newcastle disease virus for use in a method for treating cancer in a subject, wherein the chimeric NDV comprises a packaged genome comprising a transgene encoding IL-12, wherein the method further comprises administering an anti-PD-1 antibody that blocks the interaction between PD-1 and a ligand thereof (e.g., either PD-L1, PD-L2, or both) antibody.

2. BACKGROUND

2.1 Newcastle Disease Virus

Newcastle disease virus (NDV) is a member of the *Avulavirus* genus in the Paramyxoviridae family, which has been shown to infect a number of avian species (Alexander, D J (1988). Newcastle disease, Newcastle disease virus—an avian paramyxovirus. Kluwer Academic Publishers: Dordrecht, The Netherlands. pp 1-22). NDV possesses a single-stranded RNA genome in negative sense and does not undergo recombination with the host genome or with other viruses (Alexander, D J (1988). Newcastle disease, Newcastle disease virus—an avian paramyxovirus. Kluwer Academic Publishers: Dordrecht, The Netherlands. pp 1-22). The genomic RNA contains genes in the order of 3'-NP-P-M-F-HN-L-5', described in further detail below. Two additional proteins, V and W, are produced by NDV from the P gene by alternative mRNAs that are generated by RNA editing. The genomic RNA also contains a leader sequence at the 3' end.

The structural elements of the virion include the virus envelope which is a lipid bilayer derived from the cell plasma membrane. The glycoprotein, hemagglutinin-neuraminidase (HN) protrudes from the envelope allowing the virus to contain both hemagglutinin (e.g., receptor binding/fusogenic) and neuraminidase activities. The fusion glycoprotein (F), which also interacts with the viral membrane, is first produced as an inactive precursor, then cleaved post-translationally to produce two disulfide linked polypeptides. The active F protein is involved in penetration of NDV into host cells by facilitating fusion of the viral envelope with the host cell plasma membrane. The matrix protein (M), is involved with viral assembly, and interacts with both the viral membrane as well as the nucleocapsid proteins.

The main protein subunit of the nucleocapsid is the nucleocapsid protein (NP) which confers helical symmetry on the capsid. In association with the nucleocapsid are the P and L proteins. The phosphoprotein (P), which is subject to phosphorylation, is thought to play a regulatory role in transcription, and may also be involved in methylation, phosphorylation and polyadenylation. The L gene, which encodes an RNA-dependent RNA polymerase, is required for viral RNA synthesis together with the P protein. The L protein, which takes up nearly half of the coding capacity of the viral genome is the largest of the viral proteins, and plays an important role in both transcription and replication. The V protein has been shown to inhibit interferon-alpha and to contribute to the virulence of NDV (Huang et al. (2003). Newcastle disease virus V protein is associated with viral pathogenesis and functions as an Alpha Interferon Antagonist. *Journal of Virology* 77: 8676-8685).

Naturally-occurring NDV has been reported to be an effective oncolytic agent in a variety of animal tumor models (Sinkovics, J G, and Horvath, J C (2000). Newcastle disease virus (NDV): brief history of its oncolytic strains. *J Clin Virol* 16: 1-15; Zamarin et al., 2009; Mol Ther 17: 697; Elankumaran et al., 2010; J Virol 84: 3835; Schirrmacher et al., 2009; Methods Mol Biol 542: 565; Bart et al., 1973; Nat New Biol 245: 229). Naturally-occurring strains of NDV have been used in multiple clinical trials against advanced human cancers (Sinkovics, J G, and Horvath, J C (2000). Newcastle disease virus (NDV): brief history of its oncolytic strains. J Clin Virol 16: 1-15; Lorence et al. (2007). Phase 1 clinical experience using intravenous administration of PV701, an oncolytic Newcastle disease virus. *Curr Cancer Drug Targets* 7: 157-167; Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. Mol Ther 13: 221-228; Pecora et al. (2002). Phase I trial of intravenous administration of PV701, an oncolytic virus, in patients with advanced solid cancers. *J Clin Oncol* 20: 2251-2266; Csatary et al. (2004). MTH-68/H oncolytic viral treatment in human high-grade gliomas. *J Neurooncol* 67: 83-93). However, the success of naturally-occurring strains of NDV in these clinical trials for advanced human cancers was only marginal (Hotte et al. (2007). An optimized clinical regimen for the oncolytic virus PV701. *Clin Cancer Res* 13: 977-985; Freeman et al. (2006). Phase I/II trial of intravenous NDV-HUJ oncolytic virus in recurrent glioblastoma multiforme. *Mol Ther* 13: 221-228; Pecora et al. (2002). Phase I trial of intravenous administration of PV701, an oncolytic virus, in patients with advanced solid cancers. *J Clin Oncol* 20: 2251-2266). As such, there remains a need for NDV-based therapies useful in the treatment of cancer, especially advanced cancer.

2.2 PD-1 Antagonists

Anti-PD-1-blocking antibodies and anti-PD-L1 blocking antibodies have been approved for treating certain types of cancer. For example, pembrolizumab has been approved for treatment of several types of cancer, including (1) refractory classical Hodgkin lymphoma, (2) recurrent or metastatic head and neck squamous cell cancer, (3) unresectable or metastatic melanoma, (4) locally or advanced or metastatic urothelial carcinoma, (5) recurrent locally advanced or metastatic gastric or gastroesophageal adenocarcinoma with tumors expressing programmed death-ligand 1 ("PD-L1"), (6) unresectable or metastatic, microsatellite instability-high cancer or mismatch repair deficient solid tumors that have progressed following prior treatment and who have no satisfactory alternative treatment options, or colorectal cancer that has progessed following treatment with a fluoropyrimidine, oxaliplatin and irinotecan, and (7) metastatic non-small cell lung cancers having tumors which express PD-L1; and nivolumab has been approved for the treatment of different types of cancer, including unresectable or metastatic melanoma. Although these therapies have shown some success, there remains a need for therapies to treat cancer.

3. SUMMARY

In one aspect the present disclosure provides chimeric NDV comprising a packaged genome which encodes interleukin-12 ("IL-12") (e.g., the p35 and p40 subunits of IL-12) or a derivative thereof. In a specific embodiment the IL-12 transgene is an IL-12 transgene disclosed herein (see, e.g., Sections 5.2, 5.2.1, 5.7, 5.10, and 6). In a specific embodiment, the transgene comprises the nucleotide sequence set forth in SEQ ID NO: 26, 53, 61, 63, 66, or 68. In a specific embodiment, the transgene encodes a polypeptide, said polypeptide comprising the amino acid sequence set forth in SEQ ID NO: 22, 39, 42, or 43. In a specific embodiment, the IL-12 is human IL-12. In a specific embodiment, the IL-12 or derivative thereof is expressed by cells infected with the chimeric NDV. In a specific embodiment, the chimeric NDV can be used for the treatment of, e.g., cancer. A chimeric NDV disclosed herein unexpectedly significantly increases the Gene Expression Profiling Score of the 18-gene signature in Table 15 (see Section 6.3.1.14, infra) for tumor samples.

In another aspect, presented herein are methods for treating cancer utilizing a chimeric NDV or a composition comprising such a chimeric NDV in combination with an antagonist of PD-1 (e.g., human PD-1) or a ligand thereof or composition comprising such an antagonist, wherein the chimeric NDV comprises a packaged genome which encodes IL-12 (e.g., the p35 and p40 subunits of IL-12) or a derivative thereof. In a specific embodiment, the IL-12 or derivative thereof is expressed by cells infected with the chimeric NDV.

The methods of treating cancer described herein are based, in part, on the robust antitumor activity seen in subjects intratumorally administered a chimeric NDV comprising a packaged genome engineered to encode an IL-12 transgene ("NDV-IL-12"), in combination with the administration of an anti-PD-1 antibody that blocks the interaction between PD-1 and PD-L1. The robust antitumor activity in the treated subjects was observed in both the NDV-IL-12-injected and non-injected tumor, hence, an abscopal effect was observed. The methods of treating cancer described herein are also based, in part, on gene expression observed in subjects administered NDV-IL-12, alone or in combination with an anti-PD-1 antibody that blocks the interaction between PD-1 and a ligand thereof (e.g., PD-L1, PD-L2 or both PD-L1 and PD-L2).

In one embodiment, presented herein are methods for treating cancer comprising administering to a subject a chimeric NDV and an antagonist of PD-1 (e.g., human PD-1) or a ligand thereof, wherein the chimeric NDV comprises a packaged genome comprising a transgene encoding IL-12 or a derivative thereof. In a specific embodiment, the IL-12 or derivative thereof is expressed by cells infected with the chimeric NDV. In another embodiment, presented herein are methods for treating cancer comprising administering to a subject an effective amount of a chimeric NDV and an effective amount of an antagonist of PD-1 (e.g., human PD-1) or a ligand thereof, wherein the chimeric NDV comprises a packaged genome comprising a transgene encoding IL-12 or a derivative thereof. In a specific embodiment, the IL-12 or derivative thereof is expressed by cells infected with the chimeric NDV. The chimeric NDV and antagonist may be administered concurrently or sequentially to the subject. In certain embodiments, the chimeric NDV and antagonist are administered in the same composition. In other embodiments, the chimeric NDV and antagonist are administered in different compositions. The NDV and the antagonist may be administered by the same or different routes of administration to the subject. In a specific embodiment, the chimeric NDV is administered to a subject intratumorally and the antagonist is administered to the subject intravenously.

In another embodiment, presented herein is a method for treating cancer, comprising administering to a subject in need thereof a first composition comprising a chimeric NDV and a second composition comprising an antagonist of PD-1 (e.g., human PD-1) or a ligand thereof, wherein the chimeric NDV comprises a packaged genome comprising a transgene encoding IL-12, wherein the transgene encodes an IL-12 p40 subunit and an IL-12 p35 subunit. In another embodiment, presented herein is a method for treating cancer, comprising administering to a subject in need thereof a chimeric NDV and an antagonist of PD-1 (e.g., human PD-1) or a ligand thereof, wherein the chimeric NDV comprises a packaged genome which encodes IL-12, and wherein the antagonist of PD-1 is an anti-PD-1 antibody that blocks the interaction between PD-1 and a ligand thereof (e.g., PD-L1, PD-L2 or both PD-L1 and PD-L2). In another embodiment, presented herein is a method for treating cancer, comprising administering to a subject in need thereof a first composition comprising a chimeric NDV and a second composition comprising an anti-PD-1 antibody that blocks the interaction between PD-1 and a ligand thereof (e.g., PD-L1, PD-L2 or both PD-L1 and PD-L2), wherein the chimeric NDV comprises a packaged genome comprising a transgene encoding IL-12 (e.g., human IL-12), wherein the transgene encodes an IL-12 p40 subunit and an IL-12 p35 subunit. In a specific embodiment, presented herein is a method for treating cancer, comprising administering to a human subject in need thereof a first composition comprising a chimeric NDV and a second composition comprising an anti-PD-1 antibody that blocks the interaction between PD-1 and a ligand thereof (e.g., PD-L1, PD-L2 or both PD-L1 and PD-L2), wherein the chimeric NDV comprises a packaged genome comprising a transgene encoding human IL-12, wherein the transgene encodes a human IL-12 p40 subunit and a human IL-12 p35 subunit. The first and second compositions may be administered by same or different routes of administration. In a specific embodiment, the first composition is administered intratumorally and the second composition is administered intravenously. See, e.g., Sections 5.1, 5.2 and 6, infra for information regarding NDV, Sections 5.5 and 6, infra, for information regarding antagonists of PD-1 or a ligand thereof (including PD-1 blocking antibodies), Section 5.5.1, infra, for information regarding compositions and routes of administration, and Sections 5.7 and 6, infra, for information regarding methods for treating cancer.

In another aspect, provided herein is a chimeric NDV for use in a method of treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit, and wherein the method further comprises administering an antagonist of PD-1 (e.g., human PD-1) or a ligand thereof. In another embodiment, presented herein is a chimeric NDV for use in a method of treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit, wherein the method further comprises administering an antagonist of PD-1 or a ligand thereof, and wherein the antagonist of PD-1 (e.g., human PD-1) is an anti-PD-1 antibody that blocks the interaction between PD-1 and a ligand thereof (e.g., PD-L1, PD-L2 or both PD-L1 and PD-L2). In another embodiment, presented herein is a chimeric NDV for use in a method of treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit, and wherein the method further comprises administering an anti-PD-1 antibody that blocks the interaction between PD-1 and a ligand thereof (e.g., PD-L1, PD-L2 or both PD-L1 and PD-L2). The chimeric NDV and the antagonist of PD-1 or a ligand thereof or the anti-PD-1 antibody may be administered by same or different routes of administration. In a specific embodiment, the chimeric NDV is administered intratumorally and the antagonist of PD-1 or a ligand thereof or the anti-PD-1 antibody is administered intravenously. See, e.g., Sections 5.1, 5.2 and 6, infra for information regarding NDV, Sections 5.5 and 6, infra, for information regarding antagonists of PD-1 or a ligand thereof (including PD-1 blocking antibodies), Section 5.5.1, infra, for information regarding compositions and routes of administration, and Sections 5.7 and 6, infra, for information regarding methods for treating cancer.

In another embodiment, presented herein is a use of a chimeric NDV in the preparation of a medicament for use in combination with an antagonist of PD-1 (e.g., human PD-1) or a ligand thereof for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit. In another embodiment, presented herein is a use of a chimeric NDV in the preparation of a medicament for use in combination with an antagonist of PD-1 (e.g., human PD-1) or a ligand thereof for treating cancer in a subject (e.g., a human subject), wherein the chimeric NDV comprises a packaged genome which encodes IL-12, and wherein the antagonist of PD-1 is an anti-PD-1 antibody that blocks the interaction between PD-1 and a ligand thereof (e.g., PD-L1, PD-L2 or both PD-L1 and PD-L2). In another embodiment, presented herein is a use of a chimeric NDV in the preparation of a medicament for use in combination with an anti-PD-1 antibody that blocks the interaction between PD-1 and a ligand thereof (e.g., PD-L1, PD-L2 or both PD-L1 and PD-L2) for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit. The chimeric NDV and the antagonist of PD-1 or a ligand thereof or the anti-PD-1 antibody may be administered by same or different routes of administration. In a specific embodiment, the chimeric NDV is administered intratumorally and the and the antagonist of PD-1 or a ligand thereof or the anti-PD-1 antibody is administered intravenously. See, e.g., Sections 5.1, 5.2 and 6, infra for information regarding NDV, Sections 5.5 and 6, infra, for information regarding antagonists of PD-1 or a ligand thereof (including PD-1 blocking antibodies), Section 5.5.1, infra, for information regarding compositions and routes of administration, and Sections 5.7 and 6, infra, for information regarding methods for treating cancer.

The chimeric NDV may have the backbone of any NDV type or strain, including, but not limited to, naturally-occurring strains, variants or mutants, mutagenized viruses, reassortants and/or genetically engineered viruses. In a specific embodiment, the NDV that serves as the backbone for genetic engineering of the chimeric NDV is a lentogenic strain. In a specific embodiment, the NDV that serves as the backbone for genetic engineering of the chimeric NDV is a mesogenic strain. In a specific embodiment, the NDV that serves as the backbone for genetic engineering of the chimeric NDV is a velogenic strain. In one embodiment, the chimeric NDV comprises a packaged genome comprising a nucleotide sequence encoding a mutated F protein with a mutated cleavage site. In a specific embodiment, the chimeric NDV comprises a packaged genome comprising a nucleotide sequence encoding a mutated F protein in which the cleavage site of the F protein is mutated to produce a polybasic amino acid sequence, which allows the protein to be cleaved by intracellular proteases, which makes the virus more effective in entering cells and forming syncytia. In another specific embodiment, the chimeric NDV comprises a packaged genome comprising a nucleotide sequence encoding a mutated F protein in which the cleavage site of the F protein is replaced with one containing one or two extra arginine residues, allowing the mutant cleavage site to be activated by ubiquitously expressed proteases of the furin family. Specific examples of NDVs that express such a mutated F protein include, but are not limited to, rNDV/F2aa and rNDV/F3aa. For a description of mutations introduced into a NDV F protein to produce a mutated F protein with a mutated cleavage site, see, e.g., Park et al. (2006) Engineered viral vaccine constructs with dual specificity: avian influenza and Newcastle disease. PNAS USA 103: 8203-2808, which is incorporated herein by reference in its entirety. In certain embodiments, the chimeric NDV comprises a mutated F protein with an F protein cleavage site of NDV LaSota strain or glycoprotein B of cytomegalovirus (CMV). In a specific embodiment, the chimeric NDV comprises a mutated F protein with an F protein cleavage site derived from glycoprotein B of cytomegalovirus, said F protein cleavage site comprising the amino acid sequence $^{111}$H-N-R-T-K-S/F$^{117}$ (SEQ ID NO: 56), such as described in International Patent Application Publication No. WO 2015/032755. In a specific embodiment, the chimeric NDV comprises a mutated F protein with an F protein cleavage site having one of the following sequences: S116: $^{111}$H-N-R-T-K-S/F$^{117}$ (SEQ ID NO: 56); S116K: $^{111}$H-N-K-T-K-S/F$^{117}$ (SEQ ID NO: 58); S116m: $^{111}$H-N-R-M-K-S/F$^{117}$ (SEQ ID NO: 69); S116KM: $^{111}$H-N-K-M-S/F-I$^{118}$ (SEQ ID NO: 70); or R116: $^{111}$H-N-R-T-K-R/F-I$^{118}$ (SEQ ID NO: 71), such as described in International Patent Application No. WO 2015/032755. See, e.g., International Patent Application Publication No. WO 2015/032755 for a description of the types of mutated F protein cleavage sites that may be engineered into an NDV F protein, which is incorporated herein by reference in its entirety. In some embodiments, the chimeric NDV comprises a packaged genome comprising a nucleotide sequence encoding a mutated F protein, wherein the mutated F protein comprises the amino acid mutation L289A (i.e., an L to A mutation at the amino acid position corresponding to L289 of the LaSota F protein). In specific embodiments, the L289A mutated F protein possesses one, two or three arginine residues in the cleavage site. In certain embodiments, the mutated F protein is from a different type or strain of NDV than the backbone NDV. In other embodiments, the mutated F protein is from the same type or strain of NDV as the backbone NDV. In some embodiments, the mutated F protein is in addition to the backbone NDV F protein. In specific embodiments, the mutated F protein replaces the backbone NDV F protein.

The antagonist of PD-1 or a ligand thereof for use in combination with an NDV described herein (see, e.g., Section 5.1, Section 5.2, Section 5.5, Section 5.7, and/or Section 6) may be any antagonist of PD-1 or a ligand thereof known to one of skill in the art. Specific examples of ligands for PD-1 include PD-L1 and PD-L2. In a specific embodiment, the antagonist of PD-1 or a ligand thereof blocks (completely or partially) the interaction between a native ligand of PD-1 (e.g., PD-L1, PD-L2 or both PD-L1 and PD-L2) and PD-1. In a preferred embodiment, the antagonist of PD-1 or a ligand thereof blocks (completely or partially) the interaction between a native ligand of PD-1 (e.g., PD-L1, PD-L2 or both PD-L1 and PD-L2) and PD-1, and prevents or reduces the transduction of an inhibitory signal(s) induced by the interaction of PD-1 and native ligand of PD-1 (e.g., PD-L1 and/or PD-L2).

In a particular aspect, an antagonist of PD-1 or a ligand thereof is an antagonist of PD-1. In a specific embodiment, the antagonist of PD-1 or a ligand thereof is an antibody that binds to PD-1. In a specific embodiments, the antagonist of PD-1 or a ligand thereof is an antibody that binds to PD-1 and blocks (completely or partially) the interaction between PD-1 and PD-L1. In a specific embodiments, the antagonist of PD-1 or a ligand thereof is an antibody that binds to PD-1, blocks (completely or partially) the interaction between PD-1 and PD-L1, and prevents or reduces the transduction of an inhibitory signal(s). In a preferred embodiment, the antagonist of PD-1 or a ligand thereof is an antibody that binds to PD-1 and blocks (completely or partially) the interaction between PD-1 and its ligands, PD-L1 and PD-L2. In another preferred embodiment, the antagonist of PD-1 or a ligand thereof is an antibody that binds to PD-1, blocks the interaction between PD-1 and its ligands, PD-L1 and PD-L2, and prevents or reduces the transduction of an inhibitory signal(s). In certain embodiments, the antibody is a camelized antibody, human antibody or humanized antibody. In a specific embodiment, the antibody is a monoclonal antibody. In another specific embodiment, the antibody is a scFv.

In another aspect, an antagonist of PD-1 or a ligand thereof is an antagonist of a ligand of PD-1 (e.g., PD-L1 or PD-L2). In a specific embodiment, an antagonist of PD-1 or a ligand thereof is an antagonist of PD-L1. In certain embodiments, an antagonist of PD-1 or a ligand thereof is an antagonist of PD-L1, which binds to PD-L1 and blocks (completely or partially) the interaction between PD-1 to PD-L1. In some embodiments, an antagonist of PD-1 or a ligand thereof is an antagonist of PD-L1, which binds to PD-L1, blocks (completely or partially) the interaction between PD-1 to PD-L1 and prevents or reduces the transduction of an inhibitory signal(s). In some embodiments, an antagonist of PD-L1 also blocks (completely or partially) the interaction between PD-L1 and CD80 (B7.1).

In a specific embodiment, an antagonist of PD-1 or a ligand thereof is an antagonist of PD-L2. In certain embodiments, an antagonist of PD-1 or a ligand thereof is an antagonist of PD-L2, which binds to PD-L2 and blocks (completely or partially) the interaction between PD-1 to PD-L2. In certain embodiments, an antagonist of PD-1 or a ligand thereof is an antagonist of PD-L2, which binds to PD-L2 and blocks (completely or partially) the interaction between PD-1 to PD-L2 and prevents or reduces the transduction of an inhibitory signal(s).

In a specific embodiment, the antagonist of PD-1 or a ligand thereof is an antibody or a soluble receptor that specifically binds to a native ligand of PD-1. In a specific embodiment, the antagonist of PD-1 or a ligand thereof is an antibody or a soluble receptor that specifically binds to a native ligand of PD-1 and blocks (completely or partially) the native ligand from binding PD-1 and transducing an inhibitory signal(s). In certain specific embodiments, the soluble receptor is a fragment of PD-1 or a fragment of a derivative of PD-1 that binds to a ligand of PD-1 (e.g., the extracellular domain of PD-1 or a derivative of PD-1). In some specific embodiments, the soluble receptor is a fusion protein comprising at least a portion of PD-1 or a derivative of PD-1 (e.g., the extracellular domain of PD-1 or a derivative of PD-1), and a heterologous amino acid sequence. In a specific embodiment, the fusion protein comprises at least a portion of PD-1 or a derivative of PD-1, and the Fc portion of an immunoglobulin or a fragment thereof. In a specific embodiment, the portion of the PD-1 or a derivaitive thereof is e.g., the extracellular domain of PD-1 or a derivative thereof.

In a specific embodiment, the antagonist of PD-1 or a ligand thereof is an antibody that binds to a native ligand of PD-1. The antibody may bind to PD-L1 or PD-L2. In certain embodiments, the antibody is camelized antibody, human antibody or humanized antibody. In a specific embodiment, the antibody may be a monoclonal antibody. In another specific embodiment, the antibody may be a single-chain variable fragment (scFv). In a specific embodiment, the antagonist of PD-1 or a ligand thereof is an antibody or ligand that binds to PD-1, but does not transduce an inhibitory signal(s). In another embodiment, the antagonist of PD-1 or a ligand thereof is a ligand that binds to PD-1, but does not transduce an inhibitory signal(s). In certain specific embodiments, the ligand is a fusion protein comprising at least a portion of a ligand of PD-1 or a derivative of a ligand of PD-1, and a heterologous amino acid sequence. In specific embodiments, the fusion protein comprises at least a portion of a ligand of PD-1 or a derivative of a ligand of PD-1, and the Fc portion of an immunoglobulin or a fragment thereof.

In a specific embodiment, an antagonist of PD-1 or a ligand thereof is a PD-1 blocking antibody. In another specific embodiment, an antagonist of PD-1 or a ligand thereof is nivolumab. In a preferred embodiment, an antagonist of PD-1 or a ligand thereof is pembrolizumab. In another specific embodiment, an antagonist of PD-1 or a ligand thereof is a PD-L1 blocking antibody (e.g., duralumab or avelumab).

In one aspect, provided herein is a method for treating cancer, comprising administering to a human subject in need thereof a first composition comprising a chimeric Newcastle disease virus (NDV) and a second composition comprising an antagonist of human PD-1 or a ligand thereof, wherein the chimeric NDV comprises a packaged genome comprising a transgene encoding human interleukin-12 ("IL-12"), wherein the transgene encodes a human IL-12 p40 subunit and a human IL-12 p35 subunit. In a specific embodiment, the packaged genome of the chimeric NDV further comprises a nucleotide sequence encoding a mutated F protein and the mutated F protein is incorporated into the virion of the chimeric NDV, wherein the mutated F protein comprises a mutated cleavage site. In a specific embodiment, the mutated cleavage site is $^{111}$H-N-R-T-K-R/F-I$^{118}$ (SEQ ID NO: 71). In another specific embodiment, the packaged genome of the chimeric NDV further comprises a nucleotide sequence encoding a mutated F protein with the amino acid mutation L289A, wherein the mutated F protein is incorporated into the virion of the chimeric NDV. In a specific embodiment, the transgene comprises the nucleotide sequence set forth in SEQ ID NO:26. In another specific embodiment, the IL-12 p40 subunit comprises the amino acid sequence set forth in SEQ ID NO: 38. In another specific embodiment, the IL-12 p40 subunit comprises the amino acid sequence set forth in SEQ ID NO: 40. In another specific embodiment, the IL-12 p40 subunit comprises the amino acid sequence set forth in SEQ ID NO: 23. In another specific embodiment, the IL-12 p35 subunit comprises the amino acid sequence set forth in SEQ ID NO: 41. In another specific embodiment, the IL-12 p35 subunit comprises the amino acid sequence set forth in SEQ ID NO: 25. In another specific embodiment, the IL-12 p40 subunit comprises the amino acid sequence set forth in SEQ ID NO: 38 and the IL-12 p35 subunit comprises the amino acid sequence set forth in SEQ ID NO: 41. In another specific embodiment, the IL-12 p40 subunit comprises the amino acid sequence set forth in SEQ ID NO: 38 and the IL-12 p35 subunit comprises the amino acid sequence set forth in SEQ ID NO: 25. In a specific embodiment, the transgene encodes an amino acid sequence set forth in SEQ ID NO: 42. In a specific embodiment, the transgene encodes an amino acid sequence set forth in SEQ ID NO: 22. In a specific embodiment, the transgene encodes an amino acid sequence comprising the amino acid sequence set forth in SEQ ID NO: 43. In a specific embodiment, the transgene encodes an amino acid sequence comprising the amino acid sequence set forth in SEQ ID NO: 39. In another specific embodiment, the IL-12 p40 subunit comprises the amino acid sequence set forth in SEQ ID NO: 40 and the IL-12 p35 subunit comprises the amino acid sequence set forth in SEQ ID NO: 41. In a specific embodiment, the transgene is inserted between two transcription units of the packaged genome. In a particular embodiment, the two transcription units of the packaged genome are the transcription units for the NDV P gene and the NDV M gene. In a specific embodiment, the first composition is administered to the subject intratumorally or intra-nodally. In another specific embodiment, the second composition is administered to the subject intravenously.

In another aspect, provided herein is a chimeric NDV for use in a method for treating cancer in a human subject, wherein the chimeric NDV comprises a packaged genome comprising a transgene encoding human interleukin-12 ("IL-12"), wherein the transgene encodes a human IL-12 p40 subunit and a human IL-12 p35 subunit, and wherein the method further comprises administering an antagonist of human PD-1 or a ligand thereof. In a specific embodiment, the packaged genome of the chimeric NDV further comprises a nucleotide sequence encoding a mutated F protein and the mutated F protein is incorporated into the virion of the chimeric NDV, wherein the mutated F protein comprises a mutated cleavage site. In a specific embodiment, the mutated cleavage site is $^{111}$H-N-R-T-K-R/F-$^{118}$ (SEQ ID NO: 71). In another specific embodiment, the packaged genome of the chimeric NDV further comprises a nucleotide sequence encoding a mutated F protein with the amino acid mutation L289A, wherein the mutated F protein is incorporated into the virion of the chimeric NDV. In a specific embodiment, the transgene comprises the nucleotide sequence set forth in SEQ ID NO:26. In another specific embodiment, the IL-12 p40 subunit comprises the amino acid sequence set forth in SEQ ID NO: 38. In another specific embodiment, the IL-12 p40 subunit comprises the amino acid sequence set forth in SEQ ID NO: 23. In another specific embodiment, the IL-12 p35 subunit comprises the amino acid sequence set forth in SEQ ID NO: 25. In another specific embodiment, the IL-12 p40 subunit comprises the amino acid sequence set forth in SEQ ID NO: 38 and the IL-12 p35 subunit comprises the amino acid sequence set forth in SEQ ID NO: 25. In a specific embodiment, the transgene encodes an amino acid sequence set forth in SEQ ID NO: 22. In a specific embodiment, the transgene encodes an amino acid sequence comprising the amino acid sequence set forth in SEQ ID NO: 39. In another specific embodiment, the IL-12 p35 subunit comprises the amino acid sequence set forth in SEQ ID NO: 41. In another specific embodiment, the IL-12 p40 subunit comprises the amino acid sequence set forth in SEQ ID NO: 38 and the IL-12 p35 subunit comprises the amino acid sequence set forth in SEQ ID NO: 41. In a specific embodiment, the transgene encodes an amino acid sequence set forth in SEQ ID NO: 42. In another specific embodiment, the IL-12 p40 subunit comprises the amino acid sequence set forth in SEQ ID NO: 40 and the IL-12 p35 subunit comprises the amino acid sequence set forth in SEQ ID NO: 41. In a specific embodiment, the transgene is inserted between two transcription units of the packaged genome. In a particular embodiment, the two transcription units of the packaged genome are the transcription units for the NDV P gene and the NDV M gene. In a specific embodiment, the sequence of the packaged genome is as set forth in SEQ ID NO: 51. In a specific embodiment, the sequence of the packaged genome is as set forth in SEQ ID NO: 52. In a specific embodiment, the first composition is administered to the subject intratumorally or intra-nodally. In another specific embodiment, the second composition is administered to the subject intravenously.

In a specific embodiment, the chimeric NDV comprises an NDV backbone which is lentogenic. In another specific embodiment, the chimeric NDV comprises an NDV backbone of LaSota strain. In another specific embodiment, the chimeric NDV comprises an NDV backbone of Hitchner B1 strain. In another specific embodiment, the chimeric NDV comprises an NDV backbone of a r73T-R116 virus.

In a specific embodiment, the antagonist of human PD-1 or a ligand thereof is an antibody that binds to human PD-1. In another specific embodiment, the antagonist of human PD-1 or a ligand thereof is an antibody that binds to human PD-1 and blocks the interaction between human PD-1 and its ligands, PD-L1 and PD-L2. In a preferred embodiment, the antibody is pembrolizumab. In another embodiment, the antibody is nivolumab or MEDI0680. In a specific embodiment, the antibody comprises a variable light chain region (VLCR) complementarity determining region (CDR)1 comprising the amino acid sequence RASKGVSTSGYSYLH (SEQ ID NO: 1), a VLCR CDR2 comprising the amino acid sequence LASYLES (SEQ ID NO: 2), a VLCR CDR3 comprising the amino acid sequence QHSRDLPLT(SEQ ID NO: 3), a variable heavy chain region (VHCR) CDR 1 comprising the amino acid sequence NYYMY (SEQ ID NO: 6), a VHCR CDR2 comprising the amino acid sequence GINPSNGGTNFNEKFKN (SEQ ID NO: 7), and a VHCR CDR3 comprising the amino acid sequence RDYRFDMGFDY (SEQ ID NO: 8). In another embodiment, the antibody comprises: (a) a VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In another embodiment, the antibody comprises: (a) a light chain comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIKRTVAAPSVFI FPPSDEQLKSGTASVVCLLNNFYPREAKVQWKVDNALQSGNSQESVTEQDSKDSTYSLS STLTLSKADYEKHKVYACEVTHQGLSSPVTKSFNRGEC (SEQ ID NO: 5); and (b) a heavy chain comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSSASTKGPSVFPLAPCSRSTSESTAALGCLVKDYFPEPVTVSWNSGALTSGVHTF PAVLQSSGLYSLSSVVTVPSSSLGTKTYTCNVDHKPSNTKVDKRVESKYGPPCPPCPAPE FLGGPSVFLFPPKPKDTLMISRTPEVTCVVVDVSQEDPEVQFNWYVDGVEVHNAKTKPR EEQFNSTYRVVSVLTVLHQDWLNGKEYKCKVSNKGLPSSIEKTISKAKGQPREPQVYTL PPSQEEMTKNQVSLTCLVKGFYPSDIAVEWESNGQPENNYKTTPPVLDSDGSFFLYSRLT VDKSRWQEGNVFSCSVMHEALHNHYTQKSLSLSLGK (SEQ ID NO: 10). In another embodiment, the antibody comprises a VLCR CDR1 comprising the amino acid sequence RASQSVSSYLA (SEQ ID NO: 11), a VLCR CDR2 comprising the amino acid sequence DASNRAT (SEQ ID NO: 12), a VLCR CDR3 comprising the amino acid sequence QQSSNWPRT (SEQ ID NO: 13), a VHCR CDR1 comprising the amino acid sequence NSGMH (SEQ ID NO: 16), a VHCR CDR2 comprising the amino acid sequence VIWYDGSKRYYADSVKG (SEQ ID NO: 17), and a VHCR CDR3 comprising the amino acid sequence NDDY (SEQ ID NO: 18). In another embodiment, the antibody comprises: (a) a VLCR comprising the amino acid sequence EIVLTQSPATLSLSPGERATLSCRASQSVSSYLAWYQQKPGQAPRLLIYDASNRATGIPA RFSGSGSGTDFTLTISSLEPEDFAVYYCQQSSNWPRTFGQGTKVEIK (SEQ ID NO: 14); and (b) a VHCR comprising the amino acid sequence QVQLVESGGGVVQPGRSLRLDCKASGITFSNSGMHWVRQAPGKGLEWVAVIWYDGSK RYYADSVKGRFTISRDNSKNTLFLQMNSLRAEDTAVYYCATNDDYWGQGTLVTVSS (SEQ ID NO: 19). In another embodiment, the antibody comprises: (a) a light chain comprising the amino acid sequence EIVLTQSPATLSLSPGERATLSCRASQSVSSYLAWYQQKPGQAPRLLIYDASNRATGIPA RFSGSGSGTDFTLTISSLEPEDFAVYYCQQSSNWPRTFGQGTKVEIKRTVAAPSVFIFPPS DEQLKSGTASVVCLLNNFYPREAKVQWKVDNALQSGNSQESVTEQDSKDSTYSLSSTL TLSKADYEKHKVYACEVTHQGLSSPVTKSFNRGEC (SEQ ID NO: 15); and (b) a heavy chain comprising the amino acid sequence (SEQ ID NO: 20)

```
QVQLVESGGGVVQPGRSLRLDCKASGITFSNSGMHWVRQAPGKGLEWVA
VIWYDGSKRYYADSVKGRFTISRDNSKNTLFLQMNSLRAEDTAVYYCAT
NDDYWGQGTLVTVSSASTKGPSVFPLAPCSRSTSESTAALGCLVKDYFP
EPVTVSWNSGALTSGVHTFPAVLQSSGLYSLSSVVTVPSSSLGTKTYTC
NVDHKPSNTKVDKRVESKYGPPCPPCPAPEFLGGPSVFLFPPKPKDTLM
ISRTPEVTCVVVDVSQEDPEVQFNWYVDGVEVHNAKTKPREEQFNSTYR
VVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLD
SDGSFFLYSRLTVDKSRWQEGNVFSCSVMHEALHNHYTQKSLSLSLGK.
```

In a specific embodiment, the antagonist of human PD-1 or a ligand thereof is an antibody that binds to human PD-L1. In a particular embodiment, the antibody is durvalumab, avelumab, bms-936559, or atezolizumab.

In a specific embodiment, the administration of a chimeric NDV described herein in a method of treating cancer provided herein induces IL-12p70, IFN-γ expression, or both IL-12p70 and IFN-γ expression. In a specific embodiment, the administration of a chimeric NDV described herein in a method of treating cancer provided herein increases the gene expression profile (GEP) score. See, for example, Example 6.3, infra, regarding the GEP score. In a specific embodiment, provided herein is a method of increasing the response to anti-PD-1 therapy.

In a specific embodiment, the patient treated in accordance with the methods disclosed herein exhibits cutaneous or subcutaneous tumors or tumors within the lymph node.

In another specific embodiment, the cancer is melanoma, kidney cancer, lung cancer (e.g., non-small cell lung cancer), bladder cancer, ovarian cancer, colon cancer, pancreatic cancer, renal cancer (e.g., renal cell carcinoma), colorectal cancer (e.g., colorectal carcinoma), breast cancer (e.g., breast carcinoma), or head and neck cancer (e.g., squamous cell carcinoma of the head and neck). In a particular embodiment, the cancer is a solid tumor selected from the group consisting of melanoma, head and neck squamous cell carcinoma, and breast carcinoma. In another specific embodiment, the cancer is non-Hodgkin lymphoma or Hodgkin lymphoma. In another specific embodiment, the cancer is metastatic. In another specific embodiment, the cancer is unresectable. In particular embodiments, the cancer comprises a dermal, subcutaneous, or nodal metastasis. In a specific embodiment, the cancer is refractory or relapsed, or both. In a specific embodiment, a biopsy of the cancer is PD-L1-positive. In a particular embodiment, the biopsy has a tumor proportion score of at least 1%. In other specific embodiments, a biopsy of the cancer is PD-L1-negative. In a particular embodiment, the biopsy has a tumor proportion score of less than 1%.

In a specific embodiment, the subject is refractory to monotherapy treatment with an antibody that binds to PD-1 and blocks the interaction between PD-1 and its ligands, PD-L1 and PD-L2. In another specific embodiment, the subject is refractory or unresponsive to monotherapy treatment with an antagonist of human PD-1 or a ligand thereof. In a particular embodiment, the subject is refractory or unresponsive to monotherapy with nivolumab, AMP-224, MEDI0680, pembrolizumab, durvalumab, avelumab, bms-936559, or atezolizumab.

3.1 Terminology

As used herein, the term “about” or “approximately” when used in conjunction with a number refers to any number within 1, 5 or 10% of the referenced number.

As used herein, the term “agonist(s)” refers to a molecule (s) that binds to another molecule and induces a biological reaction. In a specific embodiment, an agonist is a molecule that binds to a receptor on a cell and triggers one or more signal transduction pathways. For example, an agonist includes an antibody or ligand that binds to a receptor on a cell and induces one or more signal transduction pathways. In certain embodiments, the antibody or ligand binds to a receptor on a cell and induces one or more signal transduction pathways. In other embodiments, the agonist facilitates the interaction of the native ligand with the native receptor.

The term “amino acid sequence identity” refers to the degree of identity or similarity between a pair of aligned amino acid sequences, usually expressed as a percentage. Percent identity is the percentage of amino acid residues in a candidate sequence that are identical (i.e., the amino acid residues at a given position in the alignment are the same residue) or similar (i.e., the amino acid substitution at a given position in the alignment is a conservative substitution, as discussed below), to the corresponding amino acid residue in the peptide (or polypeptide or protein) after aligning the sequences and introducing gaps, if necessary, to achieve the maximum percent sequence homology.

As used herein, the term “antagonist(s)” refers to a molecule(s) that inhibits the action of another molecule without provoking a biological response itself. In a specific embodiment, an antagonist is a molecule that binds to a receptor on a cell and blocks or dampens the biological activity of an agonist. For example, an antagonist includes an antibody or ligand that binds to a receptor on a cell and blocks or dampens binding of the native ligand to the receptor without inducing one or more signal transduction pathways. Another example of an antagonist includes an antibody or soluble receptor that competes with the native receptor on cells for binding to the native ligand, and thus, blocks or dampens one or more signal transduction pathways induced when the native receptor binds to the native ligand. Another example of an antagonist includes an antibody or soluble receptor that does not prevent the binding of the native receptor with the native ligand, but prevents signal transduction by other means (e.g., through inhibition of receptor multimerization).

As used herein, the terms “antibody” and “antibodies” refer to molecules that contain an antigen binding site, e.g., immunoglobulins. Antibodies include, but are not limited to, monoclonal antibodies, bispecific antibodies, multispecific antibodies, human antibodies, humanized antibodies, synthetic antibodies, chimeric antibodies, polyclonal antibodies, single domain antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies), and epitope-binding fragments of any of the above. In particular, antibodies include immunoglobulin molecules and immunologically active fragments of immunoglobulin molecules. Immunoglobulin molecules can be of any type (e.g., IgG, IgE, IgM, IgD, IgA and IgY), class (e.g., IgG1, IgG2, IgG3, IgG4, IgA1 and IgA2) or subclass. In a specific embodiment, an antibody is a human or humanized antibody. In another specific embodiment, an antibody is a monoclonal antibody or scFv. In certain embodiments, an antibody is a human or humanized monoclonal antibody or scFv. In other specific embodiments, the antibody is a bispecific antibody. In certain embodiments, the bispecific antibody specifically binds to a co-stimulatory receptor of an immune cell or an inhibitory receptor of an immune cell, and a receptor on a cancer cell. In some embodiments, the bispecific antibody specifically binds to two receptors on immune cells, e.g., two co-stimulatory receptors on immune cells, two inhibitory receptors on immune cells, or one co-stimulatory receptor on immune cells and one inhibitory receptor on immune cells.

“Conservative substitution” is a term understood by those of skill in the art and generally refers to replacement of an amino acid of one class with another amino acid of the same class. In particular embodiments, a conservative substitution does not alter the structure or function, or both, of a polypeptide. Classes of amino acids for the purposes of conservative substitution may include hydrophobic, neutral hydrophilic, acidic, basic, conformation disrupters, and aromatic. Hydrophobic amino acids may include Met, Ala, Val, Leu, and Ile. Neutral hydrophilic amino acids may include Cys, Ser, and Thr. Acidic amino acids may include Asp and Glu. Basic amino acids may include Asn, Gln, His, Lys, and Arg. Conformation disrupter amino acids may include Gly and Pro. Aromatic amino acids may include Trp, Tyr, and Phe.

As used herein, the term “derivative” in the context of proteins or polypeptides refers to: (a) a polypeptide that is at least 80%, 85%, 90%, 95%, 98%, or 99% or is 80% to 85%, 80% to 90%, 80% to 95%, 90% to 95%, 85% to 99%, or 95% to 99% identical to a native polypeptide; (b) a polypeptide encoded by a nucleic acid sequence that is at least 80%, 85%, 90%, 95%, 98%, or 99% or is 80% to 85%, 80% to 90%, 80% to 95%, 90% to 95%, 85% to 99%, or 95% to 99% identical to a nucleic acid sequence encoding a native polypeptide; (c) a polypeptide that contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native polypeptide; (d) a polypeptide encoded by nucleic acid sequence that can hybridize under high, moderate or typical stringency hybridization conditions to a nucleic acid sequence encoding a native polypeptide; (e) a polypeptide encoded by a nucleic acid sequence that can hybridize under high, moderate or typical stringency hybridization conditions to a nucleic acid sequence encoding a fragment of a native polypeptide of at least 10 contiguous amino acids, at least 12 contiguous amino acids, at least 15 contiguous amino acids, at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, at least 150 contiguous amino acids, or 10 to 20, 20 to 50, 25 to 75, 25 to 100, 25 to 150, 50 to 75, 50 to 100, 75 to 100, 50 to 150, 75 to 150, 100 to 150, or 100 to 200 contiguous amino acids; or (f) a fragment of a native polypeptide. Derivatives also include a polypeptide that comprises the amino acid sequence of a naturally occurring mature form of a mammalian polypeptide and a heterologous signal peptide amino acid sequence. In addition, derivatives include polypeptides that have been chemically modified by, e.g., glycosylation, acetylation, pegylation, phosphorylation, amidation, derivitization by known protecting/blocking groups, proteolytic cleavage, linkage to a cellular ligand or other protein moiety, etc. Further, derivatives include polypeptides comprising one or more non-classical amino acids. In one embodiment, a derivative is isolated. In specific embodiments, a derivative retains one or more functions of the native polypeptide from which it was derived.

Percent identity can be determined using any method known to one of skill in the art. In a specific embodiment, the percent identity is determined using the "Best Fit" or "Gap" program of the Sequence Analysis Software Package (Version 10; Genetics Computer Group, Inc., University of Wisconsin Biotechnology Center, Madison, Wisconsin). Information regarding hybridization conditions (e.g., high, moderate, and typical stringency conditions) have been described, see, e.g., U.S. Patent Application Publication No. US 2005/0048549 (e.g., paragraphs 72-73).

As used herein, the term "fragment" is the context of a fragment of a proteinaceous agent (e.g., a protein) refers to a fragment that is 8 or more contiguous amino acids, 10 or more contiguous amino acids, 15 or more contiguous amino acids, 20 or more contiguous amino acids, 25 or more contiguous amino acids, 50 or more contiguous amino acids, 75 or more contiguous amino acids, 100 or more contiguous amino acids, 150 or more contiguous amino acids, 200 or more contiguous amino acids, or in the range of between 10 to 300 contiguous amino acids, 10 to 200 contiguous amino acids, 10 to 250 contiguous amino acids, 10 to 150 contiguous amino acids, 10 to 100 contiguous amino acids, 10 to 50 contiguous amino acids, 50 to 100 contiguous amino acids, 50 to 150 contiguous amino acids, 50 to 200 contiguous amino acids, 50 to 250 contiguous amino acids, 50 to 300 contiguous amino acids, 25 to 50 contiguous amino acids, 25 to 75 contiguous amino acids, 25 to 100 contiguous amino acids, or 75 to 100 contiguous amino acids of a proteinaceous agent. In a specific embodiment, a fragment of a proteinaceous agent retains one or more functions of the proteinaceous agent—in other words, it is a functional fragment. For example, a fragment of a proteinaceous agent retains the ability to interact with another protein and/or to induce, enhance or activate one or more signal transduction pathways.

As used herein, the term "functional fragment," in the context of a proteinaceous agent, refers to a portion of a proteinaceous agent that retains one or more activities or functions of the proteinaceous agent. For example, a functional fragment of an inhibitory receptor may retain the ability to bind one or more of its ligands. A functional fragment of a ligand of a co-stimulatory receptor may retain the ability to bind to the receptor and/or induce, enhance or activate one or more signal transduction pathways mediated by the ligand binding to its co-stimulatory receptor.

As used herein, the term "GEP score" refers to RNA Gene Expressiong Profiling of human tumor histoculture samples based on the 18-gene signature in Table 15. Gene expression data of isolated RNA for each individual sample is normalized by HK (housekeeping) normalization. For each tumor sample, raw counts are log 10 transformed and then each gene normalized by subtracting off the arithmetic mean of all housekeeping genes (Table 15). Gene Expression Profiling (GEP) Signature scores are calculated as a weighted sum of the housekeeping normalized values of the 18 gene Up-Down Signature (Table 15). The house keeping normalized value for each gene is multiplied by the coefficient for that gene from the set of scoring weights to generate a weighted RNA value for each of the genes in the 18 gene signature, and adding the weighted RNA values to produce the signature score for the tumor sample.

As used herein, the term "heterologous" to refers an entity not found in nature to be associated with (e.g., encoded by and/or expressed by the genome of) a naturally occurring NDV.

As used herein, the term "elderly human" refers to a human 65 years or older.

As used herein, the term "human adult" refers to a human that is 18 years or older.

As used herein, the term "human child" refers to a human that is 1 year to 18 years old.

As used herein, the term "human toddler" refers to a human that is 1 year to 3 years old.

As used herein, the term "human infant" refers to a newborn to 1-year-old year human.

In certain embodiments, the term "highly fusogenic" and the like, as used herein, refers to an increase in the ability of the NDV to form syncytia involving a large number of cells. In a specific embodiment, cells infected with an NDV described herein that is engineered to express a mutated F protein have an increased ability to form syncytia relative to cells infected with the parental virus from which the virus is derived, which parental virus has an unmutated F protein. In another specific embodiment, about 10% to about 25%, about 25% to about 50%, about 25% to about 75%, about 50% to about 75%, about 50% to about 95%, or about 75% to about 99% or about 10%, 15%, 20%, 25%, 30%, 35%, 40%, 45%, 50%, 55%, 60%, 65%, 70%, 75%, 80%, 85%, 90%, 95%, or 99% more cells infected with an NDV described herein that is engineered to express a mutated F protein form syncytia relative to the number of cells forming syncytia that are infected with the parental virus from the chimeric virus is derived which has an unmutated F protein. In certain embodiments, the syncytia are quantitated microscopically by counting the number of nuclei per syncytium after a certain period of time (e.g., about 8 hours to about 12 hours, about 12 hours to about 24 hours, about 24 hours to about 36 hours, or about 36 hours to about 48 hours).

As used herein, the term "interferon antagonist" refers to an agent that reduces or inhibits the cellular interferon immune response. In one embodiment, an interferon antagonist is a proteinaceous agent that reduces or inhibits the cellular interferon immune response. In a specific embodiment, an interferon antagonist is a viral protein or polypeptide that reduces or inhibits the cellular interferon response.

In a specific embodiment, an interferon antagonist is an agent that reduces or inhibits interferon expression and/or activity. In one embodiment, the interferon antagonist reduces or inhibits the expression and/or activity of type I IFN. In another embodiment, the interferon antagonist reduces or inhibits the expression and/or activity of type II IFN. In another embodiment, the interferon antagonist reduces or inhibits the expression and/or activity of type III IFN. In a specific embodiment, the interferon antagonist reduces or inhibits the expression and/or activity of either IFN-α, IFN-β or both. In another specific embodiment, the interferon antagonist reduces or inhibits the expression and/or activity of IFN-γ. In another embodiment, the interferon antagonist reduces or inhibits the expression and/or activity of one, two or all of IFN-α, IFN-β, and IFN-γ.

In certain embodiments, the expression and/or activity of IFN-α, IFN-β and/or IFN-γ in an embryonated egg or cell is reduced approximately 1 to approximately 100 fold, approximately 5 to approximately 80 fold, approximately 20 to approximately 80 fold, approximately 1 to approximately 10 fold, approximately 1 to approximately 5 fold, approximately 40 to approximately 80 fold, or 1, 2, 3, 4, 5, 7, 10, 15, 20, 25, 30, 35, 40, 45, 50, 55, 60, 65, 70, 75, 80, 85, 90, 95 or 100 fold by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art. In other embodiments, the expression and/or activity of IFN-α, IFN-β and/or IFN-γ in an embryonated egg or cell is reduced by at least 20% to 25%, at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80% to 85%, at least 85% to 90%, at least 90% to 95%, at least 95% to 99% or by 20%, 25%, 30%, 35%, 40%, 45%, 50%, 55%, 60%, 65%, 70%, 75%, 80%, 85%, 90%, 95%, or 99% by an interferon antagonist relative to the expression and/or activity of IFN-α, IFN-β, and/or IFN-γ in a control embryonated egg or a cell not expressing or not contacted with such an interferon antagonist as measured by the techniques described herein or known to one skilled in the art.

As used herein, the phrases "IFN deficient systems" or "IFN-deficient substrates" refer to systems, e.g., cells, cell lines and animals, such as mice, chickens, turkeys, rabbits, rats, horses etc., which do not produce one, two or more types of IFN, or do not produce any type of IFN, or produce low levels of one, two or more types of IFN, or produce low levels of any IFN (i.e., a reduction in any IFN expression of 5-10%, 10-20%, 20-30%, 30-40%, 40-50%, 50-60%, 60-70%, 70-80%, 80-90% or more when compared to IFN-competent systems under the same conditions), do not respond or respond less efficiently to one, two or more types of IFN, or do not respond to any type of IFN, have a delayed response to one, two or more types of IFN, and/or are deficient in the activity of antiviral genes induced by one, two or more types of IFN, or induced by any type of IFN.

"Interleukin-12" and "IL-12" refer to any IL-12 known to those of skill in the art. In certain embodiments, the IL-12 may be human, dog, cat, horse, pig, or cow IL-12. In a specific embodiment, the IL-12 is human IL-12. A typical IL-12 consists of a heterodimer encoded by two separate genes, IL-12A (the p35 subunit) and IL-12B (the p40 subunit), known to those of skill in the art. GenBank™ accession number NM_000882.3 (GI number 325974478) provides an exemplary human IL-12A nucleic acid sequence. GenBank™ accession number NM_002187.2 (GI number 24497437) provides an exemplary human IL-12B nucleic acid sequence. GenBank™ accession number NP_000873.2 (GI number 24430219) provides an exemplary human IL-12A (the p35 subunit) amino acid sequence. GenBank™ accession number NP_002178.2 (GI number 24497438) provides an exemplary human IL-12B (the p40 subunit) amino acid sequence. In certain embodiments, an IL-12 consists of a single polypeptide chain, comprising the p35 subunit and the p40 subunit, optionally separated by a linker sequence (such as, e.g., any one of SEQ ID NOs: 24 and 46-49). In a preferred embodiment, an IL-12 comprises the p35 and p40 subunit sequences provided in Section 6, e.g., SEQ ID NOs: 25 and 23, respectively, or SEQ ID NOs: 41 and 40, respectively. In certain embodiments, an IL-12 consists of more than one polypeptide chain in quaternary association, e.g., p35 and p40. As used herein, the terms "interleukin-12" and "IL-12" encompass interleukin-12 polypeptides that are modified by post-translational processing such as signal peptide cleavage, disulfide bond formation, glycosylation (e.g., N-linked glycosylation), protease cleavage and lipid modification (e.g., S-palmitoylation). In some embodiments, one or both of the subunits of IL-12 or IL-12 consisting of a single polypeptide chain includes a signal sequence. In other embodiments, one or both of the subunits of IL-12 or IL-12 consisting of a single polypeptide chain does not include a signal sequence. The signal sequence can be the naturally occurring signal peptide sequence or a variant thereof. In some embodiments, the signal peptide is an IL-12 signal peptide. In some embodiments, the signal peptide is heterologous to an IL-12 signal peptide.

As used herein, the terms "immunospecifically binds," "immunospecifically recognizes," "specifically binds," and "specifically recognizes" are analogous terms in the context of antibodies and refer to molecules that specifically bind to an antigen (e.g., epitope or immune complex) as understood by one skilled in the art. A molecule that specifically binds to an antigen may bind to other peptides or polypeptides with lower affinity as determined by, e.g., immunoassays (e.g., ELISA), surface plasmon resonance (e.g., BIAcore®), a KinEx assay (using, e.g., a KinExA 3000 instrument (Sapidyne Instruments, Boise, ID)), or other assays known in the art. In a specific embodiment, molecules that specifically bind to an antigen bind to the antigen with a dissociation constant (i.e., Ka) that is at least 2 logs, 2.5 logs, 3 logs, 3.5 logs, 4 logs or greater than the Ka when the molecules bind to another antigen.

As used herein, the term "monoclonal antibody" is a term of the art and generally refers to an antibody obtained from a population of homogenous or substantially homogeneous antibodies, and each monoclonal antibody will typically recognize a single epitope (e.g., single conformation epitope) on the antigen.

As used herein, the phrase "multiplicity of infection" or "MOI" is the average number of virus per infected cell. The MOI is determined by dividing the number of virus added (ml added×Pfu) by the number of cells added (ml added×cells/ml).

As used herein, the term "native ligand" refers to any naturally occurring ligand that binds to a naturally occurring receptor. In a specific embodiment, the ligand is a mammalian ligand. In another specific embodiment, the ligand is a human ligand.

As used herein, the term "native polypeptide(s)" in the context of proteins or polypeptides refers to any naturally occurring amino acid sequence, including immature or precursor and mature forms of a protein. In a specific embodiment, the native polypeptide is a human protein or polypeptide.

As used herein, the term "native receptor" refers to any naturally occurring receptor that binds to a naturally occurring ligand. In a specific embodiment, the receptor is a mammalian receptor. In another specific embodiment, the receptor is a human receptor.

"Programmed cell death protein 1", "PD1", and "PD-1" refer to any PD-1 known to those of skill in the art. In certain embodiments, the PD-1 may be human, dog, cat, horse, pig, or cow PD-1. In a specific embodiment, the PD-1 is human PD-1. GenBank™ accession number NM_005018.2 (GI number 167857791) provides an exemplary human PD-1 nucleic acid sequence. GenBank™ accession number NP_005009.2 (GI number 167857792) provides an exemplary human PD-1 amino acid sequence. Ligands of PD-1 include programmed death-ligand 1 (also referred to as "PD-L1", "PDL1", "cluster of differentiation 274", "CD274", "B7 homolog 1", and "B7-H1") and programmed cell death 1 ligand 2 (also referred to as "PDL2", "PD-L2", and "B7-DC"). PD-L1 refers to any PD-L1 known to those of skill in the art. In certain embodiments, the PD-L1 may be human, dog, cat, horse, pig, or cow PD-L1. In a specific embodiment, the PD-L1 is human PD-L1. GenBank™ accession numbers NM_001314029.1, NM_001267706.1, and NM_014143.3 (GI numbers 930425328, 390979638, and 292658763, respectively) provide exemplary human PD-L1 nucleic acid sequences. GenBank™ accession numbers NP_001300958.1, NP_001254635.1, and NP_054862.1 (GI numbers 930425329, 390979639, and 7661534, respectively) provide exemplary human PD-L1 amino acid sequences. PD-L2 refers to any PD-L2 known to those of skill in the art. In certain embodiments, the PD-L2 may be human, dog, cat, horse, pig, or cow PD-L2. In a specific embodiment, the PD-L2 is human PD-L2. GenBank™ accession number NM_025239.3 (GI number 190014604) provides an exemplary human PD-L2 nucleic acid sequence. GenBank™ accession number NP_079515.2 (GI number 190014605) provides an exemplary human PD-L2 amino acid sequence. As used herein, PD-1, PD-L1, and PD-L2 encompass PD-1, PD-L1 and PD-L2 polypeptides, respectively, that are modified by post-translational processing such as signal peptide cleavage, disulfide bond formation, glycosylation (e.g., N-linked glycosylation), protease cleavage and lipid modification (e.g., S-palmitoylation). In some embodiments, PD-1, PD-L1 and PD-L2 includes PD-1, PD-L1 and PD-L2 polypeptides, respectively, with a signal sequence. In other embodiments, PD-1, PD-L1 and PD-L2 includes PD-1, PD-L1 and PD-L2 polypeptides, respectively, that do not include a signal sequence. See, e.g., Ishida et al., 1992, EMBO J. 11: 3887-3895 and Shinohara et al., 1994, Genomics 23: 704-706 (each which is incorporated herein by reference in its entirety) for information regarding the structure of PD-1, including information regarding the signal sequence for PD-1. When used in the context of an antibody of PD-1 or ligand thereof, the antibody is directed to the mature form of PD-1, PD-L1 or PD-L2.

"Refractory" is an art recognized term which typically means a cancer that does not respond to treatment, i.e., does not receive a beneficial effect as described under "treatment". The cancer may be resistant at the beginning of treatment or it may become resistant during treatment.

"Relapsed" is an art-recognized term, which typically means the return of a disease or the signs and symptoms of a disease after a period of improvement through treatment as described below.

As used herein, the terms "subject" or "patient" are used interchangeably. As used herein, the terms "subject" and "subjects" refers to an animal. In some embodiments, the subject is a mammal including a non-primate (e.g., a camel, donkey, zebra, cow, horse, horse, cat, dog, rat, and mouse) and a primate (e.g., a monkey, chimpanzee, and a human). In some embodiments, the subject is a non-human mammal. In certain embodiments, the subject is a pet (e.g., dog or cat) or farm animal (e.g., a horse, pig or cow). In other embodiments, the subject is a human. In certain embodiments, the mammal (e.g., human) is 0 to 6 months old, 6 to 12 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, the subject is an animal that is not avian.

As used herein, the terms "treat", "treatment" and "treating" in the context of the administration of a therapy refers to a treatment/therapy from which a subject may receive a beneficial effect, such as the reduction, decrease, attenuation, diminishment, stabilization, remission, suppression, inhibition or arrest of the development or progression of cancer, or a symptom thereof. In certain embodiments, the treatment/therapy that a subject receives results in at least one or more of the following effects: (i) the reduction or amelioration of the severity of cancer and/or a symptom associated therewith; (ii) the reduction in the duration of a symptom associated with cancer; (iii) the prevention in the recurrence of a symptom associated with cancer; (iv) the regression of cancer and/or a symptom associated therewith; (v) the reduction in hospitalization of a subject; (vi) the reduction in hospitalization length; (vii) the increase in the survival of a subject; (viii) the inhibition of the progression of cancer and/or a symptom associated therewith; (ix) the enhancement or improvement of the therapeutic effect of another therapy; (x) a reduction or elimination in the cancer cell population; (xi) a reduction in the growth of a tumor or neoplasm; (xii) a decrease in tumor size; (xiii) a reduction in the formation of a tumor; (xiv) eradication, removal, or control of primary, regional and/or metastatic cancer; (xv) a decrease in the number or size of metastases; (xvi) a reduction in mortality; (xvii) an increase in cancer-free survival rate of patients; (xviii) an increase in relapse-free survival; (xix) an increase in the number of patients in remission; (xx) a decrease in hospitalization rate; (xxi) the size of the tumor is maintained and does not increase in size or increases the size of the tumor by less than 5% or 10% after administration of a therapy as measured by conventional methods available to one of skill in the art, such as MRI, X-ray, CT Scan and PET scan; (xxii) the prevention of the development or onset of cancer and/or a symptom associated therewith; (xxiii) an increase in the length of remission in patients; (xxiv) the reduction in the number of symptoms associated with cancer; (xxv) an increase in symptom-free survival of cancer patients; (xxvi) limitation of or reduction in metastasis; (xxvii) overall survival; (xxviii) progression-free survival (as assessed, e.g., by RECIST v1.1.); (xxix) overall response rate; and/or (xxx) an increase in response duration. In some embodiments, the treatment/therapy that a subject receives does not cure cancer, but prevents the progression or worsening of the disease. In certain embodiments, the treatment/therapy that a subject receives does not prevent the onset/development of cancer, but may prevent the onset of cancer symptoms. Any method known to the skilled artisan may be utilized to evaluate the treatment/therapy that a subject receives. In a specific embodiment, the treatment/therapy is evaluated according to the Response Evaluation Criteria In Solid Tumors ("RECIST") published rules. In a specific embodiment, the treatment/therapy is evaluated according to the RECIST rules published in February 2000 (also referred to as "RECIST 1") (see, e.g., Therasse et al., 2000, Journal of National Cancer Institute, 92(3):205-216, which is incorporated by reference herein in its entirety). In a specific embodiment, the treatment/therapy is evaluated according to the RECIST rules published in January 2009 (also referred to as "RECIST 1.1") (see, e.g., Eisenhauer et al., 2009, European Journal of Cancer, 45:228-247, which is incorporated by reference herein in its entirety). In a specific embodiment, the treatment/therapy is evaluated according to the RECIST rules utilized by the skilled artisan at the time of the evaluation. In a specific embodiment, the treatment/therapy is evaluated according to the immune related RECIST ("irRECIST") published rules (see, e.g., Bohnsack et al., 2014, ESMO Abstract 4958, which is incorporated by reference herein in its entirety). In a specific embodiment, the treatment/therapy is evaluated according to the irRECIST rules utilized by the skilled artisan at the time of the evaluation. In a specific embodiment, the treatment/therapy is evaluated according to the Lugano criteria. In a specific embodiment, the treatment/therapy is evaluated through a reduction in tumor-associated serum markers, such as, e.g., CA-125, CEA, CA-19-9, PSA, AFP, inhibin A, inhibin B, HCG, CA 15-3, thyroglobulin, HE4.

As used herein, the term "in combination" in the context of the administration of (a) therapy(ies) to a subject, refers to the use of more than one therapy. The use of the term "in combination" does not restrict the order in which therapies are administered to a subject. A first therapy can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject. For example, a chimeric NDV described herein may be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of an antagonist of PD-1 or a ligand thereof.

As used herein, the terms "therapies" and "therapy" can refer to any protocol(s), method(s), and/or agent(s) that can be used in the treatment of cancer. In certain embodiments, the terms "therapies" and "therapy" refer to biological therapy, supportive therapy, hormonal therapy, chemotherapy, immunotherapy and/or other therapies useful in the treatment of cancer. In a specific embodiment, a therapy includes adjuvant therapy. For example, using a therapy in conjunction with a drug therapy, biological therapy, surgery, and/or supportive therapy. In certain embodiments, the term "therapy" refers to a chimeric NDV described herein. In other embodiments, the term "therapy" refers to an agent that is not a chimeric NDV. In certain embodiments, the term "therapy" refers to an antagonist of PD-1 or a ligand thereof. In other embodiments, the term "therapy" refers to an agent that is not an antagonist of PD-1 or a ligand thereof. In certain embodiments, the term "therapy" refers to a chimeric NDV described herein and an antagonist of PD-1 or a ligand thereof. In certain embodiments, the term "therapy" refers to an agent that is neither a chimeric NDV described herein nor an antagonist of PD-1 or a ligand thereof.

4. BRIEF DESCRIPTION OF THE FIGURES

FIG. 1. NDV infection upregulates the expression of MHC I, MHC II, and ICAM-1 on the surface of in vitro infected B16F10 cells (24 hours post-infection).

Figures 2A, 2B, 2C:
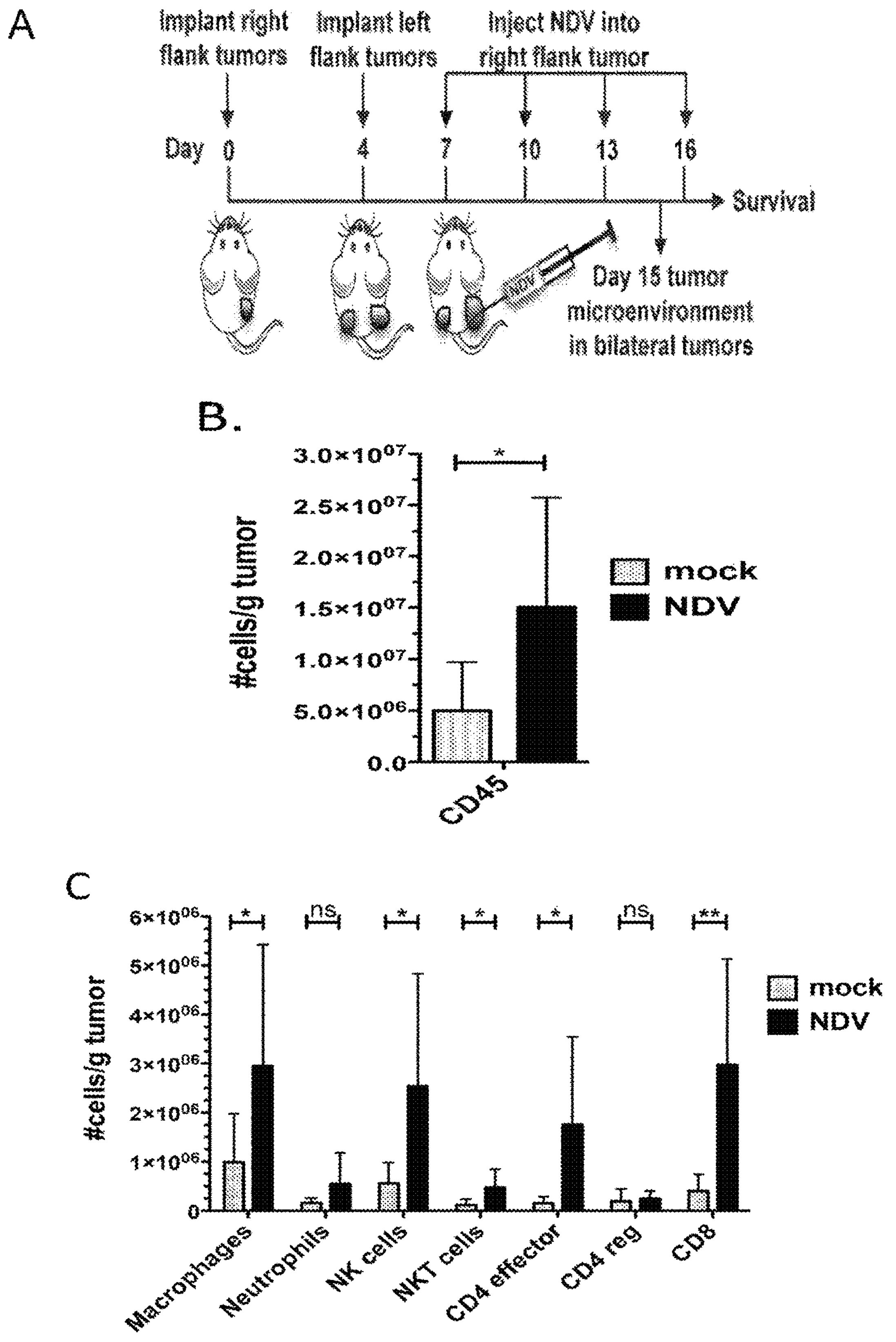
Figures 2D, 2E:
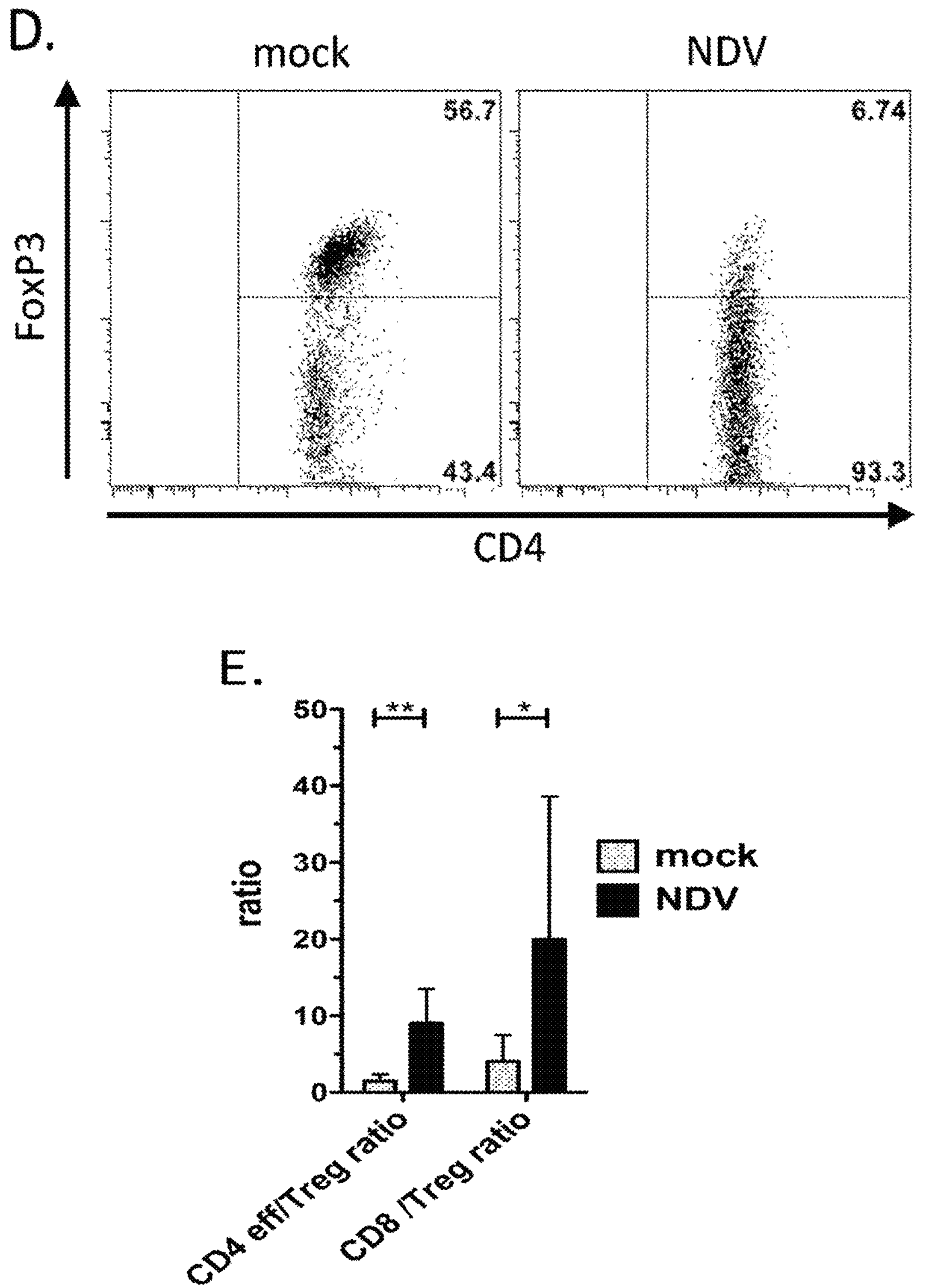

FIGS. 2A-2E. Intratumoral NDV treatment leads to infiltration with macrophages, NK cells, CD8 and CD4 effector cells and decreases the frequency of Tregs. FIG. 2A) Overall study scheme. FIG. 2B) Total CD45+ infiltrates. FIG. 2C) Total immune cell infiltrates. FIG. 2D) Representative flow cytometry dot plots of relative CD4 FoxP3+ and FoxP3− subsets. FIG. 2E) Teff/Treg and CD8/Treg ratios.

Figures 3A, 3B:
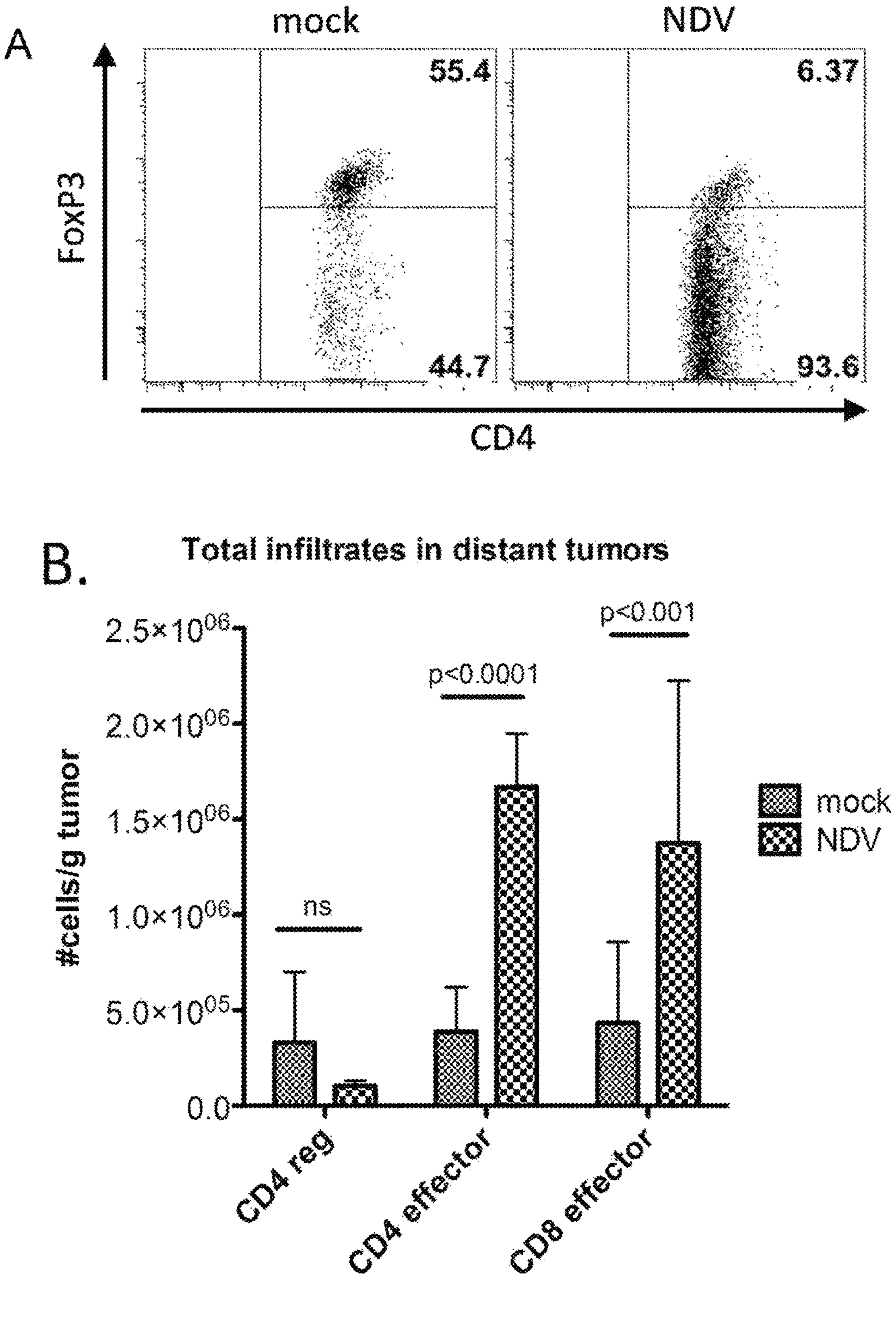
Figure 3C:
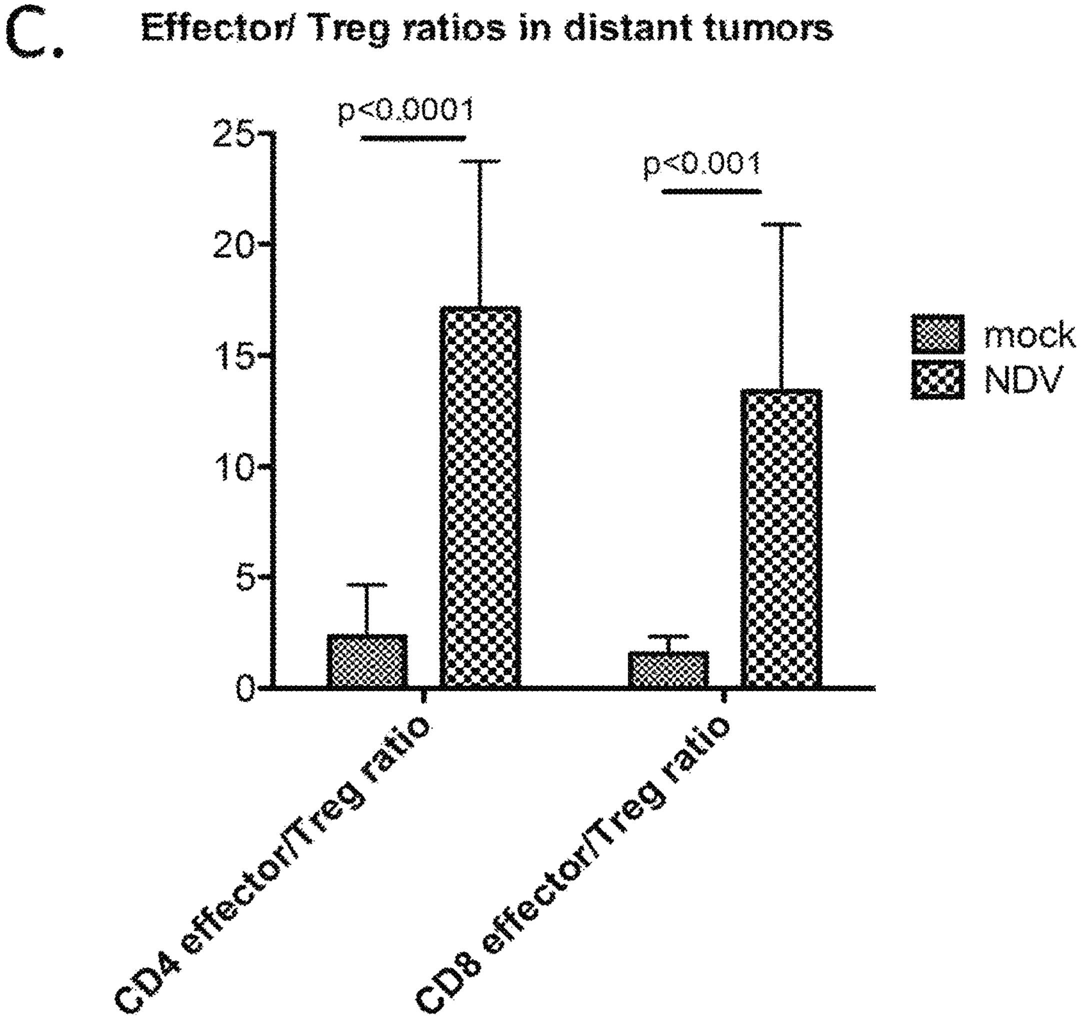

FIGS. 3A-3C. Therapy with NDV exhibits favorable effects on tumor microenvironment of distant tumors. FIG. 3A) Representative flow cytometry dot plots of relative CD4 FoxP3+ and FoxP3− subsets. FIG. 3B) Absolute numbers of CD4 effector, Treg, and CD8 cells per gram of tumor. FIG. 3C) Teff/Treg and CD8/Treg ratios.

Figure 4A:
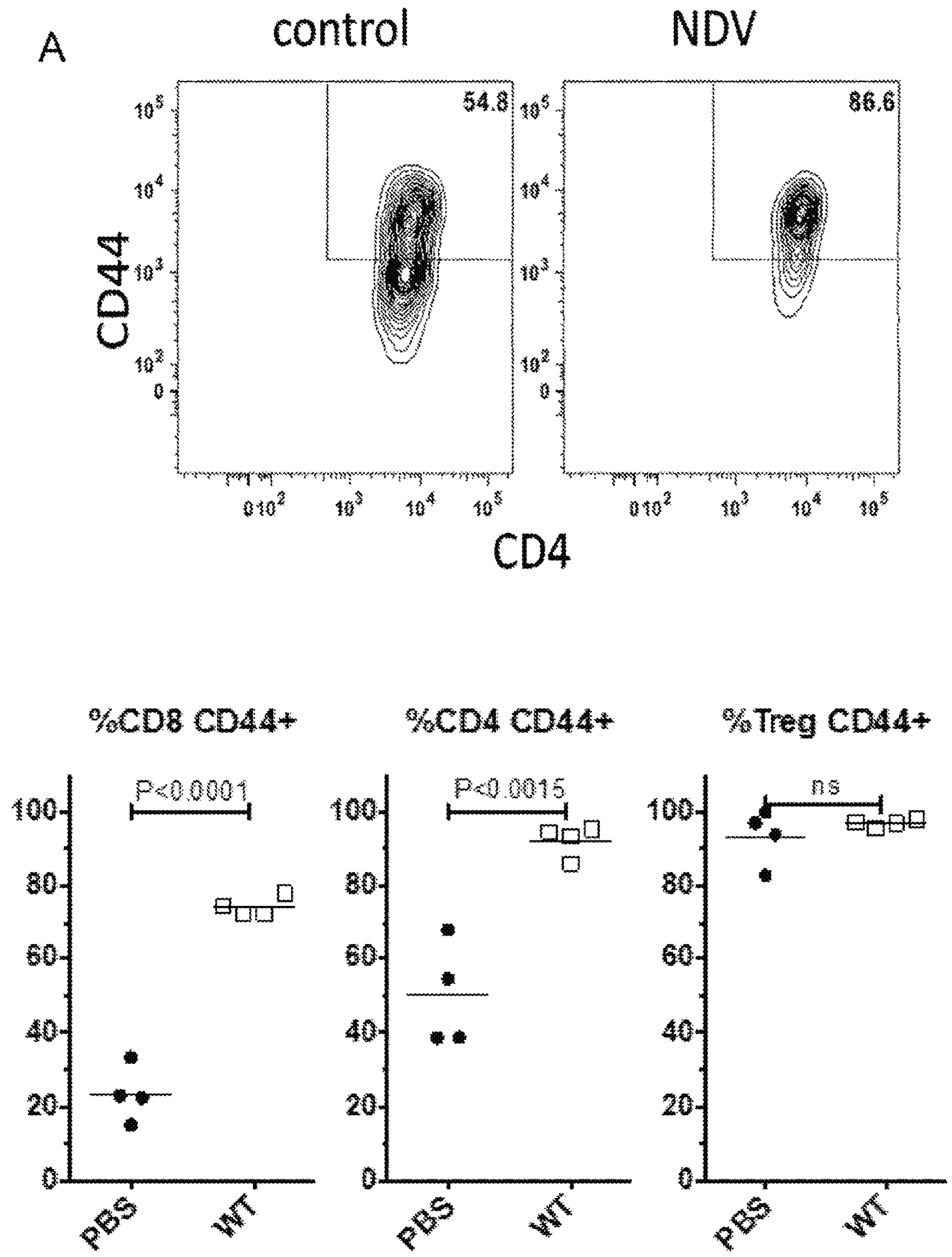
Figure 4B:
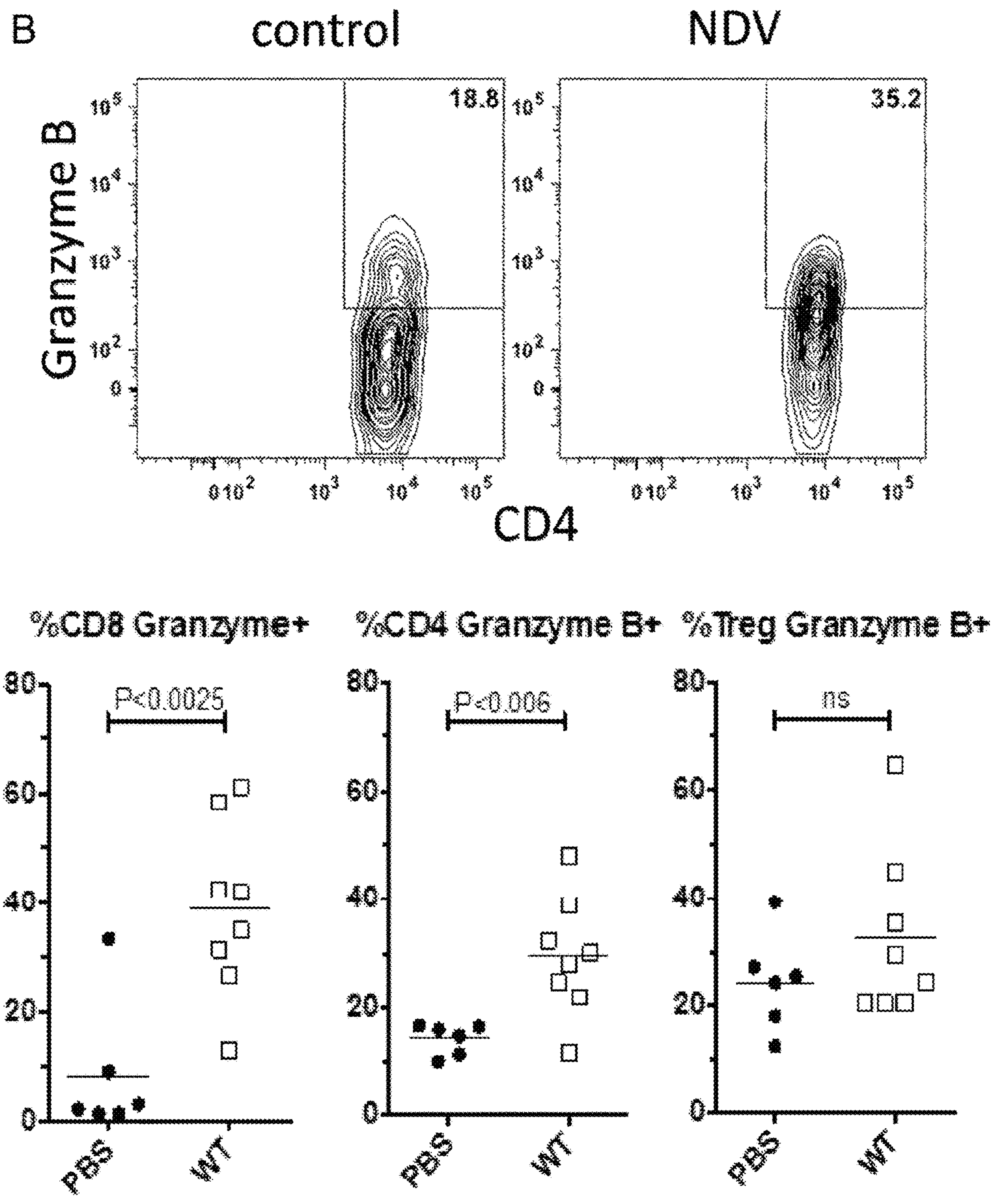
Figure 4C:
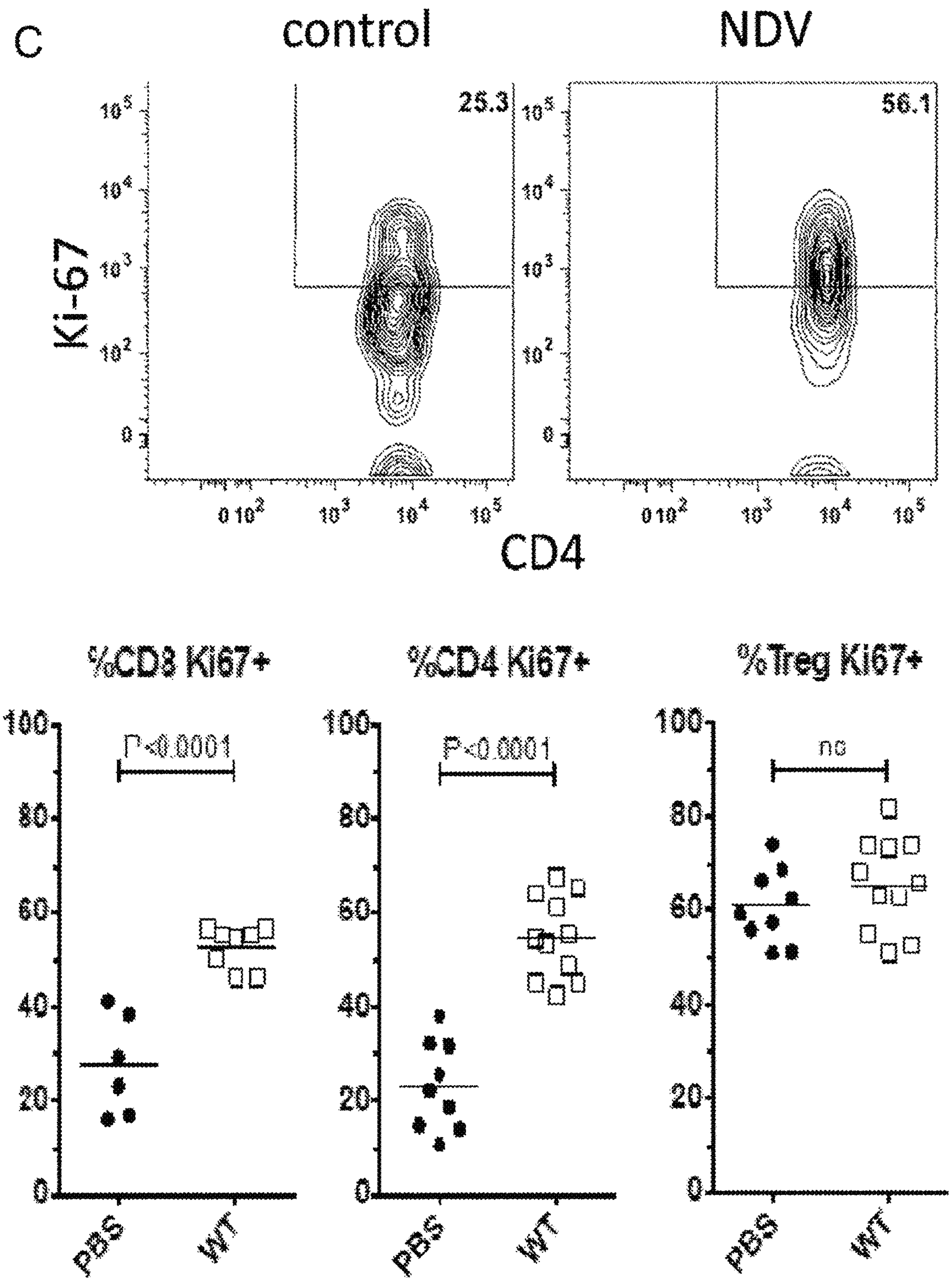

FIGS. 4A-4C. Lymphocytes infiltrating distant tumors upregulate activation, lytic, and proliferation markers. Representative expression plots on CD4 effector cells (top) and the corresponding percentages in the CD4 effector, CD8, Tregs (bottom) are shown for FIG. 4A) CD44, FIG. 4B) Granzyme B, and FIG. 4C) Ki-67.

Figures 5A, 5B:
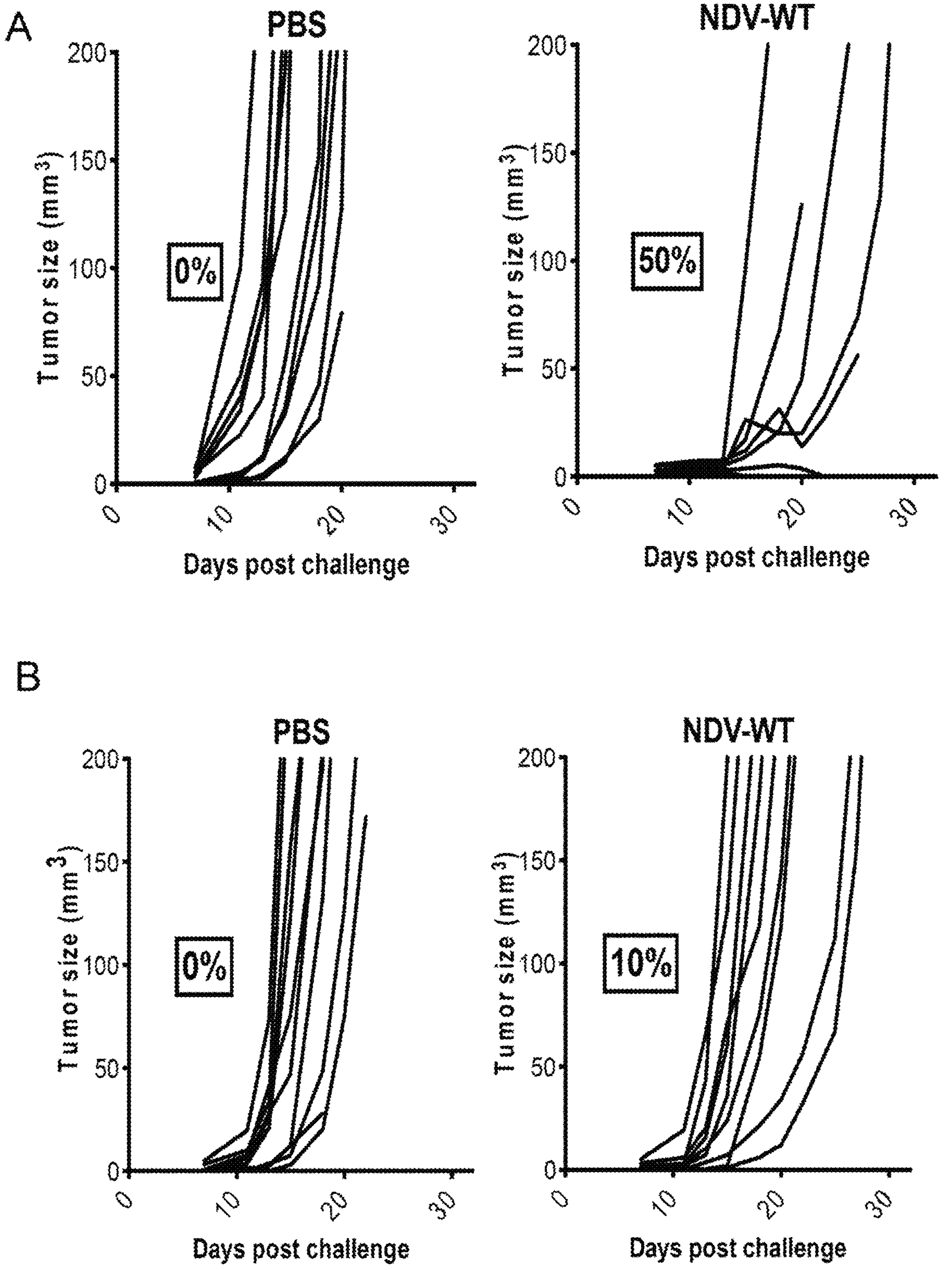
Figure 5C:
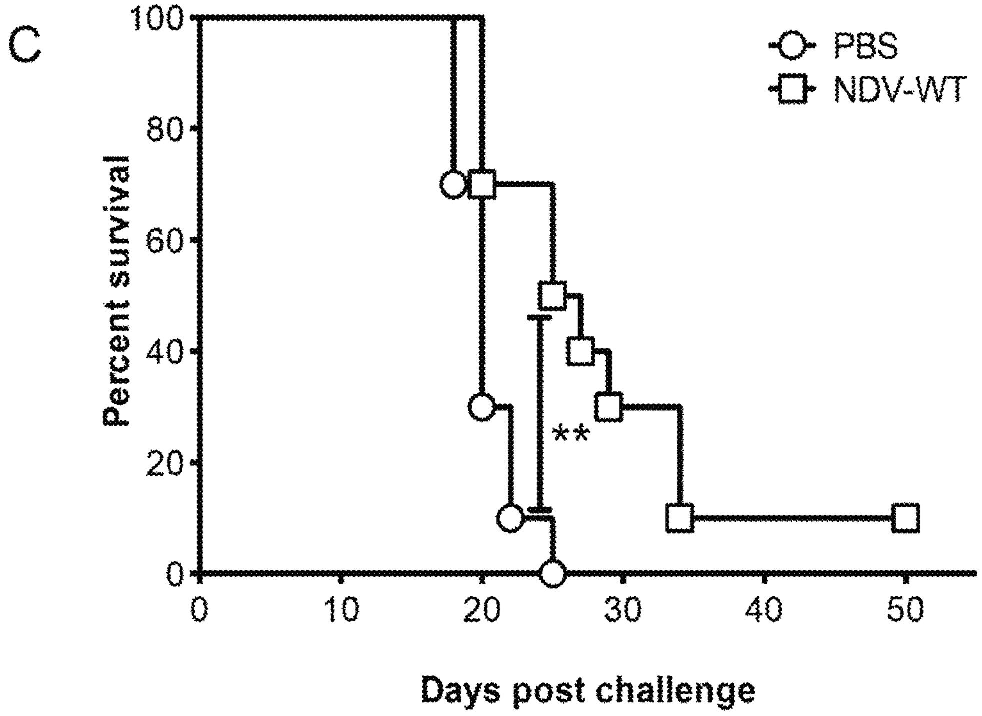
Figure 5D:
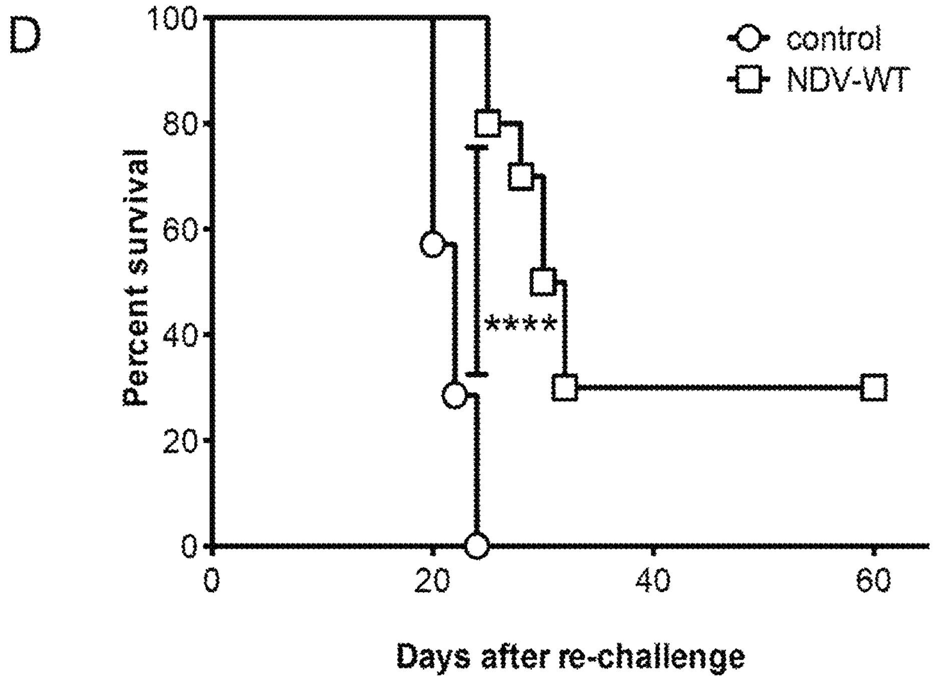

FIGS. 5A-D. NDV Monotherapy delays the growth of distant tumors and provides some protection against tumor rechallenge. Bilateral flank tumors were established as described in FIG. 2A and the animals were treated and followed for survival. FIG. 5A) Growth of right flank (treated) tumors. FIG. 5B) Growth of left flank (non-treated) tumors. FIG. 5C) Overall survival. Numbers in boxes indicate percent of animals free of tumors. FIG. 5D) Survival in animals cured of B16F10 melanoma by NDV re-challenged on day 75 with B16F10 melanoma cells. Representative results of two different experiments with 10 mice per group.

Figure 5E:
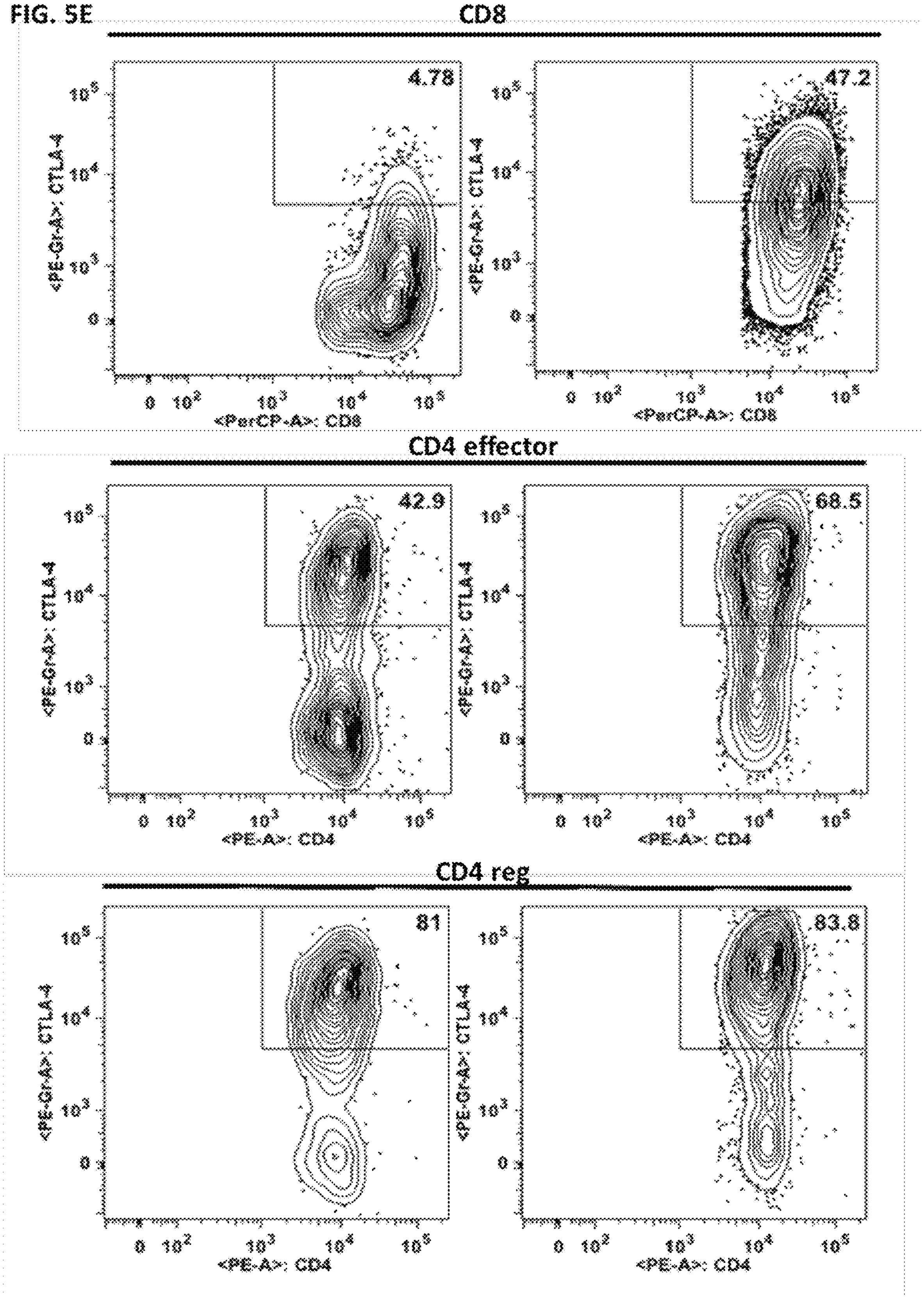
Figure 5F:
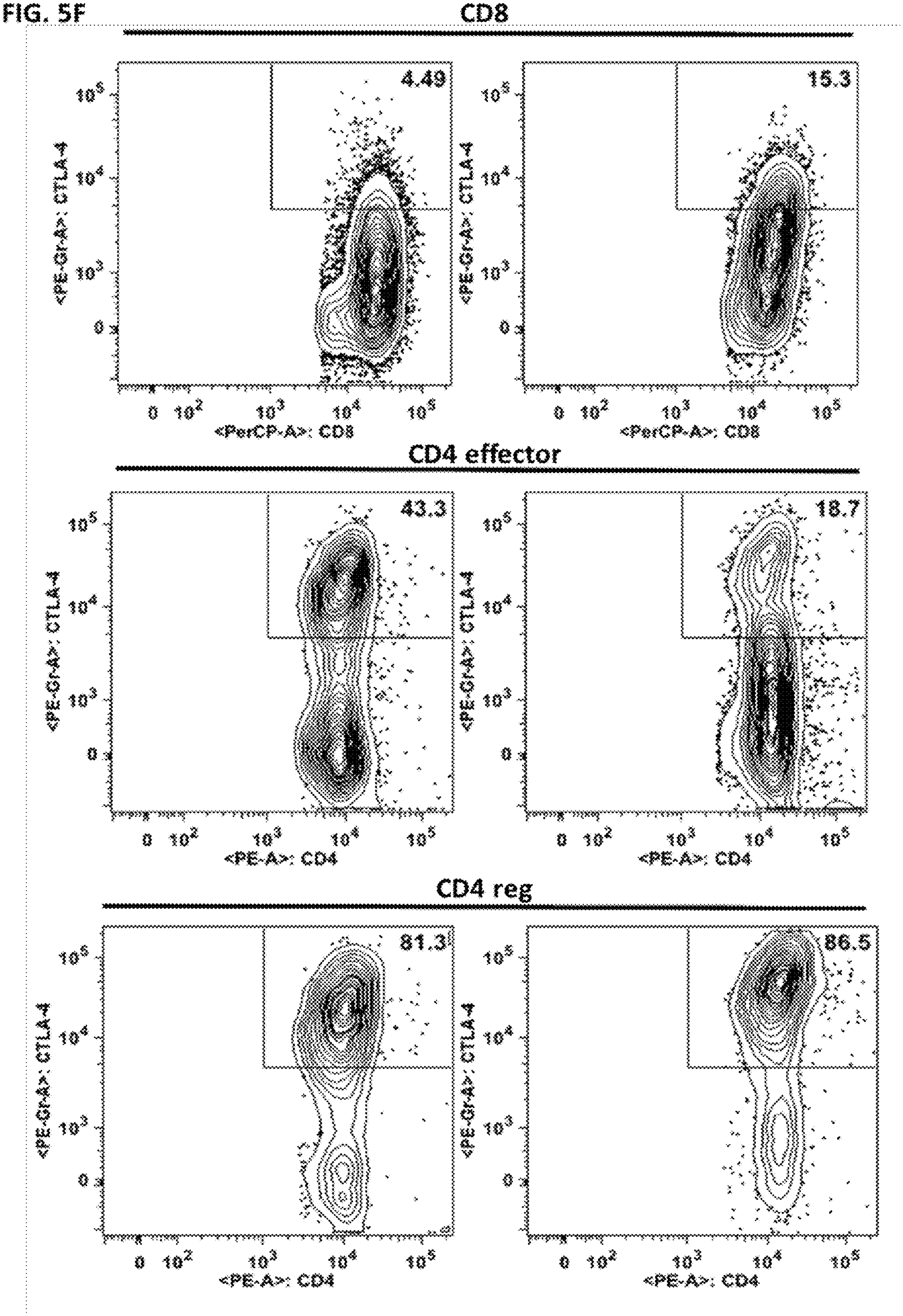

FIGS. 5E-5F. Tumor-infiltrating lymphocytes from both treated and non-treated tumors upregulate CTLA-4 in response to NDV therapy. FIG. 5E) Representative dot plots of CTLA-4 expression in CD8, CD4 effector, and Tregs in right (treated) tumors. FIG. 5F) Representative dot plots of CTLA-4 expression in CD8, CD4 effector, and Tregs in left (non-treated) tumors.

Figures 6A, 6B:
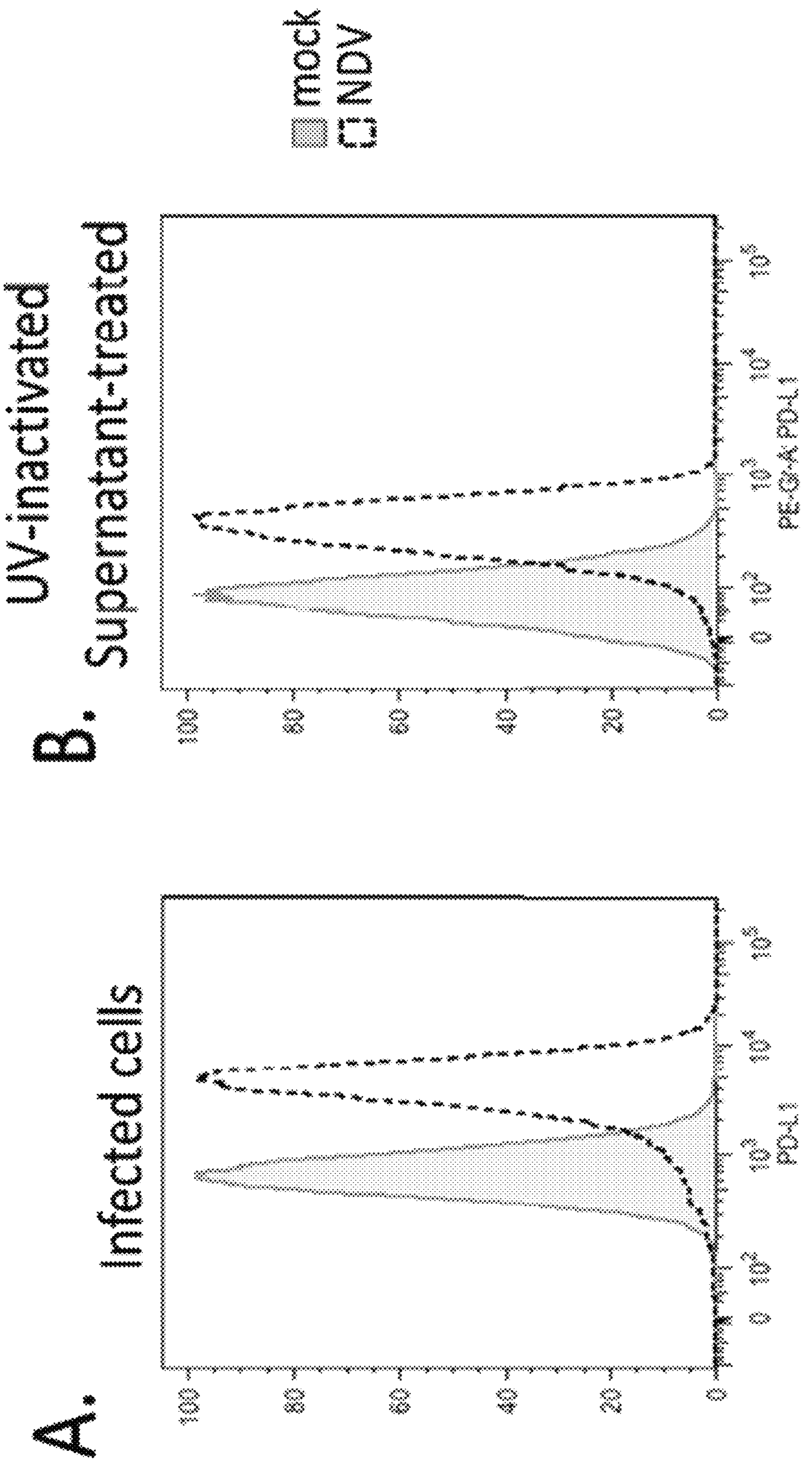
Figure 6C:
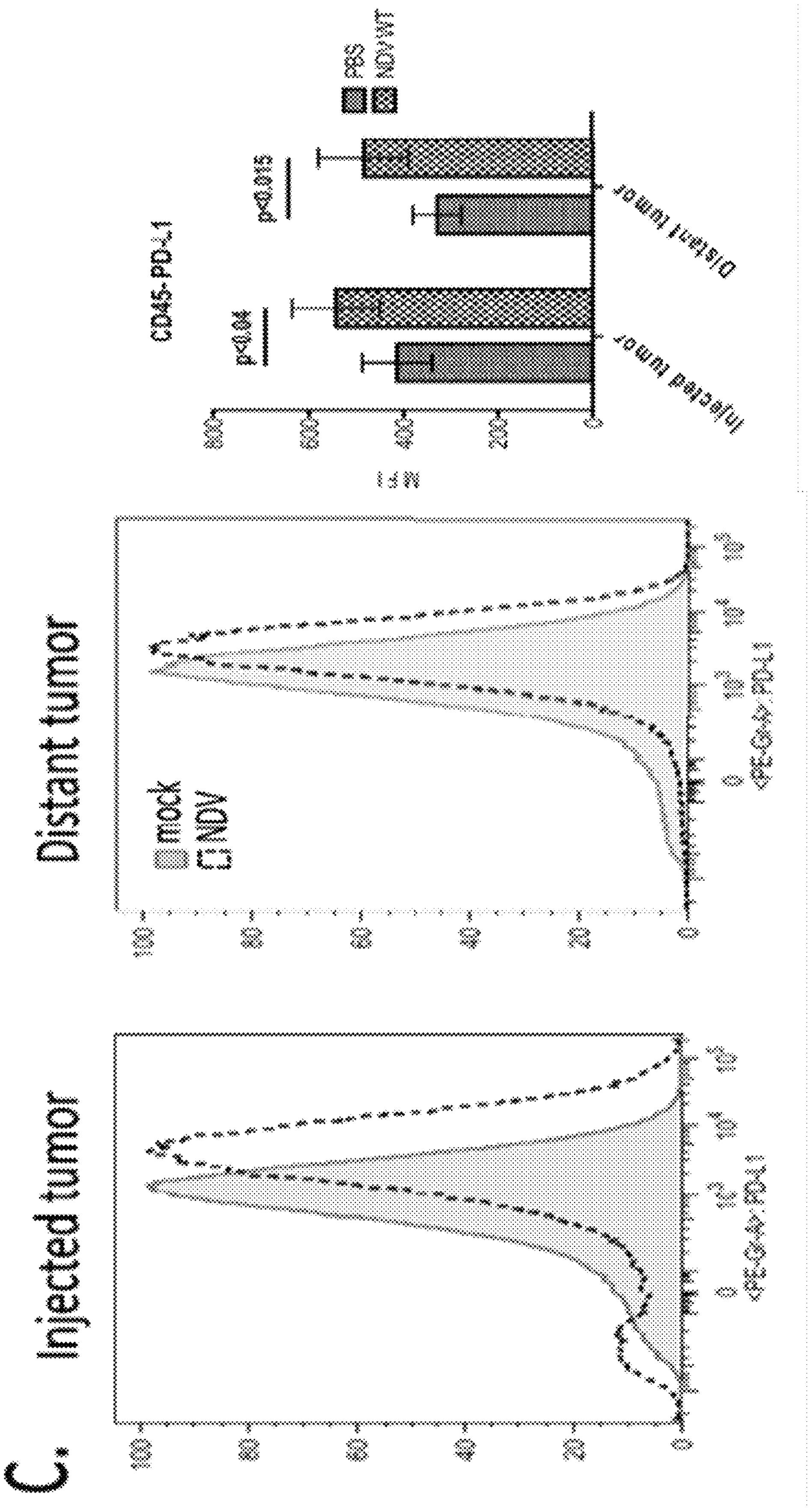

FIGS. 6A-6C. NDV infection upregulates expression of PD-L1 in B16F10 tumors. FIG. 6A) Surface PD-L1 expression on B16F10 cells infected with NDV for 24 hours. FIG. 6B) Surface PD-L1 expression on B16F10 cells treated with UV-inactivated supernatant from infected B16F10 cells. FIG. 6C) Upregulation of PD-L1 on the surface of tumor cells isolated from injected and distant tumors from the animals treated as in FIG. 2A (2 left panels—representative flow cytometry plots, right panel—calculated averages of 5 mice per group).

Figures 7A, 7B, 7C:
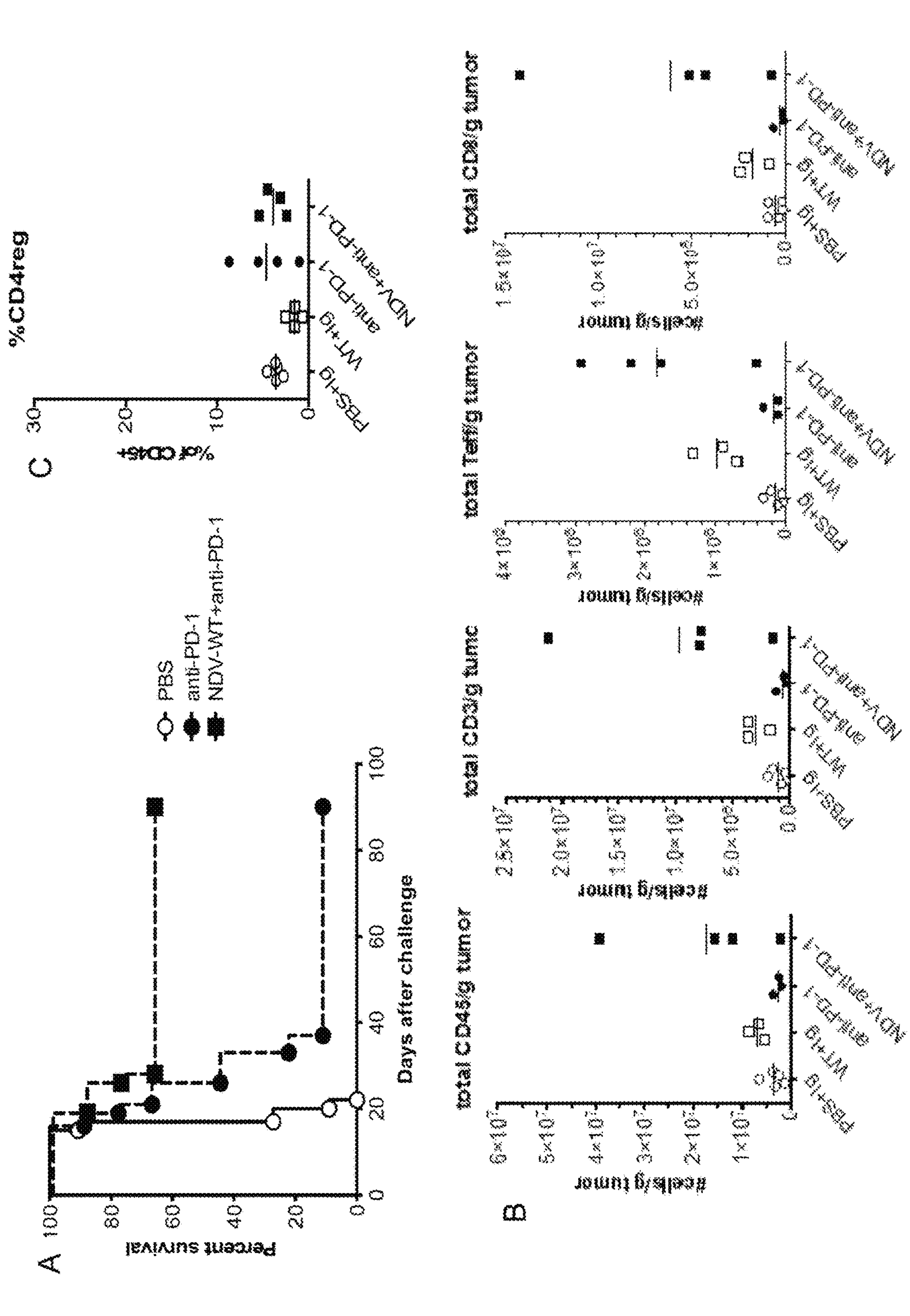
Figures 7D, 7E, 7F:
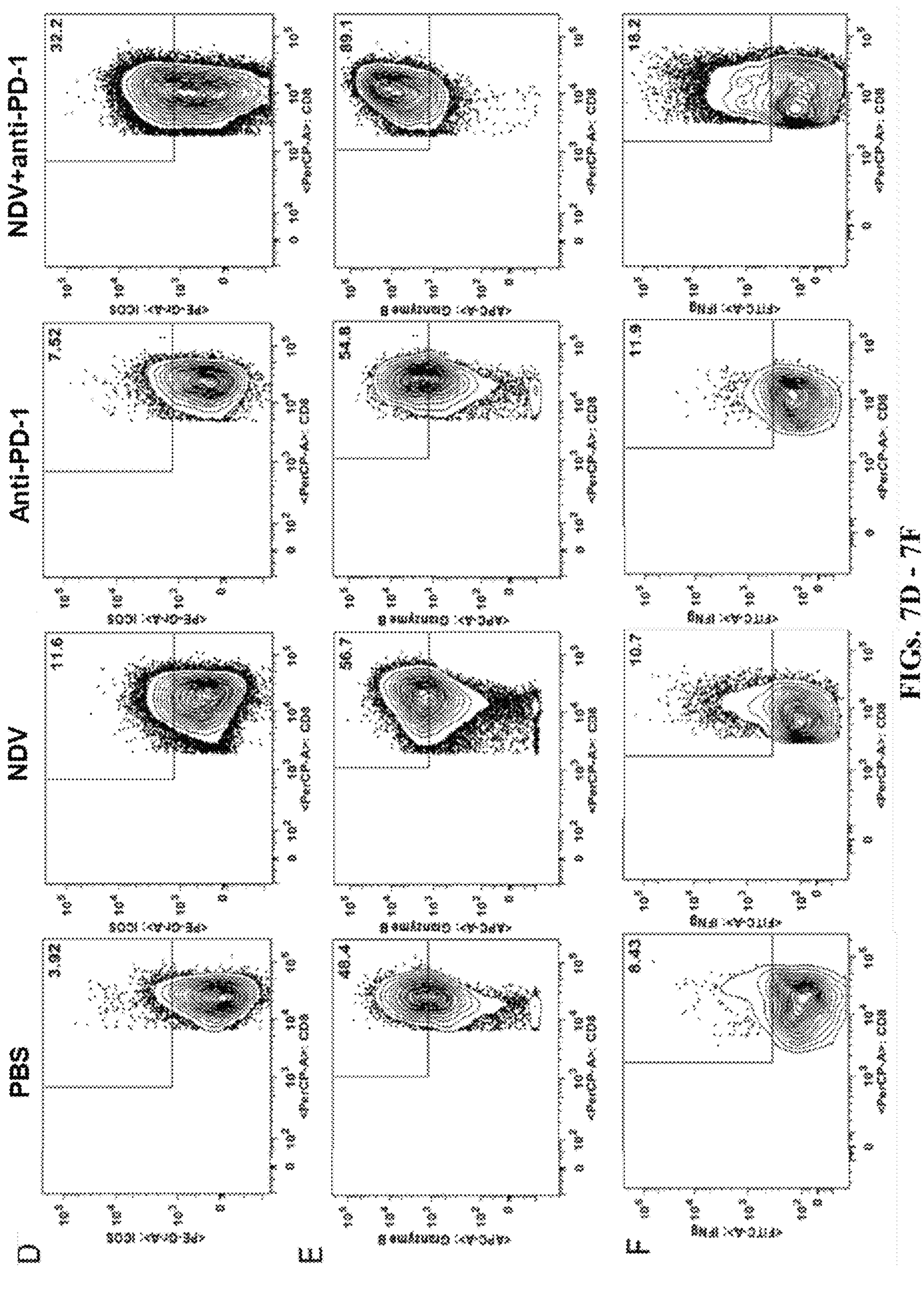

FIGS. 7A-7F. Combination therapy with NDV and anti-PD-1 is effective systemically against B16 melanoma and results in increased T cell infiltration with upregulation of activation markers. FIG. 7A) Overall survival. Animals were treated as described in FIG. 2A with or without anti-PD-1 antibody. FIG. 7B) Absolute numbers of CD45, CD3, CD8, and CD4 effector cells in tumors. FIG. 7C) Relative percentage of regulatory T cells in tumor-infiltrating lymphocytes. FIG. 7D and FIG. 7E) Tumor-infiltrating lymphocytes from distant tumors were isolated and stained for expression of ICOS (FIG. 7D) and Granzyme B (FIG. 7E). FIG. 7F) Tumor infiltrating lymphocytes were re-stimulated with dendritic cells loaded with tumor lysates and assessed for expression of IFN gamma by intracellular cytokine staining.

Figures 8A, 8B, 8C, 8D:
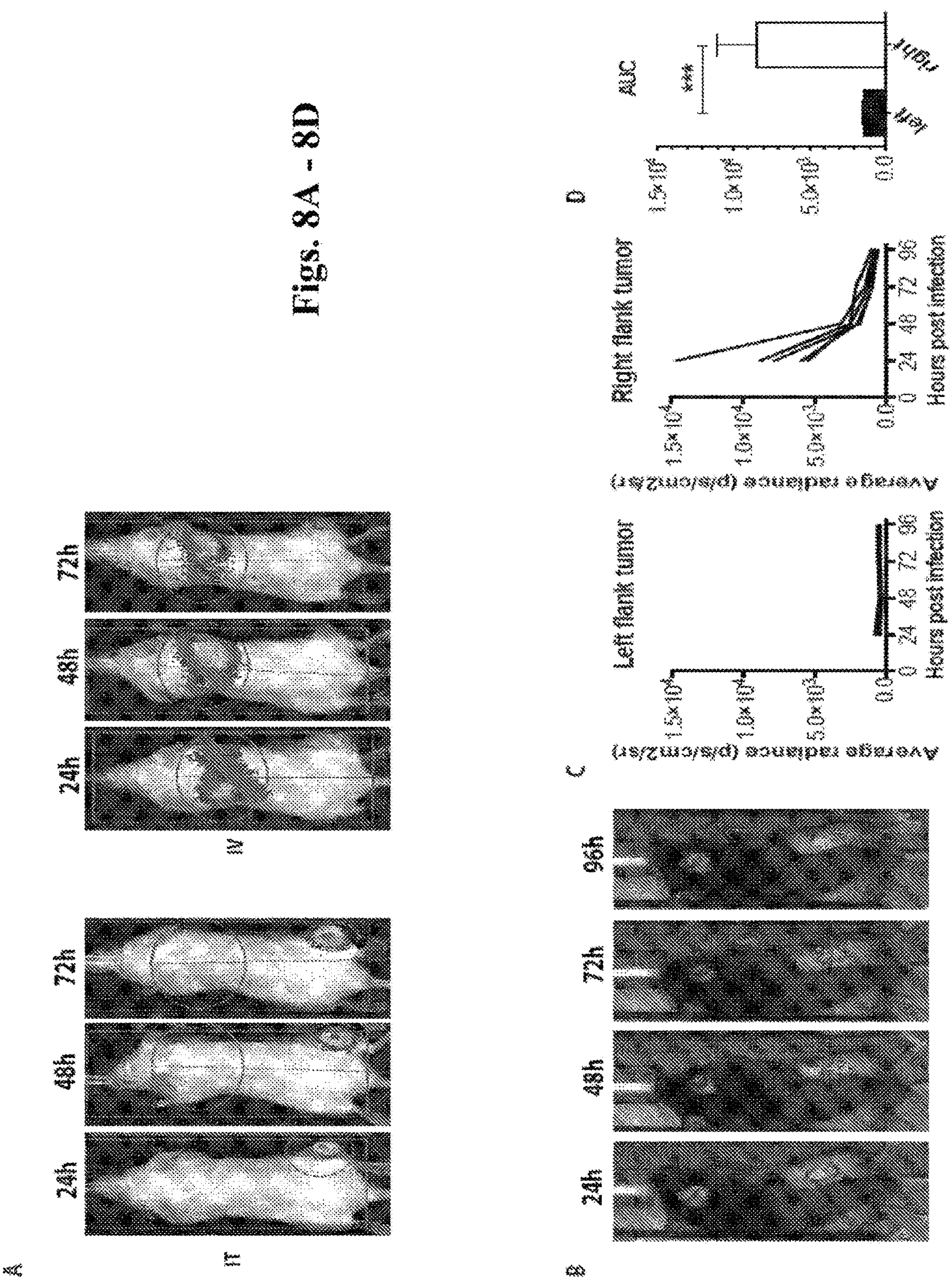

FIGS. 8A-8D. NDV infection is restricted to the injected tumor. FIG. 8A) Recombinant NDV-Flue was administered intratumorally (IT) or intravenously (IV) into Balb/C animals bearing CT26 tumors and images were acquired over the next 72 hours. FIG. 8B) NDV-Fluc was administered to C57BL/6 mice bearing bilateral B16F10 melanoma tumors and animals were monitored for 120 hours. Representative luminescence images are shown. FIG. 8C) Quantification of luminescence from the tumor site normalized to background luminescence. FIG. 8D) Area under the curve (AUC) calculated from the data in panel (FIG. 8C). Data show representative results from 1 of 3 independent experiments with 3-5 mice/group. ***$p<0.001$ ($p<0.05$ indicates statistical significance).

Figures 9A, 9B, 9C, 9D, 9E, 9F:
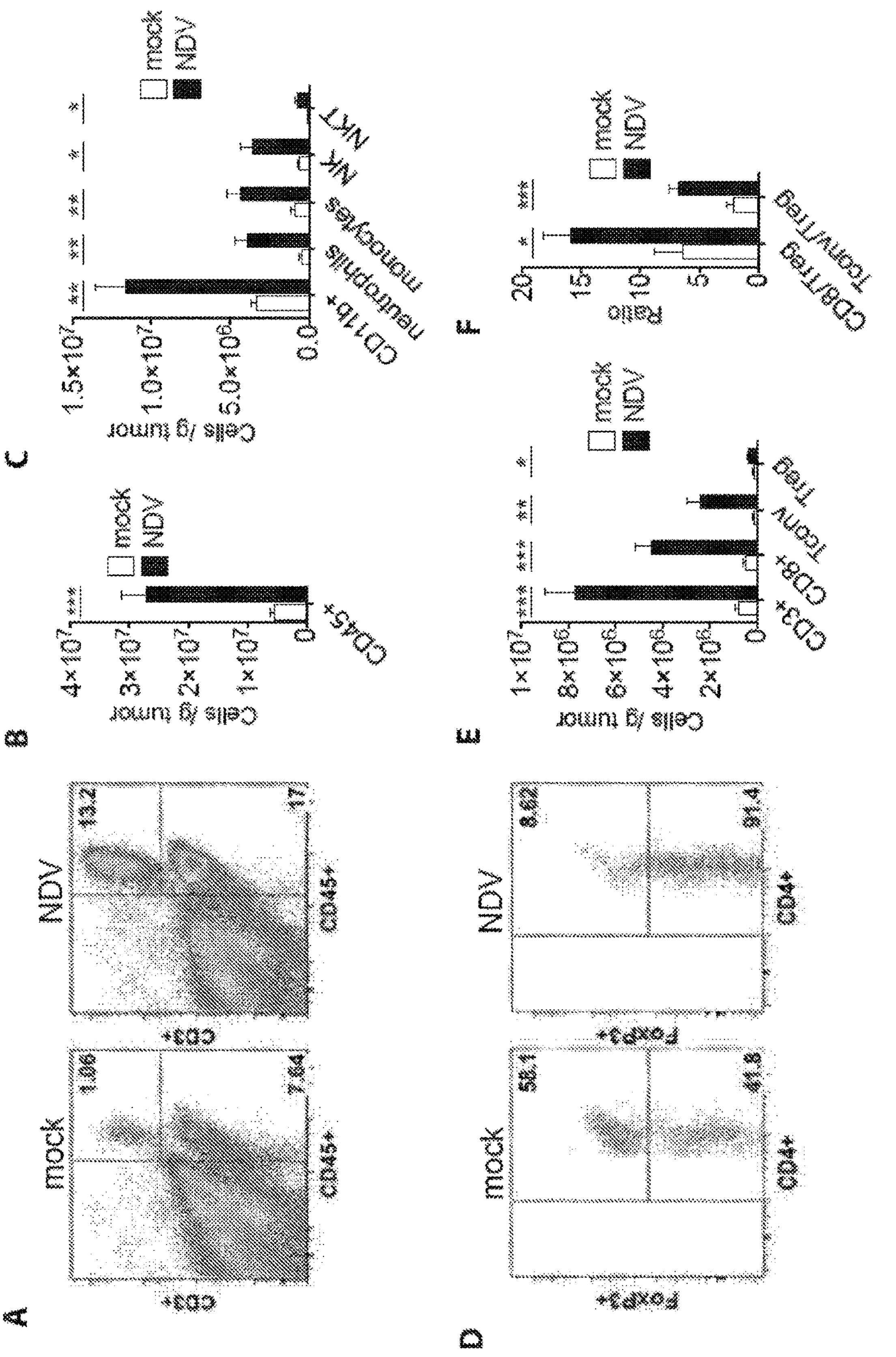

FIGS. 9A-9F. NDV infection increases tumor leukocyte infiltration in the virus-injected tumors. Animals were treated according to the scheme described in FIG. 10A. Tumors were excised on day 15, and TILs were labeled and analyzed by flow cytometry. FIG. 9A) Representative flow cytometry plots of percentages of tumor-infiltrating CD45+ and CD3+ cells. FIG. 9B) Absolute numbers of CD45+ cells/g tumor. FIG. 9C) Absolute numbers of innate immune cells/g tumor. FIG. 9D) Representative plots of percentages of CD4+FoxP3+(Treg) and CD4+FoxP3− (T cony) cells. FIG. 9E) Absolute numbers of conventional and regulatory CD4+ cells and CD8+ cells/g tumor. FIG. 9F) Calculated Tconv/Treg and CD8+/Treg ratios from the tumors. Data represent cumulative results from 3 independent experiments with 3-5 mice/group. Mean+/−SEM is shown. *$p<0.05$, $p<0.01$, *$p<0.001$, ****$p<0.0001$.

Figures 10A, 10B, 10C, 10D, 10E, 10F:
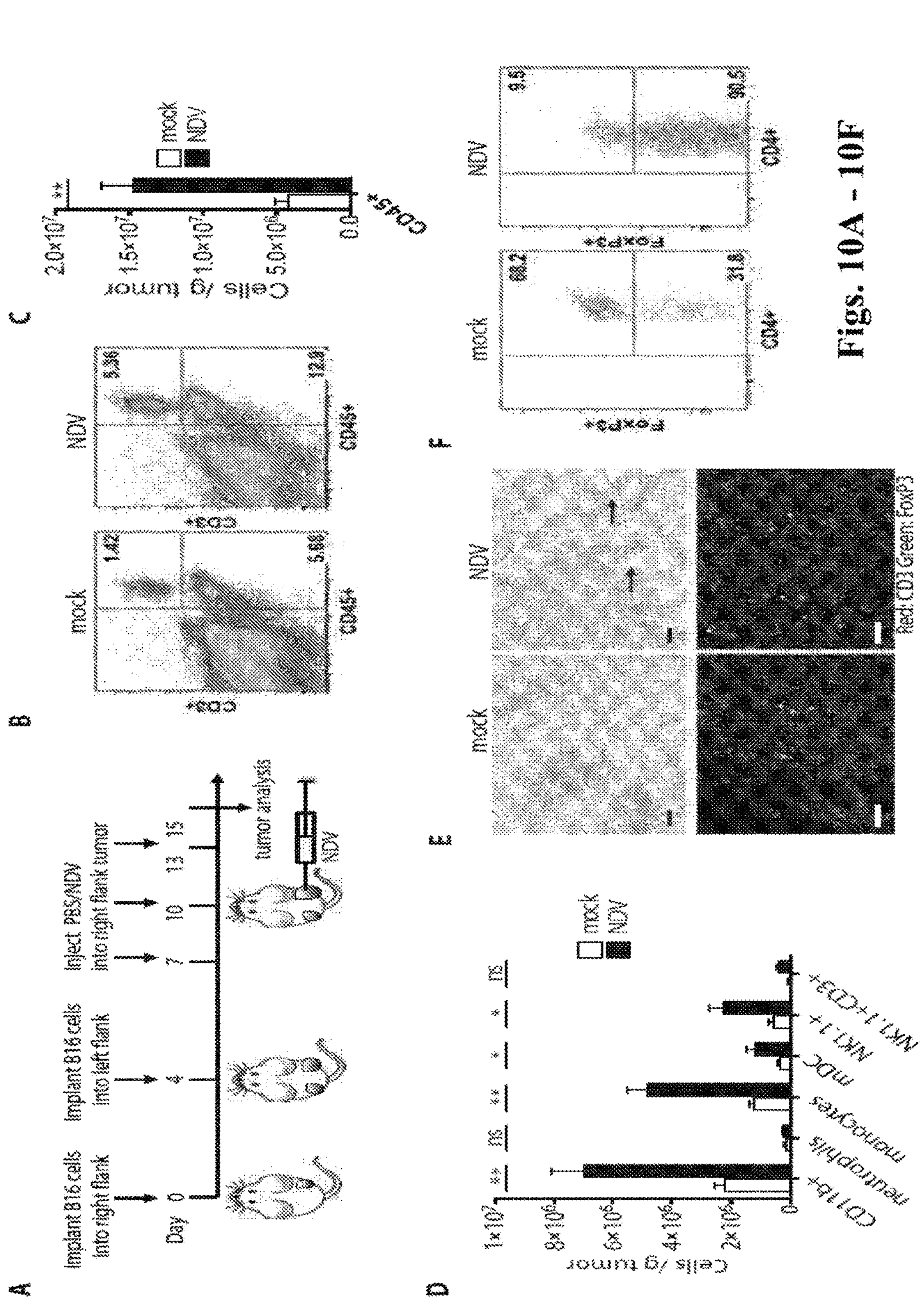
Figures 10G, 10H, 10I, 10J, 10K, 10L, 10M:
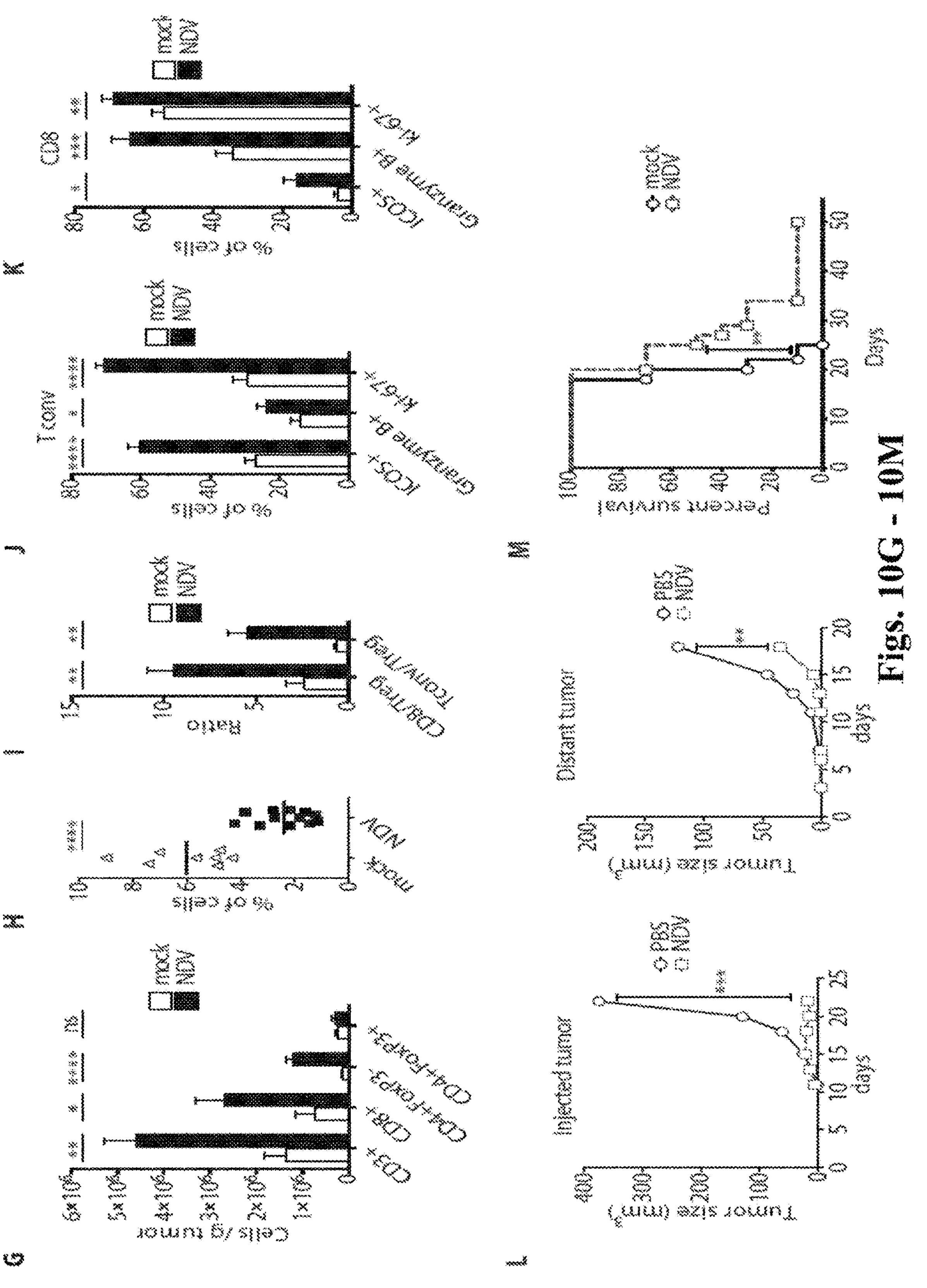

FIGS. 10A-10M. NDV increases distant tumor lymphocyte infiltration and delays tumor growth. FIG. 10A) Treatment scheme. FIG. 10B) Representative flow cytometry plots of percentages of tumor-infiltrating CD45+ and CD3+ cells. FIG. 10C) Absolute numbers of CD45+ cells/g tumor. FIG. 10D) Absolute numbers of innate immune cells/g tumor. FIG. 10E) Tumor sections from distant tumors were stained with H&E (upper panels) or labeled for CD3 and FoxP3 (bottom panels) and analyzed by microscopy. Areas denoted by arrows indicate areas of necrosis and inflammatory infiltrates. Scale bars represent 200 μm. FIG. 10F) Representative flow cytometry plots of percentages of CD4+ FoxP3+ (Treg) and CD4+FoxP3− (Tconv) cells. FIG. 10G) Absolute numbers of conventional and regulatory CD4+ cells and CD8+ cells/g tumor calculated from flow cytometry. FIG. 10H) Relative percentages of Tregs out of CD45+ cells. FIG. 10I) Calculated Tconv/Treg and CD8+/Treg ratios. (FIG. 10J and FIG. 10K) Upregulation of ICOS, Granzyme B, and Ki-67 on tumor-infiltrating Tconv (FIG. 10J) and CD8+ cells (FIG. 10K). FIG. 10L) Growth of NDV-injected and distant tumors. FIG. 10M) Overall animal survival. Data represent cumulative results from 3 (FIGS. 10B-10K) or 2 (FIGS. 10L-10M) independent experiments with n=3-5 per group. Mean+/−SEM is shown. *$p<0.05$, $p<0.01$, *$p<0.001$, ****$p<0.0001$.

Figures 11A, 11B, 11C, 11D, 11E:
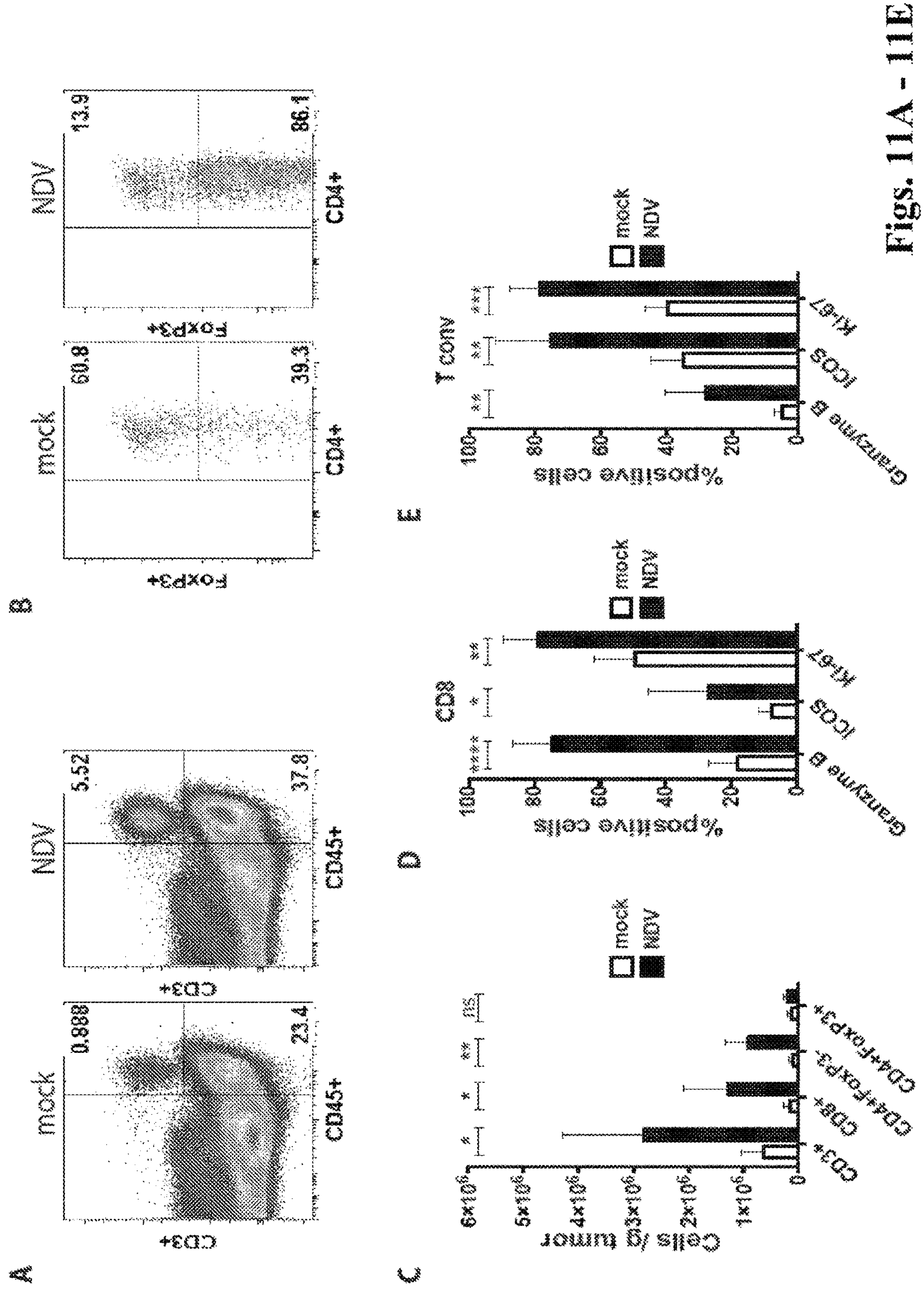

FIGS. 11A-11E. NDV therapy increases distant tumor lymphocyte infiltration in bilateral footpad melanoma model. Animals bearing bilateral footpad melanoma tumors were treated according to the schedule described in FIG. 10A. Distant tumors were excised on day 15 and TILs were labeled and analyzed by flow cytometry. FIG. 11A) Representative flow cytometry plots of percentages of tumor-infiltrating CD45+ and CD3+ cells. FIG. 11B) Representative flow cytometry plots of percentages of CD4+FoxP3+ and CD4+FoxP3− cells. FIG. 11C) Absolute numbers of conventional and regulatory CD4+ cells and CD8+ cells/g tumor. FIG. 11D and FIG. 11E) Upregulation of ICOS, Granzyme B, and Ki-67 on tumor-infiltrating CD8+ (FIG. 11D) and Tconv (FIG. 11E) lymphocytes. Data show representative results from 1 of 2 independent experiments with 5 mice/group. *$p<0.05$, $p<0.01$, *$p<0.001$, ****$p<0.0001$.

Figures 12A, 12B, 12C:
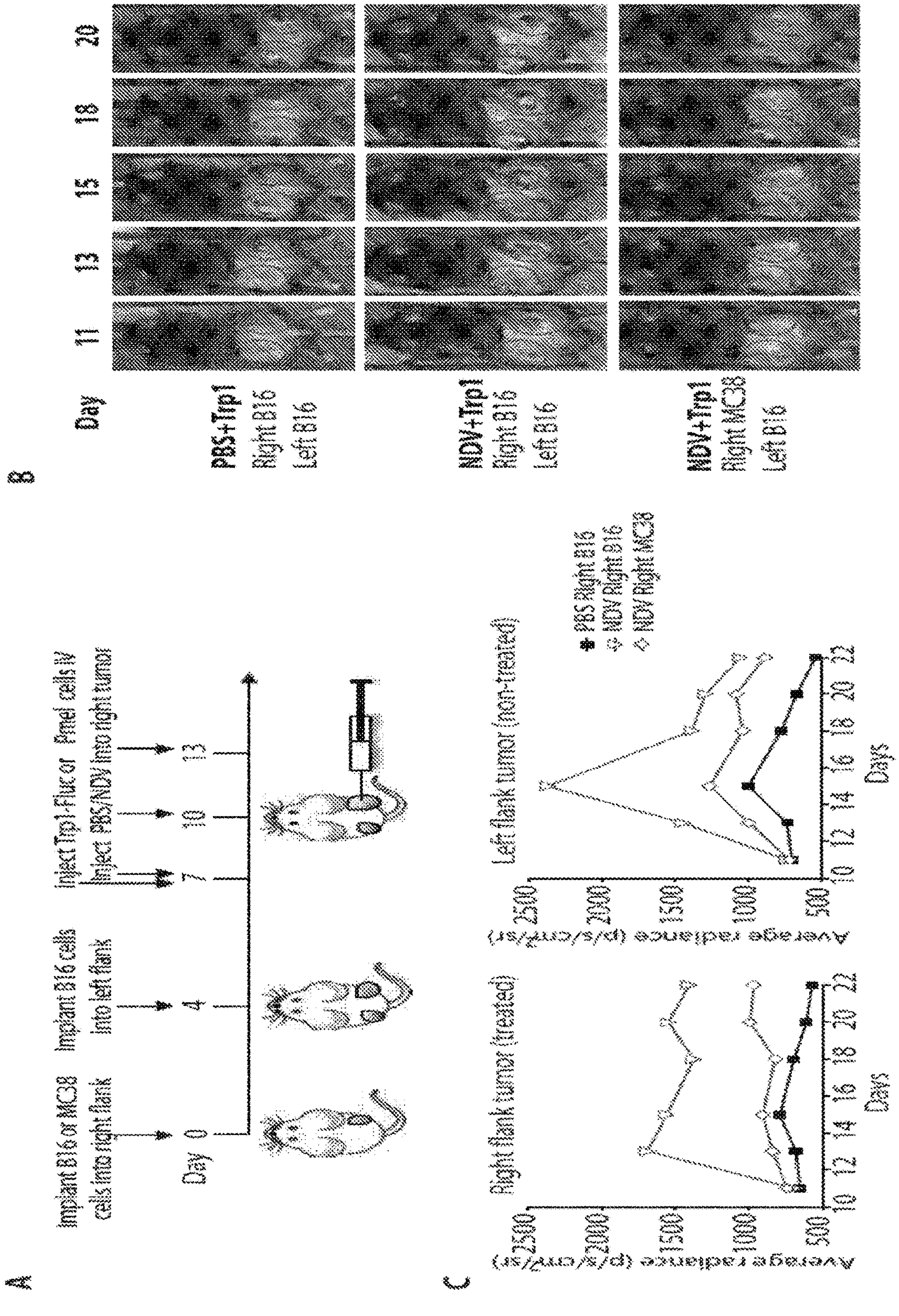
Figures 12D, 12E, 12F, 12G, 12H, 12I:
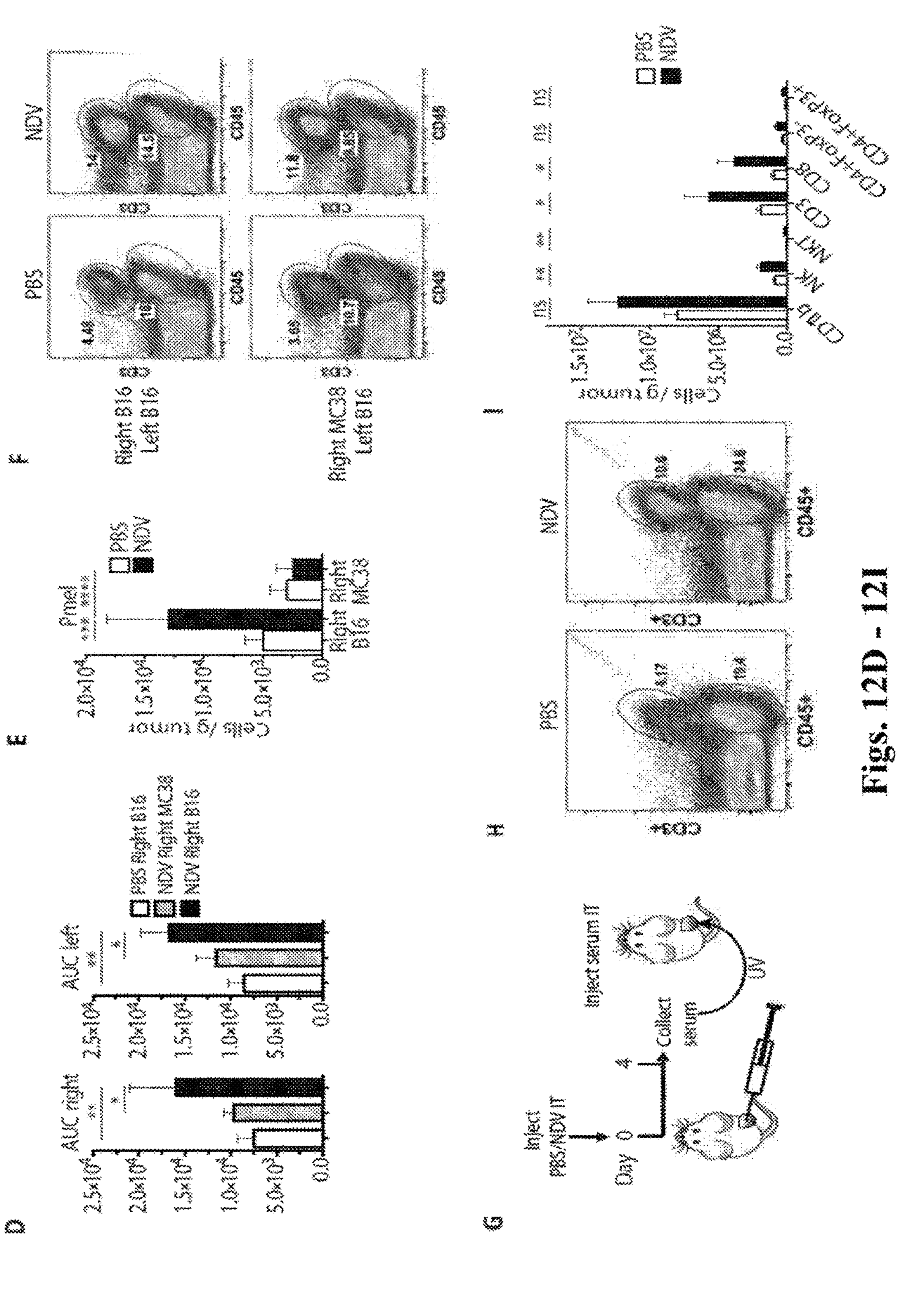

FIGS. 12A-12I. NDV induces infiltration of adoptively-transferred tumor-specific lymphocytes and facilitates tumor inflammation. FIG. 12A) Treatment scheme. FIG. 12B) Representative luminescence images from animals treated with NDV and adoptively-transferred Trp1-Fluc lymphocytes. FIG. 12C) Quantification of average luminescence from the tumor sites. FIG. 12D) The area under the curve (AUC) calculated from the data in panel FIG. 12C. FIG. 12E) Absolute number of Pmel lymphocytes from distant tumors calculated from flow cytometry. FIG. 12F) Representative flow cytometry plots of percentages of CD45+ and CD3+ cells infiltrating distant tumors of animals treated per treatment scheme in FIG. 12A. FIG. 12G) Experimental scheme for serum transfer from animals treated intratumorally with single injection of NDV or PBS. FIG. 12H) Representative flow cytometry plots of percentages of CD45+ and CD3+ cells infiltrating serum-injected tumors. FIG. 12I) Absolute numbers of the indicated cell subsets in serum-injected tumors calculated from flow cytometry. Data for FIGS. 12B-12E represent 1 of 3 experiments with n=4-5 per group. Data for FIGS. 12G-12I represent pooled data from 2 independent experiments with n=5 per group. Mean+/−SEM is shown. *$p<0.05$, $p<0.01$, *$p<0.001$, ****$p<0.0001$.

Figure 13:
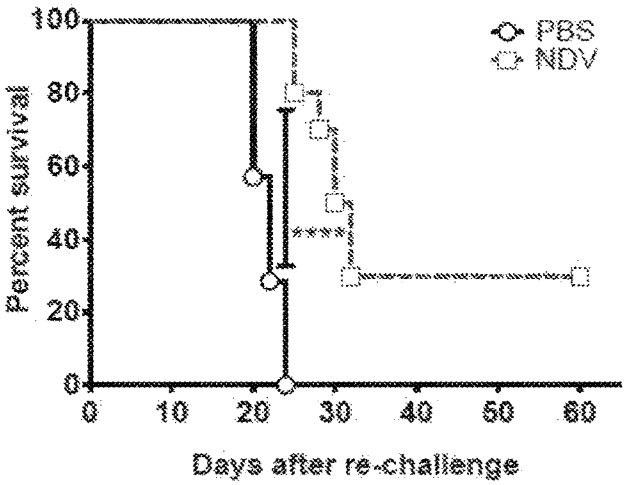

FIG. 13. Intratumoral NDV provides protection from tumor rechallenge. Animals cured of B16F10 melanoma by NDV were injected on day 75 with $1\times10^5$B16F10 melanoma cells, monitored for tumor growth, and euthanized when the tumors reached 1000 $mm^3$. Overall animal survival is shown. Data show cumulative results from 1 of 2 independent experiments with 10 mice/group. ****$p<0.0001$.

Figures 14A, 14B:
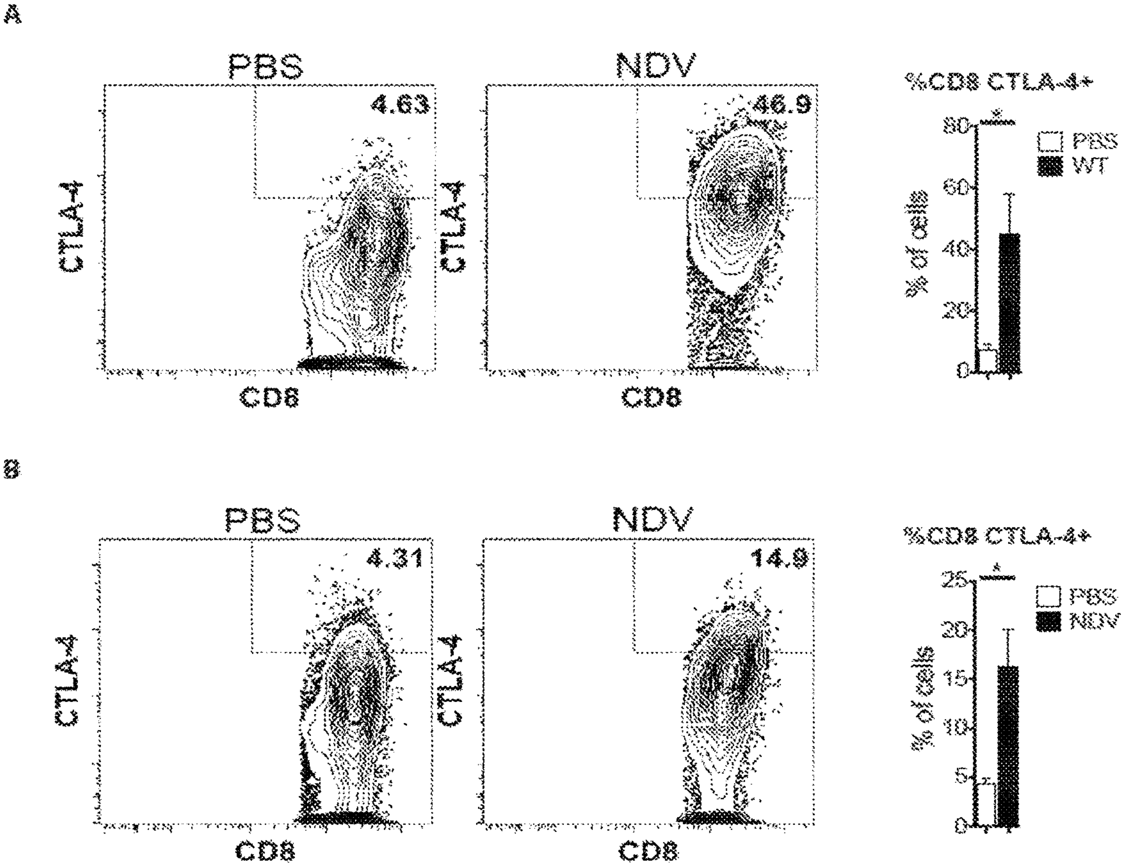

FIGS. 14A-14B. Tumor-infiltrating CD8+ lymphocytes upregulate CTLA-4 in response to NDV therapy. Representative dot plots (left) and cumulative results (right) of CTLA-4 expression in CD8+ cells in NDV-treated (FIG. 14A), and distant (FIG. 14B) tumors. Representative results from 1 of 3 experiments with 3 mice per group. *$p<0.05$.

Figure 15A:
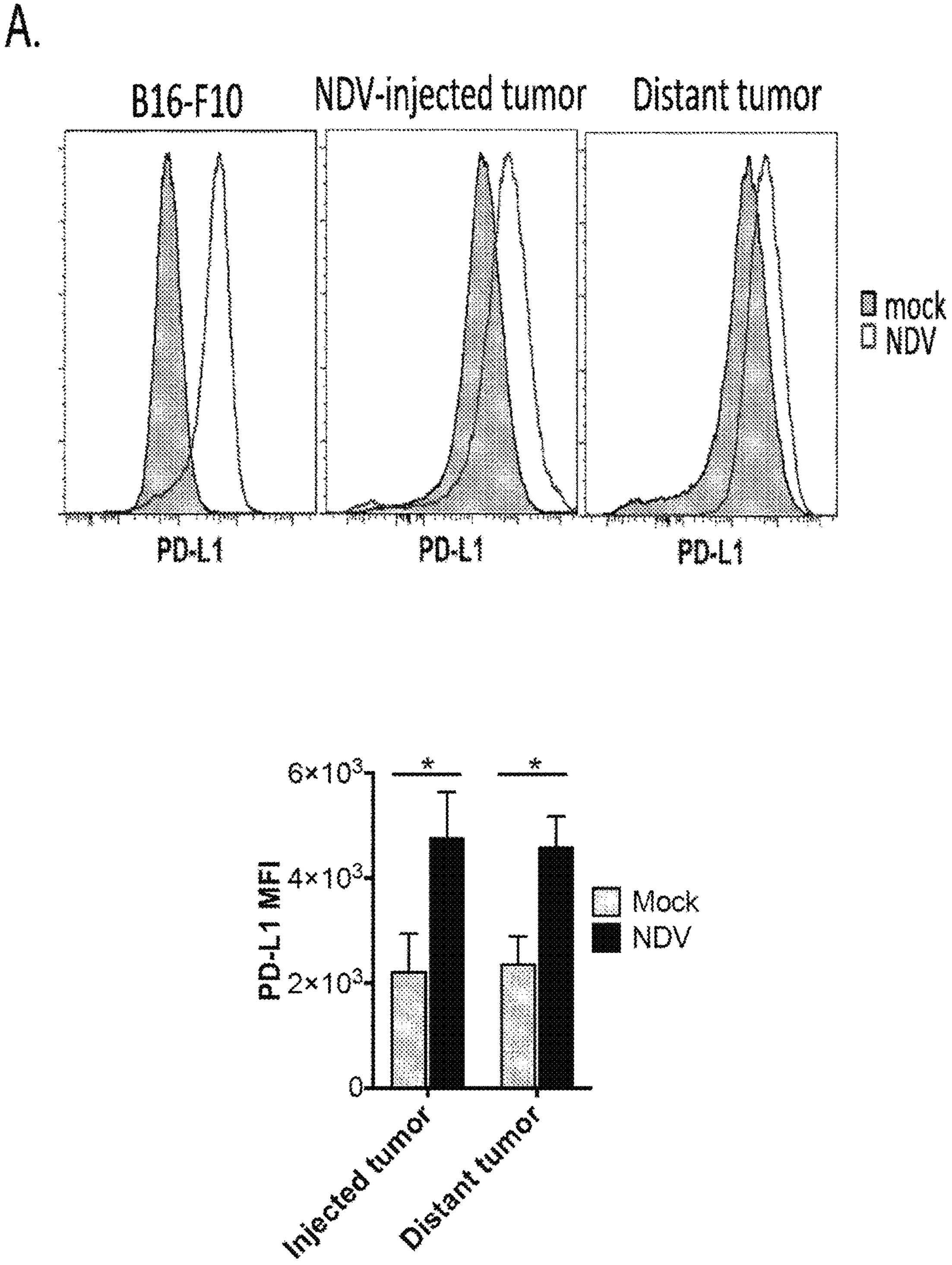
Figure 15B:
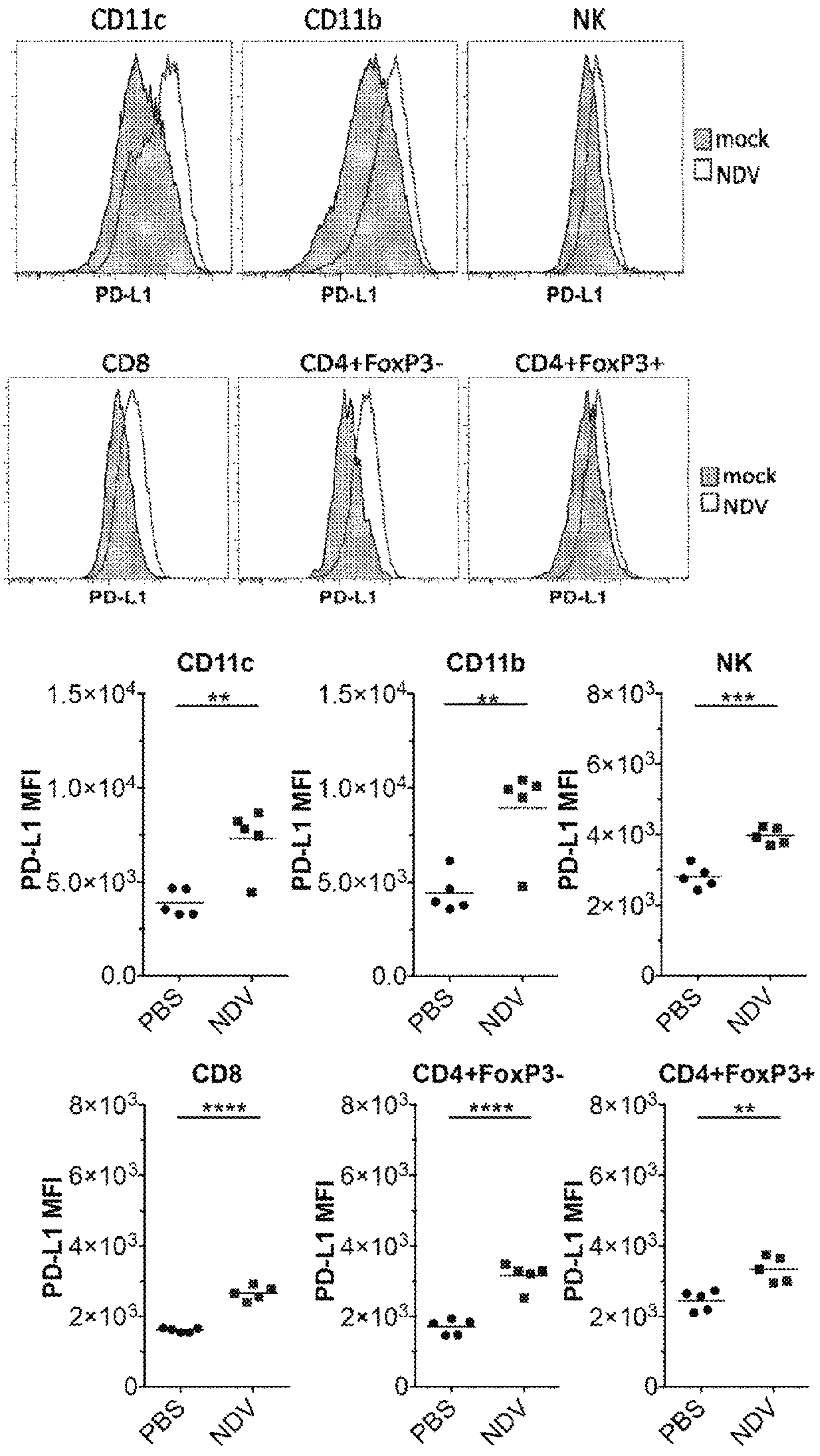

FIGS. 15A-15B. NDV therapy leads to upregulation of PD-L1 on tumors and tumor-infiltrating leukocytes. FIG. 15A) PD-L1 expression on B16F10 cells infected in vitro (left panel), and in vivo in virus injected and distant tumors. Top, representative flow cytometry histograms, bottom, average median fluorescence intensity (MFI) of PD-L1 expression on B16F10 cells from tumors. FIG. 15B) PD-L1 expression on the surface of tumor-infiltrating leukocytes isolated from distant tumors. Top: representative flow cytometry histograms, bottom: calculated average MFI for each cell subset.

Figure 16A:
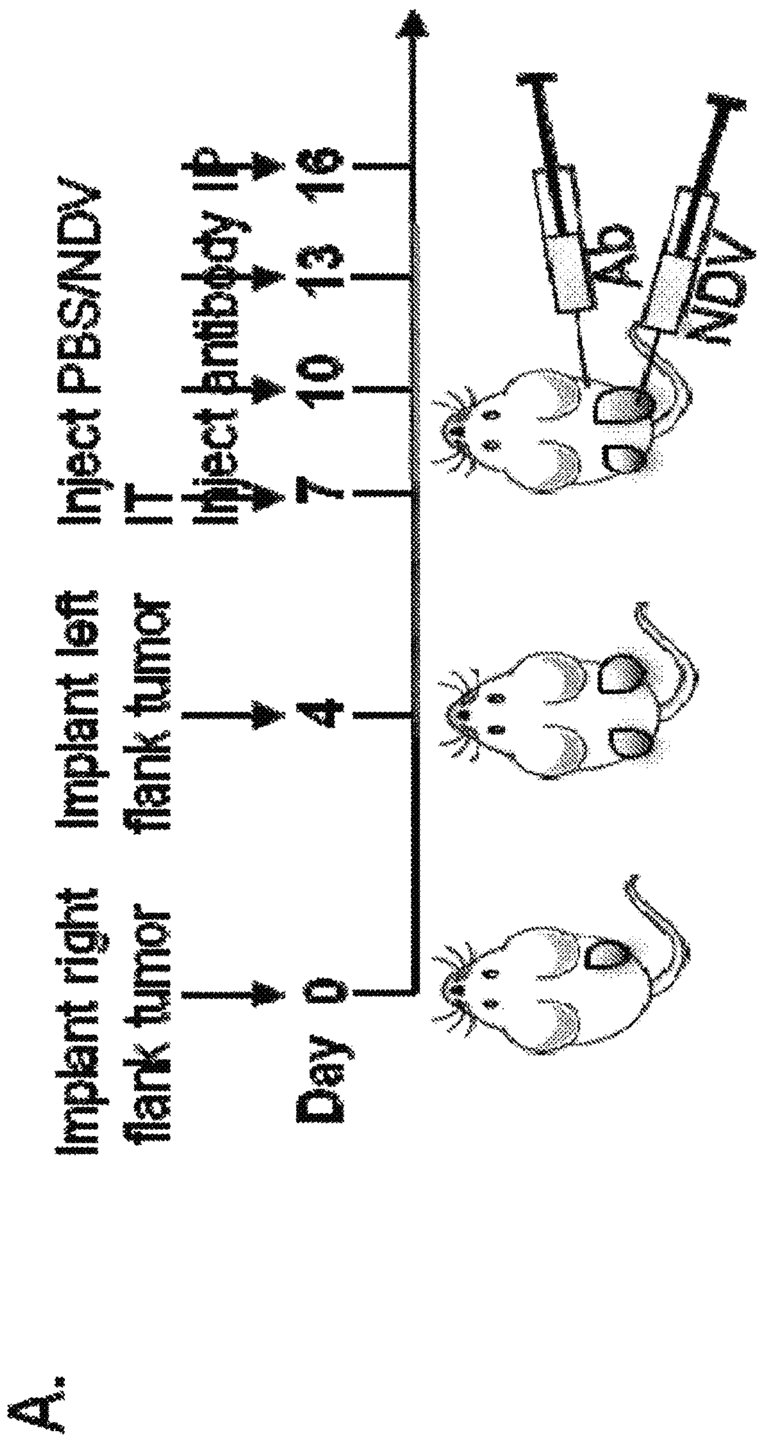
Figures 16B, 16C:
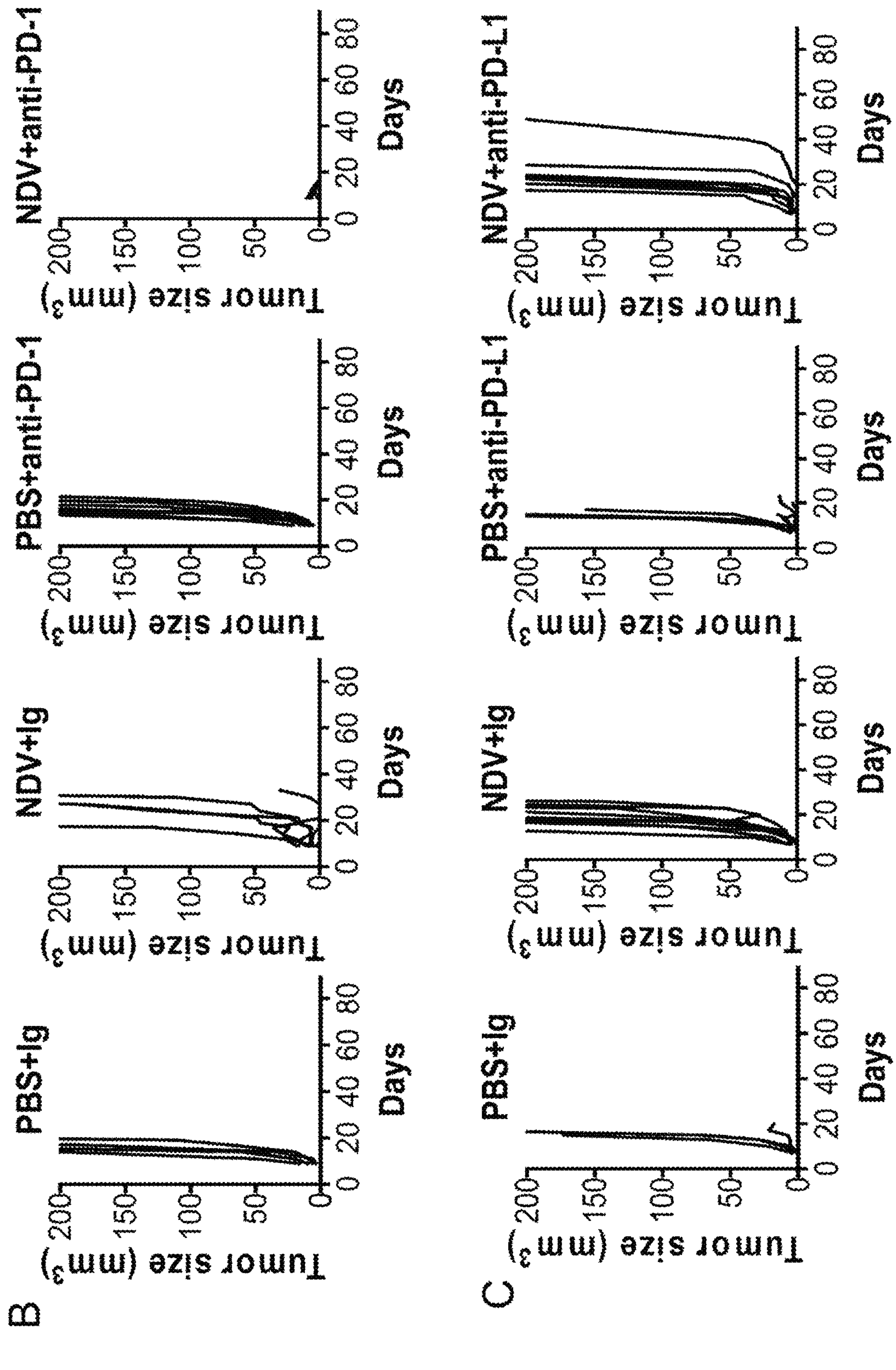
Figure 16D:
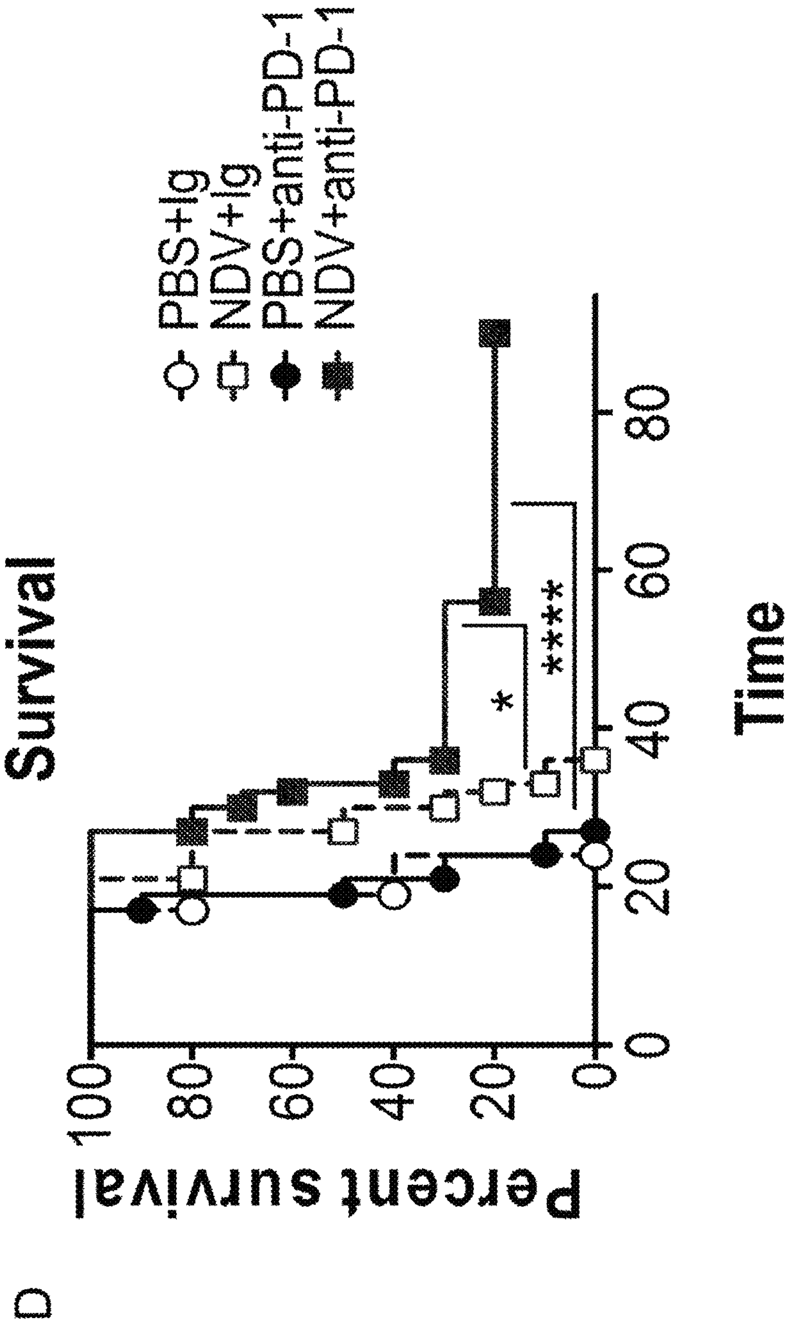

FIGS. 16A-16D. Combination therapy of NDV with antibodies blocking PD-1 leads to enhanced anti-tumor efficacy in bilateral flank B16 melanoma model. FIG. 16A) Treatment scheme. FIG. 16B) Right flank (NDV-injected) tumor growth. FIG. 16C) Left flank (distant) tumor growth. FIG. 16D) Overall survival.

Figure 17A:
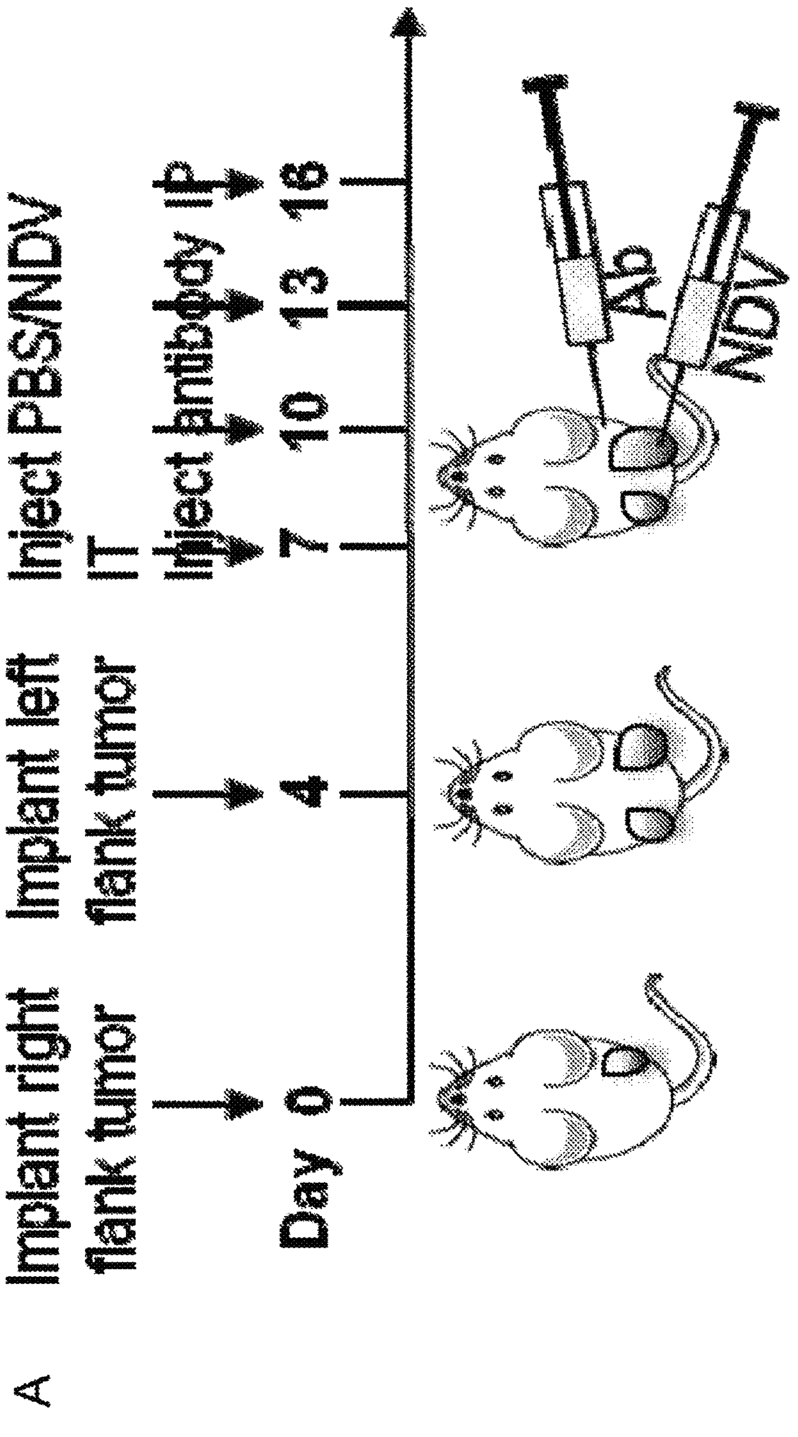
Figures 17B, 17C:
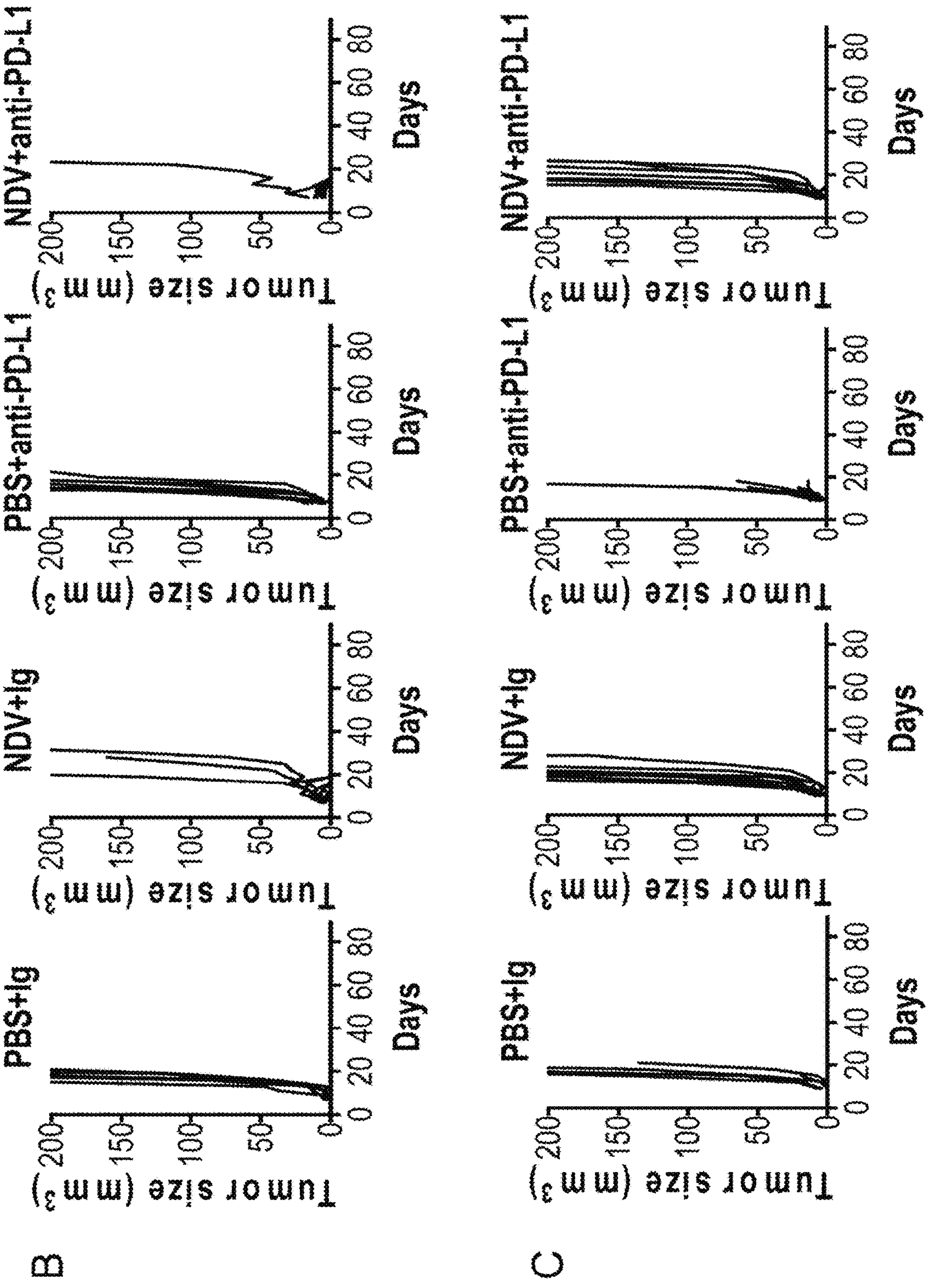
Figure 17D:
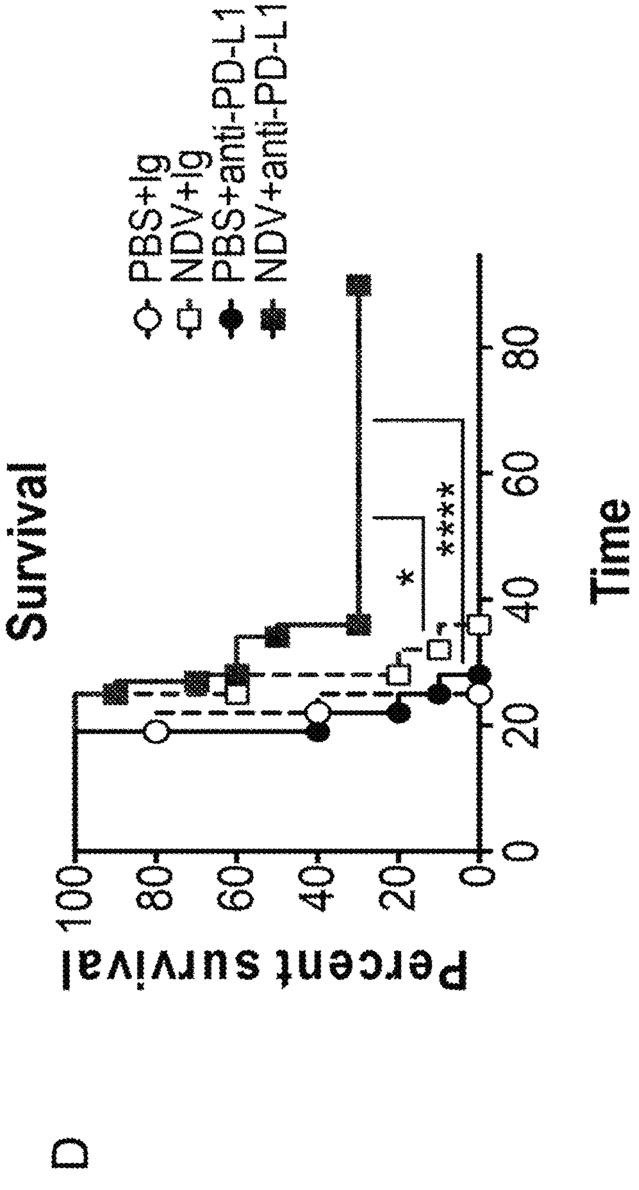

FIGS. 17A-17D. Combination therapy of NDV with antibodies blocking PD-L1 leads to enhanced anti-tumor efficacy in bilateral flank B16 melanoma model. FIG. 17A) Treatment scheme. FIG. 17B) Right flank (NDV-injected) tumor growth. FIG. 17C) Left flank (distant) tumor growth. FIG. 17D) Overall survival.

Figures 18A, 18B:
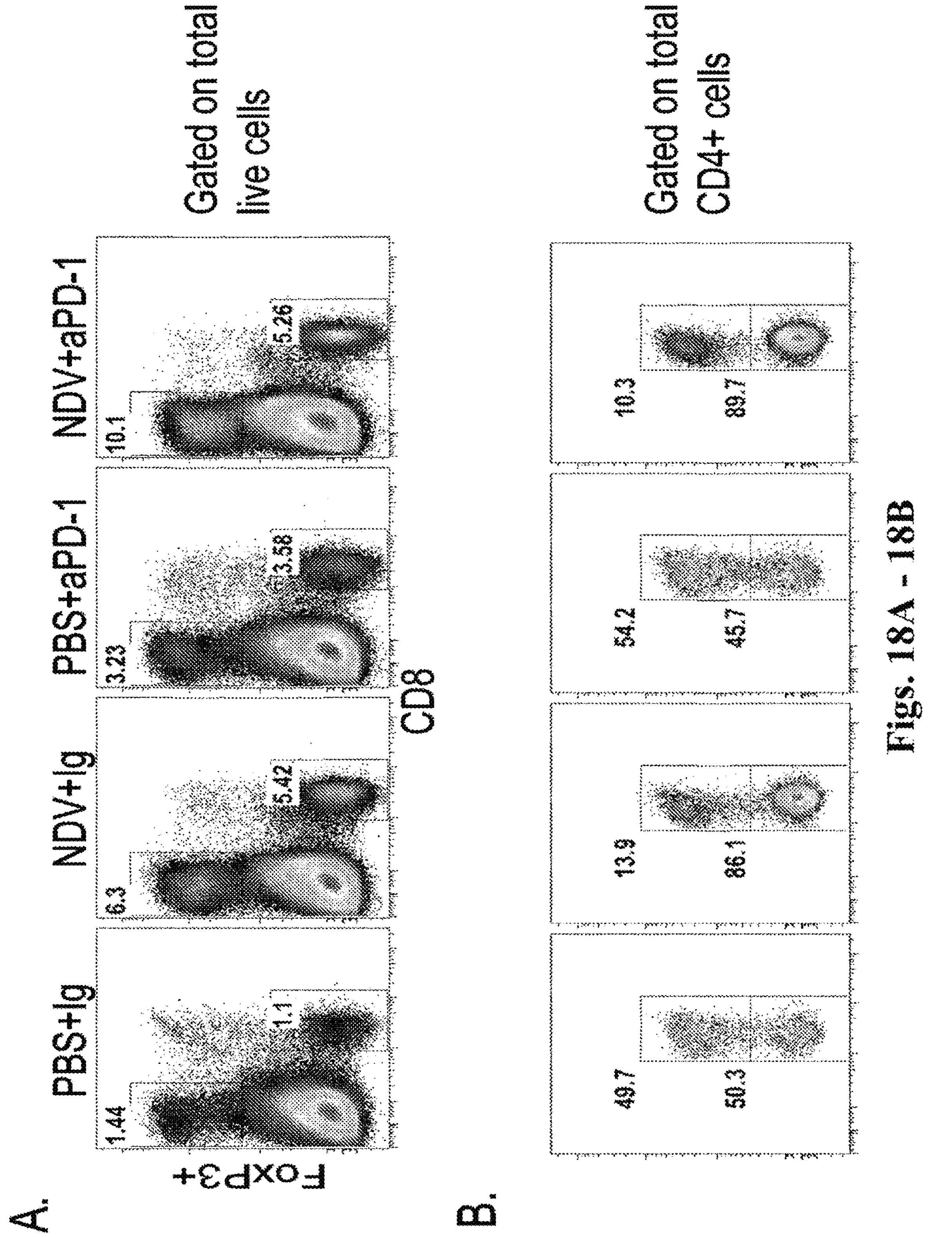
Figures 18C, 18D, 18E:
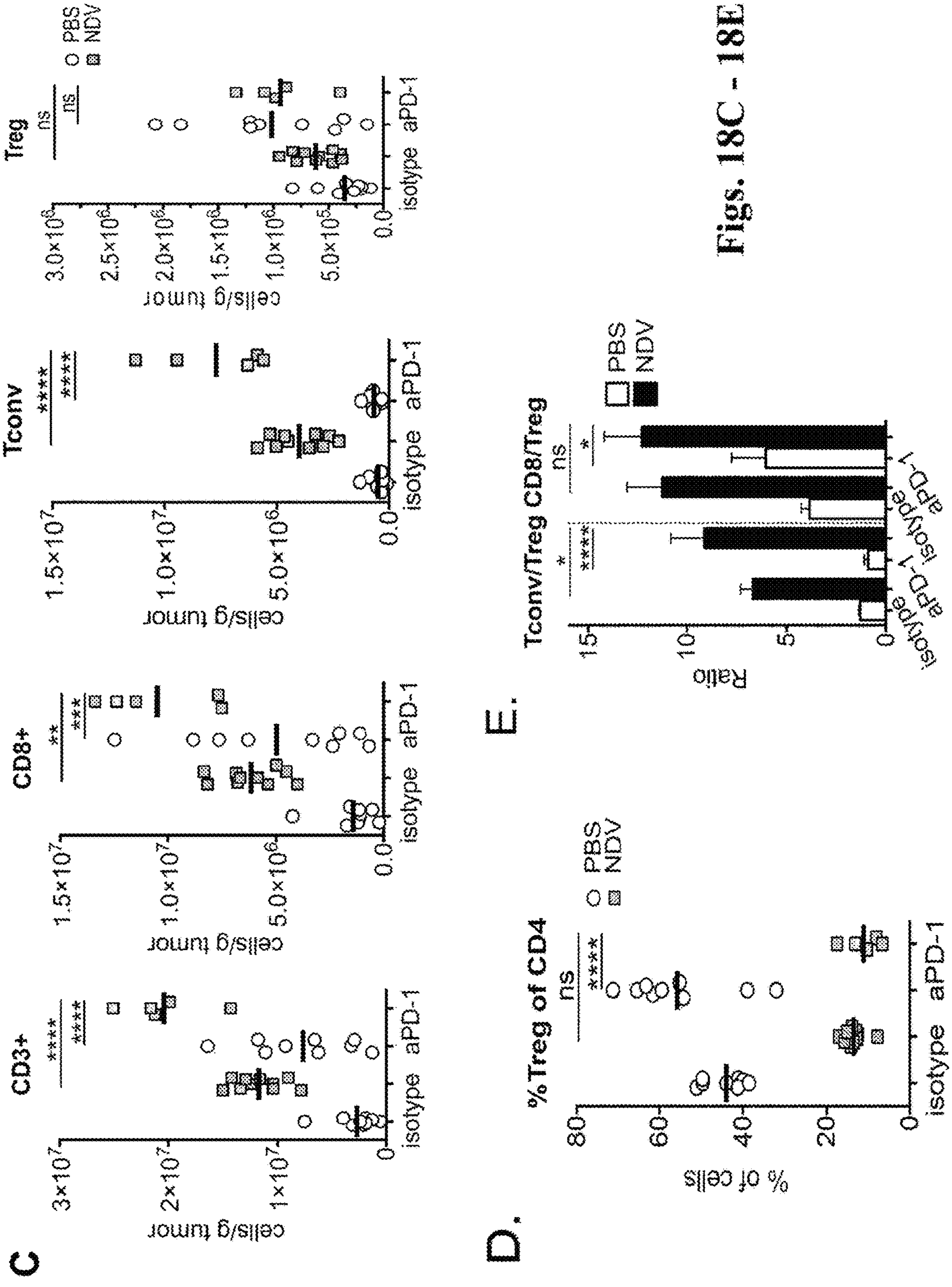

FIGS. 18A-18E. Combination therapy with NDV and anti-PD-1 therapy results in increased distant tumor infiltration with effector but not regulatory T cells. FIG. 18A) Representative flow cytometry plots of percentages of CD4+ and CD8+ cells in tumors. FIG. 18B) Representative flow cytometry plots of percentages of Tconv (CD4+FoxP3−) and Treg (CD4+FoxP3+) cells. FIG. 18C) Absolute numbers of T cell subsets per gram of tumor, calculated from flow cytometry. FIG. 18D) Relative percentages of Tregs from CD4+ T cells. FIG. 18E) Calculated Tconv/Treg and CD8/Treg ratios.

Figure 19A:
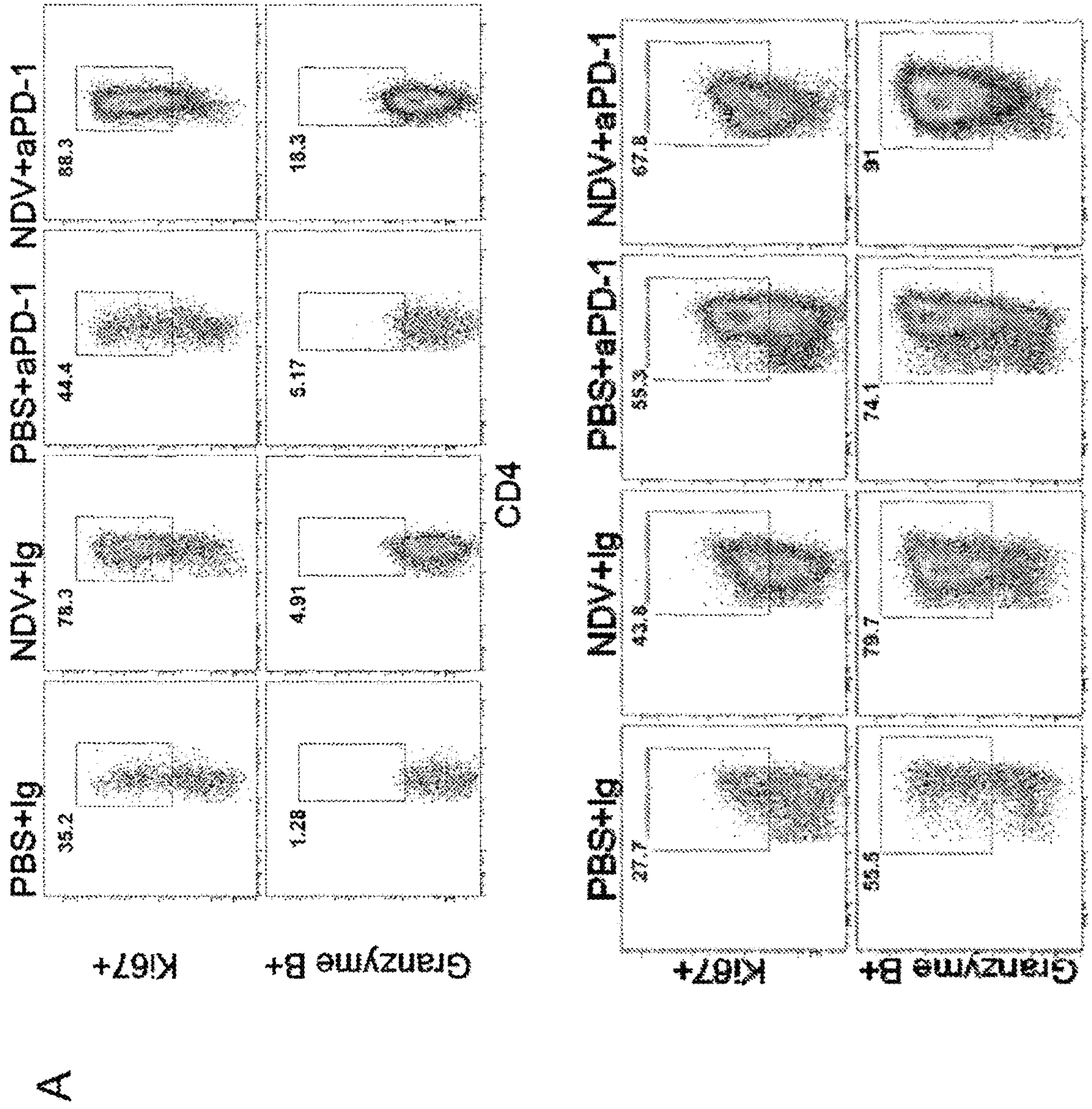
Figure 19B:
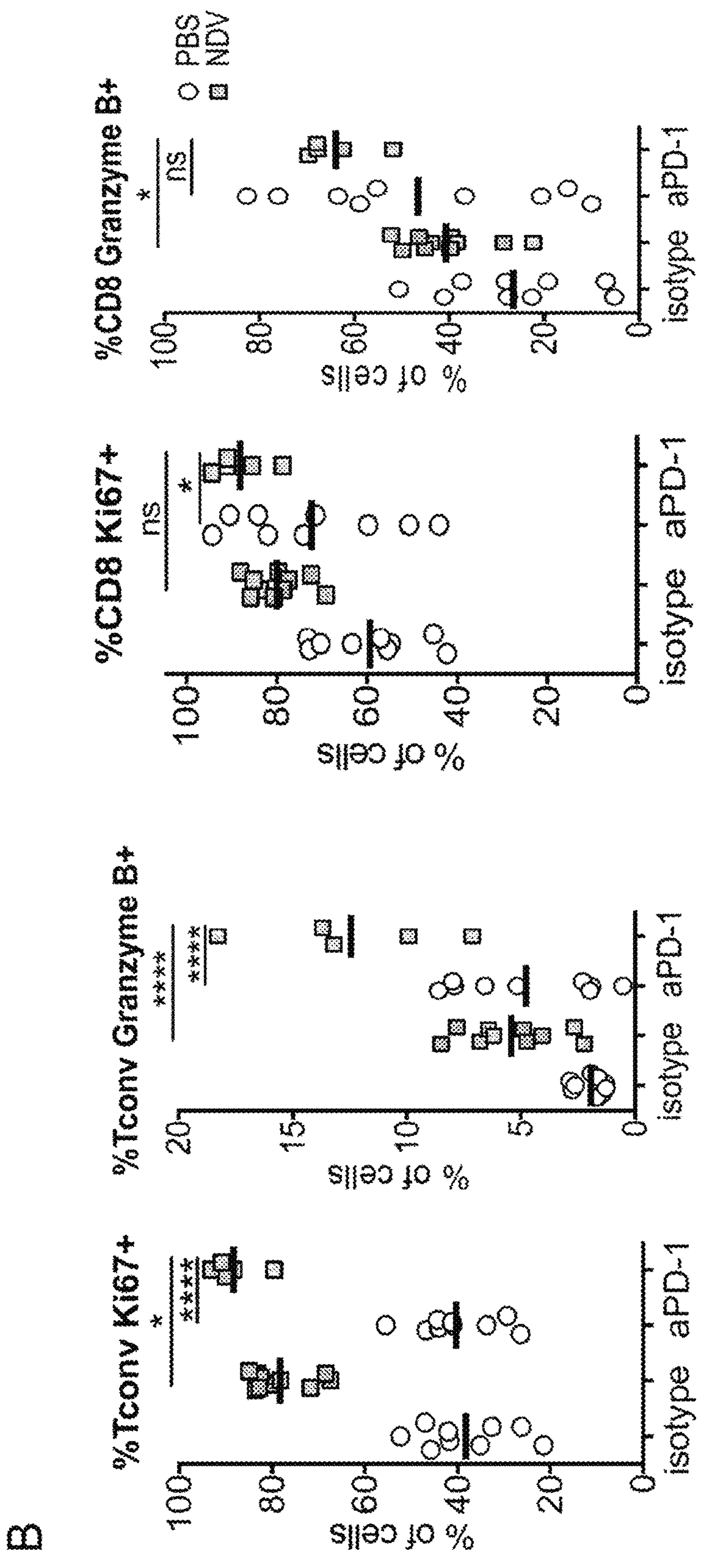

FIGS. 19A-19B. TILs from distant tumors in animals treated with combination NDV and anti-PD-1 therapy upregulate lytic and proliferation markers. FIG. 19A) Representative flow cytometry plots of percentages of Tconv and CD8 lymphocytes positive for Granzyme B and Ki67. FIG. 19B) Percentages of Tconv and CD8+ T cells positive for Granzyme B and Ki67.

Figure 20A:
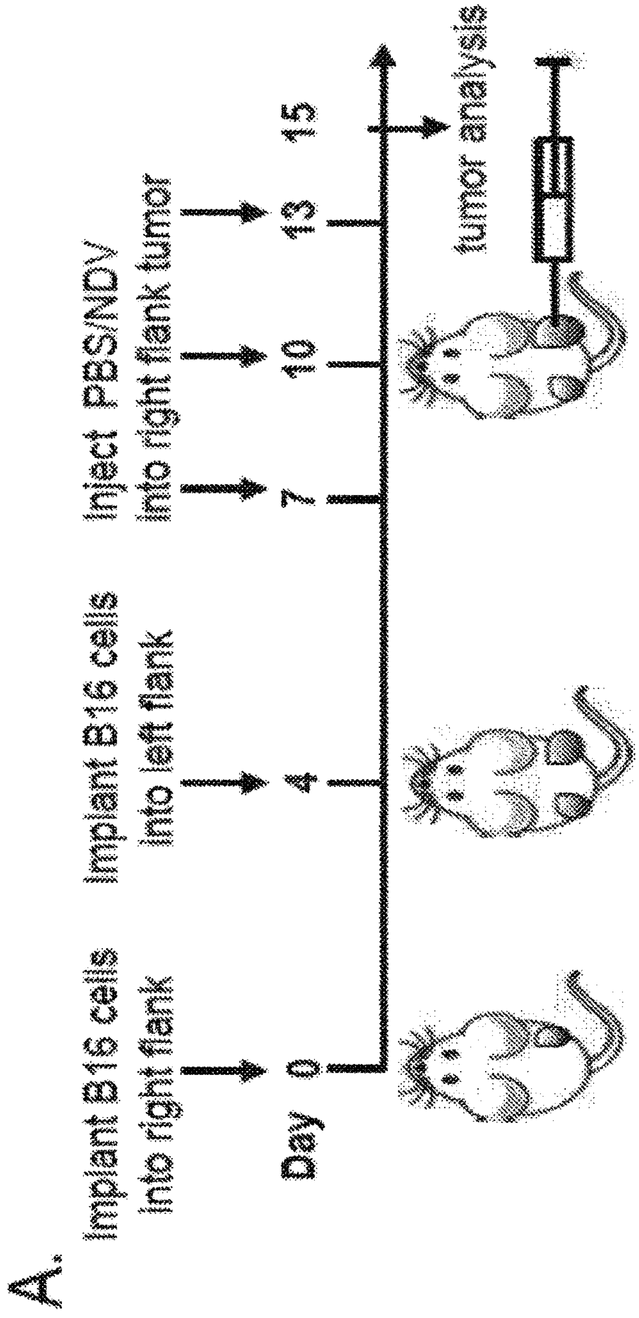
Figures 20B, 20C:
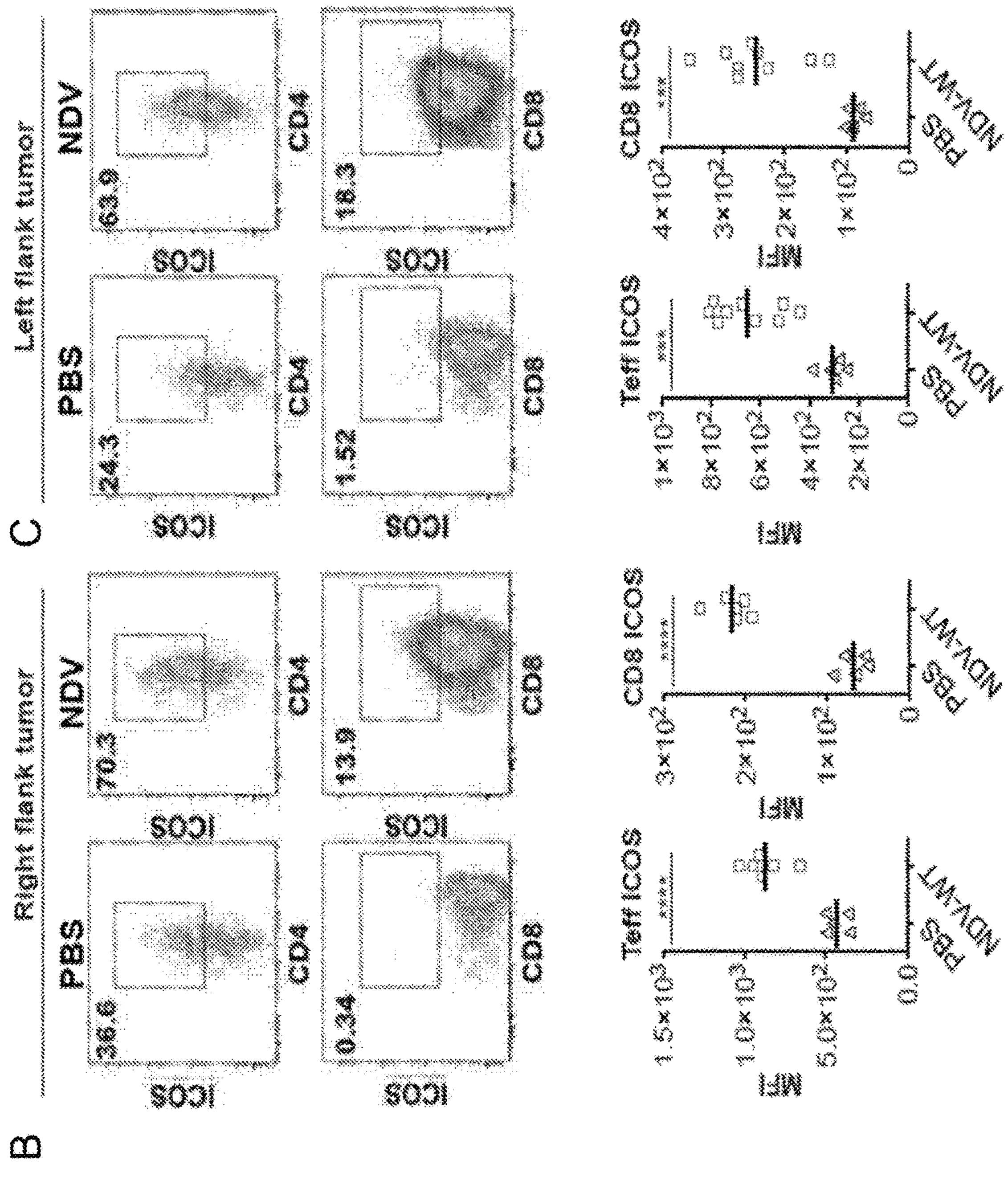

FIGS. 20A-20C. NDV induces tumor immune infiltration and upregulation of ICOS on CD4 and CD8 cells in the virus-injected and distant tumors. FIG. 20A) Treatment scheme. FIG. 20B) Expression of ICOS on tumor-infiltrating CD4+FoxP3− and CD8+ cells isolated from NDV-injected (right flank) tumors. Representative flow cytometry plots (top) and median fluorescence intensities (MFI) (bottom) are shown. FIG. 20C) Expression of ICOS on tumor-infiltrating CD4+FoxP3− and CD8+ cells isolated from distant (left flank) tumors. Representative flow cytometry plots (top) and median fluorescence intensities (MFI) (bottom) are shown.

Figure 21:
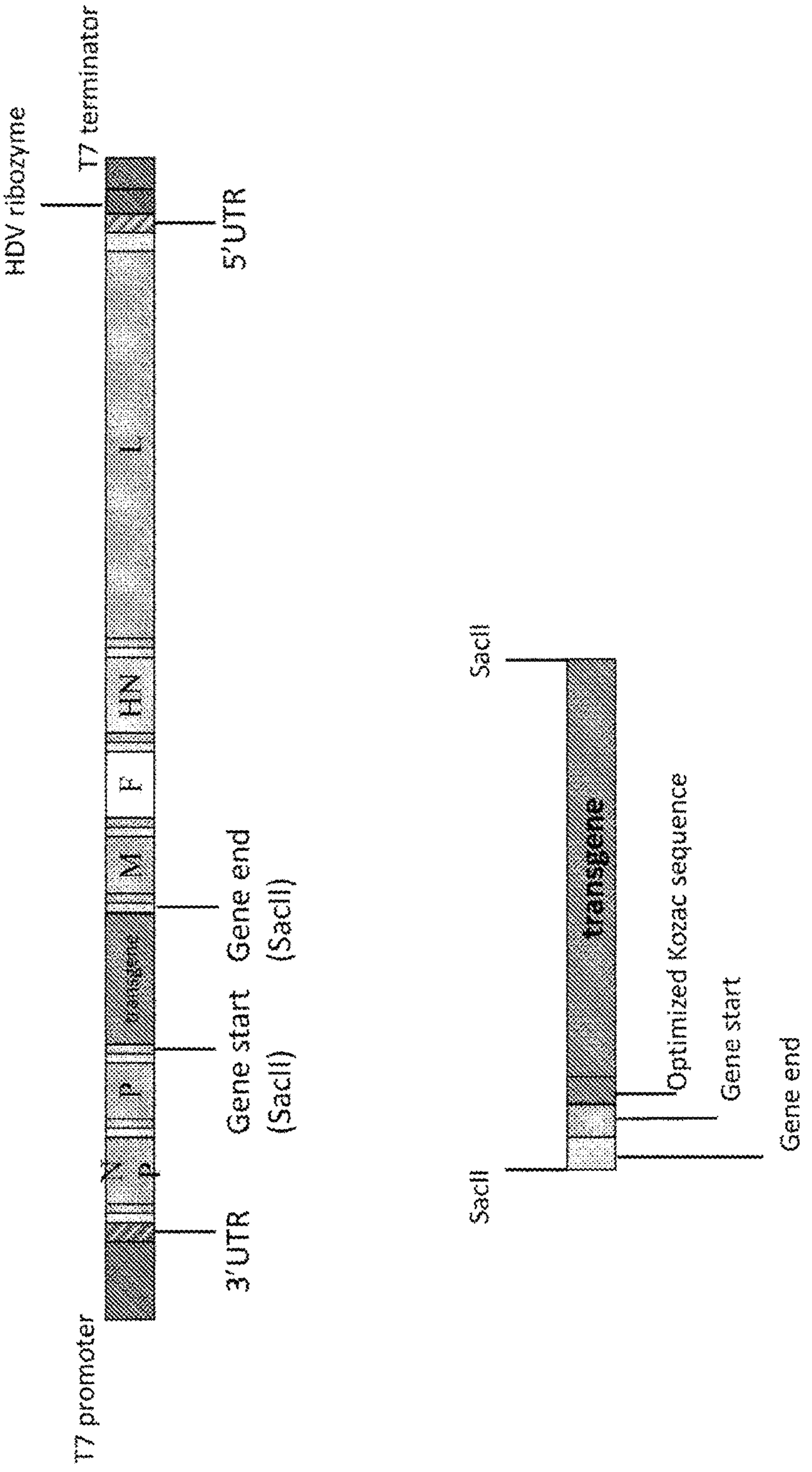

FIG. 21: Schematic of pT7NDV-LS-L289A plasmid.

Figures 22A, 22B, 22C, 22D:
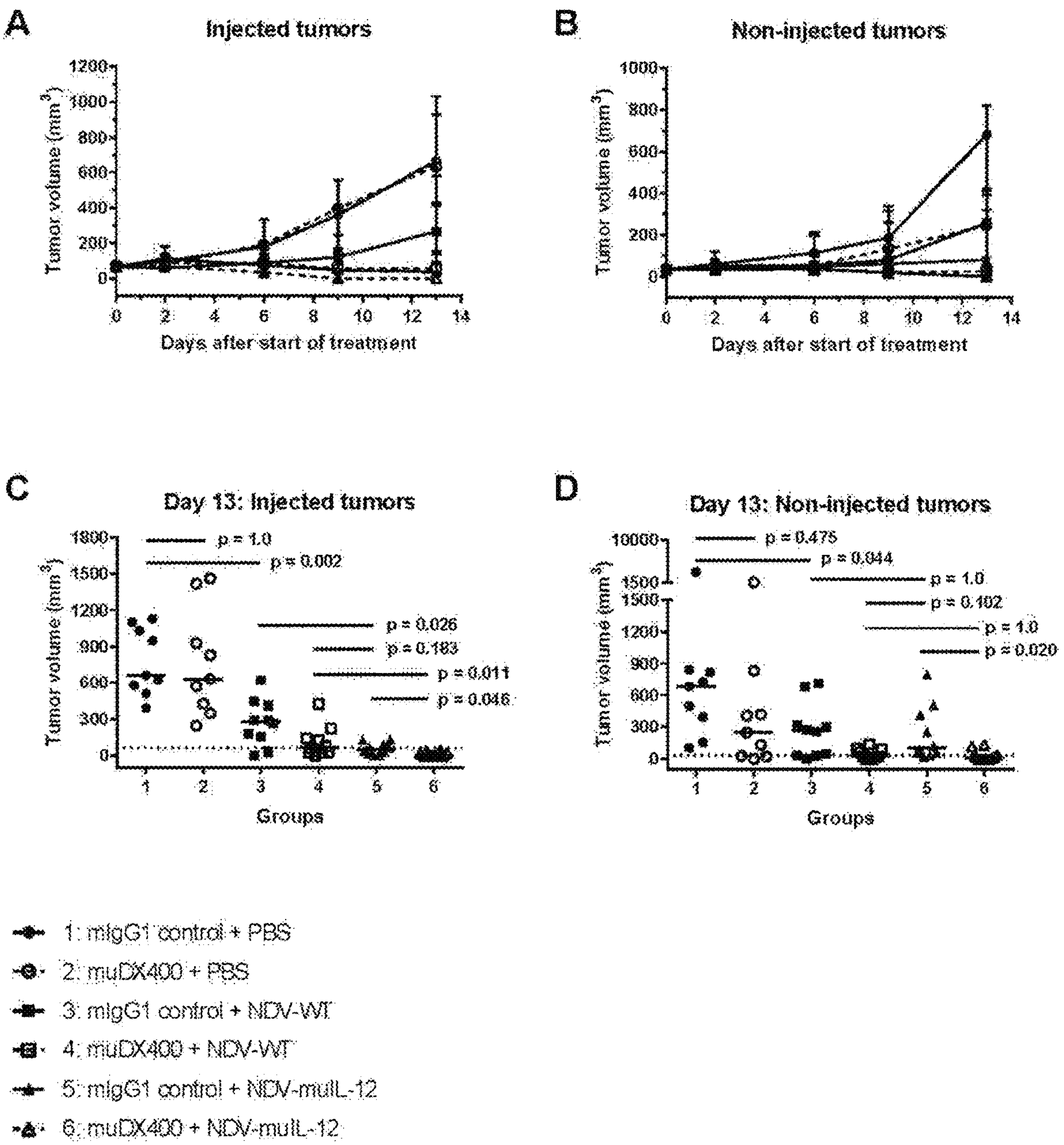

FIGS. 22A-22D: Enhanced anti-tumor efficacy with intratumoral NDV-muIL-12 in combination with anti-muPD-1 mAb muDX400 in B16F10 bilateral tumor model. Mouse B16F10 cells were subcutaneously implanted into the right flanks ($2\times10^5$ cells) and left flanks ($1\times10^5$ cells) of immunocompetent C57BL/6J mice. Animals were assigned into groups 9 days after implantation (Day 0) based on tumor volume (TV) in the right flanks (injected tumors) with median TV=65 $mm^3$. The median TV in the left flanks (non-injected tumors) of the 6 groups ranged from 31 to 38 $mm^3$. Dosing was initiated on Day 0. Mouse IgG1 isotype control and muDX400 at 10 mg/kg were administered intraperitoneally every 4 days for a total of 3 doses. PBS, NDV WT, and NDV-muIL-12 at $1\times10^7$ pfu were administered into the tumors on the right flanks every 2 days for a total of 4 doses. There were 10 animals in each group. FIG. 22A-22B: growth curves for injected tumors and non-injected tumors, respectively, are presented. Tumor volumes (“TVs”) are presented as median with 68% confidence intervals. FIGS. 22C and 22D: individual animal TV on Day 13 for injected and non-injected tumors, respectively, are presented. Dotted lines indicate Day 0 median TVs. P-values for key comparisons are indicated ($p<0.05$ indicates statistical significance). Group 1: mIgG1 control+PBS; Group 2: muDX400+PBS; Group 3: mIgG1 control+NDV-WT; Group 4: muDX400+NDV-WT; Group 5: mIgG1 control+NDV-muIL-12; Group 6: muDX400+NDV-muIL-12. For injected tumors, the number of complete regressions were as follows: Group 1: 0; Group 2: 0; Group 3: 1; Group 4: 1; Group 5: 2; and Group 6: 6. For non-injected tumors, the number of complete regressions were as follows: Group 1: 0; Group 2: 1; Group 3: 1; Group 4: 3; Group 5: 0; and Group 6: 5.

FIGS. 23A-23D: Induction of immune genes in injected tumors with intratumoral NDV-muIL 12 in combination with anti-muPD-1 mAb muDX400 in B16F10 bilateral tumor model as described in legend for FIGS. 22A-22D. Experimental design is described in Sections 6.3.1.9 and 6.3.1.13. Tumors were harvested on Day 14, and gene expression in tumor tissues were assessed by RTqPCR and normalized to ubiquitin. Individual animal expression levels of genes for T cell markers (FIG. 23A), cytokines (FIG. 23B), IFN-inducible genes (FIG. 23C), and Pd-1 and Pd-l1 (FIG. 23D) in injected tumors are presented. Lines denote mean values. For comparisons between Groups 3 and 5, 4 and 6, and 5 and 6, p-values<0.05 are indicated.

FIGS. 24A-24D: Induction of immune genes in non-injected tumors with intratumoral NDV-muIL-12 in combination with anti-muPD-1 mAb muDX400 in B16F10 bilateral tumor model as described in legend for FIGS. 22A-22D. Experimental design is described in Sections 6.3.1.9 and 6.3.1.13. Tumors were harvested on Day 14, and gene expression in tumor tissues were assessed by RTqPCR and normalized to ubiquitin. Individual animal expression levels of genes for T-cell markers (FIG. 24A), cytokines (FIG. 24B), and IFN-inducible genes (FIG. 24C), and Pd-1 and Pd-l1 (FIG. 24D) in non-injected tumors are presented. Lines denote mean values. P-values<0.05 are indicated.

Figures 25A, 25B:
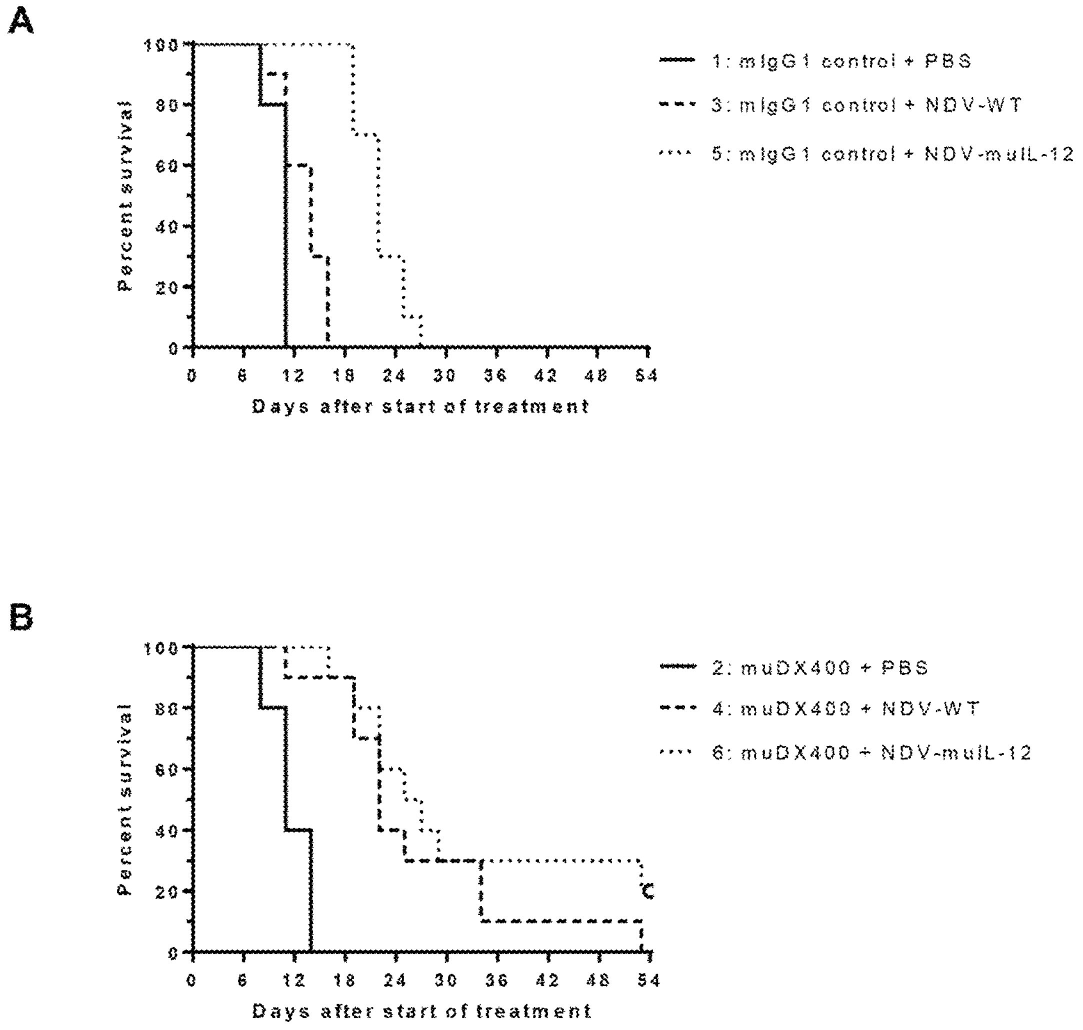

FIGS. 25A and 25B: Treatment with NDV-muIL 12 in combination with anti-muPD-1 mAb muDX400 increased survival of B16F10-bearing animals. Mouse B16-F10 cells were subcutaneously implanted into the right flanks ($2\times10^5$ cells) and left flanks ($1\times10^5$ cells) of immunocompetent C57BL/6J mice. Animals were assigned into groups 7 days after implantation (Day 0) based on tumor volume (TV) in the right flanks (injected tumors) with median TV=56 $mm^3$. The median TV in the left flanks (non-injected tumors) was 38 $mm^3$. Dosing was initiated on Day 0. Mouse IgG1 isotype control and muDX400 at 10 mg/kg were administered intraperitoneally every 4 days for a total of 3 doses. PBS, NDV-WT, and NDV-muIL-12 at $1\times10^7$ pfu were administered into the tumors on the right flanks every 2 days for a total of 4 doses. Animals were followed up to Day 54. Animals were euthanized when the sum of volumes of injected and non-injected tumors was ≥2000 $mm^3$ or body weight loss was ≥20%. There were 10 animals in each group. FIG. 25A shows survival curves for Groups 1 (mIgG1 control+PBS), 3 (mIgG1 control+NDV-WT), and 5 (mIgG1 control+NDV-muIL-12). FIG. 25B shows survival curves for Groups 2 (muDX400+PBS), 4 (muDX400+NDV-WT), and 6 (muDX400+NDV-muIL-12).

Figures 26A, 26B:
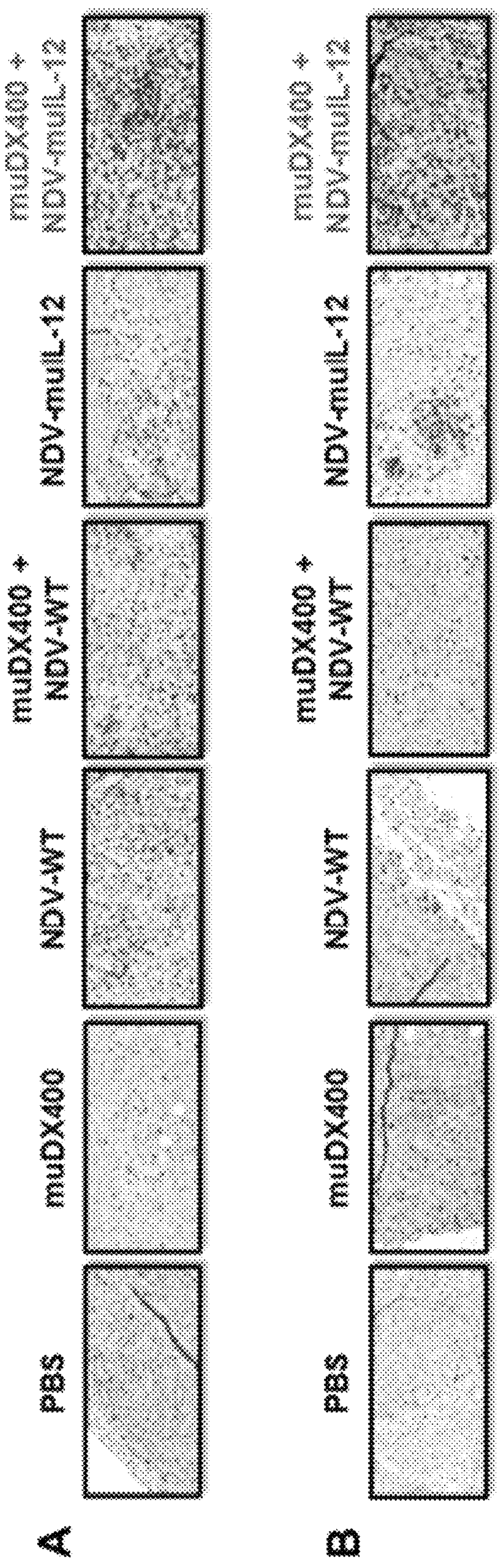

FIGS. 26A and 26B: Increased infiltration of CD3+ T cells in injected and non-injected tumors with intratumoral NDV-muIL-12 in combination with anti-muPD-1 mAb muDX400 in B16F10 bilateral tumor model. Mouse B16F10 cells were subcutaneously implanted into the right flanks ($2\times10^5$ cells) and left flanks ($1\times10^5$ cells) of immunocompetent C57BL/6J mice. Animals were assigned into groups 8 days after implantation (Day 0) based on tumor volume (TV) in the right flanks (injected tumors) with mean TV=108 $mm^3$. The mean TV=63 $mm^3$ in the left flanks. Dosing was initiated on Day 0. Mouse IgG1 isotype control and muDX400 at 10 mg/kg were administered intraperitoneally every 6 days for a total of 2 doses. PBS, NDV WT, and NDV-muIL-12 at $1\times10^7$ pfu were administered into the tumors on the right flanks every 2 days for a total of 4 doses. Experimental design is described in Sections 6.3.1.9 and 6.3.1.10. Representative images are shown for injected tumors (FIG. 26A) and non-injected tumors (FIG. 26B) on Day 8.

Figure 27A:
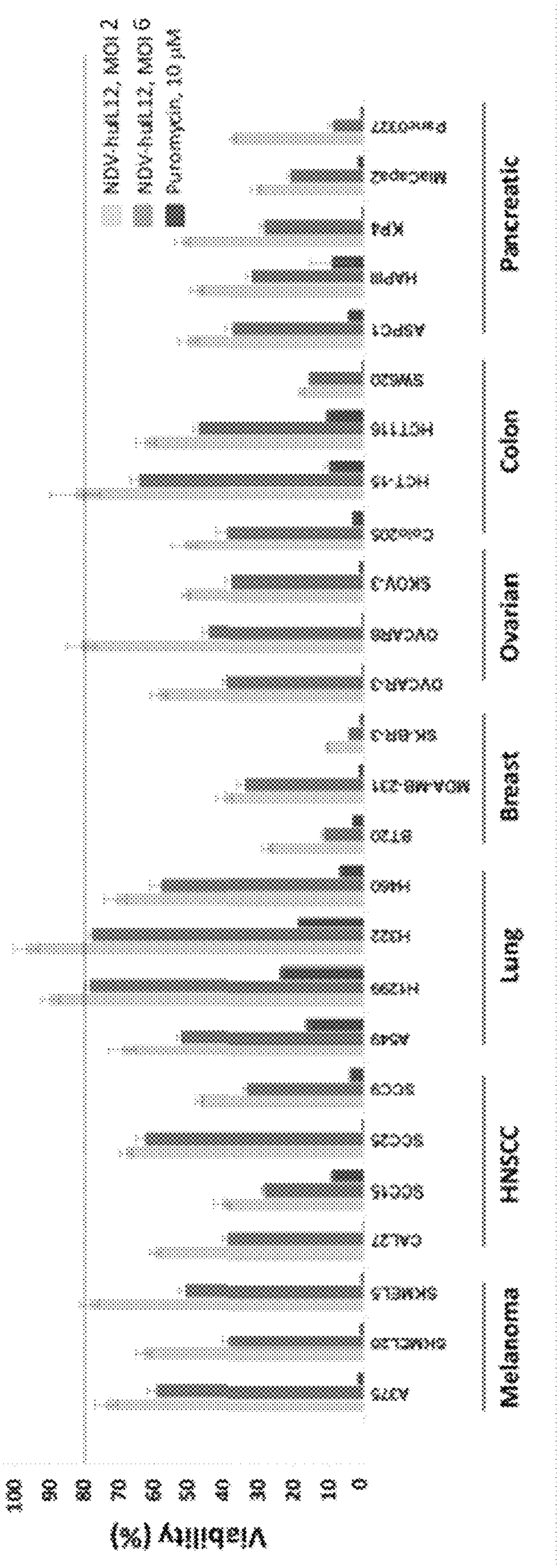

FIG. 27A: Lytic activity of NDV-huIL-12 in panel of 26 human cancer cell lines: melanoma (n=3), head and neck squamous cell carcinoma (HNSCC, n=4), lung (n=4), breast (n=3), ovarian (n=3), colon (n=4), and pancreatic (n=5). Cells were infected with NDV-huIL-12 at MOI of 2 and 6, and cell viability was determined 48 hours following infection. Viability is expressed as the percentage of viable cells in infected cells relative to uninfected cells. Treatment with 10 μM puromycin in DMSO was included as a positive control for cell killing; viability is expressed as the percentage of viable cells relative to treatment with DMSO. Values are presented as mean of 8 replicates±standard error of the mean. The dotted line indicates cut-off of 20% reduction in cell viability. DMSO=dimethyl sulfoxide. MOI=multiplicity of infection.

Figure 27B:
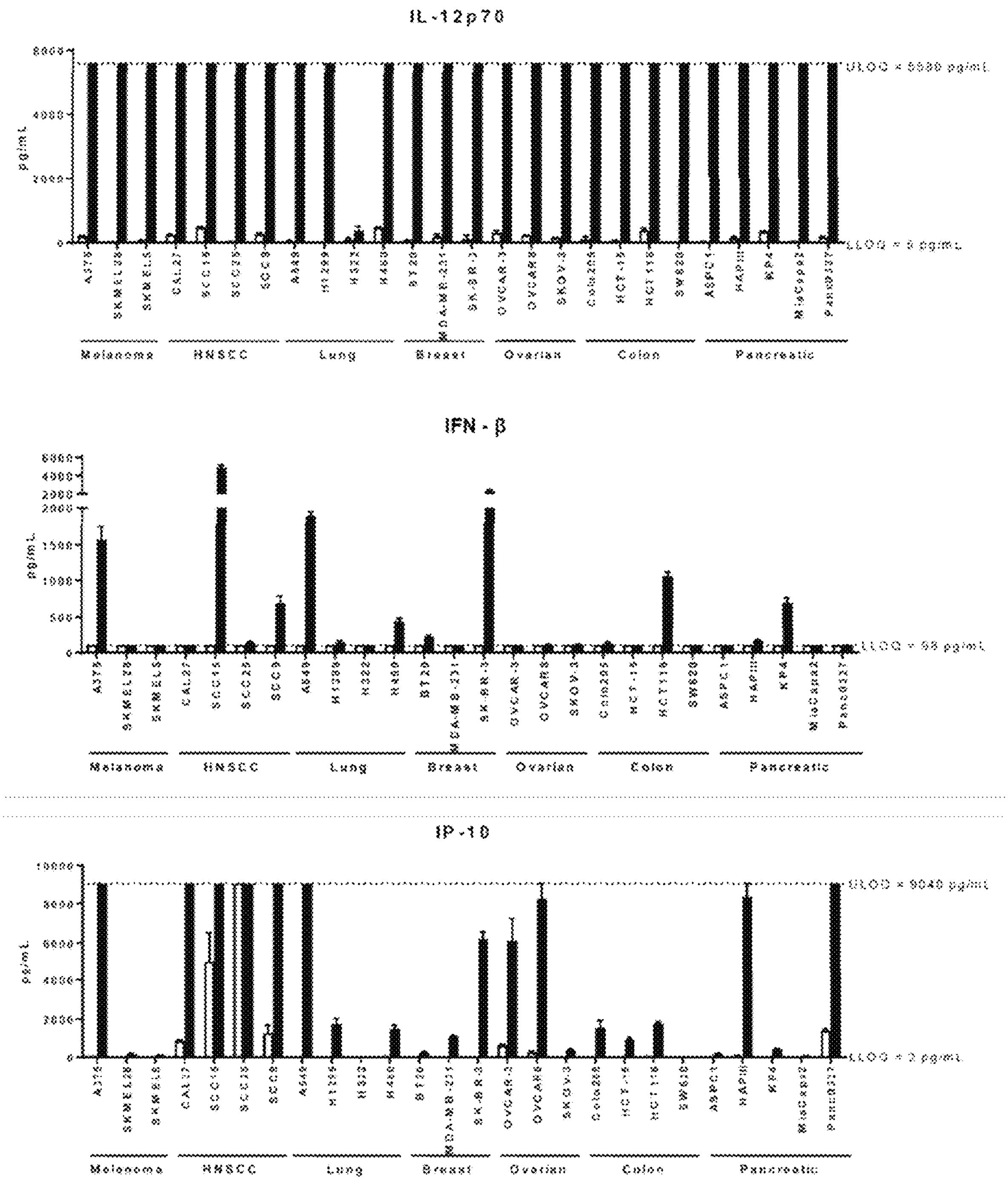

FIG. 27B: Induction of IL-12p70, IFN-γ, and IP-10 in panel of 26 human cancer cell lines. Supernatants were harvested 48 hours following mock infection (white bars) or infection with NDV-huIL-12 (MOI=2) (black bars) in a range of human tumor cell lines: melanoma (n=3), head and neck squamous cell carcinoma (HNSCC, n=4), lung (n=4), breast (n=3), ovarian (n=3), colon (n=4), and pancreatic (n=5). Supernatants were tested for protein concentrations of various cytokines and chemokines using immunoassays. Shown are the mean of 4 replicates±standard error of the mean for IL-12p70 (top), IFN-β (middle), and IP-10 (bottom). Dotted lines indicate LLOQ and ULOQ: IL 12p'70 (LLOQ=5 pg/mL and ULOQ=5580 pg/mL), IFN-β (LLOQ=98 pg/mL), and IP-10 (LLOQ=2 pg/mL and ULOQ=9040 pg/mL). LLOQ=lower limit of quantitation; MOI=multiplicity of infection; and ULOQ=upper limit of quantitation.

Figure 28:
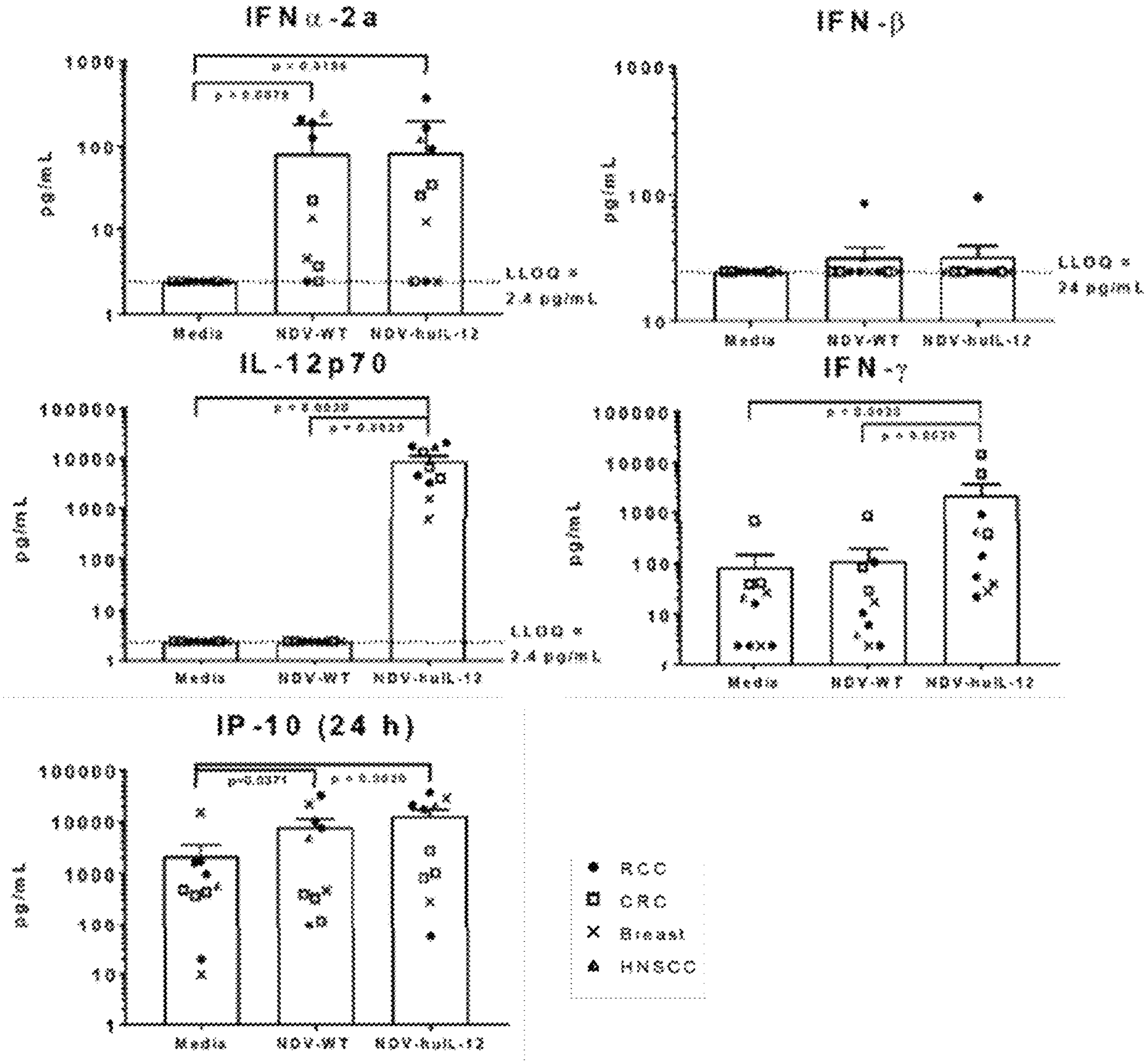
Figures 29A, 29B, 29C, 29D:
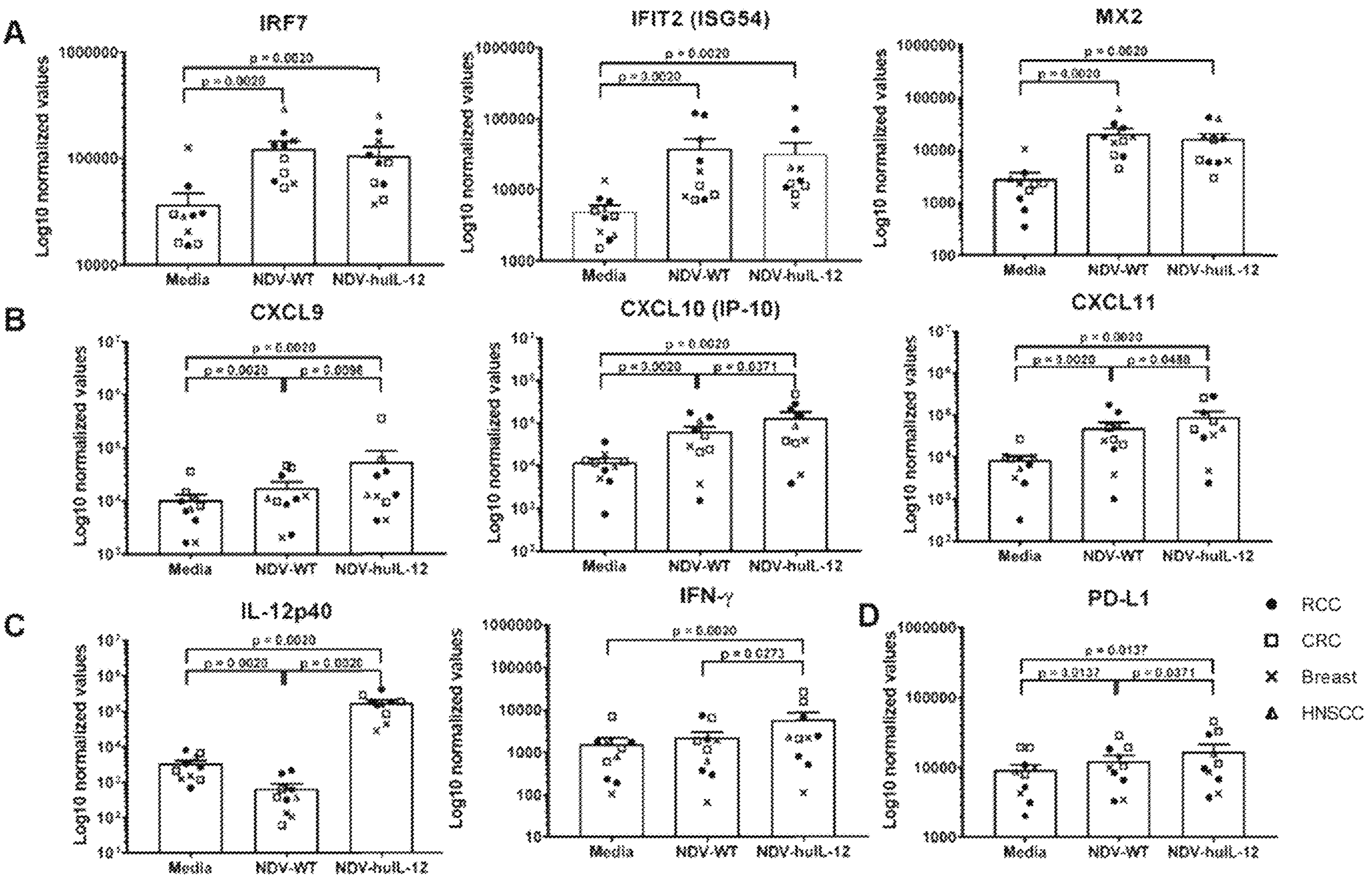

FIG. 28: Induction of IFN-α-2a, IL-12, IFN-γ, and IP-10 in human tumor histoculture with treatment with NDV-huIL-12. Samples of renal cell carcinoma (RCC, n=4), colorectal carcinoma (CRC, n=3), breast carcinoma (n=2), and head and neck squamous cell carcinoma (HNSCC; n=1) were untreated (media) or treated with $3\times10^7$ pfu NDV-WT or NDV-huIL-12 for up to 48 hours. Supernatants were collected from the histoculture for assessment of protein concentrations of various cytokines and chemokines using immunoassays. Shown are the mean±standard error of the mean (Wilcoxon signed rank test, p-values<0.05 are indicated) for IFN-α-2a, IFN-β, IL-12p70, IFN-γ, and IP-10. Dotted lines indicate LLOQ values: IFN-α-2a=2.4 pg/mL, IFN-β=24 pg/mL, IL-12p70=2.4 pg/mL. With the exception of IP-10, where supernatants were collected at 24 hours and assayed at 1:15 dilution, data are shown for undiluted supernatant collected at 48-hour time point. LLOQ=lower limit of quantitation.

FIGS. 29A-29D: Induction of gene expression of IFN-inducible genes, chemokines, Il-12p40, Ifn-γ, and Pd-11 (gene encoding PD-L1) in human tumor histoculture with treatment with NDV-huIL-12. Samples of renal cell carcinoma (RCC, n=4), colorectal carcinoma (CRC, n=3), breast carcinoma (n=2), and head and neck squamous cell carcinoma (HNSCC, n=1) were untreated (media) or treated with $3\times10^7$ pfu NDV-WT or NDV-huIL-12 for up to 48 hours. The samples were snap-frozen, and following RNA isolation, gene expression of panel of immune genes was analyzed using the Fluidigm RTqPCR platform. Shown are the mean of the values normalized to ubiquitin±standard error of the mean (Wilcoxon signed rank test, p values<0.05 are indicated) for IFN-inducible genes (FIG. 29A), chemokines (FIG. 29B), Il-12p40 and Ifn-γ (FIG. 29C), and Pd-11 (FIG. 29D) for 48-hour time point.

Figure 30:
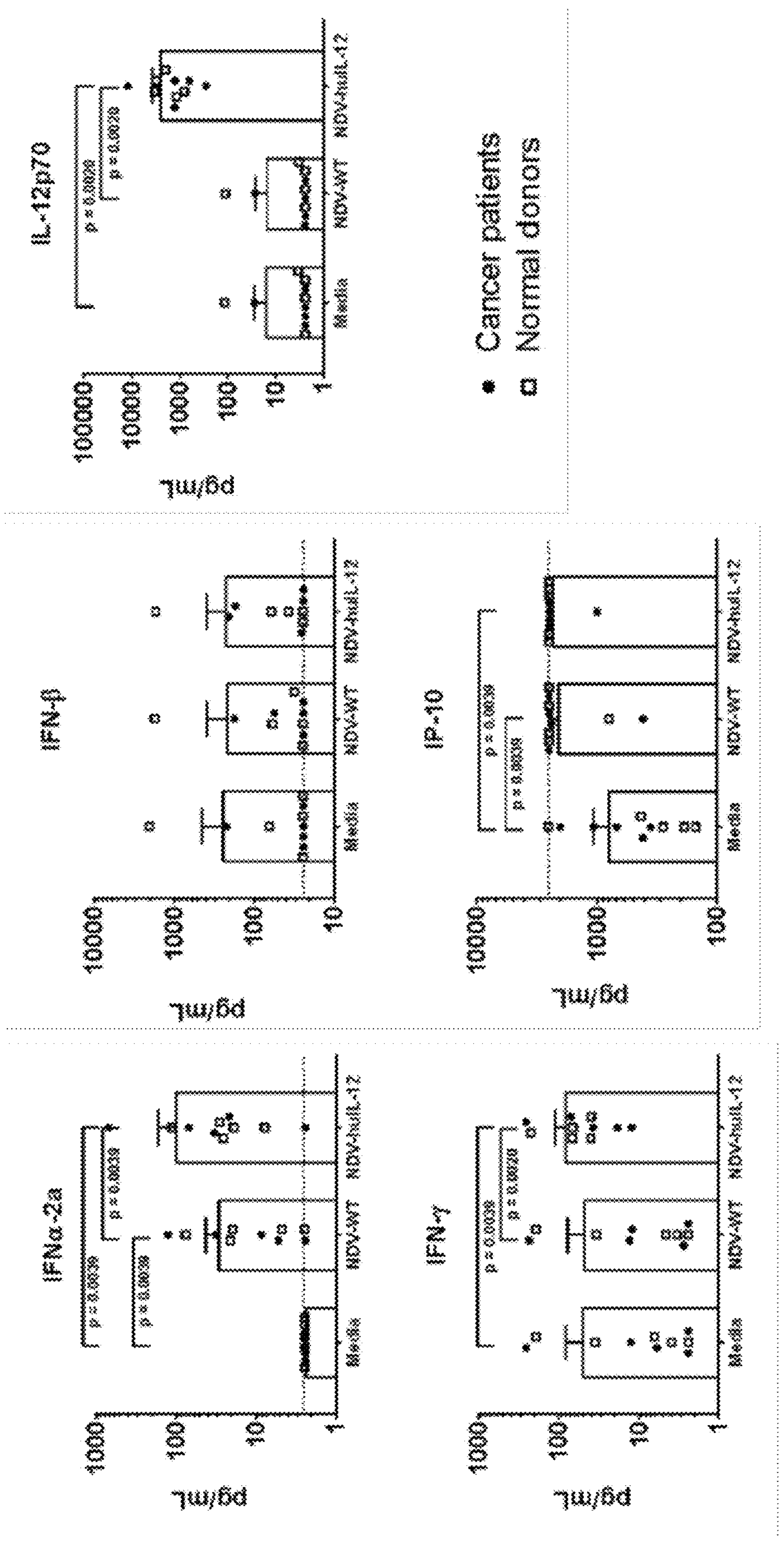
Figures 31A, 31B, 31C, 31D:
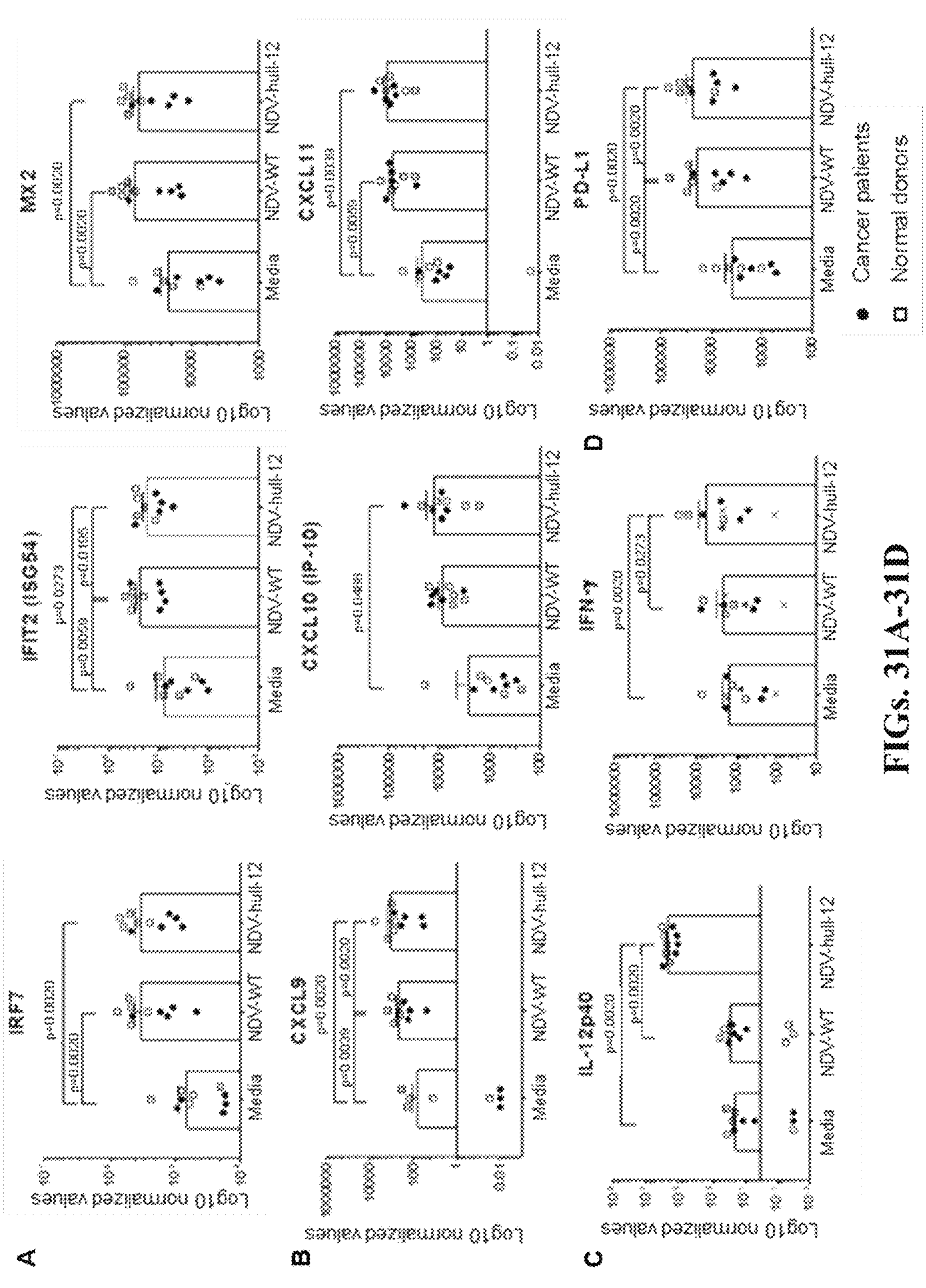

FIG. 30: Induction of IFN-α-2a, IL-12p70, IFN-γ, and IP-10 in human whole blood with NDV-huIL 12 treatment. Whole blood (1 mL) from patients with solid cancers (n=5) and normal healthy donors (n=5) were untreated (media) or treated with $3\times10^7$ pfu NDV-WT or NDV-huIL-12 for 48 hours. Plasma was collected for assessment of protein concentrations of various cytokines and chemokines using immunoassays. Shown are the mean±standard error of the mean (Wilcoxon signed rank test, p values<0.05 are indicated) for IFN-α-2a, IFN-β, IL-12p70, IFN-γ, and IP-10. Dotted lines indicate either LLOQ or ULOQ values: IFN-α-2a (LLOQ)=2.4 pg/mL, IFN-β (LLOQ)=24 pg/mL, IP-10 (ULOQ)=2610 pg/mL. Values are shown for undiluted supernatant collected at the 48-hour time point. LLOQ=lower limit of quantitation; ULOQ=upper limit of quantitation.

FIGS. 31A-31D: Induction of gene expression of IFN-inducible genes, chemokines, Il-12p40, Ifn-γ, and Pd-11 in human whole blood with NDV-huIL 12 treatment. Whole blood (4 mL) from patients with solid cancers (n=5) and normal healthy donors (n=5) were untreated (media) or treated with $12\times10^7$ pfu NDV-WT or NDV-huIL-12 for 24 hours. Whole blood was collected into PAXgene blood RNA tubes, and following RNA isolation, gene expression of panel of immune genes was analyzed using the Fluidigm RTqPCR platform. Shown are the mean of the values normalized to ubiquitin±standard error of the mean (Wilcoxon signed rank test, p-values<0.05 are indicated) for IFN-inducible genes (FIG. 31A), chemokines (FIG. 31B), Il-12p40 and Ifn-γ (FIG. 31C), and Pd-11 (FIG. 31D) for 24-hour time point.

Figure 32:
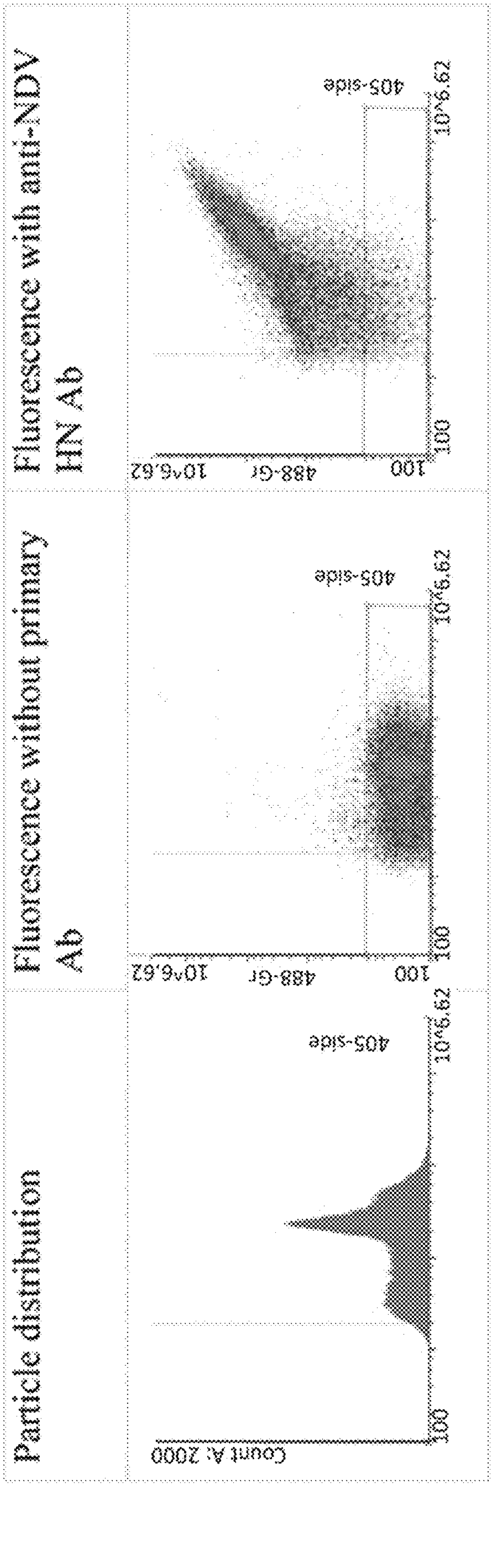

FIG. 32: Analysis of NDV-huIL-12 by flow virometry.

Figure 33:
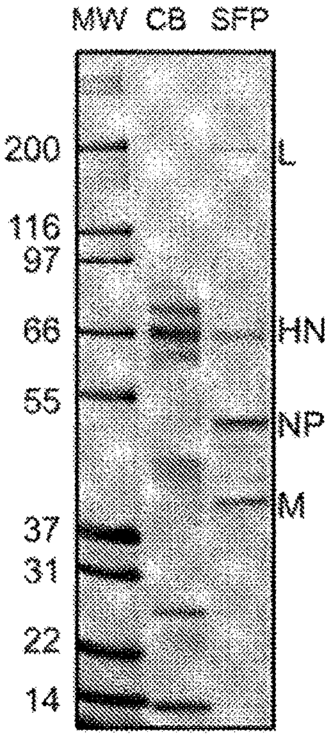

FIG. 33: Analysis of NDV-huIL-12 by reducing SDS-PAGE. MW: Molecular weight marker; CB: clarified bulk; and SFP: sterile filtered product.

Figure 34:
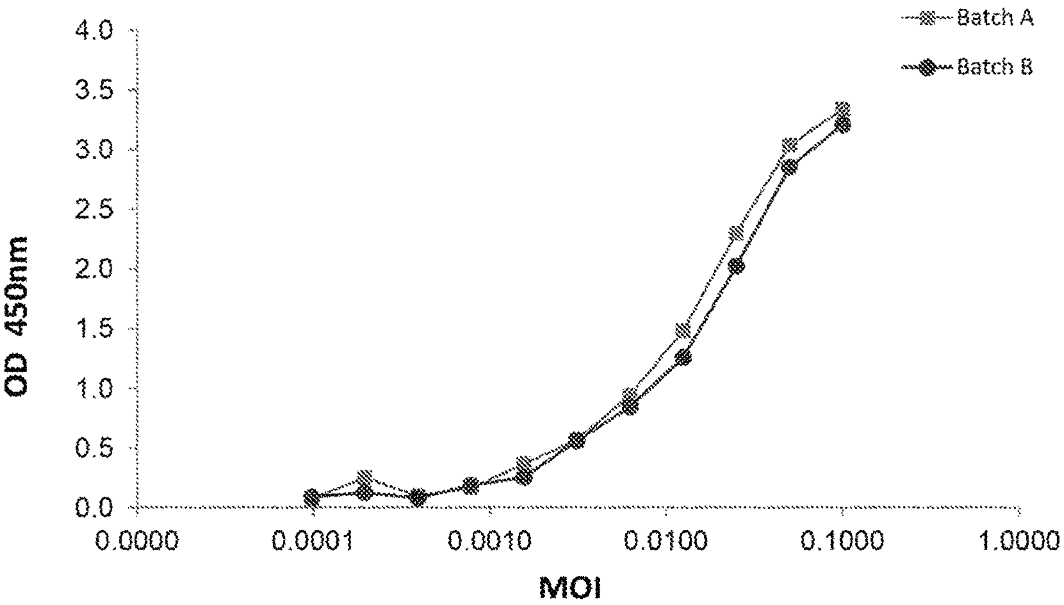

FIG. 34: MOI-dependent huIL-12 expression curve following 24-hour Vero cell infection by NDV-huIL-12.

Figure 35:
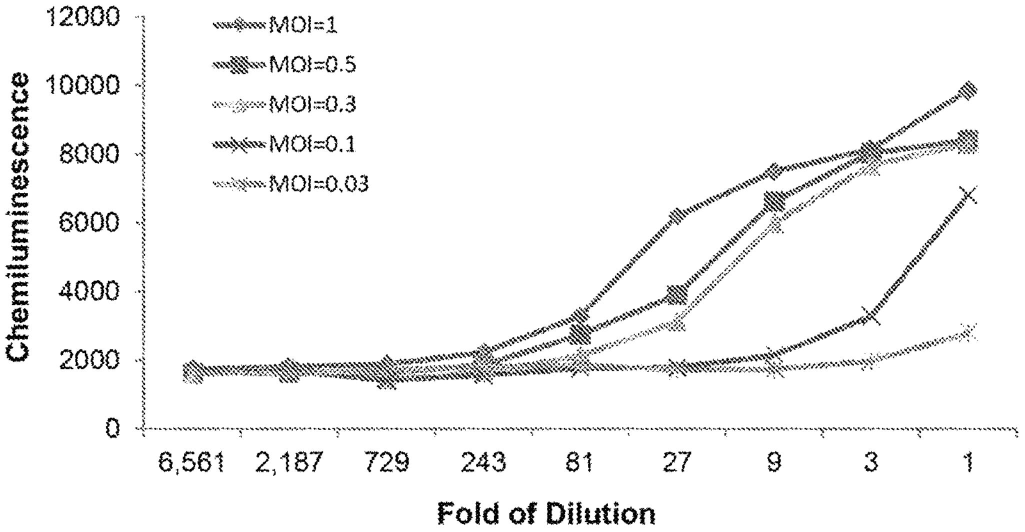

FIG. 35: huIL-12 induced receptor dimerization using PathHunter® Bioassay Detection kit. Each curve represents the titration of huIL-12 produced by Vero cells following 24-hour infection of NDV-huIL-12 at the indicated MOI.

Figure 36:
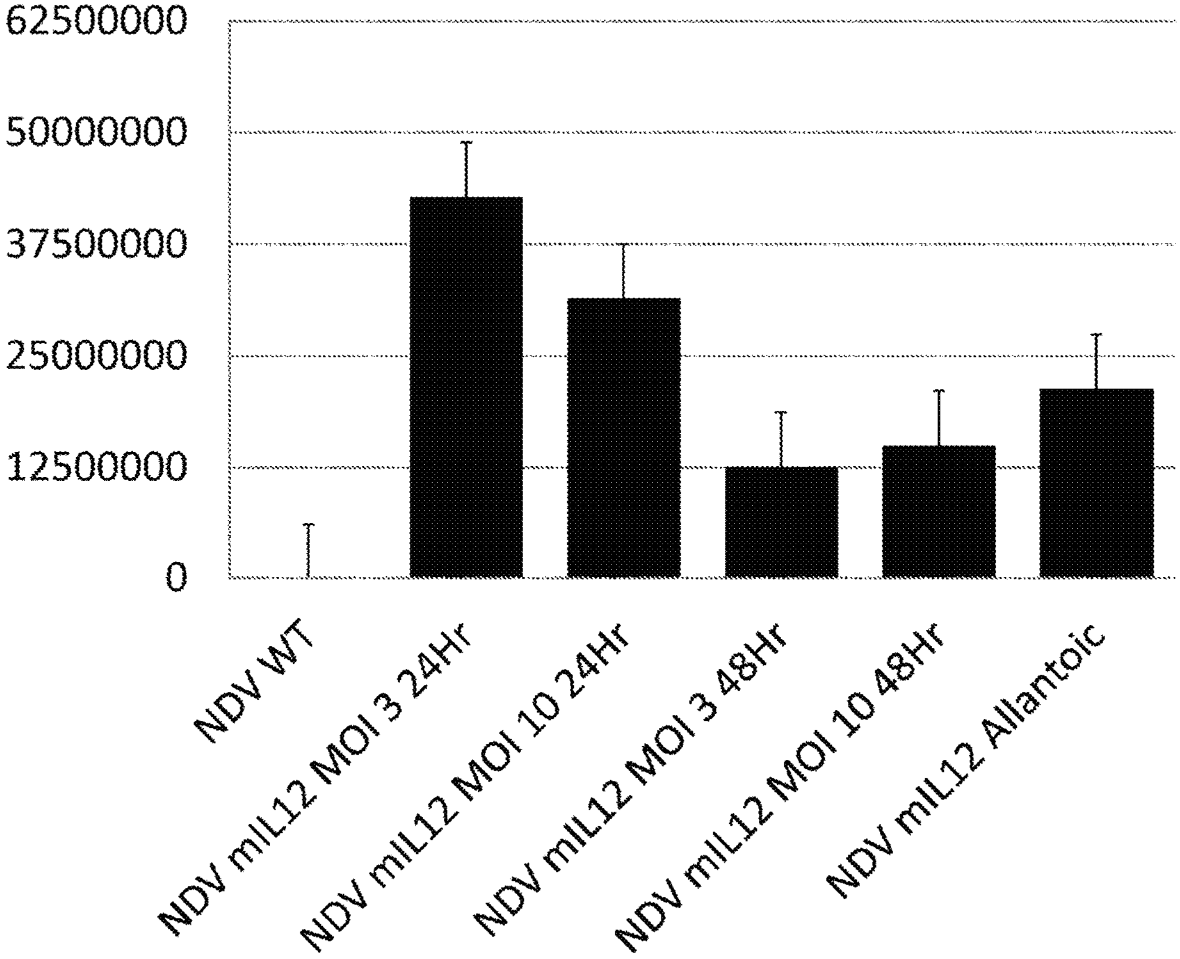

FIG. 36: rNDV-mIL12 Expression in BSRT7 cells and allantoic fluid. Y axis is concentration of muIL-12 in pg/mL as determined using the commercially available ELISA kit (Mouse IL-12p70 QUANTIKINE® ELISA Kit, R&D Systems, Catalog No. M1270). From left to right: BSRT7 cells infected with NDV-WT (negative control), NDV-muIL-12 (MOI=3, 24 hpi), NDV-muIL-12 (MOI=10, 24 hpi), NDV-muIL-12 (MOI=3, 48 hpi), or NDV-muIL-12 (MOI=10, 48 hpi), or allantoic fluid from NDV-muIL-12 infected eggs. MOI=multiplicity of infection. Hpi=hours post-infection.

Figures 37A, 37B, 37C, 37D, 37E, 37F, 37G:
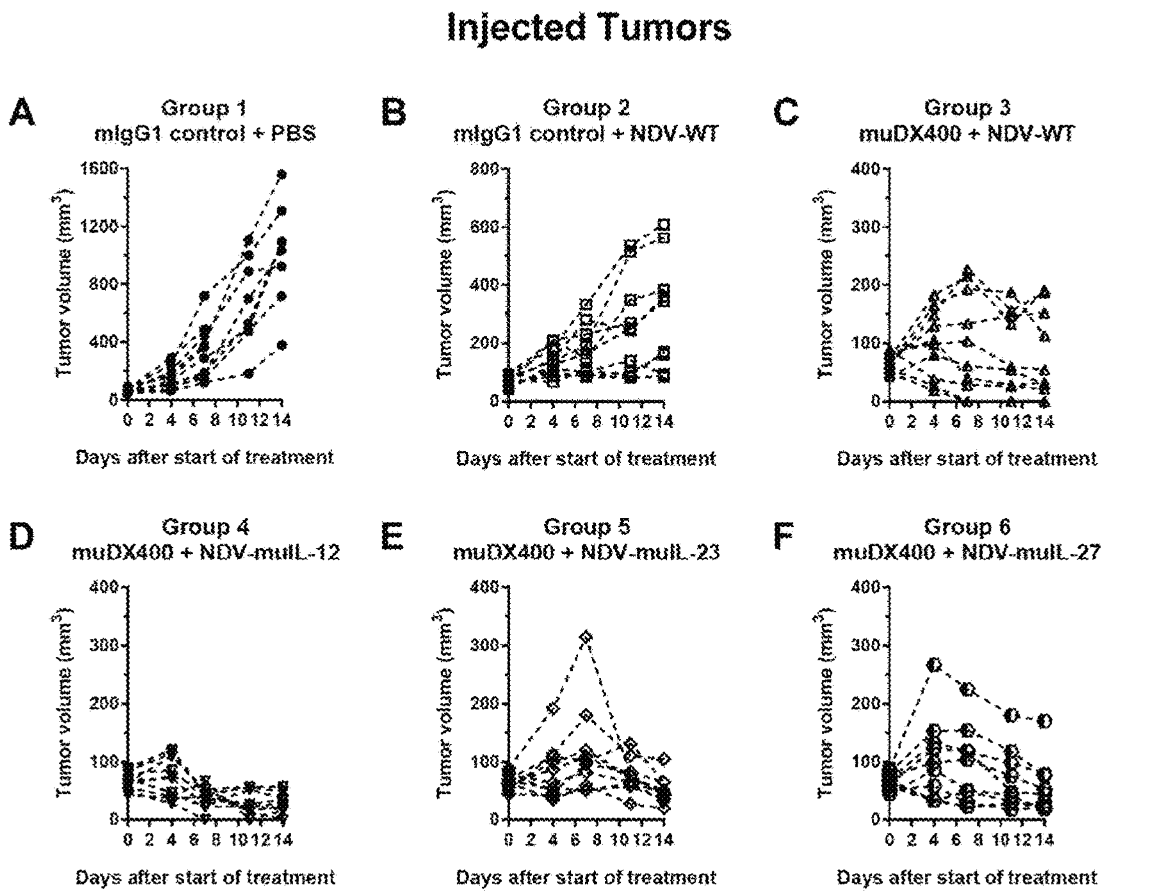
Figures 37H, 37I, 37J, 37K, 37L, 37M, 37N:
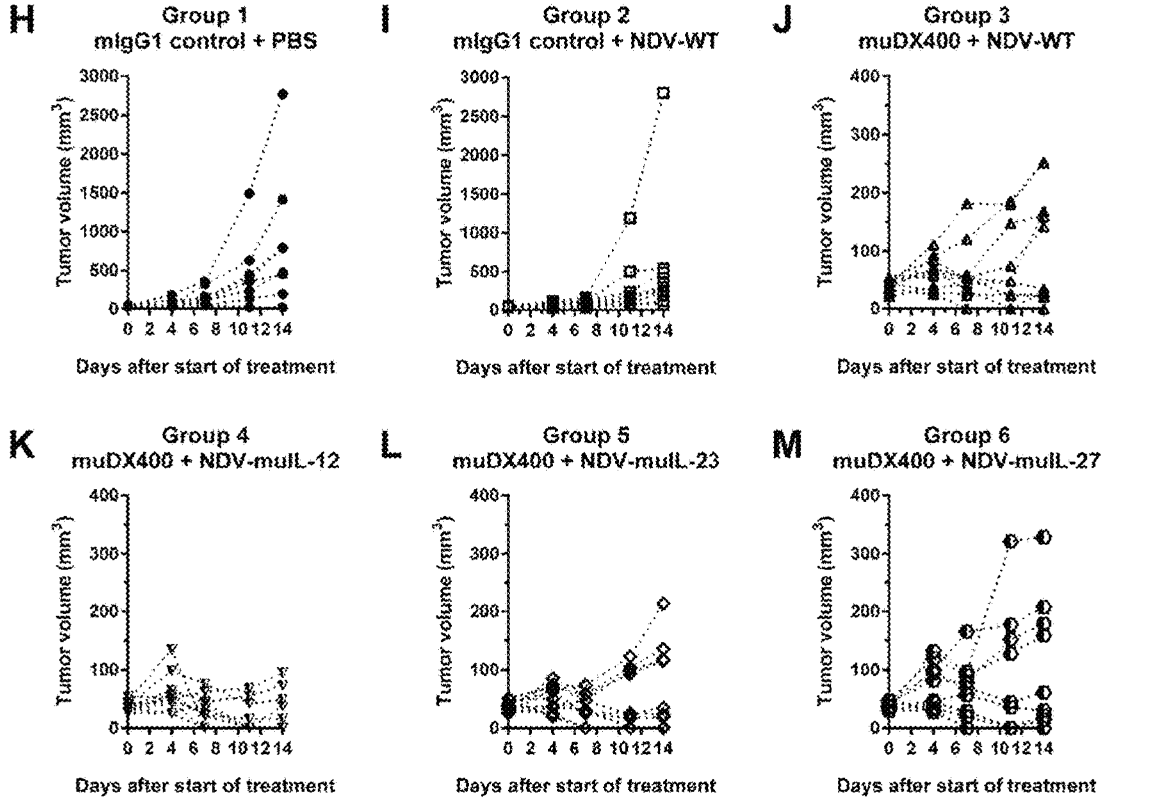

FIGS. 37A-37N: Enhanced anti-tumor efficacy with NDV-muIL-12 versus NDV-muIL-23 or NDV-muIL-27 in combination with anti-muPD-1 mAb muDX400 in B16F10 bilateral tumor model. Mouse B16F10 cells were subcutaneously implanted into the right flanks ($2\times10^5$ cells) and left flanks ($1\times10^5$ cells) of immunocompetent C57BL/6J mice. Animals were assigned into groups 9 days after implantation (Day 0) based on tumor volume (TV) in the right flanks (injected tumors) with median TV=65 $mm^3$. The median TV in the left flanks (non-injected tumors) of the 6 groups ranged from 31 to 43 $mm^3$. Dosing was initiated on Day 0. Mouse IgG1 isotype control and muDX400 at 10 mg/kg were administered intraperitoneally every 4 days for a total of 3 doses. PBS, NDV-WT, NDV-muIL-12, NDV-muIL-23, and NDV-muIL-27 at $1\times10^7$ pfu were administered into the tumors on the right flanks every 2 days for a total of 5 doses. There were 10 animals in each group. Individual animal growth curves for injected are presented: Group 1: mIgG1 control+PBS (FIG. 37A); Group 2: muDX400+PBS (FIG. 37B); Group 3: muDX400+NDV-WT (FIG. 37C); Group 4: muDX400+NDV-muIL-12 (FIG. 37D); Group 5: muDX400+NDV-muIL-23 (FIG. 37E); Group 6: muDX400+NDV-muIL-27 (FIG. 37F). Day 14 tumor volume (median with 68% confidence intervals) and the number of complete and partial regressions for injected tumors are presented in FIG. 37G. Individual animal growth curves for non-injected are presented: Group 1: mIgG1 control+PBS (FIG. 37H); Group 2: muDX400+PBS (FIG. 37I); Group 3: muDX400+NDV-WT (FIG. 37J); Group 4:

muDX400+NDV-muIL-12 (FIG. 37K); Group 5: muDX400+NDV-muIL-23 (FIG. 37L); Group 6: muDX400+NDV-muIL-27 (FIG. 37M). Day 14 tumor volume (median with 68% confidence intervals) and the number of complete and partial regressions for non-injected tumor are presented in FIG. 37N.

Figures 38A, 38B, 38C, 38D, 38E, 38F, 38G, 38H:
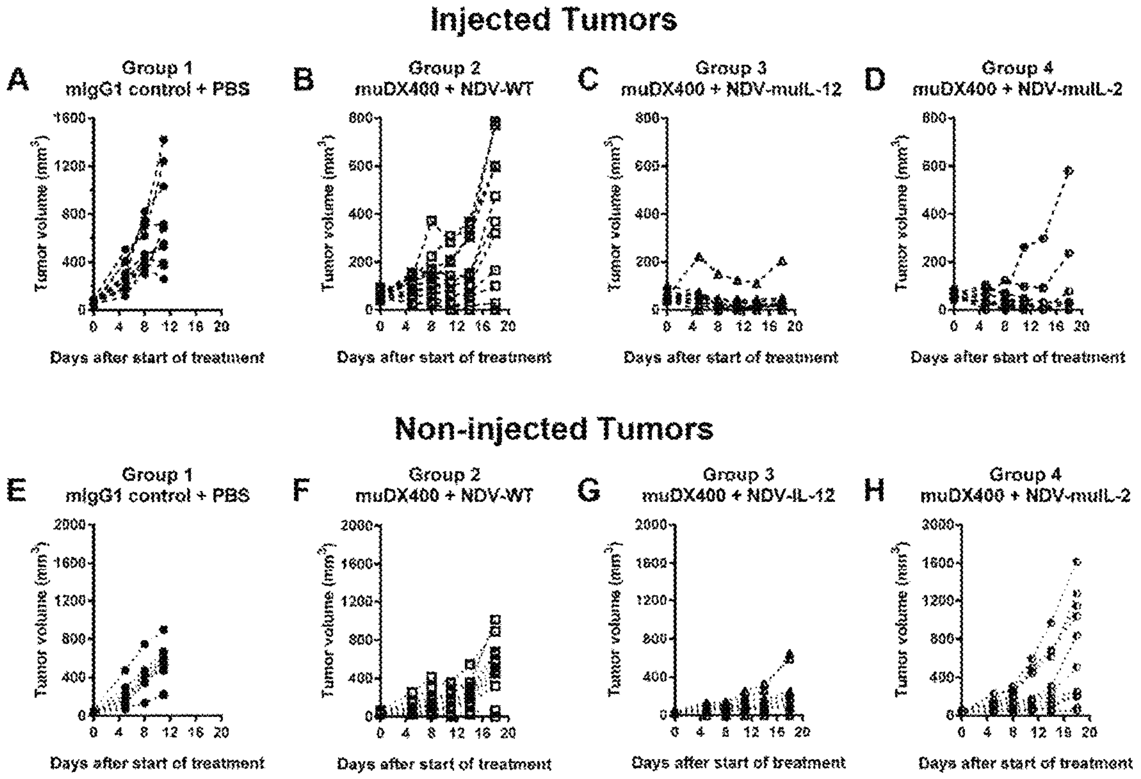

FIGS. 38A-38J: Enhanced anti-tumor efficacy with NDV-muIL-12 versus NDV-muIL-2 with anti-muPD-1 mAb muDX400 in B16F10 bilateral tumor model. Mouse B16F10 cells were subcutaneously implanted into the right flanks ($2\times10^5$ cells) and left flanks ($1\times10^5$ cells) of immunocompetent C57BL/6J mice. Animals were assigned into groups 10 days after implantation (Day 0) based on tumor volume (TV) in the right flanks (injected tumors) with median TV=55 $mm^3$. The median TV in the left flanks (non-injected tumors) was 34 $mm^3$. Dosing was initiated on Day 0. Mouse IgG1 isotype control and muDX400 at 10 mg/kg were administered intraperitoneally every 4 days for a total of 5 doses. PBS, NDV-WT, NDV-muIL-12, and NDV-muIL-2 at $1\times10^7$ pfu were administered into the tumors on the right flanks every 2 days for a total of 4 doses. There were 12 animals in each group. Individual animal growth curves for injected are presented: Group 1: mIgG1 control+PBS (FIG. 38A); Group 2: muDX400+NDV-WT (FIG. 38B); Group 3: muDX400+NDV-muIL-12 (FIG. 38C); Group 4: muDX400+NDV-muIL-2 (FIG. 38D). Individual animal growth curves for non-injected are presented: Group 1: mIgG1 control+PBS (FIG. 38E); Group 2: muDX400+NDV-WT (FIG. 38F); Group 3: muDX400+NDV-muIL-12 (FIG. 38G); Group 4: muDX400+NDV-muIL-2 (FIG. 38H). For injected and non-injected tumors, tumor volume of the last measurement (median with 68% confidence intervals) and the number of complete and partial regressions are presented in FIG. 38I and FIG. 38J, respectively.

Figure 39:
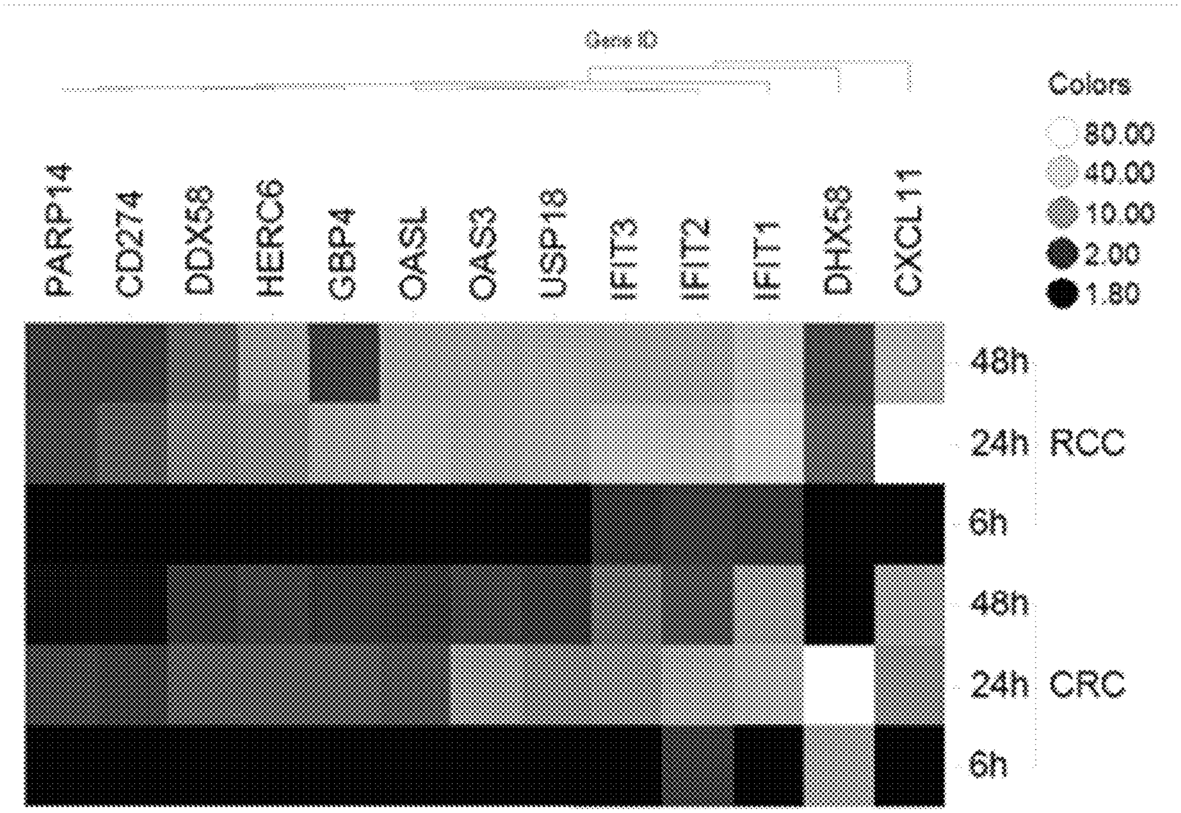

FIG. 39: Induction of NDV-huIL-12 response signature in human tumor histoculture with treatment with NDV-huIL-12. Samples of renal cell carcinoma (RCC, n=7) and colorectal carcinoma (CRC, n=7) were untreated (media) or treated with $3\times10^7$ pfu NDV-huIL-12 for up to 48 hours. The samples were snap-frozen, and following RNA isolation, gene expression of panel of immune genes was analyzed using the Fluidigm Biomark RTqPCR platform. Shown are the mean fold change in expression between NDV-huIL-12 and untreated (media) at 6, 24 and 48 hours; values normalized to ubiquitin were used in calculating fold change.

Figure 40A:
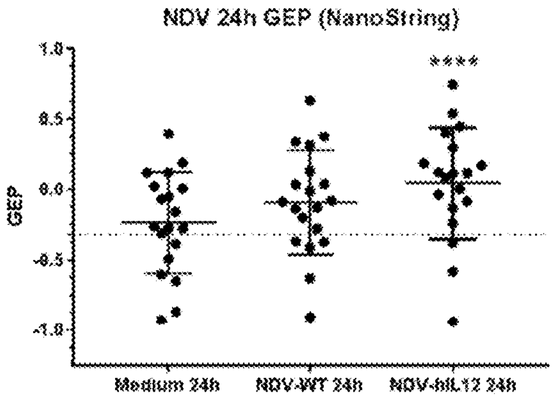
Figure 40B:
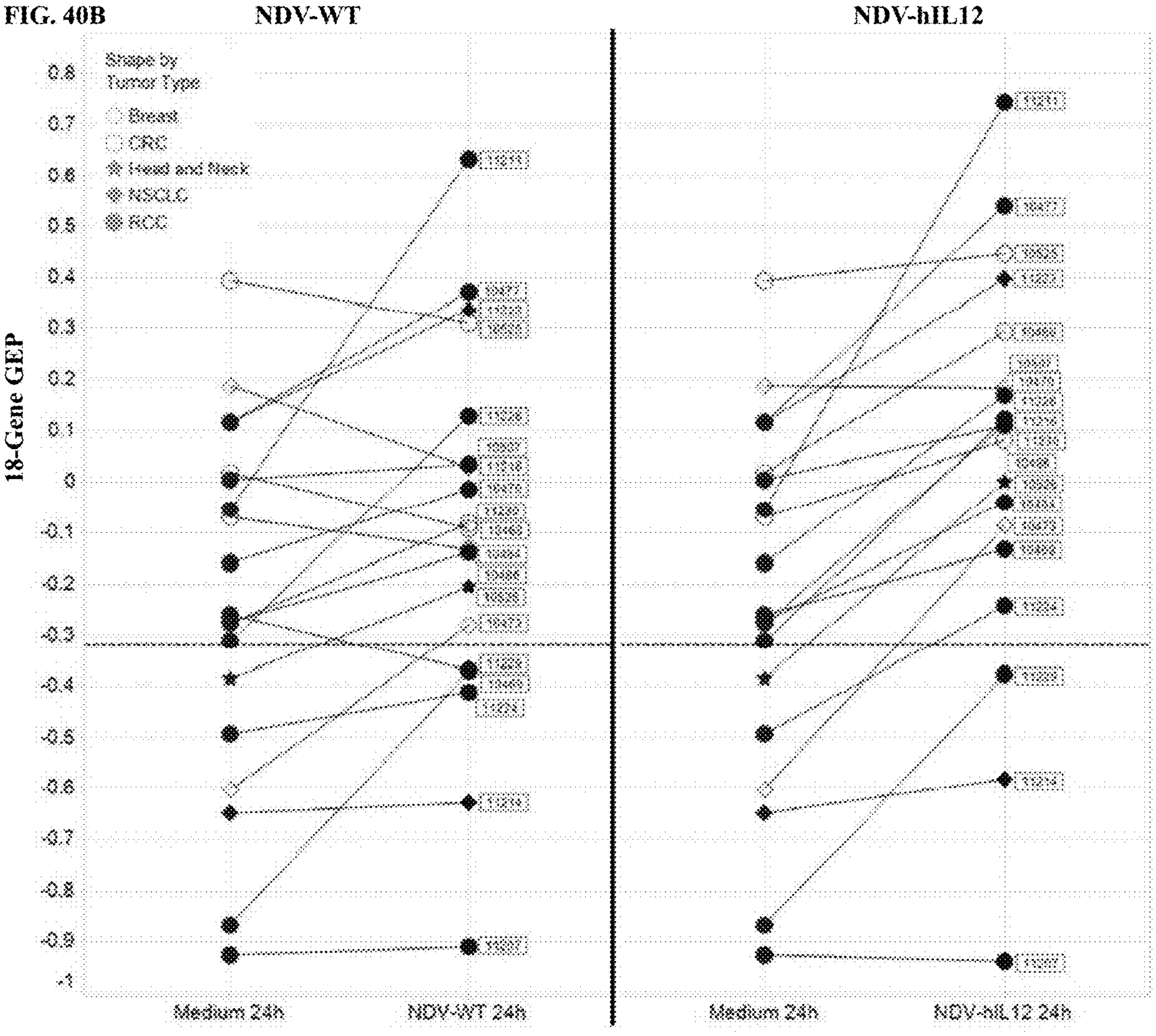

FIGS. 40A-B: Induction of the T-cell inflamed, IFN-γ-related gene signature (18-GEP) score with NDV and NDV-huIL-12 in both GEP-negative and GEP-positive tumors. Samples of renal cell carcinoma (RCC, n=10), colorectal carcinoma (CRC, n=4), breast carcinoma (n=2), non-small cell lung caricinoma (n=2), and head and neck squamous cell carcinoma (HNSCC, n=1) were untreated (media) or treated with either $3\times10^7$ pfu NDV-WT or $3\times10^7$ pfu NDV-huIL-12 for up to 24 hours. The samples were snap-frozen, and following RNA isolation, 18-gene GEP signature was analyzed using the NanoString platform. Shown are the mean GEP score with standard deviation and p-value (ANOVA Friedman Test, followed by Dunn's multiple comparison test) (FIG. 40A) and individual GEP score (FIG. 40B).

Figure 41A:
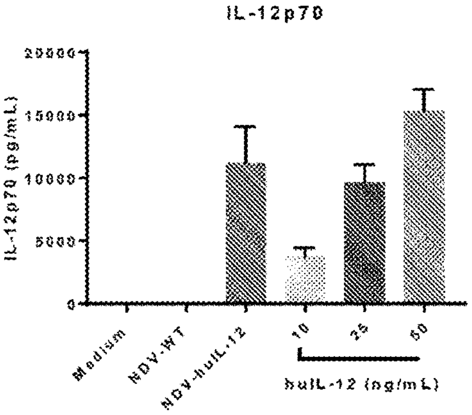
Figure 41B:
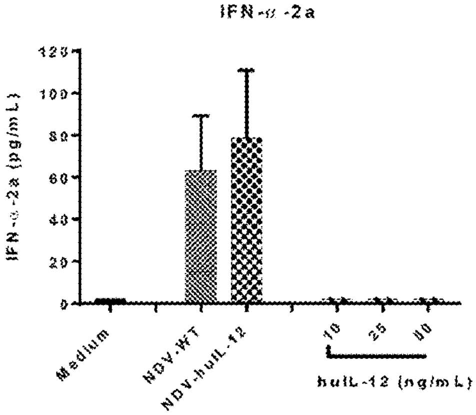
Figure 41C:
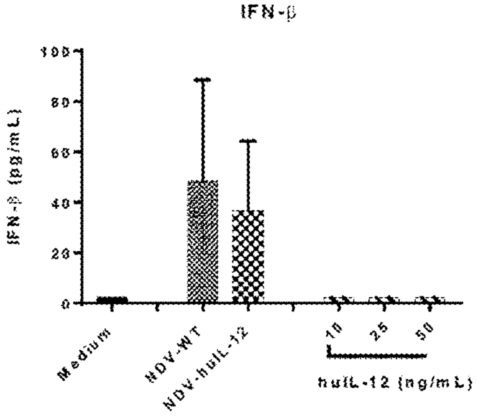
Figure 41D:
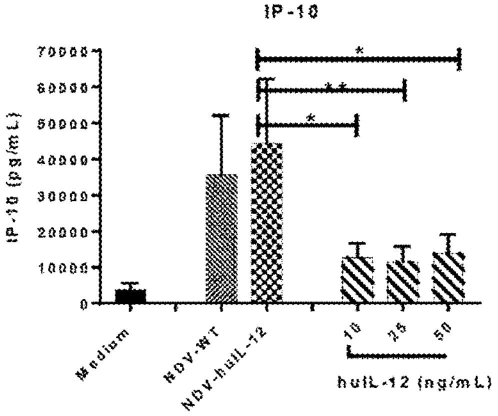

FIGS. 41A-D: Induction of Type I interferons and IP-10 by recombinant IL-12 and NDV-huIL 12. Histoculture samples from renal cell carcinoma (RCC, n=6), colorectal carcinoma (CRC, n=1), and non-small cell lung cancer (NSCLC, n=2) were untreated (media) or treated with $3\times10^7$ pfu NDV-WT, $3\times10^7$ NDV-huIL-12, or recombinant human IL-12 (10, 25, and 50 ng/mL) for up to 48 hours. The supernatants were collected and analyzed for secretion of IL-12p70 (FIG. 41A), IFN-α-2a (FIG. 41B), IFN-β (FIG. 41C), and IP-10 (FIG. 41D). Shown are the mean value with SEM and p-value (ANOVA Friedman Test, followed by Dunn's multiple comparison test).

5. DETAILED DESCRIPTION

In one aspect, presented herein are methods for treating cancer utilizing an NDV described herein (e.g., an NDV or a chimeric NDV described in Section 5.1 or Section 5.2, infra) or a composition comprising such a chimeric NDV. In a specific embodiment, a method for treating cancer comprises infecting a cancer cell in a subject with a chimeric NDV described herein (e.g., a chimeric NDV described in Section 5.2, infra) or a composition thereof. In another embodiment, a method for treating cancer comprises administering to a subject in need thereof a chimeric NDV described herein (e.g., a chimeric NDV described in Section 5.2, infra) or a composition thereof. In specific embodiments, an effective amount of a chimeric NDV described herein (e.g., a chimeric NDV described in Section 5.2, infra) or a composition comprising an effective amount of a chimeric NDV described herein is administered to a subject to treat cancer. In a specific embodiment, the chimeric NDV comprises a packaged genome that encodes IL-12 (e.g., the IL-12 p35 and IL-12 p40 subunits). In a specific embodiment, the IL-12 (e.g., human IL-12) is expressed by cells infected with the chimeric NDV. In certain embodiments, the genome of the NDV also encodes a mutated F protein. In certain embodiments, two or more chimeric NDVs are administered to a subject to treat cancer.

In another embodiment, a method for treating cancer comprises administering to a subject in need thereof cancer cells infected with an NDV described herein (e.g., an NDV or a chimeric NDV described in Section 5.1 and/or Section 5.2, infra) or composition thereof. In specific embodiments, the cancer cells have been treated with gamma radiation prior to administration to the subject or incorporation into the composition. In another embodiment, a method for treating cancer comprises administering to a subject in need thereof a protein concentrate or plasma membrane fragments from cancer cells infected with a chimeric NDV (e.g., a chimeric NDV described in Section 5.2, infra) or a composition thereof. In specific embodiments, the chimeric NDV comprises a packaged genome which encodes IL-12 (e.g., human IL-12), wherein the IL-12 is expressed by the NDV. In certain embodiments, the genome of the NDV also encodes a mutated F protein, which is expressed by the NDV.

In another aspect, presented herein are methods for treating cancer utilizing an NDV described herein (e.g., a chimeric NDV such as described in Section 5.2, infra) or a composition comprising the NDV in combination with one or more other therapies. In one embodiment, presented herein are methods for treating cancer comprising administering to a subject (e.g., a human subject) an NDV described herein (e.g., a chimeric NDV, such as described in Section 5.2, infra) and one or more other therapies. In another embodiment, presented herein are methods for treating cancer comprising administering to a subject (e.g., a human subject) an effective amount of an NDV described herein or a composition comprising an effective amount of an NDV described herein, and one or more other therapies. In a specific embodiment, presented herein are uses of an NDV described herein (e.g., a chimeric NDV such as described in Section 5.2, infra) in the preparation of a medicament for use in combination with one or more other therapies for treating cancer in a subject (e.g., a human subject). In another specific embodiment, presented herein are an NDV described herein (e.g., a chimeric NDV such as described in Section 5.2, infra) for use in a method for treating cancer in a subject (e.g., a human subject), wherein the method further comprises administering one or more other therapies.

In a preferred embodiment, the one or more therapies includes an antagonist of PD-1 or a ligand thereof (e.g., an anti-PD-1 antibody that blocks the interaction between PD-1 and a ligand thereof (e.g., PD-L1, PD-L2 or both PD-L1 and PD-L2) or anti-PD-1 L1 antibody that blocks the interaction between PD-L1 and PD-1). The NDV and one or more other therapies can be administered concurrently or sequentially to the subject. In certain embodiments, the NDV and one or more other therapies are administered in the same composition. In other embodiments, the NDV and one or more other therapies are administered in different compositions. The NDV and one or more other therapies can be administered by the same or different routes of administration to the subject.

In another aspect, presented herein are methods for treating cancer utilizing a chimeric NDV described herein (e.g., a chimeric NDV such as described in Section 5.2, infra), or a composition comprising such the chimeric NDV, in combination with an antagonist of PD-1 or a ligand thereof, wherein the chimeric NDV comprises a packaged genome comprising a transgene encoding IL-12 (e.g., human IL-12). In one embodiment, presented herein are methods for treating cancer comprising administering to a subject (e.g., a human subject) a chimeric NDV described herein (e.g., a chimeric NDV, such as described in Section 5.2, infra) and an antagonist of PD-1 or a ligand thereof, wherein the chimeric NDV comprises a packaged genome comprising a transgene encoding IL-12 (e.g., human IL-12). In another embodiment, presented herein are methods for treating cancer comprising administering to a subject (e.g., a human subject) an effective amount of a chimeric NDV described herein or a composition comprising an effective amount of a chimeric NDV described herein, and an antagonist of PD-1 or a ligand thereof, wherein the chimeric NDV comprises a packaged genome comprising a transgene encoding IL-12 (e.g., human IL-12). The chimeric NDV and antagonist of PD-1 or a ligand thereof can be administered concurrently or sequentially to the subject. In certain embodiments, the chimeric NDV and antagonist of PD-1 or a ligand thereof are administered in the same composition. In other embodiments, the chimeric NDV and antagonist of PD-1 or a ligand thereof are administered in different compositions. The chimeric NDV and antagonist of PD-1 or a ligand thereof can be administered by the same or different routes of administration to the subject. In a specific embodiment, the chimeric NDV is administered intratumorally and the antagonist is administered intravenously.

In one embodiment, presented herein are uses of a chimeric NDV in the preparation of a medicament for use in combination with an antagonist of PD-1 or a ligand thereof for use in treating cancer in a subject (e.g., a human subject) a chimeric NDV described herein, wherein the chimeric NDV comprises a packaged genome comprising a transgene encoding IL-12 (e.g., human IL-12). In another embodiment, presented herein are a chimeric NDV for use in a method for treating cancer in a subject (e.g., a human subject), wherein the chimeric NDV comprises a packaged genome comprising a transgene encoding IL-12 (e.g., human IL-12), and wherein the method further comprises administering an antagonist of PD-1 or a ligand thereof. The chimeric NDV and antagonist of PD-1 or a ligand thereof can be administered concurrently or sequentially to the subject. In certain embodiments, the chimeric NDV and antagonist of PD-1 or a ligand thereof are administered in the same composition. In other embodiments, the chimeric NDV and antagonist of PD-1 or a ligand thereof are administered in different compositions. The chimeric NDV and antagonist of PD-1 or a ligand thereof can be administered by the same or different routes of administration to the subject. In a specific embodiment, the chimeric NDV is administered intratumorally and the antagonist is administered intravenously.

International Patent Application Publication No. WO 2014/158811 and U.S. Patent Application Publication Nos. 2016/0015760 A1 and 2014/0271677 A1 are each incorporated by reference herein in their entireties. For example, the summary, the description of NDVs, the description of chimeric NDVs, the description of compositions, the description of routes of administration, and the description of anti-cancer and other uses described in, e.g., Sections 3, 5.1, 5.2, 5.5, and 5.6, of International Patent Application Publication No. WO 2014/158811 and U.S. Patent Application Publication Nos. 2016/0015760 A1 and 2014/0271677 A1 are incorporated by reference herein in their entireties.

5.1 Newcastle Disease Virus

Any NDV type or strain may be used in a combination therapy disclosed herein, including, but not limited to, naturally-occurring strains, variants or mutants, mutagenized viruses, reassortants and/or genetically engineered viruses. One skilled in the art would understand that viruses may undergo mutation when cultured, passaged or propagated. The NDV may contain these naturally occurring mutations, in addition to mutations introduced for cloning purposes. The NDV may be a homogenous or heterogeneous population with none, or one or more of these mutations. In a specific embodiment, the NDV used in a combination therapy disclosed herein is a naturally-occurring strain. In certain embodiments, the NDV is a lytic strain. In other embodiments, the NDV used in a combination therapy disclosed herein is a non-lytic strain. In certain embodiments, the NDV used in a combination therapy disclosed herein is lentogenic strain. In some embodiments, the NDV is a mesogenic strain. In other embodiments, the NDV used in a combination therapy disclosed herein is a velogenic strain. See, e.g., Newcastle Disease, Avian Paramyoxvirus-1 Infection, Goose Paramyoxvirus Infection, Ranikhet disease, the Center for Food Security & Public Health, Iowa State University, Institute for International Cooperation in Animal Biologics, College of Veterinary Medicine, Iowa State University, pp. 1-9 (January 2016) for a discussion regarding lentogenic, mesogenic and velogenic NDV strains, which is incorporated herein by reference in its entirety. Specific examples of NDV strains include, but are not limited to, the 73-T strain, NDV HUJ strain, Ulster strain (see, e.g., GenBank No. U25837), MTH-68 strain, Italien strain (see, e.g., GenBank No. EU293914), Hickman strain (see, e.g., Genbank No. AF309418), PV701 strain, Hitchner B1 strain (see, e.g., GenBank No. AF309418 or NC 002617), La Sota strain (see, e.g., GenBank Nos. AY845400 and JF950510.1 and GI No. 56799463), YG97 strain (see, e.g., GenBank Nos. AY351959 or AY390310), MET95 strain (see, e.g., GenBank No. AY143159), Roakin strain (see, e.g., GenBank No. AF124443), and F48E9 strain (see, e.g., GenBank Nos. AF163440 and U25837). In a specific embodiment, the NDV used in a combination therapy disclosed herein that is the Hitchner B1 strain. In another specific embodiment, the NDV used in a combination therapy disclosed herein is a B1 strain as identified by GenBank No. AF309418 or NC_002617. In another specific embodiment, the NDV used in a combination therapy disclosed herein is the NDV identified by ATCC No. VR2239. In another specific embodiment, the NDV used in a combination therapy disclosed herein is the La Sota strain. In a specific embodiment, the nucleotide sequence of the La Sota genome is as set forth in SEQ ID NO: 50. One skilled in the art will understand that the NDV genomic RNA sequence is the reverse complement of a cDNA sequence encoding the NDV genome. Thus, any program that generates a nucleotide sequence to its reverse complement sequence may be utilized to convert a cDNA sequence encoding an NDV genome into the genomic RNA sequence (see, e.g., www.bioinformatics.org/sms/rev_comp.html, www.fr33.net/seqedit.php, and DNAStar).

In specific embodiments, the NDV used in a combination therapy disclosed herein is not pathogenic in birds as assessed by a technique known to one of skill. In certain specific embodiments, the NDV used in a combination therapy is not pathogenic as assessed by intracranial injection of 1-day-old chicks with the virus, and disease development and death as scored for 8 days. In some embodiments, the NDV used in a combination therapy disclosed herein has an intracranial pathogenicity index of less than 0.7, less than 0.6, less than 0.5, less than 0.4, less than 0.3, less than 0.2 or less than 0.1. In certain embodiments, the NDV used in a combination therapy disclosed herein has an intracranial pathogenicity index of zero.

In certain embodiments, the NDV used in a combination therapy disclosed herein is a mesogenic strain that has been genetically engineered so as not be a considered pathogenic in birds as assessed by techniques known to one skilled in the art. In certain embodiments, the NDV used in a combination therapy disclosed herein is a velogenic strain that has been genetically engineered so as not be a considered pathogenic in birds as assessed by techniques known to one skilled in the art.

In certain embodiments, the NDV used in a combination therapy disclosed herein expresses a mutated F protein. In a specific embodiment, the NDV used in a combination therapy expresses a mutated F protein is highly fusogenic and able to form syncytia. In another specific embodiment, the mutated F protein is incorporated into the virion.

In one embodiment, a genome of a NDV used in a combination therapy disclosed herein is engineered to express a mutated F protein with a mutated cleavage site. In a specific embodiment, the NDV used in a combination therapy disclosed herein is engineered to express a mutated F protein in which the cleavage site of the F protein is mutated to produce a polybasic amino acid sequence, which allows the protein to be cleaved by intracellular proteases, which makes the virus more effective in entering cells and forming syncytia. In another specific embodiment, the NDV used in a combination therapy disclosed herein is engineered to express a mutated F protein in which the cleavage site of the F protein is replaced with a mutated cleavage site containing one or two extra arginine residues, allowing the mutant cleavage site to be activated by ubiquitously expressed proteases of the furin family. Specific examples of NDVs that express such a mutated F protein include, but are not limited to, rNDV/F2aa and rNDV/F3aa. For a description of mutations introduced into a NDV F protein to produce a mutated F protein with a mutated cleavage site, see, e.g., Park et al. (2006) Engineered viral vaccine constructs with dual specificity: avian influenza and Newcastle disease. PNAS USA 103: 8203-2808, which is incorporated herein by reference in its entirety. In some embodiments, the NDV used in a combination therapy disclosed herein is engineered to express a mutated F protein with the amino acid mutation L289A (i.e., an L to A mutation at the amino acid position corresponding to L289 of the LaSota F protein). For a description of the L289A mutation, see, e.g., Sergel et al. (2000) A Single Amino Acid Change in the Newcastle Disease Virus Fusion Protein Alters the Requirement for HN Protein in Fusion. Journal of Virology 74(11): 5101-5107, which is incorporated herein by reference in its entirety. In specific embodiments, the L289A mutated F protein possesses one, two or three arginine residues in the cleavage site. In some embodiments, the NDV used in a combination therapy disclosed herein is the LaSota strain, which has been engineered to express a mutated F protein with the amino acid mutation L289A (i.e., an L to A mutation at the amino acid position corresponding to L289 of the LaSota F protein). In certain embodiments, the NDV used in a combination therapy disclosed herein is the LaSota strain, which has been engineered to express a mutated F protein with the amino acid mutation L289A (i.e., an L to A mutation at the amino acid position corresponding to L289 of the LaSota F protein) and with the LaSota strain F protein cleavage site (GRQGRL (SEQ ID NO: 72)). In some embodiments, the NDV used in a combination therapy disclosed herein is the NDV disclosed in Kim et al., 2017, PLOS ONE 12(3): e0173965 and Kim et al., 2016, J. of General Virology 97: 1297-1303, each of which is incorporated herein by reference in its entirety. In certain embodiments, the mutated F protein is from a different type or strain of NDV than the backbone NDV. In certain embodiments, the mutated F protein is from the same strain of NDV as the backbone NDV. In some embodiments, the mutated F protein is in addition to the backbone NDV F protein. In specific embodiments, the mutated F protein replaces the backbone NDV F protein. In a specific embodiment, the NDV used in a combination therapy disclosed herein comprises a La Sota strain backbone that is engineered to express a mutated F protein with the amino acid mutation L289A. In a specific embodiment, the nucleotide sequence of the La Sota strain genome is as set forth in SEQ ID NO: 50.

In certain embodiments, the NDV used in a combination therapy disclosed herein comprises a mutated F protein with an F protein cleavage site of NDV LaSota strain or glycoprotein B of cytomegalovirus (CMV). In a specific embodiment, the NDV used in a combination therapy disclosed herein comprises a mutated F protein with an F protein cleavage having one of the following sequence modifications: S116: $^{11}$H-N-R-T-K-S/F$^{117}$ (SEQ ID NO: 56); S116K: $^{111}$H-N-$\underline{K}$-T-K-S/F$^{117}$ (SEQ ID NO: 58); S116m: $^{111}$H-N-R-$\underline{M}$-K-$\overline{S}$/F$^{117}$ (SEQ ID NO: 69); S116KM: $^{111}$H-N-$\underline{K}$-$\underline{M}$-S/F-I$^{118}$ (SEQ ID NO: 70); or R116: $^{111}$H-N-R-T-K-$\underline{R}$/F-I$^{118}$ (SEQ ID NO: 71), such as described in International Patent Application No. WO 2015/032755. See, e.g., International Patent Application Publication No. WO 2015/032755 for a description of the types of mutated F protein cleavage sites that may be engineered into an NDV F protein, which is incorporated herein by reference in its entirety. In some embodiments, the mutated F protein is in addition to the backbone NDV F protein. In specific embodiments, the mutated F protein replaces the backbone NDV F protein.

In another specific embodiment, the NDV used in a combination therapy disclosed herein is the modified 73T strain described in International Patent Application No. WO 2015/032755, which is incorporated herein by reference in its entirety. In another specific embodiment, the NDV used in a combination therapy disclosed herein is the r73T-R116 virus (r73T strain with F protein cleavage site $^{111}$H-N-R-T-K-R/F-I$^{118}$ (SEQ ID NO: 71)) described in International Patent Application No. WO 2015/032755, which is incorporated herein by referene in its entirety. In a further embodiment, the NDV comprises an HN and L intergenic non-coding sequence of 60, 102, 144, 198 or 318 nt in length.

In certain embodiments, the NDV used in a combination therapy disclosed herein is attenuated such that the NDV remains, at least partially, infectious and can replicate in vivo, but only generates low titers resulting in subclinical levels of infection that are non-pathogenic (see, e.g., Khattar et al., 2009, J. Virol. 83:7779-7782). Such attenuated NDVs may be especially suited for embodiments wherein the virus is administered to a subject in order to act as an immunogen, e.g., a live vaccine. The viruses may be attenuated by any method known in the art. In a specific embodiment, the NDV genome comprises sequences necessary for infection and replication of the attenuated virus such that progeny is produced and the infection level is subclinical. In a specific embodiment, the NDV is replication competent in human cells.

In certain embodiments, the NDV used in a combination therapy disclosed herein does not comprise an NDV V protein encoding sequence. In other embodiments, the NDV used in a combination therapy disclosed herein expresses a mutated V protein. See, e.g., Elankumaran et al., 2010, J. Virol. 84(8): 3835-3844, which is incorporated herein by reference, for examples of mutated V proteins. In certain embodiments, a mesogenic or velogenic NDV strain used in a combination therapy disclosed herein expresses a mutated V protein, such as disclosed by Elankumaran et al., 2010, J. Virol. 84(8): 3835-3844.

In certain embodiments, the NDV used in a combination therapy disclosed herein is an NDV disclosed in U.S. Pat. Nos. 7,442,379, 6,451,323, 6,146,642, U.S. Patent Application Publication No. 2014/0271677 A1, International Patent Application Publication No. WO 2014/0158811, or U.S. Patent Application Publication No. 2016/0015760 A1, each of which is incorporated herein by reference in its entirety. In a specific embodiment, the NDV used in a combination therapy disclosed herein is an NDV described in Section 5.1 of U.S. Patent Application Publication No. 2014/0271677 A1, International Patent Application Publication No. WO 2014/0158811, or U.S. Patent Application Publication No. 2016/0015760 A1, each of which is incorporated herein by reference in its entirety. In specific embodiments, the NDV used in a combination therapy disclosed herein is genetically engineered to encode and express a heterologous peptide or protein. In certain embodiments, the NDV used in a combination therapy disclosed herein is a chimeric NDV known to one of skill in the art, or a chimeric NDV disclosed herein (see, e.g., Section 5.2 and/or Section 6, infra). In certain embodiments, the NDV used in a combination therapy disclosed herein is a chimeric NDV disclosed in U.S. Patent Application Publication Nos. 2012/0058141, 2012/0122185, 2016/0015760 A1, or 2014/0271677 A1, or International Patent Application Publication No. WO 2014/158811, each of which is incorporated herein by reference in its entirety. In specific embodiments, the NDV used in a combination therapy disclosed herein is a chimeric NDV comprising a genome engineered to express a cytokine, such as, e.g., IL-12.

5.2 Chimeric Newcastle Disease Virus

In one aspect, described herein are chimeric NDVs, comprising a packaged genome comprising a transgene encoding IL-12 or an IL-12 derivative (see, e.g., Section 5.2.1). In other words, the NDV serves as the "backbone" that is engineered to encode IL-12 or an IL-12 derivative, which is expressed in cells infected with the virus. In a specific embodiment, the chimeric NDV comprises IL-12 or a derivative thereof. Any NDV type or strain may serve as the backbone of a chimeric NDV described herein, including, but not limited to, naturally-occurring strains, variants or mutants, mutagenized viruses, reassortants and/or genetically engineered viruses. In a specific embodiment, the NDV that serves as the backbone for genetic engineering of the chimeric NDV is an NDV described in Section 5.1, supra. In a specific embodiment, the chimeric NDV preferentially replicates in cancer cells as compared to non-cancer cells. In a specific embodiment, the chimeric NDV is attenuated but remains, at least, partially infectious and can replicate in vivo, but is non-pathogenic and only generates low titers of NDV progeny, resulting in subclinical levels of infection. In a specific embodiment, the chimeric NDV genome comprises sequences necessary for infection and replication of the virus such that progeny is produced and the infection level is subclinical. Techniques for attenuating NDV are known in the art, such as, e.g., mutations or substitutions within the genome and modification or deletion of the NDV V protein, and can be used to attenuate a chimeric NDV described herein. In a specific embodiment, the chimeric NDV is replication competent in human cells.

In a specific aspect, described herein are chimeric NDVs, comprising a packaged genome comprising a transgene encoding IL-12 or a derivative thereof, which may be expressed in cells infected with the virus. In another specific embodiment, described herein are chimeric NDVs, comprising a packaged genome comprising a transgene encoding IL-12 or a derivative thereof and a nucleotide sequence encoding a mutated F protein. In a particular embodiment, the mutated F protein is highly fusogenic. In a specific embodiment, the mutated F protein has a mutant cleavage site (such as described herein). In some embodiments, the mutated F protein comprises the amino acid mutation L289A (i.e., an L to A substitution at the amino acid position corresponding to L289 of the LaSota F protein). In some embodiments, the chimeric NDV comprise a packaged genome comprising a nucleotide sequence encoding a mutated F protein with the amino acid mutation L289A (i.e., an L to A substitution at the amino acid position corresponding to L289 of the LaSota F protein). In certain embodiments, the mutated F protein is from a different type or strain of NDV than the backbone NDV. In other embodiments, the mutated F protein is from the same type or strain of NDV as the backbone NDV. In specific embodiments, the L289A mutated F protein possesses one, two or three arginine residues in the cleavage site. In some embodiments, the mutated F protein is in addition to the backbone NDV F protein. In specific embodiments, the mutated F protein replaces the backbone NDV F protein. In specific embodiments, the mutated F protein is incorporated into the virion. In a specific embodiment, the chimeric NDV comprises a packaged genome comprising a nucleotide sequence encoding a mutated F protein and a nucleotide sequence comprising a transgene encoding IL-12 (e.g., human IL-12), wherein the NDV that serves as the backbone of the chimeric NDV is lentogenic. In a specific embodiment, the chimeric NDV comprises a packaged genome comprising a nucleotide sequence encoding a mutated F protein and a nucleotide sequence comprising a transgene encoding IL-12 (e.g., human IL-12), wherein the nucleotide sequence encoding the mutated F protein replaces the F protein of the genome of the NDV that serves as the backbone of the chimeric NDV. In a specific embodiment, the chimeric NDV comprises a packaged genome comprising a nucleotide sequence encoding a mutated F protein and a nucleotide sequence comprising a transgene encoding IL-12 (e.g., human IL-12), wherein the NDV that serves as the backbone of the chimeric NDV is La Sota strain. In another specific embodiment, the chimeric NDV comprises a packaged genome comprising a nucleotide sequence encoding a mutated NDV F protein and a nucleotide sequence comprising a transgene encoding IL-12 (e.g., human IL-12), wherein the NDV that serves as the backbone of the chimeric NDV is La Sota strain, wherein the nucleotide sequence encoding the mutated F protein replaces the F protein of the genome of the NDV that serves as the backbone of the chimeric NDV, and wherein the mutated NDV F protein has the amino acid mutation L289A (i.e., an L to A substitution at the amino acid position corresponding to L289 of the LaSota F protein). In another specific embodiment, the chimeric NDV comprises a packaged genome comprising a nucleotide sequence encoding a mutated NDV F protein and a nucleotide sequence comprising a transgene encoding IL-12 (e.g., human IL-12), wherein the NDV that serves as the backbone of the chimeric NDV is La Sota strain, wherein the nucleotide sequence encoding the mutated F protein replaces the F protein of the genome of the NDV that serves as the backbone of the chimeric NDV, and wherein the mutated NDV F protein has the amino acid mutation L289A (i.e., an L to A substitution at the amino acid position corresponding to L289 of the LaSota F protein) and the LaSota strain F protein cleavage site (GRQGRL (SEQ ID NO: 72)).

In some embodiments, described herein are chimeric NDVs, comprising a packaged genome comprising a transgene encoding IL-12 or a derivative thereof, wherein the NDV that serves as the backbone of the chimeric NDV is an NDV disclosed in Kim et al., 2017, PLOS ONE 12(3): e0173965 and Kim et al., 2016, J. of General Virology 97: 1297-1303, each of which is incorporated herein by reference in its entirety.

In some embodiments, described herein are chimeric NDVs, comprising a packaged genome comprising a transgene encoding IL-12 or a derivative thereof, wherein the NDV that serves as the backbone of the chimeric NDV comprises a genome having the sequence set forth in SEQ ID NO: 50. In specific embodiments, described herein is a chimeric NDV comprising a packaged genome, wherein the packaged genome comprises or consists of the nucleotide sequence of SEQ ID NO:50 and a transgene encoding IL-12 (e.g., human IL-12). In particular embodiments, the transgene is inserted between the transcription units for two NDV genes (e.g., the P and M transcription units).

In some embodiments, described herein are chimeric NDV comprising a packaged genome comprising (i) a transgene encoding IL-12 or a derivative thereof and (ii) a nucleotide sequence encoding a mutated NDV V protein-encoding sequence, such as disclosed by Elankumaran et al., 2010, J. Virol. 84(8): 3835-3844. In other embodiments, a chimeric NDV comprising a packaged genome comprising a transgene encoding IL-12 or a derivative thereof does not comprise an NDV V protein-encoding sequence. In certain embodiments, the parental backbone of the chimeric NDV is a mesogenic or velogenic NDV strain that is engineered to encode a mutated V protein, such as disclosed by Elankumaran et al., 2010, J. Virol. 84(8): 3835-3844.

In certain embodiments, provided herein are chimeric NDV comprising a packaged genome comprising a transgene encoding IL-12 or a derivative thereof and a nucleotide sequence encoding a mutated F protein, wherein the mutated F protein has an F protein cleavage site of NDV LaSota strain or glycoprotein B of cytomegalovirus (CMV). In a specific embodiment, provided herein are chimeric NDV comprising a packaged genome comprising a transgene encoding IL-12 or a derivative thereof and a nucleotide sequence encoding a mutated F protein, wherein the mutated F protein has an F protein cleavage having one of the following sequences: S116: $^{111}$H-N-R-T-K-S/F$^{117}$ (SEQ ID NO: 56); S116K: $^{111}$H-N-K-T-K-S/F$^{117}$ (SEQ ID NO: 58); S116m: $^{111}$H-N-R-M-K-S/F$^{117}$ (SEQ ID NO: 69); S116KM: $^{111}$H-N-K-M-S/F-I$^{118}$ (SEQ ID NO: 70); or R116: $^{111}$H-N-R-T-K-R/F-I$^{118}$ (SEQ ID NO: 71), such as described in International Patent Application No. WO 2015/032755. See, e.g., International Patent Application Publication No. WO 2015/032755 for a description of the types of mutated F protein cleavage sites that may be engineered into an NDV F protein, which is incorporated herein by reference in its entirety. In some embodiments, the mutated F protein is in addition to the backbone NDV F protein. In specific embodiments, the mutated F protein replaces the backbone NDV F protein.

In certain embodiments, provided herein are chimeric NDV comprising a packaged genome comprising a transgene encoding IL-12 or a derivative thereof, wherein the NDV that serves as the backbone of the chimeric NDV is the modified 73T strain described in International Patent Application No. WO 2015/032755, which is incorporated herein by referene in its entirety. In another specific embodiment, provided herein are chimeric NDV comprising a packaged genome comprising a transgene encoding IL-12 or a derivative thereof, wherein the NDV that serves as the backbone of the chimeric NDV is the r73T-R116 virus (r73T strain with F protein cleavage site $^{111}$H-N-R-T-K-R/F-I$^{118}$ (SEQ ID NO: 71)) described in International Patent Application No. WO 2015/032755, which is incorporated herein by referene in its entirety. In a further embodiment, the chimeric NDV comprises an HN and L intergenic non-coding sequence of 60, 102, 144, 198 or 318 nucleotide in length.

In a specific embodiment, the chimeric NDV is a chimeric NDV described in Section 6, infra. In a preferred embodiment, the chimeric NDV is the NDV-huIL-12 described in Section 6, infra. In another preferred embodiment, the chimeric NDV comprises a genome having the sequence set forth in SEQ ID NO: 51. In another embodiment, the chimeric NDV comprises a genome having the sequence set forth in SEQ ID NO: 52. In another preferred embodiment, the chimeric NDV comprises a genome having the sequence set forth in SEQ ID NO: 60.

In a specific embodiment, the chimeric NDV comprises a packaged genome, said packaged genome comprising a transgene encoding a human IL-12, wherein the IL-12 comprises the amino acid sequence set forth in SEQ ID NO:39. In a specific embodiment, the transgene comprises the nucleotide sequence set forth in SEQ ID NO:61.

In a specific embodiment, the chimeric NDV comprises a packaged genome, said packaged genome comprising a transgene encoding a human IL-12, wherein the IL-12 comprises the amino acid sequence set forth in SEQ ID NO:22, wherein said IL-12 comprises a signal peptide. In a specific embodiment, the transgene comprises the nucleotide sequence set forth in SEQ ID NO:26.

In a specific embodiment, the chimeric NDV comprises a packaged genome, said packaged genome comprising a transgene encoding a human IL-12, wherein the IL-12 comprises the amino acid sequence set forth in SEQ ID NO:43. In a specific embodiment, the transgene comprises the nucleotide sequence set forth in SEQ ID NO:63. In a specific embodiment, the transgene comprises the nucleotide sequence set forth in SEQ ID NO:68.

In a specific embodiment, the chimeric NDV comprises a packaged genome, said packaged genome comprising a transgene encoding a human IL-12, wherein the IL-12 comprises the amino acid sequence set forth in SEQ ID NO:42, wherein said IL-12 comprises a signal peptide. In a specific embodiment, the transgene comprises the nucleotide sequence set forth in SEQ ID NO:53. In a specific embodiment, the transgene comprises the nucleotide sequence set forth in SEQ ID NO:66.

In a specific embodiment, a chimeric NDV comprising a packaged genome comprising a transgene encoding IL-12 or a derivative thereof induces the expression of IL-12p70, IFN-T expression, or both IL-12p70 and IFN-γ in an assay described herein (e.g., an assay described in Section 6, infra). In another specific embodiment, treatment of a tumor sample with a chimeric NDV comprising a packaged genome comprising a transgene encoding IL-12 or a derivative thereof results in an increase in the gene expression profile (GEP) relative to the GEP score of the tumor sample prior to treatment with the chimeric NDV. See, for example, Example 6.3, infra, regarding the GEP score. In another specific embodiment, treatment of a tumor sample, such as described in Section 6, infra, with a chimeric NDV comprising a packaged genome comprising a transgene encoding IL-12 increases the GEP score of the tumor sample relative to the GEP score of the tumor sample prior to treatment with the chimeric NDV, such as described in Section 6, infra. In one embodiment, the tumor sample of a subject has a Gene Expression Profile (GEP) score of the 18-gene signature of Table 15 at less than −0.318. In another embodiment, the tumor of the subject has a Gene Expression Profile (GEP) score of the 18-gene signature of Table 15 at greater than −0.318. Without being bound by any theory, it is believed that an increase in GEP score will result in the tumor being more likely to be responsive to treatment with an anti-PD-1 antibody (e.g., an anti-PD-1 blocking antibody), such as pembrolizumab. Thus, in a specific embodiment, the administration of a chimeric NDV comprising a packaged genome comprising a transgene encoding IL-12 to a patient with cancer refractory, relapsed or unresponsive to treatment with an anti-PD-1 antibody (e.g., an anti-PD-1 blocking antibody, such as pembrolizumab or another antibody described in Section 5.5) may result in the patient becoming responsive to treatment with the anti-PD-1 antibody (e.g., an anti-PD-1 blocking antibody, such as pembrolizumab or another antibody described in Section 5.5). In particular, administration of a a chimeric NDV comprising a packaged genome comprising a transgene encoding IL-12 to a patient with cancer refractory, relapsed or unresponsive to treatment with pembrolizumab (KEYTRUDA®, Merck & Co., Inc. Kenilworth, NJ) may result in the patient becoming responsive to treatment with pembrolizumab. Therefore, in one embodiment, provided herein is a method of increasing response to anti-PD-1 therapy in a subject with cancer.

In another embodiment, described herein are chimeric NDVs, comprising a packaged genome comprising (i) a transgene encoding IL-12 or a derivative thereof, and (ii) a transgene encoding a heterologous interferon antagonist. See, e.g., U.S. Patent Application Publication No. 2012-0058141, which is incorporated herein by reference, for examples of chimeric NDV engineered to express heterologous interferon antagonists.

Interferon antagonists may be identified using any technique known to one of skill in the art, including, e.g., the techniques described in U.S. Pat. Nos. 6,635,416; 7,060,430; and 7,442,527; each of which is incorporated herein by reference in their entirety. In a specific embodiment, the heterologous interferon antagonist is a viral protein. Such viral proteins may be obtained or derived from any virus and the virus may infect any species (e.g., the virus may infect humans or non-human mammals). Exemplary heterologous interferon antagonists include, without limitation, Nipah virus W protein, Nipah V protein, Ebola virus VP35 protein, vaccinia virus E3L protein, influenza virus NS1 protein, respiratory syncytial virus (RSV) NS2 protein, herpes simplex virus (HSV) type 1 ICP34.5 protein, Hepatitis C virus NS3-4 protease, dominant-negative cellular proteins that block the induction or response to innate immunity (e.g., STAT1, MyD88, IKK and TBK), and cellular regulators of the innate immune response (e.g., SOCS proteins, PIAS proteins, CYLD proteins, IkB protein, Atg5 protein, Pinl protein, IRAK-M protein, and UBP43). See, e.g., U.S. patent application publication No. 2012-0058141, which is incorporated herein by reference in its entirety, for additional information regarding heterologous interferon antagonist.

Any NDV type or strain may serve as the backbone for the chimeric NDV comprising a packaged genome that is engineered to encode IL-12 (e.g., human IL-12) and, in certain embodiments, a heterologous interferon antagonist and/or mutated F protein, including, but not limited to, naturally-occurring strains, variants or mutants, mutagenized viruses, reassortants and/or genetically engineered viruses. In a specific embodiment, the NDV that serves as the backbone for genetic engineering of the chimeric NDV is an NDV described in Section 5.1. In a specific embodiment, the NDV that serves as the backbone for genetic engineering of the chimeric NDV is a naturally-occurring strain. In certain embodiments, the NDV that serves as the backbone for genetic engineering of the chimeric NDV is a lytic strain. In other embodiments, the NDV that serves as the backbone for genetic engineering of the chimeric NDV is a non-lytic strain. In certain embodiments, the NDV that serves as the backbone for genetic engineering of the chimeric NDV is a lentogenic strain. In some embodiments, the NDV that serves as the backbone for genetic engineering of the chimeric NDV is a mesogenic strain. In other embodiments, the NDV that serves as the backbone for genetic engineering of the chimeric NDV is a velogenic strain. Specific examples of NDV strains include, but are not limited to, the 73-T strain, NDV HUJ strain, Ulster strain (see, e.g., GenBank No. U25837), MTH-68 strain, Italien strain (see, e.g., GenBank No. EU293914), Hickman strain (see, e.g., Genbank No. AF309418), PV701 strain, Hitchner B1 strain (see, e.g., GenBank No. AF309418 or NC_002617), La Sota strain (see, e.g., GenBank Nos. AY845400 and JF950510.1 and GI No. 56799463), YG97 strain (see, e.g., GenBank Nos. AY351959 or AY390310), MET95 strain (see, e.g., GenBank No. AY143159), Roakin strain (see, e.g., GenBank No. AF124443), and F48E9 strain (see, e.g., GenBank Nos. AF163440 and U25837). In a specific embodiment, the NDV that serves as the backbone for genetic engineering of the chimeric NDV is the Hitchner B1 strain. In another specific embodiment, the NDV that serves as the backbone for genetic engineering of the chimeric NDV is a B1 strain as identified by GenBank No. AF309418 or NC_002617. In another specific embodiment, the NDV that serves as the backbone for genetic engineering of the chimeric NDV is the NDV identified by ATCC No. VR2239. In another specific embodiment, the NDV that serves as the backbone for genetic engineering is the La Sota strain.

In certain embodiments, attenuation, or further attenuation, of the chimeric NDV is desired such that the chimeric NDV remains, at least partially, infectious and can replicate in vivo, but only generates low titers resulting in subclinical levels of infection that are non-pathogenic (see, e.g., Khattar et al., 2009, J. Virol. 83:7779-7782). In a specific embodiment, the chimeric NDV is attenuated by deletion of the V protein. Such attenuated chimeric NDVs may be especially suited for embodiments wherein the virus is administered to a subject in order to act as an immunogen, e.g., a live vaccine. The viruses may be attenuated by any method known in the art.

In a specific embodiment of the chimeric NDV comprising a packaged genome comprising a transgene encoding IL-12 or a derivative thereof, the packaged genome also comprises one or more other transgenes, such as, e.g., an antagonist of an inhibitory receptor of an immune cell, an agonist of a co-stimulatory receptor of an immune cell, an additional cytokine, a tumor antigen, a pro-apoptotic molecule, an anti-apoptotic molecule, a suicide gene, or a heterologous interferon antagonist. Nonlimiting examples of inhibitory receptors of an immune cell are provided in Section 5.7.6.1. Nonlimiting examples of co-stimulatory receptors of an immune cell are provided in Section 5.7.6.1. Nonlimiting examples of cytokines include IL-2 (e.g., Genbank Accession No. NM_000586.3 and GI No. 125661059), IL-7 (e.g., Genbank Accession Nos. NM_000880.3, NM_001199886.1, NM_001199887.1 and NM_001199888.1 and GI Nos. 315467865, 315467866, 315467868, and 315467870), IL-9 (e.g., Genbank Accession No. NM_000590.1 and GI No. 10834979), IL-15 (e.g., Genbank Accession Nos. NM_172175.2 and NM_000585.4 and GI Nos. 323098328 and 323098327), IL-17 (e.g., Genbank Accession No. NM_002190.2 and GI No. 27477085), IL-21 (e.g., Genbank Accession Nos. NM_021803.3 and NM_001207006.2 and GI Nos. 365733583 and 365733582), IL-22 (e.g., Genbank Accession No. NM_020525.4 and GI No. 41393566), IFN-gamma (e.g., Genbank Accession No. NM_000619.2 and GI No. 56786137), GM-CSF (e.g., Genbank Accession No. M11220_1 and GI No. 183363), and TNF-alpha (e.g., Genbank Accession No. NM_000594.3). Nonlimiting examples of tumor antigens include MAGE-1, MAGE-3, BAGE, GAGE-1, GAGE-2, N-acetylglucosaminyltransferase-V, p-15, gp100, MART-1/MelanA, TRP-1 (gp75), Tyrosinase, cyclin-dependent kinase 4, β-catenin, MUM-1, CDK4, HER-2/neu, human papillomavirus-E6, human papillomavirus E7, CD20, carcinoembryonic antigen (CEA), epidermal growth factor receptor, MUC-1, caspase-8, CD5, mucin-1, Lewisx, CA-125, p185HER2, IL-2R, Fap-α, tenascin, antigens associated with a metalloproteinase, and CAMPATH-1. Other examples of tumor antigens include, but are not limited to, KS 1/4 pan-carcinoma antigen, ovarian carcinoma antigen (CA125), prostatic acid phosphate, prostate specific antigen, melanoma-associated antigen p97, melanoma antigen gp75, high molecular weight melanoma antigen (HMW-MAA), prostate specific membrane antigen, CEA, polymorphic epithelial mucin antigen, milk fat globule antigen, colorectal tumor-associated antigens (such as: CEA, TAG-72, C017-1A, GICA 19-9, CTA-1 and LEA), Burkitt's lymphoma antigen-38.13, CD19, B-lymphoma antigen-CD20, CD33, melanoma specific antigens (such as ganglioside GD2, ganglioside GD3, ganglioside GM2, ganglioside GM3), tumor-specific transplantation type of cell-surface antigen (TSTA) (such as virally-induced tumor antigens including T-antigen DNA tumor viruses and Envelope antigens of RNA tumor viruses), oncofetal antigen-alpha-fetoprotein such as CEA of colon, bladder tumor oncofetal antigen, differentiation antigen (such as human lung carcinoma antigen L6 and L20), antigens of fibrosarcoma, leukemia T cell antigen-Gp37, neoglycoprotein, sphingolipids, breast cancer antigens (such as EGFR (Epidermal growth factor receptor), HER2 antigen ($^{p185}$HER2) and HER2 neu epitope), polymorphic epithelial mucin (PEM), malignant human lymphocyte antigen-APO-1, differentiation antigen (such as I antigen found in fetal erythrocytes, primary endoderm, I antigen found in adult erythrocytes, preimplantation embryos, I(Ma) found in gastric adenocarcinomas, M18, M39 found in breast epithelium, SSEA-1 found in myeloid cells, VEP8, VEP9, Myl, VIM-D5, $D_{156-22}$ found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, E1 series (blood group B) found in pancreatic cancer, FC10.2 found in embryonal carcinoma cells, gastric adenocarcinoma antigen, CO-514 (blood group Lea) found in Adenocarcinoma, NS-10 found in adenocarcinomas, CO-43 (blood group Leb), G49 found in EGF receptor of A431 cells, MH2 (blood group ALeb/Ley) found in colonic adenocarcinoma, 19.9 found in colon cancer, gastric cancer mucins, T5A7 found in myeloid cells, R24 found in melanoma, 4.2, GD3, D1.1, OFA-1, GM2, OFA-2, GD2, and M1:22:25:8 found in embryonal carcinoma cells, and SSEA-3 and SSEA-4 found in 4 to 8-cell stage embryos), T cell receptor derived peptide from a cutaneous T cell lymphoma, C-reactive protein (CRP), cancer antigen-50 (CA-50), cancer antigen 15-3 (CA15-3) associated with breast cancer, cancer antigen-19 (CA-19) and cancer antigen-242 associated with gastrointestinal cancers, carcinoma associated antigen (CAA), chromogranin A, epithelial mucin antigen (MC5), human epithelium specific antigen (E1A), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM. Nonlimiting examples of pro-apoptotic molecules include Bax, Bak, Bad, BID, Bcl-xS, Bim, Noxa, Puma, AIF, FasL, and TRAIL. Nonlimiting examples of anti-apoptotic molecules include Bcl-2, Bcl-xL, Mcl-1, and XIAP. A nonlimiting example of a suicide gene includes thymidine kinase.

In certain embodiments, a chimeric NDV described herein comprises a packaged genome comprising a transgene encoding IL-12 or a derivative thereof and one, two, three, or more, or all of the following transgenes: (1) an agonist of a co-stimulatory signal of an immune cell; (2) an antagonist of an inhibitory signal of an immune cell; (3) a cytokine; (4) a tumor antigen; (5) a heterologous interferon antagonist; (6) a pro-apoptotic molecule; (7) an anti-apoptotic molecule; and/or (8) a suicide gene. In addition, the packaged genome may comprise a nucleotide sequence encoding a mutated F protein (such as, e.g., a mutated F protein described herein). In specific embodiments, in addition to the packaged genome comprising a transgene encoding IL-12 or a derivative thereof, and in certain embodiments, the packaged genome comprising a nucleotide sequence encoding a mutated F protein and/or a nucleotide sequence encoding a heterologous interferon antagonist, the packaged genome of a chimeric NDV comprises a transgene encoding a suicide gene (e.g., thymidine kinase) or another molecule that inhibits NDV replication or function (a gene that makes NDV sensitive to an antibiotic or an anti-viral agent). In some embodiments, in addition to the packaged genome comprising a transgene encoding IL-12 or a derivative thereof, and in certain embodiments, the packaged genome comprising a nucleotide sequence encoding a mutated F protein and/or a nucleotide sequence encoding a heterologous interferon antagonist, the packaged genome of a chimeric NDV comprise nucleotide sequence encoding tissue-specific microRNA (miRNA) target sites (e.g., sites targeted by miR-21, miR-184, miR-133a/133b, miR-137, and/or miR-193a microRNAs). In some embodiments, the packaged genome does not comprise a nucleotide sequence encoding a miRNA target site(s).

In certain embodiments, a chimeric NDV described herein comprises a packaged genome comprising a transgene encoding IL-12 or a derivative thereof, wherein the packaged genome does not encode a heterologous interferon antagonist.

In certain embodiments, the tropism of the chimeric NDV is altered. In a specific embodiment, the tropism of the virus is altered by modification of the F protein cleavage site to be recognized by tissue-specific or tumor-specific proteases such as matrix metalloproteases (MMP) and urokinase. In other embodiments, tropism of the virus is altered by introduction of tissue-specific miRNA target sites. In certain embodiments, NDV HN protein is mutated to recognize tumor-specific receptor.

In certain embodiments, a chimeric NDV described herein comprises a packaged genome comprising a transgene encoding IL-12 or a derivative therein, wherein the packaged genome of a chimeric NDV described herein does not comprise an additional transgene(s). In certain embodiments, the packaged genome of a chimeric NDV described herein does not comprise a transgene(s) encoding a heterologous interferon antagonist(s). In certain embodiments, the packaged genome of a chimeric NDV described herein does not comprise a transgene(s) encoding one, two, or more, or all of the following: (1) a transgene(s) encoding one or more cytokines other than IL-12; (2) a transgene(s) encoding one or more tumor antigens; (3) a transgene(s) encoding one or more anti-apoptotic molecule(s); (4) a transgene(s) encoding a suicide gene; (5) a transgene(s) encoding an agonist(s) of a co-stimulatory signal of an immune cell; (6) a transgene(s) encoding one or more antagonist(s) of an inhibitory signal of an immune cell; or (7) a transgene(s) encoding one or more pro-apoptotic molecule(s).

In certain embodiment, the genome of the chimeric NDV does not comprise a heterologous sequence encoding a heterologous protein other than IL-12 or a derivative thereof (e.g., human IL-12). In certain embodiments, a chimeric NDV described herein comprises a packaged genome, wherein the genome comprises the genes found in NDV and a transgene encoding IL-12 or a derivative thereof. In some embodiments, a chimeric NDV described herein comprises a packaged genome, wherein the genome comprises the genes found in NDV and a transgene encoding IL-12 or a derivative thereof but does not include any other transgenes.

In particular embodiments, the genome of the chimeric NDV does not comprises a heterologous sequence encoding a heterologous protein other than IL-12 or a derivative thereof and a mutated NDV F protein, wherein the mutated NDV F protein replaces the naturally occurring NDV F protein. In certain embodiments, a chimeric NDV described herein comprises a packaged genome, wherein the genome comprises: (1) the genes found in NDV other than an NDV F protein; (2) a transgene encoding IL-12 or a derivative thereof (e.g., human IL-12), and (3) a mutated NDV F protein, such as described herein, which replaces the NDV F protein. In some embodiments, a chimeric NDV described herein comprises a packaged genome, wherein the genome comprises (1) the genes found in NDV other than an NDV F protein; (2) a transgene encoding IL-12 or a derivative thereof (e.g., human IL-12), and (3) a mutated NDV F protein, such as described herein, which replaces the NDV F protein, but does not include any other transgenes.

In certain embodiments, one or more of the following are expressed by a chimeric NDV in cells as a chimeric protein or fusion protein: (1) IL-12 or a derivative thereof; (2) a heterologous interferon antagonist; and/or (3) a mutated F protein. In specific embodiments, IL-12 or a derivative thereof is expressed by a chimeric NDV in cells as a chimeric protein or fusion protein. In specific embodiments, a mutated F protein is expressed by a chimeric NDV as a chimeric protein or a fusion protein. In specific embodiments, the chimeric protein or fusion protein comprises the transmembrane and cytoplasmic domains or fragments thereof of the NDV F or NDV HN protein and an extracellular domain that comprises one of the molecules referenced in the previous sentence. See U.S. Patent Application No. 2012-0122185 for a description of such chimeric proteins or fusion proteins, and International Application Publication No. WO 2007/064802, each of which is incorporated herein by reference.

In embodiments herein, the transgene encoding IL-12 or a derivative thereof may be inserted into the genome of the backbone NDV between two transcription units. In a specific embodiment, the transgene encoding IL-12 or a derivative thereof is inserted into the genome of the backbone NDV between the M and P transcription units or between the HN and L transcription units. In accordance with other embodiments herein, one or more other transgenes or nucleotide sequences described herein, such as those encoding a heterologous interferon antagonist and/or a mutated F protein may be inserted into the genome of the backbone NDV between two or more transcription units (e.g., between the M and P transcription units or between the HN and L transcription units).

In some embodiments, the chimeric NDV is an NDV described in Section 5.2 of U.S. Patent Application Publication No. 2014/0271677 A1 or 2016/0015760 A1, or International Patent Application Publication No. WO 2014/158811, each of which is incorporated herein by reference in its entirety.

5.2.1 IL-12

In one aspect, provided herein is a chimeric NDV comprising a packaged genome, wherein the packaged genome comprises a transgene encoding IL-12 or a derivative thereof (e.g., human IL-12). The chimeric NDV may be used alone or in combination with one or more other therapies, such as an antagonist of PD-1 or a ligand thereof, to treat cancer.

In another aspect, presented herein are methods for treating cancer utilizing a chimeric NDV or a composition comprising the chimeric NDV in combination with an antagonist of PD-1 or a ligand thereof or a composition comprising such an antagonist, wherein the chimeric NDV comprises a packaged genome comprising a transgene encoding interleukin-12 ("IL-12") (e.g., the p35 and p40 subunits of IL-12) or a derivative thereof. In specific embodiments, the chimeric NDV comprises a packaged genome comprising a first transgene encoding the IL-12 p35 subunit or a derivative thereof and a second transgene encoding the IL-12 p40 subunit or a derivative thereof. In a specific embodiment, the IL-12 or derivative thereof is expressed by cells infected with the chimeric NDV. In specific embodiments, the antagonist is a PD-1 blocking antibody (e.g., nivolumab or pembrolizumab). In some embodiments, the antagonist is a PD-L1 blocking antibody (e.g., avelumab).

In another aspect, presented herein are a chimeric NDV or a composition comprising the chimeric NDV for use in a method for treating cancer in a subject (e.g., a human subject), wherein the chimeric NDV comprises a packaged genome comprising a transgene encoding IL-12 (e.g., the p35 and p40 subunits of IL-12) or a derivative thereof, and wherein the method further comprises administering an antagonist of PD-1 or a ligand thereof or a composition comprising such an antagonist. In a specific embodiment, the IL-12 or derivative thereof is expressed by cells infected with the chimeric NDV. In specific embodiments, the antagonist is a PD-1 blocking antibody (e.g., nivolumab or pembrolizumab). In some embodiments, the antagonist is a PD-L1 blocking antibody (e.g., avelumab).

The IL-12 or derivative thereof encoded by a transgene in a packaged genome of a chimeric NDV described herein may be any IL-12 known to those of skill in the art. In certain embodiments, the IL-12 or a derivative thereof is human, dog, cat, horse, pig, or cow IL-12 or a derivative thereof. In a specific embodiment, the IL-12 or a derivative thereof is human IL-12 or a derivative thereof. A typical IL-12 consists of a heterodimer encoded by two separate genes, IL-12A (the p35 subunit) and IL-12B (the p40 subunit), known to those of skill in the art. GenBank™ accession number NM_000882.3 (GI number 325974478) provides an exemplary human IL-12A nucleic acid sequence. GenBank™ accession number NM_002187.2 (GI number 24497437) provides an exemplary human IL-12B nucleic acid sequence. GenBank™ accession number NP_000873.2 (GI number 24430219) provides an exemplary human IL-12A (the p35 subunit) amino acid sequence. GenBank™ accession number NP_002178.2 (GI number 24497438) provides an exemplary human IL-12B (the p40 subunit) amino acid sequence. In certain embodiments, the IL-12 or a derivative thereof encoded by a packaged genome of a chimeric NDV described herein consists of a single polypeptide chain, comprising the IL-12 p35 subunit (also referred to as "IL-12A") or a derivative thereof and the IL-12 p40 subunit (also referred to as "IL-12B") or a derivative thereof, optionally separated by a linker sequence. In certain embodiments, the IL-12 or a derivative thereof encoded by a packaged genome of a chimeric NDV described herein consists of two polypeptide chains: (i) a first polypeptide comprising the IL-12 p35 subunit or a derivative thereof, and (ii) a second polypeptide comprising the IL-12 p40 subunit or a derivative thereof. In certain embodiments, the transgene encoding the IL-12 or a derivative thereof comprises a nucleotide sequence encoding the IL-12 p35 subunit and a nucleotide sequence encoding the IL-12 p40 subunit, wherein the nucleotide sequence encoding the IL-12 p35 subunit and the nucleotide sequence encoding the IL-12 p40 subunit are separated by an internal ribosome entry site. SEQ ID NOs: 29, 55, and 65 provide exemplary nucleotide sequences encoding the IL-12 p35 subunit. SEQ ID NOs: 27, 54, 57, 59, and 64 provide exemplary nucleotide sequences encoding the IL-12 p40 subunit. In a specific embodiment, an IL-12 comprises the p35 and p40 subunit sequences set forth in SEQ ID NOs: 41 and 38, respectively. In another specific embodiment, an IL-12 comprises the p35 and p40 subunit sequences set forth in SEQ ID NOs: 25 and 38. In a preferred embodiment, an IL-12 comprises the p35 and p40 subunit sequences provided in Section 6, e.g., SEQ ID NOs: 25 and 23, respectively, or SEQ ID NOs: 41 and 40, respectively. In a specific embodiment, the IL-12 encoded by a packaged genome of a chimeric NDV described herein consists of a single polypeptide chain comprising the amino acid sequence set forth in SEQ ID NO: 43. In a specific embodiment, the IL-12 encoded by a packaged genome of a chimeric NDV described herein consists of a single polypeptide chain comprising the amino acid sequence set forth in SEQ ID NO: 42. In a specific embodiment, the IL-12 encoded by a packaged genome of a chimeric NDV described herein consists of a single polypeptide chain comprising the amino acid sequence set forth in SEQ ID NO: 39. In a preferred embodiment, the IL-12 encoded by a packaged genome of a chimeric NDV described herein consists of a single polypeptide chain comprising an amino acid sequence provided in Section 6, e.g., SEQ ID NO: 22. In a specific embodiment, the nucleotide sequence of the transgene is as set forth in SEQ ID NO: 26, 53, 61, 63, 66, or 68. In a specific embodiment, the nucleotide sequence of the transgene comprises the nucleotide sequence set forth in SEQ ID NO: 26, 53, 61, 63, 66, or 68. In a specific embodiment, the IL-12 p35 subunit and IL-12 p40 subunit or derivative(s) thereof are directly fused to each other. In specific embodiments, a polypeptide comprising the IL-12 p35 subunit and IL-12 p40 subunit or derivative(s) thereof directly fused to each other is functional (e.g., capable of specifically binding to the IL-12 receptor and inducing IL-12-mediated signal transduction and/or IL-12-mediated immune function). In a specific embodiment, the IL-12 p35 subunit and IL-12 p40 subunit or derivative(s) thereof are indirectly fused to each other using one or more linkers. Linkers suitable for preparing the IL-12 p35 subunit/p40 subunit fusion protein may comprise one or more amino acids (e.g., a peptide). In specific embodiments, a polypeptide comprising the IL-12 p35 subunit and IL-12 p40 subunit or derivative(s) thereof indirectly fused to each other using an amino acid linker (e.g., a peptide linker) is functional (e.g., capable of specifically binding to the IL-12 receptor and inducing IL-12-mediated signal transduction and/or IL-12-mediated immune function). In a specific embodiment, the linker is long enough to preserve the ability of the IL-12 p35 subunit and IL-12 p40 subunit or derivative(s) thereof to form a functional IL-12 heterodimer complex, which is capable of binding to the IL-12 receptor and inducing IL-12-mediated signal transduction. In some embodiments, the linker is an amino acid sequence (e.g., a peptide) that is 1, 2, 3, 4, 5, 6, 7, 8, 9, 10, 11, 12, 13, 14, 15, 16, 17, 18, 19, 20 or more amino acids long. In some embodiments, the linker is an amino acid sequence (e.g., a peptide) that is between 5 and 20 or 5 and 15 amino acids in length. In certain embodiments, an IL-12 or a derivative thereof encoded by a transgene in a packaged genome of a chimeric NDV described herein consists of more than one polypeptide chain in quaternary association, e.g., a polypeptide chain comprising the IL-12 p35 subunit or a derivative thereof in quaternary association with a polypeptide chain comprising the IL-12 p40 subunit or a derivative thereof. In certain embodiments, the linker is the amino acid sequence set forth in SEQ ID NO: 24. In certain embodiments, the linker is the amino acid sequence set forth in SEQ ID NO: 46. In certain embodiments, the linker is the amino acid sequence set forth in SEQ ID NO: 47. In certain embodiments, the linker is the amino acid sequence set forth in SEQ ID NO: 48. In certain embodiments, the linker is the amino acid sequence set forth in SEQ ID NO: 49. In certain embodiments, the linker is an elastin-like polypeptide sequence. In certain embodiments, the elastin-like polypeptide sequence comprises the amino acid sequence VPGXG (SEQ ID NO:44), wherein X is any amino acid except proline. In certain embodiments, the elastin-like polypeptide sequence comprises the amino acid sequence VPGXGVPGXG (SEQ ID NO:45), wherein X is any amino acid except proline. In certain embodiments, the linker may be a linker described in U.S. Pat. No. 5,891,680, which is incorporated by reference herein in its entirety.

In a specific embodiment, IL-12 encoded by a transgene in a packaged genome of a chimeric NDV described herein comprises the amino acid sequence of a sequence set forth in Table 7. In another specific embodiment, IL-12 encoded by a transgene in a packaged genome of a chimeric NDV described herein consists of the amino acid sequence set forth in Table 7. In a specific embodiment, a transgene encoding IL-12 in a packaged genome of a chimeric NDV described herein comprises the nucleotide sequence of a sequence set forth in Table 8. In a specific embodiment, a transgene encoding IL-12 in a packaged genome of a chimeric NDV described herein consists of the nucleotide sequence of a sequence set forth in Table 8.

In a specific embodiment, a transgene encoding a derivative of IL-12 in a packaged genome of a chimeric NDV described herein is a derivative of any IL-12 known to those of skill in the art. In a specific embodiment, the IL-12 derivative has at least 70%, 75%, 80%, 85%, 90%, 95%, 96%, 98%, or 99% amino acid sequence identity to an IL-12 known to those of skill in the art. In a specific embodiment, the IL-12 derivative comprises deleted forms of a known IL-12, wherein up to about 20, 15, 10, 9, 8, 7, 6, 5, 4, 3, 2 or 1 amino acid residues are deleted from the known IL-12. Also provided herein are IL-12 derivatives comprising deleted forms of a known IL-12, wherein about 1-3, 3-5, 5-7, 7-10, 10-15, or 15-20 amino acid residues are deleted from the known IL-12. Further provided herein are IL-12 derivatives comprising altered forms of a known IL-12, wherein up to about 20, 15, 10, 9, 8, 7, 6, 5, 4, 3, 2 or 1 amino acid residues of the known IL-12 are substituted (e.g., conservatively substituted) with other amino acids. In some embodiments, the IL-12 derivative comprises up to about 20, 15, 10, 9, 8, 7, 6, 5, 4, 3, 2 or 1 conservatively substituted amino acids (see, e.g., Huang et al., 2016, Preclinical validation: LV/IL-12 transduction of patient leukemia cells for immunotherapy of AML, Molecular Therapy—Methods & Clinical Development, 3, 16074; doi:10.1038/mtm.2016.74, which is incorporated by reference herein in its entirety). In some embodiments, the conservatively substituted amino acids are not projected to be in the cytokine/receptor interface (see, e.g., Huang et al., 2016, Preclinical validation: LV/IL-12 transduction of patient leukemia cells for immunotherapy of AML, Molecular Therapy—Methods & Clinical Development, 3, 16074; doi:10.1038/mtm.2016.74; Jones & Vignali, 2011, Molecular Interactions within the IL-6/IL-12 cytokine/receptor superfamily, Immunol Res., 51(1):5-14, doi:10.1007/s12026-011-8209-y; each of which is incorporated by reference herein in its entirety). In some embodiments, the IL-12 derivative comprises an IL-12 p35 subunit having the amino acid substitution L165S (i.e., leucine at position 165 of the IL-12 p35 subunit in the IL-12 derivative is substituted with a serine). In some embodiments, the IL-12 derivative comprises an IL-12 p40 subunit having the amino acid substitution of C2G (i.e., cysteine at position 2 of the immature IL-12 p40 subunit (i.e., the IL-12 p40 subunit containing the signal peptide) in the IL-12 derivative is substituted with a glycine).

In a specific embodiment, the IL-12 derivative is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a native IL-12. In another specific embodiment, the IL-12 derivative is a polypeptide encoded by a nucleic acid sequence that is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a nucleic acid sequence encoding a native IL-12. In a specific embodiment, the IL-12 derivative comprises an IL-12 p35 subunit that is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a native IL-12 p35 subunit. In another specific embodiment, the IL-12 derivative is a polypeptide encoded by a nucleic acid sequence, wherein a portion of nucleic acid sequences encodes an IL-12 p35 subunit, wherein said the nucleic acid sequence of said portion is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a nucleic acid sequence encoding a native IL-12 p35 subunit. In a specific embodiment, the IL-12 derivative comprises an IL-12 p40 subunit that is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a native IL-12 p40 subunit. In another specific embodiment, the IL-12 derivative is a polypeptide encoded by a nucleic acid sequence, wherein a portion of nucleic acid sequences encodes an IL-12 p40 subunit, wherein said the nucleic acid sequence of said portion is at least 80%, 85%, 90%, 95%, 98%, or 99% or is 80% to 85%, 80% to 90%, 80% to 95%, 90% to 95%, 85% to 99%, or 95% to 99% identical (e.g., sequence identity) to a nucleic acid sequence encoding a native IL-12 p40 subunit. In another specific embodiment, the IL-12 derivative contains 1, 2, 3, 4, 5, 6, 7, 8, 9, 10, 11, 12, 13, 14, 15, 16, 17, 18, 19, 20 or more, or 2 to 5, 2 to 10, 5 to 10, 5 to 15, 5 to 20, 10 to 15, or 15 to 20 amino acid mutations (i.e., additions, deletions and/or substitutions) relative to a native IL-12. In another specific embodiment, the IL-12 derivative is a polypeptide encoded by nucleic acid sequence that can hybridize under high, moderate or typical stringency hybridization conditions to a nucleic acid sequence encoding a native IL-12. In another specific embodiment, the IL-12 derivative is a polypeptide encoded by a nucleic acid sequence that can hybridize under high, moderate or typical stringency hybridization conditions to a nucleic acid sequence encoding a fragment of a native IL-12 of at least 10 contiguous amino acids, at least 12 contiguous amino acids, at least 15 contiguous amino acids, at least 20 contiguous amino acids, at least 30 contiguous amino acids, at least 40 contiguous amino acids, at least 50 contiguous amino acids, at least 75 contiguous amino acids, at least 100 contiguous amino acids, at least 125 contiguous amino acids, at least 150 contiguous amino acids, or 10 to 20, 20 to 50, 25 to 75, 25 to 100, 25 to 150, 50 to 75, 50 to 100, 75 to 100, 50 to 150, 75 to 150, 100 to 150, or 100 to 200 contiguous amino acids. In another specific embodiment, the IL-12 derivative is a fragment of a native IL-12. In another specific embodiment, the IL-12 derivative comprises a subunit (e.g., p35 or p40) encoded by a nucleotide sequence that hybridizes over its full length to the nucleotide encoding the native subunit (e.g., native p40 subunit or native p35 subunit). In a specific embodiment, the IL-12 derivative comprises a native IL-12 p40 subunit and a derivative of an IL-12 p35 subunit. In a specific embodiment, the IL-12 derivative comprises a native IL-12 p35 subunit and a derivative of an IL-12 p40 subunit. IL-12 derivatives also include polypeptides that comprise the amino acid sequence of a naturally occurring mature form of IL-12 and a heterologous signal peptide amino acid sequence. In addition, IL-12 derivatives include polypeptides that have been chemically modified by, e.g., glycosylation, acetylation, pegylation, phosphorylation, amidation, derivitization by known protecting/blocking groups, proteolytic cleavage, linkage to a cellular ligand or other protein moiety, etc. Further, IL-12 derivatives include polypeptides comprising one or more non-classical amino acids. In specific embodiments, the IL-12 derivative retains one, two, or more, or all of the functions of the native IL-12 from which it was derived. Tests for determining whether or not an IL-12 derivative retains one or more functions of the native IL-12 from which it was derived are known to one of skill in the art and examples are provided herein.

In specific embodiments, the transgene encoding IL-12 or a derivative thereof in a packaged genome of a chimeric NDV described herein is codon optimized. In a specific embodiment, the nucleotide sequence(s) encoding one or both subunits of a native IL-12 may be codon optimized. A nonlimiting example of a codon-optimized sequence encoding IL-12 p35 or a derivative thereof includes SEQ ID NO:55. Nonlimiting examples of codon-optimized sequences encoding IL-12 p40 or a derivative thereof include SEQ ID NO:54 and 59. Methods of codon optimization are known in the art, e.g., the OptimumGene™ (GenScript®) protocol and U.S. Pat. No. 8,326,547, which is incorporated by reference herein in its entirety.

5.3 Construction of NDVs

The NDVs described herein (see, e.g., Sections 5.1, 5.2, and 6) can be generated using the reverse genetics technique. The reverse genetics technique involves the preparation of synthetic recombinant viral RNAs that contain the non-coding regions of the negative-strand, viral RNA which are essential for the recognition by viral polymerases and for packaging signals necessary to generate a mature virion. The recombinant RNAs are synthesized from a recombinant DNA template and reconstituted in vitro with purified viral polymerase complex to form recombinant ribonucleoproteins (RNPs) which can be used to transfect cells. A more efficient transfection is achieved if the viral polymerase proteins are present during transcription of the synthetic RNAs either in vitro or in vivo. The synthetic recombinant RNPs can be rescued into infectious virus particles. The foregoing techniques are described in U.S. Pat. No. 5,166,057 issued Nov. 24, 1992; in U.S. Pat. No. 5,854,037 issued Dec. 29, 1998; in U.S. Pat. No. 6,146,642 issued Nov. 14, 2000; in European Patent Publication EP 0702085A1, published Feb. 20, 1996; in U.S. patent application Ser. No. 09/152,845; in International Patent Publications PCT WO97/12032 published Apr. 3, 1997; WO96/34625 published Nov. 7, 1996; in European Patent Publication EP A780475; WO 99/02657 published Jan. 21, 1999; WO 98/53078 published Nov. 26, 1998; WO 98/02530 published Jan. 22, 1998; WO 99/15672 published Apr. 1, 1999; WO 98/13501 published Apr. 2, 1998; WO 97/06270 published Feb. 20, 1997; and EPO 780 475A1 published Jun. 25, 1997, each of which is incorporated by reference herein in its entirety.

The helper-free plasmid technology can also be utilized to engineer a NDV described herein. Briefly, a complete cDNA of a NDV (e.g., the Hitchner B1 strain) is constructed, inserted into a plasmid vector and engineered to contain a unique restriction site between two transcription units (e.g., the NDV P and M genes; or the NDV HN and L genes). A nucleotide sequence encoding a heterologous amino acid sequence (e.g., an IL-12 transgene or other sequence such as, e.g., a nucleotide sequence encoding an agonist of a co-stimulatory signal and/or an antagonist of an inhibitory signal of an immune cell) may be inserted into the viral genome at the unique restriction site. Alternatively, a nucleotide sequence encoding a heterologous amino acid sequence (e.g., an IL-12 transgene or other sequence such as, e.g., a nucleotide sequence encoding an agonist of a co-stimulatory signal and/or an antagonist of an inhibitory signal of an immune cell) may be engineered into a NDV transcription unit so long as the insertion does not affect the ability of the virus to infect and replicate. The single segment is positioned between a T7 promoter and the hepatitis delta virus ribozyme to produce an exact negative or positive transcript from the T7 polymerase. The plasmid vector and expression vectors comprising the necessary viral proteins are transfected into cells leading to production of recombinant viral particles (see, e.g., International Publication No. WO 01/04333; U.S. Pat. Nos. 7,442,379, 6,146,642, 6,649,372, 6,544,785 and 7,384,774; Swayne et al. (2003). Avian Dis. 47:1047-1050; and Swayne et al. (2001). J. Virol. 11868-11873, each of which is incorporated by reference in its entirety).

Techniques for the production of a chimeric NDV that express an antibody are known in the art. See, e.g., Puhler et al., Gene Ther. 15(5): 371-283 (2008) for the generation of a recombinant NDV expressing a full IgG from two transgenes.

Bicistronic techniques to produce multiple proteins from a single mRNA are known to one of skill in the art. Bicistronic techniques allow the engineering of coding sequences of multiple proteins into a single mRNA through the use of IRES sequences. IRES sequences direct the internal recruitment of ribosomes to the RNA molecule and allow downstream translation in a cap independent manner. Briefly, a coding region of one protein is inserted downstream of the ORF of a second protein. The insertion is flanked by an IRES and any untranslated signal sequences necessary for proper expression and/or function. The insertion must not disrupt the open reading frame, polyadenylation or transcriptional promoters of the second protein (see, e.g., Garcia-Sastre et al., 1994, J. Virol. 68:6254-6261 and Garcia-Sastre et al., 1994 Dev. Biol. Stand. 82:237-246, each of which are incorporated by reference herein in their entirety).

Methods for cloning chimeric NDV to encode a transgene and express a heterologous protein encoded by the transgene (e.g., IL-12) are known to one skilled in the art, such as, e.g., insertion of the transgene into a restriction site that has been engineered into the NDV genome, inclusion an appropriate signals in the transgene for recognition by the NDV RNA-dependent-RNA polymerase (e.g., sequences upstream of the open reading frame of the transgene that allow for the NDV polymerase to recognize the end of the previous gene and the beginning of the transgene, which may be, e.g., spaced by a single nucleotide intergenic sequence), inclusion of a valid Kozak sequence (e.g., to improve eukaryotic ribosomal translation); incorporation of a transgene that satisfies the "rule of six" for NDV cloning; and inclusion of silent mutations to remove extraneous gene end and/or gene start sequences within the transgene. Regarding the Rule of Six, one skilled in the art will understand that efficient replication of NDV (and more generally, most members of the paramyxoviridae family) is dependent on the genome length being a multiple of six, known as the "rule of six" (see, e.g., Calain, P. & Roux, L. The rule of six, a basic feature of efficient replication of Sendai virus defective interfering RNA. J. Virol. 67, 4822-4830 (1993)). Thus, when constructing a chimeric NDV described herein, care should be taken to satisfy the "Rule of Six" for NDV cloning. Methods known to one skilled in the art to satisfy the Rule of Six for NDV cloning may be used, such as, e.g., addition of nucleotides downstream of the transgene. See, e.g., Ayllon et al., Rescue of Recombinant Newcastle Disease Virus from cDNA. J. Vis. Exp. (80), e50830, doi: 10.3791/50830 (2013) for a discussion of methods for cloning and rescuing of NDV (e.g., chimeric NDV), which is incorporated by reference herein in its entirety.

In a specific embodiment, an NDV described herein (see, e.g., Sections 5.1, 5.2, and 6) can be generated according to a method described in Section 6.

In a specific embodiment, a chimeric NDV comprising a packaged genome comprising a transgene encoding IL-12 or a derivative thereof described herein comprises a La Sota strain backbone. In a specific embodiment, the genomic sequence of the La Sota strain backbone (i.e., without the transgene) is as set forth in SEQ ID NO: 50. In a specific embodiment, a chimeric NDV comprises a packaged genome comprising the nucleotide sequence set forth in SEQ ID Nos: 51, 52 or 60. In a specific embodiment, a chimeric NDV comprises a packaged genome with the nucleotide sequence set forth in SEQ ID Nos: 51, 52 or 60. In some embodiments, a plasmid comprising the nucleotide sequence set forth in a sequence in Table 10 is used to produce a chimeric NDV. In specific embodiments, a plasmid with the nucleotide sequence set forth in a sequence in Table 10 is used to produce a chimeric NDV. See, e.g., Section 6, infra, for techniques that may be used to generate a chimeric NDV using such a plasmid.

5.4 Propagation of NDVs

The NDVs described herein (e.g., the chimeric NDVs; see, also, e.g., Sections 5.1, 5.2, and 6) can be propagated in any substrate that allows the virus to grow to titers that permit the uses of the viruses described herein. In one embodiment, the substrate allows the NDVs described herein (e.g., the chimeric NDVs) to grow to titers comparable to those determined for the corresponding wild-type viruses.

The NDVs described herein (e.g., the chimeric NDVs; see, also, e.g., Sections 5.1, 5.2, and 6) may be grown in cells (e.g., avian cells, chicken cells, etc.) that are susceptible to infection by the viruses, embryonated eggs (e.g., chicken eggs or quail eggs) or animals (e.g., birds). Such methods are well-known to those skilled in the art. In a specific embodiment, the NDVs described herein (e.g., the chimeric NDVs) may be propagated in cancer cells, e.g., carcinoma cells (e.g., breast cancer cells and prostate cancer cells), sarcoma cells, leukemia cells, lymphoma cells, and germ cell tumor cells (e.g., testicular cancer cells and ovarian cancer cells). In another specific embodiment, the NDVs described herein (e.g., the chimeric NDVs) may be propagated in cell lines, e.g., cancer cell lines such as HeLa cells, MCF7 cells, THP-1 cells, U87 cells, DU145 cells, Lncap cells, and T47D cells. In certain embodiments, the cells or cell lines (e.g., cancer cells or cancer cell lines) are obtained and/or derived from a human(s). In another embodiment, the NDVs described herein (e.g., the chimeric NDVs) are propagated in chicken cells or embryonated eggs. Representative chicken cells include, but are not limited to, chicken embryo fibroblasts and chicken embryo kidney cells. In a specific embodiment, the NDVs described herein (e.g., the chimeric NDVs) are propagated in Vero cells. In another specific embodiment, the NDVs described herein (e.g., the chimeric NDVs) are propagated in cancer cells in accordance with the methods described in Section 6, infra. In another specific embodiment, the NDVs described herein (e.g., the chimeric NDVs) are propagated in chicken eggs or quail eggs. In certain embodiments, a NDV virus described herein (e.g., a chimeric NDV) is first propagated in embryonated eggs and then propagated in cells (e.g., a cell line).

The NDVs described herein (e.g., the chimeric NDVs) may be propagated in embryonated eggs, e.g., from 6 to 14 days old, 6 to 12 days old, 6 to 10 days old, 6 to 9 days old, 6 to 8 days old, 8 to 10 days old, or 10 to 12 days old. Young or immature embryonated eggs can be used to propagate the NDVs described herein (e.g., the chimeric NDVs). Immature embryonated eggs encompass eggs which are less than ten day old eggs, e.g., eggs 6 to 9 days old or 6 to 8 days old that are IFN-deficient. Immature embryonated eggs also encompass eggs which artificially mimic immature eggs up to, but less than ten day old, as a result of alterations to the growth conditions, e.g., changes in incubation temperatures; treating with drugs; or any other alteration which results in an egg with a retarded development, such that the IFN system is not fully developed as compared with ten to twelve day old eggs. In a specific embodiment, the NDVs described herein (e.g., the chimeric NDVs) are propagated in 10 day old embryonated chicken eggs. The NDVs described herein (e.g., the chimeric NDVs) can be propagated in different locations of the embryonated egg, e.g., the allantoic cavity. For a detailed discussion on the growth and propagation viruses, see, e.g., U.S. Pat. Nos. 6,852,522 and 7,494,808, both of which are hereby incorporated by reference in their entireties.

In a specific embodiment, provided herein is a method for propagating an NDV described herein (e.g., a chimeric NDV described herein), the method comprising culturing a substrate (e.g., a cell line or embryonated egg) infected with the NDV. In another specific embodiment, provided herein is a method for propagating an NDV described herein (e.g., a chimeric NDV described herein), the method comprising: (a) culturing a substrate (e.g., a cell line or embryonated egg) infected with the NDV; and (b) isolating or purifying the NDV from the substrate. In certain embodiments, these methods involve infecting the substrate with the NDV prior to culturing the substrate. See, e.g., Section 6, infra, for methods that may be used to propagate an NDV described herein (e.g., a chimeric NDV described herein).

For virus isolation, the NDVs described herein (e.g., the chimeric NDVs) can be removed from embryonated eggs or cell culture and separated from cellular components, typically by well known clarification procedures, e.g., such as centrifugation, depth filtration, and microfiltration, and may be further purified as desired using procedures well known to those skilled in the art, e.g., tangential flow filtration (TFF), density gradient centrifugation, differential extraction, or chromatography.

In a specific embodiment, virus isolation from allantoic fluid of an infected egg (e.g., a chicken egg) begins with harvesting allantoic fluid, which is clarified using a filtration system (comprising, e.g., a 1.2 μm glass fiber dead end filtration) to remove cells and other large debris, specifically, comprising a membrane having a net positive charge such that there is a measurable reduction in host cell DNA. The clarified bulk is subsequently processed by tangential flow filtration, e.g., by using 750 kD hollow fiber membranes, concentrating the clarified bulk approximately five-fold. The concentrated clarified bulk is then diafiltered against four diavolumes of high salt buffer, followed by four diavolumes of low salt formulation buffer and subsequently concentrated approximately 10-fold. Accordingly, residual egg proteins, e.g., primarily ovalbumin, and residual DNA are reduced to acceptable levels, and the buffer is exchanged to a buffer compatible with formulation of the chimeric NDV for a composition to be administered to a subject. The resulting product is then sterile filtered through a filter, e.g., a 0.2 μm filter, dispensed into appropriate sterile storage containers, frozen, and stored at −70 degrees Celsius.

In a specific embodiment, an NDV described herein (see, e.g., Sections 5.1, 5.2, and 6) is propagated, isolated, and/or purified according to a method described in Section 6. In a specific embodiment, an NDV described herein (see, e.g., Sections 5.1, 5.2, and 6) is either propagated, isolated, or purified, or any two or all of the foregoing, using a method described in Section 6.

5.5 Antagonists of PD-1 or a Ligand Thereof

Also provided herein are antagonists of PD-1 or a ligand thereof for use in combination with an NDV described herein (see, e.g., Section 5.1, Section 5.2, Section 5.5, Section 5.7, and/or Section 6). Any antagonist of PD-1 or a ligand thereof known to one of skill in the art may be utilized in the methods described herein (see, e.g., Section 5.5, Section 5.7 and/or Section 6). Specific examples of ligands for PD-1 include PD-L1 and PD-L2.

In another embodiment, the antagonist of PD-1 or a ligand thereof is an antibody (or an antigen-binding fragment) or a soluble receptor that specifically binds to a ligand of PD-1 (e.g., PD-L1, PD-L2 or both PD-L1 and PD-L2). In a specific embodiment, the antagonist blocks the ligand of PD-1 (e.g., PD-L1, PD-L2 or both PD-L1 and PD-L2) from binding to PD-1 and transducing an inhibitory signal(s). In certain embodiments, the soluble receptor is a fragment of PD-1 or a fragment of a derivative of PD-1 that binds to a ligand of PD-1 (e.g., the extracellular domain of PD-1 or a derivative of PD-1). In some embodiments, the soluble receptor is a fusion protein comprising at least a portion of PD-1 or a derivative of PD-1 (e.g., the extracellular domain of PD-1 or a derivative of PD-1), and a heterologous amino acid sequence. In specific embodiments, the fusion protein comprises at least a portion of PD-1 or a derivative of PD-1, and the Fc portion of an immunoglobulin or a fragment thereof.

In specific embodiments, the antagonist of PD-1 or a ligand thereof is an antibody (or an antigen-binding fragment) that binds to a ligand of PD-1 (e.g., PD-L1, PD-L2 or both PD-L1 and PD-L2). In a specific embodiment, the antagonist blocks (completely or partially) the ligand of PD-1 (e.g., PD-L1, PD-L2 or both PD-L1 and PD-L2) from interacting with PD-1 and transducing an inhibitory signal (s). In certain specific embodiments, the antibody is a monoclonal antibody. In some specific embodiments, the antibody is an scFv. In certain specific embodiments, the antibody is a camelized antibody. In particular embodiments, the antibody is a human or humanized antibody. Nonlimiting examples of antibodies that bind to a ligand of PD-1 include durvalumab (also referred to as "medi-4736"; see, e.g., Lutzky et al., J Clin Oncol. 2014; 32(suppl 5S): abstr 3001), avelumab (e.g., for Merkel cell carcinoma) (also referred to as "MSB0010718C"; see, e.g., Heery et al. J Clin Oncol. 2014; 32(suppl 5S):abstr 3064), bms-936559 (see, e.g., Brahmer et al. N. Engl. J. Med. 2012; 366, 2455-2465), and atezolizumab (also referred to as "mpd13280A" or "TECENTRIQ®"; see, e.g., McDermott et al., J Clin Oncol. 2016; 34(8):833-842, Herbst et al., J Clin Oncol. 2013; 31(suppl):abstr 3000, and Full Prescribing Information for TECENTRIQ, Reference ID: 3933242).

In a specific embodiment in which the antagonist of PD-1 or a ligand thereof is an antibody that binds to a ligand of PD-1 (e.g., PD-L1 or PD-L2), the antibody is a PD-1 ligand blocking antibody. In a specific embodiment, the anti-PD-1 ligand antibody (e.g., an anti-PD-L1 or an anti-PD-L2 antibody) specifically binds to the PD-1 ligand (e.g., PD-L1 or PD-L2). In a specific embodiment, the PD-1 ligand is human PD-L1. In another specific embodiment, the PD-1 ligand is human PD-L2. In a specific embodiment, an anti-PD-L1 or anti-PD-L2 antibody inhibits or reduces the interaction between PD-L1 or PD-L2, respectively, and PD-1. In a specific embodiment, an anti-PD-L1 or anti-PD-L2 antibody is an antibody that binds to PD-L1 or PD-L2, respectively, and blocks (completely or partially) the interaction between PD-L1 or PD-L2, respectively, and PD-1, thereby releasing PD-1 pathway-mediated inhibition of the immune response, including the anti-tumor response. In a specific embodiment, the blocking of the interaction between PD-L1 or PD-L2 and PD-1 is complete. In a specific embodiment, the blocking of the interaction between PD-L1 or PD-L2 and PD-1 refers to at least 5%, 10%, 15%, 20%, 25%, 30%, 35%, 40%, 45%, 50%, 55%, 60%, 65%, 70%, 75%, 80%, 85%, 90%, 95%, 98%, or 99% blocking of the interaction between PD-L1 or PD-L2 and PD-1 as assessed by any method known to one of skill in the art, such as, e.g., co-immunoprecipitation or co-localization assays, as compared to interaction between PD-L1 or PD-L2, respectively, and PD-1 in the presence of a negative control therapy (e.g., an anti-IgG antibody). In a specific embodiment, an anti-PD-L1 or anti-PD-L2 antibody inhibits or reduces PD-L1- or PD-L2-dependent, respectively, activation of PD-1. In a specific embodiment, the inhibition of ligand-dependent activation is complete. In a specific embodiment, the inhibition of ligand-dependent activation refers to at least 5%, 10%, 15%, 20%, 25%, 30%, 35%, 40%, 45%, 50%, 55%, 60%, 65%, 70%, 75%, 80%, 85%, 90%, 95%, 98%, or 99% inhibition of ligand-dependent activation as assessed by any method known to one of skill in the art, such as, e.g., a phosphorylation assay, as compared to ligand-dependent PD-1 activation in the presence of a negative control therapy (e.g., an anti-IgG antibody).

In some embodiments, an antagonist of PD-1 or a ligand thereof is an antibody that binds to PD-L1, blocks (completely or partially) the interaction between PD-L1 and PD-1, and blocks (completely or partially) the interaction between PD-L1 and CD80 (B7.1). In certain embodiments, the antibody is an IgG1 monoclonal antibody. In a specific embodiment, the antibody is durvalumab.

In another embodiment, the antagonist of PD-1 or a ligand thereof is an antibody or ligand that binds to PD-1 (e.g., human PD-1), but does not transduce an inhibitory signal(s), as measured by techniques described herein or known to one of skill in the art. In a specific embodiment, the antibody or ligand binds to human PD-1. In a particular embodiment, the antibody or ligand specifically binds to PD-1 (e.g., human PD-1). In certain specific embodiments, the antibody is a monoclonal antibody. In some specific embodiments, the antibody is an scFv. In certain specific embodiments, the antibody is a camelized antibody. In particular embodiments, the antibody is a human or humanized antibody. Nonlimiting examples of antibodies that bind to PD-1 include pembrolizumab ("KEYTRUDA®"; see, e.g., Hamid et al., N Engl J Med. 2013; 369:134-44 and Full Prescribing Information for KEYTRUDA, Reference ID: 3862712), nivolumab ("OPDIVO®"; see, e.g., Topalian et al., N Engl J Med. 2012; 366:2443-54 and Full Prescribing Information for OPDIVO (nivolumab), Reference ID: 3677021), and MEDI0680 (also referred to as "AMP-514"; see, e.g., Hamid et al., Ann Oncol. 2016; 27(suppl_6):1050PD). In a preferred embodiment, the anti-PD-1 antibody is pembrolizumab.

In a specific embodiment in which the antagonist of PD-1 or a ligand thereof is an antibody that binds to PD-1 (e.g., human PD-1), the antibody is an anti-PD-1 antibody that blocks or reduces the interaction between PD-1 (e.g., human PD-1) and a ligand thereof (e.g., PD-L1, PD-L2 or both PD-L1 and PD-L2). In a specific embodiment, a PD-1 blocking antibody binds to PD-1 and inhibits or reduces the interaction between PD-1 (e.g., human PD-1) and a ligand thereof (e.g., either PD-L1, PD-L2, or both). In a specific embodiment, the PD-1 blocking antibody specifically binds to PD-1. In some embodiments, an anti-PD-1 is an antibody that binds to PD-1 (e.g., human PD-1) and blocks (completely or partially) the interaction between PD-1 (e.g., human PD-1) and either PD-L1, PD-L2, or both, thereby releasing PD-1 pathway-mediated inhibition of the immune response, including the anti-tumor response. In a specific embodiment, an anti-PD-1 is an antibody that binds to PD-1 (e.g., human PD-1) and blocks (completely or partially) the interaction between PD-1 (e.g., human PD-1) and its ligands, PD-L1 and PD-L2, thereby releasing PD-1 pathway-mediated inhibition of the immune response, including the anti-tumor response. In a specific embodiment, the blocking of the interaction between PD-1 (e.g., human PD-1) and either PD-L1, PD-L2, or both is complete. In a specific embodiment, the blocking of the interaction between PD-1 (e.g., human PD-1) and either PD-L1, PD-L2, or both refers to at least 5%, 10%, 15%, 20%, 25%, 30%, 35%, 40%, 45%, 50%, 55%, 60%, 65%, 70%, 75%, 80%, 85%, 90%, 95%, 98%, or 99% blocking of the interaction between PD-1 (e.g., human PD-1) and either PD-L1, PD-L2, or both as assessed by any method known to one of skill in the art, such as, e.g., co-immunoprecipitation or co-localization assays, as compared to interaction between PD-1 (e.g., human PD-1) and either PD-L1, PD-L2, or both in the presence of a negative control therapy (e.g., an anti-IgG antibody). In a specific embodiment, an anti-PD-1 antibody inhibits ligand-dependent (e.g., either PD-L1, PD-L2, or both) activation of PD-1 (e.g., human PD-1). In a specific embodiment, the inhibition of ligand-dependent activation is complete. In a specific embodiment, the inhibition of ligand-dependent activation refers to at least 5%, 10%, 15%, 20%, 25%, 30%, 35%, 40%, 45%, 50%, 55%, 60%, 65%, 70%, 75%, 80%, 85%, 90%, 95%, 98%, or 99% inhibition of ligand-dependent activation as assessed by any method known to one of skill in the art, such as, e.g., a phosphorylation assay, as compared to ligand-dependent PD-1 (e.g., human PD-1) activation in the presence of a negative control therapy (e.g., an anti-IgG antibody).

In another embodiment, the antagonist of PD-1 or a ligand thereof is a ligand that binds to PD-1 (e.g., human PD-1), but does not transduce an inhibitory signal(s). In another embodiment, the antagonist of PD-1 or a ligand thereof is a ligand that binds to PD-1 (e.g., human PD-1), but only nominally transduces an inhibitory signal(s). In certain specific embodiments, the ligand is a fusion protein comprising at least a portion of a ligand of PD-1 (e.g., human PD-1) or a derivative of a ligand of PD-1, and a heterologous amino acid sequence. In specific embodiments, the fusion protein comprises at least a portion of a ligand of PD-1 or a derivative of a ligand of PD-1, and the Fc portion of an immunoglobulin or a fragment thereof. An example of such a fusion protein is AMP-224 (see, e.g., Infante et al., J Clin Oncol. 2013; 31(suppl):abstr 3044).

In some embodiments, an antagonist of PD-1 or a ligand thereof (e.g., selectively) inhibits or reduces one or more of the signal transduction pathways induced by the binding of PD-1 (e.g., human PD-1) to its ligand(s). In specific embodiments, an antagonist of PD-1 or a ligand thereof inhibits or reduces one or more of the signal transduction pathways induced by the binding of PD-1 (e.g., human PD-1) to one or more of its ligands (e.g., either PD-L1, PD-L2, or both) by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of PD-1 (e.g., human PD-1) to one or more of its ligands (e.g., either PD-L1, PD-L2, or both) in the absence of the antagonist. In specific embodiments, an antagonist of PD-1 or its ligand: (i) inhibits or reduces one or more of the signal transduction pathways induced by the binding of PD-1 (e.g., human PD-1) to one particular ligand (e.g., PD-L1) by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of PD-1 (e.g., human PD-1) to the one particular ligand (e.g., PDLI) in the absence of the antagonist; and (ii) does not inhibit or reduce, or inhibits or reduces one or more of the signal transduction pathways induced by the binding of PD-1 (e.g., human PD-1) to one or more other ligands (e.g., PD-L2) by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of PD-1 to such one or more other ligands in the absence of the antagonist.

In specific embodiments, an antagonist of PD-1 or a ligand thereof inhibits or reduces one or more of the signal transduction pathways induced by the binding of PD-1 (e.g., human PD-1) to either PD-L1, PD-L2, or both by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of PD-1 (e.g., human PD-1) to either PD-L1, PD-L2, or both in the absence of the antagonist. In specific embodiments, an antagonist of PD-1 or a ligand thereof induces, activates and/or enhances one or more immune activities, functions or responses. The one or more immune activities, functions or responses can be in the form of, e.g., an antibody response (humoral response) or a cellular immune response, e.g., cytokine secretion (e.g., interferon-gamma), helper activity or cellular cytotoxicity. In one embodiment, expression of an activation marker on immune cells (e.g., CD44, Granzyme, or Ki-67), expression of a co-stimulatory receptor on immune cells (e.g., ICOS, CD28, OX40, or CD27), expression of a ligand for a co-stimulatory receptor (e.g., B7HRP1, CD80, CD86, OX40L, or CD70), cytokine secretion, infiltration of immune cells (e.g., T-lymphocytes, B lymphocytes and/or NK cells) to a tumor, antibody production, effector function, T cell activation, T cell differentiation, T cell proliferation, B cell differentiation, B cell proliferation, and/or NK cell proliferation is induced, activated and/or enhanced following contact with an antagonist of PD-1 or a ligand thereof. In another embodiment, myeloid-derived suppressor cell (MDSC) tumor infiltration and proliferation, Treg tumor infiltration, activation and proliferation, peripheral blood MDSC and Treg counts are inhibited following contact with an antagonist of PD-1 or a ligand thereof. In another embodiment, expression of a ligand of PD-1 (e.g., PD-L1, PD-L2 or both PD-L1 and PD-L2) is induced, activated and/or enhanced following contact with an antagonist of PD-1 or a ligand thereof. In a particular embodiment, the expression of PD-L1 is induced and/or increased following contact with an antagonist of PD-1 or a ligand thereof. In another embodiment, one, two, or more of the effects described in Section 6, infra, occurs following contact with an antagonist of PD-1 or a ligand thereof.

Nonlimiting examples of antagonists of PD-1 or a ligand thereof include pembrolizumab ("KEYTRUDA®"; see, e.g., Hamid et al., N Engl J Med. 2013; 369:134-44 and Full Prescribing Information for KEYTRUDA (pembrolizumab), Reference ID: 3862712), nivolumab ("OPDIVO®"; see, e.g., Topalian et al., N Engl J Med. 2012; 366:2443-54 and Full Prescribing Information for OPDIVO (nivolumab), Reference ID: 3677021), AMP-224 (see, e.g., Infante et al., J Clin Oncol. 2013; 31(suppl):abstr 3044), MEDI0680 (also referred to as "AMP-514"; see, e.g., Hamid et al., Ann Oncol. 2016; 27(suppl 6):1050PD), durvalumab (also referred to as "medi-4736"; see, e.g., Lutzky et al., J Clin Oncol. 2014; 32(suppl 5S):abstr 3001), avelumab (e.g., for Merkel cell carcinoma) (also referred to as "MSB0010718C"; see, e.g., Heery et al. J Clin Oncol. 2014; 32(suppl 5S):abstr 3064), bms-936559 (see, e.g., Brahmer et al. N. Engl. J. Med. 2012; 366, 2455-2465), and atezolizumab (also referred to as "mpd13280A" and "TECENTRIQ®"; see, e.g., McDermott et al., J Clin Oncol. 2016; 34(8):833-842, Herbst et al., J Clin Oncol. 2013; 31(suppl): abstr 3000, and Full Prescribing Information for TECENTRIQ, Reference ID: 3933242). In a specific embodiment, the antagonist of PD-1 or a ligand thereof is a therapy approved by the U.S. FDA for treatment of one or more cancers. Nonlimiting examples of an antagonist of PD-1 or a ligand thereof approved by the U.S. FDA for treatment of cancer include pembrolizumab, nivolumab, atezolizumab, and avelumab. In a specific embodiment, the antagonist of PD-1 or a ligand thereof is a therapy approved by the EMA for treatment of one or more cancers. Nonlimiting examples of an antagonist of PD-1 or a ligand thereof approved by the EMA for treatment of cancer include pembrolizumab, nivolumab, and atezolizumab. In a specific embodiment, the antagonist of PD-1 or a ligand thereof is nivolumab. In a specific embodiment, the antagonist of PD-1 or a ligand thereof is anti-PD-1 antibody described in International Patent Application Publication No WO 2008/156712, or U.S. Pat. Nos. 8,354,509, 8,952,136, or U.S. Pat. No. 8,900,587, each of which is incorporated by reference in its entirety. In a preferred embodiment, the antagonist of PD-1 or a ligand thereof is pembrolizumab.

In a specific embodiment, provided herein is an antibody that binds to human PD-1, which antibody comprises a variable light chain region (VLCR) complementarity determining region (CDR)1 comprising the amino acid sequence RASKGVSTSGYSYLH (SEQ ID NO: 1), a VLCR CDR2 comprising the amino acid sequence LASYLES (SEQ ID NO: 2), a VLCR CDR3 comprising the amino acid sequence QHSRDLPLT (SEQ ID NO: 3), a variable heavy chain region (VHCR) CDR1 comprising the amino acid sequence NYYMY (SEQ ID NO: 6), a VHCR CDR2 comprising the amino acid sequence GINPSNGGTNFNEKFKN (SEQ ID NO: 7), and a VHCR CDR3 comprising the amino acid sequence RDYRFDMGFDY (SEQ ID NO: 8). In another specific embodiment, provided herein is an antibody that binds to human PD-1, which antibody comprises (a) a VLCR comprising (i) a VLCR CDR1 comprising the amino acid sequence RASKGVSTSGYSYLH (SEQ ID NO: 1), (ii) a VLCR CDR2 comprising the amino acid sequence LASYLES (SEQ ID NO: 2), and (iii) a VLCR CDR3 comprising the amino acid sequence QHSRDLPLT (SEQ ID NO: 3); and (b) a VHCR comprising (i) a VHCR CDR1 comprising the amino acid sequence NYYMY (SEQ ID NO: 6), (ii) a VHCR CDR2 comprising the amino acid sequence GINPSNGGTNFNEKFKN (SEQ ID NO: 7), and (iii) a VHCR CDR3 comprising the amino acid sequence RDYRFDMGFDY (SEQ ID NO: 8). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1, which antibody comprises: (a) a VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a VHCR comprising (i) a VHCR CDR1 comprising the amino acid sequence NYYMY (SEQ ID NO: 6), (ii) a VHCR CDR2 comprising the amino acid sequence GINPSNGGTNFNEKFKN (SEQ ID NO: 7), and (iii) a VHCR CDR3 comprising the amino acid sequence RDYRFDMGFDY (SEQ ID NO: 8). In another specific embodiment, provided herein is an antibody that binds to human PD-1, which antibody comprises: (a) a VLCR comprising (i) a VLCR CDR1 comprising the amino acid sequence RASKGVSTSGYSYLH (SEQ ID NO: 1), (ii) a VLCR CDR2 comprising the amino acid sequence LASYLES (SEQ ID NO: 2), and (iii) a VLCR CDR3 comprising the amino acid sequence QHSRDLPLT (SEQ ID NO: 3); and (b) a VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a preferred embodiment, provided herein is an antibody that binds to human PD-1, which antibody comprises: (a) a VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a VHCR comprising the amino acid sequence QVQLVQSGVEVKKPGASVKVSCKASGYTFTNYYMYWVRQAPGQGLEWMGGINPSNG GTNFNEKFKNRVTLTTDSSTT- TAYMELKSLQFDDTAVYYCARRDYRFDMGFDYWGQG TTVTVSS (SEQ ID NO: 9). In a preferred embodiment, the antibody is an IgG4 kappa immunoglobulin.

In a specific embodiment, provided herein is an antibody that binds to human PD-1 and blocks the interaction between human PD-1 and its ligands, PD-L1 and PD-L2, which antibody comprises a variable light chain region (VLCR) complementarity determining region (CDR)1 comprising the amino acid sequence RASKGVSTSGYSYLH (SEQ ID NO: 1), a VLCR CDR2 comprising the amino acid sequence LASYLES (SEQ ID NO: 2), a VLCR CDR3 comprising the amino acid sequence QHSRDLPLT (SEQ ID NO: 3), a variable heavy chain region (VHCR) CDR1 comprising the amino acid sequence NYYMY (SEQ ID NO: 6), a VHCR CDR2 comprising the amino acid sequence GINPSNGGTNFNEKFKN (SEQ ID NO: 7), and a VHCR CDR3 comprising the amino acid sequence RDYRFDMGFDY (SEQ ID NO: 8). In another specific embodiment, provided herein is an antibody that binds to human PD-1 and blocks the interaction between human PD-1 and its ligands, PD-L1 and PD-L2, which antibody comprises (a) a VLCR comprising (i) a VLCR CDR1 comprising the amino acid sequence RASKGVSTSGYSYLH (SEQ ID NO: 1), (ii) a VLCR CDR2 comprising the amino acid sequence LASYLES (SEQ ID NO: 2), and (iii) a VLCR CDR3 comprising the amino acid sequence QHSRDLPLT (SEQ ID NO: 3); and (b) a VHCR comprising (i) a VHCR CDR1 comprising the amino acid sequence NYYMY (SEQ ID NO: 6), (ii) a VHCR CDR2 comprising the amino acid sequence GINPSNGGTNFNEKFKN (SEQ ID NO: 7), and (iii) a VHCR CDR3 comprising the amino acid sequence RDYRFDMGFDY (SEQ ID NO: 8). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1 and blocks the interaction between human PD-1 and its ligands, PD-L1 and PD-L2, which antibody comprises: (a) a VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a VHCR comprising (i) a VHCR CDR1 comprising the amino acid sequence NYYMY (SEQ ID NO: 6), (ii) a VHCR CDR2 comprising the amino acid sequence GINPSNGGTNFNEKFKN (SEQ ID NO: 7), and (iii) a VHCR CDR3 comprising the amino acid sequence RDYRFDMGFDY (SEQ ID NO: 8). In another specific embodiment, provided herein is an antibody that binds to human PD-1 and blocks the interaction between human PD-1 and its ligands, PD-L1 and PD-L2, which antibody comprises: (a) a VLCR comprising (i) a VLCR CDR1 comprising the amino acid sequence RASKGVSTSGYSYLH (SEQ ID NO: 1), (ii) a VLCR CDR2 comprising the amino acid sequence LASYLES (SEQ ID NO: 2), and (iii) a VLCR CDR3 comprising the amino acid sequence QHSRDLPLT (SEQ ID NO: 3); and (b) a VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1 and blocks the interaction between human PD-1 and its ligands, PD-L1 and PD-L2, which antibody comprises: (a) a VLCR CDR1, a VLCR CDR2, and a VLCR CDR3 comprising the amino acid sequences of the VLCR CDR1, VLCR CDR2, and VLCR CDR3, respectively, of the VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a VHCR CDR1, a VHCR CDR2, and a VHCR CDR3 comprising the amino acid sequences of the VHCR CDR1, VHCR CDR2, and VHCR CDR3, respectively, of the VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In certain aspects, the CDRs of an antibody can be determined according to the Kabat numbering system. In a specific embodiment, the VLCR CDR1 comprising the amino acid sequence RASKGVSTSGYSYLH (SEQ ID NO: 1), the VLCR CDR2 comprising the amino acid sequence LASYLES (SEQ ID NO: 2), the VLCR CDR3 comprising the amino acid sequence QHSRDLPLT (SEQ ID NO: 3), the VHCR CDR1 comprising the amino acid sequence NYYMY (SEQ ID NO: 6), the VHCR CDR2 comprising the amino acid sequence GINPSNGGTNFNEKFKN (SEQ ID NO: 7), and the VHCR CDR3 comprising the amino acid sequence RDYRFDMGFDY (SEQ ID NO: 8), as determined according to the Kabat numbering system. In some aspects, the CDRs of an antibody can be determined according to the Chothia numbering scheme, which refers to the location of immunoglobulin structural loops (see, e.g., Chothia and Lesk, 1987, J. Mol. Biol., 196:901-917; Al-Lazikani et al., 1997, J. Mol. Biol., 273:927-948; Chothia et al., 1992, J. Mol. Biol., 227:799-817; Tramontano A et al., 1990, J. Mol. Biol. 215(1):175-82; and U.S. Pat. No. 7,709,226). In certain aspects, the CDRs of an antibody can be determined according to the IMGT numbering system as described in Lefranc, M.-P., 1999, The Immunologist, 7:132-136 and Lefranc, M.-P. et al., 1999, Nucleic Acids Res., 27:209-212. In certain aspects, the CDRs of an antibody can be determined according to MacCallum et al., 1996, J. Mol. Biol., 262:732-745. See also, e.g., Martin, A., "Protein Sequence and Structure Analysis of Antibody Variable Domains," in Antibody Engineering, Kontermann and Dübel, eds., Chapter 31, pp. 422-439, Springer-Verlag, Berlin (2001). In certain aspects, the CDRs of an antibody can be determined according to the AbM numbering scheme, which refers AbM hypervariable regions, which represent a compromise between the Kabat CDRs and Chothia structural loops, and are used by Oxford Molecular's AbM antibody modeling software. In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

The terms "Kabat numbering," and like terms are recognized in the art and refer to a system of numbering amino acid residues in the heavy and light chain variable regions of an antibody, or an antigen-binding portion thereof. In certain aspects, the CDRs of an antibody can be determined according to the Kabat numbering system (see, e.g., Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). With respect to the Kabat numbering system, (i) the VH CDR1 is typically present at amino acid positions 31 to 35 of the heavy chain, which can optionally include one or two additional amino acids following amino acid position 35 (referred to in the Kabat numbering scheme as 35A and 35B); (ii) the VH CDR2 is typically present at amino acid positions 50 to 65 of the heavy chain; and (iii) the VH CDR2 is typically present at amino acid positions 95 to 102 of the heavy chain (Kabat, Elvin A. et al., Sequences of Proteins of Immunological Interest. Bethesda: National Institutes of Health, 1983). With respect to the Kabat numbering system, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (Kabat, Elvin A. et al., Sequences of Proteins of Immunological Interest. Bethesda: National Institutes of Health, 1983). As is well known to those of skill in the art, using the Kabat numbering system, the actual linear amino acid sequence of the antibody variable domain can contain fewer or additional amino acids due to a shortening or lengthening of a FR and/or CDR and, as such, an amino acid's Kabat number is not necessarily the same as its linear amino acid number.

The Chothia definition is based on the location of the structural loop regions (Chothia et al., (1987) J Mol Biol 196: 901-917; and U.S. Pat. No. 7,709,226). The term "Chothia CDRs," and like terms are recognized in the art and refer to antibody CDR sequences as determined according to the method of Chothia and Lesk, 1987, J. Mol. Biol., 196:901-917, which will be referred to herein as the "Chothia CDRs" (see also, e.g., U.S. Pat. No. 7,709,226 and Martin, A., "Protein Sequence and Structure Analysis of Antibody Variable Domains," in Antibody Engineering, Kontermann and Dübel, eds., Chapter 31, pp. 422-439, Springer-Verlag, Berlin (2001)). With respect to the Chothia numbering system, using the Kabat numbering system of numbering amino acid residues in the VH region, (i) the VH CDR1 is typically present at amino acid positions 26 to 32 of the heavy chain; (ii) the VH CDR2 is typically present at amino acid positions 53 to 55 of the heavy chain; and (iii) the VH CDR3 is typically present at amino acid positions 96 to 101 of the heavy chain. In a specific embodiment, with respect to the Chothia numbering system, using the Kabat numbering system of numbering amino acid residues in the VH region, (i) the VH CDR1 is typically present at amino acid positions 26 to 32 or 34 of the heavy chain; (ii) the VH CDR2 is typically present at amino acid positions 52 to 56 (in one embodiment, CDR2 is at positions 52A-56, wherein 52A follows position 52) of the heavy chain; and (iii) the VH CDR3 is typically present at amino acid positions 95 to 102 of the heavy chain (in one embodiment, there is no amino acid at positions numbered 96-100). With respect to the Chothia numbering system, using the Kabat numbering system of numbering amino acid residues in the VL region, (i) the VL CDR1 is typically present at amino acid positions 26 to 33 of the light chain; (ii) the VL CDR2 is typically present at amino acid positions 50 to 52 of the light chain; and (iii) the VL CDR3 is typically present at amino acid positions 91 to 96 of the light chain. In a specific embodiment, with respect to the Chothia numbering system, using the Kabat numbering system of numbering amino acid residues in the VL region, (i) the VL CDR1 is typically present at amino acid positions 24 to 34 of the light chain; (ii) the VL CDR2 is typically present at amino acid positions 50 to 56 of the light chain; and (iii) the VL CDR3 is typically present at amino acid positions 89 to 97 of the light chain (in one embodiment, there is no amino acid at positions numbered 96-100). These Chothia CDR positions may vary depending on the antibody, and may be determined according to methods known in the art.

The IMGT definition is from the IMGT ("IMGT®, the international ImMunoGeneTics information System® website imgt.org, founder and director: Marie-Paule Lefranc, Montpellier, France; see, e.g., Lefranc, M.-P., 1999, The Immunologist, 7:132-136 and Lefranc, M.-P. et al., 1999, Nucleic Acids Res., 27:209-212, both of which are incorporated herein by reference in their entirety). With respect to the IMGT numbering system, (i) the VH CDR1 is typically present at amino acid positions 25 to 35 of the heavy chain; (ii) the VH CDR2 is typically present at amino acid positions 51 to 57 of the heavy chain; and (iii) the VH CDR2 is typically present at amino acid positions 93 to 102 of the heavy chain. With respect to the IMGT numbering system, (i) the VL CDR1 is typically present at amino acid positions 27 to 32 of the light chain; (ii) the VL CDR2 is typically present at amino acid positions 50 to 52 of the light chain; and (iii) the VL CDR3 is typically present at amino acid positions 89 to 97 of the light chain.

In a preferred embodiment, provided herein is an antibody that binds to human PD-1 and blocks the interaction between human PD-1 and its ligands, PD-L1 and PD-L2, which antibody comprises: (a) a VLCR comprising the amino acid sequence EIVLTQSPATLSLSPGERATLSCRASKGVSTSGYSYLHWYQQKPGQAPRLLIYLASYLESGVPARFSGSGSGTDFTLTISSLEPEDFAVYYCQHSRDL PLTFGGGTKVEIK (SEQ ID NO: 4); and (b) a VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In a preferred embodiment, the antibody is an IgG4 kappa immunoglobulin.

In a specific embodiment, provided herein is an antibody that binds to human PD-1 and blocks the interaction between human PD-1 and its ligands, PD-L1 and PD-L2, which antibody comprises: (a) a light chain comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIKRTVAAPSVFI FPPSDEQLKSGTASVVCLLNNFYPREAKVQWKVDNALQSGNSQESVTEQDSKDSTYSLS STLTLSKADYEKHKVYACEVTHQGLSSPVTKSFNRGEC (SEQ ID NO: 5); and (b) a heavy chain comprising a VHCR comprising the amino acid sequence QVQLVQSGVEVKKPGASVKVSCKASGYTFTNYYMYWVRQAPGQGLEWMGGINPSNG GTNFNEKFKNRVTLTTDSSTTTAYMELKSLQFDDTAVYYCARRDYRFDMGFDYWGQG TTVTVSS (SEQ ID NO: 9). In another specific embodiment, provided herein is an antibody that binds to human PD-1 and blocks the interaction between human PD-1 and its ligands, PD-L1 and PD-L2, which antibody comprises: (a) a light chain comprising a VLCR comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIK (SEQ ID NO: 4); and (b) a heavy chain comprising the amino acid sequence

```
                                            (SEQ ID NO: 10)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.
```

In a preferred embodiment, provided herein is an antibody that binds to human PD-1 and blocks the interaction between human PD-1 and its ligands, PD-L1 and PD-L2, which antibody comprises: (a) a light chain comprising the amino acid sequence EIVLTQSPATLSLSPGERATLSCRASKGVSTSGYSYLHWYQQKPGQAPRLLIYLASYLES GVPARFSGSGSGTDFTLTISSLEPEDFAVYYCQHSRDLPLTFGGGTKVEIKRTVAAPSVFI FPPSDEQLKSGTASVVCLLNNFYPREAKVQWKVDNALQSGNSQESVTEQDSKDSTYSLS STLTLSKADYEKHKVYACEVTHQGLSSPVTKSFNRGEC (SEQ ID NO: 5); and (b) a heavy chain comprising the amino acid sequence

```
                                            (SEQ ID NO: 10)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK.
```

In a specific embodiment, provided herein is an antibody that binds to human PD-1, which antibody comprises a VLCR CDR1 comprising the amino acid sequence RASQSVSSYLA (SEQ ID NO: 11), a VLCR CDR2 comprising the amino acid sequence DASNRAT (SEQ ID NO: 12), a VLCR CDR3 comprising the amino acid sequence QQSSNWPRT (SEQ ID NO: 13), a VHCR CDR1 comprising the amino acid sequence NSGMH (SEQ ID NO: 16), a VHCR CDR2 comprising the amino acid sequence VIWYDGSKRYYADSVKG (SEQ ID NO: 17), and a VHCR CDR3 comprising the amino acid sequence NDDY (SEQ ID NO: 18). In another specific embodiment, provided herein is an antibody that binds to human PD-1, which antibody comprises: (a) a VLCR comprising (i) a VLCR CDR1 comprising the amino acid sequence RASQSVSSYLA (SEQ ID NO: 11), (ii) a VLCR CDR2 comprising the amino acid sequence DASNRAT (SEQ ID NO: 12), and (iii) a VLCR CDR3 comprising the amino acid sequence QQSSNWPRT (SEQ ID NO: 13); and (b) a VHCR comprising (i) a VHCR CDR1 comprising the amino acid sequence NSGMH (SEQ ID NO: 16), (ii) a VHCR CDR2 comprising the amino acid sequence VIWYDGSKRYYADSVKG (SEQ ID NO: 17), and (iii) a VHCR CDR3 comprising the amino acid sequence NDDY (SEQ ID NO: 18). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1, which antibody comprises: (a) a VLCR comprising the amino acid sequence

```
                                            (SEQ ID NO: 14)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK;
```

and (b) a VHCR comprising (i) a VHCR CDR1 comprising the amino acid sequence NSGMH (SEQ ID NO: 16), (ii) a VHCR CDR2 comprising the amino acid sequence VIWYDGSKRYYADSVKG (SEQ ID NO: 17), and (iii) a VHCR CDR3 comprising the amino acid sequence NDDY (SEQ ID NO: 18). In another specific embodiment, provided herein is an antibody that binds to human PD-1, which antibody comprises: (a) a VLCR comprising (i) a VLCR CDR1 comprising the amino acid sequence RASQSVSSYLA (SEQ ID NO: 11), (ii) a VLCR CDR2 comprising the amino acid sequence DASNRAT (SEQ ID NO: 12), and (iii) a VLCR CDR3 comprising the amino acid sequence QQSSNWPRT (SEQ ID NO: 13); and (b) a VHCR comprising QVQLVESGGGVVQPGRSLRLDCKASGITFSNSGMHWVRQAPGKGLEWVAVIWYDGSK RYYADSVKGRFTISRDNSKNTLFLQMNSLRAEDTAVYYCATNDDYWGQGTLVTVSS (SEQ ID NO: 19). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1 and blocks the binding of human PD-1 to its ligands, PD-L1 and PD-L2, which antibody comprises a VLCR CDR1 comprising the amino acid sequence RASQSVSSYLA (SEQ ID NO: 11), a VLCR CDR2 comprising the amino acid sequence DASNRAT (SEQ ID NO: 12), a VLCR CDR3 comprising the amino acid sequence QQSSNWPRT (SEQ ID NO: 13), a VHCR CDR1 comprising the amino acid sequence NSGMH (SEQ ID NO: 16), a VHCR CDR2 comprising the amino acid sequence VIWYDGSKRYYADSVKG (SEQ ID NO: 17), and a VHCR CDR3 comprising the amino acid sequence NDDY (SEQ ID NO: 18). In another specific embodiment, provided herein is an antibody that binds to human PD-1 and blocks the binding of human PD-1 to its ligands, PD-L1 and PD-L2, which antibody comprises: (a) a VLCR comprising (i) a VLCR CDR1 comprising the amino acid sequence RASQSVSSYLA (SEQ ID NO: 11), (ii) a VLCR CDR2 comprising the amino acid sequence DASNRAT (SEQ ID NO: 12), and (iii) a VLCR CDR3 comprising the amino acid sequence QQSSNWPRT (SEQ ID NO: 13); and (b) a VHCR comprising (i) a VHCR CDR1 comprising the amino acid sequence NSGMH (SEQ ID NO: 16), (ii) a VHCR CDR2 comprising the amino acid sequence VIWYDGSKRYYADSVKG (SEQ ID NO: 17), and (iii) a VHCR CDR3 comprising the amino acid sequence NDDY (SEQ ID NO: 18). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1 and blocks the binding of human PD-1 to its ligands, PD-L1 and PD-L2, which antibody comprises: (a) a VLCR comprising the amino acid sequence

```
                                    (SEQ ID NO: 14)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK;
```

and (b) a VHCR comprising (i) a VHCR CDR1 comprising the amino acid sequence NSGMH (SEQ ID NO: 16), (ii) a VHCR CDR2 comprising the amino acid sequence VIWYDGSKRYYADSVKG (SEQ ID NO: 17), and (iii) a VHCR CDR3 comprising the amino acid sequence NDDY (SEQ ID NO: 18). In another specific embodiment, provided herein is an antibody that binds to human PD-1 and blocks the binding of human PD-1 to its ligands, PD-L1 and PD-L2, which antibody comprises: (a) a VLCR comprising (i) a VLCR CDR1 comprising the amino acid sequence RASQSVSSYLA (SEQ ID NO: 11), (ii) a VLCR CDR2 comprising the amino acid sequence DASNRAT (SEQ ID NO: 12), and (iii) a VLCR CDR3 comprising the amino acid sequence QQSSNWPRT (SEQ ID NO: 13); and (b) a VHCR comprising QVQLVESGGGVVQPGRSLRLDCKASGITFSNSGMHWVRQAPGKGLEWVAVIWYDGSK RYYADSVKGRFTISRDNSKNTLFLQMNSLRAEDTAVYYCATNDDYWGQGTLVTVSS (SEQ ID NO: 19). In a specific embodiment, the antibody is an IgG (e.g., an IgG1, IgG2, IgG3, or IgG4) antibody. In a preferred embodiment, the antibody is an IgG4 antibody. In certain embodiments, the antibody is a humanized or chimeric antibody. In a preferred embodiment, the antibody is a humanized monoclonal antibody. In another preferred embodiment, the antibody is an IgG4 kappa immunoglobulin.

In a specific embodiment, provided herein is an antibody that binds to human PD-1 and blocks the binding of human PD-1 to its ligands, PD-L1 and PD-L2, which antibody comprises: (a) a VLCR CDR1, a VLCR CDR2, and a VLCR CDR3 comprising the amino acid sequences of the VLCR CDR1, VLCR CDR2, and VLCR CDR3, respectively, of the VLCR comprising the amino acid sequence

```
                                    (SEQ ID NO: 14)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIK;
```

and (b) a VHCR CDR1, a VHCR CDR2, and a VHCR CDR3 comprising the amino acid sequences of the VHCR CDR1, VHCR CDR2, and VHCR CDR3, respectively, of the VHCR comprising the amino acid sequence QVQLVESGGGVVQPGRSLRLDCKASGITFSNSGMHWVRQAPGKGLEWVAVIWYDGSK RYYADSVKGRFTISRDNSKNTLFLQMNSLRAEDTAVYYCATNDDYWGQGTLVTVSS (SEQ ID NO: 19). In certain aspects, the CDRs of an antibody can be determined according to the Kabat numbering system. In some aspects, the CDRs of an antibody can be determined according to the Chothia numbering scheme. In certain aspects, the CDRs of an antibody can be determined according to MacCallum et al., 1996, J. Mol. Biol., 262:732-745. In some aspects, the CDRs of an antibody can be determined according to the IMGT numbering system as described in Lefranc, M.-P., 1999, The Immunologist, 7:132-136 and Lefranc, M.-P. et al., 1999, Nucleic Acids Res., 27:209-212. In certain aspects, the CDRs of an antibody can be determined according to the AbM numbering scheme. In a specific embodiment, the antibody is an IgG (e.g., an IgG1, IgG2, IgG3, or IgG4) antibody. In a preferred embodiment, the antibody is an IgG4 antibody. In another preferred embodiment, the antibody is an IgG4 kappa immunoglobulin.

In a specific embodiment, provided herein is an antibody that binds to human PD-1 and blocks the binding of human PD-1 to its ligands, PD-L1 and PD-L2, which antibody comprises: (a) a VLCR comprising the amino acid sequence

```
                                    (SEQ ID NO: 14)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK;
```

and (b) a VHCR comprising the amino acid sequence QVQLVESGGGVVQPGRSLRLDCKASGITF SNSGMHWVRQAPGKGLEWVAVIWYDGSK RYYADSVKGRFTISRDNSKNTLFLQMNSLRAEDTAVYYCATNDDYWGQGTLVTVSS (SEQ ID NO: 19). In a specific embodiment, the antibody is an IgG (e.g., an IgG1, IgG2, IgG3, or IgG4) antibody. In a preferred embodiment, the antibody is an IgG4 antibody. In another preferred embodiment, the antibody is an IgG4 kappa immunoglobulin.

In a specific embodiment, provided herein is an antibody that binds to human PD-1 and blocks the interaction between human PD-1 and its ligands, PD-L1 and PD-L2, which antibody comprises: (a) a light chain comprising the amino acid sequence EIVLTQSPATLSLSPGERATLSCRASQSVSSYLAWYQQKPGQAPRLLIYDASNRATGIPA RFSGSGSGTDFTLTISSLEPEDFAVYYCQQSSNWPRTFGQGTKVEIKRTVAAPSVFIFPPS DEQLKSGTASVVCLLNNFYPREAKVQWKVDNALQSGNSQESVTEQDSKDSTYSLSSTL TLSKADYEKHKVYACEVTHQGLSSPVTKSFNRGEC (SEQ ID NO: 15); and (b) a heavy chain comprising a VHCR comprising the amino acid sequence QVQLVESGGGVVQPGRSLRLDCK- ASGITFSNSGMHWVRQAPGKGLEWVAVIWYDGSK RYYADSVKGRFTISRDNSKNTLFLQMNSLRAED-TAVYYCATNDDYWGQGTLVTVSS (SEQ ID NO: 19). In another specific embodiment, provided herein is an antibody that binds to human PD-1 and and blocks the interaction between human PD-1 and its ligands, PD-L1 and PD-L2, which antibody comprises: (a) a light chain comprising a VLCR comprising the amino acid sequence EIVLTQSPATLSLSPGERATLSCRASQSVSSYLAWYQ-QKPGQAPRLLIYDASNRATGIPA RFSGSGSGTDFTL-TISSLEPEDFAVYYCQQSSNWPRTFGQGTKVEIK (SEQ ID NO: 14) and (b) a heavy chain comprising the amino acid sequence

```
                                       (SEQ ID NO: 20)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK.
```

In a preferred embodiment, provided herein is an antibody that binds to human PD-1 and and blocks the interaction between human PD-1 and its ligands, PD-L1 and PD-L2, which antibody comprises: (a) a light chain comprising the amino acid sequence EIVLTQSPATLSLSPGER-ATLSCRASQSVSSYLAWYQQKPGQAPRLLIYDASN-RATGIPA RFSGSGSGTDFTLTISSLEPEDFAVYYCQ-QSSNWPRTFGQGTKVEIKRTVAAPSVFIFPPS DEQL-KSGTASVVCLLNNFYPREAKVQWKVDNALQSGN-SQESVTEQDSKDSTYSLSSTL TLSKADYEKHKVY-ACEVTHQGLSSPVTKSFNRGEC (SEQ ID NO: 15) and (b) a heavy chain comprising the amino acid sequence

```
                                       (SEQ ID NO: 20)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK.
```

Antagonists of PD-1 or a ligand thereof may be produced by techniques known by one skilled in the art. See, e.g., U.S. Pat. Nos. 9,642,298, 8,952,136, 8,900,587, 8,168,757, 7,488,802, U.S. Patent Application Publication No. 2016/0137721, and International Patent Application Publication No. WO 2014/159960 for examples of techniques that may be used to produce antagonists of PD-1; or a ligand thereof. In a specific embodiment, an antagonist of PD-1 or a ligand thereof is isolated.

5.5.1 Antibody Production

In one aspect, provided herein are methods for making an antibody or other proteinacous antagonist of PD-1 or a ligand thereof described herein. In a specific embodiment, an antibody or other proteinacous antagonist of PD-1 or a ligand thereof described herein may be prepared, expressed, created or isolated by any means that involves creation, e.g., via synthesis or genetic engineering of sequences. In a specific embodiment, such an antibody or other proteinacous antagonist of PD-1 or a ligand thereof comprises sequences that are encoded by DNA sequences that do not naturally exist within the antibody germline repertoire of an animal or mammal (e.g., a human).

In certain aspects, a method for making an antibody or other proteinacous antagonist of PD-1 or a ligand thereof described herein comprises the step of culturing a cell (e.g., host cell or hybridoma cell) that expresses the antibody or other proteinacous antagonist of PD-1 or a ligand thereof. In certain embodiments, the method for making an antibody or other proteinacous antagonist of PD-1 or a ligand thereof described herein further comprises the step of purifying the antibody or other proteinacous antagonist of PD-1 or a ligand thereof expressed by the cell. In certain aspects, a method for making an antibody or other proteinacous antagonist of PD-1 or a ligand thereof described herein, comprises the step of culturing a cell (e.g., host cell or hybridoma cell) that comprises polynucleotides or vectors encoding the antibody or other proteinacous antagonist of PD-1 or a ligand thereof. In a particular aspect, provided herein are methods for producing an antibody described herein, comprising expressing such antibody from a host cell. The cells may be primary cells or cell lines. In a particular embodiment, the host cell is isolated from other cells. In another embodiment, the host cell is not found within the body of a subject.

Standard methods in molecular biology are described Sambrook, Fritsch and Maniatis (1982 & 1989 $2^{nd}$ Edition, 2001 3rd Edition) *Molecular Cloning, A Laboratory Manual*, Cold Spring Harbor Laboratory Press, Cold Spring Harbor, NY; Sambrook and Russell (2001) *Molecular Cloning, $3^{rd}$ ed.*, Cold Spring Harbor Laboratory Press, Cold Spring Harbor, NY; Wu (1993) *Recombinant DNA*, Vol. 217, Academic Press, San Diego, CA). Standard methods also appear in Ausbel, et al. (2001) *Current Protocols in Molecular Biology, Vols.* 1-4, John Wiley and Sons, Inc. New York, NY, which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, MO; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, NY; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

In certain aspects, provided herein are cells (e.g., host cells) expressing (e.g., recombinantly expressing) the antibodies described herein and related expression vectors. In another aspect, provided herein are vectors (e.g., expression vectors) comprising polynucleotides comprising nucleotide sequences encoding antibodies for recombinant expression in host cells, preferably in mammalian cells. Also provided herein are host cells comprising a polynucleotide encoding an antibody, or vectors comprising a polynucleotide encoding an antibody for recombinantly expressing an antibody described herein. In a specific embodiment, provided herein is a host cell comprising two vectors, wherein the first vector comprises a polynucleotide encoding the variable heavy chain region of an antibody described herein and the second vector comprises a polynucleotide encoding the variable light chain region of an antibody for recombinantly expressing an antibody described herein. The cells may be primary cells or cell lines. In a particular embodiment, the host cell is isolated from other cells. In another embodiment, the host cell is not found within the body of a subject.

Antibodies described herein (e.g., monoclonal antibodies, such as chimeric or humanized antibodies, or an antigen-binding fragment thereof) can be produced by any method known in the art for the synthesis of antibodies, for example, by chemical synthesis or by recombinant expression techniques. The methods described herein employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (1989), *Molecular Cloning: A Laboratory Manual*, Second Edition, Cold Spring Harbor Laboratory Press; Sambrook et al. (2001) *Molecular Cloning: A Laboratory Manual*, Cold Spring Harbor Laboratory Press, Cold Spring Harbor, NY; Ausubel et al., *Current Protocols in Molecular Biology*, John Wiley & Sons (1987 and annual updates); *Current Protocols in Immunology*, John Wiley & Sons (1987 and annual updates) Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) (1999) *Genome Analysis: A Laboratory Manual*, Cold Spring Harbor Laboratory Press.

Monoclonal, polyclonal, and humanized antibodies can be prepared by techniques known in the art (see, e.g., Sheperd and Dean (eds.) (2000) Monoclonal Antibodies, Oxford Univ. Press, New York, NY; Kontermann and Dubel (eds.) (2001) Antibody Engineering, Springer-Verlag, New York; Harlow and Lane (1988) Antibodies A Laboratory Manual, Cold Spring Harbor Laboratory Press, Cold Spring Harbor, NY, pp. 139-243; Carpenter, et al. (2000) J. Immunol. 165:6205; He, et al. (1998) J. Immunol. 160:1029; Tang et al. (1999) J. Biol. Chem. 274:27371-27378; Baca et al. (1997) J. Biol. Chem. 272:10678-10684; Chothia et al. (1989) Nature 342:877-883; Foote and Winter (1992) J. Mol. Biol. 224:487-499; U.S. Pat. No. 6,329,511).

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563 681 (Elsevier, N.Y., 1981). The term "monoclonal antibody" as used herein is not limited to antibodies produced through hybridoma technology.

Methods for producing and screening for specific antibodies using hybridoma technology are routine and well known in the art. For example, in the hybridoma method, a mouse or other appropriate host animal, such as a sheep, goat, rabbit, rat, hamster or macaque monkey, is immunized to elicit lymphocytes that produce or are capable of producing antibodies that will bind to the protein (e.g., PD-1) used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)). Additionally, a RIMMS (repetitive immunization multiple sites) technique can be used to immunize an animal (Kilptrack et al., 1997 Hybridoma 16:381-9, incorporated by reference in its entirety).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Specific embodiments employ myeloma cells that fuse efficiently, support stable high-level production of antibody by the selected antibody-producing cells, and are sensitive to a medium such as HAT medium. Among these myeloma cell lines are murine myeloma lines, such as those derived from MOPC-21 and MPC-11 mouse tumors available from the Salk Institute Cell Distribution Center, San Diego, CA, USA, and SP-2 or X63-Ag8.653 cells available from the American Type Culture Collection, Rockville, MD, USA. Human myeloma and mouse-human heteromyeloma cell lines also have been described for the production of human monoclonal antibodies (Kozbor, *J. Immunol.,* 133:3001 (1984); Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen of interest (e.g., PD-1). The binding specificity of monoclonal antibodies produced by hybridoma cells is determined by methods known in the art, for example, immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice, pp.* 59-103 (Academic Press, 1986)). Suitable culture media for this purpose include, for example, D-MEM or RPMI 1640 medium. Alternatively, clonal cells can be isolated using a semi-solid agar supplemented with HAT (Stemcell Technologies). In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

In some embodiments, mice (or other animals, such as rats, monkeys, donkeys, pigs, sheep, goats, hamsters, or dogs) can be immunized with an antigen (e.g., human PD-1) and once an immune response is detected, e.g., antibodies specific for the antigen are detected in the mouse serum, the mouse spleen is harvested and splenocytes isolated. The splenocytes are then fused by well known techniques to any suitable myeloma cells, for example cells from cell line SP20 available from the American Type Culture Collection (ATCC®) (Manassas, VA), to form hybridomas. Hybridomas are selected and cloned by limited dilution. In certain embodiments, lymph nodes of the immunized mice are harvested and fused with NS0 myeloma cells.

The hybridoma clones are then assayed by methods known in the art for cells that secrete antibodies capable of binding a polypeptide of the antigen (e.g., human PD-1). Ascites fluid, which generally contains high levels of antibodies, can be generated by immunizing mice with positive hybridoma clones.

Accordingly, described herein are methods of making antibodies described herein by culturing a hybridoma cell secreting an antibody. In certain embodiments, the method of making an antibody described herein further comprises the step of purifying the antibody.

In specific embodiments, the hybridoma is generated by fusing splenocytes isolated from a mouse (or other animal, such as rat, monkey, donkey, pig, sheep, or dog) immunized with an antigen of interest (e.g., human PD-1) with myeloma cells and then screening the hybridomas resulting from the fusion for hybridoma clones that secrete an antibody able to bind to the antigen. In certain embodiments, the hybridoma is generated by fusing lymph nodes isolated from a mouse (or other animal, such as rat, monkey, donkey, pig, sheep, or dog) immunized with an antigen of interest (e.g., human PD-1) with myeloma cells, and then screening the hybridomas resulting from the fusion for hybridoma clones that secrete an antibody able to bind to the antigen.

Antibodies described herein include antibody fragments which recognize an antigen of interest (e.g., human PD-1) and can be generated by any technique known to those of skill in the art. For example, Fab and $F(ab')_2$ fragments described herein can be produced by proteolytic cleavage of immunoglobulin molecules, using enzymes such as papain (to produce Fab fragments) or pepsin (to produce $F(ab')_2$ fragments). A Fab fragment corresponds to one of the two identical arms of an antibody molecule and contains the complete light chain paired with the VH and CH1 domains of the heavy chain. A $F(ab')_2$ fragment contains the two antigen-binding arms of an antibody molecule linked by disulfide bonds in the hinge region.

Further, the antibodies described herein can also be generated using various phage display methods known in the art. In phage display methods, functional antibody domains are displayed on the surface of phage particles which carry the polynucleotide sequences encoding them. In particular, DNA sequences encoding VHCR and VLCR are amplified from animal cDNA libraries (e.g., human or murine cDNA libraries of affected tissues). The DNA encoding the VHCR and VLCR are recombined together with an scFv linker by PCR and cloned into a phagemid vector. The vector is electroporated in *E. coli* and the *E. coli* is infected with helper phage. Phage used in these methods are typically filamentous phage including fd and M13, and the VHCR and VLCR are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies described herein include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce antibody fragments such as Fab, Fab' and $F(ab')_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043.

In one aspect, to generate whole antibodies, PCR primers including VHCR or VLCR nucleotide sequences, a restriction site, and a flanking sequence to protect the restriction site can be used to amplify the VHCR or VLCR sequences from a template, e.g., scFv clones. Utilizing cloning techniques known to those of skill in the art, the PCR amplified VHCR can be cloned into vectors expressing a variable heavy constant region, and the PCR amplified VLCR can be cloned into vectors expressing a variable light constant region, e.g., human kappa or lambda constant regions. The VHCR and VLCR can also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it can be preferable to use human, humanized or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741.

A chimeric antibody is a molecule in which different portions of the antibody are derived from different immunoglobulin molecules. For example, a chimeric antibody can contain a variable region of a mouse monoclonal antibody fused to a constant region of a human antibody. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415.

In some embodiments, humanized antibodies are produced. A humanized antibody is capable of binding to a predetermined antigen and comprises a framework region having substantially the amino acid sequence of a human immunoglobulin and CDRs having substantially the amino acid sequence of a non-human immunoglobulin (e.g., a murine immunoglobulin). Humanized antibodies can be produced using a variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety.

Human antibodies can be produced using any method known in the art. For example, transgenic mice which are incapable of expressing functional endogenous immunoglobulins, but which can express human immunoglobulin genes, can be used. In particular, the human heavy and light chain immunoglobulin gene complexes can be introduced randomly or by homologous recombination into mouse embryonic stem cells. Alternatively, the human variable region, constant region, and diversity region can be introduced into mouse embryonic stem cells in addition to the human heavy and light chain genes. The mouse heavy and light chain immunoglobulin genes can be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of an antigen (e.g., human PD-1). Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, Int. Rev. Immunol. 13:65-93. For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598.

In some embodiments, human antibodies can be produced using mouse-human hybridomas. For example, human peripheral blood lymphocytes transformed with Epstein-Barr virus (EBV) can be fused with mouse myeloma cells to produce mouse-human hybridomas secreting human monoclonal antibodies, and these mouse-human hybridomas can be screened to determine ones which secrete human monoclonal antibodies that bind to a target antigen (e.g., an influenza B virus NA). Such methods are known and are described in the art, see, e.g., Shinmoto et al., Cytotechnology, 2004, 46:19-23; Naganawa et al., Human Antibodies, 2005, 14:27-31.

In some embodiments, human antibodies can be generated by inserting polynucleotides encoding human CDRs (e.g., VLCR CDRs and/or VHCR CDRs) of an antibody into an expression vector containing nucleotide sequences encoding human framework region sequences. In certain embodiments, such expression vectors further comprise nucleotide sequences encoding a constant region of a human light and/or heavy chain. In some embodiments, human antibodies can be generated by inserting human CDRs (e.g., VLCR CDRs and/or VHCR CDRs) of an antibody obtained from a phage library into such human expression vectors.

In certain embodiments, a human antibody can be generated by selecting human CDR sequences that are homologous (or substantially homologous) to non-human CDR sequences of a non-human antibody, and selecting human framework sequences that are homologous (or substantially homologous) to non-human framework sequences of a non-human antibody.

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301.

Bispecific antibodies are antibodies that have binding specificities for at least two different epitopes. Exemplary bispecific antibodies may bind to two different epitopes of an antigen or to two different epitopes of two different antigens. In specific embodiments, a bispecific antibody has two distinct antigen-binding domains, wherein each domain specifically binds to a different antigen. Other such antibodies may bind a first antigen (e.g., human PD-1) and further bind a second antigen. Bispecific antibodies can be prepared as full-length antibodies or antibody fragments (e.g., F(ab'): bispecific antibodies).

Methods for making bispecific antibodies are known in the art. (See, for example, Millstein et al., Nature, 305:537-539 (1983); Traunecker et al., EMBO J., 10:3655-3659 (1991); Suresh et al., Methods in Enzymology, 121:210 (1986); Kostelny et al., J. Immunol., 148(5):1547-1553 (1992); Hollinger et al., Proc. Natl. Acad. Sci. USA, 90:6444-6448 (1993); Gruber et al., J. Immunol., 152:5368

(1994); U.S. Pat. Nos. 4,474,893; 4,714,681; 4,925,648; 5,573,920; 5,601,81; 95,731,168; 4,676,980; and 4,676,980, WO 94/04690; WO 91/00360; WO 92/200373; WO 93/17715; WO 92/08802; and EP 03089.)

Recombinant expression of an antibody described herein (e.g., a full-length antibody, heavy and/or light chain of an antibody, or a single chain antibody described herein) that binds to an antigen of interest (e.g., human PD-1), can for example, involve construction of vectors (e.g., expression vectors) containing a polynucleotide that encodes the antibody or fragments thereof (e.g., VLCR and/or VHCR). Once a polynucleotide encoding an antibody molecule, heavy and/or light chain of an antibody, or antigen-binding fragment thereof described herein has been obtained, a vector for the production of the antibody molecule can be produced by recombinant DNA technology using techniques well-known in the art. Methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Also provided are replicable vectors comprising a nucleotide sequence encoding an antibody molecule described herein, a heavy or light chain of an antibody, a heavy or light chain variable domain of an antibody or a fragment thereof, or a heavy or light chain CDR, operably linked to a promoter. Such vectors can, for example, include the nucleotide sequence encoding the constant region of the antibody molecule (see, e.g., International Publication Nos. WO 86/05807 and WO 89/01036; and U.S. Pat. No. 5,122,464) and the variable domain of the antibody can be cloned into such a vector for expression of the entire heavy, the entire light chain, or both the entire heavy and light chains.

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, MD); GCG Wisconsin Package (Accelrys, Inc., San Diego, CA); DeCypher® (TimeLogic Corp., Crystal Bay, Nevada); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

An expression vector can be transferred to a cell (e.g., host cell) by conventional techniques and the resulting cells can then be cultured by conventional techniques to produce an antibody described herein or a fragment thereof. Thus, provided herein are host cells containing a polynucleotide encoding an antibody described herein or fragments thereof, or a heavy or light chain thereof, or antigen-binding fragment thereof, or a single chain antibody described herein, operably linked to a promoter for expression of such sequences in the host cell. In certain embodiments, e.g., for the expression of double-chained antibodies, vectors encoding both the heavy and light chains individually can be co-expressed in the host cell for expression of the entire immunoglobulin molecule, as detailed below. In certain embodiments, a host cell contains a vector comprising a polynucleotide encoding both the heavy chain and light chain of an antibody described herein, or a fragment thereof. In specific embodiments, a host cell contains two different vectors, a first vector comprising a polynucleotide encoding a heavy chain of an antibody described herein, or a fragment thereof, and a second vector comprising a polynucleotide encoding a light chain of an antibody described herein, or a fragment thereof. In other embodiments, a first host cell comprises a first vector comprising a polynucleotide encoding a heavy chain of an antibody described herein, or a fragment thereof, and a second host cell comprises a second vector comprising a polynucleotide encoding a light chain of an antibody described herein.

A variety of host-expression vector systems can be utilized to express antibody molecules described herein (see, e.g., U.S. Pat. No. 5,807,715). Such host-expression systems represent vehicles by which the coding sequences of interest can be produced and subsequently purified, but also represent cells which can, when transformed or transfected with the appropriate nucleotide coding sequences, express an antibody molecule described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, MDCK, HEK 293, NS0, PER.C6, VERO, CRL7O3O, HsS78Bst, HeLa, and NIH 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, a mammalian expression vector is pOptiVEC™ or pcDNA3.3. Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary (CHO) cells, in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In certain embodiments, antibodies described herein are produced by CHO cells or NS0 cells. In a specific embodiment, the expression of nucleotide sequences encoding antibodies described herein (or fragments thereof) which bind to antigen of interest (e.g., human PD-1) is regulated by a constitutive promoter, inducible promoter or tissue specific promoter.

In bacterial systems, a number of expression vectors can be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., 1983, EMBO 12:1791), in which the antibody coding sequence can be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, e.g., Bittner et al., 1987, Methods in Enzymol. 153:51-544).

As used herein, the term "host cell" refers to any type of cell, e.g., a primary cell or a cell from a cell line. In specific embodiments, the term "host cell" refers a cell transfected with a polynucleotide and the progeny or potential progeny of such a cell. Progeny of such a cell may not be identical to the parent cell transfected with the polynucleotide due to mutations or environmental influences that may occur in succeeding generations or integration of the polynucleotide into the host cell genome.

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, Hela, COS, MDCK, HEK 293, NIH 3T3, W138, BT483, Hs578T, HTB2, BT2O and T47D, NS0 (a murine myeloma cell line that does not endogenously produce any immunoglobulin chains), CRL7O3O and HsS78Bst cells. In certain embodiments, humanized monoclonal antibodies described herein are produced in mammalian cells, such as CHO cells.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compositions that interact directly or indirectly with the antibody molecule.

A number of selection systems can be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology can be routinely applied to select the desired recombinant clone, and such methods are described, for example, in Ausubel et al. (eds.), *Current Protocols in Molecular Biology*, John Wiley & Sons, N Y (1993); Kriegler, *Gene Transfer and Expression*, A Laboratory Manual, Stockton Press, N Y (1990); and in Chapters 12 and 13, Dracopoli et al. (eds.), *Current Protocols in Human Genetics*, John Wiley & Sons, N Y (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3 (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell can be co-transfected with two or more expression vectors described herein, the first vector encoding a heavy chain derived polypeptide and the second vector encoding a light chain derived polypeptide. The two vectors can contain identical selectable markers which enable equal expression of heavy and light chain polypeptides.

Alternatively, a single vector can be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2197-2199). The coding sequences for the heavy and light chains can comprise cDNA or genomic DNA. The expression vector can be monocistronic or multicistronic. A multicistronic nucleic acid construct can encode 2, 3, 4, 5, 6, 7, 8, 9, 10 or more, or in the range of 2-5, 5-10 or 10-20 genes/nucleotide sequences. For example, a bicistronic nucleic acid construct can comprise in the following order a promoter, a first gene (e.g., heavy chain of an antibody described herein), and a second gene and (e.g., light chain of an antibody described herein). In such an expression vector, the transcription of both genes can be driven by the promoter, whereas the translation of the mRNA from the first gene can be by a cap-dependent scanning mechanism and the translation of the mRNA from the second gene can be by a cap-independent mechanism, e.g., by an IRES.

Once an antibody molecule described herein has been produced by recombinant expression, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies described herein can be fused to heterologous polypeptide sequences described herein or otherwise known in the art to facilitate purification.

In specific embodiments, an antibody (e.g., a monoclonal antibody, such as a humanized or chimeric antibody or an antigen-binding fragment thereof) described herein is isolated or purified. Generally, an isolated antibody is one that is substantially free of other antibodies with different antigenic specificities than the isolated antibody. For example, in a particular embodiment, a preparation of an antibody described herein is substantially free of cellular material and/or chemical precursors. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, 5%, 2%, 1%, 0.5%, or 0.1% (by dry weight) of heterologous protein (also referred to herein as a "contaminating protein") and/or variants of an antibody, for example, different post-translational modified forms of an antibody or other different versions of an antibody (e.g., antibody fragments). When the antibody is recombinantly produced, it is also generally substantially free of culture medium, i.e., culture medium represents less than about 20%, 10%, 2%, 1%, 0.5%, or 0.1% of the volume of the protein preparation. When the antibody is produced by chemical synthesis, it is generally substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a specific embodiment, antibodies described herein are isolated or purified.

5.6 Compositions & Routes of Administration

Encompassed herein is the use of a NDV described herein (e.g., the chimeric NDVs; see, e.g., Sections 5.1, 5.2, and/or 6) in compositions. Also encompassed herein is the use of plasma membrane fragments from NDV infected cells or whole cancer cells infected with NDV in compositions. In a specific embodiment, the compositions are pharmaceutical compositions, such as immunogenic formulations (e.g., vaccine formulations). The compositions may be used in methods of treating cancer.

In one embodiments, a pharmaceutical composition comprises a NDV described herein (e.g., the chimeric NDVs; see, e.g., Sections 5.1, 5.2, and/or 6), in an admixture with a pharmaceutically acceptable carrier. In a specific embodiment, the chimeric NDV comprises a packaged genome, wherein the genomic RNA sequence of the packaged genome is as set forth in SEQ ID NO: 51, 52, or 60. In some embodiments, the pharmaceutical composition further comprises one or more additional prophylactic or therapeutic agents, such as described in Section 5.7.6, infra. In a specific embodiment, a pharmaceutical composition comprises an effective amount of a NDV described herein (e.g., the chimeric NDVs; see, e.g., Sections 5.1, 5.2, and/or 6), and optionally one or more additional prophylactic or therapeutic agents, in a pharmaceutically acceptable carrier. In some embodiments, the NDV (e.g., a chimeric NDV; see, e.g., Sections 5.1, 5.2, and/or 6) is the only active ingredient included in the pharmaceutical composition.

In another embodiment, a pharmaceutical composition (e.g., an oncolysate vaccine) comprises a protein concentrate or a preparation of plasma membrane fragments from NDV infected cancer cells, in an admixture with a pharmaceutically acceptable carrier. In some embodiments, the pharmaceutical composition further comprises one or more additional prophylactic or therapeutic agents, such as described in Section 5.7.6, infra. In another embodiment, a pharmaceutical composition (e.g., a whole cell vaccine) comprises cancer cells infected with NDV, in an admixture with a pharmaceutically acceptable carrier. In some embodiments, the pharmaceutical composition further comprises one or more additional prophylactic or therapeutic agents, such as described in Section 5.7.6, infra.

In another embodiment, a pharmaceutical composition comprises an antagonist of PD-1 or a ligand thereof described herein (see, e.g., Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of an antagonist of PD-1 or a ligand thereof described herein (see, e.g., Section 5.5), and optionally one or more additional prophylactic or therapeutic agents, in a pharmaceutically acceptable carrier. In some embodiments, the antagonist of PD-1 or a ligand thereof (see, e.g., Section 5.5) is the only active ingredient included in the pharmaceutical composition.

In another embodiment, a pharmaceutical composition comprises a PD-1 blocking antibody (see, e.g., Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of a PD-1 blocking antibody described herein (see, e.g., Section 5.5), and optionally one or more additional prophylactic or therapeutic agents, in a pharmaceutically acceptable carrier. In certain embodiments, the pharmaceutical composition further comprises a chimeric NDV described herein (e.g., a chimeric NDV comprising a packaged genome comprising a transgene encoding IL-12 or derivative thereof). In certain embodiments, the pharmaceutical composition further comprises a chimeric NDV described herein (e.g., a chimeric NDV comprising a packaged genome comprising a transgene encoding human IL-12). In some embodiments, the PD-1 blocking antibody (see, e.g., Section 5.5) is the only active ingredient included in the pharmaceutical composition. In a specific embodiment, the PD-1 blocking antibody is nivolumab. In a preferred embodiment, the PD-1 blocking antibody is pembrolizumab. In a specific embodiment, the PD-1 blocking comprises: (a) a VLCR CDR1 comprising the amino acid sequence RASKGVSTSGYSYLH (SEQ ID NO: 1), (b) a VLCR CDR2 comprising the amino acid sequence LASYLES (SEQ ID NO: 2), (c) a VLCR CDR3 comprising the amino acid sequence QHSRDLPLT (SEQ ID NO: 3), (d) a VHCR CDR1 comprising the amino acid sequence NYYMY (SEQ ID NO: 6), (e) a VHCR CDR2 comprising the amino acid sequence GINPSNGGTNFNEKFKN (SEQ ID NO: 7), and (f) a VHCR CDR3 comprising the amino acid sequence RDYRFDMGFDY (SEQ ID NO: 8), as determined according to the Kabat numbering system. In another specific embodiment, the PD-1 blocking comprises: (a) a VLCR CDR1 comprising the amino acid sequence RASQSVSSYLA (SEQ ID NO: 11), (b) a VLCR CDR2 comprising the amino acid sequence DASNRAT (SEQ ID NO: 12), (c) a VLCR CDR3 comprising the amino acid sequence QQSSNWPRT (SEQ ID NO: 13), (d) a VHCR CDR1 comprising the amino acid sequence NSGMH (SEQ ID NO: 16), (e) a VHCR CDR2 comprising the amino acid sequence VIWYDGSKRYYADSVKG (SEQ ID NO: 17), and (f) a VHCR CDR3 comprising the amino acid sequence NDDY (SEQ ID NO: 18).

In another embodiment, a pharmaceutical composition comprises a PD-L1 blocking antibody (see, e.g., Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of a PD-L1 blocking antibody described herein (see, e.g., Section 5.5), and optionally one or more additional prophylactic or therapeutic agents, in a pharmaceutically acceptable carrier. In certain embodiments, the pharmaceutical composition further comprises a chimeric NDV described herein (e.g., a chimeric NDV comprising a packaged genome comprising a transgene encoding IL-12 or derivative thereof). In certain embodiments, the pharmaceutical composition further comprises a chimeric NDV described herein (e.g., a chimeric NDV comprising a packaged genome comprising a transgene encoding human IL-12). In some embodiments, the PD-L1 blocking antibody (see, e.g., Section 5.5) is the only active ingredient included in the pharmaceutical composition. In a specific embodiment, the PD-L1 blocking antibody is duralumab or azelumab.

In a specific embodiment of the pharmaceutical composition comprising an antagonist of PD-1 or a ligand thereof, the pharmaceutical composition is formulated as a lyophilized powder or cake. In a specific embodiment, the lyophilized powder or cake is packaged in a single-use vial for reconstitution. In a specific embodiment, the lyophilized powder or cake is formulated in L-histidine, polysorbate 80, and sucrose, and optionally, hydrochloric acid and/or sodium hydroxide to adjust the pH to 5.5. In a specific embodiment, the lyophilized powder or cake is reconstituted with an amount Sterile Water for Injection to achieve the desired concentration of the antagonist of PD-1 or ligand thereof, by, e.g., injecting the Sterile Water for Injection into the vial comprising the lyophilized powder or cake, slowly swirling the vial to allow for reconstitution of the lyophilized powder or cake, and waiting a period of time for the lyophilized powder or cake to be fully reconstituted. In a specific embodiment, 2 mL of reconstituted antagonist contains 50 mg of the antagonist and is formulated in L-histidine (3.1 mg), polysorbate 80 (0.4 mg), and sucrose (140 mg), and optionally, hydrochloric acid and/or sodium hydroxide to adjust pH to 5.5. See, e.g., the Full Prescribing Information for KETRUDA (pembrolizumab), Reference ID: 3862712, which is incorporated by referenced herein in its entirety. Once reconstituted, the pharmaceutical composition should be stored at room temperature for no more than six hours from the time of reconstitution, or under refrigeration at 2 degrees Celsius to 8 degrees Celsius for no more than 24 hours from the time of reconstitution. See, e.g., the Full Prescribing Information for KETRUDA (pembrolizumab), Reference ID: 3862712, which is incorporated by referenced herein in its entirety. In a specific embodiment, the reconstituted pharmaceutical composition is further formulated for intravenous infusion. For example, a desired amount of the reconstituted antagonist of PD-1 or ligand thereof is transferred into a sterile intravenous bag containing, e.g., 0.9% sodium chloride or 5% dextrose in a volume suitable to achieve a desired concentration of the antagonist of PD-1 or ligand thereof.

In another specific embodiment of the pharmaceutical composition comprising an antagonist of PD-1 or a ligand thereof, the pharmaceutical composition is formulated as a liquid solution. In a specific embodiment, the pharmaceutical composition is further formulated for intravenous infusion. For example, a desired amount of the pharmaceutical composition is transferred into a sterile intravenous bag containing, e.g., 0.9% sodium chloride or 5% dextrose in a volume suitable to achieve a desired concentration of the antagonist of PD-1 or ligand thereof. See, e.g., the Full Prescribing Information for OPDIVO (nivolumab), Reference ID: 3677021, which is incorporated by referenced herein in its entirety.

In another embodiment, a pharmaceutical composition comprises (i) an NDV described herein (see, e.g., Sections 5.1, 5.2, and/or 6), and (ii) an antagonist of PD-1 or a ligand thereof described herein (see, e.g., Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of (i) an NDV described herein (see, e.g., Sections 5.1, 5.2, and/or 6), and (ii) an antagonist of PD-1 or a ligand thereof described herein (see, e.g., Section 5.5), and optionally one or more additional prophylactic or therapeutic agents, in a pharmaceutically acceptable carrier. In some embodiments, the NDV (see, e.g., Sections 5.1, 5.2, and/or 6) and the antagonist of PD-1 or a ligand thereof are the only active ingredients included in the pharmaceutical composition.

In another embodiment, a pharmaceutical composition comprises (i) a chimeric NDV comprising a packaged genome comprising a transgene encoding IL-12 (e.g., human IL-12) or a derivative thereof, and (ii) an antagonist of PD-1 or a ligand thereof described herein (see, e.g., Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of (i) an NDV described herein (see, e.g., Sections 5.1, 5.2, and/or 6), and (ii) an antagonist of PD-1 or a ligand thereof described herein (see, e.g., Section 5.5), and optionally one or more additional prophylactic or therapeutic agents, in a pharmaceutically acceptable carrier. In a specific embodiment, a pharmaceutical composition comprises an effective amount of (i) a chimeric NDV comprising a packaged genome comprising a transgene encoding IL-12 (e.g., human IL-12) or a derivative thereof, and (ii) an antagonist of PD-1 or a ligand thereof described herein (see, e.g., Section 5.5), and optionally one or more additional prophylactic or therapeutic agents, in a pharmaceutically acceptable carrier. In some embodiments, the NDV (see, e.g., Sections 5.1, 5.2, and/or 6) and the antagonist of PD-1 or a ligand thereof are the only active ingredients included in the pharmaceutical composition. In specific embodiments, the chimeric NDV comprising a packaged genome comprising a transgene encoding IL-12 (e.g., human IL-12) or a derivative thereof and the antagonist of PD-1 or a ligand thereof are the only active ingredients included in the pharmaceutical composition.

In another embodiment, a pharmaceutical composition comprises (i) a chimeric NDV comprising a packaged genome comprising a transgene encoding IL-12 (e.g., human IL-12) or a derivative thereof, and (ii) a PD-1 blocking antibody (such as described, e.g., in Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of (i) an NDV described herein (see, e.g., Sections 5.1, 5.2, and/or 6), and (ii) a PD-1 blocking antibody described herein (see, e.g., Section 5.5), and optionally one or more additional prophylactic or therapeutic agents, in a pharmaceutically acceptable carrier. In a specific embodiment, a pharmaceutical composition comprises an effective amount of (i) a chimeric NDV comprising a packaged genome comprising a transgene encoding IL-12 (e.g., human IL-12) or a derivative thereof, and (ii) a PD-1 blocking antibody described herein (see, e.g., Section 5.5), and optionally one or more additional prophylactic or therapeutic agents, in a pharmaceutically acceptable carrier. In some embodiments, the NDV (see, e.g., Sections 5.1, 5.2, and/or 6) and the antagonist of PD-1 or a ligand thereof are the only active ingredients included in the pharmaceutical composition. In specific embodiments, the chimeric NDV comprising a packaged genome comprising a transgene encoding IL-12 (e.g., human IL-12) or a derivative thereof and the PD-1 blocking antibody are the only active ingredients included in the pharmaceutical composition. In a specific embodiment, the PD-1 blocking antibody is nivolumab. In a preferred embodiment, the PD-1 blocking antibody is pembrolizumab. In a specific embodiment, the pharmaceutical composition comprises: (i) an antibody comprising: (a) a VLCR CDR1 comprising the amino acid sequence RASKGVSTSGYSYLH (SEQ ID NO: 1), (b) a VLCR CDR2 comprising the amino acid sequence LASYLES (SEQ ID NO: 2), (c) a VLCR CDR3 comprising the amino acid sequence QHSRDLPLT (SEQ ID NO: 3), (d) a VHCR CDR1 comprising the amino acid sequence NYYMY (SEQ ID NO: 6), (e) a VHCR CDR2 comprising the amino acid sequence GINPSNGGTNFNEKFKN (SEQ ID NO: 7), and (f) a VHCR CDR3 comprising the amino acid sequence RDYRFDMGFDY (SEQ ID NO: 8), as determined according to the Kabat numbering system; and (ii) a chimeric NDV comprising a packaged genome comprising the nucleotide sequence set forth in SEQ ID NO: 51. In a specific embodiment, the pharmaceutical composition comprises: (i) an antibody comprising: (a) a VLCR CDR1 comprising the amino acid sequence RASKGVSTSGYSYLH (SEQ ID NO: 1), (b) a VLCR CDR2 comprising the amino acid sequence LASYLES (SEQ ID NO: 2), (c) a VLCR CDR3 comprising the amino acid sequence QHSRDLPLT (SEQ ID NO: 3), (d) a VHCR CDR1 comprising the amino acid sequence NYYMY (SEQ ID NO: 6), (e) a VHCR CDR2 comprising the amino acid sequence GINPSNGGTNFNEKFKN (SEQ ID NO: 7), and (f) a VHCR CDR3 comprising the amino acid sequence RDYRFDMGFDY (SEQ ID NO: 8), as determined according to the Kabat numbering system; and (ii) a chimeric NDV comprising a packaged genome comprising the nucleotide sequence set forth in SEQ ID NO: 52. In a specific embodiment, the pharmaceutical composition comprises: (i) an antibody comprising: (a) a VLCR CDR1 comprising the amino acid sequence RASKGVSTSGYSYLH (SEQ ID NO: 1), (b) a VLCR CDR2 comprising the amino acid sequence LASYLES (SEQ ID NO: 2), (c) a VLCR CDR3 comprising the amino acid sequence QHSRDLPLT (SEQ ID NO: 3), (d) a VHCR CDR1 comprising the amino acid sequence NYYMY (SEQ ID NO: 6), (e) a VHCR CDR2 comprising the amino acid sequence GINPSNGGTNFNEKFKN (SEQ ID NO: 7), and (f) a VHCR CDR3 comprising the amino acid sequence RDYRFDMGFDY (SEQ ID NO: 8), as determined according to the Kabat numbering system; and (ii) a chimeric NDV comprising a packaged genome comprising the nucleotide sequence set forth in SEQ ID NO: 60.

In another embodiment, a pharmaceutical composition comprises (i) a chimeric NDV comprising a packaged genome comprising a transgene encoding IL-12 (e.g., human IL-12) or a derivative thereof, and (ii) a PD-L1 blocking antibody (such as described, e.g., in Section 5.5), in an admixture with a pharmaceutically acceptable carrier. In some embodiments, the pharmaceutical composition further comprises one or more additional prophylactic or therapeutic agents, such as described in Section 5.7.6, infra. In a specific embodiment, a pharmaceutical composition comprises an effective amount of (i) an NDV described herein (see, e.g., Sections 5.1, 5.2, and/or 6), and (ii) a PD-L1 blocking antibody described herein (see, e.g., Section 5.5), and optionally one or more additional prophylactic or therapeutic agents, in a pharmaceutically acceptable carrier. In a specific embodiment, a pharmaceutical composition comprises an effective amount of (i) a chimeric NDV comprising a packaged genome comprising a transgene encoding IL-12 (e.g., human IL-12) or a derivative thereof, and (ii) a PD-L1 blocking antibody described herein (see, e.g., Section 5.5), and optionally one or more additional prophylactic or therapeutic agents, in a pharmaceutically acceptable carrier. In some embodiments, the NDV (see, e.g., Sections 5.1, 5.2, and/or 6) and the antagonist of PD-L1 or a ligand thereof are the only active ingredients included in the pharmaceutical composition. In specific embodiments, the chimeric NDV comprising a packaged genome comprising a transgene encoding IL-12 (e.g., human IL-12) or a derivative thereof and the PD-L1 blocking antibody are the only active ingredients included in the pharmaceutical composition. In a specific embodiment, the PD-L1 blocking antibody is duralumab or avelumab.

The pharmaceutical compositions provided herein can be in any form that allows for the composition to be administered to a subject. In a specific embodiment, the pharmaceutical compositions are suitable for veterinary and/or human administration. As used herein, the term "pharmaceutically acceptable" means approved by a regulatory agency of the Federal or a state government or listed in the U.S. Pharmacopeia or other generally recognized pharmacopeiae for use in animals, and more particularly in humans. The term "carrier" refers to a diluent, adjuvant, excipient, or vehicle with which the pharmaceutical composition is administered. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Examples of suitable pharmaceutical carriers are described in "Remington's Pharmaceutical Sciences" by E. W. Martin. The formulation should suit the mode of administration.

In a specific embodiment, the pharmaceutical compositions are formulated to be suitable for the intended route of administration to a subject. For example, the pharmaceutical composition may be formulated to be suitable for parenteral, intravenous, intraarterial, intrapleural, inhalation, intraperitoneal, oral, intradermal, colorectal, intraperitoneal, intracranial, and intratumoral administration. In a specific embodiment, the pharmaceutical composition may be formulated for intravenous, intraarterial, oral, intraperitoneal, intranasal, intratracheal, intrapleural, intracranial, subcutaneous, intramuscular, topical, pulmonary, or intratumoral administration.

In a specific embodiment, the pharmaceutical composition comprising an NDV described herein (see, e.g., Sections 5.1, 5.2, and/or 6) is formulated to be suitable for intratumoral administration to the subject (e.g., human subject). In a specific embodiment, the pharmaceutical composition comprising a chimeric NDV comprising a packaged genome comprising a transgene encoding IL-12 (e.g., human IL-12) or a derivative thereof is formulated to be suitable for intratumoral administration to the subject (e.g., human subject). In a specific embodiment, the sequence of the packaged genome comprising a transgene encoding IL-12 comprises or consists of the sequence set forth in SEQ ID NO: 51. In a specific embodiment, the sequence of the packaged genome comprising a transgene encoding IL-12 comprises or consists of the sequence set forth in SEQ ID NO: 52. In a specific embodiment, the sequence of the packaged genome comprising a transgene encoding IL-12 comprises or consists of the sequence set forth in SEQ ID NO: 60.

In a specific embodiment, the pharmaceutical composition comprising an NDV described herein (see, e.g., Sections 5.1, 5.2, and/or 6) is formulated to be suitable for intravenous administration to the subject (e.g., human subject). In a specific embodiment, the pharmaceutical composition comprising a chimeric NDV comprising a packaged genome comprising a transgene encoding IL-12 (e.g., human IL-12) or a derivative thereof is formulated to be suitable for intravenous administration to the subject (e.g., human subject). In a specific embodiment, the sequence of the packaged genome comprising a transgene encoding IL-12 is as set forth in SEQ ID NO: 51. In a specific embodiment, the sequence of the packaged genome comprising a transgene encoding IL-12 is as set forth in SEQ ID NO: 52. In a specific embodiment, the sequence of the packaged genome comprising a transgene encoding IL-12 is as set forth in SEQ ID NO: 60.

In a specific embodiment, the pharmaceutical composition comprising an antagonist of PD-1 or a ligand thereof described herein (see, e.g., Section 5.5) is formulated to be suitable for intravenous administration to the subject (e.g., human subject). In a specific embodiment, the pharmaceutical composition comprising a PD-1 blocking antibody described herein (see, e.g., Section 5.5) is formulated to be suitable for intravenous administration to the subject (e.g., human subject). In a specific embodiment, the PD-1 blocking antibody is nivolumab. In a preferred embodiment, the PD-1 blocking antibody is pembrolizumab. In a specific embodiment, the pharmaceutical composition comprising a PD-L1 blocking antibody described herein (see, e.g., Section 5.5) is formulated to be suitable for intravenous administration to the subject (e.g., human subject). In a specific embodiment, the PD-L1 blocking antibody is duralumab or avelumab.

5.7 Anti-Cancer Uses and Other Uses

5.7.1 Methods of Treating Cancer with NDV-IL12 and an Antagonist of PD-1 or a Ligand Thereof In one aspect, presented herein are methods for treating cancer utilizing a chimeric NDV described herein (e.g., a chimeric NDV described in Section 5.2 and/or Section 6) or a composition comprising such a chimeric NDV in combination with an antagonist of PD-1 or a ligand thereof (e.g., an antagonist described in Section 5.5 and/or Section 6) or composition comprising such an antagonist, wherein the chimeric NDV comprises a packaged genome which encodes IL-12 or a derivative thereof. In a specific embodiment, the IL-12 or derivative thereof is expressed by cells infected with the chimeric NDV. The chimeric NDV, or a composition thereof, and the antagonist of PD-1 or a ligand thereof, or a composition thereof, may be used as any line of therapy (e.g., a first, second, third, fourth or fifth line therapy). In a specific embodiment, the method of treatment further comprises administering to the subject one or more additional therapies described in Section 5.7.6, e.g., Section 5.7.6.1.

In one embodiment, presented herein are methods for treating cancer comprising administering to a subject a chimeric NDV and an antagonist of PD-1 or a ligand thereof, wherein the chimeric NDV comprises a packaged genome comprising a transgene encoding IL-12 or a derivative thereof (e.g., human IL-12). In a specific embodiment, the IL-12 or derivative thereof is expressed by cells infected with the chimeric NDV. In another embodiment, presented herein are methods for treating cancer comprising administering to a subject an effective amount of a chimeric NDV and an effective amount of an antagonist of PD-1 or a ligand thereof, wherein the chimeric NDV comprises a packaged genome comprising a transgene encoding IL-12 or a derivative thereof (e.g., human IL-12). In a specific embodiment, the IL-12 or derivative thereof is expressed by cells infected with the chimeric NDV. The chimeric NDV and antagonist may be administered concurrently or sequentially to the subject. In certain embodiments, the chimeric NDV and antagonist are administered in the same composition. In other embodiments, the chimeric NDV and antagonist are administered in different compositions. The chimeric NDV and antagonist may be administered by the same or different routes of administration to the subject. Any route known to one of skill in the art or described herein may be used to administer the chimeric NDV and antagonist. In a specific embodiment, the chimeric NDV is administered intratumorally and the antagonist is administered intravenously. In some embodiments, the chimeric NDV and the antagonist are administered intravenously.

In another aspect, presented herein are uses of a chimeric NDV in the preparation of a medicament for use in combination with an antagonist of PD-1 or a ligand thereof for treating cancer in a subject (e.g., a human subject), wherein the chimeric NDV comprises a packaged genome comprising a transgene encoding IL-12 or a derivative thereof (e.g., human IL-12). In another aspect, presented herein is a chimeric NDV for use in a method for treating cancer in a subject (e.g., a human subject), wherein the chimeric NDV comprises a packaged genome comprising a transgene encoding IL-12 or a derivative thereof, and wherein the method further comprising administering an antagonist of PD-1 or a ligand thereof (e.g., human IL-12). In a specific embodiment, the IL-12 or derivative thereof is expressed by cells infected with the chimeric NDV. The chimeric NDV and antagonist may be administered concurrently or sequentially to the subject. In certain embodiments, the chimeric NDV and antagonist are administered in the same composition. In other embodiments, the chimeric NDV and antagonist are administered in different compositions. The chimeric NDV and antagonist may be administered by the same or different routes of administration to the subject. Any route known to one of skill in the art or described herein may be used to administer the chimeric NDV and antagonist. In a specific embodiment, the chimeric NDV is administered intratumorally and the antagonist is administered intravenously. In some embodiments, the chimeric NDV and the antagonist are administered intravenously. In another embodiment, the chimeric NDV is administered intra-nodally and the antagonist are administered intravenously.

In another embodiment, presented herein is a method for treating cancer, comprising administering to a subject (e.g., a human subject) in need thereof a first composition comprising a chimeric NDV and a second composition comprising an antagonist of PD-1 or a ligand thereof, wherein the chimeric NDV comprises a packaged genome comprising a transgene encoding IL-12 (e.g., human IL-12), wherein the transgene encodes an IL-12 p40 subunit and an IL-12 p35 subunit. In another embodiment, presented herein is a method for treating cancer, comprising administering to a subject (e.g., a human subject) in need thereof a chimeric NDV and an antagonist of PD-1 or a ligand thereof, wherein the chimeric NDV comprises a packaged genome which encodes IL-12, and wherein the antagonist of PD-1 is an antibody that binds to PD-1 and blocks (completely or partially) the interaction between PD-1 and a ligand thereof (e.g., either PD-L1, PD-L2, or both) (sometimes referred herein as a "PD-1 blocking antibody"). In another embodiment, presented herein is a method for treating cancer, comprising administering to a subject (e.g., a human subject) in need thereof a first composition comprising a chimeric NDV and a second composition comprising a PD-1-blocking antibody, wherein the chimeric NDV comprises a packaged genome comprising a transgene encoding IL-12 (e.g., human IL-12), wherein the transgene encodes an IL-12 p40 subunit and an IL-12 p35 subunit. In another embodiment, presented herein is a method for treating cancer, comprising administering to a human subject in need thereof a first composition comprising a chimeric Newcastle disease virus (NDV) and a second composition comprising a PD-1-blocking antibody, wherein the chimeric NDV comprises a packaged genome comprising a transgene encoding human IL-12, wherein the transgene encodes a human IL-12 p40 subunit and a human IL-12 p35 subunit. In a specific embodiment, the sequence of the packaged genome comprising a transgene encoding human IL-12 is as set forth in SEQ ID NO: 51. In a specific embodiment, the sequence of the packaged genome comprising a transgene encoding human IL-12 is as set forth in SEQ ID NO: 52. In a specific embodiment, the sequence of the packaged genome comprising a transgene encoding human IL-12 is as set forth in SEQ ID NO: 60. In a preferred embodiment, the PD-1 blocking antibody is pembrolizumab. In other embodiments, the PD-1 blocking antibody is nivolumab, MEDI0680, PDR001, or atezolizumab. The first and second compositions may be administered by same or different routes of administration. Any route known to one of skill in the art or described herein may used to administer the first and second compositions. In a specific embodiment, the first composition is administered intratumorally and the second composition is administered intravenously. In some embodiments, the first and second compositions are administered intravaneously. See, e.g., Sections 5.1 and 5.2, supra, and Section 6, infra, for information regarding NDV, Section 5.5, supra, and Section 6, infra, for information regarding antagonists of PD-1 or a ligand thereof, and Section 5.5.1, supra, for information regarding compositions and routes of administration.

In another embodiment, presented herein is a use of a chimeric NDV in the preparation of a medicament for use in combination with an antagonist of PD-1 or a ligand thereof for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit. In another embodiment, presented herein is a use of a chimeric NDV in the preparation of a medicament for use in combination with an antagonist of PD-1 or a ligand thereof for treating cancer in a subject (e.g., a human subject), wherein the chimeric NDV comprises a packaged genome which encodes IL-12 (e.g., human IL-12), and wherein the antagonist of PD-1 is an antibody that binds to PD-1 (e.g., human PD-1) and blocks (completely or partially) the interaction between PD-1 and a ligand thereof (e.g., either PD-L1, PD-L2, or both) (sometimes referred herein as a "PD-1 blocking antibody"). In another embodiment, presented herein is a use of a chimeric NDV in the preparation of a medicament for use in combination with a PD-1 blocking antibody for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit. In another embodiment, presented herein is a use of a chimeric NDV in the preparation of a medicament for use in combination with a PD-1 blocking antibody for treating cancer in a subject (e.g., a human subject), wherein the chimeric NDV comprises a packaged genome comprising a transgene encoding human IL-12, wherein the transgene encodes a human IL-12 p40 subunit and a human IL-12 p35 subunit. In a specific embodiment, the sequence of the packaged genome comprising a transgene encoding IL-12 is as set forth in SEQ ID NO: 51. In a specific embodiment, the sequence of the packaged genome comprising a transgene encoding IL-12 is as set forth in SEQ ID NO: 52. In a specific embodiment, the sequence of the packaged genome comprising a transgene encoding IL-12 is as set forth in SEQ ID NO: 60. In a specific embodiment, the transgene encodes an IL-12 amino acid sequence with sequence set forth in Table 7. In a specific embodiment, the transgene encodes an IL-12 amino acid sequence comprising an amino acid sequence set forth in Table 7. In a specific embodiment, the transgene encoding IL-12 comprising a nucleotide sequence of a sequence set forth in Table 8. In a specific embodiment, the transgene encoding IL-12 consists of a sequence set forth in Table 8. In a preferred embodiment, the PD-1 blocking antibody is pembrolizumab. In other embodiments, the PD-1 blocking antibody is nivolumab, MEDI0680, PDR001, or atezolizumab. The first and second compositions (i.e., the chimeric NDV and the antagonist) may be administered by same or different routes of administration. Any route known to one of skill in the art or described herein may be used to administer the first and second compositions (i.e., the chimeric NDV and the antagonist). In a specific embodiment, the first composition (i.e., the chimeric NDV) is administered intratumorally and the second composition (i.e., the antagonist) is administered intravenously. In another specific embodiment, the first composition (i.e., the chimeric NDV) is administered intra-nodally and the second composition (i.e., the antagonist) is administered intravenously. In some embodiments, the first and second compositions (i.e., the chimeric NDV and the antagonist) are administered intravenously. See, e.g., Sections 5.1 and 5.2, supra, and Section 6, infra, for information regarding NDV, Section 5.5, supra, and Section 6, infra, for information regarding antagonists of PD-1 or a ligand thereof, and Section 5.5.1, supra, for information regarding compositions and routes of administration.

In another embodiment, presented herein is a chimeric NDV for use in method for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit, and wherein the method further comprises administering an antagonist of PD-1 or a ligand thereof. In another embodiment, presented herein is a chimeric NDV for use in method for treating cancer in a subject (e.g., a human subject), wherein the chimeric NDV comprises a packaged genome comprising a transgene encoding IL-12 (e.g., human IL-12), wherein the transgene encodes an IL-12 p40 subunit and an IL-12 p35 subunit, wherein the method further comprises administering an antagonist of PD-1 or a ligand thereof, and wherein the antagonist of PD-1 is an antibody that binds to PD-1 (e.g., human PD-1) and blocks (completely or partially) the interaction between PD-1 and a ligand thereof (e.g., either PD-L1, PD-L2, or both) (sometimes referred herein as a "PD-1 blocking antibody"). In another embodiment, presented herein is a chimeric NDV for use in method for treating cancer in a subject (e.g., a human subject), wherein the chimeric NDV comprises a packaged genome comprising a transgene encoding IL-12 (e.g.e.g., human IL-12), wherein the transgene encodes an IL-12 p40 subunit and an IL-12 p35 subunit, and wherein the method further comprises administering PD-1 blocking antibody. In another embodiment, presented herein is a chimeric NDV for use in method for treating cancer in a subject (e.g., a human subject), wherein the chimeric NDV comprises a packaged genome comprising a transgene encoding human IL-12, wherein the transgene encodes a human IL-12 p40 subunit and a human IL-12 p35 subunit, and wherein the method further comprises administering PD-1 blocking antibody. In a specific embodiment, the sequence of the packaged genome comprising a transgene encoding IL-12 is as set forth in SEQ ID NO: 51. In a specific embodiment, the sequence of the packaged genome comprising a transgene encoding IL-12 is as set forth in SEQ ID NO: 52. In a specific embodiment, the sequence of the packaged genome comprising a transgene encoding IL-12 is as set forth in SEQ ID NO: 60. In a preferred embodiment, the PD-1 blocking antibody is pembrolizumab. In other embodiments, the PD-1 blocking antibody is nivolumab, PDR001, MEDI0680, or atezolizumab. The first and second compositions (i.e., the chimeric NDV and the antagonist) may be administered by same or different routes of administration. Any route known to one of skill in the art or described herein may be used to administer the first and second compositions (i.e., the chimeric NDV and the antagonist). In a specific embodiment, the first composition (i.e., the chimeric NDV) is administered intratumorally and the second composition (i.e., the antagonist) is administered intravenously. In another specific embodiment, the first composition (i.e., the chimeric NDV) is administered intra-nodally and the second composition (i.e., the antagonist) is administered intravenously. In some embodiments, the first and second compositions (i.e., the chimeric NDV and the antagonist) are administered intravenously. See, e.g., Sections 5.1 and 5.2, supra, and Section 6, infra, for information regarding NDV, Section 5.5, supra, and Section 6, infra, for information regarding antagonists of PD-1 or a ligand thereof, and Section 5.5.1, supra, for information regarding compositions and routes of administration.

In a specific embodiment, the chimeric NDV comprises a packaged genome comprising a transgene encoding a human IL-12 transgene, wherein the transgene encodes an IL-12 p40 subunit and an IL-12 p35 subunit. See, e.g., Sections 5.2.1, 5.7, and 6 for examples of IL-12 trangenes. In a specific embodiment, the chimeric NDV comprises an NDV backbone of LaSota strain. In a specific embodiment, the chimeric NDV comprises an NDV backbone which is lentogenic. In a specific embodiment, the packaged genome comprises a nucleotide sequence encoding a mutated F protein and the mutated F protein is expressed by the chimeric NDV, wherein the mutated F protein comprises a mutated cleavage site. In a specific embodiment, the packaged genome comprises a nucleotide sequence encoding a mutated F protein with the amino acid mutation L289A (i.e., an L to A mutation at the amino acid position corresponding to L289 of the NDV La Sota strain F protein), wherein the mutated F protein is expressed by the chimeric NDV. In a specific embodiment, the chimeric NDV comprises an NDV backbone which is LaSota strain, and wherein the packaged genome encodes a mutated F protein with the amino acid mutation L289A (i.e., an L to A mutation at the amino acid position corresponding to L289 of the NDV La Sota strain F protein), wherein the mutated F protein is expressed by the chimeric NDV. See, e.g., Sections 5.2 and 6 for examples of chimeric NDV encoding IL-12 or a derivative thereof. In a specific embodiment, the chimeric NDV comprises a packaged genome having the nucleotide sequence set forth in SEQ ID NO: 51, 52 or 60.

In a specific embodiment, the antagonist of PD-1 or a ligand thereof is an antagonist described in Sections 5.5 and/or 6. In a specific embodiment, the antagonist of PD-1 or a ligand thereof is an antibody (or an antigen-binding fragment) or a soluble receptor that specifically binds to a ligand of PD-1. In certain embodiments, the soluble receptor is a fragment of PD-1 or a fragment of a derivative of PD-1 that specifically binds to a ligand of PD-1 (e.g., the extracellular domain of PD-1 or a derivative of PD-1). In some embodiments, the soluble receptor is a fusion protein comprising at least a portion of PD-1 or a derivative of PD-1 (e.g., the extracellular domain of PD-1 or a derivative of PD-1), and a heterologous amino acid sequence. In specific embodiments, the fusion protein comprises at least a portion of PD-1 or a derivative of PD-1, and the Fc portion of an immunoglobulin or a fragment thereof. In specific embodiments, the antagonist of PD-1 or a ligand thereof is an antibody (or an antigen-binding fragment) that specifically binds to a ligand of PD-1. In another embodiment, the antagonist of PD-1 or a ligand thereof is an antibody (or an antigen-binding fragment) or ligand that binds to PD-1, but does not transduce an inhibitory signal(s). In another embodiment, the antagonist of PD-1 or a ligand thereof is a ligand that binds to PD-1, but does not transduce an inhibitory signal(s). In certain specific embodiments, the ligand is a fusion protein comprising at least a portion of a ligand of PD-1 or a derivative of a ligand of PD-1, and a heterologous amino acid sequence. In specific embodiments, the fusion protein comprises at least a portion of a ligand of PD-1 or a derivative of a ligand of PD-1, and the Fc portion of an immunoglobulin or a fragment thereof. Nonlimiting examples of antagonists of PD-1 or a ligand thereof include pembrolizumab ("KEYTRUDA®"; see, e.g., Hamid et al., N Engl J Med. 2013; 369:134-44 and Full Prescribing Information for KEYTRUDA (pembrolizumab), Reference ID: 3862712), nivolumab ("OPDIVO®"; see, e.g., Topalian et al., N Engl J Med. 2012; 366:2443-54 and Full Prescribing Information for OPDIVO (nivolumab), Reference ID: 3677021), AMP-224 (see, e.g., Infante et al., J Clin Oncol. 2013; 31(suppl):abstr 3044), MEDI0680 (also referred to as "AMP-514"; see, e.g., Hamid et al., Ann Oncol. 2016; 27(suppl_6):1050PD), durvalumab (also referred to as "medi-4736"; see, e.g., Lutzky et al., J Clin Oncol. 2014; 32(suppl 5S):abstr 3001), avelumab (e.g., for Merkel cell carcinoma) (also referred to as "MSB0010718C"; see, e.g., Heery et al. J Clin Oncol. 2014; 32(suppl 5S):abstr 3064), bms-936559 (see, e.g., Brahmer et al. N. Engl. J. Med. 2012; 366, 2455-2465), and atezolizumab (also referred to as "mpdl3280A" and "TECENTRIQ®"; see, e.g., McDermott et al., J Clin Oncol. 2016; 34(8):833-842, Herbst et al., J Clin Oncol. 2013; 31(suppl):abstr 3000, and Full Prescribing Information for TECENTRIQ, Reference ID: 3933242). In a specific embodiment, the antagonist of PD-1 or a ligand thereof is a therapy approved by the U.S. FDA for treatment of one or more cancers. Nonlimiting examples of an antagonist of PD-1 or a ligand thereof approved by the U.S. FDA for treatment of cancer include pembrolizumab, nivolumab, atezolizumab, and avelumab. In a specific embodiment, the antagonist of PD-1 or a ligand thereof is a therapy approved by the EMA for treatment of one or more cancers. Nonlimiting examples of an antagonist of PD-1 or a ligand thereof approved by the EMA for treatment of cancer include pembrolizumab, nivolumab, and atezolizumab. In a specific embodiment, the antagonist of PD-1 or a ligand thereof is nivolumab, MEDI0680, or pembrolizumab. In a preferred embodiment, the antagonist of PD-1 or a ligand thereof is pembrolizumab. In another embodiment, the antagonist of PD-1 or a ligand thereof is nivolumab, AMP-224, MEDI0680, PDR001, durvalumab, avelumab, bms-936559, or atezolizumab.

In a specific embodiment, the IL-12 transgene encodes an amino acid sequence set forth in SEQ ID NO: 42. In a specific embodiment, the nucleotide sequence encoding the IL-12 transgene comprises the nucleotide sequence set forth in SEQ ID NO: 53. In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 40. In a specific embodiment, the nucleotide sequence encoding the IL-12 p40 subunit comprises the nucleotide sequence set forth in SEQ ID NO: 54. In a specific embodiment, the IL-12 p35 subunit comprises the amino acid sequence set forth in SEQ ID NO: 41. In a specific embodiment, the nucleotide sequence encoding the IL-12 p35 subunit comprises the nucleotide sequence set forth in SEQ ID NO: 55.

In a specific embodiment, the IL-12 transgene encodes an amino acid sequence comprising the amino acid sequence set forth in SEQ ID NO: 43. In a specific embodiment, the nucleotide sequence encoding the IL-12 transgene comprises the nucleotide sequence set forth in SEQ ID NO: 63. In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 38. In a specific embodiment, the nucleotide sequence encoding the IL-12 p40 subunit comprises the nucleotide sequence set forth in SEQ ID NO: 59. In a specific embodiment, the IL-12 p35 subunit comprises the amino acid sequence set forth in SEQ ID NO: 41. In a specific embodiment, the nucleotide sequence encoding the IL-12 p35 subunit is as set forth in SEQ ID NO: 55.

In a specific embodiment, the IL-12 transgene encodes an amino acid sequence set forth in SEQ ID NO: 22. In a specific embodiment, the nucleotide sequence encoding the IL-12 transgene is as set forth in SEQ ID NO: 26. In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 23. In a specific embodiment, the nucleotide sequence encoding the IL-12 p40 subunit comprises the nucleotide sequence set forth in SEQ ID NO: 27. In a specific embodiment, the IL-12 p35 subunit comprises the amino acid sequence set forth in SEQ ID NO: 25. In a specific embodiment, the nucleotide sequence encoding the IL-12 p35 subunit is as set forth in SEQ ID NO: 29.

In a specific embodiment, the IL-12 transgene encodes an amino acid sequence comprising the amino acid sequence set forth in SEQ ID NO: 39. In a specific embodiment, the nucleotide sequence encoding the IL-12 transgene comprises the nucleotide sequence set forth in SEQ ID NO: 61.

In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 38. In a specific embodiment, the nucleotide sequence encoding the IL-12 p40 subunit comprises the nucleotide sequence set forth in SEQ ID NO: 57. In a specific embodiment, the IL-12 p35 subunit comprises the amino acid sequence set forth in SEQ ID NO: 25. In a specific embodiment, the nucleotide sequence encoding the IL-12 p35 subunit comprises the nucleotide sequence set forth in SEQ ID NO: 29.

In a specific embodiment, the IL-12 transgene encodes an amino acid sequence comprising the amino acid sequence set forth in SEQ ID NO: 42. In a specific embodiment, the nucleotide sequence encoding the IL-12 transgene comprises the nucleotide sequence set forth in SEQ ID NO: 66. In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 40. In a specific embodiment, the nucleotide sequence encoding the IL-12 p40 subunit comprises the nucleotide sequence set forth in SEQ ID NO: 64. In a specific embodiment, the IL-12 p35 subunit comprises the amino acid sequence set forth in SEQ ID NO: 41. In a specific embodiment, the nucleotide sequence encoding the IL-12 p35 subunit comprises the nucleotide sequence set forth in SEQ ID NO: 65.

In a specific embodiment, the IL-12 transgene encodes an amino acid sequence comprising the amino acid sequence set forth in SEQ ID NO: 43. In a specific embodiment, the nucleotide sequence encoding the IL-12 transgene comprises the nucleotide sequence set forth in SEQ ID NO: 68. In a specific embodiment, the transgene is inserted between two transcription units of the packaged genome. In a specific embodiment, the transgene is inserted between two transcription units of the packaged genome, wherein the two transcription units of the packaged genome are the transcription units for the NDV P gene and the NDV M gene. In a specific embodiment, the IL-12 p40 subunit comprises the amino acid sequence set forth in SEQ ID NO: 38. In a specific embodiment, the nucleotide sequence encoding the IL-12 p40 subunit comprises the nucleotide sequence set forth in SEQ ID NO: 57. In a specific embodiment, the IL-12 p35 subunit comprises the amino acid sequence set forth in SEQ ID NO: 41. In a specific embodiment, the nucleotide sequence encoding the IL-12 p35 subunit comprises the nucleotide sequence set forth in SEQ ID NO: 65.

In a specific embodiment, the sequence of the packaged genome comprising a transgene encoding IL-12 comprises the nucleotide sequence set forth in SEQ ID NO: 51.

In a specific embodiment, the sequence of the packaged genome comprising a transgene encoding IL-12 comprises the nucleotide sequence set forth in SEQ ID NO: 52.

In a specific embodiment, the sequence of the packaged genome comprising a transgene encoding IL-12 comprises the nucleotide sequence set forth in SEQ ID NO: 60.

In a specific embodiment, the chimeric NDV (or composition comprising the chimeric NDV) is administered to the subject via a route described in Section 5.5.1 and/or Section 6. In a specific embodiment, the chimeric NDV is administered to the subject intratumorally. In a specific embodiment, the intratumoral administration is subcutaneous. In another specific embodiment, the chimeric NDV is administered to the subject intra-nodally. In another embodiment, the chimeric NDV is administered to the subject intravenously.

In a specific embodiment, the antagonist of PD-1 or a ligand thereof (or composition comprising the antagonist) is administered to the subject via routes described in Section 5.5.1 and/or Section 6. In a specific embodiment, the antagonist of PD-1 or a ligand thereof (or composition comprising the antagonist) is administered to the subject intravenously.

In a specific embodiment, the cancer treated is a cancer described in Section 5.7.5 and/or Section 6. In a specific embodiment, the cancer is melanoma, kidney cancer, lung cancer, bladder cancer, or head and neck cancer. In a specific embodiment, the lung cancer is non-small cell lung cancer. In a specific embodiment, the head and neck cancer is squamous cell cancer of the head and neck. In a specific embodiment, the cancer is uterine cancer, gastric cancer, esophageal cancer, liver cancer, brain cancer or sarcoma. In a specific embodiment, the cancer is recurrent or relapsed. In a specific embodiment, the cancer is metastatic. In a specific embodiment, the cancer is unresectable. In a specific embodiment, the cancer comprises a dermal, subcutaneous, or nodal metastasis. In a specific embodiment, a biopsy of the cancer is PD-L1-positive as assessed by a technique known in the art or described herein, such as immunohistochemistry or the PD-L1 IHC 22C3 pharmDx (Agilent Technologies Inc.). In a specific embodiment, a biopsy is PD-L1-positive if the tumor proportion score (TPS), the percentage of cells staining for PD-L1 is at least 1%, 2%, 3%, 5%, 7%, 8%, 10%, 15%, 20%, 25%, 30%, 35%, 40%, 45%, 50%, 55%, 60%, 65%, 70%, 75%, 80%, 85%. 90%, 95%, 98%, or 100% as assessed by a technique known in the art or described herein such as immunohistochemistry or the PD-L1 IHC 22C3 pharmDx (Agilent Technologies Inc.). In another specific embodiment, a biopsy is PD-L1-positive if the tumor proportion score (TPS), the percentage of cells staining for PD-L1 is 1% to 100%, 25% to 50%, 25% to 100%, 50% to 75%, 50% to 100%, or 75% to 100%, as assessed by a technique known in the art or described herein such as immunohistochemistry or the PD-L1 IHC 22C3 pharmDx (Agilent Technologies Inc.). In other embodiments, a biopsy of the cancer is PD-L1-negative as assessed by a technique known in the art or described herein, such as immunohistochemistry or the PD-L1 IHC 22C3 pharmDx (Agilent Technologies Inc.). In a specific embodiment, a biopsy is PD-L1-negative if the tumor proportion score (TPS) is less than 1% as assessed by a technique known in the art or described herein, such as immunohistochemistry or the PD-L1 IHC 22C3 pharmDx (Agilent Technologies Inc.).

In a specific embodiment, the subject is a subject described in Section 5.7.3 and/or Section 6. In a specific embodiment, the subject is refractory to treatment with an antagonist of PD-1 or a ligand thereof. In a specific embodiment, the subject is refractory to treatment with nivolumab, AMP-224, MEDI0680, pembrolizumab, durvalumab, avelumab, bms-936559, or atezolizumab. In a specific embodiment, the subject is refractory to treatment with pembrolizumab alone. In a specific embodiment, the subject is unresponsive to treatment with pembrolizumab alone.

In a specific embodiment, the subject has relapsed cancer and is refractory to treatment with an antagonist of PD-1 or a ligand thereof. In a specific embodiment, the subject has relapsed cancer and is refractory to treatment with nivolumab, AMP-224, MEDI0680, pembrolizumab, durvalumab, avelumab, bms-936559, or atezolizumab. In a specific embodiment, the subject has relapsed cancer and is refractory to treatment with pembrolizumab.

5.7.2 Additional Methods

In one aspect, a chimeric NDV described herein (e.g., a chimeric NDV described in Section 5.2, supra) may be used in the treatment of cancer. In one embodiment, provided herein are methods for treating cancer, comprising administering to a subject in need thereof a chimeric NDV described herein (e.g., a chimeric NDV described in Section 5.2, supra) or a composition thereof. In a specific embodiment, provided herein is a method for treating cancer, comprising administering to a subject in need thereof an effective amount of a chimeric NDV described herein (e.g., a chimeric NDV described in Section 5.2, supra) or a composition thereof.

In a specific embodiment, the chimeric NDV used in the treatment of cancer comprises a packaged genome which encodes IL-12 (see, e.g., Section 5.2 and/or Section 6).

A chimeric NDV (e.g., a chimeric NDV described in Section 5.2, supra) described herein or a composition thereof, an oncolysate vaccine, or a whole cell cancer vaccine used in a method for treating cancer may be used as any line of therapy (e.g., a first, second, third, fourth or fifth line therapy).

In certain embodiments, a chimeric NDV described herein (e.g., a chimeric NDV described in Section 5.2, supra) is the only active ingredient administered to treat cancer. In specific embodiments, a chimeric NDV described herein (e.g., a chimeric NDV described in Section 5.2, supra) is the only active ingredient in a composition administered to treat cancer.

The chimeric NDV (e.g., a chimeric NDV described in Section 5.2, supra) or a composition thereof may be administered locally or systemically to a subject. For example, the chimeric NDV (e.g., a chimeric NDV described in Section 5.2, supra) or a composition thereof may be administered parenterally (e.g., intravenously, intraarterially, or subcutaneously), intratumorally, intra-nodally, intrapleurally, intranasally, intraperitoneally, intracavitary, intracranially, orally, rectally, by inhalation, intramuscularly, topically or intradermally to a subject. In a specific embodiment, the chimeric NDV is administered via the hepatic artery, by, e.g., hepatic artery injection, which can be performed by interventional radiology or through placement of an arterial infusion pump. In another specific embodiment, the chimeric NDV is administered intraoperatively, laparoscopically, endoscopically, or by image-guidance. In a specific embodiment, intraperitoneal administration of the chimeric NDV is performed by direct injection, infusion via catheter, or injection during laparoscopy. In a specific embodiment, the chimeric NDV is administered intratumorally. In certain embodiments, image-guidance is used to administer the chimeric NDV. In a specific embodiment, the chimeric NDV is administered intravenously. In another specific embodiment, the chimeric NDV is administered intra-nodally.

In certain embodiments, the methods described herein include the treatment of cancer for which no treatment is available. In some embodiments, a chimeric NDV described herein (e.g., a chimeric NDV described in Section 5.2, supra) or a composition thereof is administered to a subject to treat cancer as an alternative to other conventional therapies.

In one embodiment, provided herein is a method for treating cancer, comprising administering to a subject in need thereof a chimeric NDV described herein (e.g., a chimeric NDV described in Section 5.2, supra) or a composition thereof and one or more additional therapies, such as described in Section 5.7.6, infra. In a particular embodiment, one or more therapies are administered to a subject in combination with a chimeric NDV described herein (e.g., a chimeric NDV described in Section 5.2, supra) or a composition thereof to treat cancer. In a specific embodiment, the additional therapies are currently being used, have been used or are known to be useful in treating cancer. In another embodiment, a chimeric NDV described herein (e.g., a chimeric NDV described in Section 5.2, supra) or a composition thereof is administered to a subject in combination with a supportive therapy, a pain relief therapy, or other therapy that does not have a therapeutic effect on cancer. In a specific embodiment, the one or more additional therapies administered in combination with a chimeric NDV described herein (e.g., a chimeric NDV described in Section 5.2, supra) is one or more of the therapies described in Section 5.7.6.1, infra. In certain embodiments, a chimeric NDV described herein (e.g., a chimeric NDV described in Section 5.2, supra) and one or more additional therapies are administered in the same composition. In other embodiments, a chimeric NDV and one or more additional therapies are administered in different compositions.

In certain embodiments, two, three or multiple NDVs (including one, two or more chimeric NDVs described herein, such as one, two or more of the chimeric NDVs described in Section 5.2, supra) are administered to a subject to treat cancer. The second or more chimeric NDVs used in accordance with methods described herein that comprise administration of two, three or multiple NDVs to a subject to treat cancer may be naturally occurring chimeric NDVs or engineered chimeric NDVs that have been engineered to express heterologous amino acid sequence (e.g., a cytokine). The first and second chimeric NDVs may be part of the same pharmaceutical composition or different pharmaceutical compositions. In certain embodiments, the first chimeric NDV and the second chimeric NDV are administered by the same route of administration (e.g., both are administered intratumorally or intravenously). In other embodiments, the first chimeric NDV and the second chimeric NDV are administered by different routes of administration (e.g., one is administered intratumorally and the other is administered intravenously).

In another aspect, an NDV described herein (e.g., an NDV described in Section 5.1, supra) may be used in combination with one or more additional therapies, such as described herein in Section 5.7.6, infra (e.g., Section 5.7.6.1, infra), in the treatment of cancer. In one embodiment, provided herein are methods for treating cancer, comprising administering to a subject in need thereof an NDV described herein (e.g., an NDV described in Section 5.1, supra) or a composition thereof and one or more additional therapies, such as described herein in Section 5.7.6, infra. (e.g., Section 5.7.6.1). In a specific embodiment, provided herein is a method for treating cancer, comprising administering to a subject in need thereof an effective amount of an NDV described herein (e.g., an NDV described in Section 5.1, supra) or a composition thereof and an effective amount of one or more additional therapies, such as described in Section 5.7.6, infra. (e.g., Section 5.7.6.1). In certain embodiments, an NDV described herein (e.g., an NDV described in Section 5.1, supra) and one or more additional therapies, such as described in Section 5.7.6, infra (e.g., Section 5.7.6.1), are administered in the same composition. In other embodiments, an NDV (e.g., an NDV described in Section 5.1, supra) and one or more additional therapies are administered in different compositions.

The NDV used in combination with one or more additional therapies can be administered systemically or locally. For example, the NDV or composition thereof may be administered parenterally (e.g., intravenously, intraarterially, or subcutaneously), intratumorally, intra-nodally, intrapleurally, intranasally, intraperitoneally, intracranially, orally, rectally, by inhalation, intramuscularly, topically or intradermally to a subject. In a specific embodiment, the NDV is administered via the hepatic artery, by, e.g., hepatic artery injection, which can be performed by interventional radiology or through placement of an arterial infusion pump. In another specific embodiment, the NDV is administered intraoperatively, laparoscopically, or endoscopically. In a specific embodiment, intraperitoneal administration of the NDV is performed by direct injection, infusion via catheter, or injection during laparoscopy.

An NDV (e.g., an NDV described in Section 5.1, supra) described herein or a composition thereof, an oncolysate vaccine, or a whole cell cancer vaccine in combination with one or more additional therapies, such as described herein in Section 5.7.6, infra, may be used as any line of therapy (e.g., a first, second, third, fourth or fifth line therapy) for treating cancer in accordance with a method described herein.

In another aspect, whole cancer cells infected with a chimeric NDV described herein (e.g., a chimeric NDV described in Section 5.2, supra) can be used to treat cancer. In a specific embodiment, a chimeric NDV described herein (e.g., a chimeric NDV described in Section 5.2, supra) may be contacted with a cancer cell or a population of cancer cells and the infected cancer cell or population of cancer cells may be administered to a subject to treat cancer. In one embodiment, the cancer cells are subjected to gamma radiation prior to infection with a chimeric NDV described herein (e.g., a chimeric NDV described in Section 5.2, supra). In another embodiment, the cancer cells are subjected to gamma radiation after infection with a chimeric NDV described herein (e.g., a chimeric NDV described in Section 5.2, supra). In a particular embodiment, the cancer cells are treated prior to administration to a subject so that the cancer cells cannot multiply in the subject. In a specific embodiment, the cancer cells cannot multiply in the subject and the virus cannot infect the subject. In one embodiment, the cancer cells are subjected to gamma radiation prior to administration to subject. In another embodiment, the cancer cells are sonicated prior to administration to a subject. In another embodiment, the cancer cells are treated with mitomycin C prior to administration to a subject. In another embodiment, the cancer cells are treated by freezing and thawing prior to administration to a subject. In another embodiment, the cancer cells are treated with heat treatment prior to administration to a subject. The cancer cells may be administered locally or systemically to a subject. For example, the cancer cells may be administered parenterally (e.g., intravenously or subcutaneously), intratumorally, intra-nodally, intranasally, orally, by inhalation, intrapleurally, topically or intradermally to a subject. In a specific embodiment, the cancer cells are administered intratumorally or to the skin (e.g., intradermally) of a subject. The cancer cells used may be autologous or allogeneic. In a specific embodiment, the backbone of the chimeric NDV is a non-lytic strain. The cancer cells may be administered to a subject alone or in combination with an additional therapy. The cancer cells are preferably in a pharmaceutical composition. In certain embodiments, the cancer cells are administered in combination with one or more additional therapies, such as described in Section 5.7.6, infra. In certain embodiments, the cancer cells and one or more additional therapies are administered in the same composition. In other embodiments, the cancer cells and one or more additional therapies are administered in different compositions.

In another aspect, whole cancer cells infected with an NDV described herein (e.g., an NDV described in Section 5.1, supra) may be used in combination with one or more additional therapies described herein in Section 5.7.6, infra, in the treatment of cancer. In one embodiment, provided herein are methods for treating cancer, comprising administering to a subject in need thereof whole cancer cells infected with an NDV described herein (e.g., an NDV described in Section 5.1, supra) in combination with one or more additional therapies described herein in Section 5.7.6, infra. In a specific embodiment, provided herein is a method for treating cancer, comprising administering to a subject in need thereof an effective amount of whole cancer cells infected with an NDV described herein (e.g., an NDV described in Section 5.1, supra) in combination with an effective amount of one or more additional therapies described in Section 5.7.6, infra. In certain embodiments, whole cancer cells infected with an NDV described herein (e.g., an NDV described in Section 5.1, supra) and one or more additional therapies described in Section 5.7.6.1, infra, are administered in the same composition. In other embodiments, whole cancer cells infected with an NDV described herein (e.g., an NDV described in Section 5.1, supra) and one or more additional therapies are administered in different compositions.

In another aspect, a protein concentrate or plasma membrane preparation from lysed cancer cells infected with a chimeric NDV (e.g., a chimeric NDV described in Section 5.2, supra) can be used to treat cancer. In one embodiment, a plasma membrane preparation comprising fragments from cancer cells infected with a chimeric NDV described herein can be used to treat cancer. In another embodiment, a protein concentrate from cancer cells infected with a chimeric NDV described herein can be used to treat cancer. Techniques known to one of skill in the art may be used to produce the protein concentrate or plasma membrane preparation. In a specific embodiment, a chimeric NDV described herein (e.g., a chimeric NDV described in Section 5.2, supra) may be contacted with a cancer cell or a population of cancer cells and the infected cancer cell or population of cancer cells may be lysed using techniques known to one of skill in the art to obtain protein concentrate or plasma membrane fragments of the NDV-infected cancer cells, and the protein concentrate or plasma membrane fragments of the NDV-infected cancer cells may be administered to a subject to treat cancer. The protein concentrate or plasma membrane fragments may be administered locally or systemically to a subject. For example, the protein concentrate or plasma membrane fragments may be administered parenterally, intratumorally, intra-nodally, intranasally, intrapleurally, orally, by inhalation, topically or intradermally to a subject. In a specific embodiment, such a protein concentrate or plasma membrane preparation is administered intratumorally or to the skin (e.g., intradermally) of a subject. The cancer cells used to produce the protein concentrate or plasma membrane preparation may be autologous or allogeneic. In a specific embodiment, the backbone of the chimeric NDV is a lytic strain. The protein concentrate or plasma membrane preparation may be administered to a subject alone or in combination with an additional therapy.

The protein concentrate or plasma membrane preparation is preferably in a pharmaceutical composition. In certain embodiments, the protein concentrate or plasma membrane preparation is administered in combination with one or more additional therapies, such as described in Section 5.7.6, infra (e.g., Section 5.7.6.1) In certain embodiments, the protein concentrate or plasma membrane preparation and one or more additional therapies are administered in the same composition. In other embodiments, the protein concentrate or plasma membrane preparation and one or more additional therapies are administered in different compositions.

In another aspect, a protein concentrate or plasma membrane preparation from lysed cancer cells infected with an NDV (e.g., an NDV described in Section 5.1, supra) may be used in combination with one or more additional therapies, such as described herein in Section 5.7.6, infra (e.g., Section 5.7.6.1), in the treatment of cancer. In one embodiment, provided herein are methods for treating cancer, comprising administering to a subject in need thereof a protein concentrate or plasma membrane preparation from lysed cancer cells infected with an NDV (e.g., an NDV described in Section 5.1, supra) in combination with one or more additional therapies, such as described herein in Section 5.7.6, infra. (e.g., Section 5.7.6.1). In a specific embodiment, provided herein is a method for treating cancer, comprising administering to a subject in need thereof an effective amount of a protein concentrate or plasma membrane preparation from lysed cancer cells infected with an NDV (e.g., an NDV described in Section 5.1, supra) in combination with an effective amount of one or more additional therapies, such as described in Section 5.7.6, infra. (e.g., Section 5.7.6.1). In certain embodiments, the protein concentrate or plasma membrane preparation and one or more additional therapies, such as described in Section 5.7.6, infra, are administered in the same composition. In other embodiments, the protein concentrate or plasma membrane preparation and one or more additional therapies are administered in different compositions.

In certain embodiments, the methods for treating cancer include those described in Section 5.6 of International Patent Application Publication No. WO 2014/158811 and U.S. Patent Application Publication Nos. 2016/0015760 A1 and 2014/0271677 A1, each of which is incorporated by reference herein in its entirety.

5.7.3 Patient Population

In some embodiments, an NDV (e.g., a chimeric NDV) described herein or a composition thereof, an oncolysate vaccine described herein, or a whole cell vaccine described herein, or a combination therapy described herein is administered to a subject suffering from cancer. In other embodiments, an NDV (e.g., a chimeric NDV) described herein or a composition thereof, an oncolysate vaccine described herein, or a whole cell vaccine described herein, or a combination therapy described herein is administered to a subject predisposed or susceptible to cancer. In some embodiments, an NDV (e.g., a chimeric NDV) or a composition thereof, an oncolysate vaccine described herein, or a whole cell vaccine described herein, or a combination therapy described herein is administered to a subject diagnosed with cancer. Specific examples of the types of cancer are described herein (see, e.g., Section 5.7.5 and Section 6). In an embodiment, the subject has metastatic cancer. In another embodiment, the subject has stage 1, stage 2, stage 3, or stage 4 cancer. In another embodiment, the subject is in remission. In yet another embodiment, the subject has a recurrence of cancer.

In certain embodiments, an NDV (e.g., a chimeric NDV) or a composition thereof, an oncolysate vaccine described herein, or a whole cell vaccine described herein, or a combination therapy described herein is administered to a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In specific embodiments, an NDV (e.g., a chimeric NDV) or a composition thereof, an oncolysate vaccine described herein, or a whole cell vaccine described herein, or a combination therapy described herein is administered to a pediatric patient that is, e.g., 1 years old, 2 years old, 3 years, 4 years old, 5 years old, 6 years old, 7 years old, 8 years old, 9 years old, 10 years old, 11 years old, 12 years old, 13 years old, 14 years old, 15 years old, 16 years or 17 years old. In certain embodiments, an NDV (e.g., a chimeric NDV) or a composition thereof, an oncolysate vaccine described herein, or a whole cell vaccine described herein, or a combination therapy described herein is administered to a human pediatric patient that is 1 to 5 years old, 2 to 5 years old, 1 to 10 years old, 2 to 10 years old, 5 to 10 years old, 1 to 18 years old, 2 to 18 years old, 5 to 18 years old, or 10 to 18 years old. In some embodiments, an NDV (e.g., a chimeric NDV) or a composition thereof, an oncolysate vaccine described herein, or a whole cell vaccine described herein, or a combination therapy described herein is administered to a human infant. In other embodiments, an NDV (e.g., a chimeric NDV) or a composition thereof, an oncolysate vaccine described herein, or a whole cell vaccine described herein, or a combination therapy described herein is administered to a human toddler. In other embodiments, an NDV (e.g., a chimeric NDV) or a composition thereof, an oncolysate vaccine described herein, or a whole cell vaccine described herein, or a combination therapy described herein is administered to a human child. In some embodiments, an NDV (e.g., a chimeric NDV) or a composition thereof, an oncolysate vaccine described herein, or a whole cell vaccine described herein, or a combination therapy described herein is administered to an adult patient that is 18 years of age or older. In other embodiments, an NDV (e.g., a chimeric NDV) or a composition thereof, an oncolysate vaccine described herein, or a whole cell vaccine described herein, or a combination therapy described herein is administered to a human adult. In yet other embodiments, an NDV (e.g., a chimeric NDV) or a composition thereof, an oncolysate vaccine described herein, or a whole cell vaccine described herein, or a combination therapy described herein is administered to an elderly human. In a specific embodiment, an NDV (e.g., a chimeric NDV) or a composition thereof, an oncolysate vaccine described herein, or a whole cell vaccine described herein, or a combination therapy described herein is administered to a patient exhibits cutaneous or subcutaneous tumors or tumors within the lymp node.

In certain embodiments, an NDV (e.g., a chimeric NDV) or a composition thereof, an oncolysate vaccine described herein, or a whole cell vaccine described herein, or a combination therapy described herein is administered to a subject in an immunocompromised state or immunosuppressed state or at risk for becoming immunocompromised or immunosuppressed. In certain embodiments, an NDV (e.g., a chimeric NDV) or a composition thereof, an oncolysate vaccine described herein, or a whole cell vaccine described herein, or a combination therapy described herein is administered to a subject receiving or recovering from immunosuppressive therapy. In certain embodiments, an NDV (e.g., a chimeric NDV) or a composition thereof, an oncolysate vaccine described herein, or a whole cell vaccine described herein, or a combination therapy described herein is administered to a subject that has or is at risk of getting cancer. In certain embodiments, the subject is, will or has undergone surgery, chemotherapy and/or radiation therapy. In certain embodiments, the patient has undergone surgery to remove the tumor or neoplasm. In specific embodiments, the patient is administered an NDV (e.g., a chimeric NDV) or a composition thereof, an oncolysate vaccine described herein, or a whole cell vaccine described herein, or a combination therapy described herein following surgery to remove a tumor or neoplasm. In other embodiment, the patient is administered an NDV (e.g., a chimeric NDV) or a composition thereof, an oncolysate vaccine described herein, or a whole cell vaccine described herein, or a combination therapy described herein prior to undergoing surgery to remove a tumor or neoplasm. In certain embodiments, an NDV (e.g., a chimeric NDV) or a composition thereof, an oncolysate vaccine described herein, or a whole cell vaccine described herein, or a combination therapy described herein is administered to a subject that has, will have or had a tissue transplant, organ transplant or transfusion.

In some embodiments, an NDV (e.g., a chimeric NDV) or a composition thereof, an oncolysate vaccine described herein, or a whole cell vaccine described herein, or a combination therapy described herein is administered to a patient who has proven refractory to therapies other than the chimeric NDV or composition thereof, oncolysate, whole cell vaccine, or a combination therapy but are no longer on these therapies. In a specific embodiment, an NDV (e.g., a chimeric NDV) or a composition thereof, an oncolysate vaccine described herein, or a whole cell vaccine described herein, or a combination therapy described herein is administered to a patient who has proven refractory to chemotherapy. In a specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to treatment with an antagonist of PD-1 or a ligand thereof. In a specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to monotherapy treatment with an antagonist of PD-1 or a ligand thereof. In a specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to treatment with a PD-1-blocking antibody (e.g., pembrolizumab or nivolumab). In a specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to monotherapy treatment with a PD-1-blocking antibody (e.g., pembrolizumab or nivolumab). In a specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to treatment with a PD-L1-blocking antibody (e.g., atezolizumab). In another specific embodiment, an NDV (e.g., a chimeric NDV) or a composition thereof, an oncolysate vaccine described herein, or a whole cell vaccine described herein, or a combination therapy described herein is administered to a patient who has proven refractory or unresponsive to monotherapy treatment with a PD-L1-blocking antibody (e.g., atezolizumab). In a specific embodiment, the therapy to which the patient has proven refractory is part of the combination therapy. For example, in a specific embodiment, the patient has proven refractory to treatment with an antagonist of PD-1 or a ligand thereof; however, without being bound to any particular theory, the patient is responsive to treatment with the antagonist of PD-1 or a ligand thereof in combination with an NDV (e.g., a chimeric NDV) or a composition thereof, an oncolysate vaccine described herein, or a whole cell vaccine described herein, or a combination therapy described herein. The determination of whether cancer is refractory can be made by any method known in the art. In a certain embodiment, refractory patient is a patient refractory to a standard therapy. In some embodiments, a patient with cancer is initially responsive to therapy, but subsequently becomes refractory.

In certain embodiments, the patient to be treated in accordance with the methods described herein is a patient that has relapsed after treatment with therapies other than the chimeric NDV or composition thereof, oncolysate, whole cell vaccine, or a combination therapy. In some embodiments, the patient to be treated in accordance with the methods described herein is a patient that has relapsed after treatment with an antagonist of PD-1 or a ligand thereof. In certain embodiments, the patient to be treated in accordance with the methods described herein is a patient that has relapsed after monotherapy treatment with an antagonist of PD-1 or a ligand thereof. In some embodiments, the patient to be treated in accordance with the methods described herein is a patient that has relapsed after treatment with a PD-1-blocking antibody (e.g., pembrolizumab or nivolumab). In certain embodiments, the patient to be treated in accordance with the methods described herein is a patient that has relapsed after monotherapy treatment with a PD-1-blocking antibody (e.g., pembrolizumab or nivolumab). In some embodiments, the patient to be treated in accordance with the methods described herein is a patient that has relapsed after treatment with a PD-L1-blocking antibody (e.g., atezolizumab). In certain embodiments, the patient to be treated in accordance with the methods described herein is a patient that has relapsed after monotherapy treatment with a PD-L1-blocking antibody (e.g., atezolizumab).

In certain embodiments, the patient to be treated in accordance with the methods described herein is a patient that has relapsed after treatment with therapies other than the chimeric NDV or composition thereof, oncolysate, whole cell vaccine, or a combination therapy and is refractory or unresponsive to treatment with an antagonist of PD-1 or a ligand thereof. In some embodiments, the patient to be treated in accordance with the methods described herein is a patient that has relapsed after treatment with an antagonist of PD-1 or a ligand thereof and is refractory or unresponsive to monotherapy treatment with an antagonist of PD-1 or a ligand thereof. In certain embodiments, the patient to be treated in accordance with the methods described herein is a patient that has relapsed after treatment with a PD-1-blocking antibody (e.g., pembrolizumab or nivolumab) and is refractory or unresponsive to monotherapy treatment with a PD-1 blocking antibody. In certain embodiments, the patient to be treated in accordance with the methods described herein is a patient that has relapsed after treatment with with a PD-L1-blocking antibody (e.g., atezolizumab) and is refractory or unresponsive to monotherapy treatment with a PD-L1-blocking antibody.

In certain embodiments, the patient to be treated in accordance with the methods described herein is a patient already being treated with antibiotics, anti-virals, anti-fungals, or other biological therapy/immunotherapy or anti-cancer therapy. Among these patients are refractory patients, and patients who are too young for conventional therapies. In some embodiments, the subject being administered an NDV (e.g., a chimeric NDV), an oncolysate vaccine described herein, or a whole cell vaccine described herein, or a combination therapy described herein has not received therapy prior to the administration of the chimeric NDV or composition, the oncolysate vaccine, or the whole cell vaccine, or the combination therapy.

In some embodiments, an NDV (e.g., a chimeric NDV) or a composition thereof, an oncolysate vaccine described herein, or a whole cell vaccine described herein, or a combination therapy described herein is administered to a patient to prevent the onset of cancer in a patient at risk of developing cancer. In some embodiments, compounds are administered to a patient who are susceptible to adverse reactions to conventional therapies.

In some embodiments, the subject being administered an NDV (e.g., a chimeric NDV) or a composition thereof, an oncolysate vaccine described herein, or a whole cell vaccine described herein, or a combination therapy described herein has not received prior therapy. In other embodiments, an NDV (e.g., a chimeric NDV) or a composition thereof, an oncolysate vaccine described herein, or a whole cell vaccine described herein, or a combination therapy described herein is administered to a subject who has received a therapy prior to administration of the NDV (e.g., a chimeric NDV) or composition, the oncolysate vaccine, the whole cell vaccine, or the combination therapy. In some embodiments, the subject administered an NDV (e.g., a chimeric NDV) or a composition thereof, an oncolysate vaccine described herein, or a whole cell vaccine described herein, or a combination therapy described herein experienced adverse side effects to a prior therapy or a prior therapy was discontinued due to unacceptable levels of toxicity to the subject.

In a specific embodiment, the subject being administered an NDV (e.g., a chimeric NDV) or a composition thereof, an oncolysate vaccine described herein, or a whole cell vaccine described herein, or a combination therapy described herein has one or more PD-L1 positive tumors or malignancies. In a specific embodiment, a tumor or malignancy is PD-L1-positive. In a specific embodiment, a tumor or malignancy is PD-L1-positive if the tumor proportion score (TPS) of a biopsy of the tumor or malignancy, the percentage of cells staining for PD-L1 is at least 1%, 2%, 3%, 5%, 7%, 8%, 10%, 15%, 20%, 25%, 30%, 35%, 40%, 45%, 50%, 55%, 60%, 65%, 70%, 75%, 80%, 85%. 90%, 95%, 98%, or 100% as assessed by a technique known in the art or described herein such as immunohistochemistry or the PD-L1 IHC 22C3 pharmDx (Agilent Technologies Inc.). In another specific embodiment, a tumor or malignancy is PD-L1-positive if the tumor proportion score (TPS) of a biopsy of the tumor or malignancy, the percentage of cells staining for PD-L1 is 1% to 100%, 25% to 50%, 25% to 100%, 50% to 75%, 50% to 100%, or 75% to 100%, as assessed by a technique known in the art or described herein such as immunohistochemistry or the PD-L1 IHC 22C3 pharmDx (Agilent Technologies Inc.).

In a specific embodiment, a tumor or malignancy is PD-L1-positive if the combined positive score (CPS) of a biopsy of the tumor or malignancy, the percentage of cells staining for PD-L1 is at least 1%, 2%, 3%, 5%, 7%, 8%, 10%, 15%, 20%, 25%, 30%, 35%, 40%, 45%, 50%, 55%, 60%, 65%, 70%, 75%, 80%, 85%. 90%, 95%, 98%, or 100% as assessed by a technique known in the art or described herein such as immunohistochemistry or the PD-L1 IHC 22C3 pharmDx (Agilent Technologies Inc.). In another specific embodiment, a tumor or malignancy is PD-L1-positive if the combined positive score (CPS) of a biopsy of the tumor or malignancy, the percentage of cells staining for PD-L1 is 1% to 100%, 25% to 50%, 25% to 100%, 50% to 75%, 50% to 100%, or 75% to 100%, as assessed by a technique known in the art or described herein such as immunohistochemistry or the PD-L1 IHC 22C3 pharmDx (Agilent Technologies Inc.). In order to determine the CPS, the number of viable PD-L1 positive tumor cells, the number of viable PD-L1 negative tumor cells, and the number of viable PD-L1 positive mononuclear inflammatory cells (MIC) in a tumor tissue sample from a subject is determined, and then the formula is used to calculate the combined positive score (CPS): CPS=(number of PD-L1 positive tumor cells+number of PD-L1 positive mononuclear inflammatory cells (MIC)/number of PD-L-1 positive tumor cells+PD-L1 negative tumor cells)×100%. See, e.g., U.S. Patent Application Publication No. 2017/0285037 and Kulangara et al., Journal of Clinical Oncology 2017 35:15_suppl, e14589-e14589 for a description of the combined positive score (CPS), each of which is incorporated herein by reference in its entirety.

In some embodiments, the subject being administered an NDV (e.g., a chimeric NDV) or a composition thereof, an oncolysate vaccine described herein, or a whole cell vaccine described herein, or a combination therapy described herein has one or more PD-L1 negative tumors or malignancies. In a specific embodiment, a tumor or malignancy is PD-L1 negative. In a specific embodiment, a biopsy of the cancer is PD-L1-negative as assessed by a technique known in the art or described herein, such as immunohistochemistry or the PD-L1 IHC 22C3 pharmDx (Agilent Technologies Inc.). In a specific embodiment, a tumor or malignancy is PD-L1-negative if the tumor proportion score (TPS) of a biopsy of the tumor or malignancy, the percentage of cells staining for PD-L1 is less than 1% as assessed by a technique known in the art or described herein, such as immunohistochemistry or the PD-L1 IHC 22C3 pharmDx (Agilent Technologies Inc.).

In a specific embodiment, a tumor or malignancy is PD-L1-negative if the combined positive score (CPS) of a biopsy of the tumor or malignancy, the percentage of cells staining for PD-L1 is less than 1% as assessed by a technique known in the art or described herein, such as immunohistochemistry or the PD-L1 IHC 22C3 pharmDx (Agilent Technologies Inc.).

In a specific embodiment, the subject being administered an NDV (e.g., a chimeric NDV) or a composition thereof, an oncolysate vaccine described herein, or a whole cell vaccine described herein, or a combination therapy described herein has one or more tumors or malignancies that has low levels of PD-L1. In a specific embodiment, a tumor or malignancy has low levels of PD-L1 expression if a biopsy of the tumor or malignancy has the tumor proportion score (TPS) of between 1% to 50%, or 1% to 40%, 1% to 30%, 1% to 25%, 1% to 15%, or 1% to 10% as assessed by a technique known in the art or described herein, such as immunohistochemistry or the PD-L1 IHC 22C3 pharmDx (Agilent Technologies Inc.). In a specific embodiment, a tumor or malignancy has low levels of PD-L1 expression if a biopsy of the tumor or malignancy has the tumor proportion score (TPS) of less than 50% but 1% or greater as assessed by a technique known in the art or described herein, such as immunohistochemistry or the PD-L1 IHC 22C3 pharmDx (Agilent Technologies Inc.)

In a specific embodiment, a tumor or malignancy has low levels of PD-L1 expression if a biopsy of the tumor or malignancy has the combined positive score (CPS) of between 1% to 50%, or 1% to 40%, 1% to 30%, 1% to 25%, 1% to 15%, or 1% to 10% as assessed by a technique known in the art or described herein, such as immunohistochemistry or the PD-L1 IHC 22C3 pharmDx (Agilent Technologies Inc.). In a specific embodiment, a tumor or malignancy has low levels of PD-L1 expression if a biopsy of the tumor or malignancy has the combined positive score (CPS) of less than 50% but 1% or greater as assessed by a technique known in the art or described herein, such as immunohistochemistry or the PD-L1 IHC 22C3 pharmDx (Agilent Technologies Inc.)

In a specific embodiment, an ELISA is used to determine if tumor cells are PD-L1-positive and/or to determine if a tumor or malignancy has low levels of PD-L1. In a specific embodiment, immunohistochemistry is used to determine if tumor cells are PD-L1-negative, PD-L1-positive and/or if a tumor or malignancy has low levels of PD-L1. In a specific embodiment, a tumor or malignancy (or a biopsy thereof) is determined to be PD-L1-negative, PD-L1-positive, and/or have low levels of PD-L1 according to one or more assays approved by the U.S. Food and Drug Administration for determining the level of PD-L1. Nonlimiting examples of U.S. Food and Drug Administration-approved assays for determining the level of PD-L1 include PD-L1 IHC 22C3 pharmDx (manufactured by Dako North America, Inc.) and Ventana PD-L1 (SP142) Assay (manufactured by Ventana Medical Systems, Inc.). In another specific embodiment, the level of PD-L1 in a tumor or malignancy (or a biopsy thereof) is determined according to a laboratory-developed test performed in a Clinical Laboratory Improvement Amendments-certified laboratory.

5.7.4 Dosage & Frequency

The amount of an NDV or a composition thereof, an oncolysate vaccine, or a whole cell vaccine which will be effective in the treatment of cancer will depend on the nature of the cancer, the route of administration, the general health of the subject, etc. and should be decided according to the judgment of a medical practitioner. Standard clinical techniques, such as in vitro assays, may optionally be employed to help identify optimal dosage ranges. However, suitable dosage ranges of an NDV for administration are generally about $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ pfu, and most preferably about $10^4$ to about $10^{12}$, $10^6$ to $10^{12}$, $10^8$ to $10^{12}$, $10^9$ to $10^{12}$ or $10^9$ to $10^{11}$ pfu, and can be administered to a subject once, twice, three, four or more times with intervals as often as needed. Dosage ranges of oncolysate vaccines for administration may include 0.001 mg, 0.005 mg, 0.01 mg, 0.05 mg. 0.1 mg. 0.5 mg, 1.0 mg, 2.0 mg. 3.0 mg, 4.0 mg, 5.0 mg, 10.0 mg, 0.001 mg to 10.0 mg, 0.01 mg to 1.0 mg, 0.1 mg to 1 mg, and 0.1 mg to 5.0 mg, and can be administered to a subject once, twice, three or more times with intervals as often as needed. Dosage ranges of whole cell vaccines for administration may include $10^2$, $5\times10^2$, $10^3$, $5\times10^3$, $10^4$, $5\times10^4$, $10^5$, $5\times10^5$, $10^6$, $5\times10^6$, $10^7$, $5\times10^7$, $10^8$, $5\times10^8$, $1\times10^9$, $5\times10^9$, $1\times10^{10}$, $5\times10^{10}$, $1\times10^{11}$, $5\times10^{11}$ or $10^{12}$ cells, and can be administered to a subject once, twice, three or more times with intervals as often as needed. In certain embodiments, dosages similar to those currently being used in clinical trials for NDV, oncolysate vaccines or whole cell vaccines are administered to a subject. Effective doses may be extrapolated from dose response curves derived from in vitro or animal model test systems.

In certain embodiments, an NDV (e.g., a chimeric NDV) or a composition thereof is administered to a subject as a single dose followed by a second dose 1 to 6 weeks, 1 to 5 weeks, 1 to 4 weeks, 1 to 3 weeks, 1 to 2 weeks later. In accordance with these embodiments, booster inoculations may be administered to the subject at 6 to 12 month intervals following the second inoculation. In certain embodiments, an oncolysate vaccine or a whole cell vaccine is administered to a subject as a single dose followed by a second dose 1 to 6 weeks, 1 to 5 weeks, 1 to 4 weeks, 1 to 3 weeks, 1 to 2 weeks later.

In certain embodiments, administration of the same NDV (e.g., chimeric NDV) or a composition thereof, oncolysate vaccine, or whole cell vaccine may be repeated and the administrations may be separated by at least 1 day, 2 days, 3 days, 5 days, 6 says, 7 days, 10 days, 14 days, 15 days, 21 days, 28 days, 30 days, 45 days, 2 months, 75 days, 3 months, or at least 6 months. In other embodiments, administration of the same NDV (e.g., a NDV) or a composition thereof, oncolysate vaccine, or whole cell vaccine may be repeated and the administrations may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months. In some embodiments, a first NDV (e.g., a first chimeric NDV) or a composition thereof is administered to a subject followed by the administration of a second NDV (e.g., a second chimeric NDV) or a composition thereof. In certain embodiments, the first and second NDVs (e.g., the first and second chimeric NDVs) or compositions thereof may be separated by at least 1 day, 2 days, 3 days, 5 days, 6 days, 7 days, 10 days, 14 days, 15 days, 21 days, 28 days, 30 days, 45 days, 2 months, 75 days, 3 months, or at least 6 months. In other embodiments, the first and second NDVs (e.g., the first and second chimeric NDVs) or compositions thereof may be separated by 1 to 14 days, 1 to 7 days, 7 to 14 days, 1 to 30 days, 15 to 30 days, 15 to 45 days, 15 to 75 days, 15 to 90 days, 1 to 3 months, 3 to 6 months, 3 to 12 months, or 6 to 12 months.

In certain embodiments, an NDV or composition thereof, or oncolysate vaccine or whole cell vaccine is administered to a subject in combination with one or more additional therapies, such as a therapy described in Section 5.7.6, infra. The dosage of the other one or more additional therapies will depend upon various factors including, e.g., the therapy, the nature of the cancer, the route of administration, the general health of the subject, etc. and should be decided according to the judgment of a medical practitioner. In specific embodiments, the dose of the other therapy is the dose and/or frequency of administration of the therapy recommended for the therapy for use as a single agent is used in accordance with the methods disclosed herein. In other embodiments, the dose of the other therapy is a lower dose and/or less frequent administration of the therapy than recommended for the therapy for use as a single agent is used in accordance with the methods disclosed herein. Recommended doses for approved therapies can be found in the Physician's Desk Reference.

In certain embodiments, an NDV or composition thereof, or oncolysate vaccine or whole cell vaccine is administered to a subject concurrently with the administration of one or more additional therapies. In other embodiments, an NDV or composition thereof, or oncolysate vaccine or whole cell vaccine is administered to a subject every 3 to 7 days, 1 to 6 weeks, 1 to 5 weeks, 1 to 4 weeks, 2 to 4 weeks, 1 to 3 weeks, or 1 to 2 weeks and one or more additional therapies (such as described in Section 5.7.6, infra) is administered every 3 to 7 days, 1 to 6 weeks, 1 to 5 weeks, 1 to 4 weeks, 1 to 3 weeks, or 1 to 2 weeks. In certain embodiments, an NDV or composition thereof, or oncolysate vaccine or whole cell vaccine is administered to a subject every 1 to 2 weeks and one or more additional therapies (such as described in Section 5.7.6, infra) is administered every 2 to 4 weeks. In some embodiments, an NDV or composition thereof, or oncolysate vaccine or whole cell vaccine is administered to a subject every week and one or more additional therapies (such as described in Section 5.7.6, infra) is administered every 2 weeks.

The dosage of the antagonist of PD-1 or a ligand thereof used to treat a subject will depend upon various factors including, e.g., the therapy, the nature of the cancer, the route of administration, the general health of the subject, etc. and should be decided according to the judgment of a medical practitioner. In specific embodiments, the dose of the antagonist of PD-1 or a ligand thereof is the dose and/or frequency of administration of the antagonist of PD-1 or a ligand thereof recommended for the antagonist of PD-1 or a ligand thereof for use as a single agent is used in accordance with the methods disclosed herein. In some embodiments, the dose of the antagonist of PD-1 or a ligand thereof is a lower dose and/or less frequent administration of the therapy than recommended for the antagonist of PD-1 or a ligand thereof for use as a single agent is used in accordance with the methods disclosed herein. Recommended doses for approved therapies can be found in the Physician's Desk Reference.

In a specific embodiment in which the antagonist of PD-1 or a ligand thereof is nivolumab, the dosage of nivolumab may be 240 mg as an intravenous infusion over a period of time, e.g., 30 minutes, every two weeks. See, e.g., Full Prescribing Information for OPDIVO, as revised April 2018, which is incorporated by reference herein in its entirety. In another specific embodiment in which the antagonist of PD-1 or a ligand thereof is nivolumab, the dosage of nivolumab may be 480 mg as an intravenous infusion over a period of time, e.g., 30 minutes, every four weeks. Id. In another specific embodiment in which the antagonist of PD-1 or a ligand thereof is nivolumab, the dosage of nivolumab may be 3 mg/kg as an intravenous infusion over a period of time, e.g., 60 minutes, every two weeks. See, e.g., Full Prescribing Information for OPDIVO, Reference ID: 3677021, which is incorporated by reference herein in its entirety. In a specific embodiment in which the antagonist of PD-1 or a ligand thereof is pembrolizumab, the dosage of pembrolizumab may be 200 mg as an intravenous infusion over a period of time, e.g., 30 minutes, every three weeks. See, e.g., Full Prescribing Information for KEYTRUDA, as revised November 2017, which is incorporated by reference herein in its entirety. In another specific embodiment in which the antagonist of PD-1 or a ligand thereof is pembrolizumab, the dosage of pembrolizumab may be 2 mg/kg as an intravenous infusion over a period of time, e.g., 30 minutes, every three weeks. See, e.g., Full Prescribing Information for KEYTRUDA, Reference ID: 3862712, which is incorporated by reference herein in its entirety. In another specific embodiment in which the antagonist of PD-1 or a ligand thereof is pembrolizumab, the dosage of pembrolizumab may be between 2 mg/kg and up to 200 mg/kg as an intravenous infusion over a period of time, e.g., 30 minutes, every three weeks. See, e.g., Full Prescribing Information for KEYTRUDA, Reference ID: 3862712, which is incorporated by reference herein in its entirety. In a specific embodiment in which the antagonist of PD-1 or a ligand thereof is atezolizumab, the dosage of atezolizumab may be 1,200 mg as an intravenous infusion over a period of time, e.g., 60 minutes, every three weeks. See, e.g., Full Prescribing Information for TECENTRIQ, Reference ID: 4000525, which is incorporated by reference herein in its entirety.

5.7.5 Types of Cancer

Specific examples of cancers that can be treated in accordance with the methods described herein include, but are not limited to: leukemias, such as but not limited to, acute leukemia, acute lymphocytic leukemia, acute myelocytic leukemias, such as, myeloblastic, promyelocytic, myelomonocytic, monocytic, and erythroid leukemias and myelodysplastic syndrome; myelofibrisis, chronic leukemias, such as but not limited to, chronic myelocytic (granulocytic) leukemia, chronic lymphocytic leukemia, hairy cell leukemia; polycythemia vera; lymphomas such as but not limited to Hodgkin disease, non-Hodgkin disease; multiple myelomas such as but not limited to smoldering multiple myeloma, nonsecretory myeloma, osteosclerotic myeloma, placancer cell leukemia, solitary placancercytoma and extramedullary placancercytoma; Waldenstrom's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors such as but not limited to, glioma, astrocytoma, brain stem glioma, ependymoma, oligodendroglioma, nonglial tumor, glioblastoma multiforme, acoustic neurinoma, craniopharyngioma, medulloblastoma, meningioma, pineocytoma, pineoblastoma, primary brain lymphoma; breast cancer including but not limited to triple negative breast cancer, ER+/HER2− breast cancer, ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipidus; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and cancer-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America).

In a specific embodiment, the chimeric NDVs described herein or compositions thereof, an oncolysate vaccine described herein, a whole cell vaccine herein, or a combination therapy described herein are useful in the treatment of a variety of cancers and abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, teratocarcinoma, neuroblastoma and glioma; tumors of the central and peripheral nervous system, including astrocytoma, neuroblastoma, glioma, and schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma.

In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma or melanoma is treated in accordance with the methods described herein.

In a specific embodiment, the cancer being treated in accordance with the methods described herein is leukemia, lymphoma or myeloma (e.g., multiple myeloma). Specific examples of leukemias and other blood-borne cancers that can be treated in accordance with the methods described herein include, but are not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CIVIL", chronic lymphocytic leukemia "CLL", and hairy cell leukemia.

Specific examples of lymphomas that can be treated in accordance with the methods described herein include, but are not limited to, Hodgkin disease, non-Hodgkin lymphoma such as diffuse large B-cell lymphoma, multiple myeloma, Waldenstrom's macroglobulinemia, heavy chain disease, and polycythemia vera.

In another embodiment, the cancer being treated in accordance with the methods described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, cancer cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma. In another embodiment, the cancer being treated in accordance with the methods described herein is a metastatic. In another embodiment, the cancer being treated in accordance with the methods described herein is malignant.

In a specific embodiment, the cancer being treated in accordance with the methods described herein is melanoma (e.g. advanced melanoma), non-small cell lung cancer (NSCLC), head and neck squamous cell cancer (HNSCC), classical Hodgkin lymphoma, advanced urothelial cancer, a microsatellite instability-high cancer, or gastric or gastroesophageal junction adenocarcinoma. In a specific embodiment, the cancer being treated in accordance with the methods described herein is uterine cancer, gastric cancer, esophageal cancer, liver cancer, brain cancer, or sarcoma. In a specific embodiment, the cancer being treated in accordance with the methods described herein is (1) refractory classical Hodgkin lymphoma, (2) recurrent or metastatic head and neck squamous cell cancer, (3) unresectable or metastatic melanoma, (4) locally or advanced or metastatic urothelial carcinoma, (5) recurrent locally advanced or metastatic gastric or gastroesophageal adenocarcinoma with tumors expressing programmed death-ligand 1 ("PD-L1") (e.g., tumors having a CPS≥1), (6) unresectable or metastatic, microsatellite instability-high cancer or mismatch repair deficient solid tumors that have progressed following prior treatment and who have no satisfactory alternative treatment options, or colorectal cancer that has progessed following treatment with a fluoropyrimidine, oxaliplatin and irinotecan, or (7) metastatic non-small cell lung cancers having tumors which express PD-L1 (e.g., tumors having a TPS≥1% or 50%).

In a specific embodiment, the cancer being treated in accordance with the methods described herein is melanoma, non-small cell lung cancer, head and neck cancer (HNSCC head and neck squamous cell carcinoma), Urothelial cancer, Triple negative breast cancer, gastric cancer, classical Hodgkin lymphoma, non-Hodgkin lymphoma, primary mediastinal B-cell lymphoma, mesothelioma, ovarian cancer, small cell lung cancer, esophageal cancer, nasopharyngeal cancer, anal cancer, biliary tract cancer, colorectal cancer, ER+/HER2− breast cancer, cervical cancer, thyroid cancer, salivary cancer, endometrial cancer, prostate cancer, glioblastoma, microsatellite instability-high (MSI-H) or mismatch repair deficient cancer (tissue agnostic), or tumors with high tumor mutational burden (tissue agnostic).

In a specific embodiment, the cancer being treated in accordance with the methods described herein is a cancer that has a poor prognosis and/or has a poor response to conventional therapies, such as chemotherapy and radiation. In another specific embodiment, the cancer being treated in accordance with the methods described herein is malignant melanoma, malignant glioma, renal cell carcinoma, pancreatic adenocarcinoma, malignant pleural mesothelioma, lung adenocarcinoma, lung small cell carcinoma, lung squamous cell carcinoma, anaplastic thyroid cancer, and head and neck squamous cell carcinoma. In another specific embodiment, the cancer being treated in accordance with the methods described herein is a type of cancer described in Section 6, infra.

In a specific embodiment, the cancer being treated in accordance with the methods described herein is refractory Hodgkin lymphoma, recurrent or metastatic head and neck squamous cell cancer, unresectable or metastatic melanoma, or metastatic non-small cell lung cancer.

In a specific embodiment, a cancer being treated in accordance with the methods described herein is PD-L1-positive. In a specific embodiment, a cancer is PD-L1-positive if the tumor proportion score (TPS), the percentage of cells staining for PD-L1 in a biopsy of the cancer is at least 1%, 2%, 3%, 5%, 7%, 8%, 10%, 15%, 20%, 25%, 30%, 35%, 40%, 45%, 50%, 55%, 60%, 65%, 70%, 75%, 80%, 85%. 90%, 95%, 98%, or 100% as assessed by a technique known in the art or described herein such as immunohistochemistry or the PD-L1 IHC 22C3 pharmDx (Agilent Technologies Inc.). In another specific embodiment, a cancer is PD-L1-positive if the TPS, the percentage of cells staining for PD-L1 in a biopsy of the cancer is at least 1% or 1% to 100%, as assessed by a technique known in the art or described herein such as immunohistochemistry or the PD-L1 IHC 22C3 pharmDx (Agilent Technologies Inc.). In another specific embodiment, a cancer is PD-L1-positive if the TPS, the percentage of cells staining for PD-L1 in a biopsy of the cancer is 1% to 100%, 25% to 50%, 25% to 100%, 50% to 75%, 50% to 100%, or 75% to 100%, as assessed by a technique known in the art or described herein such as immunohistochemistry or the PD-L1 IHC 22C3 pharmDx (Agilent Technologies Inc.). In a specific embodiment, the cancer that is determined to be PD-L1 positive using the TPS score is non-small cell lung cancer.

In a specific embodiment, a cancer is PD-L1-positive if the combined positive score (CPS), the percentage of cells staining for PD-L1 in a biopsy of the cancer is at least 1%, 2%, 3%, 5%, 7%, 8%, 10%, 15%, 20%, 25%, 30%, 35%, 40%, 45%, 50%, 55%, 60%, 65%, 70%, 75%, 80%, 85%. 90%, 95%, 98%, or 100% as assessed by a technique known in the art or described herein such as immunohistochemistry or the PD-L1 IHC 22C3 pharmDx (Agilent Technologies Inc.). In another specific embodiment, a cancer is PD-L1-positive if the CPS, the percentage of cells staining for PD-L1 in a biopsy of the cancer is at least 1% or 1% to 100%, as assessed by a technique known in the art or described herein such as immunohistochemistry or the PD-L1 IHC 22C3 pharmDx (Agilent Technologies Inc.). In another specific embodiment, a cancer is PD-L1-positive if the CPS, the percentage of cells staining for PD-L1 in a biopsy of the cancer is 1% to 100%, 25% to 50%, 25% to 100%, 50% to 75%, 50% to 100%, or 75% to 100%, as assessed by a technique known in the art or described herein such as immunohistochemistry or the PD-L1 IHC 22C3 pharmDx (Agilent Technologies Inc.). In a specific embodiment, the cancer that is determined to be PD-L1 positive using the CPS score is gastric cancer (e.g., recurrent locally advanced metastatic gastric or gastroesophageal junction adenocarcinoma).

In some specific embodiments, a cancer being treated in accordance with the methods described herein is PD-L1-negative. In a specific embodiment, a cancer is PD-L1-negative if the TPS, the percentage of cells staining for PD-L1 in a biopsy of the cancer is less than 1% as assessed by a technique known in the art or described herein, such as immunohistochemistry or the PD-L1 IHC 22C3 pharmDx (Agilent Technologies Inc.). In a specific embodiment, the cancer that is determined to be PD-L1 negative using the TPS score is non-small cell lung cancer.

In specific embodiments, a cancer being treated in accordance with the methods described herein has low levels of PD-L1 expression. In a specific embodiment, a cancer has low levels of PD-L1 expression if the TPS, the percentage of cells staining for PD-L1 in a biopsy of the cancer is between 1% to 50%, or 1% to 40%, 1% to 30%, 1% to 25%, 1% to 15%, or 1% to 10% as assessed by a technique known in the art or described herein, such as immunohistochemistry or the PD-L1 IHC 22C3 pharmDx (Agilent Technologies Inc.). In a specific embodiment, a cancer has low levels of PD-L1 expression if the TPS, the percentage of cells staining for PDL1 in a biopsy of the cancer is less than 50% but 1% or greater as assessed by a technique known in the art or described herein, such as immunohistochemistry or the PD-L1 IHC 22C3 pharmDx (Agilent Technologies Inc.)

In a specific embodiment, ELISA is used to determine if a biopsy of cancer is PD-L1-positive, PD-L1-negative, and/or have low levels of PD-L1 expression. In a specific embodiment, immunohistochemistry is used to determine if a biopsy of cancer is PD-L1-positive, PD-L1-negative, and/or have low levels of PD-L1 expression. In a specific embodiment, a tumor or malignancy (or a biopsy thereof) is determined to be PD-L1-positive, PD-L1 negative, and/or have low levels of PD-L1 expression according to one or more assays approved by the U.S. Food and Drug Administration for determining the level of PD-L1. Non-limiting examples of U.S. Food and Drug Administration-approved assays for determining the level of PD-L1 include PD-L1 IHC 22C3 pharmDx (manufactured by Dako North America, Inc.) and Ventana PD-L1 (SP142) Assay (manufactured by Ventana Medical Systems, Inc.). In another specific embodiment, the level of PD-L1 in a tumor or malignancy (or a biopsy thereof) is determined according to a laboratory-developed test performed in a Clinical Laboratory Improvement Amendments-certified laboratory. In another specific embodiment, the level of PD-L1 in a tumor or malignancy (or a biopsy thereof) is determined using PCR. In another specific embodiment, the level of PD-L1 in a tumor or malignancy (or a biopsy thereof) is determined by assessing the gene expression profile of certain tumor-associated genes using kits from NanoString Technologies.

In specific embodiments, a cancer being treated in accordance with the methods described herein is refractory or unresponsive to monotherapy treatment with an antagonist of PD-1 or a ligand thereof. In a specific embodiment, a cancer being treated in accordance with the methods described herein is refractory or unresponsive to monotherapy treatment with an PD-1 blocking antibody (e.g., nivolumab or pembrolizumab). In specific embodiments, a cancer being treated in accordance with the methods described herein is refractory or unresponsive to monotherapy treatment with a PD-L1 blocking antibody (e.g., avelumab).

In specific embodiments, a cancer being treated in accordance with the methods described herein is PD-L1-negative and refractory or unresponsive to monotherapy treatment with an antagonist of PD-1 or a ligand thereof. In a specific embodiment, a cancer being treated in accordance with the methods described herein is PD-L1-negative and refractory or unresponsive to monotherapy treatment with a PD-1 blocking antibody (e.g., nivolumab or pembrolizumab). In specific embodiments, a cancer being treated in accordance with the methods described herein is PD-L1-negative and refractory or unresponsive to monotherapy treatment with a PD-L1 blocking antibody (e.g., avelumab).

In specific embodiments, a cancer being treated in accordance with the methods described herein has low levels of PD-L1 expression and is refractory or unresponsive to monotherapy treatment with an antagonist of PD-1 or a ligand thereof. In a specific embodiment, a cancer being treated in accordance with the methods described herein has low levels of PD-L1 expression and is refractory or unresponsive to monotherapy treatment with a PD-1 blocking antibody (e.g., nivolumab or pembrolizumab). In specific embodiments, a cancer being treated in accordance with the methods described herein has low levels of PD-L1 expression and is refractory or unresponsive to monotherapy treatment with a PD-L1 blocking antibody (e.g., avelumab).

In specific embodiments, a cancer being treated in accordance with the methods described herein is relapsed. In a specific embodiment, a cancer being treated in accordance with the methods described herein is relapsed and refractory or unresponsive to monotherapy treatment with an antagonist of PD-1 or a ligand thereof. In another specific embodiment, a cancer being treated in accordance with the methods described herein is relapsed and refractory or unresponsive to monotherapy treatment with a PD-1 blocking antibody (e.g., nivolumab or pembrolizumab). In specific embodiments, a cancer being treated in accordance with the methods described herein is relapsed and refractory or unresponsive to monotherapy treatment with a PD-L1 blocking antibody (e.g., avelumab).

In specific embodiments, a cancer being treated in accordance with the methods described herein is PD-L1-negative and relapsed. In specific embodiments, a cancer being treated in accordance with the methods described herein has low levels of PD-L1 expression and is relapsed.

In a specific embodiment, a cancer being treated in accordance with the methods described herein is relapsed, PD-L1-negative and refractory or unresponsive to monotherapy treatment with an antagonist of PD-1 or a ligand thereof. In a specific embodiment, a cancer being treated in accordance with the methods described herein is relapsed, PD-L1-negative and refractory or unresponsive to monotherapy treatment with a PD-1 blocking antibody (e.g., nivolumab or pembrolizumab). In specific embodiments, a cancer being treated in accordance with the methods described herein is relapsed, PD-L1-negative and refractory or unresponsive to monotherapy treatment with a PD-L1 blocking antibody (e.g., avelumab).

In specific embodiments, a cancer being treated in accordance with the methods described herein has low levels of PD-L1 expression, and is relapsed and refractory or unresponsive to monotherapy treatment with an antagonist of PD-1 or a ligand thereof. In a specific embodiment, a cancer being treated in accordance with the methods described herein has low levels of PD-L1 expression, and is relapsed and is refractory or unresponsive to monotherapy treatment with a PD-1 blocking antibody (e.g., nivolumab or pembrolizumab). In specific embodiments, a cancer being treated in accordance with the methods described herein has low levels of PD-L1 expression, and is relapsed and is refractory or unresponsive to monotherapy treatment with a PD-L1 blocking antibody (e.g., avelumab).

In specific embodiments, a cancer being treated in accordance with the methods described herein is refractory or unresponsive to monotherapy treatment with an antagonist of PD-1 or a ligand thereof. In a specific embodiment, a cancer being treated in accordance with the methods described herein is refractory or unresponsive to monotherapy treatment with a PD-1 blocking antibody (e.g., nivolumab or pembrolizumab). In specific embodiments, a cancer being treated in accordance with the methods described herein is refractory or unresponsive to monotherapy treatment with a PD-L1 blocking antibody (e.g., avelumab).

In a specific embodiment, the cancer being treated in accordance with the methods described herein is a cancer that is metastatic. In a specific embodiment, the cancer comprises a dermal, subcutaneous, or nodal metastasis. In a specific embodiment, the cancer comprises peritoneal or pleural metastasis. In a specific embodiment, the cancer comprises visceral organ metastasis, such as liver, kidney, spleen, or lung metastasis.

In a specific embodiment, the cancer being treated in accordance with the methods described herein is relapsed/refractory solid tumor types, such as melanoma, sarcoma, squamous cell cancer of the head and neck (SSCHN), breast carcinoma with dermal metastases and other malignancies with accessible dermal/SC/nodal metastases In a specific embodiment, the cancer being treated in accordance with the methods described herein is a cancer that is unresectable. Any method known to the skilled artisan may be utilized to determine if a cancer is unresectable.

5.7.6 Additional Therapies

Additional therapies that can be used in a combination with an NDV described herein or a composition thereof, an oncolysate vaccine, or a whole cell vaccine for the treatment of cancer include, but are not limited to, small molecules, synthetic drugs, peptides (including cyclic peptides), polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules. In a specific embodiment, the additional therapy is a chemotherapeutic agent.

In some embodiments, an NDV described herein or a composition thereof, an oncolysate vaccine, or a whole cell vaccine is used in combination with radiation therapy comprising the use of x-rays, gamma rays and other sources of radiation to destroy cancer cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed inside the body close to cancer cells and/or a tumor mass.

In certain embodiments, an NDV described herein or a composition thereof, an oncolysate vaccine, or a whole cell cancer vaccine is used in combination with adoptive T cell therapy. In a specific embodiment, the T cells utilized in the adoptive T cell therapy are tumor infiltrating lymphocytes that have been isolated from a subject and a particular T cell or clone has been expanded for use thereof. In some embodiments, the T cells utilized in the adoptive T cell therapy are T cells taken from a patient's blood after they have received a cancer vaccine and expanded in vitro before use. In another specific embodiment, the T cells utilized in the adoptive T cell therapy are T cells that have been influenced to potently recognize and attack tumors. In another specific embodiment, the T cells utilized in the adoptive T cell therapy have been genetically modified to express tumor-antigen specific T cell receptor or a chimeric antigen receptor (CAR). In a specific embodiment, the adoptive T cell therapy utilized is analogous to that described in Section 6.2 of International Publication No. WO 2014/158811 and U.S. Patent Application Publication No. 2016/0015760, each of which is incorporated by reference herein in its entirety.

In certain embodiments, an NDV described herein or a composition thereof, an oncolysate vaccine, or a whole cell cancer vaccine is used in combination with a cytokine. In a specific embodiment, an NDV described herein or a composition thereof, an oncolysate vaccine, or a whole cell cancer vaccine is used in combination with interferon (e.g., IFN-γ).

Currently available cancer therapies and their dosages, routes of administration and recommended usage are known in the art and have been described in such literature as the Physician's Desk Reference (67th ed., 2013).

Specific examples of anti-cancer agents that may be used in combination with an NDV described herein or a composition thereof include: hormonal agents (e.g., aromatase inhibitor, selective estrogen receptor modulator (SERM), and estrogen receptor antagonist), chemotherapeutic agents (e.g., microtubule disassembly blocker, antimetabolite, topoisomerase inhibitor, and DNA crosslinker or damaging agent), anti-angiogenic agents (e.g., VEGF antagonist, receptor antagonist, integrin antagonist, vascular targeting agent (VTA)/vascular disrupting agent (VDA)), radiation therapy, and conventional surgery.

Non-limiting examples of hormonal agents that may be used in combination with an NDV described herein or a composition thereof include aromatase inhibitors, SERMs, and estrogen receptor antagonists. Hormonal agents that are aromatase inhibitors may be steroidal or nonsteroidal. Non-limiting examples of nonsteroidal hormonal agents include letrozole, anastrozole, aminoglutethimide, fadrozole, and vorozole. Non-limiting examples of steroidal hormonal agents include aromasin (exemestane), formestane, and testolactone. Non-limiting examples of hormonal agents that are SERMs include tamoxifen (branded/marketed as Nolvadex®), afimoxifene, arzoxifene, bazedoxifene, clomifene, femarelle, lasofoxifene, ormeloxifene, raloxifene, and toremifene. Non-limiting examples of hormonal agents that are estrogen receptor antagonists include fulvestrant. Other hormonal agents include but are not limited to abiraterone and lonaprisan.

Non-limiting examples of chemotherapeutic agents that may be used in combination with an NDV described herein or a composition thereof, an oncolysate vaccine, or a whole cell vaccine include microtubule disasssembly blocker, antimetabolite, topoisomerase inhibitor, and DNA crosslinker or damaging agent. Chemotherapeutic agents that are microtubule disassembly blockers include, but are not limited to, taxenes (e.g., paclitaxel (branded/marketed as TAXOL®), docetaxel, abraxane, larotaxel, ortataxel, and tesetaxel); epothilones (e.g., ixabepilone); and vinca alkaloids (e.g., vinorelbine, vinblastine, vindesine, and vincristine (branded/marketed as ONCOVIN®)).

Chemotherapeutic agents that are antimetabolites include, but are not limited to, folate antimetabolites (e.g., methotrexate, aminopterin, pemetrexed, raltitrexed); purine antimetabolites (e.g., cladribine, clofarabine, fludarabine, mercaptopurine, pentostatin, thioguanine); pyrimidine antimetabolites (e.g., 5-fluorouracil, capecitabine, gemcitabine (GEMZAR®), cytarabine, decitabine, floxuridine, tegafur); and deoxyribonucleotide antimetabolites (e.g., hydroxyurea).

Chemotherapeutic agents that are topoisomerase inhibitors include, but are not limited to, class I (camptotheca) topoisomerase inhibitors (e.g., topotecan (branded/marketed as HYCAMTIN®) irinotecan, rubitecan, and belotecan);

class II (podophyllum) topoisomerase inhibitors (e.g., etoposide or VP-16, and teniposide); anthracyclines (e.g., doxorubicin, epirubicin, Doxil, aclarubicin, amrubicin, daunorubicin, idarubicin, pirarubicin, valrubicin, and zorubicin); and anthracenediones (e.g., mitoxantrone, and pixantrone).

Chemotherapeutic agents that are DNA crosslinkers (or DNA damaging agents) include, but are not limited to, alkylating agents (e.g., cyclophosphamide, mechlorethamine, ifosfamide (branded/marketed as IFEX®), trofosfamide, chlorambucil, melphalan, prednimustine, bendamustine, uramustine, estramustine, carmustine (branded/marketed as BiCNU®), lomustine, semustine, fotemustine, nimustine, ranimustine, streptozocin, busulfan, mannosulfan, treosulfan, carboquone, N,N'N'-triethylenethiophosphoramide, triaziquone, triethylenemelamine); alkylating-like agents (e.g., carboplatin (branded/marketed as PARAPLATIN®), cisplatin, oxaliplatin, nedaplatin, triplatin tetranitrate, satraplatin, picoplatin); nonclassical DNA crosslinkers (e.g., procarbazine, dacarbazine, temozolomide (branded/marketed as TEMODAR®), altretamine, mitobronitol); and intercalating agents (e.g., actinomycin, bleomycin, mitomycin, and plicamycin).

5.7.6.1 Immune Modulators

In specific embodiments, an NDV described herein (e.g., a chimeric NDV) or a composition thereof, an oncolysate vaccine, or a whole cell vaccine are administered to a subject in combination with one or more of the following: any agonist of a co-stimulatory signal of an immune cell (such as, e.g., a T-lymphocyte, NK cell or antigen-presenting cell (e.g., a dendritic cell or macrophage) and/or any antagonist of an inhibitory signal of an immune cell (such as, e.g., a T-lymphocyte, NK cell or antigen-presenting cell (e.g., a dendritic cell or macrophage), known to one of skill in the art.

In specific embodiments, the agonist and/or antagonist is an agonist of a human co-stimulatory signal of an immune cell and/or antagonist of a human inhibitory signal of an immune cell.

In certain embodiments, the agonist of a co-stimulatory signal is an agonist of a co-stimulatory molecule (e.g., co-stimulatory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of co-stimulatory molecules include glucocorticoid-induced tumor necrosis factor receptor (GITR), Inducible T-cell costimulator (ICOS or CD278), OX40 (CD134), CD27, CD28, 4-1BB (CD137), CD40, lymphotoxin alpha (LT alpha), LIGHT (lymphotoxin-like, exhibits inducible expression, and competes with herpes simplex virus glycoprotein D for HVEM, a receptor expressed by T lymphocytes), CD226, cytotoxic and regulatory T cell molecule (CRTAM), death receptor 3 (DR3), lymphotoxin-beta receptor (LTBR), transmembrane activator and CAML interactor (TACI), B cell-activating factor receptor (BAFFR), and B cell maturation protein (BCMA). In specific embodiments, the agonist is an agonist of a human co-stimulatory receptor of an immune cell. In certain embodiments, the agonist of a co-stimulatory receptor is not an agonist of ICOS.

In a specific embodiment, the agonist of a co-stimulatory receptor is an antibody or antigen-binding fragment thereof that specifically binds to the co-stimulatory receptor. Specific examples of co-stimulatory receptors include GITR, ICOS, OX40, CD27, CD28, 4-1BB, CD40, LT alpha, LIGHT, CD226, CRTAM, DR3, LTBR, TACI, BAFFR, and BCMA. In certain specific embodiments, the antibody is a monoclonal antibody. In other specific embodiments, the antibody is an sc-Fv. In other specific embodiments, the antibody is a camelized antibody. In a specific embodiment, the antibody is a bispecific antibody that binds to two receptors on an immune cell. In other embodiments, the bispecific antibody binds to a receptor on an immune cell and to another receptor on a cancer cell. In specific embodiments, the antibody is a human or humanized antibody. In some embodiments, the antibody is expressed as a chimeric protein with NDV F protein or fragment thereof, or NDV HN protein or fragment thereof. See, e.g., U.S. patent application Publication No. 2012/0122185, which is incorporated herein by reference for a description regarding generation of chimeric F or chimeric HN proteins.

In another embodiment, the agonist of a co-stimulatory receptor is a ligand of the co-stimulatory receptor. In certain embodiments, the ligand is fragment of a native ligand. Specific examples of native ligands include ICOSL, B7RP1, CD137L, OX40L, CD70, herpes virus entry mediator (HVEM), CD80, and CD86. The nucleotide sequences encoding native ligands as well as the amino acid sequences of native ligands are known in the art. For example, the nucleotide and amino acid sequences of B7RP1 (otherwise known as ICOSL; GenBank human: NM_015259.4, NP_056074.1 murine: NM_015790.3, NP_056605.1), CD137L(GenBank human: NM_003811.3, NP_003802.1, murine: NM_009404.3, NP_033430.1), OX40L(GenBank human: NM_003326.3, NP_003317.1, murine: NM_009452.2, NP_033478.1), CD70(GenBank human: NM_001252.3, NP_001243.1, murine: NM_011617.2, AAD00274.1), CD80(GenBank human: NM_005191.3, NP_005182.1, murine: NM_009855.2, NP_033985.3), and CD86(GenBank human: NM_005191.3, CAG46642.1, murine: NM_019388.3, NP_062261.3) can be found in GenBank. In other embodiments, the ligand is a derivative of a native ligand. In some embodiments, the ligand is a fusion protein comprising at least a portion of the native ligand or a derivative of the native ligand that specifically binds to the co-stimulatory receptor, and a heterologous amino acid sequence. In specific embodiments, the fusion protein comprises at least a portion of the native ligand or a derivative of the native ligand that specifically binds to the co-stimulatory receptor, and the Fc portion of an immunoglobulin or a fragment thereof. An example of a ligand fusion protein is a 4-1BB ligand fused to Fc portion of immunoglobulin (described by Meseck M et al., J Immunother. 2011 34:175-82).

In some embodiments, the antagonist is an antagonist of an inhibitory molecule (e.g., inhibitory receptor) found on immune cells, such as, e.g., T-lymphocytes (e.g., CD4+ or CD8+ T-lymphocytes), NK cells and/or antigen-presenting cells (e.g., dendritic cells or macrophages). Specific examples of inhibitory molecules include cytotoxic T-lymphocyte-associated antigen 4 (CTLA-4 or CD52), programmed cell death protein 1 (PD-1 or CD279), B and T-lymphocyte attenuator (BTLA), killer cell immunoglobulin-like receptor (KIR), lymphocyte activation gene 3 (LAG3), T-cell membrane protein 3 (TIM3), CD160, adenosine A2a receptor (A2aR), T cell immunoreceptor with immunoglobulin and ITIM domains (TIGIT), leukocyte-associated immunoglobulin-like receptor 1 (LAIR1), and CD160. In specific embodiments, the antagonist is an antagonist of a human inhibitory receptor of an immune cell. In a specific embodiment, the antagonist of an inhibitory molecule is an antagonist of PD-1 or a ligand thereof (such as, e.g., as described in Section 5.5, supra).

In another embodiment, the antagonist of an inhibitory receptor is an antibody (or an antigen-binding fragment) or a soluble receptor that specifically binds to the native ligand for the inhibitory receptor and blocks the native ligand from binding to the inhibitory receptor and transducing an inhibitory signal(s). Specific examples of native ligands for inhibitory receptors include PDL-1, PDL-2, B7-H3, B7-H4, HVEM, Gal9 and adenosine. Specific examples of inhibitory receptors that bind to a native ligand include CTLA-4, PD-1, BTLA, KIR, LAG3, TIM3, and A2aR.

In specific embodiments, the antagonist of an inhibitory receptor is a soluble receptor that specifically binds to the native ligand for the inhibitory receptor and blocks the native ligand from binding to the inhibitory receptor and transducing an inhibitory signal(s). In certain embodiments, the soluble receptor is a fragment of a native inhibitory receptor or a fragment of a derivative of a native inhibitory receptor that specifically binds to native ligand (e.g., the extracellular domain of a native inhibitory receptor or a derivative of an inhibitory receptor). In some embodiments, the soluble receptor is a fusion protein comprising at least a portion of the native inhibitory receptor or a derivative of the native inhibitory receptor (e.g., the extracellular domain of the native inhibitory receptor or a derivative of the native inhibitory receptor), and a heterologous amino acid sequence. In specific embodiments, the fusion protein comprises at least a portion of the native inhibitory receptor or a derivative of the native inhibitory receptor, and the Fc portion of an immunoglobulin or a fragment thereof. An example of a soluble receptor fusion protein is a LAG3-Ig fusion protein (described by Huard B et al., Eur J Immunol. 1995 25:2718-21).

In specific embodiments, the antagonist of an inhibitory receptor is an antibody (or an antigen-binding fragment) that specifically binds to the native ligand for the inhibitory receptor and blocks the native ligand from binding to the inhibitory receptor and transducing an inhibitory signal(s). In certain specific embodiments, the antibody is a monoclonal antibody. In other specific embodiments, the antibody is an scFv. In particular embodiments, the antibody is a human or humanized antibody. A specific example of an antibody to inhibitory ligand is anti-PD-L1 antibody (Iwai Y, et al. PNAS 2002; 99:12293-12297).

In another embodiment, the antagonist of an inhibitory receptor is an antibody (or an antigen-binding fragment) or ligand that binds to the inhibitory receptor, but does not transduce an inhibitory signal(s). Specific examples of inhibitory receptors include CTLA-4, PD-1, BTLA, KIR, LAG3, TIM3, and A2aR. In certain specific embodiments, the antibody is a monoclonal antibody. In other specific embodiments, the antibody is an scFv. In particular embodiments, the antibody is a human or humanized antibody. A specific example of an antibody to inhibitory receptor is anti-CTLA-4 antibody (Leach D R, et al. Science 1996; 271: 1734-1736). Another example of an antibody to inhibitory receptor is anti-PD-1 antibody (Topalian S L, NEJM 2012; 28:3167-75).

In certain embodiments, an antagonist of an inhibitory receptor is an antagonist of CTLA-4, such as, e.g., Ipilimumab or Tremelimumab. In certain embodiments, the antagonist of an inhibitory receptor is an antagonist of PD-1, such as, e.g., MDX-1106 (BMS-936558), MK3475, CT-011, AMP-224, or MDX-1105. In certain embodiments, an antagonist of an inhibitory receptor is an antagonist of LAG3, such as, e.g., IMP321. In certain embodiments, an antagonist of a inhibitory receptor is an antibody (e.g., a monoclonal antibody or an antigen-binding fragment thereof, or scFv) that binds to B7-H3, such as, e.g., MGA271. In specific embodiments, an agonist of a co-stimulatory receptor is anti-CD28 scvFv, ICOSL, CD40L, OX40L, CD137L, GITRL, and/or CD70.

In certain embodiments, an agonist of a co-stimulatory signal of an immune cell induces (e.g., selectively) induces one or more of the signal transduction pathways induced by the binding of a co-stimulatory receptor to its ligand. In specific embodiments, an agonist of a co-stimulatory receptor induces one or more of the signal transduction pathways induced by the binding of the co-stimulatory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to one or more of its ligands in the absence of the agonist. In specific embodiments, an agonist of a co-stimulatory receptor: (i) induces one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not induce, or induces one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In certain embodiments, an agonist of a co-stimulatory signal of an immune cell activates or enhances (e.g., selectively activates or enhances) one or more of the signal transduction pathways induced by the binding of a co-stimulatory receptor to its ligand. In specific embodiments, an agonist of a co-stimulatory receptor activates or enhances one or more of the signal transduction pathways induced by the binding of the co-stimulatory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of co-stimulatory receptor to one or more of its ligands in the absence of the agonist. In specific embodiments, an agonist of a co-stimulatory receptor: (i) an agonist of a co-stimulatory signal activates or enhances one or more of the signal transduction pathways induced by the binding of the co-stimulatory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the co-stimulatory receptor to the particular ligand in the absence of the agonist; and (ii) does not activate or enhance, or activates or enhances one or more of the signal transduction pathways induced by the binding of the co-stimulatory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of the co-stimulatory receptor to such one or more other ligands in the absence of the agonist.

In some embodiments, an antagonist of an inhibitory signal of an immune cell (e.g., selectively) inhibits or reduces one or more of the signal transduction pathways induced by the binding of an inhibitory receptor to its ligand. In specific embodiments, an antagonist of an inhibitory receptor inhibits or reduces one or more of the signal transduction pathways induced by the binding of the inhibitory receptor to one or more of its ligands by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to one or more of its ligands in the absence of the antagonist. In specific embodiments, an antagonist of an inhibitory receptor: (i) inhibits or reduces one or more of the signal transduction pathways induced by the binding of the inhibitory receptor to one particular ligand by at least 25%, 30%, 40%, 50%, 60%, 75%, 80%, 85%, 90%, 95%, 98% or 99%, or in the range of between 25% to 50%, 25% to 75%, 50% to 75%, 50% to 95%, 75% to 95%, or 75% to 100% relative to the one or more signal transduction pathways induced by the binding of the inhibitory receptor to the one particular ligand in the absence of the antagonist; and (ii) does not inhibit or reduce, or inhibits or reduces one or more of the signal transduction pathways induced by the binding of the inhibitory receptor to one or more other ligands by less than 20%, 15%, 10%, 5%, or 2%, or in the range of between 2% to 5%, 2% to 10%, 5% to 10%, 5% to 15%, 5% to 20%, 10% to 15%, or 15% to 20% relative to the one or more signal transduction pathways induced by the binding of inhibitory receptor to such one or more other ligands in the absence of the antagonist.

In specific embodiments, an agonist of a co-stimulatory signal of an immune cell and/or an antagonist of an inhibitory signal of an immune cell induces, activates and/or enhances one or more immune activities, functions or responses. The one or more immune activities, functions or responses can be in the form of, e.g., an antibody response (humoral response) or a cellular immune response, e.g., cytokine secretion (e.g., interferon-gamma), helper activity or cellular cytotoxicity. In one embodiment, expression of an activation marker on immune cells (e.g., CD44, Granzyme, or Ki-67), expression of a co-stimulatory receptor on immune cells (e.g., ICOS, CD28, OX40, or CD27), expression of a ligand for a co-stimulatory receptor (e.g., B7HRP1, CD80, CD86, OX40L, or CD70), cytokine secretion, infiltration of immune cells (e.g., T-lymphocytes, B lymphocytes and/or NK cells) to a tumor, antibody production, effector function, T cell activation, T cell differentiation, T cell proliferation, B cell differentiation, B cell proliferation, and/or NK cell proliferation is induced, activated and/or enhanced following contact with an agonist of a co-stimulatory signal of an immune cell and/or an antagonist of an inhibitory signal of an immune cell. In another embodiment, myeloid-derived suppressor cell (MDSC) tumor infiltration and proliferation, Treg tumor infiltration, activation and proliferation, peripheral blood MDSC and Treg counts are inhibited following contact with an agonist of a co-stimulatory signal of an immune cell and/or an antagonist of an inhibitory signal of an immune cell.

5.8 Biological Assays

In certain embodiments, an assay described in Section 6, infra, is used to characterize/assess, e.g., the production of a chimeric NDV, the expression, function or both of IL-12 expressed by a chimeric NDV, or the efficacy of a method described herein.

5.8.1 In Vitro Viral Assays

Viral assays include those that indirectly measure viral replication (as determined, e.g., by plaque formation) or the production of viral proteins (as determined, e.g., by western blot analysis) or viral RNAs (as determined, e.g., by RT-PCR or northern blot analysis) in cultured cells in vitro using methods which are well known in the art.

Growth of the NDVs described herein can be assessed by any method known in the art or described herein (e.g., in cell culture (e.g., cultures of chicken embryonic kidney cells or cultures of chicken embryonic fibroblasts (CEF)) (see, e.g., Section 6). Viral titer may be determined by inoculating serial dilutions of a NDV described herein into cell cultures (e.g., CEF, MDCK, EFK-2 cells, Vero cells, primary human umbilical vein endothelial cells (HUVEC), H292 human epithelial cell line or HeLa cells), chick embryos, or live animals (e.g., avians). After incubation of the virus for a specified time, the virus is isolated using standard methods. Physical quantitation of the virus titer can be performed using PCR applied to viral supernatants (Quinn & Trevor, 1997; Morgan et al., 1990), hemagglutination assays, tissue culture infectious doses (TCID50) or egg infectious doses (EID50). An exemplary method of assessing viral titer is described in Section 6, below.

Incorporation of nucleotide sequences encoding a heterologous peptide or protein (e.g., a cytokine, a mutated F protein, a mutated V protein, or miRNA target site into the genome of a chimeric NDV described herein can be assessed by any method known in the art or described herein (e.g., in cell culture, an animal model or viral culture in embryonated eggs). For example, viral particles from cell culture of the allantoic fluid of embryonated eggs can be purified by centrifugation through a sucrose cushion and subsequently analyzed for fusion protein expression by Western blotting using methods well known in the art.

Immunofluorescence-based approaches may also be used to detect virus and assess viral growth. Such approaches are well known to those of skill in the art, e.g., fluorescence microscopy and flow cytometry (see Section 6, infra). Methods for flow cytometry, including fluorescence activated cell sorting (FACS), are available (see, e.g., Owens, et al. (1994) Flow Cytometry Principles for Clinical Laboratory Practice, John Wiley and Sons, Hoboken, NJ; Givan (2001) Flow Cytometry, 2nd ed.; Wiley-Liss, Hoboken, NJ; Shapiro (2003) Practical Flow Cytometry, John Wiley and Sons, Hoboken, NJ). Fluorescent reagents suitable for modifying nucleic acids, including nucleic acid primers and probes, polypeptides, and antibodies, for use, e.g., as diagnostic reagents, are available (Molecular Probesy (2003) Catalogue, Molecular Probes, Inc., Eugene, OR; Sigma-Aldrich (2003) Catalogue, St. Louis, MO).

Standard methods of histology of the immune system are described (see, e.g., Muller-Harmelink (ed.) (1986) *Human Thymus: Histopathology and Pathology*, Springer Verlag, New York, NY; Hiatt, et al. (2000) *Color Atlas of Histology*, Lippincott, Williams, and Wilkins, Phila, PA; Louis, et al. (2002) *Basic Histology: Text and Atlas*, McGraw-Hill, New York, NY).

5.8.2 IFN Assays

IFN induction and release by an NDV described herein may be determined using techniques known to one of skill in the art or described herein (see, e.g., Section 6). For example, the amount of IFN induced in cells following infection with an NDV described herein may be determined using an immunoassay (e.g., an ELISA or Western blot assay) to measure IFN expression or to measure the expression of a protein whose expression is induced by IFN. Alternatively, the amount of IFN induced may be measured at the RNA level by assays, such as Northern blots and quantitative RT-PCR, known to one of skill in the art. In specific embodiments, the amount of IFN released may be measured using an ELISPOT assay. (See, e.g., the methods described in Section 6, below). Further, the induction and release of cytokines and/or interferon-stimulated genes may be determined by, e.g., an immunoassay or ELISPOT assay at the protein level and/or quantitative RT-PCR or northern blots at the RNA level. See Section 6, infra, regarding assays to measure cytokine and/or interferon-stimulated gene induction and release.

5.8.3 Activation Marker Assays

Techniques for assessing the expression of activation marker, co-stimulatory molecule, ligand, or inhibitory molecule by immune cells are known to one of skill in the art. For example, the expression of an activation marker, co-stimulatory molecule, ligand, or inhibitory molecule by an immune cell (e.g., T lymphocyte or NK cell) can be assessed by flow cytometry. In a specific embodiment, techniques described in Section 6, infra, are used to assess the expression of an activation marker, co-stimulatory molecule, ligand, or inhibitory molecule by an immune cell.

5.8.4 Immune Cell Infiltration Assays

Techniques for assessing immune cell infiltration are known to one of skill in the art. In a specific embodiment, techniques described in Section 6, infra, are used to assess immune cell infiltration.

5.8.5 Toxicity Studies

In some embodiments, the NDVs described herein or compositions thereof, oncolysate vaccines described herein, whole cell vaccines described herein, or combination therapies described herein are tested for cytotoxicity in mammalian, preferably human, cell lines (see, e.g., the cytotoxicity assay described in Section 6, infra). In certain embodiments, cytotoxicity is assessed in one or more of the following non-limiting examples of cell lines: U937, a human monocyte cell line; primary peripheral blood mononuclear cells (PBMC); Huh7, a human hepatoblastoma cell line; HL60 cells, HT1080, HEK 293T and 293H, MLPC cells, human embryonic kidney cell lines; human melanoma cell lines, such as SkMel2, SkMel-119 and SkMel-197; THP-1, monocytic cells; a HeLa cell line; and neuroblastoma cells lines, such as MC-IXC, SK-N-MC, SK-N-MC, SK-N-DZ, SH-SY5Y, and BE(2)-C. In certain embodiments, cytotoxicity is assessed in various cancer cells. In some embodiments, the ToxLite assay is used to assess cytotoxicity.

Many assays well-known in the art can be used to assess viability of cells or cell lines following infection with an NDV described herein or composition thereof, or treatment with an oncolysate vaccine described herein, a whole cell vaccine described herein, or a combination therapy described herein and, thus, determine the cytotoxicity of the NDV or composition thereof, oncolysate vaccine, whole cell vaccine, or combination therapy. For example, cell proliferation can be assayed by measuring Bromodeoxyuridine (BrdU) incorporation, ($^3$H) thymidine incorporation, by direct cell count, or by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art. For example, protein can be quantitated by known immunodiagnostic methods such as ELISA, Western blotting or immunoprecipitation using antibodies, including commercially available antibodies. mRNA can be quantitated using methods that are well known and routine in the art, for example, using northern analysis, RNase protection, or polymerase chain reaction in connection with reverse transcription. Cell viability can be assessed by using trypan-blue staining or other cell death or viability markers known in the art. In a specific embodiment, the level of cellular ATP is measured to determined cell viability. In preferred embodiments, an NDV described herein or composition thereof, oncolysate vaccine, whole cell vaccine, or combination therapy kills cancer cells but does not kill healthy (i.e., non-cancerous) cells. In one embodiment, an NDV described herein or composition thereof, oncolysate vaccine, whole cell vaccine, or combination therapy preferentially kills cancer cells but does not kill healthy (i.e., non-cancerous) cells.

In specific embodiments, cell viability is measured in three-day and seven-day periods using an assay standard in the art, such as the CellTiter-Glo Assay Kit (Promega) which measures levels of intracellular ATP. A reduction in cellular ATP is indicative of a cytotoxic effect. In another specific embodiment, cell viability can be measured in the neutral red uptake assay. In other embodiments, visual observation for morphological changes may include enlargement, granularity, cells with ragged edges, a filmy appearance, rounding, detachment from the surface of the well, or other changes.

The NDVs described herein or compositions thereof, oncolysate vaccines, whole cell vaccines or combination therapies can be tested for in vivo toxicity in animal models (see, e.g., the animal models described in Section 6, below). For example, animal models, described herein and/or others known in the art, used to test the effects of compounds on cancer can also be used to determine the in vivo toxicity of the NDVs described herein or compositions thereof, oncolysate vaccines, whole cell vaccines, or combination therapies. For example, animals are administered a range of pfu of an NDV described herein (e.g., a chimeric NDV described in Section 5.2, infra). Subsequently, the animals are monitored over time for lethality, weight loss or failure to gain weight, and/or levels of serum markers that may be indicative of tissue damage (e.g., creatine phosphokinase level as an indicator of general tissue damage, level of glutamic oxalic acid transaminase or pyruvic acid transaminase as indicators for possible liver damage). These in vivo assays may also be adapted to test the toxicity of various administration mode and/or regimen in addition to dosages.

The toxicity and/or efficacy of an NDV described herein or a composition thereof, an oncolysate vaccine described herein, a whole cell vaccine described herein, or a combination therapy described herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibits large therapeutic indices are preferred. While therapies that exhibits toxic side effects may be used, care should be taken to design a delivery system that targets such therapies to the site of affected tissue in order to minimize potential damage to noncancerous cells and, thereby, reduce side effects.

The data obtained from the cell culture assays and animal studies can be used in formulating a range of dosage of the therapies for use in subjects. The dosage of such agents lies preferably within a range of circulating concentrations that include the ED50 with little or no toxicity. The dosage may vary within this range depending upon the dosage form employed and the route of administration utilized. For any therapy described herein, the therapeutically effective dose can be estimated initially from cell culture assays. A dose may be formulated in animal models to achieve a circulating plasma concentration range that includes the IC50 (i.e., the concentration of the chimeric NDV that achieves a half-maximal inhibition of symptoms) as determined in cell culture. Such information can be used to more accurately determine useful doses in subjects. Levels in plasma may be measured, for example, by high performance liquid chromatography.

5.8.6 Anti-Cancer Studies

The NDVs described herein or compositions thereof, oncolysate vaccines described herein, whole cell vaccines described herein, or combination therapies described herein can be tested for biological activity using animal models for cancer (see, e.g., Section 6). Such animal model systems include, but are not limited to, rats, mice, chicken, cows, monkeys, pigs, dogs, rabbits, etc. In a specific embodiment, the anti-cancer activity of an NDV described herein or combination therapy is tested in a mouse model system. Such model systems are widely used and well-known to the skilled artisan such as the SCID mouse model or transgenic mice.

The anti-cancer activity of an NDV described herein or a composition thereof, oncolysate vaccine described herein, whole cell vaccine described herein, or a combination therapy described herein can be determined by administering the NDV or composition thereof, oncolysate vaccine, whole cell vaccine, or combination therapy to an animal model and verifying that the NDV or composition thereof, oncolysate vaccine, whole cell vaccine, or combination therapy is effective in reducing the severity of cancer, reducing the symptoms of cancer, reducing cancer metastasis, and/or reducing the size of a tumor in said animal model (see, e.g., Section 6, below). Examples of animal models for cancer in general include, include, but are not limited to, animal models refractory or unresponsive to treatment with an antagonist of PD-1 or a ligand thereof, such as, e.g., the B16F10 mouse model (e.g., as described in Section 6), and spontaneously occurring tumors of companion animals (see, e.g., Vail & MacEwen, 2000, Cancer Invest 18(8):781-92). Examples of animal models for lung cancer include, but are not limited to, lung cancer animal models described by Zhang & Roth (1994, In-vivo 8(5):755-69) and a transgenic mouse model with disrupted p53 function (see, e.g.e.g., Morris et al., 1998, J La State Med Soc 150(4): 179-85). An example of an animal model for breast cancer includes, but is not limited to, a transgenic mouse that over expresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res. 61(6):2395-8). Examples of animal models for pancreatic cancer include, but are not limited to, a metastatic model of PancO2 murine pancreatic adenocarcinoma (see, e.g., Wang et al., 2001, Int. J. Pancreatol. 29(1):37-46) and nu-nu mice generated in subcutaneous pancreatic tumors (see, e.g., Ghaneh et al., 2001, Gene Ther. 8(3):199-208). Examples of animal models for non-Hodgkin lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc. Natl. Acad. Sci. USA 95(23):13853-8). An example of an animal model for esophageal cancer includes, but is not limited to, a mouse transgenic for the human papillomavirus type 16 E7 oncogene (see, e.g., Herber et al., 1996, J. Virol. 70(3):1873-81). Examples of animal models for colorectal carcinomas include, but are not limited to, Apc mouse models (see, e.g., Fodde & Smits, 2001, Trends Mol Med 7(8):369 73 and Kuraguchi et al., 2000) and ID8 ovarian cancer model. In a specific embodiment, the animal models for cancer described in Section 6, infra, are used to assess efficacy of an NDV or composition thereof, an oncolysate, a whole cell vaccine, or a combination therapy.

5.8.7 Expression of IL-12

Assays for testing the expression of IL-12 or a derivative thereof in cells infected with a chimeric NDV comprising a packaged genome comprising a transgene encoding IL-12 or a derivative thereof may be conducted using any assay known in the art, such as, e.g., western blot, immunofluorescence, and ELISA, or any assay described herein (see, e.g., Section 6).

In a specific aspect, ELISA is utilized to detect expression of IL-12 or a derivative thereof in cells infected with a chimeric NDV comprising a packaged genome comprising a transgene encoding IL-12 or a derivative thereof. For example, cells (e.g., Vero cells) are seeded in a tissue culture plate (e.g., a 96-well plate) at the appropriate concentration (e.g., $1\times10^4$ vero cells/well of a 96-well plate) in serum free medium (e.g., OptiPRO serum free medium (Gibco, Cat. No. 12309-019) supplemented with 2% glutamine (e.g., Corning, Cat. No. 25-005-CI) and incubated under standard conditions (e.g., 37±2° C., 5±2% $CO_2$) for a period of time (e.g., approximately 24 hours). Test samples of the chimeric NDV are pre-diluted in reduced serum medium (e.g., Opti-MEM (1×) reduced serum medium (Gibco, Cat. No. 31985-070)) to a desired titer (e.g., $2\times10^4$ pfu/mL). A volume of the pre-diluted test sample (e.g., 300 μL) is added to, e.g., a row of, a 0.5 mL Assay Block (Costar, Cat. No. 3956) and serial dilutions (e.g., 2-fold serial dilutions) are performed across rows by transferring a volume of sample into a volume of reduced serum medium (e.g., 150 μL of sample into 150 μL Opti-MEM (1×) reduced serum medium). Two replicates per sample may be prepared. The tissue culture plates (e.g., 96-well plates) containing the cells (e.g., Vero cells) are removed from the incubator a period of time after seeding (e.g., approximately 24 hours post seeding) and spent medium is removed from the plate. The cells are inoculated with a volume (e.g., 100 μL) of the serially diluted test samples and incubated under standard conditions (e.g., 37° C., 5% $CO_2$). After a period of time of incubation (e.g., approximately 24 hours), a volume of the supernatant fluid (e.g., 90 μL) is removed from the infection plates, transferred to an ELISA plate pre-coated with anti-human IL-12 p70 capture antibody (e.g., Affymetrix eBioscience, Cat. No. 14-7128-68) and incubated for a period of time (e.g., two hours at room temperature). The captured huIL-12 is detected with anti-human IL-12 p70 detection antibody (e.g., Affymetrix eBioscience, Cat. No. 33-8261-68A) and, e.g., Avidin-HRP and visualized with, e.g., a HRP substrate TMB following vendor's procedure (Affymetrix eBioscience, Human IL-12 p70 ELISA Ready-SET-Go! ELISA kit, Cat. No. 88-7126-88). In a specific embodiment, human IL-12 is quantitied using an ELISA such as described in Section 6.3.1.19, infra.

In one embodiment, an IL-12 or a derivative thereof encoded by a packaged genome of a chimeric NDV described herein is assayed for proper folding and functionality by testing its ability to bind specifically to an anti-IL-12 antibody using any assay for antibody-antigen interaction known in the art. In another embodiment, an IL-12 or a derivative thereof encoded by a packaged genome of a chimeric NDV described herein is assayed for proper folding by determination of the structure or conformation of the IL-12 or derivative thereof using any method known in the art such as, e.g., NMR, X-ray crystallographic methods, or secondary structure prediction methods, e.g., circular dichroism.

Assays for testing the functionality of IL-12 or a derivative thereof in cells infected with a chimeric NDV comprising a packaged genome comprising a transgene encoding IL-12 or a derivative thereof may be conducted using any assay known in the art, such as, e.g., PathHunter® Bioassay Detection Kit (DiscoverX, Cat #93-0933). For example, to evaluate the functionality of hulL-12 produced from a chimeric NDV comprising a packaged genome comprising a transgene encoding hulL-12 or a derivative thereof in cells infected with the chimeric NDV, cells (e.g., vero cells) are seeded in plates (e.g., $5\times10^5$ vero cells/well of a 6-well tissue culture plate) and incubated for a period of time, e.g., 24 hours, under standard conditions known to the skilled artisan for the cell type (e.g., 37° C., 5% $CO_2$). Test samples of the chimeric NDV are diluted (e.g., to $1\times10^6$ pfu/mL) in reduced serum medium (e.g., Opti-MEM (1×) reduced serum medium) and various amounts of the diluted samples are transferred to the cell plate to target MOI between 0.03-1. Medium is then then added to each well to a final volume appropriate for the size of the tissue culture plate (e.g., 2 mL per well of a 6-well tissue culture plate). The infected cell plate is incubated at 37° C., 5% $CO_2$ for 24 hours and the function of the produced hulL-12 or derivative thereof in the supernatant is assayed using the PathHunter® Bioassay Detection kit (DiscoverX, Cat #93-0933) according to the manufacturer's instructions. Briefly, U2OS IL12RB1/IL12RB2 cells are seeded in a 96-well cell plate (e.g., at $5\times10^3$ cells/well) and are incubated under standard conditions (e.g., 37° C., 5% $CO_2$) for a period of time (e.g., 4-6 hours). A volume of supernatant fluids (e.g., 60 μL) from each plate of the chimeric NDV-infected plate is transferred to a second column of a 96-well sample dilution plate and a 3-fold serial dilution in AssayComplete Cell Plating Reagent (DiscoverX, 93-0563R5A) is carried out. A portion (e.g., 10 μL) of each diluted supernatant is transferred to the U2OS cell plate and the plate is incubated under standard conditions (e.g., at 37° C., 5% $CO_2$) for a period of time (e.g., 16-20 hours). Detection Reagent 1 (e.g., 10 μL) is added to each well and the plate is incubated for a period of time (e.g., 15 minutes) at room temperature. Detection Reagent 2 (e.g., 40 μL) is added to each well and the plate is further incubated for a period of time (e.g., 60 minutes) at room temperature. The chemiluminescence signal is detected using a plate reader (e.g., a SpectraMax M5 plate reader). In a specific embodiment, the functionality of human IL-12 is assessed using an assay described in Section 6.3.1.18, infra.

5.9 Kits

In one aspect, provided herein is a pharmaceutical pack or kit comprising one or more containers filled with one or more of the ingredients of a composition (e.g., a pharmaceutical compositions) described herein. In a specific embodiment, provided herein is a pharmaceutical pack or kit comprising a first container and a second container, wherein the first container comprises an antagonist of PD-1 or a ligand thereof as described herein, or a pharmaceutical composition comprising the antagonist, and the second container comprises a chimeric NDV comprising a packaged genome comprising a transgene encoding IL-12 (e.g., human IL-12) or a derivative thereof, or a pharmaceutical composition comprising the chimeric NDV. In another specific embodiment, provided herein is a pharmaceutical pack or kit comprising a first container and a second container, wherein the first container comprises a PD-1 blocking antibody as described herein, or a pharmaceutical composition comprising the PD-1 blocking antibody, and the second container comprises a chimeric NDV comprising a packaged genome comprising a transgene encoding IL-12 (e.g., human IL-12) or a derivative thereof, or a pharmaceutical composition comprising the chimeric NDV. In one embodiment, the PD-1 blocking antibody is nivolumab. In a preferred embodiment, the PD-1 blocking antibody is pembrolizumab. In another specific embodiment, provided herein is a pharmaceutical pack or kit comprising a first container and a second container, wherein the first container comprises a PD-L1 blocking antibody as described herein, or a pharmaceutical composition comprising the PD-L1 blocking antibody, and the second container comprises a chimeric NDV comprising a packaged genome comprising a transgene encoding IL-12 (e.g., human IL-12) or a derivative thereof, or a pharmaceutical composition comprising the chimeric NDV. In certain embodiments, the PD-L1 blocking antibody is duralumab or avelumab. Optionally associated with such container(s) can be a notice in the form prescribed by a governmental agency regulating the manufacture, use or sale of pharmaceuticals or biological products, which notice reflects approval by the agency of manufacture, use or sale for human administration.

5.10 Sequences

TABLE 1

Exemplary p40 sequences (amino acid)

| Name | Sequence | SEQ ID NO. |
|---|---|---|
| Version 1: human IL12B (p40 subunit) with signal peptide (bold) | **MGHQQLVISWFSLVFLASPLVA**IWELKKDVYVVELDWY PDAPGEMVVLTCDTPEEDGITWTLDQSSEVLGSGKTLTIQ VKEFGDAGQYTCHKGGEVLSHSLLLLHKKEDGIWSTDILK DQKEPKNKTFLRCEAKNYSGRFTCWWLTTISTDLTFSVKS SRGSSDPQGVTCGAATLSAERVRGDNKEYEYSVECQEDS | 23 |

TABLE 1-continued

| Exemplary p40 sequences (amino acid) | | |
|---|---|---|
| Name | Sequence | SEQ ID NO. |
| | ACPAAEESLPIEVMVDAVHKLKYENYTSSFFIRDIIKPDPPK NLQLKPLKNSRQVEVSWEYPDTWSTPHSYFSLTFCVQVQ GKSKREKKDRVFTDKTSATVICRKNASISVRAQDRYYSSS WSEWASVPCS | |
| Version 1/Version 2.1/Version 3: human IL12B (p40 subunit) without signal peptide | IWELKKDVYVVELDWYPDAPGEMVVLTCDTPEEDGITWT LDQSSEVLGSGKTLTIQVKEFGDAGQYTCHKGGEVLSHSL LLLHKKEDGIWSTDILKDQKEPKNKTFLRCEAKNYSGRFT CWWLTTISTDLTFSVKSSRGSSDPQGVTCGAATLSAERVR GDNKEYEYSVECQEDSACPAAEESLPIEVMVDAVHKLKY ENYTSSFFIRDIIKPDPPKNLQLKPLKNSRQVEVSWEYPDT WSTPHSYFSLTFCVQVQGKSKREKKDRVFTDKTSATVICR KNASISVRAQDRYYSSSWSEWASVPCS | 38 |
| Version 2.1/Version 3: human IL12B (p40 subunit) with signal peptide (bold) | **MCHQQLVISWFSLVFLASPLVA**IWELKKDVYVVELDWY PDAPGEMVVLTCDTPEEDGITWTLDQSSEVLGSGKTLTIQ VKEFGDAGQYTCHKGGEVLSHSLLLLHKKEDGIWSTDILK DQKEPKNKTFLRCEAKNYSGRFTCWWLTTISTDLTFSVKS SRGSSDPQGVTCGAATLSAERVRGDNKEYEYSVECQEDS ACPAAEESLPIEVMVDAVHKLKYENYTSSFFIRDIIKPDPPK NLQLKPLKNSRQVEVSWEYPDTWSTPHSYFSLTFCVQVQ GKSKREKKDRVFTDKTSATVICRKNASISVRAQDRYYSSS WSEWASVPCS | 40 |

TABLE 2

| Exemplary p40 sequences (nucleic acid) | | |
|---|---|---|
| Name | Sequence | SEQ ID NO. |
| Version 1: nucleic acid sequence encoding human IL12B (p40 subunit) with signal peptide (exemplary nucleic acid sequence encoding SEQ ID NO: 23) | ATGGGTCACCAGCAGTTGGTCATCTCTTGGTTTTCCCTG GTTTTTCTGGCATCTCCCCTCGTGGCCATATGGGAACTG AAGAAAGATGTTTATGTCGTAGAATTGGATTGGTATCC GGATGCCCCTGGAGAAATGGTGGTCCTCACCTGTGACA CCCCTGAAGAAGATGGTATCACCTGGACCTTGGACCAG AGCAGTGAGGTCTTAGGCTCTGGCAAAACCCTGACCAT CCAAGTCAAAGAGTTTGGAGATGCTGGCCAGTACACCT GTCACAAAGGAGGCGAGGTTCTAAGCCATTCGCTCCTG CTGCTTCACAAAAAGGAAGATGGAATTTGGTCCACTGA TATTTTAAAGGACCAGAAAGAACCCAAAAATAAGACCT TTCTAAGATGCGAGGCCAAGAATTATTCTGGACGTTTCA CCTGCTGGTGGCTGACGACAATCAGTACTGATTTGACAT TCAGTGTCAAAAGCAGCAGAGGCTCTTCTGACCCCCAA GGGGTGACGTGCGGAGCTGCTACACTCTCTGCAGAGAG AGTCAGAGGGGACAACAAGGAGTATGAGTACTCAGTG GAGTGCCAGGAGGACAGTGCCTGCCCAGCTGCTGAGGA GAGTCTGCCCATTGAGGTCATGGTGGATGCCGTTCACA AGCTCAAGTATGAAAACTACACCAGCAGCTTCTTCATC AGGGACATCATCAAACCTGACCCACCCAAGAACTTGCA GCTGAAGCCATTAAAGAATTCTCGGCAGGTGGAGGTCA GCTGGGAGTACCCTGACACCTGGAGTACTCCACATTCCT ACTTCTCCCTGACATTCTGCGTTCAGGTCCAGGGCAAGA GCAAGAGAGAAAAGAAAGATAGAGTCTTCACGGACAA GACCTCAGCCACGGTCATCTGCCGCAAAAATGCCAGCA TTAGCGTGCGGGCCCAGGACCGCTACTATAGCTCATCTT GGAGCGAATGGGCATCTGTGCCCTGCAGT | 27 |
| Version 1/Version 3: nucleic acid sequence encoding human IL12B (p40 subunit) without signal peptide (exemplary nucleic acid sequence encoding SEQ ID NO: 38) | ATATGGGAACTGAAGAAAGATGTTTATGTCGTAGAATT GGATTGGTATCCGGATGCCCCTGGAGAAATGGTGGTCC TCACCTGTGACACCCCTGAAGAAGATGGTATCACCTGG ACCTTGGACCAGAGCAGTGAGGTCTTAGGCTCTGGCAA AACCCTGACCATCCAAGTCAAAGAGTTTGGAGATGCTG GCCAGTACACCTGTCACAAAGGAGGCGAGGTTCTAAGC CATTCGCTCCTGCTGCTTCACAAAAAGGAAGATGGAAT TTGGTCCACTGATATTTTAAAGGACCAGAAAGAACCCA AAAATAAGACCTTTCTAAGATGCGAGGCCAAGAATTAT TCTGGACGTTTCACCTGCTGGTGGCTGACGACAATCAGT ACTGATTTGACATTCAGTGTCAAAAGCAGCAGAGGCTC TTCTGACCCCCAAGGGGTGACGTGCGGAGCTGCTACAC TCTCTGCAGAGAGAGTCAGAGGGGACAACAAGGAGTAT | 57 |

TABLE 2-continued

Exemplary p40 sequences (nucleic acid)

| Name | Sequence | SEQ ID NO. |
| --- | --- | --- |
| | GAGTACTCAGTGGAGTGCCAGGAGGACAGTGCCTGCCC<br>AGCTGCTGAGGAGAGTCTGCCCATTGAGGTCATGGTGG<br>ATGCCGTTCACAAGCTCAAGTATGAAAACTACACCAGC<br>AGCTTCTTCATCAGGGACATCATCAAACCTGACCCACCC<br>AAGAACTTGCAGCTGAAGCCATTAAAGAATTCTCGGCA<br>GGTGGAGGTCAGCTGGGAGTACCCTGACACCTGGAGTA<br>CTCCACATTCCTACTTCTCCCTGACATTCTGCGTTCAGG<br>TCCAGGGCAAGAGCAAGAGAGAAAAGAAAGATAGAGT<br>CTTCACGGACAAGACCTCAGCCACGGTCATCTGCCGCA<br>AAAATGCCAGCATTAGCGTGCGGGCCCAGGACCGCTAC<br>TATAGCTCATCTTGGAGCGAATGGGCATCTGTGCCCTGC<br>AGT | |
| Version 2.1: codon-optimized nucleic acid sequence encoding human IL12B (p40 subunit) with signal peptide (exemplary codon-optimized nucleic acid sequence encoding SEQ ID NO: 40) | ATGTGCCATCAGCAGCTGGTCATCTCATGGTTCTCCCTG<br>GTGTTTCTGGCCTCACCTCTGGTCGCAATCTGGGAACTG<br>AAAAAGGATGTGTACGTGGTGGAGCTGGACTGGTATCC<br>CGATGCCCCTGGCGAGATGGTGGTGCTGACCTGCGACA<br>CACCCGAGGAGGATGGCATCACCTGGACACTGGATCAG<br>AGCTCCGAGGTGCTGGGAAGCGGCAAGACCCTGACAAT<br>CCAGGTGAAGGAGTTCGGCGACGCCGGCCAGTACACCT<br>GTCACAAGGGAGGAGAGGTGCTGAGCCACTCCCTGCTG<br>CTGCTGCACAAGAAGGAGGATGGCATCTGGTCCACAGA<br>CATCCTGAAGGATCAGAAGGAGCCAAAGAACAAGACC<br>TTCCTGCGGTGCGAGGCCAAGAATTATAGCGGCCGGTT<br>CACCTGTTGGTGGCTGACCACAATCTCCACCGATCTGAC<br>ATTTTCTGTGAAGTCTAGCAGGGGATCCTCTGACCCACA<br>GGGAGTGACATGCGGAGCAGCCACCCTGAGCGCCGAG<br>AGGGTGCGCGGCGATAACAAGGAGTACGAGTATTCCGT<br>GGAGTGCCAGGAGGACTCTGCCTGTCCAGCAGCAGAGG<br>AGTCCCTGCCTATCGAAGTGATGGTGGATGCCGTGCAC<br>AAGCTGAAGTACGAGAATTATACCAGCTCCTTCTTTATC<br>CGGGACATCATCAAGCCCGATCCCCCTAAGAACCTGCA<br>GCTGAAGCCTCTGAAGAATAGCAGACAGGTGGAGGTGT<br>CCTGGGAGTACCCTGACACCTGGAGCACACCACACTCC<br>TATTTCTCTCTGACCTTTTGCGTGCAGGTGCAGGGCAAG<br>TCCAAGCGGGAGAAGAAGGACAGAGTGTTCACCGATA<br>AGACATCTGCCACCGTGATCTGTAGAAAGAACGCCTCT<br>ATCAGCGTGAGGGCCCAGGACCGCTACTATTCTAGCTC<br>CTGGTCCGAGTGGGCCTCTGTGCCTTGCAGC | 54 |
| Version 2.1: nucleic acid sequence encoding human IL12B (p40 subunit) without signal peptide (exemplary nucleic acid sequence encoding SEQ ID NO: 38) | atctgggaactgaaaaaggatgtgtacgtggtggagctggactggtatcccgatgcccctgg<br>cgagatggtggtgctgacctgcgacacacccgaggaggatggcatcacctggacactgga<br>tcagagctccgaggtgctgggaagcggcaagaccctgacaatccaggtgaaggagttcgg<br>cgacgccggccagtacacctgtcacaagggaggagaggtgctgagccactccctgctgct<br>gctgcacaagaaggaggatggcatctggtccacagacatcctgaaggatcagaaggagcc<br>aaagaacaagaccttcctgcggtgcgaggccaagaattatagcggccggttcacctgttggt<br>ggctgaccacaatctccaccgatctgacattttctgtgaagtctagcaggggatcctctgacc<br>cacagggagtgacatgcggagcagccaccctgagcgccgagagggtgcgcggcgataa<br>caaggagtacgagtattccgtggagtgccaggaggactctgcctgtccagcagcagagga<br>gtccctgcctatcgaagtgatggtggatgccgtgcacaagctgaagtacgagaattatacca<br>gctccttctttatccgggacatcatcaagcccgatccccctaagaacctgcagctgaagcctc<br>tgaagaatagcagacaggtggaggtgtcctgggagtaccctgacacctggagcacaccac<br>actcctatttctctctgaccttttgcgtgcaggtgcagggcaagtccaagcgggagaagaag<br>gacagagtgttcaccgataagacatctgccaccgtgatctgtagaaagaacgcctctatcag<br>cgtgagggcccaggaccgctactattctagctcctggtccgagtgggcctctgtgccttgca<br>gc | 59 |
| Version 3: (non-codon-optimized) nucleic acid sequence encoding human IL12B (p40 subunit) with signal peptide (exemplary non-codon-optimized nucleic acid sequence encoding SEQ ID NO: 40) | atgtgtcaccagcagttggtcatctcttggttttccctggtttttctggcatctcccctcgtggcca<br>tatgggaactgaagaaagatgtttatgtcgtagaattggattggtatccggatgcccctggag<br>aaatggtggtcctcacctgtgacacccctgaagaagatggtatcacctggaccttggaccag<br>agcagtgaggtcttaggctctggcaaaaccctgaccatccaagtcaaagagtttggagatgc<br>tggccagtacacctgtcacaaaggaggcgaggttctaagccattcgctcctgctgcttcaca<br>aaaaggaagatggaatttggtccactgatattttaaaggaccagaaagaacccaaaaataag<br>acctttctaagatgcgaggccaagaattattctggacgtttcacctgctggtggctgacgaca<br>atcagtactgatttgacattcagtgtcaaaagcagcagaggctcttctgacccccaaggggtg<br>acgtgcggagctgctacactctctgcagagagagtcagaggggacaacaaggagtatgag<br>tactcagtggagtgccaggaggacagtgcctgcccagctgctgaggagagtctgcccattg<br>aggtcatggtggatgccgttcacaagctcaagtatgaaaactacaccagcagcttcttcatca<br>gggacatcatcaaacctgacccacccaagaacttgcagctgaagccattaaagaattctcgg<br>caggtggaggtcagctgggagtaccctgacacctggagtactccacattcctacttctccctg<br>acattctgcgttcaggtccagggcaagagcaagagagaaaagaaagatagagtcttcacgg<br>acaagacctcagccacggtcatctgccgcaaaaatgccagcattagcgtgcgggcccagg<br>accgctactatagctcatcttggagcgaatgggcatctgtgccctgcagt | 64 |

TABLE 3

| Exemplary p35 sequences (amino acid) | | |
|---|---|---|
| Name | Sequence | SEQ ID NO. |
| Version 1: human IL12A (p35 subunit) | RNLPVATPDPGMFPCLHHSQNLLRAVSNMLQKARQTLEF YPCTSEEIDHEDITKDKTSTVEACLPLELTKNESCLNSRETS FITNGSCLASRKTSFMMALCLSSIYEDSKMYQVEFKTMNA KLLMDPKRQIFLDQNMLAVIDELMQALNFNSETVPQKSSL EEPDFYKTKIKLCILLHAFRIRAVTIDRVMSYLNAS | 25 |
| Version 2.1/Version 3: human IL12A (p35 subunit) | RNLPVATPDPGMFPCLHHSQNLLRAVSNMLQKARQTLEF YPCTSEEIDHEDITKDKTSTVEACLPLELTKNESCLNSRETS FITNGSCLASRKTSFMMALCLSSIYEDLKMYQVEFKTMNA KLLMDPKRQIFLDQNMLAVIDELMQALNFNSETVPQKSSL EEPDFYKTKIKLCILLHAFRIRAVTIDRVMSYLNAS | 41 |

TABLE 4

| Exemplary p35 sequences (nucleic acid) | | |
|---|---|---|
| Name | Sequence | SEQ ID NO. |
| Version 1: nucleic acid sequence encoding human IL12A (p35 subunit) (exemplary nucleic acid sequence encoding SEQ ID NO: 25) | agaaacctccccgtggccactccagacccaggaatgttcccatgccttcaccactcccaaaa cctgctgagggccgtcagcaacatgctccagaaggccagacaaactctagaattttaccctt gcacttctgaagagattgatcatgaagatatcacaaaagataaaaccagcacagtggaggc ctgtttaccattggaattaaccaagaatgagagttgcctaaattccagagagacctctttcataa ctaatgggagttgcctggcctccagaaagacctcttttatgatggccctgtgccttagtagtatt tatgaagactcgaagatgtaccaggtggagttcaagaccatgaatgcaaagcttctgatggat cctaagaggcagatctttctagatcaaaacatgctggcagttattgatgagctgatgcaggcc ctgaatttcaacagtgagactgtgccacaaaaatcctcccttgaagaaccggatttttataaaa ctaaaatcaagctctgcatacttcttcatgctttcagaattcgggcagtgactattgatagagtg atgagctatctgaatgcttcctaa | 29 |
| Version 2.1: codon-optimized nucleic acid sequence encoding human IL12A (p35 subunit) (exemplary codon-optimized nucleic acid sequence encoding SEQ ID NO: 41) | aggaatctgccagtggcaacccctgacccaggcatgttcccctgcctgcaccacagccaga acctgctgagggccgtgtccaatatgctgcagaaggcccgccagacactggagttttaccct tgtaccagcgaggagatcgaccacgaggacatcacaaaggataagacctccacagtggag gcctgcctgccactggagctgaccaagaacgagtcctgtctgaacagccgggagacaagc ttcatcaccaacggctcctgcctggcctctagaaagacaagctttatgatggccctgtgcctgt ctagcatctacgaggacctgaagatgtatcaggtggagttcaagaccatgaacgccaagct gctgatggaccccaagaggcagatctttctggatcagaatatgctggccgtgatcgacgagc tgatgcaggccctgaacttcaatagcgagacagtgcctcagaagtcctctctggaggagcc agatttctacaagaccaagatcaagctgtgcatcctgctgcacgcctttcggatcagagccgt gacaatcgaccgcgtgatgtcctatctgaatgcttcctaa | 55 |
| Version 3: non-codon-optimized nucleic acid sequence encoding human IL12A (p35 subunit) (exemplary non-codon-optimized nucleic acid sequence encoding SEQ ID NO: 41) | agaaacctccccgtggccactccagacccaggaatgttcccatgccttcaccactcccaaaa cctgctgagggccgtcagcaacatgctccagaaggccagacaaactctagaattttaccctt gcacttctgaagagattgatcatgaagatatcacaaaagataaaaccagcacagtggaggc ctgtttaccattggaattaaccaagaatgagagttgcctaaattccagagagacctctttcataa ctaatgggagttgcctggcctccagaaagacctcttttatgatggccctgtgccttagtagtatt tatgaagacttgaagatgtaccaggtggagttcaagaccatgaatgcaaagcttctgatggat cctaagaggcagatctttctagatcaaaacatgctggcagttattgatgagctgatgcaggcc ctgaatttcaacagtgagactgtgccacaaaaatcctcccttgaagaaccggatttttataaaa ctaaaatcaagctctgcatacttcttcatgctttcagaattcgggcagtgactattgatagagtg atgagctatctgaatgcttcctaa | 65 |

TABLE 5

Exemplary linker sequences (amino acid)

| Name | Sequence | SEQ ID NO. |
|---|---|---|
| GS Linker | GGGGGGS | 24 |
| Elastin-like polypeptide linker | VPGXG, wherein X is any amino acid except proline | 44 |
| Elastin-like polypeptide linker (multimerized) | $VPGX_1GVPGX_2G$, wherein $X_1$ is any amino acid except proline and $X_2$ is any amino acid except proline | 45 |
| $G_4S$ linker | GGGGS | 46 |
| $(G_4S)_2$ linker | GGGGSGGGGS | 47 |

TABLE 5-continued

Exemplary linker sequences (amino acid)

| Name | Sequence | SEQ ID NO. |
|---|---|---|
| $(G_4S)_3$ linker | GGGGSGGGGSGGGGS | 48 |
| $(G_4S)_4$ linker | GGGGSGGGGSGGGGSGGGGS | 49 |

TABLE 6

Exemplary linker sequences (nucleic acid)

| Name | Sequence | SEQ ID NO. |
|---|---|---|
| Exemplary nucleic acid sequence encoding GS Linker of SEQ ID NO: 24 | GGTGGCGGTGGCGGCGGATCT | 28 |

TABLE 7

Exemplary IL-12 transgene sequences (amino acid)

| Name | Sequence | SEQ ID NO. |
|---|---|---|
| Version 1: Human IL12 transgene (Signal peptide-IL12B (P40 Subunit)-GS Linker-IL12A (P35 Subunit)) | **MGHQQLVISWFSLVFLASPLVA**IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCS**GGGGGGS***RNLPVATPDPGMFPCLHHSQNLLRAVSNMLQKARQTLEFYPCTSEEIDHEDITKDKTSTVEACLPLELTKNESCLNSRETSFITNGSCLASRKTSFMMALCLSSIYEDSKMYQVEFKTMNAKLLMDPKRQIFLDQNMLAVIDELMQALNFNSETVPQKSSLEEPDFYKTKIKLCILLHAFRIRAVTIDRVMSYLNAS* | 22 |
| Version 1: Human IL12 transgene (IL12B (P40 Subunit)-GS Linker-IL12A (P35 Subunit)) | IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCS**GGGGGGS***RNLPVATPDPGMFPCLHHSQNLLRAVSNMLQKARQTLEFYPCTSEEIDHEDITKDKTSTVEACLPLELTKNESCLNSRETSFITNGSCLASRKTSFMMALCLSSIYEDSKMYQVEFKTMNAKLLMDPKRQIFLDQNMLAVIDELMQALNFNSETVPQKSSLEEPDFYKTKIKLCILLHAFRIRAVTIDRVMSYLNAS* | 39 |
| Version 2.1/Version 3: Human IL12 transgene (Signal peptide-IL12B (P40 Subunit)-GS Linker-IL12A (P35 Subunit)) | **MCHQQLVISWFSLVFLASPLVA**IWELKKDVYVVELDWYPDAPGEMVVLTCDTPEEDGITWTLDQSSEVLGSGKTLTIQVKEFGDAGQYTCHKGGEVLSHSLLLLHKKEDGIWSTDILKDQKEPKNKTFLRCEAKNYSGRFTCWWLTTISTDLTFSVKSSRGSSDPQGVTCGAATLSAERVRGDNKEYEYSVECQEDSACPAAEESLPIEVMVDAVHKLKYENYTSSFFIRDIIKPDPPKNLQLKPLKNSRQVEVSWEYPDTWSTPHSYFSLTFCVQVQGKSKREKKDRVFTDKTSATVICRKNASISVRAQDRYYSSSWSEWASVPCS**GGGGGGS***RNLPVATPDPGMFPCLHHSQNLLRAVSNMLQKARQTLEFYPCTSEEIDHEDITKDKTSTVEACLPLELTKNESCLNSRETSFITNGSCLASRKTSFMMALCLSSIYEDL* | 42 |

TABLE 7-continued

| Exemplary IL-12 transgene sequences (amino acid) | | |
|---|---|---|
| Name | Sequence | SEQ ID NO. |
| | *KMYQVEFKTMNAKLLMDPKRQIFLDQNMLAVIDELMQALNF*<br>*NSETVPQKSSLEEPDFYKTKIKLCILLHAFRIRAVTIDRVMSYLN*<br>*AS* | |
| Version 2.1/Version 3: Human IL12 transgene (IL12B (P40 Subunit)-GS Linker-IL12A (P35 Subunit)) | IWELKKDVYVVELDWYPDAPGEMVVLTCDTPEEDGITWT<br>LDQSSEVLGSGKTLTIQVKEFGDAGQYTCHKGGEVLSHSL<br>LLLHKKEDGIWSTDILKDQKEPKNKTFLRCEAKNYSGRFT<br>CWWLTTISTDLTFSVKSSRGSSDPQGVTCGAATLSAERVR<br>GDNKEYEYSVECQEDSACPAAEESLPIEVMVDAVHKLKY<br>ENYTSSFFIRDIIKPDPPKNLQLKPLKNSRQVEVSWEYPDT<br>WSTPHSYFSLTFCVQVQGKSKREKKDRVFTDKTSATVICR<br>KNASISVRAQDRYYSSSWSEWASVPCS**GGGGGGS***RNLPV*<br>*ATPDPGMFPCLHHSQNLLRAVSNMLQKARQTLEFYPCTSEEI*<br>*DHEDITKDKTSTVEACLPLELTKNESCLNSRETSFITNGSCLAS*<br>*RKTSFMMALCLSSIYEDLKMYQVEFKTMNAKLLMDPKRQIFL*<br>*DQNMLAVIDELMQALNFNSETVPQKSSLEEPDFYKTKIKLCIL*<br>*LHAFRIRAVTIDRVMSYLNAS* | 43 |

TABLE 8

| Exemplary IL-12 transgene sequences (nucleic acid) | | |
|---|---|---|
| Name | Sequence | SEQ ID NO. |
| Version 1: nucleic acid sequence of human IL12 transgene (Human IL12 transgene (Signal peptide-IL12B (P40 Subunit)-GS Linker-IL12A (P35 Subunit)) (exemplary nucleic acid sequence encoding SEQ ID NO: 22) | atgggtcaccagcagttggtcatctcttggttttccctggtttttctggcatctcccctcgtggcc<br>atatgggaactgaagaaagatgtttatgtcgtagaattggattggtatccggatgcccctgga<br>gaaatggtggtcctcacctgtgacacccctgaagaagatggtatcacctggaccttggacca<br>gagcagtgaggtcttaggctctggcaaaaccctgaccatccaagtcaaagagtttggagatg<br>ctggccagtacacctgtcacaaaggaggcgaggttctaagccattcgctcctgctgcttcac<br>aaaaaggaagatggaatttggtccactgatattttaaaggaccagaaagaacccaaaaataa<br>gacctttctaagatgcgaggccaagaattattctggacgtttcacctgctggtggctgacgac<br>aatcagtactgatttgacattcagtgtcaaaagcagcagaggctcttctgacccccaaggggt<br>gacgtgcggagctgctacactctctgcagagagagtcagaggggacaacaaggagtatga<br>gtactcagtggagtgccaggaggacagtgcctgcccagctgctgaggagagtctgcccatt<br>gaggtcatggtggatgccgttcacaagctcaagtatgaaaactacaccagcagcttcttcatc<br>agggacatcatcaaacctgacccacccaagaacttgcagctgaagccattaaagaattctcg<br>gcaggtggaggtcagctgggagtaccctgacacctggagtactccacattcctacttctccct<br>gacattctgcgttcaggtccagggcaagagcaagagagaaaagaaagatagagtcttcacg<br>gacaagacctcagccacggtcatctgccgcaaaaatgccagcattagcgtgcgggcccag<br>gaccgctactatagctcatcttggagcgaatgggcatctgtgccctgcagt**ggtggcggtgg**<br>**cggcggatct***agaaacctccccgtggccactccagacccaggaatgttcccatgccttca*<br>*ccactcccaaaacctgctgagggccgtcagcaacatgctccagaaggccagacaaact*<br>*ctagaattttacccttgcacttctgaagagattgatcatgaagatatcacaaaagataaaa*<br>*ccagcacagtggaggcctgtttaccattggaattaaccaagaatgagagttgcctaaattc*<br>*cagagagacctctttcataactaatgggagttgcctggcctccagaaagacctcttttatga*<br>*tggccctgtgccttagtagtatttatgaagactcgaagatgtaccaggtggagttcaagac*<br>*catgaatgcaaagcttctgatggatcctaagaggcagatctttctagatcaaaacatgctg*<br>*gcagttattgatgagctgatgcaggccctgaatttcaacagtgagactgtgccacaaaaa*<br>*tcctcccttgaagaaccggatttttataaaactaaaatcaagctctgcatacttcttcatgctt*<br>*tcagaattcgggcagtgactattgatagagtgatgagctatctgaatgcttcctaa* | 26 |
| Version 1: nucleic acid sequence of human IL12 transgene (IL12B (P40 Subunit)-GS Linker-IL12A (P35 Subunit)) (exemplary nucleic acid sequence encoding SEQ ID NO: 39) | atatgggaactgaagaaagatgtttatgtcgtagaattggattggtatccggatgcccctgga<br>gaaatggtggtcctcacctgtgacacccctgaagaagatggtatcacctggaccttggacca<br>gagcagtgaggtcttaggctctggcaaaaccctgaccatccaagtcaaagagtttggagatg<br>ctggccagtacacctgtcacaaaggaggcgaggttctaagccattcgctcctgctgcttcac<br>aaaaaggaagatggaatttggtccactgatattttaaaggaccagaaagaacccaaaaataa<br>gacctttctaagatgcgaggccaagaattattctggacgtttcacctgctggtggctgacgac<br>aatcagtactgatttgacattcagtgtcaaaagcagcagaggctcttctgacccccaaggggt<br>gacgtgcggagctgctacactctctgcagagagagtcagaggggacaacaaggagtatga<br>gtactcagtggagtgccaggaggacagtgcctgcccagctgctgaggagagtctgcccatt<br>gaggtcatggtggatgccgttcacaagctcaagtatgaaaactacaccagcagcttcttcatc<br>agggacatcatcaaacctgacccacccaagaacttgcagctgaagccattaaagaattctcg<br>gcaggtggaggtcagctgggagtaccctgacacctggagtactccacattcctacttctccct<br>gacattctgcgttcaggtccagggcaagagcaagagagaaaagaaagatagagtcttcacg<br>gacaagacctcagccacggtcatctgccgcaaaaatgccagcattagcgtgcgggcccag<br>gaccgctactatagctcatcttggagcgaatgggcatctgtgccctgcagt**ggtggcggtgg**<br>**cggcggatct***agaaacctccccgtggccactccagacccaggaatgttcccatgccttca*<br>*ccactcccaaaacctgctgagggccgtcagcaacatgctccagaaggccagacaaact*<br>*ctagaattttacccttgcacttctgaagagattgatcatgaagatatcacaaaagataaaa*<br>*ccagcacagtggaggcctgtttaccattggaattaaccaagaatgagagttgcctaaattc*<br>*cagagagacctctttcataactaatgggagttgcctggcctccagaaagacctcttttatga* | 61 |

TABLE 8-continued

Exemplary IL-12 transgene sequences (nucleic acid)

| Name | Sequence | SEQ ID NO. |
|---|---|---|
| | tggccctgtgccttagtagtatttatgaagactcgaagatgtaccaggtggagttcaagac<br>catgaatgcaaagcttctgatggatcctaagaggcagatctttctagatcaaaacatgctg<br>gcagttattgatgagctgatgcaggccctgaatttcaacagtgagactgtgccacaaaaa<br>tcctcccttgaagaaccggattttataaaactaaaatcaagctctgcatacttcttcatgctt<br>tcagaattcgggcagtgactattgatagagtgatgagctatctgaatgcttcctaa | |
| Version 2.1: codon-optimized nucleic acid sequence of human IL12 transgene (Signal peptide-IL12B (P40 Subunit)-GS Linker-IL12A (P35 Subunit)) (exemplary codon-optimized nucleic acid sequence encoding SEQ ID NO: 42) | atgtgccatcagcagctggtcatctcatggttctccctggtgtttctggcctcacctctggtcgc<br>aatctgggaactgaaaaaggatgtgtacgtggtggagctggactggtatcccgatgcccctg<br>gcgagatggtggtgctgacctgcgacacacccgaggaggatggcatcacctggacactgg<br>atcagagctccgaggtgctgggaagcggcaagaccctgacaatccaggtgaaggagttcg<br>gcgacgccggccagtacacctgtcacaagggaggagaggtgctgagccactccctgctgc<br>tgctgcacaagaaggaggatggcatctggtccacagacatcctgaaggatcagaaggagc<br>caaagaacaagaccttcctgcggtgcgaggccaagaattatagcggccggttcacctgttg<br>gtggctgaccacaatctccaccgatctgacattttctgtgaagtctagcaggggatcctctgac<br>ccacagggagtgacatgcggagcagccaccctgagcgccgagagggtgcgcggcgata<br>acaaggagtacgagtattccgtggagtgccaggaggactctgcctgtccagcagcagagg<br>agtccctgcctatcgaagtgatggtggatgccgtgcacaagctgaagtacgagaattatacc<br>agctccttctttatccgggacatcatcaagcccgatccccctaagaacctgcagctgaagcct<br>ctgaagaatagcagacaggtggaggtgtcctgggagtaccctgacacctggagcacacca<br>cactcctatttctctctgaccttttgcgtgcaggtgcagggcaagtccaagcgggagaagaa<br>ggacagagtgttcaccgataagacatctgccaccgtgatctgtagaaagaacgcctctatca<br>gcgtgagggcccaggaccgctactattctagctcctggtccgagtgggcctctgtgccttgc<br>agc**ggcggaggaggaggaggatct**aggaatctgccagtggcaacccctgacccaggc<br>atgttcccctgcctgcaccacagccagaacctgctgagggccgtgtccaatatgctgcag<br>aaggcccgccagacactggagttttacccttgtaccagcgaggagatcgaccacgagg<br>acatcacaaaggataagacctccacagtggaggcctgcctgccactggagctgaccaa<br>gaacgagtcctgtctgaacagccgggagacaagcttcatcaccaacggctcctgcctgg<br>cctctagaaagacaagctttatgatggccctgtgcctgtctagcatctacgaggacctgaa<br>gatgtatcaggtggagttcaagaccatgaacgccaagctgctgatggaccccaagagg<br>cagatctttctggatcagaatatgctggccgtgatcgacgagctgatgcaggccctgaact<br>tcaatagcgagacagtgcctcagaagtcctctctggaggagccagatttctacaagacca<br>agatcaagctgtgcatcctgctgcacgcctttcggatcagagccgtgacaatcgaccgcg<br>tgatgtcctatctgaatgcttcctaa | 53 |
| Version 2.1: codon-optimized nucleic acid sequence of human IL12 transgene (IL12B (P40 Subunit)-GS Linker-IL12A (P35 Subunit)) (exemplary codon-optimized nucleic acid sequence encoding SEQ ID NO: 43) | atctgggaactgaaaaaggatgtgtacgtggtggagctggactggtatcccgatgcccctgg<br>cgagatggtggtgctgacctgcgacacacccgaggaggatggcatcacctggacactgga<br>tcagagctccgaggtgctgggaagcggcaagaccctgacaatccaggtgaaggagttcgg<br>cgacgccggccagtacacctgtcacaagggaggagaggtgctgagccactccctgctgct<br>gctgcacaagaaggaggatggcatctggtccacagacatcctgaaggatcagaaggagcc<br>aaagaacaagaccttcctgcggtgcgaggccaagaattatagcggccggttcacctgttggt<br>ggctgaccacaatctccaccgatctgacattttctgtgaagtctagcaggggatcctctgacc<br>cacagggagtgacatgcggagcagccaccctgagcgccgagagggtgcgcggcgataa<br>caaggagtacgagtattccgtggagtgccaggaggactctgcctgtccagcagcagagga<br>gtccctgcctatcgaagtgatggtggatgccgtgcacaagctgaagtacgagaattatacca<br>gctccttctttatccgggacatcatcaagcccgatccccctaagaacctgcagctgaagcctc<br>tgaagaatagcagacaggtggaggtgtcctgggagtaccctgacacctggagcacaccac<br>actcctatttctctctgaccttttgcgtgcaggtgcagggcaagtccaagcgggagaagaag<br>gacagagtgttcaccgataagacatctgccaccgtgatctgtagaaagaacgcctctatcag<br>cgtgagggcccaggaccgctactattctagctcctggtccgagtgggcctctgtgccttgca<br>gc**ggcggaggaggaggaggatctaggaatct**gccagtggcaacccctgacccaggca<br>tgttcccctgcctgcaccacagccagaacctgctgagggccgtgtccaatatgctgcaga<br>aggcccgccagacactggagttttacccttgtaccagcgaggagatcgaccacgagga<br>catcacaaaggataagacctccacagtggaggcctgcctgccactggagctgaccaag<br>aacgagtcctgtctgaacagccgggagacaagcttcatcaccaacggctcctgcctggc<br>ctctagaaagacaagctttatgatggccctgtgcctgtctagcatctacgaggacctgaag<br>atgtatcaggtggagttcaagaccatgaacgccaagctgctgatggaccccaagaggc<br>agatctttctggatcagaatatgctggccgtgatcgacgagctgatgcaggccctgaactt<br>caatagcgagacagtgcctcagaagtcctctctggaggagccagatttctacaagacca<br>agatcaagctgtgcatcctgctgcacgcctttcggatcagagccgtgacaatcgaccgcg<br>tgatgtcctatctgaatgcttcctaa | 63 |
| Version 3: non-codon-optimized nucleic acid sequence of human IL12 transgene (Signal peptide-IL12B (P40 Subunit)-GS Linker-IL12A (P35 Subunit)) (exemplary non-codon-optimized nucleic acid | atgtgtcaccagcagttggtcatctcttggttttccctggtttttctggcatctcccctcgtggcca<br>tatgggaactgaagaaagatgtttatgtcgtagaattggattggtatccggatgcccctggag<br>aaatggtggtcctcacctgtgacacccctgaagaagatggtatcacctggaccttggaccag<br>agcagtgaggtcttaggctctggcaaaaccctgaccatccaagtcaaagagtttggagatgc<br>tggccagtacacctgtcacaaaggaggcgaggttctaagccattcgctcctgctgcttcaca<br>aaaaggaagatggaatttggtccactgatattttaaaggaccagaaagaacccaaaaataag<br>acctttctaagatgcgaggccaagaattattctggacgtttcacctgctggtggctgacgaca<br>atcagtactgatttgacattcagtgtcaaaagcagcagaggctcttctgacccccaaggggtg<br>acgtgcggagctgctacactctctgcagagagagtcagaggggacaacaaggagtatgag<br>tactcagtggagtgccaggaggacagtgcctgcccagctgctgaggagagtctgcccattg<br>aggtcatggtggatgccgttcacaagctcaagtatgaaaactacaccagcagcttcttcatca<br>gggacatcatcaaacctgacccacccaagaacttgcagctgaagccattaaagaattctcgg<br>caggtggaggtcagctgggagtaccctgacacctggagtactccacattcctacttctccctg<br>acattctgcgttcaggtccagggcaagagcaagagagaaaagaaagatagagtcttcacgg | 66 |

TABLE 8-continued

Exemplary IL-12 transgene sequences (nucleic acid)

| Name | Sequence | SEQ ID NO. |
|---|---|---|
| sequence encoding SEQ ID NO: 42) | acaagacctcagccacggtcatctgccgcaaaaatgccagcattagcgtgcgggcccagg<br>accgctactatagctcatcttggagcgaatgggcatctgtgccctgcagt**ggtggcggtggc**<br>**ggcggatct**agaaacctccccgtggccactccagacccaggaatgttcccatgccttcacc<br>actcccaaaacctgctgagggccgtcagcaacatgctccagaaggccagacaaactctag<br>aattttacccttgcacttctgaagagattgatcatgaagatatcacaaaagataaaaccagcac<br>agtggaggcctgtttaccattggaattaaccaagaatgagagttgcctaaattccagagagac<br>ctctttcataactaatgggagttgcctggcctccagaaagacctcttttatgatggccctgtgcc<br>ttagtagtatttatgaagacttgaagatgtaccaggtggagttcaagaccatgaatgcaaagct<br>tctgatggatcctaagaggcagatctttctagatcaaaacatgctggcagttattgatgagctg<br>atgcaggccctgaatttcaacagtgagactgtgccacaaaaatcctcccttgaagaaccgga<br>tttttataaaactaaaatcaagctctgcatacttcttcatgctttcagaattcgggcagtgactatt<br>gatagagtgatgagctatctgaatgcttcctaa | |
| Version 3: non-codon-optimized nucleic acid sequence of human IL12 transgene (IL12B (P40 Subunit)-GS Linker-IL12A (P35 Subunit)) (exemplary non-codon-optimized nucleic acid sequence encoding SEQ ID NO: 43) | atatgggaactgaagaaagatgtttatgtcgtagaattggattggtatccggatgcccctgga<br>gaaatggtggtcctcacctgtgacacccctgaagaagatggtatcacctggaccttggacca<br>gagcagtgaggtcttaggctctggcaaaaccctgaccatccaagtcaaagagtttggagatg<br>ctggccagtacacctgtcacaaaggaggcgaggttctaagccattcgctcctgctgcttcac<br>aaaaaggaagatggaatttggtccactgatattttaaaggaccagaaagaacccaaaaataa<br>gacctttctaagatgcgaggccaagaattattctggacgtttcacctgctggtggctgacgac<br>aatcagtactgatttgacattcagtgtcaaaagcagcagaggctcttctgacccccaaggggt<br>gacgtgcggagctgctacactctctgcagagagagtcagaggggacaacaaggagtatga<br>gtactcagtggagtgccaggaggacagtgcctgcccagctgctgaggagagtctgcccatt<br>gaggtcatggtggatgccgttcacaagctcaagtatgaaaactacaccagcagcttcttcatc<br>agggacatcatcaaacctgacccacccaagaacttgcagctgaagccattaaagaattctcg<br>gcaggtggaggtcagctgggagtaccctgacacctggagtactccacattcctacttctccct<br>gacattctgcgttcaggtccagggcaagagcaagagagaaaagaaagatagagtcttcacg<br>gacaagacctcagccacggtcatctgccgcaaaaatgccagcattagcgtgcgggcccag<br>gaccgctactatagctcatcttggagcgaatgggcatctgtgccctgcagtggtggcggtgg<br>cggcggatctagaaacctccccgtggccactccagacccaggaatgttcccatgccttcacc<br>actcccaaaacctgctgagggccgtcagcaacatgctccagaaggccagacaaactctag<br>aattttacccttgcacttctgaagagattgatcatgaagatatcacaaaagataaaaccagcac<br>agtggaggcctgtttaccattggaattaaccaagaatgagagttgcctaaattccagagagac<br>ctctttcataactaatgggagttgcctggcctccagaaagacctcttttatgatggccctgtgcc<br>ttagtagtatttatgaagacttgaagatgtaccaggtggagttcaagaccatgaatgcaaagct<br>tctgatggatcctaagaggcagatctttctagatcaaaacatgctggcagttattgatgagctg<br>atgcaggccctgaatttcaacagtgagactgtgccacaaaaatcctcccttgaagaaccgga<br>tttttataaaactaaaatcaagctctgcatacttcttcatgctttcagaattcgggcagtgactatt<br>gatagagtgatgagctatctgaatgcttcctaa | 68 |
| Nucleic acid sequence of mouse IL12 transgene | atgtctgcacttctgatcctagctcttgttggagctgcagttgctgactacaaagacgatgacg<br>acaagctttgggagctggagaaagacgtttatgttgtagaggtggactggactcccgatgcc<br>cctggagaaacagtgaacctcacctgtgacacgcctgaagaagatgacatcacctggacct<br>cagaccagagacatggagtcataggctctggaaagaccctgaccatcactgtcaaagagttt<br>ctggatgctggccagtacacctgccacaaaggaggcgagactctgagccactcacatctgc<br>tgctccacaagaaggaaaatggaatttggtccactgaaattttaaaaaatttcaaaaacaaga<br>ctttcctgaagtgtgaagcaccaaattactccggacggttcacgtgctcatggctggtgcaaa<br>gaaacatggacttgaagttcaacatcaagagcagtagcagttcccctgactctcgggcagtg<br>acatgtggaatggcgtctctgtctgcagagaaggtcacactggaccaaagggactatgaga<br>agtattcagtgtcctgccaggaggatgtcacctgcccaactgctgaggagaccctgcccatt<br>gaactggcgttggaagcacggcagcagaataaatatgagaactacagcaccagcttcttcat<br>cagggacatcatcaaaccagacccgcccaagaacttgcagatgaagcctttgaagaactca<br>caggtggaggtcagctgggagtaccctgactcctggagcactccccattcctacttctccctc<br>aagttctttgttcgaatccagcgcaagaaagaaaagatgaaggagacagaggaggggtgta<br>accagaaaggtgcgttcctcgtagagaagacatctaccgaagtccaatgcaaaggcggga<br>atgtctgcgtgcaagctcaggatcgctattacaattcctcgtgcagcaagtgggcatgtgttcc<br>ctgcagggtccgatcctctagaggtagtggatccggtggcagtggaggttctggatctggta<br>agcttagggtcattccagtctctggacctgccaggtgtcttagccagtcccgaaacctgctga<br>agaccacagatgacatggtgaagacggccagagaaaaactgaaacattattcctgcactgc<br>tgaagacatcgatcatgaagacatcacacgggaccaaaccagcacattgaagacctgtttac<br>cactggaactacacaagaacgagagttgcctggctactagagagacttcttccacaacaaga<br>gggagctgcctgcccccacagaagacgtctttgatgatgaccctgtgccttggtagcatctat<br>gaggacttgaagatgtaccagacagagttccaggccatcaacgcagcacttcagaatcaca<br>accatcagcagatcattctagacaagggcatgctggtggccatcgatgagctgatgcagtct<br>ctgaatcataatggcgagactctgcgccagaaacctcctgtgggagaagcagacccttaca<br>gagtgaaaatgaagctctgcatcctgcttcacgccttcagcacccgcgtcgtgaccatcaac<br>agggtgatgggctatctgagctccgcctaa | 30 |

TABLE 9

Exemplary chimeric NDV genomic RNA sequences

| Name | Sequence | SEQ ID NO. |
|---|---|---|
| NDV La Sota genomic RNA | accaaacaaagauuuggugaaugacgagacuacacucaagaauaauugugcgcaac<br>cuuuuuuuaagacauuuauuugaguucgaauucgaguccuaaggagucaggguuc<br>aacuuuuuucuaacauaauaugauuaaaucaacaagaauacaauuggccaaaaaag<br>gagccuauuaauaugugauuuucguuaagagucacaguuacuguaauauccuuug<br>acugcauugccuauaguuuucauguagaauuuuuguugagcacgagucaaguaca<br>guacagaagugucuguaaacauuucuuugaguugguaauaccuaggacagccuu<br>caaauauuuagggcagguacuaugcuucaaguauguccuuaguggauaagguccc<br>uccauggagaucaugccuuuaagcacuaggcugauuauaucgccuauuuuauuga<br>gauuuucgacucuaagaccuaguauuguaaccucuaggaucugucucgugcacug<br>uuuaagugauguccucuuuuucccgucaguagagagauuguaagggguaaauaga<br>aauacugugucagcgagaucacccucagcuuccauauauaucacagaccggauaac<br>ugugucaaugugacuagcgaugaucuggguuaucugaguuauguucgcuagcgu<br>gcucaccagacucuccgcacagaauggacggacgggcugucccccggcuucaauca<br>gcgcagugucaauauucuuccucaaguacuuuauuaaucuugguaaaggacugga<br>uaggaugucugucacacgcugccgcugugaggugaauaaccuggucagugugauc<br>ucaucugauuuagacaaaagcguaccgugccgcugcaccagaguuucgccauccu<br>caccaccucauguacaaauguaggcccgcccagguaacccaugacaaauaccaggua<br>acacuccauaucuccucgacaugcauaaccauuagagagaauauauccuuuugugg<br>aacacggagcaaacaaguucaugaguagaugaaaguaguaucccauugcauacaac<br>acuuugaugauuacuaccccgcccucccuuacagaaugcauggcaaucagagauaa<br>auugauagcuaguugaucuaguaagcuuugauuggacccuggaggaauuucaaug<br>ucacaaugcagcaaugauacagaucuguagggcacugcagauguaauauaccccac<br>uacuuuaucugaggucaggucgcuuuccucuguauuuucucuccauaauggacgg<br>aacucuuggacaaauccaucuuugcauguuaccuccgccuguagauuccuauaaac<br>aaccgaauucaaaaacugaguuggggucggcccgaaaugucguugcggggggguuc<br>aucucauuugaaaagagcguauuguaauagauaguuucaugugguacaugcaguu<br>cgagaagacucaugauggcuccgcucccuucagcuaaguauaaggaguucccgugu<br>cuugcacaucuuaccucggguacagaaaggagaugagaugccuuauaccaagagga<br>agaugcagucccuaucccucugaacaaguaucguacuaaguagucuuccuccggau<br>uuggagaugugaguucaggaugaaucugacuaagugugaaugcgucauaccuugc<br>uggagcacucaaaucuaacucuugcaaaaaugccgcagguugucgggugaaugga<br>ucuuucacucgagcaccaauaucuugcacagaagggaacucuaauaaugg cucuug<br>ggggaacaacaacgccaggauaguaucccuguccucccuuucccugaucaaauuga<br>ggcucuuccgagacauguaguacagauuagcugggaauguaauuauguuaggaga<br>caugauagagcucacuugaucggggcuaaguaaugguuucacagcauccgacagua<br>aauacucagugaguauugaacauuucucuucugcaguuaagccucuuauuuucgg<br>gauuucucuuguuguagcaaagaguaccguguacagacagcauaaccgggauauca<br>gcugaagcaucuucucauucagguuaucaucuaagacagaugggaacagcagauca<br>uacuuauuuccugaauauaagccggagaucacacgucgggugcaagauacuaauag<br>uuuugcagacauuucgauaaaauccguaucugcaaguuggugugauccgucaugg<br>uugaccaggcccacugcauguaaccuugaaugaaugacgggaugagauauuguag<br>cugcaauguuggaaaguagaauuccuggcauauucuuguauaaaucacccauauau<br>aagacaauauuguccaggccucuuacucucagguaauagaguugguaagaacaguc<br>gaggagcacuucaagugcugcauauucaaauaggcggaccacaucugaauucugag<br>cuucacugauccaauuucggguauugucauacacuauuauggcgucauucuuuau<br>ggagguaucuucaucauaagaaaccacagacuggccaaucaacuucccgcuggaua<br>uugaaagaauguucauuagcucuaucgugggauaugacuccagauuaagcucaua<br>acucuugaagauagcuaagucaagucucgcaaagucucccuccgauacagggcuag<br>gaucauacauaaacuuauuugaggucacuguccucaguuccgguaccaccccaagu<br>agcucgaaaggaaccgcaacaggugcuucucugauacagcaacuaaauuuacuaug<br>uaggugcagugugaucucaucauauguccugguuguugucauuggaaagaucgau<br>ucgauuagagauaaacccaagagcaugaucuguugguaaaccacauuccccucuuu<br>gacuccuucuucagugaacagccuuugagaaucauuggauaugugaauguaaggu<br>gacacccuguagagagaugcaggggugaaugucaucugaguuauaccaucaucua<br>gucuauguugaagauucccagccgugggguaaaggggacaguaaccgaagauacuc<br>uaaguuuacauuacaccgagauuuugcaaucguaagagcagcaguccaauuuacuu<br>cauuauccccauaagcccagaucaacacggaugaugcccuuagggcagccuuuaca<br>uguggcgacauaugagcuauuuuugcaagugaggcagcucuccucuccugugucu<br>uugacccgagauaugguacccucaucggaggauucuugcuggugucaucggucaa<br>uucuauauugcuuggaagauggaaccaaguaaauuguucaucuccgcugucacau<br>cuuguacacccuccgcuuacacuaagaaucucacccucuacgaguucuaucguauc<br>aggauuagauacacccaguauuuuccugccucccgucaaaggugaccagcuucuau<br>uccgugcauagucugccagugucagagaacacauauuagaagagacuaaggggug<br>guuggaucuacuggaggaaaaaacaucgucucuaaacagcauugcaugcaugcuag<br>aauaauugacuauccgcaucagccucuugaugccuaauggccuccuaguaagcgca<br>aucuuaauuacgguguuuguugugucaacaagcccuugaauuugcuuucuccuac<br>cuacagagcuugccuccaugauggcaugcgcaacgcggggaugaaucaccucuuga<br>uuaagcaagaauucagccaaugccuucucuucugccucauuauccucugugugcac<br>uccagacaauaagggauuugaacaaguuucaaauaggacucuuugcguauguuuc<br>uuaagaacaauauuugggcuugcaacagucucaaaauugaaagaguaugggucgu<br>ugcacagacuggcccaaucuccauucccaggcggccuaguuaagauauuagucaua<br>auguuaggacucaguaaucccacugcuucuagucgcuugaucucugcaaaagcagu<br>aguccccgggucaccgauauuucuaguguagagccuugaguauugaagguuacuc<br>agucccccuaauugggcaggagucagaacauaugagugcacaaaagagauguccuc<br>aauccacgacugauuaagaucggggugcgaauuguuggugauggagaacucagag | 50 |

TABLE 9-continued

Exemplary chimeric NDV genomic RNA sequences

| Name | Sequence | SEQ ID NO. |
|---|---|---|
| | ucaaaguaugucugcacacaacucauuauauaguuuaaauaguaacagaagucuuu | |
| | gggaagcccguucucgcauagccgugcuacaguagaggcaauguuggcacaggaca | |
| | uuacgguguuuucacugagaucaccugacacuagcacuaauuuagaugaauuuuu | |
| | gaggacuugacugaggauugcuccaucuuugaagauucguuugcuguauaugaag | |
| | aaugugucugaccugaugguuucacgauccuucaaauuauggccaaucaaaugau | |
| | ugacaugaauuaauuccuugaagaaauuaucacuggcuugaugcaacugugucaac | |
| | accaucuccggagagucgucugaucuuaccucucucguuacugcuauuacuugau | |
| | uaucacccuguaccauacaggcaacacgacaaugcgaucuagcugcagcaaguugg | |
| | auugcagcaauugagaucauuguccauagcuucuggcauaauccuucgauaccccc | |
| | ucuggcacugacaauauauaugucaucauuagggacucuugagaggucacaguca | |
| | guagggucacuuggaggauugaaaggucuccuacgaacaucguaguguccauca | |
| | gucuuaggugaauccauucgaagaagugagguaggcccaucaacugauugauggc | |
| | augagcgaacaauuugauugucugauaucuccaauuaagacaguacuuuugcagg | |
| | ucaguuguuaugaagguugcaacucuccgacgguucuugcuuuucggaucaugau | |
| | ugcgguuugaagauacucuuucuuuacagucagugauacguuucuuauugcuguu | |
| | aaaagacaguugacucaucgcuagcauacucuuggucaaggauaugcuauccugaa | |
| | ugacuccauuucccugaaagaaaggugcaaucugaucggcuaggaucccuuccgcc | |
| | aucaccugacaguuccuuaacuucuuugucagcuuagcgaagauccguccauuaac | |
| | uuucacuuccuucuccuugagcgaguaugauacugccacauugucaucucuaagg | |
| | uacucaagggucgucagauauuccaucucuuuauauggaucaaaaucauuugacuc | |
| | uaaaaacucuaucaagaggcgauuagucgaaguugcuucuuuuacauguuucuuc | |
| | uggucuucggagagaagguuccgccuaaacgaggcaagccaauuaucguuggggu | |
| | gugcgauugccuugucuuuuaggaacaugcucagguuggugacagggucauauuc | |
| | uauacauggcucaaauucaagugcagauaaacucuuauacucucucaacaugauau | |
| | cgugugaaaucucugcugaaucugcauguaguugcccaaugaccuucccauauau | |
| | uguauccacuuugacucgcggccacacaccugcauucuucuuucuguacccguuga | |
| | ugauuguucccuugaagaaagacaguaccugaaggaucauaucaaagucuaccauu | |
| | uucggugcgcacauuuggcuccugacugccuuugcugcaauacgggacucaagca | |
| | gugggugaccccacagacgcaacagacacaacaucucagcugcuugauucuguucu | |
| | aaaccagagaauacaguagcgauugcaugagucacggauucugcuauaucauuggg | |
| | gaggaggccaauuagaaugucuuuaagcuccugcagguugaaugcgaagaaaucu | |
| | ccugcaaauguaccugacggcucgaguagcuggacagcuccguaugcaaaucccuc | |
| | cauuagugauacaacaucguagacuugauuacccaagucuuuugccagagcgucua | |
| | uuaaccgcaaaaugucaucaauuuucucugauaagcuucugagaugcaccgccgug | |
| | guugauauuauguugaccauaucucugcccuccaucauaucugcauacaucaauac | |
| | aaguuccugguaagacaugugaacuuguucucauucguaugcgucacaacgacaa | |
| | guucaggagugacaaagacuuggccuaccuuaugguuagcaucaccaauuuguu | |
| | ggccgcagaccuuguccuagcugccaccaucagaugccucuggaucuguuuuaua | |
| | uggagccaugcaaacuuggcuguggaccauuuugagugaaaccagaaugccggau | |
| | ccguacgaaugcugcugaacuccucugaccggggacauuguuagaccaagaugac | |
| | cccagcaguuucuucucuauaugcguacacagccuugugaacaguucuccauaucu | |
| | cguguugugaauuuggaucuucuucucaaucuuccgaaauuuguugguugaaucu | |
| | gggaccucaauauuagccaguucuucuaaacaccugggguggagcacuccgguua | |
| | uucuggaauugugguuaagaguuugguguacugcccuuccgaguuuuaucauuc | |
| | ucucaguaucaggagaggccgauucaaguauuuuuuuccauugucggcugagaau | |
| | gagguggucgaagucacauucaucaggaagcgguagcccaguuaauuuccaguaa | |
| | uagaguaguuugugcuugaccaauggugaagacaggugugacucugguaggauaa | |
| | ucugaugcucugcccuuucaggaccggagcucgccauguccuacccguauuguua | |
| | accaugagcuguuuugccuuguaucucauugccacuuacauuuuuucuuaaucaa | |
| | gagacuauugacaaggcuuaaucugaucgcaugagcacuggcugauuguggucaa | |
| | cuggcaacauggaauucgagcacgcgccggcauucgguuugauucuugaugucgc | |
| | agaagauaggugauacaaugccaucuuuccaacuccuuuauaauugacucaacuag | |
| | ccagaccuggcuucucuaaccccgucaucuuugaggaucucaacuaguaacgggac | |
| | gauucugaauucuccgaagagaguauuagauauuucagcaaugcugagacaauag | |
| | gucuuauuagucuugaccacuuuaaaacaaguugauguuguguaugcugcuuugg | |
| | uacugcuugaacucacucgaguaaugcgacugcgggaugugcuaucgaauacugc | |
| | agacgcaggguuaagucuugcuuguacaccaucaagcauugucccgaauaccccuc | |
| | gcaagguguggguuucuauagaagauuaggggauauggaucuguauagacuccagu | |
| | aacacacgaguuggggcaucuugcugaagccuggcaagggauacuaccuggccgag | |
| | ugaaggcauugaauguauaaggacuaugaagaguggcuguuuuguugcugacugu | |
| | cauaggauauaauaacgcgggagagaaguaugaugacccucguugauacaagaaau | |
| | gagaugucccuacugugagaauucugccuucggcccccaugagugugacuguguu | |
| | gggcgguacagucaguaccgggucuucgccuaaggauguugacaccuugauagau | |
| | aagauagccugcuguaugcguuucccaccaaaccguccaggcuuauacgaagacuu | |
| | ggccauucgaaucugguagucuugcucaucugggcaugugucauuguaucgcuug | |
| | uauaucacauauuucccuuccuguacagugucacugggugaauuggguuuuaacc | |
| | cuccguagacugagaaccauacgcggcugucaauaaaagauccacccccuacuccu | |
| | ggguaguuggccacccaguccccgaauaauguugugacaucuagguccuuuucgu | |
| | gguacuggccgucgaacccuaaccucccauguaccauccgcguagggacagcugag | |
| | uuauaaucuucuuccucugucuccgugacuuucgagcacagcauaucacaacccag | |
| | gggaguugcacucacacugcaagacuuccgauuuuggguguccgguccagguugaug | |
| | gaacgcagaguagaaaagaauacccucccuguugcagauguccggagcacaccaag | |
| | ugcuaaauacugauaugaaugugagugaucucugcauccagacaauauuacauuau | |
| | ggguguagcaguaaugguagcacucaugucaaaugagguauucgagugcaacc | |
| | ugauccuguaguaggcgccgggauaaaaauucagauguucuugaaaugcagaggga | |

TABLE 9-continued

Exemplary chimeric NDV genomic RNA sequences

| Name | Sequence | SEQ ID NO. |
|---|---|---|
| | uagaaugaugugacaucacuagcaucaucuacaaugaguucuuugccuaucccccc | |
| | uauauaaucugggucauggauaggugccccccacccacuguuguuugcagcucca | |
| | uuaaucugauaagagagagauguuauugcguucauaauuguggucucaguauuua | |
| | acaaugccaacggagacucaagggccacuugcuuauauauccuaucuacuacaucu | |
| | ugauuggaaccaaguguagauguaaucuuuucuucugcccuggaaauccuagucg | |
| | guaugccuacaagaucgcuaggugugcuagccccaugcuauauaaaagggaggcu | |
| | acagauauagccaaggucacuacuguuaagaauaagauugcaauccggaauaucaa | |
| | gcgccauguauuuuuugccucucuuucaucauucucuaacgcaacuuggcuaacg | |
| | gcgcgguccaugauugaggacuguugucggugaagcgguagaacggagguuguga | |
| | agccuggcucgcaauugaggggcggccucucuuaccguucuacccguauaucguc | |
| | cuuuggucaucuacaaccgguaguuuuuucuuaacucucugaacugacagacuacc | |
| | agaacuuucacacaaauuacuauuagggaaaccuucguuccucaucuguguucaca | |
| | uuuuuguaguggcucucaucugaucuagaguauuauucccaagccauaauaaggu | |
| | cuuuuguugcgccuuuugcuuguacauuagguagcaugcuagaaucaggcuaagu | |
| | auaccaaaaacaagagauaugauagucaaaacgauauagguaaugagagcagaugu | |
| | gcuagucaguuugacauugacuuugucuaguuuucuguugcuuuccucuaacuua | |
| | uucaaagcauuacugaucgaguuguugacauucccaagcucaguugagauaucaag | |
| | auugccuguuauuauuacuugagaaucuuguauugagauauucuucugauaaguu | |
| | acaucgaauuccccacugagccuuaaaguuaucccgccuaaggauaaaacauugca | |
| | ugauuguuuaucuauuagagacacggcuucuccauaguuuugcgauaugauaccc | |
| | gggggguuuacacaucuacauguugucaucuugcaguuggcgaugacugaaccuu | |
| | ugauagucauguaugguguaguaagugcgccuucggucuuugaguacauacaggc | |
| | cgacguauugccgcucaagcaggaauaaauaccaggggacauagggaacguuacua | |
| | uucuuguacaauauaaaucuaagucaguuucuauacaguaugaggugucaaguuc | |
| | uucuaucacagaaccgaccugugucaccacuuuugggacaagugccgaggcaaauc | |
| | cccugguugugcuuacggauaagguuuccaaguagguggcacgcauauuauuuag | |
| | guucccgacugaaggugcaguuaccuguauacccaagaguugagucugugagucg | |
| | uauagaauagguuaccggugauuaagccgcuaccgauuaaugagcugaguugau | |
| | uguucccuacaccuaacuuagucaauaaguaauccauauuuccaccagcuagauug | |
| | uaaagugccugaauagucagcuuguuuaaagcaggugaagugauuugugguccga | |
| | auacuguagucaauucgguuagguacagguugagcucuacaccaacuugcugugc | |
| | aauuuugaugcagucuaauuccugagcuguuuuauuaaauuggucauuaacaaac | |
| | ugcugcaucuucccaacugccacugcuaguugcgauaauccgucagugaccucaug | |
| | cacagccucauugguugcggcaaugcucucuuuaagucggaggauguuggcagca | |
| | uuuuguuuggcuuguaucagagcugcggccgcuguuauuugugcggcaguugca | |
| | accccaagagccacaccgccaauaauggcgccuauaaggcgccccugucuccccccu | |
| | ccagauguagucacagacucuuguauccuacggauagagucaccaaggggggguga | |
| | gcaaaguggucaauguccuguuguaugcauccaaggggggcuuucgcacaugccuc | |
| | cuuauccuugggcagauucgggaggagcuuaacuaugauugauccugucugggau | |
| | gagguguauauguugacggcuuugucuccuguaaccacaauuccugcagcugcaa | |
| | gaggccugccaucaauggaguuugccggacagaugcaacucaguaccagcgcaacc | |
| | cggauagucagcaucauaggugcugggguucuugguagaaggucuggagcccaucu | |
| | ugcaccuggagggcgccaaccgggauccagaaucuucuacccguguuuuuucuaac | |
| | uugauagacagguaaacuaacuguaaauaaucaagacagauuaguuuuuugugu c | |
| | augaugaucuggguggaguggcggagcgcaaucucagagacgcagcuuauuucuu | |
| | aaaaggauuguauuuggcaagggugugccccuucuccagcuuaguagagguaacc | |
| | ucguggucggcggucacugcgacagcgcguuggguaccugcuuggauaaugauuu | |
| | uaacgcuccgcaggcacgcgguuugacuccagaguaucuuggccaccugaggagaa | |
| | gcauuugcuaugggauagcaggcugucccacugcuagagaagaaaggugccaaaag | |
| | cuuaguccgugcaccucuugcuuuuaccaacacggaaggcccgagcacaucacuga | |
| | gcccgacagauagaucaaggcuccuuauuuucuuuuccagcuugucaaaugucacu | |
| | uucuuccccuuccuaucuacaguggucauaaguccaauaugcaagaagagguuagc | |
| | auaguauccgcugucagacuuagacagagauuuaaccaaaggacuccucgggucua | |
| | ccuccacauuaauagugacauugagcgcaagauuguacagacucgagccagaaacc | |
| | uucaauacugcagcugggaucuuguagacaucccucuucgguaccacagucaagga | |
| | gacaaaguucaccuuguauucuaggguuccacucccgggaaucuucucuggcgcu | |
| | uucacgugcuugacugcauucacugaugaguauuuguuugccacaacccuacagc | |
| | uuugcagcacuugggggugccugcacuacugagaaaaccauucucucaguauuagu | |
| | ugcacucuucuugcaugugacuaucauagugagacaggcccuugccagcucaauaa | |
| | ggucuccgguauuugggacgcuuccuaggcagagcaucgcagcggaaaguaacuc | |
| | gcgcuuggguuuaucaucgaucaugccgacgguggcuucuucauucccaacuuga | |
| | aagaugaauccauagguggugaugaauacugaguccuccuuacuaucaguccacaa | |
| | gucaaggcgcuggauccuauauugcggggcgauuugcuucuucccaucuccugug | |
| | ucuuguaggacgaucggaaaugcuaacagguugcuagaagaaugggcagaaucaaa | |
| | guacagcccaauuguccuagaugaguccaucuuggcacaauuggggcacuccaauu | |
| | cuacccguauuuuuucuuaaucuuaaauguagcuagauuaauuacgguuacgcga | |
| | ucauucaguggggcugaggaagcgagagaggauugccgcuuggagaguuggaccu | |
| | uggguccgcggggggaacucggugcagauuccgugugaugccgaguggacaggg | |
| | acccgcuacguguggcaguaguaauuagccauuuagagcaaggcgcuugauuuuc | |
| | cugauuuccucgaucgacccggcugcaucuaacuugcuuaggagcuuggcugaag | |
| | aacucgggugcauugggcgugacaugaucaaugcacggacaguguccuuuuccac | |
| | uccuauaucaggcccgcaugcaguggcggguuuaaucaauucagauggauguggc | |
| | acugguugcgaaaguuuauuaagugccauuucgccuccuugugucacauagggag | |
| | aggggucuccagggccugaaacuaaaaccgggugagaucgggcaacugcccguaga | |
| | ucacucagagaugaaauguuggcacaaccgggauccagaaucuucaucauucccaa | |

TABLE 9-continued

Exemplary chimeric NDV genomic RNA sequences

| Name | Sequence | SEQ ID NO. |
|---|---|---|
| | guuggcuuccaugacugcaacagauguuucagcuguuggauuucggaccgcauc<br>auagggauggaggaugucuguuucaagacaagaucuagcugauagucaaccuuac<br>uuacucucugugauaucgccuccaucauagacaucaucgcuugcacaaagucuaca<br>gguggcuggacaugauccgcagauacaaggguauugucuuggcucugccuugauc<br>ggagagcaugagggguugcaccagcugauaguugugacuccucccauuguccaug<br>auaugcuguguucacgucugugcccugguuuccaggggcggccuugacuugguuc<br>ugcggucuuuccugacuguuuccgcgacugguugacuccccugcuguugagucg<br>gacguuggugauuccccucuuggggcucgaccaugggcccuuuuuagcauugga<br>cgauuuauugcugagcuugucaagcaucaacagcagagaguugcuugcuccgguc<br>cugagcugugugucgacggcuucgucuguggccuggguggggggcuggucggcg<br>gauguggccggcgggcugucaugcggggucguuugcucggguguggaugguugu<br>uugucagaucuguccugucgaucgggguugucuugacuggccgguggcuggaug<br>cucccaugcuucucccaugcugcgcucagcaccuuggucuugccuugugggauug<br>cacuccuuccaacagucucugcugguuuacccugggcuguaauuauguugucaau<br>gacaguuccacuugucucaaauagcucgucgaucucugcaucuguaaagguggcca<br>uguuuguccuggucuaucagguagaggagagagcagagacucgggagacuugccc<br>ugaucucugaauaucccucuucuacccguacuuuuuucuaauucccucggcucug<br>uuuugauuguuagugagccgcauugugccugugguaucuagggcguacguaguu<br>guacagcaggggggagggaggaaagaggggauguuuguuugagggugugggucau<br>auagagccgcaaaucgaggggucgacuacgggugagggcauugggauguuuuugu<br>ggaagcaggcuggguuuuguccaucaauacccccagucggugucguuaucuuggg<br>auggcccaggaguugggggaggccccgauuggggagugcccugugcagaguugg<br>cgccucccucaugcuauuugcuaccgcucucaucagauccaggaauuggucuccc<br>cauccccggcuucugguugcccuugcgaucuauucgauccgccuuguagagcuug<br>ggaccccccucgcuaagcccagugaggacuccgacuuguugaguaggcaugucua<br>ugcugcuggucuccucggagacccguugggcagcagcugccaggccccuccuugc<br>ugcugggguuagcuuuagcucggcagccauauccucguuaaugcuacuucccuga<br>gccugagcguacucuacuccaagucuccagaaugaugugcucauaaagucccuggc<br>aaauugguauuucccaguaccuuuaucuaggacugaugccauacccauggcaaagg<br>aguaaaguugugcauacucggcaggcgcaaagcucaucuggucacuaucaccaagu<br>aaugucauguacggcgcauuaucuccuuucauccgauacaaacgcaugagcugcuu<br>caucuucuggaugucgccugagaggcuacuaagugcaagggcugaugucuuggug<br>uugauuccguacuugagugucaagaagaaugcaguaagcccgguauuccugaugu<br>augagucuacguccccuaccagguuauaauaaguagagguaccaccugccguguug<br>cggccucucuugagcucgcuaaccaaaaagaugcggacugcaagagacugucugau<br>cgugaguuggauugugcuccugcauacgggguagaggauguauuucuuuuggac<br>ccugccuugcugcauauacuuauugauucgccuuguuuccgacucaucugcaguc<br>ucauacgcagucauggcuuuugcuacugugacccauacuugagccuggauagaga<br>ggauccucuccaggguaucggugaugucuucuggugcaucaucuucggccccggc<br>ugugacgaacgggguuccguugcugcaugcccgagggagagauccugcuaucauc<br>gcaaaucucugugcucucucuucagacacuccacuccuauuguugaacuggggcg<br>ugccguuggcaaagccaucaaucucaagcacggccaauguggcuucauucuguuuc<br>ccugcaagggcaacaugguuccucauuaccugugagugggagcauaaaagagauau<br>gagagcaccuugccugagugguuuguuggcaucuucgcuaacagcaauccggagg<br>cagaauaccacaaagcuccaucuaucuucugggucaucacuguuaagagugaauac<br>cgggacgucuacuuuuaagguacucccuuuuucucccccuccaugagcuccauug<br>gggcgagucugagccgcgaggagcuguucguacucaucaaauacggaagacaugu<br>uggcagaaggcuuucucgaguuugugcuucgggcucgcacucgagauucacaccu<br>ucuacccgugcgacuucaauugcuccuucgccuuuuaucguaacucacggauucuc<br>uguuuggu | |
| Exemplary NDV-huIL-12 genomic RNA sequence (Version 1) | accaaacaaagauuuggugaaugacgagacuacacucaagaauaauugugcgcaac<br>cuuuuuuuaagacauuuauuugaguucgaauucgaguccuaaggagucaggguuc<br>aacuuuuuucuaacauaauaugauuaaaucaacaagaauacaauuggccaaaaaag<br>gagccuauuaauaugugauuuucguuaagagucacaguuacuguaauauccuuug<br>acugcauugccuauaguuuucauguagaauuuuuguugagcacgagucaaguaca<br>guacagaagugucuguaaacauuucuuugaguugguaauaccuaggacagccuu<br>caaauauuuagggcagguacuaugcuucaaguauguccuuagugggauaagguccc<br>uccauggagaucaugccuuuaagcacuaggcugauuauaucgccuauuuuauuga<br>gauuuucgacucuaagaccuaguauuguaaccucuaggaucugucucgugcacug<br>uuuaagugauguccuuuuuuucccgucaguagagagauuguaagggguaaauaga<br>aauacugugucagcgagaucacccucagcuuccauauauaucacagaccggauaac<br>ugugucaaugugacuagcgaugaucuggguuaucugaguuauguucgcuagcgu<br>gcucaccagacucuccgcacagaauggacggacgggcuguccccggcuucaauca<br>gcgcagugucaauauucuuccucaaguacuuuauuaaucuugguaaaggacugga<br>uaggaugucugucacacgcugccgcugugaggugaauaaccuggucagugugauc<br>ucaucugauuuagacaaaagcguaccgugccgcugcaccagaguuuucgccauccu<br>caccaccucauguacaaauguaggcccgcccagguaacccaugacaaauaccaggua<br>acacuccauaucuccucgacaugcauaaccauuagagagaauauauccuuuugugg<br>aacacggagcaaacaaguucaugaguagaugaaaguaguaucccauugcauacaac<br>acuuugaugauuacuaccccgcccucccuuacagaaugcauggcaaucagagauaa<br>auugauagcuaguugaucuaguaagcuuugauuggacccuggaggaauuucaaug<br>ucacaaugcagcaaugauacagaucuguagggcacugcagauguaauauaccccac<br>uacuuuaucugaggucaggucgcuuuccucuguauuuucucuccauaauggacgg<br>aacucuuggacaaauccaucuuugcauguuaccuccgccuguagauuccuauaaac | 51 |

TABLE 9-continued

Exemplary chimeric NDV genomic RNA sequences

| Name | Sequence | SEQ ID NO. |
|---|---|---|
| | aaccgaauucaaaaacugaguuggggucggcccgaaaugucguugcggggguuc | |
| | aucucauuugaaaagagcguauuguaauagauaguuucaugugguacaugcaguu | |
| | cgagaagacucaugauggcuccgcucccuucagcuaaguauaaggaguucccgugu | |
| | cuugcacaucuuaccucggguacagaaaggagaugagaugccuuauaccaagagga | |
| | agaugcagucccuaucccucugaacaaguaucguacuaaguagucuuccuccggau | |
| | uuggagaugugaguucaggaugaaucugacuaagugugaaugcgucauaccuugc | |
| | uggagcacucaaaucuaacucuugcaaaaaugccgcagguugucgggugaaugga | |
| | ucuuucacucgagcaccaauaucuugcacagaagggaacucuaauaauggcucuug | |
| | ggggaacaacaacgccaggauaguaucccuguccucccuuucccugaucaaauuga | |
| | ggcucuuccgagacauguaguacagauuagcugggaauguaauuauguuaggaga | |
| | caugauagagcucacuugaucggggcuaaguaaugguuucacagcauccgacagua | |
| | aauacucagugaguauugaacauuucucuucugcaguuaagccucuuauuuucgg | |
| | gauuucucuuguuguagcaaagaguaccguguacagacagcauaaccgggauauca | |
| | gcugaagcaucuucucauucagguuaucaucuaagacagaugggaacagcagauca | |
| | uacuuauuuccugaauauaagccggagaucacacgucgggugcaagauacuaauag | |
| | uuuugcagacauuucgauaaaauccguaucugcaaguuggugugauccgucaugg | |
| | uugaccaggcccacugcauguaaccuugaaugaaugacgggaugagauauuguag | |
| | cugcaauguuggaaaguagaauuccuggcauauucuuguauaaaucacccauauau | |
| | aagacaauauuguccaggccucuuacucucagguaauagaguugguaagaacaguc | |
| | gaggagcacuucaagugcugcauauucaaauaggcggaccacaucugaauucugag | |
| | cuucacugauccaauuucggguauugucauacacuauuauggcgucauucuuuau | |
| | ggagguaucuucaucauaagaaaccacagacuggccaaucaacuucccgcuggaua | |
| | uugaaagaauguucauuagcucuaucgugggauaugacuccagauuaagcucaua | |
| | acucuugaagauagcuaagucaagucucgcaaagucucccuccgauacagggcuag | |
| | gaucauacauaaacuuauuugaggucacuguccucaguuccgguaccaccccaagu | |
| | agcucgaaaggaaccgcaacaggugcuucucugauacagcaacuaaauuuacuaug | |
| | uaggugcagugugaucucaucauauguccugguuguugucauuggaaagaucgau | |
| | ucgauuagagauaaacccaagagcaugaucuguugguaaaccacauuccccucuuu | |
| | gacuccuucuucagugaacagccuuugagaaucauuggauaugugaauguaaggu | |
| | gacacccuguagagagaugcaggggugaaugucaucugaguuauaccaucaucua | |
| | gucuauguugaagauucccagccgugggguaaaggggacaguaaccgaagauacuc | |
| | uaaguuuacauuacaccgagauuuugcaaucguaagagcagcaguccaauuuacuu | |
| | cauuauccccauaagcccagaucaacacggaugaugcccuuagggcagccuuuaca | |
| | uguggcgacauaugagcuauuuuugcaagugaggcagcucuccucuccugugucu | |
| | uugacccgagauaugguacccucaucggaggauucuugcuggugucaucggucaa | |
| | uucuauauugcuuggaagauggaaccaaguaaauuguucaucuccgcugucacau | |
| | cuuguacacccuccgcuuacacuaagaaucucacccucuacgaguucuaucguauc | |
| | aggauuagauacacccaguauuuuccugccucccgucaaaggugaccagcuucuau | |
| | uccgugcauagucugccagugucagagaacacauauuagaagagacuaaggggug | |
| | guuggaucuacuggaggaaaaaacaucgucucuaaacagcauugcaugcaugcuag | |
| | aauaauugacuauccgcaucagccucuugaugccuaauggccuccuaguaagcgca | |
| | aucuuaauuacgguguuuguugugucaacaagcccuugaauuugcuuucuccuac | |
| | cuacagagcuugccuccaugauggcaugcgcaacgcggggaugaaucaccucuuga | |
| | uuaagcaagaauucagccaaugccuucucuucugccucauuauccucugugugcac | |
| | uccagacaauaagggauuugaacaaguuucaaauaggacucuuugcguauguuuc | |
| | uuaagaacaauauuugggcuugcaacagucucaaaauugaaagaguaugggucgu | |
| | ugcacagacuggcccaaucuccauucccaggcggccuaguuaagauauuagucaua | |
| | auguuaggacucaguaaucccacugcuucuagucgcuugaucucugcaaaagcagu | |
| | aguccccgggucaccgauauuucuaguguagagccuugaguauugaagguuacuc | |
| | aguccccccuaauugggcaggagucagaacauaugagugcacaaaagagauguccuc | |
| | aauccacgacugauuaagaucggggugcgaauuguuggugauggagaacucagag | |
| | ucaaaguaugucugcacacaacucauuauauaguuuaaauaguaacagaagucuuu | |
| | gggaagcccguucucgcauagccgugcuacaguagaggcaauguuggcacaggaca | |
| | uuacgguguuuucacugagaucaccugacacuagcacuaauuuagaugaauuuuu | |
| | gaggacuugacugaggauugcuccaucuuugaagauucguuugcuguauaugaag | |
| | aaugugucugaccugaugguuucacgauccuucaaauuauggccaaucaaaugau | |
| | ugacaugaauuaauuccuugaagaaauuaucacuggcuugaugcaacugugucaac | |
| | accaucuccggagagucgucugaucuuaccucucucguuacugcuauuacuugau | |
| | uaucacccuguaccauacaggcaacacgacaaugcgaucuagcugcagcaaguugg | |
| | auugcagcaauugagaucauuguccauagcuucuggcauaauccuucgauaccccc | |
| | ucuggcacugacaauauauaugucaucauuagggacucuugagaggucacaguca | |
| | guagggucacuuggaggauugaaagggucuccuacgaacaucguaguguccauca | |
| | gucuuaggugaauccauucgaagaagugagguaggcccaucaacugauugauggc | |
| | augagcgaacaauuugauugucugauaucuccaauuaagacaguacuuuugcagg | |
| | ucaguuguuaugaagguugcaacucuccgacgguucuugcuuuucggaucaugau | |
| | ugcgguuugaagauacucuuucuuuacagucagugauacguuucuuauugcuguu | |
| | aaaagacaguugacucaucgcuagcauacucuuggucaaggauaugcuauccugaa | |
| | ugacuccauuucccugaaagaaaggugcaaucugaucggcuaggaucccuuccgcc | |
| | aucaccugacaguuccuuaacuucuuugucagcuuagcgaagauccguccauuaac | |
| | uuucacuuccuucuccuugagcgaguaugauacugccacauugucaucucuaagg | |
| | uacucaagggucgucagauauuccaucucuuuauauggaucaaaaucauuugacuc | |
| | uaaaaacucuaucaagaggcgauuagucgaaguugcuucuuuuacauguuucuuc | |
| | uggucuucggagagaagguuccgccuaaacgaggcaagccaauuaucguuggggu | |
| | gugcgauugccuugucuuuuaggaacaugcucagguuggugacagggucauauuc | |
| | uauacauggcucaaauucaagugcagauaaacucuuauacucucucaacaugauau | |

TABLE 9-continued

Exemplary chimeric NDV genomic RNA sequences

| Name | Sequence | SEQ ID NO. |
|---|---|---|
| | cgugugaaaucucugcugaaucugcauguaguugcccaaugaccuucccauauau<br>uguauccacuuugacucgcggccacacaccugcauucuucuuucuguacccguuga<br>ugauuguucccuugaagaaagacaguaccugaaggaucauaucaaagucuaccauu<br>uucggugcgcacauuuggcuccugacugccuuugcugcaauacgggacucaagca<br>gugggugaccccacagacgcaacagacacaacaucucagcugcuugauucuguucu<br>aaaccagagaauacaguagcgauugcaugagucacggauucugcuauaucauuggg<br>gaggaggccaauuagaaugucuuuaagcuccugcagguugaaugcgaagaaaucu<br>ccugcaaauguaccugacggcucgaguagcuggacagcuccguaugcaaaucccuc<br>cauuagugauacaacaucguagacuugauuacccaagucuuuugccagagcgucua<br>uuaaccgcaaaaugucaucaauuuucucugauaagcuucugagaugcaccgccgug<br>guugauauuauguugaccauaucucugcccuccaucauaucugcauacaucaauac<br>aaguuccugguaagacaugugaacuuguucucauucguaugcgucacaacgacaa<br>guucaggagugacaaagacuuggccuaccuuaugguuagcaucaccaauuuguu<br>ggccgcagaccuuguccuagcugccaccaucagaugccucuggaucuguuuuaua<br>uggagccaugcaaacuuggcuguggaccauuuugagugaaaccagaaugccggau<br>ccguacgaaugcugcugaacuccucugaccgggggacauuguuagaccaagaugac<br>cccagcaguuucuucucuauaugcguacacagccuugugaacaguucuccauaucu<br>cguguugugaauuuggaucuucuucucaaucuuccgaaauuuguugguugaaucu<br>gggaccucaauauuagccaguucuucuaaacaccuggggguggagcacuccgguua<br>uucuggaauugugguuaagaguuugguguacugcccuuccgaguuuuaucauuc<br>ucucaguaucaggagaggccgauucaaguauuuuuuccauugucggcugagaau<br>gagguggucgaagucacauucaucaggaagcgguagcccaguuaauuuccaguaa<br>uagaguaguuugugcuugaccaauggugaagacaggugugacucugguaggauaa<br>ucugaugcucugcccuuucaggaccggagcucgccauguccuacccguauuguua<br>accaugagcuguuuugccuuguaucucauugccacuuacauuuuuucuuaaucaa<br>gagacuauugacaaggcuugaucugaucgcaugagcacuggcugauuguggucaa<br>cuggcaacauggaauucgagcacgcgccggcauucgguuugauucuugaugucgc<br>agaagauaggugauacaaugccaucuuuccaacuccuuuauaauugacucaacuag<br>ccagaccuggcuucucuaaccccgucaucuuugaggaucucaacuaguaacgggac<br>gauucugaauucuccgaagagaguauuagauauuucagcaaugcugagacaauag<br>gucuuauuagucuugaccacuuuaaaacaaguugauguuguguaugcugcuuugg<br>uacugcuugaacucacucgaguaaugcgacugcgggaugugcuaucgaauacugc<br>agacgcaggguuaagucuugcuuguacaccaucaagcauugucccgaauaccccuc<br>gcaagguguggguuucuauagaagauuaggggauauggaucuguauagacuccagu<br>aacacacgaguuggggcaucuugcugaagccuggcaagggauacuaccuggccgag<br>ugaaggcauugaauguauaaggacuaugaagaguggcuguuuuguugcugacugu<br>cauaggauauaauaacgcgggagagaaguaugaugacccucguugauacaagaaau<br>gagaugucccuacugugagaauucugccuucggcccccaugagugugacuguguu<br>gggcgguacagucaguaccgggucuucgccuaaggauguugacaccuugauagau<br>aagauagccugcuguaugcguuucccaccaaaccguccaggcuuauacgaagacuu<br>ggccauucgaaucugguagucuugcucaucugggcaugugucauuguaucgcuug<br>uauaucacauauuucccuuccuguacagugucacugggugaauuggguuuuaacc<br>cuccguagacugagaaccauacgcggcugucaauaaaagauccacccccuacuccu<br>ggguaguuggccacccaguccccgaauaauguugugacaucuagguccuuuucgu<br>gguacuggccgucgaacccuaaccucccauguaccauccgcguagggacagcugag<br>uuauaaucuucuuccucugucuccgugacuuucgagcacagcauaucacaacccag<br>gggaguugcacucacacugcaagacuuccgauuuuggguguccguccagguugaug<br>gaacgcagaguagaaaagaauacccucccuguugcagauguccggagcacaccaag<br>ugcuaaauacugauaugaaugugagugaucucugcauccagacaauauuacauuau<br>ggguguagcaguaaugguagcacucaugucaaaugaggguauucgagugcaacc<br>ugauccuguaguaggcgccgggauaaaauucagauguucuugaaaugcagaggga<br>uagaaugaugugacaucacuagcaucaucuacaaugaguucuuugccuaucccccc<br>uauauaaucugggucauggauaggugcccccacccacuguuguuugcagcucca<br>uuaaucugauaagagagagauguuauugcguucauaauuguggucucaguauuua<br>acaaugccaacggagacucaagggccacuugcuuauauauccuaucuacuacaucu<br>ugauuggaaccaaguguagauguaaucuuuucuucugcccuggaaauccuagucg<br>guaugccuacaagaucgcuaggugugcuagcccccaugcuauauaaaagggaggcu<br>acagauauagccaaggucacuacuguuaagaauaagauugcaauccggaauaucaa<br>gcgccauguauuuuuugccucucuuucaucauucucuaacgcaacuuggcuaacg<br>gcgcgguccaugauugaggacuguugucggugaagcgguagaacggagguuguga<br>agccuggcucgcaauugaggggcggccucucuuaccguucuacccguauaucguc<br>cuuuggucaucuacaaccgguaguuuuuucuuaacucucugaacugacagacuacc<br>agaacuuucacacaaauuacuauuagggaaaccuucguuccucaucuguguucaca<br>uuuuuguaguggcucucaucugaucuagaguauuauucccaagccauaauaaggu<br>cuuuuguugcgccuuuugcuuguacauuagguagcaugcuagaaucaggcuaagu<br>auaccaaaaacaagagauaugauagucaaaacgauauagguaaugagagcagaugu<br>gcuagucaguuugacauugacuuugucuaguuuucuguugcuuuccucuaacuua<br>uucaaagcauuacugaucgaguuguugacauucccaagcucaguugagauaucaag<br>auugccuguuauuauuacuugagaaucuuguauugagauauucuucugauaaguu<br>acaucgaauuccccacugagccuuaaaguuaucccgccuaaggauaaaacauugca<br>ugauuguuuaucuauuagagacacggcuucuccauaguuuugcgauaugauaccc<br>gggggguuuacacaucuacauguugucaucuugcaguuggcgaugacugaaccuu<br>ugauagucauguaugguguaguaagugcgccuucggucuuugaguacauacaggc<br>cgacguauugccgcucaagcaggaauaaauaccaggggacauagggaacguuacua<br>uucuuguacaauauaaaucuaagucaguuucuauacaguaugaggugucaaguuc | |

TABLE 9-continued

Exemplary chimeric NDV genomic RNA sequences

| Name | Sequence | SEQ ID NO. |
| --- | --- | --- |
| | uucuaucacagaaccgaccugugucaccacuuuugggacaagugccgaggcaaauc<br>cccugguugugcuuacggauaagguuuccaaguagguggcacgcauauuauuuag<br>guucccgacugaaggggcaguuaccuguauacccaagaguugagucugugagucg<br>uauagaauaggguuaccggugauuaagccgcuaccgauuaaugagcugaguugau<br>uguucccuacaccuaacuuagucaauaaguaauccauauuuccaccagcuagauug<br>uaaagugccugaauagucagcuuguuuaaagcaggugaagugauuuguggucccga<br>auacuguagucaauucgguuagguacagguugagcucuacaccaacuugcugugc<br>aauuuugaugcagucuaauuccugagcuguuuuauuaaauuggucauuaacaaac<br>ugcugcaucuucccaacugccacugcuaguugcgauaauccgucagugaccucaug<br>cacagccucauugguugcggcaaugcucucuuuaagucggaggauguuggcagca<br>uuuuguuuggcuuguaucagagcugcggccgcuguuauuugugcggcaguugca<br>accccaagagccacaccgccaauaauggcgccuauaaggcgccccugucuccccccu<br>ccagauguagucacagacucuuguauccuacggauagagucaccaaggggggguga<br>gcaaagugguucaauguccuguuguaugcauccaagggggcuuucgcacaugccuc<br>cuuauccuugggcagauucgggaggagcuuaacuaugauugauccugucugggau<br>gagguguauauguugacggcuuugucuccuguaaccacaauuccugcagcugcaa<br>gaggccugccaucaauggaguuugccggacagaugcaacucaguaccagcgcaacc<br>cggauagucagcaucauaggugcuggguucuugguagaaggucuggagcccaucu<br>ugcaccuggagggcgccaaccgggauccagaaucuucuacccguguuuuuucuaac<br>uugauagacagguaaacuaacuguaaauaaucaagacagauuaguuuuuuguguc<br>augaugaucugggugagugggcggagcgcaaucucagagacgcagcuuauuucuu<br>aaaaggauuguauuuggcaagggugugccccuucuccagcuuaguagagguaacc<br>ucguggucggcggucacugcgacagcgcguuggguaccugcuuggauaaugauuu<br>uaacgcuccgcaggcacgcgguuugacuccagaguaucuuggccaccugaggagaa<br>gcauuugcuaugggauagcaggcugucccacugcuagagaagaaaggugccaaaag<br>cuuaguccgugcaccucuugcuuuuaccaacacggaaggcccgagcacaucacuga<br>gcccgacagauagaucaaggcuccuuauuuucuuuuccagcuugucaaaugucacu<br>uucuuccccuuccuaucuacaguggucauaaguccaauaugcaagaagagguuagc<br>auaguauccgcugucagacuuagacagagauuuaaccaaaggacuccucgggucua<br>ccuccacauuaauagugacauugagcgcaagauuguacagacucgagccagaaacc<br>uucaauacugcagcugggaucuuguagacaucccucuucgguaccacagucaagga<br>gacaaaguucaccuuguauucuaggguuccacucccgggaaucuucucuggcgcu<br>uucacgugcuugacugcauucacugaugaguauuuguuugccacaacccuacagc<br>uuugcagcacuuggggugccugcacuacugagaaaaccauucucucaguauuagu<br>ugcacucuucuugcaugugacuaucauagugagacaggcccuugccagcucaauaa<br>ggucuccgguauuugggacgcuuccuaggcagagcaucgcagcggaaaguaacuc<br>gcgcuuggguuuaucaucgaucaugccgacgguggcuucuucauucccaacuuga<br>aagaugaauccauagguggugaugaauacugaguccuccuuacuaucaguccacaa<br>gucaaggcgcuggauccuauauugcggggcgauuugcuucuucccaucuccugug<br>ucuuguaggacgaucggaaaugcuaacagguugcuagaagaaugggcagaaucaaa<br>guacagcccaauuguccuagaugaguccaucuuggcacaauuggggcacuccaauu<br>cuacccguauuuuuucuuaaucuuaaauguagcuagauuaauuacgguuacgcga<br>ucauucaguggggcugaggaagcgagagaggauugccgcuuggagaguuggaccu<br>uggguccgcggaucauuaggaagcauucagauagcucaucacucuaucaauaguca<br>cugcccgaauucugaaagcaugaagaaguaugcagagcuugauuuuaguuuuaua<br>aaaauccgguucuucaagggaggauuuuuguggcacagucucacuguugaaauuc<br>agggccugcaucagcucaucaauaacugccagcauguuuugaucuagaaagaucug<br>ccucuuaggauccaucagaagcuuugcauucauggucuugaacuccaccugguaca<br>ucuucgagucuucauaaauacuacuaaggcacagggccaucauaaaagaggucuuu<br>cuggaggccaggcaacucccauuaguuaugaaagaggucucucuggaauuuaggc<br>aacucucauucuugguuaauuccaaugguaaacaggccuccacugugcugguuuu<br>aucuuuugugauaucuucaugaucaaucucuucagaagugcaaggguaaaauucu<br>agaguuugucuggccuucuggagcauguugcugacggcccucagcagguuuuggg<br>agguggugaaggcaugggaacauuccugggucuggaguggccacggggagguuucu<br>agauccgccgccaccgccaccacugcagggcacagaugcccauucgcuccaagauga<br>gcuauaguagcgguccugggcccgcacgcuaaugcuggcauuuuugcggcagaug<br>accguggcugaggucuuguccgugaagacucuaucuuucuuuucucucuugcucu<br>ugcccuggaccugaacgcagaaugucagggagaaguaggaauguggaguacucca<br>ggugucaggguacucccagcugaccuccaccugccgagaauucuuuaauggcuuca<br>gcugcaaguucuuggguggggucagguuugaugaugucccugaugaagaagcugcu<br>gguguaguuuucauacuugagcuugugaacggcauccaccaugaccucaaugggc<br>agacucuccucagcagcugggcaggcacuguccuccuggcacuccacugaguacuc<br>auacuccuuguuguccccucugacucucucugcagagaguguagcagcuccgcacg<br>ucaccccuugggggucagaagagccucugcugcuuuugacacugaaugucaaauca<br>guacugauugucgucagccaccagcaggugaaacguccagaauaauucuuggccuc<br>gcaucuuagaaaggucuuauuuuuggguucuuucugguccuuuaaaauaucagug<br>gaccaaauuccaucuuccuuuuugugaagcagcaggagcgaauggcuuagaaccuc<br>gccuccuuugugacagguguacuggccagcaucuccaaacucuuugacuuggaug<br>gucaggguuuugccagagccuaagaccucacugcucugguccaagguccagguga<br>uaccaucuucuucagggggugucacaggugaggaccaccauuucuccaggggcaucc<br>ggauaccaauccaauucuacgacauaaacaucuuucuucaguucccauauggccac<br>gaggggagaugccagaaaaaccagggaaaaccaagagaugaccaacugcuggugac<br>ccaugguggcgguucuacccguauuuuuucuaaccgcgggggggaacucggugca<br>gauuccgugugaugccgaguggacagggacccgcuacgugugggcaguaguaauua<br>gccauuuagagcaaggcgcuugauuuuccugauuuccucgaucgacccggcugca | |

TABLE 9-continued

Exemplary chimeric NDV genomic RNA sequences

| Name | Sequence | SEQ ID NO. |
|---|---|---|
| | ucuaacuugcuuaggagcuuggcugaagaacucgggugcauugggcgugacauga<br>ucaaugcacggacaguguccuuuuccacuccuauaucaggcccgcaugcaguggcg<br>gguuuaaucaauucagauggauguggcacugguugcgaaaguuuauuaagugcca<br>uuucgccuccuugugucacauagggagaggggucuccagggccugaaacuaaaacc<br>gggugagaucgggcaacugcccguagaucacucagagaugaaauguuggcacaacc<br>gggauccagaaucuucaucauucccaaguuggcuuccaugacugcaacagauguuu<br>ucagcuguuggauuucggaccgcaucauagggauggaggaugucuguuucaagac<br>aagaucuagcugauagucaaccuuacuuacucucugugauaucgccuccaucauag<br>acaucaucgcuugcacaaagucuacagguggcuggacaugauccgcagauacaagg<br>guauugucuuggcucugccuugaucggagagcaugagggguugcaccagcugaua<br>guugugacuccucccauuguccaugauaugcuguguucacgucugugcccugguu<br>uccaggggcggccuugacuugguucugcggucuuuccugacuguuuccgcgacug<br>gguugacuccccugcuguugagucggacguuggugauuccccucuuggggcucg<br>accaugggcccuuuuuagcauuggacgauuuauugcugagcuugucaagcaucaa<br>cagcagagaguugcuugcuccgguccugagcugugugucgacggcuucgucugug<br>gccugggugggggcuggucggcggauguggccggcgggcugucaugcggggguc<br>guuugcucggguguggaugguuguuugucagaucuguccugucgaucgggguug<br>ucuugacuggccgguggcuggaugcucccaugcuucucccaugcugcgcucagca<br>ccuuggucuugccuugugggauugcacuccuuccaacagucucugcugguuuacc<br>cugggcuguaauuauguugucaaugacaguuccacuugucucaaauagcucgucg<br>aucucugcaucuguaaagguggccauguuuguccuggucuaucagguagaggaga<br>gagcagagacucgggagacuugcccugaucucugaauaucccucuucuacccguac<br>uuuuuucuaauucccucggcucuguuuugauuguuagugagccgcauugugccu<br>gugguaucuagggcguacguaguuguacagcagggggagggaggaaagaggggga<br>uguuuguuugagggugugguc auauagagccgcaaaucgaggggucgacuacggg<br>ugagggcauugggauguuuuuguggaagcaggcuggguuuuguccaucaauaccc<br>ccagucggugucguuaucuugggauggcccaggaguuggggaggccccgauugg<br>ggagugcccugugcagaguuuggcgccucccucaugcuauuugcuaccgcucuca<br>ucagauccaggaauugggucuccccaucccccggcuucugguugcccuugcgaucu<br>auucgauccgccuuguagagcuugggacccccccucgcuaagcccagugaggacuc<br>cgacuuguugaguaggcaugucuaugcugcuggucuccucggagacccguugggc<br>agcagcugccaggccccuccuugcugcugggguuagcuuuagcucggcagccaua<br>uccucguuaaugcuacuucccugagccugagcguacucuacuccaagucuccagaa<br>ugaugugcucauaaagucccuggcaaauugguauuucccaguaccuuuaucuagg<br>acugaugccauacccauggcaaaggaguaaaguugugcauacucggcaggcgcaaa<br>gcucaucuggucacuaucaccaaguaaugucauguacggcgcauuaucuccuuuca<br>uccgauacaaacgcaugagcugcuucaucuucuggaugucgccugagaggcuacua<br>agugcaagggcugaugucuugguguugauuccguacuugagugucaagaagaaug<br>caguaagcccgguauuccugauguaugagucuacguccccuaccagguuauaauaa<br>guagagguaccaccugccguguugcggccucucuugagcucgcuaaccaaaaagau<br>gcggacugcaagagacugucugaucgugaguuggauugugcuccugcauacgggg<br>uagaggauguauuucuuuuggacccugccuugcugcauauacuuauugauucgcc<br>uuguuuccgacucaucugcagucucauacgcagucauggcuuuugcuacugugac<br>ccauacuugagccuggauagagaggauccucuccaggguaucggugaugucuucu<br>ggugcaucaucuucggccccggcugugacgaacgggguuccguugcugcaugccc<br>gagggagagauccugcuaucaucgcaaaucucugugcucucucuucagacacucca<br>cuccuauuguugaacuggggcgugccguuggcaaagccaucaaucucaagcacggc<br>caauguggcuucauucuguuucccugcaagggcaacaugguuccucauuaccugu<br>gagugggagcauaaaagagauaugagagcaccuugccugagugguuuguuggcau<br>cuucgcuaacagcaauccggaggcagaauaccacaaagcuccaucuaucuucuggg<br>ucaucacuguuaagagugaauaccgggacgucuacuuuuaagguacucccuuuuu<br>cucccccuccaugagcuccauuggggcgagucugagccgcgaggagcuguucgua<br>cucaucaaauacggaagacauguuggcagaaggcuuucucgaguuugugcuucgg<br>gcucgcacucgagauucacaccuucuacccgugcgacuucaauugcuccuucgccu<br>uuuaucguaacucacggauucucuguuuggu | |
| Exemplary NDV-huIL-12 genomic RNA sequence (codon-optimized) (Version 2.1) | accaaacaaagauuuggugaaugacgagacuacacucaagaauaauugugcgcaac<br>cuuuuuuuaagacauuuauuugaguucgaauucgaguccuaaggagucaggguuc<br>aacuuuuuucuaacauaauaugauuaaaucaacaagaauacaauuggccaaaaaag<br>gagccuauuaauaugugauuuucguuaagagucacaguuacuguaauauccuuug<br>acugcauugccuauaguuuucauguagaauuuuuguugagcacgagucaaguaca<br>guacagaagugucuguaaacauuucuuugaguugguaauaccuaggacagccuu<br>caaauauuuagggcagguacuaugcuucaaguauguccuuaguggauaagguccc<br>uccauggagaucaugccuuuaagcacuaggcugauuauaucgccuauuuuauuga<br>gauuuucgacucuaagaccuaguauuguaaccucuaggaucugucucgugcacug<br>uuuaagugauguccucuuuuucccgucaguagagagauuguaagggguaaauaga<br>aauacugugucagcgagaucacccucagcuuccauauauaucacagaccggauaac<br>ugugucaaugugacuagcgaugaucuggguuaucugaguuauguucgcuagcgu<br>gcucaccagacucuccgcacagaauggacggacgggcuguccccggcuucaauca<br>gcgcagugucaauauucuuccucaaguacuuuauuaaucuugguaaaggacugga<br>uaggaugucugucacacgcugccgcugugaggugaauaaccuggucagugugauc<br>ucaucugauuuagacaaaagcguaccgugccgcugcaccagaguuucgccauccu<br>caccaccucauguacaaauguaggcccgcccagguaacccaugacaaauaccaggua<br>acacuccauaucuccucgacaugcauaaccauuagagagaauauauccuuuugugg<br>aacacggagcaaacaaguucaugaguagaugaaaguaguaucccauugcauacaac | 52 |

TABLE 9-continued

Exemplary chimeric NDV genomic RNA sequences

| Name | Sequence | SEQ ID NO. |
|---|---|---|
| | acuuugaugauuacuaccccgcccucccuuacagaaugcauggcaaucagagauaa | |
| | auugauagcuaguugaucuaguaagcuuugauuggacccuggaggaauuucaaug | |
| | ucacaaugcagcaaugauacagaucuguagggcacugcagauguaauauaccccac | |
| | uacuuuaucugaggucaggucgcuuucccucuguauuuucucuccauaauggacgg | |
| | aacucuuggacaaauccaucuuugcauguuaccuccgccuguagauuccuauaaac | |
| | aaccgaauucaaaaacugaguuggggucggcccgaaaugucguugcggggguuc | |
| | aucucauuugaaaagagcguauuguaauagauaguuucaugugguacaugcaguu | |
| | cgagaagacucaugauggcuccgcucccuucagcuaaguauaaggaguucccgugu | |
| | cuugcacaucuuaccucggguacagaaaggagaugagaugccuuauaccaagagga | |
| | agaugcagucccuaucccucugaacaaguaucguacuaaguagucuucccuccggau | |
| | uuggagaugugaguucaggaugaaucugacuaagugugaaugcgucauaccuugc | |
| | uggagcacucaaaucuaacucuugcaaaaaugccgcagguugucgggugaaugga | |
| | ucuuucacucgagcaccaauaucuugcacagaagggaacucuaauaaaggcucuug | |
| | ggggaacaacaacgccaggauaguaucccugucccucccuuucccugaucaaauuga | |
| | ggcucuuccgagacauguaguacagauuagcugggaauguaauuauguuaggaga | |
| | caugauagagcucacuugaucggggcuaaguaaugguuucacagcauccgacagua | |
| | aauacucagugaguauugaacauuucucuucugcaguuaagccucuuauuuucgg | |
| | gauuucucuuguuguagcaaagaguaccguguacagacagcauaaccgggauauca | |
| | gcugaagcaucuucucauucagguuaucaucuaagacagaugggaacagcagauca | |
| | uacuuauuuccugaauauaagccggagaucacacgucgggugcaagauacuaauag | |
| | uuuugcagacauuucgauaaaauccguaucugcaaguuggugugauccgucaugg | |
| | uugaccaggcccacugcauguaaccuugaaugaaugacgggaugagauauuguag | |
| | cugcaauguuggaaaguagaauuccuggcauauucuuguauaaaucacccauauau | |
| | aagacaauauuguccaggccucuuacucucagguaauagaguugguaagaacaguc | |
| | gaggagcacuucaagugcugcauauucaaauaggcggaccacaucugaauucugag | |
| | cuucacugauccaauuucggguauugucauacacuauuauggcgucauucuuuau | |
| | ggagguaucuucaucauaagaaaccacagacuggccaaucaacuucccgcuggaua | |
| | uugaaagaauguucauuagcucuaucgugggauaugacuccagauuaagcucaua | |
| | acucuugaagauagcuaagucaagucucgcaaagucucccuccgauacagggcuag | |
| | gaucauacauaaacuuauuugaggucacugucccucaguuccgguaccaccccaagu | |
| | agcucgaaaggaaccgcaacaggugcuucucugauacagcaacuaaauuuacuaug | |
| | uaggugcagugugaucucaucauauguccugguuguugucauuggaaagaucgau | |
| | ucgauuagagauaaacccaagagcaugaucuguugguaaaccacauuccccucuuu | |
| | gacuccuucuucagugaacagccuuugagaaucauuggauaugugaauguaaggu | |
| | gacacccuguagagagaugcagggugaaugucaucugaguuauaccaucaucua | |
| | gucuauguugaagauucccagccgugggguaaaggggacaguaaccgaagauacuc | |
| | uaaguuuacauuacaccgagauuuugcaaucguaagagcagcaguccaauuuacuu | |
| | cauuauccccauaagcccagaucaacacggaugaugcccuuagggcagccuuuaca | |
| | uguggcgacauaugagcuauuuuugcaagugaggcagcucuccucuccugugucu | |
| | uugacccgagauaugguacccucaucggaggauucuugcuggugucaucggucaa | |
| | uucuauauugcuuggaagauggaaccaaguaaauuguucaucuccgcugucacau | |
| | cuuguacacccuccgcuuacacuaagaaucucacccucuacgaguucuaucguauc | |
| | aggauuagauacacccaguauuuuccugccucccgucaaaggugaccagcuucuau | |
| | uccgugcauagucugccagugucagagaacacauauuagaagagacuaaggggug | |
| | guuggaucuacuggaggaaaaaacaucgucucuaaacagcauugcaugcaugcuag | |
| | aauaauugacuauccgcaucagccucuugaugccuaauggccuccuaguaagcgca | |
| | aucuuaauuacgguguuuguugugucaacaagcccuugaauuugcuuucuccuac | |
| | cuacagagcuugccuccaugauggcaugcgcaacgcggggaugaaucaccucuuga | |
| | uuaagcaagaauucagccaaugccuucucuucugccucauuauccucugugugcac | |
| | uccagacaauaagggauuugaacaaguuucaaauaggacucuuugcguauguuuc | |
| | uuaagaacaauauuugggcuugcaacagucucaaaauugaaagaguaugggucgu | |
| | ugcacagacuggcccaaucuccauucccaggcggccuaguuaagauauuagucaua | |
| | auguuaggacucaguaaucccacugcuucuagucgcuugaucucugcaaaagcagu | |
| | aguccccgggucaccgauauuucuaguguagagccuugaguauugaagguuacuc | |
| | aguccccccuaauugggcaggagucagaacauaugagugcacaaaagagauguccuc | |
| | aauccacgacugauuaagaucggggugcgaauuguuggugauggagaacucagag | |
| | ucaaaguaugucugcacacaacucauuauauaguuuaaauaguaacagaagucuuu | |
| | gggaagcccguucucgcauagccgugcuacaguagaggcaauguuggcacaggaca | |
| | uuacgguguuuucacugagaucaccugacacuagcacuaauuuagaugaauuuuu | |
| | gaggacuugacugaggauugcuccaucuuugaagauucguuugcuguauaugaag | |
| | aaugugucugaccugaugguuucacgauccuucaaauuauggccaaucaaaugau | |
| | ugacaugaauuaauuccuugaagaaauuaucacuggcuugaugcaacugugucaac | |
| | accaucuccggagagucgucugaucuuaccucucucguuacugcuauuacuugau | |
| | uaucacccuguaccauacaggcaacacgacaaugcgaucuagcugcagcaaguugg | |
| | auugcagcaauugagaucauuguccauagcuucuggcauaauccuucgauaccccc | |
| | ucuggcacugacaauauauaugucaucauuagggacucuugagaggucacaguca | |
| | guagggucacuuggaggauugaaagggucuccuacgaacaucguaguguccauca | |
| | gucuuaggugaauccauucgaagaagugagguaggcccaucaacugauugauggc | |
| | augagcgaacaauuugauugucugauaucuccaauuaagacaguacuuuugcagg | |
| | ucaguuguuaugaagguugcaacucuccgacgguucuugcuuuucggaucaugau | |
| | ugcgguuugaagauacucuuucuuuacagucagugauacguuucuuauugcuguu | |
| | aaaagacaguugacucaucgcuagcauacucuuggucaaggauaugcuauccugaa | |
| | ugacuccauuucccugaaagaaaggugcaaucugaucggcuaggaucccuuccgcc | |
| | aucaccugacaguuccuuaacuucuuugucagcuuagcgaagauccguccauuaac | |
| | uuucacuuccuucuccuugagcgaguaugauacugccacauugucaucucuaagg | |

TABLE 9-continued

Exemplary chimeric NDV genomic RNA sequences

| Name | Sequence | SEQ ID NO. |
|---|---|---|
| | uacucaagggucgucagauauuccaucucuuuauauggaucaaaaucauuugacuc uaaaaacucuaucaagaggcgauuagucgaaguugcuucuuuuacauguuucuuc uggucuucggagagaagguuccgccuaaacgaggcaagccaauuaucguuggggu gugcgauugccuugucuuuuaggaacaugcucagguuggugacagggucauauuc uauacauggcucaaauucaagugcagauaaacucuuauacucucucaacaugauau cgugugaaaucucugcugaaucugcauguaguugcccaaugaccuucccauauau uguauccacuuugacucgcggccacacaccugcauucuucuuucuguacccguuga ugauuguucccuugaagaaagacaguaccugaaggaucauaucaaagucuaccauu uucggugcgcacauuuggcuccugacugccuuugcugcaauacgggacucaagca gugggugaccccacagacgcaacagacacaacaucucagcugcuugauucuguucu aaaccagagaauacaguagcgauugcaugagucacggauucugcuauaucauuggg gaggaggccaauuagaaugucuuuaagcuccugcagguugaaugcgaagaaaucu ccugcaaauguaccugacggcucgaguagcuggacagcuccguaugcaaaucccuc cauuagugauacaacaucguagacuugauuacccaagucuuuugccagagcgucua uuaaccgcaaaaugucaucaauuuucucugauaagcuucugagaugcaccgccgug guugauauuauguugaccauaucucugcccuccaucauaucugcauacaucaauac aaguuccugggguaagacaugugaacuuguucucauucguaugcgucacaacgacaa guucaggagugacaaagacuuggccuaccuuaugggguuagcaucaccaauuuguu ggccgcagaccuuguccuagcugccaccaucagaugccucuggaucuguuuuaua uggagccaugcaaacuuggcuguggaccauuuugagugaaaccagaaugccggau ccguacgaaugcugcugaacuccucugaccgggggacauuguuagaccaagaugac cccagcaguuucuucucuauaugcguacacagccuugugaacaguucuccauaucu cguguugugaauuuggaucuucuucucaaucuuccgaaauuuguugguugaaucu gggaccucaauauuagccaguucuucuaaacaccugggguggagcacuccgguua uucuggaauugugguuaagaguuugguguacugcccuuccgaguuuuaucauuc ucucaguaucaggagaggccgauucaaguauuuuuuuccauugucggcugagaau gagguggucgaagucacauucaucaggaagcgguagcccaguuaauuuccaguaa uagaguaguuugugcuugaccaauggugaagacaggugugacucugguaggauaa ucugaugcucugcccuuucaggaccggagcucgccauguccuacccguauuguua accaugagcuguuuugccuuguaucucauugccacuuacauuuuuucuuaaucaa gagacuauugacaaggcuuaaucugaucgcaugagcacuggcugauuguggucaa cuggcaacauggaauucgagcacgcgccggcauucgguuugauucuugaugucgc agaagauaggugauacaaugccaucuuuccaacuccuuuauaauugacucaacuag ccagaccuggcuucucuaaccccgucaucuuugaggaucucaacuaguaacgggac gauucugaauucuccgaagagaguauuagauauuucagcaaugcugagacaauag gucuuauuagucuugaccacuuuaaaacaaguugauguuguguaugcugcuuugg uacugcuugaacucacucgaguaaugcgacugcgggaugugcuaucgaauacugc agacgcaggguuaagucuugcuuguacaccaucaagcauugucccgaauaccccuc gcaaggugugguuucuauagaagauuaggggauauggaucuguauagacuccagu aacacacgaguuggggcaucuugcugaagccuggcaagggauacuaccuggccgag ugaaggcauugaauguauaaggacuaugaagaguggcuguuuuguugcugacugu cauaggauauaauaacgcgggagagaaguaugaugacccucguugauacaagaaau gagaugucccuacugugagaauucugccuucggcccccaugagugugacuguguu gggcgguacagucaguaccgggucuucgccuaaggauguugacaccuugauagau aagauagccugcuguaugcguuucccaccaaaccguccaggcuuauacgaagacuu ggccauucgaaucugguagucuugcucaucugggcaugugucauuguaucgcuug uauaucacauauuucccuuccuguacagugucacugggugaauuggguuuuaacc cuccguagacugagaaccauacgcggcugucaauaaaagauccacccccuacuccu ggguaguuggccacccaguccccgaauaauguugugacaucuagguccuuuucgu gguacuggccgucgaacccuaaccucccauguaccauccgcguagggacagcugag uuauaaaucuucuuccucugucuccgugacuuucgagcacagcauaucacaacccag gggaguugcacucacacugcaagacuucccgauuuugggugucguccagguugaug gaacgcagaguagaaaagaauacccucccuguugcagauguccggagcacaccaag ugcuaaaauacugauaugaaugugagugaucucugcauccagacaauauuacauuau ggguguagcaguaaugggguagcacucaugucaaaugaggguauucgagugcaacc ugauccuguaguaggcgccgggauaaaaauucagauguucuugaaaugcagaggga uagaaugaugugacaucacuagcaucaucuacaaugaguucuuugccuauccccccc uauauaaucugggucauggauaggugcccccccacccacuguuguuugcagcucca uuaaucugauaagagagagagauguuauugcguucauaauuguggucucaguauuua acaaugccaacggagacucaagggccacuugcuuauauauccuaucuacuacaucu ugauuggaaccaaguguagauguaaucuuuucuucugcccuggaaauccuagucg guaugccuacaagaucgcuaggugugcuagcccccaugcuauauaaaagggaggcu acagauauagccaaggucacuacuguuaagaauaagauugcaauccggaauaucaa gcgccauguauuuuuugccucucuuucaucauucucuaacgcaacuuggcuaacg gcgcgguccaugauugaggacuguugucggugaagcgguagaacggagguuguga agccuggcucgcaauugaggggcggccucucuuaccguucuacccguauaucguc cuuuggucaucuacaaccgguaguuuuuucuuaacucucugaacugacagacuacc agaacuuucacacaaauuacuauuagggaaaccuucguuccucaucuguguucaca uuuuuguaguggcucucaucugaucuagaguauuauucccaagccauaauaaggu cuuuuguugcgccuuuugcuuguacauuagguagcaugcuagaaucaggcuaagu auaccaaaaacaagagauaugauagucaaaacgauauagguaaugagagcagaugu gcuagucaguuugacauugacuuugucuaguuuucuguugcuuuccucuaacuua uucaaagcauuacugaucgaguuguugacauucccaagcucaguugagauaucaag auugccuguuauuauuacuugagaaucuuguauugagauauucuucugauaaguu acaucgaauuccccacugagccuuaaaguuaucccgccuaaggauaaaacauugca | |

TABLE 9-continued

Exemplary chimeric NDV genomic RNA sequences

| Name | Sequence | SEQ ID NO. |
|---|---|---|
| | ugauuguuuaucuauuagagacacggcuucuccauaguuuugcgauaugauaccc<br>ggggguuuacacaucuacauguugucaucuugcaguuggcgaugacugaaccuu<br>ugauagucauguaugguguaguaagugcgccuucggucuuugaguacauacaggc<br>cgacguauugccgcucaagcaggaauaaauaccaggggacauagggaacguuacua<br>uucuuguacaauauaaaucuaagucaguuucuauacaguaugaggugucaaguuc<br>uucuaucacagaaccgaccugugucaccacuuuugggacaagugccgaggcaaauc<br>cccugguugugcuuacggauaagguuuccaaguagguggcacgcauauuauuuag<br>guucccgacugaaggggcaguuaccuguauacccaagaguugagucugugagucg<br>uauagaauaggguuaccggugauuaagccgcuaccgauuaaugagcugaguugau<br>uguucccuacaccuaacuuagucaauaaguaauccauauuuccaccagcuagauug<br>uaaagugccugaauagucagcuuguuuaaagcaggugaagugauuuguggguccga<br>auacuguagucaauucgguuagguacagguugagcucuacaccaacuugcugugc<br>aauuuugaugcagucuaauuccugagcuguuuuauuaaauuggucauuaacaaac<br>ugcugcaucuucccaacugccacugcuaguugcgauaauccgucagugaccucaug<br>cacagccucauugguugcggcaaugcucucuuuaagucggaggauguuggcagca<br>uuuuguuuggcuuguaucagagcugcggccgcuguuauuugugcggcaguugca<br>accccaagagccacaccgccaauaauggcgccuauaaggcgccccugucuccccccu<br>ccagauguagucacagacucuuguauccuacggauagagucaccaagggggguga<br>gcaaagugguucaauguccuguuguaugcauccaagggggcuuucgcacaugccuc<br>cuuauccuugggcagauucgggaggagcuuaacuaugauugauccugucugggau<br>gagguguauauguugacggcuuugucuccuguaaccacaauuccugcagcugcaa<br>gaggccugccaucaauggaguuugccggacagaugcaacucaguaccagcgcaacc<br>cggauagucagcaucauaggugcugguucuugguagaaggucuggagcccaucu<br>ugcaccuggagggcgccaaccgggauccagaaucuucuacccguguuuuuucuaac<br>uugauagacagguaaacuaacuguaaauaaucaagacagauuaguuuuuuguguc<br>augaugaucugggugaguggggcggagcgcaaucucagagacgcagcuuauuucuu<br>aaaaggauuguauuuggcaagggugugccccuucuccagcuuaguagagguaacc<br>ucguggucggcggucacugcgacagcgcguuggguaccugcuuggauaaugauuu<br>uaacgcuccgcaggcacgcgguuugacuccagaguaucuuggccaccugaggagaa<br>gcauuugcuaugggauagcaggcugucccacugcuagagaagaaaggugccaaaag<br>cuuaguccgugcaccucuugcuuuuaccaacacggaaggcccgagcacaucacuga<br>gcccgacagauagaucaaggcuccuuauuuucuuuuccagcuugucaaaugucacu<br>uucuuccccuuccuaucuacaguggucauaaguccaauaugcaagaagagguuagc<br>auaguauccgcugucagacuuagacagagauuuaaccaaaggacuccucgggucua<br>ccuccacauuaauagugacauugagcgcaagauuguacagacucgagccagaaacc<br>uucaauacugcagcugggaucuuguagacaucccucuucgguaccacagucaagga<br>gacaaaguucaccuuguauucuaggguuccacucccgggaaucuucucuggcgcu<br>uucacgugcuugacugcauucacugaugaguauuuguuugccacaacccuacagc<br>uuugcagcacuuggggugccugcacuacugagaaaaccauucucucaguauuagu<br>ugcacucuucuugcaugugacuaucauagugagacaggcccuugccagcucaauaa<br>ggucuccgguauuugggacgcuuccuaggcagagcaucgcagcggaaaguaacuc<br>gcgcuuggguuuaucaucgaucaugccgacgguggcuucuucauucccaacuuga<br>aagaugaauccauagguggugaugaauacugaguccuccuuacuaucaguccacaa<br>gucaaggcgcuggauccuauauugcggggcgauuugcuucuucccaucuccugug<br>ucuuguaggacgaucggaaaugcuaacagguugcuagaagaaugggcagaaucaaa<br>guacagcccaauuguccuagaugaguccaucuuggcacaauuggggcacuccaauu<br>cuacccguauuuuuucuuaaucuuaaauguagcuagauuaauuacgguuacgcga<br>ucauucaguggggcugaggaagcgagagaggauugccgcuuggagaguuggaccu<br>uggguccgcggaucauuaggaagcauucagauaggacaucacgcggucgauuguc<br>acggcucugauccgaaaggcgugcagcaggaugcacagcuugaucuuggucuugu<br>agaaaucuggcuccuccagagaggacuucugaggcacugucucgcuauugaaguu<br>cagggccugcaucagcucgucgaucacggccagcauauucugauccagaaagaucu<br>gccucuugggguccaucagcagcuuggcguucauggucuugaacuccaccugaua<br>caucuucagguccucguagaugcuagacaggcacagggccaucauaaagcuugucu<br>uucuagaggccaggcaggagccguuggugaugaagcuugucucccggcuguucag<br>acaggacucguucuuggucagcuccaguggcaggcaggccuccacuguggagguc<br>uuauccuuugugauguccucguggucgaucuccucgcugguacaaggguaaaacu<br>ccagugucuggcgggccuucugcagcauauuggacacggcccucagcagguucug<br>gcugguggugcaggcaggggaacaugccugggucagggguugccacuggcagauuc<br>cuagauccuccuccuccuccgccgcugcaaggcacagaggcccacucggaccagga<br>gcuagaauaguagcgguccugggcccucacgcugauagaggcguucuuucuacag<br>aucacgguggcagaugucuuaucggugaacacucuguccuucuucucccgcuugg<br>acuugcccugcaccugcacgcaaaaggucagagagaaauaggagugugguguggcuc<br>caggugucaggguacucccaggacaccuccaccugucugcuauucuucagaggcuu<br>cagcugcagguucuuagggggaucgggcuugaugaugucccggauaaagaaggag<br>cugguauaauucucguacuucagcuugugcacggcauccaccaucacuucgauagg<br>cagggacuccucugcugcuggacaggcagaguccuccuggcacuccacggaauacu<br>cguacuccuuguuaucgccgcgcacccucucggcgcucaggguggcugcuccgca<br>ugucacucccugugggucagaggauccccugcuagacuucacagaaaaugucagau<br>cgguggagauugguggucagccaccaacaggugaaccggccgcuauaauucuuggc<br>cucgcaccgcaggaaggucuuguucuuuggcuccuucugauccuucaggaugucu<br>guggaccagaugccauccuccuucuugugcagcagcagcagggaguggcucagcac<br>cucuccucccuugugacagguguacuggccggcgucgccgaacuccuucaccugga<br>uugucagggucuugccgcuucccagcaccucggagcucugauccaguguccaggu<br>gaugccauccuccucggguguguccgcaggucagcaccaccaucucgccaggggcau | |

TABLE 9-continued

Exemplary chimeric NDV genomic RNA sequences

| Name | Sequence | SEQ ID NO. |
|---|---|---|
| | cgggauaccaguccagcuccaccacguacacauccuuuuucaguucccagauugcg<br>accagaggugaggccagaaacaccagggagaaccaugagaugaccagcugcugaug<br>gcacaugguggcgguucuacccguauuuuuucuaaccgcggggggaacucggug<br>cagauuccgugugaugccgaguggacagggacccgcuacgugugg cagu aguaau<br>uagccauuuagagcaaggcgcuugauuuuccugauuuccucgaucgacccggcug<br>caucuaacuugcuuaggagcuuggcugaagaacucgggugcauugggcgugacau<br>gaucaaugcacggacaguguccuuuuccacuccuauaucaggcccgcaugcagugg<br>cgguuuaaucaauucagauggauguggcacugguugcgaaaguuuauuaagugc<br>cauuucgccuccuugugucacauagggagagggucuccagggccugaaacuaaaa<br>ccgggugagaucgggcaacugcccguagaucacucagagaugaaauguuggcacaa<br>ccgggauccagaaucuucaucauucccaaguuggcuuccaugacugcaacagaugu<br>uuucagcuguuggauuucggaccgcaucauagggauggaggaugucuguuucaag<br>acaagaucuagcugauagucaaccuuacuuacucucugugauaucgccuccaucau<br>agacaucaucgcuugcacaaagucuacagguggcuggacaugauccgcagauacaa<br>ggguauugucuuggcucugccuugaucggagagcaugagggguugcaccagcuga<br>uaguugugacuccucccauuguccaugauaugcuguguucacgucugugcccugg<br>uuuccaggggcggccuugacuugguucugcggucuuuccugacuguuuccgcgac<br>uggguugacuccccugcuguugagucggacguuggugauuccccucuuggggc<br>ucgaccaugggcccuuuuuagcauuggacgauuuauugcugagcuugucaagcau<br>caacagcagagaguugcuugcuccgguccugagcugugugucgacggcuucgucu<br>guggccuggguggggggcuggucggcggauguggccggcgggcugucaugcggg<br>gucguuugcucgggugugg augguuguuugucagaucuguccugucgaucgggg<br>uugucuugacuggccgguggcuggaugcucccaugcuucucccaugcugcgcuca<br>gcaccuuggucuugccuugugggauugcacuccuuccaacagucucugcugguuu<br>acccugggcuguaauuauguugucaaugacaguuccacuugucucaaauagcucg<br>ucgaucucugcaucuguaaagguggccauguuuguccuggucuaucagguagagg<br>agagagcagagacucgggagacuugcccugaucucugaauaucccucuucuacccg<br>uacuuuuuucuaauucccucggcucuguuuugauuguuagugagccgcauugugc<br>cugugguaucuagggcguacguaguuguacagcagggggagggaggaaagagggg<br>gauguuuguuugagggugugg ucauauagagccgcaaaucgagggucgacuacg<br>ggugagggcauugggauguuuuuguggaagcaggcuggguuuuguccaucaaua<br>cccccagucggugucguuaucuugggauggcccaggaguuggggaggccccgau<br>uggggagugcccugugcagaguuuggcgccucccucaugcuauuugcuaccgcuc<br>ucaucagauccaggaauuggg ucuccccauccccggcuucugguugcccuugcga<br>ucuauucgauccgccuuguagagcuugggaccccccucgcuaagcccagugagga<br>cuccgacuuguugaguaggcaugucuaugcugcuggucuccucggagacccguug<br>ggcagcagcugccaggccccuccuugcugcugggguuagcuuuagcucggcagcc<br>auauccucguuaaugcuacuucccugagccugagcguacucuacuccaagucucca<br>gaaugaugugcucauaaagucccuggcaaauugguauuucccaguaccuuuaucu<br>aggacugaugccauacccauggcaaaggaguaaaguugugcauacucggcaggcgc<br>aaagcucaucuggucacuaucaccaaguaaugucauguacggcgcauuaucuccuu<br>ucauccgauacaaacgcaugagcugcuucaucuucuggaugucgccugagaggcua<br>cuaagugcaagggcugaugucuugguguugauuccguacuugagugucaagaaga<br>augcaguaagcccgguauuccugauguaugagucuacguccccuaccagguuauaa<br>uaaguagagguaccaccugccguguugcggccucucuugagcucgcuaaccaaaaa<br>gaugcggacugcaagagacugucugaucgugaguuggauugugcuccugcauacg<br>ggguagaggauguauuucuuuuggacccugccuugcugcauauacuuauugauuc<br>gccuuguuuccgacucaucugcagucucauacgcagucauggcuuuugcuacugu<br>gacccauacuugagccuggauagagaggauccucuccaggguaucggugaugucu<br>ucuggugcaucaucuucggccccggcugugacgaacgggguuccguugcugcaug<br>cccgagggagagauccugcuaucaucgcaaaucucugugcucucucuucagacacu<br>ccacuccuauuguugaacuggggcgugccguuggcaaagccaucaaucucaagcac<br>ggccaauguggcuucauucuguuucccugcaagggcaacaugguuccucauuacc<br>ugugagugggagcauaaaagagauaugagagcaccuugccugagugguuuguugg<br>caucuucgcuaacagcaauccggaggcagaauaccacaaagcuccaucuaucuucu<br>gggucaucacuguuaagagugaauaccgggacgucuacuuuuaagguacucccuu<br>uuucuccccuccaugagcuccauugggcgagucugagccgcgaggagcuguuc<br>guacucaucaaauacggaagacauguuggcagaaggcuuucucgaguuugugcuu<br>cgggcucgcacucgagauucacaccuucuacccgugcgacuucaauugcuccuucg<br>ccuuuuaucguaacucacggauucucuguuuggu | |
| Exemplary NDV-huIL-12 genomic RNA sequence (non-codon-optimized) (Version 3) | accaaacaaagauuuggugaaugacgagacuacacucaagaauaauugugcgcaac<br>cuuuuuuuaagacauuuauuugaguucgaauucgaguccuaaggagucaggguuc<br>aacuuuuuucuaacauaauaugauuaaaucaacaagaauacaauuggccaaaaaag<br>gagccuauuaauaugugauuuucguuaagagucacaguuacuguaauauccuuug<br>acugcauugccuauaguuuucauguagaauuuuuguugagcacgagucaaguaca<br>guacagaagugucuguaaacauuucuuugaguugguaauaccuaggacagccuu<br>caaauauuuagggcagguacuaugcuucaaguauguccuuaguggauaagguccc<br>uccauggagaucaugccuuuaagcacuaggcugauuauaucgccuauuuuauuga<br>gauuuucgacucuaagaccuaguauuguaaccucuaggaucugucucgugcacug<br>uuuaagugauguccucuuuuucccgucaguagagagauuguaagggguaaauaga<br>aauacugugucagcgagaucacccucagcuuccauauauaucacagaccggauaac<br>ugugucaaugugacuagcgaugaucuggguuaucugaguuauguucgcuagcgu<br>gcucaccagacucuccgcacagaauggacggacgggcuguccccggcuucaauca<br>gcgcagugucaauauucuuccucaaguacuuuauuaaucuugguaaaggacugga | 60 |

TABLE 9-continued

Exemplary chimeric NDV genomic RNA sequences

| Name | Sequence | SEQ ID NO. |
|---|---|---|
| | uaggaugucugucacacgcugccgcugugaggugaauaaccuggucagugugauc<br>ucaucugauuuagacaaaagcguaccgugccgcugcaccagaguuuucgccauccu<br>caccaccucauguacaaauguaggcccgcccagguaacccaugacaaauaccaggua<br>acacuccauaucuccucgacaugcauaaccauuagagagaauauauccuuuugugg<br>aacacggagcaaacaaguucaugaguagaugaaaguaguaucccauugcauacaac<br>acuuugaugauuacuaccccgcccucccuuacagaaugcauggcaaucagagauaa<br>auugauagcuaguugaucuaguaagcuuugauuggacccuggaggaauuucaaug<br>ucacaaugcagcaaugauacagaucuguagggcacugcagauguaauauaccccac<br>uacuuuaucugaggucaggucgcuuuccucuguauuuucucuccauaauggacgg<br>aacucuuggacaaauccaucuuugcauguuaccuccgccuguagauuccuauaaac<br>aaccgaauucaaaaacugaguuggggucggcccgaaaugucguugcggggguuc<br>aucucauuugaaaagagcguauuguaauagauaguuucaugugguacaugcaguu<br>cgagaagacucaugauggcuccgcucccuucagcuaaguauaaggaguucccgugu<br>cuugcacaucuuaccucggguacagaaaggagaugagaugccuuauaccaagagga<br>agaugcagucccuaucccucugaacaaguaucguacuaaguagucuuccuccggau<br>uuggagaugugaguucaggaugaaucugacuaagugugaaugcgucauaccuugc<br>uggagcacucaaaucuaacucuugcaaaaaugccgcagguugucgggugaaugga<br>ucuuucacucgagcaccaauaucuugcacagaagggaacucuaauaauggcucuug<br>ggggaacaacaacgccaggauaguaucccuguccucccuuucccugaucaaauuga<br>ggcucuuccgagacauguaguacagauuagcugggaauguaauuauguuaggaga<br>caugauagagcucacuugaucggggcuaaguaaugguuucacagcauccgacagua<br>aauacucagugaguauugaacauuucucuucugcaguuaagccucuuauuuucgg<br>gauuucucuuguuguagcaaagaguaccguguacagacagcauaaccgggauauca<br>gcugaagcaucuucucauucagguuaucaucuaagacagaugggaacagcagauca<br>uacuuauuuccugaauauaagccggagaucacacgucgggugcaagauacuaauag<br>uuuugcagacauuucgauaaaauccguaucugcaaguuggugugauccgucaugg<br>uugaccaggcccacugcauguaaccuugaaugaaugacgggaugagauauuguag<br>cugcaauguuggaaaguagaauuccuggcauauucuuguauaaaucacccauauau<br>aagacaauauuguccaggccucuuacucucagguaauagaguugguaagaacaguc<br>gaggagcacuucaagugcugcauauucaaauaggcggaccacaucugaauucugag<br>cuucacugauccaauuucggguauugucauacacuauuauggcgucauucuuuau<br>ggagguaucuucaucauaagaaaccacagacuggccaaucaacuucccgcuggaua<br>uugaaagaauguucauuagcucuaucgugggauaugacuccagauuaagcucaua<br>acucuugaagauagcuaagucaagucucgcaaagucucccuccgauacagggcuag<br>gaucauacauaaacuuauuugaggucacuguccucaguuccgguaccaccccaagu<br>agcucgaaaggaaccgcaacaggugcuucucugauacagcaacuaaauuuacuaug<br>uaggugcagugugaucucaucauauguccugguuguugucauuggaaagaucgau<br>ucgauuagagauaaacccaagagcaugaucuguugguaaaccacauuccccucuuu<br>gacuccuucuucagugaacagccuuugagaaucauuggauaugugaauguaaggu<br>gacacccuguagagagaugcaggggugaaugucaucugaguuauaccaucaucua<br>gucuauguugaagauucccagccgugggguaaaggggacaguaaccgaagauacuc<br>uaaguuuacauuacaccgagauuuugcaaucguaagagcagcaguccaauuuacuu<br>cauuauccccauaagcccagaucaacacggaugaugcccuuagggcagccuuuaca<br>uguggcgacauaugagcuauuuuugcaagugaggcagcucuccucuccugugucu<br>uugacccgagauaugguacccucaucggaggauucuugcuggugucaucggucaa<br>uucuauauugcuuggaagauggaaccaaguaaauuguucaucuccgcugucacau<br>cuuguacacccuccgcuuacacuaagaaucucacccucuacgaguucuaucguauc<br>aggauuagauacacccaguauuuccugccucccgucaaggugaccagcuucuau<br>uccgugcauagucugccagugucagagaacacauauuagaagagacuaaggggug<br>guuggaucuacuggaggaaaaaacaucgucucuaaacagcauugcaugcaugcuag<br>aauaauugacuauccgcaucagccucuugaugccuaauggccuccuaguaagcgca<br>aucuuaauuacgguguuuguugugucaacaagcccuugaauuugcuuucuccuac<br>cuacagagcuugccuccaugauggcaugcgcaacgcggggaugaaucaccucuuga<br>uuaagcaagaauucagccaaugccuucucuucugccucauuauccucugugugcac<br>uccagacaauaagggauuugaacaaguuucaaauaggacucuuugcguauguuuc<br>uuaagaacaauauuugggcuugcaacagucucaaaauugaaagaguaugggucgu<br>ugcacagacuggcccaaucuccauucccaggcggccuaguuaagauauuagucaua<br>auguuaggacucaguaaucccacugcuucuagucgcuugaucucugcaaaagcagu<br>aguccccgggucaccgauauuucuaguguagagccuugaguauugaagguuacuc<br>aguccccccuaauugggcaggagucagaacauaugagugcacaaaagagauguccuc<br>aauccacgacugauuaagaucggggugcgaauuguuggugauggagaacucagag<br>ucaaaguaugucugcacacaacucauuauauaguuuaaauaguaacagaagucuuu<br>gggaagcccguucucgcauagccgugcuacaguagaggcaauguuggcacaggaca<br>uuacgguguuuucacugagaucaccugacacuagcacuaauuuagaugaauuuuu<br>gaggacuugacugaggauugcuccaucuuugaagauucguuugcuguauaugaag<br>aaugugucugaccugaugguuucacgauccuucaaauuauggccaaucaaaugau<br>ugacaugaauuaauuccuugaagaaauuaucacuggcuugaugcaacugugucaac<br>accaucuccggagagucgucugaucuuaccucucucguuacugcuauuacuugau<br>uaucacccuguaccauacaggcaacacgacaaugcgaucuagcugcagcaaguugg<br>auugcagcaauugagaucauuguccauagcuucuggcauaauccuucgauaccccc<br>ucuggcacugacaauauauaugucaucauuagggacucuugagaggucacaguca<br>guagggucacuuggaggauugaaagggucuccuacgaacaucguaguguccauca<br>gucuuaggugaauccauucgaagaagugagguaggcccaucaacugauugauggc<br>augagcgaacaauuugauugucugauaucuccaauuaagacaguacuuuugcagg<br>ucaguuguuaugaagguugcaacucuccgacgguucuugcuuuucggaucaugau | |

TABLE 9-continued

Exemplary chimeric NDV genomic RNA sequences

| Name | Sequence | SEQ ID NO. |
| --- | --- | --- |
| | ugcgguuugaagauacucuuucuuuacagucagugauacguuucuuauugcuguu<br>aaaagacaguugacucaucgcuagcauacucuuggucaaggauaugcuauccugaa<br>ugacuccauuucccugaaagaaaggugcaaucugaucggcuaggaucccuuccgcc<br>aucaccugacaguuccuuaacuucuuugucagcuuagcgaagauccguccauuaac<br>uuucacuuccuucuccuugagcgaguaugauacugccacauugucaucucuaagg<br>uacucaagggucgucagauauuccaucucuuuauauggaucaaaaucauuugacuc<br>uaaaaacucuaucaagaggcgauuagucgaaguugcuucuuuuacauguuucuuc<br>uggucuucggagagaagguuccgccuaaacgaggcaagccaauuaucguuggggu<br>gugcgauugccuugucuuuuaggaacaugcucagguuggugacagggucauauuc<br>uauacauggcucaaauucaagugcagauaaacucuuauacucucucaacaugauau<br>cgugugaaaucucugcugaaucugcauguaguugcccaaugaccuucccauauau<br>uguauccacuuugacucgcggccacacaccugcauucuucuuucuguacccguuga<br>ugauuguucccuugaagaaagacaguaccugaaggaucauaucaaagucuaccauu<br>uucggugcgcacauuuggcuccugacugccuuugcugcaauacgggacucaagca<br>gugggugaccccacagacgcaacagacacaacaucucagcugcuugauucuguucu<br>aaaccagagaauacaguagcgauugcaugagucacggauucugcuauaucauuggg<br>gaggaggccaauuagaaugucuuuaagcuccugcagguugaaugcgaagaaaucu<br>ccugcaaauguaccugacggcucgaguagcuggacagcuccguaugcaaaucccuc<br>cauuagugauacaacaucguagacuugauuacccaagucuuuugccagagcgucua<br>uuaaccgcaaaaugucaucaauuuucucugauaagcuucugagaugcaccgccgug<br>guugauauuauguugaccauaucucugcccuccaucauaucugcauacaucaauac<br>aaguuccugguaagacaugugaacuuguucucauucguaugcgucacaacgacaa<br>guucaggagugacaaagacuuggccuaccuuaugguuagcaucaccaauuuguu<br>ggccgcagaccuuguccuagcugccaccaucagaugccucuggaucuguuuuaua<br>uggagccaugcaaacuuggcuguggaccauuuugagugaaaccagaaugccggau<br>ccguacgaaugcugcugaacuccucugaccgggggacauuguuagaccaagaugac<br>cccagcaguuucuucucuauaugcguacacagccuugugaacaguucuccauaucu<br>cguguugugaauuuggaucuucuucucaaucuuccgaaauuuguugguugaaucu<br>gggaccucaauauuagccaguucuucuaaacaccugggguggagcacuccgguua<br>uucuggaauugugguuaagaguuugguguacugcccuuccgaguuuuaucauuc<br>ucucaguaucaggagaggccgauucaaguauuuuuuccauugucggcugagaau<br>gagguggucgaagucacauucaucaggaagcgguagcccaguuaauuuccaguaa<br>uagaguaguuugugcuugaccaauggugaagacaggugugacucugguaggauaa<br>ucugaugcucugcccuuucaggaccggagcucgccauguccuacccguauuguua<br>accaugagcuguuuugccuuguaucucauugccacuuacauuuuuucuuaaucaa<br>gagacuauugacaaggcuuaaucugaucgcaugagcacuggcugauuguggucaa<br>cuggcaacauggaauucgagcacgcgccggcauucgguuugauucuugaugucgc<br>agaagauaggugauacaaugccaucuuuccaacuccuuuauaauugacucaacuag<br>ccagaccuggcuucucuaaccccgucaucuuugaggaucucaacuaguaacgggac<br>gauucugaauucuccgaagagaguauuagauauuucagcaaugcugagacaauag<br>gucuuauuagucuugaccacuuuaaaacaaguugauguuguguaugcugcuuugg<br>uacugcuugaacucacucgaguaaugcgacugcgggaugugcuaucgaauacugc<br>agacgcaggguuaagucuugcuuguacaccaucaagcauugucccgaauaccccuc<br>gcaaggugugguuucuauagaagauuaggggauauggaucuguauagacuccagu<br>aacacacgaguuggggcaucuugcugaagccuggcaagggauacuaccuggccgag<br>ugaaggcauugaauguauaaggacuaugaagaguggcuguuuuguugcugacugu<br>cauaggauauaauaacgcgggagagaaguaugaugacccucguugauacaagaaau<br>gagaugucccuacugugagaauucugccuucggcccccaugagugugacuguguu<br>gggcgguacagucaguaccgggucuucgccuaaggauguugacaccuugauagau<br>aagauagccugcuguaugcguuucccaccaaaccguccaggcuuauacgaagacuu<br>ggccauucgaaucugguagucuugcucaucugggcaugugucauuguaucgcuug<br>uauaucacauauuucccuuccuguacagugucacugggugaauuggguuuuaacc<br>cuccguagacugagaaccauacgcggcugucaauaaaagauccacccccuacuccu<br>ggguaguuggccacccaguccccgaauaauguugugacaucuagguccuuuucgu<br>gguacuggccgucgaacccuaaccucccauguaccauccgcguagggacagcugag<br>uuauaaucuucuuccucugucuccgugacuuucgagcacagcauaucacaacccag<br>gggaguugcacucacacugcaagacuuccgauuuuggugucguccagguugaug<br>gaacgcagaguagaaaagaauacccucccuguugcagauguccggagcacaccaag<br>ugcuaaauacugauaugaaugugagugaucucugcauccagacaauauuacauuau<br>ggguguagcaguaaugguagcacucaugucaaaugagguauucgagugcaacc<br>ugauccuguaguaggcgccgggauaaaauucagauguucuugaaaugcagaggga<br>uagaaugaugugacaucacuagcaucaucuacaaugaguucuuugccuaucccccc<br>uauauaaucugggucauggauaggugcccccccacccacuguuguuugcagcucca<br>uuaaucugauaagagagagauguuauugcguucauaauuguggucucaguauuua<br>acaaugccaacggagacucaagggccacuugcuuauauauccuaucuacuacaucu<br>ugauuggaaccaaguguagauguaaucuuuucuucugcccuggaaauccuagucg<br>guaugccuacaagaucgcuaggugugcuagcccccaugcuauauaaaagggaggcu<br>acagauauagccaaggucacuacuguuaagaauaagauugcaauccggaauaucaa<br>gcgccauguauuuuuugccucucuuucaucauucucuaacgcaacuuggcuaacg<br>gcgcgguccaugauugaggacuguugucggugaagcgguagaacggagguuguga<br>agccuggcucgcaauugaggggcggccucucuuaccguucuacccguauaucguc<br>cuuuggucaucuacaaccgguaguuuuuucuuaacucucugaacugacagacuacc<br>agaacuuucacacaaauuacuauuagggaaaccuucguuccucaucuguguucaca<br>uuuuuguaguggcucucaucugaucuagaguauuauucccaagccauaauaaggu<br>cuuuuguugcgccuuuugcuuguacauuagguagcaugcuagaaucaggcuaagu | |

TABLE 9-continued

Exemplary chimeric NDV genomic RNA sequences

| Name | Sequence | SEQ ID NO. |
|---|---|---|
| | auaccaaaaacaagagauaugauagucaaaacgauauagguaaugagagcagaugu | |
| | gcuagucaguuugacauugacuuugucuaguuuucuguugcuuuccucuaacuua | |
| | uucaaagcauuacugaucgaguuguugacauucccaagcucaguugagauaucaag | |
| | auugccuguuauuauuacuugagaaucuuguauugagauauucuucugauaaguu | |
| | acaucgaauuccccacugagccuuaaaguuaucccgccuaaggauaaaacauugca | |
| | ugauuguuuaucuauuagagacacggcuucuccauaguuuugcgauaugauaccc | |
| | gggggguuuacacaucuacauguugucaucuugcaguuggcgaugacugaaccuu | |
| | ugauagucauguaugguguaguaagugcgccuucggucuuugaguacauacaggc | |
| | cgacguauugccgcucaagcaggaauaaauaccaggggacauagggaacguuacua | |
| | uucuuguacaauauaaaucuaagucaguuucuauacaguaugaggugucaaguuc | |
| | uucuaucacagaaccgaccugugucaccacuuuugggacaagugccgaggcaaauc | |
| | cccugguugugcuuacggauaagguuuccaaguagguggcacgcauauuauuuag | |
| | guucccgacugaaggggcaguuaccuguauacccaagaguugagucugugagucg | |
| | uauagaauaggguuaccggugauuaagccgcuaccgauuaaugagcugaguugau | |
| | uguucccuacaccuaacuuagucaauaaguaauccauauuuccaccagcuagauug | |
| | uaaagugccugaauagucagcuuguuuaaagcaggugaagugauuugugguccga | |
| | auacuguagucaauucgguuagguacagguugagcucuacaccaacuugcugugc | |
| | aauuuugaugcagucuaauuccugagcuguuuuauuaaauuggucauuaacaaac | |
| | ugcugcaucuucccaacugccacugcuaguugcgauaauccgucagugaccucaug | |
| | cacagccucauugguugcggcaaugcucucuuuaagucggaggauguuggcagca | |
| | uuuuguuuggcuuguaucagagcugcggccgcuguuauuugugcggcaguugca | |
| | accccaagagccacaccgccaauaauggcgccuauaaggcgccccugucucccccu | |
| | ccagauguagucacagacucuuguauccuacggauagagucaccaagggggguga | |
| | gcaaaguggucaauguccuguuguaugcauccaagggggcuuucgcacaugccuc | |
| | cuuauccuugggcagauucgggaggagcuuaacuaugauugauccugucugggau | |
| | gagguguauauguugacggcuuugucuccuguaaccacaauuccugcagcugcaa | |
| | gaggccugccaucaauggaguuugccggacagaugcaacucaguaccagcgcaacc | |
| | cggauagucagcaucauaggugcugguucuugguagaaggucuggagcccaucu | |
| | ugcaccuggagggcgccaaccgggauccagaaucuucuacccguguuuuuucuaac | |
| | uugauagacagguaaacuaacuguaaauaaucaagacagauuaguuuuuuguguc | |
| | augaugaucugggugagugggcggagcgcaaucucagagacgcagcuuauuucuu | |
| | aaaaggauuguauuuggcaagggugugccccuucuccagcuuaguagagguaacc | |
| | ucguggucggcggucacugcgacagcgcguuggguaccugcuuggauaaugauuu | |
| | uaacgcuccgcaggcacgcgguuugacuccagaguaucuuggccaccugaggagaa | |
| | gcauuugcuaugggauagcaggcugucccacugcuagagaagaaaggugccaaaag | |
| | cuuaguccgugcaccucuugcuuuuaccaacacggaaggcccgagcacaucacuga | |
| | gcccgacagauagaucaaggcuccuuauuuucuuuuccagcuugucaaaugucacu | |
| | uucuuccccuuccuaucuacaguggucauaaguccaauaugcaagaagagguuagc | |
| | auaguauccgcugucagacuuagacagagauuuaaccaaaggacuccucgggucua | |
| | ccuccacauuaauagugacauugagcgcaagauuguacagacucgagccagaaacc | |
| | uucaauacugcagcugggaucuuguagacaucccucuucgguaccacagucaagga | |
| | gacaaaguucaccuuguauucuaggguuccacucccgggaaucuucucuggcgcu | |
| | uucacgugcuugacugcauucacugaugaguauuuguuugccacaacccuacagc | |
| | uuugcagcacuugggggugccugcacuacugagaaaaccauucucucaguauuagu | |
| | ugcacucuucuugcaugugacuaucauagugagacaggcccuugccagcucaauaa | |
| | ggucuccgguauuugggacgcuuccuaggcagagcaucgcagcggaaaguaacuc | |
| | gcgcuuggguuuaucaucgaucaugccgacgguggcuucuucauucccaacuuga | |
| | aagaugaauccauagguggugaugaauacugaguccuccuuacuaucaguccacaa | |
| | gucaaggcgcuggauccuauauugcggggcgauuugcuucuucccaucuccugug | |
| | ucuuguaggacgaucggaaaugcuaacagguugcuagaagaaugggcagaaucaaa | |
| | guacagcccaauuguccuagaugaguccaucuuggcacaauuggggcacuccaauu | |
| | cuacccguauuuuuucuuaaucuuaaauguagcuagauuaauuacgguuacgcga | |
| | ucauucaguggggcugaggaagcgagagaggauugccgcuuggagaguuggaccu | |
| | uggguccgcggaucauuaggaagcauucagauagcucaucacucuaucaauaguca | |
| | cugcccgaauucugaaagcaugaagaaguaugcagagcuugauuuuaguuuuaua | |
| | aaaauccgguucuucaagggaggauuuuuguggcacagucucacuguugaaauuc | |
| | agggccugcaucagcucaucaauaacugccagcauguuuugaucuagaaagaucug | |
| | ccucuuaggauccaucagaagcuuugcauucauggucuugaacuccaccugguaca | |
| | ucuucaagucuucauaaauacuacuaaggcacagggccaucauaaaagaggucuuu | |
| | cuggaggccaggcaacucccauuaguuaugaaagaggucucucuggaauuuaggc | |
| | aacucucauucuugguuaauuccaaugguaaacaggccuccacugugcugguuuu | |
| | aucuuuugugauaucuucaugaucaaucucuucagaagugcaaggguaaaauucu | |
| | agaguuugucuggccuucuggagcauguugcugacggcccucagcagguuuuggg | |
| | aguggugaaggcaugggaacauuccugggucuggaguggccacggggagguuucu | |
| | agauccgccgccaccgccaccacugcagggcacagaugcccauucgcuccaagauga | |
| | gcuauaguagcgguccugggcccgcacgcuaaugcuggcauuuuugcggcagaug | |
| | accguggcugaggucuuguccgugaagacucuaucuuucuuuucucucuugcucu | |
| | ugcccuggaccugaacgcagaaugucagggagaaguaggaauguggaguacucca | |
| | ggugucaggguacucccagcugaccuccaccugccgagaauucuuuaauggcuuca | |
| | gcugcaaguucuugggugggucagguuugaugaugucccugaugaagaagcugcu | |
| | gguguaguuuucauacuugagcuugugaacggcauccaccaugaccucaaugggc | |
| | agacucuccucagcagcugggcaggcacuguccuccuggcacuccacugaguacuc | |
| | auacuccuuguuguccccucugacucucucugcagagaguguagcagcuccgcacg | |
| | ucaccccuugggggucagaagagccucugcugcuuuugacacugaaugucaaauca | |
| | guacugauugucgucagccaccagcaggugaaacguccagaauaauucuuggccuc | |

TABLE 9-continued

Exemplary chimeric NDV genomic RNA sequences

| Name | Sequence | SEQ ID NO. |
| --- | --- | --- |
| | gcaucuuagaaaggucuuauuuuugguucuuucugguccuuuaaaauaucagug<br>gaccaaauuccaucuuccuuuuugugaagcagcaggagcgaauggcuuagaaccuc<br>gccuccuuugugacagguguacuggccagcaucuccaaacucuuugacuuggaug<br>gucaggguuuugccagagccuaagaccucacugcucugguccaagguccagguga<br>uaccaucuucuucagggugucacaggugaggaccaccauuucuccaggggcaucc<br>ggauaccaauccaauucuacgacauaaacaucuuucuucaguucccauauggccac<br>gaggggagaugccagaaaaaccagggaaaaccaagagaugaccaacugcuggugac<br>acaugguggcgguucuacccguauuuuuucuaaccgcgggggggaacucggugca<br>gauuccgugugaugccgaguggacagggacccgcuacguguggcaguaguaauua<br>gccauuuagagcaaggcgcuugauuuuccugauuuccucgaucgacccggcugca<br>ucuaacuugcuuaggagcuuggcugaagaacucgggugcauugggcgugacauga<br>ucaaugcacggacaguguccuuuuccacuccuauaucaggcccgcaugcaguggcg<br>gguuuaaucaauucagauggauguggcacugguugcgaaaguuuauuaagugcca<br>uuucgccuccuugugucacauagggagaggggucuccagggccugaaacuaaaacc<br>gggugagaucgggcaacugcccguagaucacucagagaugaaauguuggcacaacc<br>gggauccagaaucuucaucauucccaaguuggcuuccaugacugcaacagauguuu<br>ucagcuguuggauuucggaccgcaucauagggauggaggaugucuguuucaagac<br>aagaucuagcugauagucaaccuuacuuacucucugugauaucgccuccaucauag<br>acaucaucgcuugcacaaagucuacagguggcuggacaugauccgcagauacaagg<br>guauugucuuggcucugccuugaucggagagcaugaggguugcaccagcugaua<br>guugugacuccucccauuguccaugauaugcuguguucacgucugugcccugguu<br>uccaggggcggccuugacuugguucugcggucuuuccugacuguuuccgcgacug<br>gguugacuccccugcuguugagucggacguuggugauuccccucuuggggcucg<br>accaugggcccuuuuuagcauuggacgauuuauugcugagcuugucaagcaucaa<br>cagcagagaguugcuugcuccgguccugagcugugugucgacggcuucgucugug<br>gccugggugggggcuggucggcggauguggccggcgggcugucaugcggggguc<br>guuugcucggguguggaugguuguuugucagaucuguccugucgaucgggguug<br>ucuugacuggccgguggcuggaugcucccaugcuucucccaugcugcgcucagca<br>ccuuggucuugccuugugggauugcacuccuuccaacagucucugcugguuuacc<br>cugggcuguaauuauguugucaaugacaguuccacuugucucaaauagcucgucg<br>aucucugcaucuguaaagguggccauguuuguccuggucuaucagguagaggaga<br>gagcagagacucgggagacuugcccugaucucugaauaucccucuucuacccguac<br>uuuuuucuaauucccucggcucuguuuugauuguuagugagccgcauugugccu<br>gugguaucuagggcguacguaguuguacagcaggggggagggaggaaagaggggga<br>uguuuguuugagggugugguggucauauagagccgcaaaucgaggggucgacuacggg<br>ugagggcauugggauguuuuuguggaagcaggcuggguuuuguccaucaauaccc<br>ccagucggugucguuaucuugggauggcccaggaguuggggaggccccgauugg<br>ggagugcccugugcagaguuuggcgccucccucaugcuauuugcuaccgcucuca<br>ucagauccaggaauugggucuccccaucccccggcuucugguugcccuugcgaucu<br>auucgauccgccuuguagagcuugggacccccccucgcuaagcccagugaggacuc<br>cgacuuguugaguaggcaugucuaugcugcuggucuccucggagacccguugggc<br>agcagcugccaggccccuccuugcugcugggguuagcuuuagcucggcagccaua<br>uccucguuaaugcuacuucccugagccugagcguacucuacuccaagucuccagaa<br>ugaugugcucauaaagucccuggcaaauugguauuucccaguaccuuuaucuagg<br>acugaugccauacccauggcaaaggaguaaaguugugcauacucggcaggcgcaaa<br>gcucaucuggucacuaucaccaaguaaugucauguacggcgcauuaucuccuuuca<br>uccgauacaaacgcaugagcugcuucaucuucuggaugucgccugagaggcuacua<br>agugcaagggcugaugucuugguguugauuccguacuugagugucaagaagaaug<br>caguaagcccgguauuccugauguaugagucuacguccccuaccagguuauaauaa<br>guagagguaccaccugccguguugcggccucucuugagcucgcuaaccaaaaagau<br>gcggacugcaagagacugucugaucgugaguuggauugugcuccugcauacgggg<br>uagaggauguauuucuuuuggacccugccuugcugcauauacuuauugauucgcc<br>uuguuuccgacucaucugcagucucauacgcagucauggcuuuugcuacugugac<br>ccauacuugagccuggauagagaggauccucuccaggguaucggugaugucuucu<br>ggugcaucaucuucggccccggcugugacgaacgggguuccguugcugcaugccc<br>gagggagagauccugcuaucaucgcaaaucucugugcucucucuucagacacucca<br>cuccuauuguugaacuggggcgugccguuggcaaagccaucaaucucaagcacggc<br>caauguggcuucauucuguuucccugcaagggcaacaugguuccucauuaccugu<br>gagugggagcauaaaagagauaugagagcaccuugccugagugguuuguuggcau<br>cuucgcuaacagcaauccggaggcagaauaccacaaagcuccaucuaucuucuggg<br>ucaucacuguuaagagugaauaccgggacgucuacuuuuaagguacucccuuuuu<br>cucccccuccaugagcuccauugggcgagucugagccgcgaggagcuguucgua<br>cucaucaaauacggaagacauguuggcagaaggcuuucucgaguuugugcuucgg<br>gcucgcacucgagauucacaccuucuacccgugcgacuucaauugcuccuucgccu<br>uuuaucguaacucacggauucucuguuuggu | |

TABLE 10

Exemplary plasmid sequences encoding chimeric NDVs (nucleic acid)

| Name | Sequence | SEQ ID NO. |
|---|---|---|
| Nucleic acid sequence of the pT7NDV-LS-L289A plasmid containing a human IL-12 transgene (gene open reading frame in bold) (Version 1) *GCC*= codon for L289A mutation | tcagctcactcaaaggcggtaatacggttatccacagaatcaggggataacgcaggaaag<br>aacatgtgagcaaaaggccagcaaaaggccaggaaccgtaaaaaggccgcgttgctggc<br>gtttttccataggctccgcccccctgacgagcatcacaaaaatcgacgctcaagtcagagg<br>tggcgaaacccgacaggactataaagataccaggcgtttccccctggaagctccctcgtg<br>cgctctcctgttccgaccctgccgcttaccggatacctgtccgcctttctcccttcggga<br>agcgtggcgctttctcatagctcacgctgtaggtatctcagttcggtgtaggtcgttcgc<br>tccaagctgggctgtgtgcacgaaccccccgttcagcccgaccgctgcgccttatccggt<br>aactatcgtcttgagtccaacccggtaagacacgacttatcgccactggcagcagccact<br>ggtaacaggattagcagagcgaggtatgtaggcggtgctacagagttcttgaagtggtgg<br>cctaactacggctacactagaagaacagtatttggtatctgcgctctgctgaagccagtt<br>accttcggaaaaagagttggtagctcttgatccggcaaacaaaccaccgctggtagcggt<br>ggtttttttgtttgcaagcagcagattacgcgcagaaaaaaaggatctcaagaagatcct<br>ttgatcttttctacggggtctgacgctcagtggaacgaaaactcacgttaagggattttg<br>gtcatgagattatcaaaaaggatcttcacctagatccttttaaattaaaaatgaagtttt<br>aaatcaatctaaagtatatatgagtaaacttggtctgacagttaccaatgcttaatcagt<br>gaggcacctatctcagcgatctgtctatttcgttcatccatagttgcctgactccccgtc<br>gtgtagataactacgatacgggagggcttaccatctggccccagtgctgcaatgataccg<br>cgagacccacgctcaccggctccagatttatcagcaataaaccagccagccggaagggcc<br>gagcgcagaagtggtcctgcaactttatccgcctccatccagtctattaattgttgccgg<br>gaagctagagtaagtagttcgccagttaatagtttgcgcaacgttgttgccattgctaca<br>ggcatcgtggtgtcacgctcgtcgtttggtatggcttcattcagctccggttcccaacga<br>tcaaggcgagttacatgatcccccatgttgtgcaaaaaagcggttagctccttcggtcct<br>ccgatcgttgtcagaagtaagttggccgcagtgttatcactcatggttatggcagcactg<br>cataattctcttactgtcatgccatccgtaagatgcttttctgtgactggtgagtactca<br>accaagtcattctgagaatagtgtatgcggcgaccgagttgctcttgcccggcgtcaata<br>cgggataataccgcgccacatagcagaactttaaaagtgctcatcattggaaaacgttct<br>tcggggcgaaaactctcaaggatcttaccgctgttgagatccagttcgatgtaacccact<br>cgtgcacccaactgatcttcagcatcttttactttcaccagcgtttctgggtgagcaaaa<br>acaggaaggcaaaatgccgcaaaaaagggaataagggcgacacggaaatgttgaatactc<br>atactcttcctttttcaatattattgaagcatttatcagggttattgtctcatgagcgga<br>tacatatttgaatgtatttagaaaaataaacaaataggggttccgcgcacatttccccga<br>aaagtgccacctgacgtctaagaaaccattattatcatgacattaacctataaaaatagg<br>cgtatcacgaggccctttcgtctcgcgcgtttcggtgatgacggtgaaaacctctgacac<br>atgcagctcccggagacggtcacagcttgtctgtaagcggatgccgggagcagacaagcc<br>cgtcagggcgcgtcagcgggtgttggcgggtgtcggggctggcttaactatgcggcatca<br>gagcagattgtactgagagtgcaccataaaattgtaaacgttaatattttgttaaaattc<br>gcgttaaatttttgttaaatcagctcattttttaaccaataggccgaaatcggcaaaatc<br>ccttataaatcaaaagaatagcccgagatagggttgagtgttgttccagtttggaacaag<br>agtccactattaaagaacgtggactccaacgtcaaagggcgaaaaaccgtctatcagggc<br>gatggcccactacgtgaaccatcacccaaatcaagttttttggggtcgaggtgccgtaaa<br>gcactaaatcggaaccctaaagggagcccccgatttagagcttgacggggaaagccggcg<br>aacgtggcgagaaaggaagggaagaaagcgaaaggagcgggcgctagggcgctggca<br>agtgtagcggtcacgctgcgcgtaaccaccacacccgccgcgcttaatgcgccgctacag<br>ggcgcgtactatggttgctttgacgtatgcggtgtgaaataccgcacagatgcgtaaggaga<br>aaataccgcatcaggcgccattcgccattcaggctgcgcaactgttgggaagggcgatcgg<br>tgcgggcctcttcgctattacgccagctggcgaaagggggatgtgctgcaaggcgattaa<br>gttgggtaacgccagggttttcccagtcacgacgttgtaaaacgacggccagtgccaagc<br>tttaatacgactcactatagggaccaaacagagaatccgtgagttacgataaaaggcgaagg<br>agcaattgaagtcgcacgggtagaaggtgtgaatctcgagtgcgagcccgaagcacaaac<br>tcgagaaagccttctgccaacatgtcttccgtatttgatgagtacgaacagctcctcgcggctc<br>agactcgccccaatggagctcatggagggggagaaaaagggagtaccttaaaagtagacg<br>tcccggtattcactcttaacagtgatgacccagaagatagatggagctttgtggtattctgcctc<br>cggattgctgttagcgaagatgccaacaaaccactcaggcaaggtgctctcatatctcttttat<br>gctcccactcacaggtaatgaggaaccatgttgcccttgcagggaaacagaatgaagccac<br>attggccgtgcttgagattgatggctttgccaacggcacgccccagttcaacaataggagtg<br>gagtgtctgaagagagagcacagagatttgcgatgatagcaggatctctccctcgggcatg<br>cagcaacggaaccccgttcgtcacagccggggccgaagatgatgcaccagaagacatca<br>ccgataccctggagaggatcctctctatccaggctcaagtatgggtcacagtagcaaaagcc<br>atgactgcgtatgagactgcagatgagtcggaaacaaggcgaatcaataagtatatgcagc<br>aaggcagggtccaaaagaaatacatcctctaccccgtatgcaggagcacaatccaactcac<br>gatcagacagtctcttgcagtccgcatctttttggttagcgagctcaagagaggccgcaacac<br>ggcaggtggtacctctacttattataacctggtaggggacgtagactcatacatcaggaatac<br>cgggcttactgcattcttcttgacactcaagtacggaatcaacaccaagacatcagcccttgc<br>acttagtagcctctcaggcgacatccagaagatgaagcagctcatgcgtttgtatcggatgaa<br>aggagataatgcgccgtacatgacattacttggtgatagtgaccagatgagctttgcgcctgc<br>cgagtatgcacaactttactcctttgccatgggtatggcatcagtcctagataaaggtactggg<br>aaataccaatttgccagggactttatgagcacatcattctggagacttggagtagagtacgctc<br>aggctcagggaagtagcattaacgaggatatggctgccgagctaaagctaaccccagcag<br>caaggaggggcctggcagctgctgcccaacgggtctccgaggagaccagcagcatagac<br>atgcctactcaacaagtcggagtcctcactgggcttagcgagggggggtcccaagctctac<br>aaggcggatcgaatagatcgcaagggcaaccagaagccggggatggggagacccaattc<br>ctggatctgatgagagcggtagcaaatagcatgagggaggcgccaaactctgcacagggc<br>actccccaatcggggcctcccccaactcctgggccatcccaagataacgacaccgactgg<br>gggtattgatggacaaaacccagcctgcttccacaaaaacatcccaatgccctcacccgtag<br>tcgacccctcgatttgcggctctatatgaccacaccctcaaacaaacatccccctctttcctcc | 31 |

TABLE 10-continued

Exemplary plasmid sequences encoding chimeric NDVs (nucleic acid)

| Name | Sequence | SEQ ID NO. |
|---|---|---|
| | ctccccctgctgtacaactacgtacgccctagataccacaggcacaatgcggctcactaaca<br>atcaaaacagagccgagggaattagaaaaaagtacgggtagaagagggatattcagagat<br>cagggcaagtctcccgagtctctgctctctcctctacctgatagaccaggacaaacatggcc<br>acctttacagatgcagagatcgacgagctatttgagacaagtggaactgtcattgacaacata<br>attacagcccagggtaaaccagcagagactgttggaaggagtgcaatcccacaaggcaag<br>accaaggtgctgagcgcagcatgggagaagcatgggagcatccagccaccggccagtca<br>agacaaccccgatcgacaggacagatctgacaaacaaccatccacacccgagcaaacga<br>ccccgcatgacagcccgccggccacatccgccgaccagcccccacccaggccacaga<br>cgaagccgtcgacacacagctcaggaccggagcaagcaactctctgctgttgatgcttgac<br>aagctcagcaataaatcgtccaatgctaaaaagggcccatggtcgagcccccaagagggg<br>aatcaccaacgtccgactcaacagcaggggagtcaacccagtcgcggaaacagtcagga<br>aagaccgcagaaccaagtcaaggccgcccctggaaaccagggcacagacgtgaacaca<br>gcatatcatggacaatgggaggagtcacaactatcagctggtgcaacccctcatgctctccg<br>atcaaggcagagccaagacaatacccttgtatctgcggatcatgtccagccacctgtagactt<br>tgtgcaagcgatgatgtctatgatggaggcgatatcacagagagtaagtaaggttgactatca<br>gctagatcttgtcttgaaacagacatcctccatccctatgatgcggtccgaaatccaacagctg<br>aaaacatctgttgcagtcatggaagccaacttgggaatgatgaagattctggatcccggttgt<br>gccaacatttcatctctgagtgatctacgggcagttgcccgatctcacccggttttagtttcagg<br>ccctggagacccctctccctatgtgacacaaggaggcgaaatggcacttaataaactttcgc<br>aaccagtgccacatccatctgaattgattaaacccgccactgcatgcgggcctgatatagga<br>gtggaaaaggacactgtccgtgcattgatcatgtcacgcccaatgcacccgagttcttcagc<br>caagctcctaagcaagttagatgcagccgggtcgatcgaggaaatcaggaaaatcaagcg<br>ccttgctctaaatggctaattactactgccacacgtagcgggtccctgtccactcggcatcaca<br>cggaatctgcaccgagttcccccCCGCGGTTAGAAAAAATACGGGT<br>AGAACCGCCACCATGGGTCACCAGCAGTTGGTCATCT<br>CTTGGTTTTCCCTGGTTTTTCTGGCATCTCCCCTCGT<br>GGCCATATGGGAACTGAAGAAAGATGTTTATGTCGTAG<br>AATTGGATTGGTATCCGGATGCCCCTGGAGAAATGGTG<br>GTCCTCACCTGTGACACCCCTGAAGAAGATGGTATCAC<br>CTGGACCTTGGACCAGAGCAGTGAGGTCTTAGGCTCTG<br>GCAAAACCCTGACCATCCAAGTCAAAGAGTTTGGAGAT<br>GCTGGCCAGTACACCTGTCACAAAGGAGGCGAGGTTCT<br>AAGCCATTCGCTCCTGCTGCTTCACAAAAAGGAAGATG<br>GAATTTGGTCCACTGATATTTTAAAGGACCAGAAAGAA<br>CCCAAAAATAAGACCTTTCTAAGATGCGAGGCCAAGAA<br>TTATTCTGGACGTTTCACCTGCTGGTGGCTGACGACAAT<br>CAGTACTGATTTGACATTCAGTGTCAAAAGCAGCAGAG<br>GCTCTTCTGACCCCCAAGGGGTGACGTGCGGAGCTGCT<br>ACACTCTCTGCAGAGAGAGTCAGAGGGGACAACAAGG<br>AGTATGAGTACTCAGTGGAGTGCCAGGAGGACAGTGCC<br>TGCCCAGCTGCTGAGGAGAGTCTGCCCATTGAGGTCAT<br>GGTGGATGCCGTTCACAAGCTCAAGTATGAAAACTACA<br>CCAGCAGCTTCTTCATCAGGGACATCATCAAACCTGAC<br>CCACCCAAGAACTTGCAGCTGAAGCCATTAAAGAATTC<br>TCGGCAGGTGGAGGTCAGCTGGGAGTACCCTGACACCT<br>GGAGTACTCCACATTCCTACTTCTCCCTGACATTCTGCG<br>TTCAGGTCCAGGGCAAGAGCAAGAGAGAAAAGAAAGA<br>TAGAGTCTTCACGGACAAGACCTCAGCCACGGTCATCT<br>GCCGCAAAAATGCCAGCATTAGCGTGCGGGCCCAGGAC<br>CGCTACTATAGCTCATCTTGGAGCGAATGGGCATCTGTG<br>CCCTGCAGTGGTGGCGGTGGCGGCGGATCTAGAAAC<br>CTCCCCGTGGCCACTCCAGACCCAGGAATGTTCCCATGC<br>CTTCACCACTCCCAAAACCTGCTGAGGGCCGTCAGCAA<br>CATGCTCCAGAAGGCCAGACAAACTCTAGAATTTTACC<br>CTTGCACTTCTGAAGAGATTGATCATGAAGATATCACA<br>AAAGATAAAACCAGCACAGTGGAGGCCTGTTTACCATT<br>GGAATTAACCAAGAATGAGAGTTGCCTAAATTCCAGAG<br>AGACCTCTTTCATAACTAATGGGAGTTGCCTGGCCTCCA<br>GAAAGACCTCTTTTATGATGGCCCTGTGCCTTAGTAGTA<br>TTTATGAAGACTCGAAGATGTACCAGGTGGAGTTCAAG<br>ACCATGAATGCAAAGCTTCTGATGGATCCTAAGAGGCA<br>GATCTTTCTAGATCAAAACATGCTGGCAGTTATTGATGA<br>GCTGATGCAGGCCCTGAATTTCAACAGTGAGACTGTGC<br>CACAAAAATCCTCCCTTGAAGAACCGGATTTTTATAAA<br>ACTAAAATCAAGCTCTGCATACTTCTTCATGCTTTCAGA<br>ATTCGGGCAGTGACTATTGATAGAGTGATGAGCTATCT<br>GAATGCTTCCTAATGATCCGCGGacccaaggtccaactctccaagcg<br>gcaatcctctctcgcttcctcagccccactgaatgatcgcgtaaccgtaattaatctagctacat<br>ttaagattaagaaaaaatacgggtagaattggagtgccccaattgtgccaagatggactcatc<br>taggacaattgggctgtactttgattctgcccattcttctagcaacctgttagcatttccgatcgt<br>cctacaagacacaggagatgggaagaagcaaatcgccccgcaatataggatccagcgcct<br>tgacttgtggactgatagtaaggaggactcagtattcatcaccacctatggattcatctttcaag<br>ttgggaatgaagaagccaccgtcggcatgatcgatgataaacccaagcgcgagttactttcc<br>gctgcgatgctctgcctaggaagcgtcccaaataccggagaccttattgagctggcaaggg<br>cctgtctcactatgatagtcacatgcaagaagagtgcaactaatactgagagaatggttttctc | |

TABLE 10-continued

Exemplary plasmid sequences encoding chimeric NDVs (nucleic acid)

| Name | Sequence | SEQ ID NO. |
|---|---|---|
| | agtagtgcaggcaccccaagtgctgcaaagctgtagggttgtggcaaacaaatactcatca<br>gtgaatgcagtcaagcacgtgaaagcgccagagaagattcccgggagtggaaccctagaa<br>tacaaggtgaactttgtctccttgactgtggtaccgaagagggatgtctacaagatcccagct<br>gcagtattgaaggtttctggctcgagtctgtacaatcttgcgctcaatgtcactattaatgtgga<br>ggtagacccgaggagtcctttggttaaatctctgtctaagtctgacagcggatactatgctaac<br>ctcttcttgcatattggacttatgaccactgtagataggaaggggaagaaagtgacatttgaca<br>agctggaaaagaaaataaggagccttgatctatctgtcgggctcagtgatgtgctcgggcctt<br>ccgtgttggtaaaagcaagaggtgcacggactaagcttttggcacctttcttctctagcagtgg<br>gacagcctgctatcccatagcaaatgcttctcctcaggtggccaagatactctggagtcaaac<br>cgcgtgcctgcggagcgttaaaatcattatccaagcaggtacccaacgcgctgtcgcagtg<br>accgccgaccacgaggttacctctactaagctggagaaggggcacacccttgccaaataca<br>atccttttaagaaataagctgcgtctctgagattgcgctccgcccactcacccagatcatcatg<br>acacaaaaaactaatctgtcttgattatttacagttagtttacctgtctatcaagttagaaaaaac<br>acgggtagaagattctggatcccggttggcgccctccaggtgcaagatgggctccagacct<br>tctaccaagaacccagcacctatgatgctgactatccgggttgcgctggtactgagttgcatct<br>gtccggcaaactccattgatggcaggcctcttgcagctgcaggaattgtggttacaggagac<br>aaagccgtcaacatatacacctcatcccagacaggatcaatcatagttaagctcctcccgaat<br>ctgcccaaggataaggaggcatgtgcgaaagccccccttggatgcatacaacaggacattga<br>ccactttgctcacccccccttggtgactctatccgtaggatacaagagtctgtgactacatctgg<br>agggggagacaggggcgccttataggcgccattattggcggtgtggctcttggggttgca<br>actgccgcacaaataacagcggccgcagctctgatacaagccaaacaaaatgctgccaac<br>atcctccgacttaaagagagcattgccgcaaccaatgaggctgtgcatgaggtcactgacg<br>gattatcgcaactagcagtggcagttgggaagatgcagcagtttgttaatgaccaatttaataa<br>aacagctcaggaattagactgcatcaaaattgcacagcaagttggtgtagagctcaacctgta<br>cctaaccgaattgactacagtattcggaccacaaatcacttcacctgctttaaacaagctgact<br>attcaggcactttacaatctagctggtggaaatatggattacttattgactaagttaggtgtagg<br>gaacaatcaactcagctcattaatcggtagcggcttaatcaccggtaaccctattctatacgac<br>tcacagactcaactcttgggtatacaggtaact***GCC***ccttcagtcgggaacctaaataatat<br>gcgtgccacctacttggaaaccttatccgtaagcacaaccaggggatttgcctcggcacttgt<br>cccaaaagtggtgacacaggtcggttctgtgatagaagaacttgacacctcatactgtataga<br>aactgacttagatttatattgtacaagaatagtaacgttccctatgtcccctggtatttattcctgct<br>tgagcggcaatacgtcggcctgtatgtactcaaagaccgaaggcgcacttactacaccatac<br>atgactatcaaaggttcagtcatcgccaactgcaagatgacaacatgtagatgtgtaaacccc<br>ccgggtatcatatcgcaaaactatggagaagccgtgtctctaatagataaacaatcatgcaat<br>gttttatccttaggcgggataactttaaggctcagtggggaattcgatgtaacttatcagaaga<br>atatctcaatacaagattctcaagtaataataacaggcaatcttgatatctcaactgagcttggg<br>aatgtcaacaactcgatcagtaatgctttgaataagttagaggaaagcaacagaaaactaga<br>caaagtcaatgtcaaactgactagcacatctgctctcattacctatatcgttttgactatcatatct<br>cttgtttttggtatacttagcctgattctagcatgctacctaatgtacaagcaaaaggcgcaaca<br>aaagaccttattatggcttgggaataatactctagatcagatgagagccactacaaaaatgtg<br>aacacagatgaggaacgaaggtttccctaatagtaatttgtgtgaaagttctggtagtctgtca<br>gttcagagagttaagaaaaaactaccggttgtagatgaccaaaggacgatatacgggtaga<br>acggtaagagaggccgcccctcaattgcgagccaggcttcacaacctccgttctaccgcttc<br>accgacaacagtcctcaatcatggaccgcgccgttagccaagttgcgttagagaatgatgaa<br>agagaggcaaaaaatacatggcgcttgatattccggattgcaatcttattcttaacagtagtga<br>ccttggctatatctgtagcctcccttttatatagcatggggggctagcacacctagcgatcttgta<br>ggcataccgactaggatttccagggcagaagaaaagattacatctacacttggttccaatcaa<br>gatgtagtagataggatatataagcaagtggcccttgagtctccgttggcattgttaaatactg<br>agaccacaattatgaacgcaataacatctctctcttatcagattaatggagctgcaaacaacag<br>tgggtgggggcacctatccatgacccagattatataggggggataggcaaagaactcatt<br>gtagatgatgctagtgatgtcacatcattctatccctctgcatttcaagaacatctgaattttatcc<br>cggcgcctactacaggatcaggttgcactcgaataccctcatttgacatgagtgctacccatt<br>actgctacacccataatgtaatattgtctggatgcagagatcactcacattcatatcagtatttag<br>cacttggtgtgctccggacatctgcaacagggagggtattcttttctactctgcgttccatcaac<br>ctggacgacacccaaaatcggaagtcttgcagtgtgagtgcaactcccctgggttgtgatat<br>gctgtgctcgaaagtcacggagacagaggaagaagattataactcagctgtccctacgcgg<br>atggtacatgggaggttagggttcgacggccagtaccacgaaaaggacctagatgtcacaa<br>cattattcggggactgggtggccaactacccaggagtagggggtggatcttttattgacagc<br>cgcgtatggttctcagtctacggagggttaaaacccaattcacccagtgacactgtacagga<br>agggaaatatgtgatatacaagcgatacaatgacacatgcccagatgagcaagactaccag<br>attcgaatggccaagtcttcgtataagcctggacggtttggtgggaaacgcatacagcaggc<br>tatcttatctatcaaggtgtcaacatccttaggcgaagacccggtactgactgtaccgcccaac<br>acagtcacactcatgggggccgaaggcagaattctcacagtagggacatctcatttcttgtat<br>caacgagggtcatcatacttctctcccgcgttattatatcctatgacagtcagcaacaaaacag<br>ccactcttcatagtccttatacattcaatgccttcactcggccaggtagtatcccttgccaggctt<br>cagcaagatgccccaactcgtgtgttactggagtctatacagatccatatcccctaatcttctat<br>agaaaccacaccttgcgaggggtattcgggacaatgcttgatggtgtacaagcaagacttaa<br>ccctgcgtctgcagtattcgatagcacatcccgcagtcgcattactcgagtgagttcaagcag<br>taccaaagcagcatacacaacatcaacttgttttaaagtggtcaagactaataagacctattgt<br>ctcagcattgctgaaatatctaatactctcttcggagaattcagaatcgtcccgttactagttga<br>gatcctcaaagatgacggggttagagaagccaggtctggctagttgagtcaattataaagga<br>gttggaaagatggcattgtatcacctatcttctgcgacatcaagaatcaaaccgaatgccggc<br>gcgtgctcgaattccatgttgccagttgaccacaatcagccagtgctcatgcgatcagattaa<br>gccttgtcaatagtctcttgattaagaaaaaatgtaagtggcaatgagatacaaggcaaaaca<br>gctcatggttaacaatacgggtaggacatggcgagctccggtcctgaaagggcagagcatc | |

TABLE 10-continued

Exemplary plasmid sequences encoding chimeric NDVs (nucleic acid)

| Name | Sequence | SEQ ID NO. |
|---|---|---|
| | agattatcctaccagagtcacacctgtcttcaccattggtcaagcacaaactactctattactgg | |
| | aaattaactgggctaccgcttcctgatgaatgtgacttcgaccacctcattctcagccgacaat | |
| | ggaaaaaaatacttgaatcggcctctcctgatactgagagaatgataaaactcggaagggca | |
| | gtacaccaaactcttaaccacaattccagaataaccggagtgctccaccccaggtgtttagaa | |
| | gaactggctaatattgaggtcccagattcaaccaacaaatttcggaagattgagaagaagatc | |
| | caaattcacaacacgagatatggagaactgttcacaaggctgtgtacgcatatagagaagaa | |
| | actgctggggtcatcttggtctaacaatgtcccccggtcagaggagttcagcagcattcgtac | |
| | ggatccggcattctggtttcactcaaaatggtccacagccaagtttgcatggctccatataaaa | |
| | cagatccagaggcatctgatggtggcagctaggacaaggtctgcggccaacaaattggtga | |
| | tgctaacccataaggtaggccaagtctttgtcactcctgaacttgtcgttgtgacgcatacgaa | |
| | tgagaacaagttcacatgtcttacccaggaacttgtattgatgtatgcagatatgatggagggc | |
| | agagatatggtcaacataatatcaaccacggcggtgcatctcagaagcttatcagagaaaatt | |
| | gatgacattttgcggttaatagacgctctggcaaaagacttgggtaatcaagtctacgatgttg | |
| | tatcactaatggagggatttgcatacggagctgtccagctactcgagccgtcaggtacatttg | |
| | caggagatttcttcgcattcaacctgcaggagcttaaagacattctaattggcctcctccccaa | |
| | tgatatagcagaatccgtgactcatgcaatcgctactgtattctctggtttagaacagaatcaag | |
| | cagctgagatgttgtgtctgttgcgtctgtggggtcacccactgcttgagtcccgtattgcagc | |
| | aaaggcagtcaggagccaaatgtgcgcaccgaaaatggtagactttgatatgatccttcagg | |
| | tactgtctttcttcaagggaacaatcatcaacgggtacagaaagaagaatgcaggtgtgtggc | |
| | cgcgagtcaaagtggatacaatatatgggaaggtcattgggcaactacatgcagattcagca | |
| | gagatttcacacgatatcatgttgagagagtataagagtttatctgcacttgaatttgagccatg | |
| | tatagaatatgaccctgtcaccaacctgagcatgttcctaaaagacaaggcaatcgcacacc | |
| | ccaacgataattggcttgcctcgtttaggcggaaccttctctccgaagaccagaagaaacatg | |
| | taaaagaagcaacttcgactaatcgcctcttgatagagtttttagagtcaaatgattttgatccat | |
| | ataaagagatggaatatctgacgacccttgagtaccttagagatgacaatgtggcagtatcat | |
| | actcgctcaaggagaaggaagtgaaagttaatggacggatcttcgctaagctgacaaagaa | |
| | gttaaggaactgtcaggtgatggcggaagggatcctagccgatcagattgcacctttctttca | |
| | gggaaatggagtcattcaggatagcatatccttgaccaagagtatgctagcgatgagtcaact | |
| | gtcttttaacagcaataagaaacgtatcactgactgtaaagaaagagtatcttcaaaccgcaat | |
| | catgatccgaaaagcaagaaccgtcggagagttgcaaccttcataacaactgacctgcaaa | |
| | agtactgtcttaattggagatatcagacaatcaaattgttcgctcatgccatcaatcagttgatg | |
| | ggcctacctcacttcttcgaatggattcacctaagactgatggacactacgatgttcgtaggag | |
| | accctttcaatcctccaagtgaccctactgactgtgacctctcaagagtccctaatgatgacat | |
| | atatattgtcagtgccagagggggtatcgaaggattatgccagaagctatggacaatgatctc | |
| | aattgctgcaatccaacttgctgcagctagatcgcattgtcgtgttgcctgtatggtacagggt | |
| | gataatcaagtaatagcagtaacgagagaggtaagatcagacgactctccggagatggtgtt | |
| | gacacagttgcatcaagccagtgataatttcttcaaggaattaattcatgtcaatcatttgattgg | |
| | ccataatttgaaggatcgtgaaaccatcaggtcagacacattcttcatatacagcaaacgaat | |
| | cttcaaagatggagcaatcctcagtcaagtcctcaaaaattcatctaaattagtgctagtgtca | |
| | ggtgatctcagtgaaaacaccgtaatgtcctgtgccaacattgcctctactgtagcacggctat | |
| | gcgagaacgggcttcccaaagacttctgttactatttaaactatataatgagttgtgtgcagac | |
| | atactttgactctgagttctccatcaccaacaattcgcaccccgatcttaatcagtcgtggattg | |
| | aggacatctcttttgtgcactcatatgttctgactcctgcccaattaggggactgagtaacctt | |
| | caatactcaaggctctacactagaaatatcggtgacccggggactactgcttttgcagagatc | |
| | aagcgactagaagcagtgggattactgagtcctaacattatgactaatatcttaactaggccg | |
| | cctgggaatggagattgggccagtctgtgcaacgacccatactctttcaattttgagactgttg | |
| | caagcccaaatattgttcttaagaaacatacgcaaagagtcctatttgaaacttgttcaaatccc | |
| | ttattgtctggagtgcacacagaggataatgaggcagaagagaaggcattggctgaattcttg | |
| | cttaatcaagaggtgattcatccccgcgttgcgcatgccatcatggaggcaagctctgtaggt | |
| | aggagaaagcaaattcaagggcttgttgacacaacaaacaccgtaattaagattgcgcttact | |
| | aggaggccattaggcatcaagaggctgatgcggatagtcaattattctagcatgcatgcaat | |
| | gctgtttagagacgatgtttttcctccagtagatccaaccaccccttagtctcttctaatatgtgt | |
| | tctctgacactggcagactatgcacggaatagaagctggtcacctttgacgggaggcagga | |
| | aaatactgggtgtatctaatcctgatacgatagaactcgtagagggtgagattcttagtgtaag | |
| | cggagggtgtacaagatgtgacagcggagatgaacaatttacttggttccatcttccaagcaa | |
| | tatagaattgaccgatgacaccagcaagaatcctccgatgagggtaccatatctcgggtcaa | |
| | agacacaggagaggagagctgcctcacttgcaaaaatagctcatatgtcgccacatgtaaa | |
| | ggctgccctaagggcatcatccgtgttgatctgggcttatggggataatgaagtaaattggac | |
| | tgctgctcttacgattgcaaaatctcggtgtaatgtaaacttagagtatcttcggttactgtcccc | |
| | tttacccacggctgggaatcttcaacatagactagatgatggtataactcagatgacattcacc | |
| | cctgcatctctctacagggtgtcaccttacattcacatatccaatgattctcaaaggctgttcact | |
| | gaagaaggagtcaaagaggggaatgtggtttaccaacagatcatgctcttgggtttatctcta | |
| | atcgaatcgatctttccaatgacaacaaccaggacatatgatgagatcacactgcacctacat | |
| | agtaaatttagttgctgtatcagagaagcacctgttgcggttcctttcgagctacttggggtggt | |
| | accggaactgaggacagtgacctcaaataagtttatgtatgatcctagccctgtatcggaggg | |
| | agactttgcgagacttgacttagctatcttcaagagttatgagcttaatctggagtcatatccca | |
| | cgatagagctaatgaacattctttcaatatccagcgggaagttgattggccagtctgtggtttct | |
| | tatgatgaagatacctccataaagaatgacgccataatagtgtatgacaatacccgaaattgg | |
| | atcagtgaagctcagaattcagatgtggtccgcctatttgaatatgcagcacttgaagtgctcc | |
| | tcgactgttcttaccaactctattacctgagagtaagaggcctggacaatattgtcttatatatgg | |
| | gtgatttatacaagaatatgccaggaattctactttccaacattgcagctacaatatctcatccc | |
| | gtcattcattcaaggttacatgcagtgggcctggtcaaccatgacggatcacaccaacttgca | |
| | gatacggattttatcgaaatgtctgcaaaactattagtatcttgcacccgacgtgtgatctccgg | |
| | cttatattcaggaaataagtatgatctgctgttcccatctgtcttagatgataacctgaatgagaa | |
| | gatgcttcagctgatatcccggttatgctgtctgtacacggtactctttgctacaacaagagaa | |

TABLE 10-continued

| Exemplary plasmid sequences encoding chimeric NDVs (nucleic acid) | | |
|---|---|---|
| Name | Sequence | SEQ ID NO. |
| | atcccgaaaataagaggcttaactgcagaagagaaatgttcaatactcactgagtatttactgt<br>cggatgctgtgaaaccattacttagccccgatcaagtgagctctatcatgtctcctaacataatt<br>acattcccagctaatctgtactacatgtctcggaagagcctcaatttgatcagggaaagggag<br>gacagggatactatcctggcgttgttgttcccccaagagccattattagagttcccttctgtgca<br>agatattggtgctcgagtgaaagatccattcacccgacaacctgcggcatttttgcaagagtta<br>gatttgagtgctccagcaaggtatgacgcattcacacttagtcagattcatcctgaactcacat<br>ctccaaatccggaggaagactacttagtacgatacttgttcagagggatagggactgcatctt<br>cctcttggtataaggcatctcatctcctttctgtacccgaggtaagatgtgcaagacacgggaa<br>ctccttatacttagctgaagggagcggagccatcatgagtcttctcgaactgcatgtaccacat<br>gaaactatctattacaatacgctcttttcaaatgagatgaaccccccgcaacgacatttcgggc<br>cgaccccaactcagtttttgaattcggttgtttataggaatctacaggcggaggtaacatgcaa<br>agatggatttgtccaagagttccgtccattatggagagaaaatacagaggaaagcgacctga<br>cctcagataaagtagtggggtatattacatctgcagtgccctacagatctgtatcattgctgcat<br>tgtgacattgaaattcctccagggtccaatcaaagcttactagatcaactagctatcaatttatct<br>ctgattgccatgcattctgtaagggagggcggggtagtaatcatcaaagtgttgtatgcaatg<br>ggatactactttcatctactcatgaacttgtttgctccgtgttccacaaaaggatatattctctcta<br>atggttatgcatgtcgaggagatatggagtgttacctggtatttgtcatgggttacctgggcgg<br>gcctacatttgtacatgaggtggtgaggatggcgaaaactctggtgcagcggcacggtacg<br>cttttgtctaaatcagatgagatcacactgaccaggttattcacctcacagcggcagcgtgtga<br>cagacatcctatccagtcctttaccaagattaataaagtacttgaggaagaatattgacactgc<br>gctgattgaagccgggggacagcccgtccgtccattctgtgcggagagtctggtgagcacg<br>ctagcgaacataactcagataacccagatcatcgctagtcacattgacacagttatccggtct<br>gtgatatatatggaagctgagggtgatctcgctgacacagtatttctatttaccccttacaatctc<br>tctactgacgggaaaaagaggacatcacttaaacagtgcacgagacagatcctagaggtta<br>caatactaggtcttagagtcgaaaatctcaataaaataggcgatataatcagcctagtgcttaa<br>aggcatgatctccatggaggaccttatcccactaaggacatacttgaagcatagtacctgccc<br>taaatatttgaaggctgtcctaggtattaccaaactcaaagaaatgtttacagacacttctgtact<br>gtacttgactcgtgctcaacaaaaattctacatgaaaactataggcaatgcagtcaaaggatat<br>tacagtaactgtgactcttaacgaaaatcacatattaataggctcctttttttggccaattgtattctt<br>gttgatttaatcatattatgttagaaaaaagttgaaccctgactccttaggactcgaattcgaact<br>caaataaatgtcttaaaaaaaggttgcgcacaattattcttgagtgtagtctcgtcattcaccaa<br>atctttgtttggtgcgcgcggccggcatggtcccagcctcctcgctggcgccggctgggcaa<br>cattccgaggggaccgtcccctcggtaatggcgaatgggacgtcgactgctaacaaagccc<br>gaaaggaagctgagttggctgctgccaccgctgagcaataactagcataaccccttggggc<br>ctctaaacgggtcttgaggggttttttgctgaaaggaggaactatatgcgcgcagatctgtcat<br>gatgatcattgcaattggatccatatatagggcccgggttataattacctcaggtcgacgtccc<br>atggccattcgaattcgtaatcatggtcatagctgtttcctgtgtgaaattgttatccgctcacaa<br>ttccacacaacatacgagccggaagcataaagtgtaaagcctggggtgcctaatgagtgag<br>ctaactcacattaattgcgttgcgctcactgcccgctttccagtcgggaaacctgtcgtgccag<br>ctgcattaatgaatcggccaacgcgcggggagaggcggtttgcgtattgggcgc | |
| Exemplary<br>nucleic acid<br>sequence<br>encoding NDV<br>genome<br>encoding a<br>human IL-12<br>transgene<br>(Version 2.1) | accaaacagagaatccgtgagttacgataaaaggcgaaggagcaattgaagtcgcacggg<br>tagaaggtgtgaatctcgagtgcgagcccgaagcacaaactcgagaaagccttctgccaac<br>atgtcttccgtatttgatgagtacgaacagctcctcgcggctcagactcgccccaatggagct<br>catggaggggagaaaaagggagtaccttaaaagtagacgtcccggtattcactcttaaca<br>gtgatgacccagaagatagatggagctttgtggtattctgcctccggattgctgttagcgaag<br>atgccaacaaaccactcaggcaaggtgctctcatatctcttttatgctcccactcacaggtaat<br>gaggaaccatgttgcccttgcagggaaacagaatgaagccacattggccgtgcttgagattg<br>atggctttgccaacggcacgccccagttcaacaataggagtggagtgtctgaagagagagc<br>acagagatttgcgatgatagcaggatctctccctcgggcatgcagcaacggaaccccgttc<br>gtcacagccggggccgaagatgatgcaccagaagacatcaccgataccctggagaggat<br>cctctctatccaggctcaagtatgggtcacagtagcaaaagccatgactgcgtatgagactg<br>cagatgagtcggaaacaaggcgaatcaataagtatatgcagcaaggcagggtccaaaaga<br>aatacatcctctaccccgtatgcaggagcacaatccaactcacgatcagacagtctcttgcag<br>tccgcatctttttggttagcgagctcaagagaggccgcaacacggcaggtggtacctctactt<br>attataacctggtaggggacgtagactcatacatcaggaataccgggcttactgcattcttctt<br>gacactcaagtacggaatcaacaccaagacatcagcccttgcacttagtagcctctcaggcg<br>acatccagaagatgaagcagctcatgcgtttgtatcggatgaaaggagataatgcgccgtac<br>atgacattacttggtgatagtgaccagatgagctttgcgcctgccgagtatgcacaactttact<br>cctttgccatgggtatggcatcagtcctagataaaggtactgggaaataccaatttgccaggg<br>actttatgagcacatcattctggagacttggagtagagtacgctcaggctcagggaagtagc<br>attaacgaggatatggctgccgagctaaagctaaccccagcagcaaggagggcctggca<br>gctgctgcccaacgggtctccgaggagaccagcagcatagacatgcctactcaacaagtc<br>ggagtcctcactgggcttagcgagggggggtcccaagctctacaaggcggatcgaataga<br>tcgcaagggcaaccagaagccggggatggggagacccaattcctggatctgatgagagc<br>ggtagcaaatagcatgagggaggcgccaaactctgcacagggcactccccaatcggggc<br>ctcccccaactcctgggccatcccaagataacgacaccgactgggggtattgatggacaaa<br>acccagcctgcttccacaaaaacatcccaatgccctcacccgtagtcgacccctcgatttgc<br>ggctctatatgaccacaccctcaaacaaacatccccctctttcctccctcccccctgctgtacaa<br>ctacgtacgccctagataccacaggcacaatgcggctcactaacaatcaaaacagagccga<br>gggaattagaaaaaagtacgggtagaagagggatattcagagatcagggcaagtctcccg<br>agtctctgctctctcctctacctgatagaccaggacaaacatggccacctttacagatgcaga<br>gatcgacgagctatttgagacaagtggaactgtcattgacaacataattacagcccagggta<br>aaccagcagagactgttggaaggagtgcaatcccacaaggcaagaccaaggtgctgagc<br>gcagcatgggagaagcatgggagcatccagccaccggccagtcaagacaaccccgatcg | 62 |

TABLE 10-continued

Exemplary plasmid sequences encoding chimeric NDVs (nucleic acid)

| Name | Sequence | SEQ ID NO. |
|---|---|---|
| | acaggacagatctgacaaacaaccatccacacccgagcaaacgaccccgcatgacagcc | |
| | cgccggccacatccgccgaccagccccccacccaggccacagacgaagccgtcgacac | |
| | acagctcaggaccggagcaagcaactctctgctgttgatgcttgacaagctcagcaataaat | |
| | cgtccaatgctaaaaagggcccatggtcgagccccaagaggggaatcaccaacgtccga | |
| | ctcaacagcaggggagtcaacccagtcgcggaaacagtcaggaaagaccgcagaaccaa | |
| | gtcaaggccgcccctggaaaccagggcacagacgtgaacacagcatatcatggacaatgg | |
| | gaggagtcacaactatcagctggtgcaacccctcatgctctccgatcaaggcagagccaag | |
| | acaatacccttgtatctgcggatcatgtccagccacctgtagactttgtgcaagcgatgatgtc | |
| | tatgatggaggcgatatcacagagagtaagtaaggttgactatcagctagatcttgtcttgaaa | |
| | cagacatcctccatccctatgatgcggtccgaaatccaacagctgaaaacatctgttgcagtc | |
| | atggaagccaacttgggaatgatgaagattctggatcccggttgtgccaacatttcatctctga | |
| | gtgatctacgggcagttgcccgatctcacccggttttagtttcaggccctggagacccctctc | |
| | cctatgtgacacaaggaggcgaaatggcacttaataaactttcgcaaccagtgccacatcca | |
| | tctgaattgattaaacccgccactgcatgcgggcctgatataggagtggaaaaggacactgt | |
| | ccgtgcattgatcatgtcacgcccaatgcacccgagttcttcagccaagctcctaagcaagtt | |
| | agatgcagccgggtcgatcgaggaaatcaggaaaatcaagcgccttgctctaaatggctaa | |
| | ttactactgccacacgtagcgggtccctgtccactcggcatcacacggaatctgcaccgagtt | |
| | cccccCCGCGGTTAGAAAAAATACGGGTAGAACCGCCAC | |
| | CATGTGCCATCAGCAGCTGGTCATCTCATGGTTCTCCCT | |
| | GGTGTTTCTGGCCTCACCTCTGGTCGCAATCTGGGAACT | |
| | GAAAAAGGATGTGTACGTGGTGGAGCTGGACTGGTATC | |
| | CCGATGCCCCTGGCGAGATGGTGGTGCTGACCTGCGAC | |
| | ACACCCGAGGAGGATGGCATCACCTGGACACTGGATCA | |
| | GAGCTCCGAGGTGCTGGGAAGCGGCAAGACCCTGACAA | |
| | TCCAGGTGAAGGAGTTCGGCGACGCCGGCCAGTACACC | |
| | TGTCACAAGGGAGGAGAGGTGCTGAGCCACTCCCTGCT | |
| | GCTGCTGCACAAGAAGGAGGATGGCATCTGGTCCACAG | |
| | ACATCCTGAAGGATCAGAAGGAGCCAAAGAACAAGAC | |
| | CTTCCTGCGGTGCGAGGCCAAGAATTATAGCGGCCGGT | |
| | TCACCTGTTGGTGGCTGACCACAATCTCCACCGATCTGA | |
| | CATTTTCTGTGAAGTCTAGCAGGGGATCCTCTGACCCAC | |
| | AGGGAGTGACATGCGGAGCAGCCACCCTGAGCGCCGA | |
| | GAGGGTGCGCGGCGATAACAAGGAGTACGAGTATTCCG | |
| | TGGAGTGCCAGGAGGACTCTGCCTGTCCAGCAGCAGAG | |
| | GAGTCCCTGCCTATCGAAGTGATGGTGGATGCCGTGCA | |
| | CAAGCTGAAGTACGAGAATTATACCAGCTCCTTCTTTAT | |
| | CCGGGACATCATCAAGCCCGATCCCCCTAAGAACCTGC | |
| | AGCTGAAGCCTCTGAAGAATAGCAGACAGGTGGAGGTG | |
| | TCCTGGGAGTACCCTGACACCTGGAGCACACCACACTC | |
| | CTATTTCTCTCTGACCTTTTGCGTGCAGGTGCAGGGCAA | |
| | GTCCAAGCGGGAGAAGAAGGACAGAGTGTTCACCGAT | |
| | AAGACATCTGCCACCGTGATCTGTAGAAAGAACGCCTC | |
| | TATCAGCGTGAGGGCCCAGGACCGCTACTATTCTAGCT | |
| | CCTGGTCCGAGTGGGCCTCTGTGCCTTGCAGCGGCGGA | |
| | GGAGGAGGAGGATCTAGGAATCTGCCAGTGGCAACCCC | |
| | TGACCCAGGCATGTTCCCCTGCCTGCACCACAGCCAGA | |
| | ACCTGCTGAGGGCCGTGTCCAATATGCTGCAGAAGGCC | |
| | CGCCAGACACTGGAGTTTTACCCTTGTACCAGCGAGGA | |
| | GATCGACCACGAGGACATCACAAAGGATAAGACCTCCA | |
| | CAGTGGAGGCCTGCCTGCCACTGGAGCTGACCAAGAAC | |
| | GAGTCCTGTCTGAACAGCCGGGAGACAAGCTTCATCAC | |
| | CAACGGCTCCTGCCTGGCCTCTAGAAAGACAAGCTTTA | |
| | TGATGGCCCTGTGCCTGTCTAGCATCTACGAGGACCTGA | |
| | AGATGTATCAGGTGGAGTTCAAGACCATGAACGCCAAG | |
| | CTGCTGATGGACCCCAAGAGGCAGATCTTTCTGGATCA | |
| | GAATATGCTGGCCGTGATCGACGAGCTGATGCAGGCCC | |
| | TGAACTTCAATAGCGAGACAGTGCCTCAGAAGTCCTCT | |
| | CTGGAGGAGCCAGATTTCTACAAGACCAAGATCAAGCT | |
| | GTGCATCCTGCTGCACGCCTTTCGGATCAGAGCCGTGAC | |
| | AATCGACCGCGTGATGTCCTATCTGAATGCTTCCTAATG | |
| | ATCCGCGGacccaaggtccaactctccaagcggcaatcctctctcgcttcctcagccc | |
| | cactgaatgatcgcgtaaccgtaattaatctagctacatttaagattaagaaaaaatacgggta | |
| | gaattggagtgccccaattgtgccaagatggactcatctaggacaattgggctgtactttgatt | |
| | ctgcccattcttctagcaacctgttagcatttccgatcgtcctacaagacacaggagatggga | |
| | agaagcaaatcgccccgcaatataggatccagcgccttgacttgtggactgatagtaagga | |
| | ggactcagtattcatcaccacctatggattcatctttcaagttgggaatgaagaagccaccgtc | |
| | ggcatgatcgatgataaacccaagcgcgagttactttccgctgcgatgctctgcctaggaag | |
| | cgtcccaaataccggagaccttattgagctggcaagggcctgtctcactatgatagtcacatg | |
| | caagaagagtgcaactaatactgagagaatggttttctcagtagtgcaggcaccccaagtgc | |
| | tgcaaagctgtagggttgtggcaaacaaatactcatcagtgaatgcagtcaagcacgtgaaa | |
| | gcgccagagaagattcccgggagtggaaccctagaatacaaggtgaactttgtctccttgac | |
| | tgtggtaccgaagagggatgtctacaagatcccagctgcagtattgaaggtttctggctcgag | |
| | tctgtacaatcttgcgctcaatgtcactattaatgtggaggtagacccgaggagtcctttggtta | |
| | aatctctgtctaagtctgacagcggatactatgctaacctcttcttgcatattggacttatgacca | |
| | ctgtagataggaaggggaagaaagtgacatttgacaagctggaaaagaaaataaggagcc | |

TABLE 10-continued

Exemplary plasmid sequences encoding chimeric NDVs (nucleic acid)

| Name | Sequence | SEQ ID NO. |
|---|---|---|
| | ttgatctatctgtcgggctcagtgatgtgctcgggccttccgtgttggtaaaagcaagaggtgc<br>acggactaagcttttggcacctttcttctctagcagtgggacagcctgctatcccatagcaaat<br>gcttctcctcaggtggccaagatactctggagtcaaaccgcgtgcctgcggagcgttaaaat<br>cattatccaagcaggtacccaacgcgctgtcgcagtgaccgccgaccacgaggttacctct<br>actaagctggagaaggggcacacccttgccaaatacaatccttttaagaaataagctgcgtct<br>ctgagattgcgctccgcccactcacccagatcatcatgacacaaaaaactaatctgtcttgatt<br>atttacagttagtttacctgtctatcaagttagaaaaaacacgggtagaagattctggatcccg<br>gttggcgccctccaggtgcaagatgggctccagaccttctaccaagaacccagcacctatg<br>atgctgactatccgggttgcgctggtactgagttgcatctgtccggcaaactccattgatggca<br>ggcctcttgcagctgcaggaattgtggttacaggagacaaagccgtcaacatatacacctca<br>tcccagacaggatcaatcatagttaagctcctcccgaatctgcccaaggataaggaggcatg<br>tgcgaaagccccccttggatgcatacaacaggacattgaccactttgctcacccccccttggtga<br>ctctatccgtaggatacaagagtctgtgactacatctggagggggagacaggggcgcctt<br>ataggcgccattattggcggtgtggctcttggggttgcaactgccgcacaaataacagcggc<br>cgcagctctgatacaagccaaacaaaatgctgccaacatcctccgacttaaagagagcattg<br>ccgcaaccaatgaggctgtgcatgaggtcactgacggattatcgcaactagcagtggcagtt<br>gggaagatgcagcagtttgttaatgaccaatttaataaaacagctcaggaattagactgcatc<br>aaaattgcacagcaagttggtgtagagctcaacctgtacctaaccgaattgactacagtattc<br>ggaccacaaatcacttcacctgctttaaacaagctgactattcaggcactttacaatctagctg<br>gtggaaatatggattacttattgactaagttaggtgtagggaacaatcaactcagctcattaatc<br>ggtagcggcttaatcaccggtaaccctattctatacgactcacagactcaactcttgggtatac<br>aggtaactGCCccttcagtcgggaacctaaataatatgcgtgccacctacttggaaacctta<br>tccgtaagcacaaccaggggatttgcctcggcacttgtcccaaaagtggtgacacaggtcg<br>gttctgtgatagaagaacttgacacctcatactgtatagaaactgacttagatttatattgtacaa<br>gaatagtaacgttccctatgtcccctggtatttattcctgcttgagcggcaatacgtcggcctgt<br>atgtactcaaagaccgaaggcgcacttactacaccatacatgactatcaaaggttcagtcatc<br>gccaactgcaagatgacaacatgtagatgtgtaaaccccccgggtatcatatcgcaaaacta<br>tggagaagccgtgtctctaatagataaacaatcatgcaatgttttatccttaggcgggataactt<br>taaggctcagtggggaattcgatgtaacttatcagaagaatatctcaatacaagattctcaagt<br>aataataacaggcaatcttgatatctcaactgagcttgggaatgtcaacaactcgatcagtaat<br>gctttgaataagttagaggaaagcaacagaaaactagacaaagtcaatgtcaaactgactag<br>cacatctgctctcattacctatatcgttttgactatcatatctcttgtttttggtatacttagcctgatt<br>ctagcatgctacctaatgtacaagcaaaaggcgcaacaaaagaccttattatggcttgggaat<br>aatactctagatcagatgagagccactacaaaaatgtgaacacagatgaggaacgaaggttt<br>ccctaatagtaatttgtgtgaaagttctggtagtctgtcagttcagagagttaagaaaaaactac<br>cggttgtagatgaccaaaggacgatatacgggtagaacggtaagagaggccgcccctcaa<br>ttgcgagccaggcttcacaacctccgttctaccgcttcaccgacaacagtcctcaatcatgga<br>ccgcgccgttagccaagttgcgttagagaatgatgaaagagaggcaaaaaatacatggcgc<br>ttgatattccggattgcaatcttattcttaacagtagtgaccttggctatatctgtagcctccctttt<br>atatagcatgggggctagcacacctagcgatcttgtaggcataccgactaggatttccaggg<br>cagaagaaaagattacatctacacttggttccaatcaagatgtagtagataggatatataagca<br>agtggcccttgagtctccgttggcattgttaaatactgagaccacaattatgaacgcaataaca<br>tctctctcttatcagattaatggagctgcaaacaacagtgggtgggggcacctatccatgac<br>ccagattatataggggggataggcaaagaactcattgtagatgatgctagtgatgtcacatca<br>ttctatccctctgcatttcaagaacatctgaattttatcccggcgcctactacaggatcaggttgc<br>actcgaataccctcatttgacatgagtgctacccattactgctacacccataatgtaatattgtct<br>ggatgcagagatcactcacattcatatcagtatttagcacttggtgtgctccggacatctgcaa<br>cagggagggtattcttttctactctgcgttccatcaacctggacgacacccaaaatcggaagt<br>cttgcagtgtgagtgcaactcccctgggttgtgatatgctgtgctcgaaagtcacggagacag<br>aggaagaagattataactcagctgtccctacgcggatggtacatgggaggttagggttcgac<br>ggccagtaccacgaaaaggacctagatgtcacaacattattcggggactgggtggccaact<br>acccaggagtaggggggtggatcttttattgacagccgcgtatggttctcagtctacggagggt<br>taaaacccaattcacccagtgacactgtacaggaagggaaatatgtgatatacaagcgatac<br>aatgacacatgcccagatgagcaagactaccagattcgaatggccaagtcttcgtataagcc<br>tggacggtttggtgggaaacgcatacagcaggctatcttatctatcaaggtgtcaacatcctta<br>ggcgaagacccggtactgactgtaccgcccaacacagtcacactcatgggggccgaagg<br>cagaattctcacagtagggacatctcatttcttgtatcaacgagggtcatcatacttctctcccg<br>cgttattatatcctatgacagtcagcaacaaaacagccactcttcatagtccttatacattcaatg<br>ccttcactcggccaggtagtatcccttgccaggcttcagcaagatgccccaactcgtgtgtta<br>ctggagtctatacagatccatatcccctaatcttctatagaaaccacaccttgcgaggggtatt<br>cgggacaatgcttgatggtgtacaagcaagacttaaccctgcgtctgcagtattcgatagcac<br>atcccgcagtcgcattactcgagtgagttcaagcagtaccaaagcagcatacacaacatcaa<br>cttgttttaaagtggtcaagactaataagacctattgtctcagcattgctgaaatatctaatactct<br>cttcggagaattcagaatcgtcccgttactagttgagatcctcaaagatgacggggttagaga<br>agccaggtctggctagttgagtcaattataaaggagttggaaagatggcattgtatcacctatc<br>ttctgcgacatcaagaatcaaaccgaatgccggcgcgtgctcgaattccatgttgccagttga<br>ccacaatcagccagtgctcatgcgatcagattaagccttgtcaatagtctcttgattaagaaaa<br>aatgtaagtggcaatgagatacaaggcaaaacagctcatggttaacaatacgggtaggacat<br>ggcgagctccggtcctgaaagggcagagcatcagattatcctaccagagtcacacctgtctt<br>caccattggtcaagcacaaactactctattactggaaattaactgggctaccgcttcctgatga<br>atgtgacttcgaccacctcattctcagccgacaatggaaaaaaatacttgaatcggcctctcct<br>gatactgagagaatgataaaactcggaagggcagtacaccaaactcttaaccacaattccag<br>aataaccggagtgctccaccccaggtgtttagaagaactggctaatattgaggtcccagattc<br>aaccaacaaatttcggaagattgagaagaagatccaaattcacaacacgagatatggagaa<br>ctgttcacaaggctgtgtacgcatatagagaagaaactgctggggtcatcttggtctaacaat | |

TABLE 10-continued

Exemplary plasmid sequences encoding chimeric NDVs (nucleic acid)

| Name | Sequence | SEQ ID NO. |
|---|---|---|
| | gtcccccggtcagaggagttcagcagcattcgtacggatccggcattctggtttcactcaaaa<br>tggtccacagccaagtttgcatggctccatataaaacagatccagaggcatctgatggtggc<br>agctaggacaaggtctgcggccaacaaattggtgatgctaacccataaggtaggccaagtc<br>tttgtcactcctgaacttgtcgttgtgacgcatacgaatgagaacaagttcacatgtcttaccca<br>ggaacttgtattgatgtatgcagatatgatggagggcagagatatggtcaacataatatcaac<br>cacggcggtgcatctcagaagcttatcagagaaaattgatgacattttgcggttaatagacgc<br>tctggcaaaagacttgggtaatcaagtctacgatgttgtatcactaatggagggatttgcatac<br>ggagctgtccagctactcgagccgtcaggtacatttgcaggagatttcttcgcattcaacctg<br>caggagcttaaagacattctaattggcctcctccccaatgatatagcagaatccgtgactcatg<br>caatcgctactgtattctctggtttagaacagaatcaagcagctgagatgttgtgtctgttgcgt<br>ctgtggggtcacccactgcttgagtcccgtattgcagcaaaggcagtcaggagccaaatgtg<br>cgcaccgaaaatggtagactttgatatgatccttcaggtactgtctttcttcaagggaacaatca<br>tcaacgggtacagaaagaagaatgcaggtgtgtggccgcgagtcaaagtggatacaatata<br>tgggaaggtcattgggcaactacatgcagattcagcagagatttcacacgatatcatgttgag<br>agagtataagagtttatctgcacttgaatttgagccatgtatagaatatgaccctgtcaccaacc<br>tgagcatgttcctaaaagacaaggcaatcgcacaccccaacgataattggcttgcctcgttta<br>ggcggaaccttctctccgaagaccagaagaaacatgtaaaagaagcaacttcgactaatcg<br>cctcttgatagagtttttagagtcaaatgattttgatccatataaagagatggaatatctgacgac<br>ccttgagtaccttagagatgacaatgtggcagtatcatactcgctcaaggagaaggaagtga<br>aagttaatggacggatcttcgctaagctgacaaagaagttaaggaactgtcaggtgatggcg<br>gaagggatcctagccgatcagattgcacctttctttcagggaaatggagtcattcaggatagc<br>atatccttgaccaagagtatgctagcgatgagtcaactgtcttttaacagcaataagaaacgta<br>tcactgactgtaaagaaagagtatcttcaaaccgcaatcatgatccgaaaagcaagaaccgt<br>cggagagttgcaaccttcataacaactgacctgcaaaagtactgtcttaattggagatatcag<br>acaatcaaattgttcgctcatgccatcaatcagttgatgggcctacctcacttcttcgaatggatt<br>cacctaagactgatggacactacgatgttcgtaggagaccctttcaatcctccaagtgaccct<br>actgactgtgacctctcaagagtccctaatgatgacatatatattgtcagtgccagagggggt<br>atcgaaggattatgccagaagctatggacaatgatctcaattgctgcaatccaacttgctgca<br>gctagatcgcattgtcgtgttgcctgtatggtacagggtgataatcaagtaatagcagtaacga<br>gagaggtaagatcagacgactctccggagatggtgttgacacagttgcatcaagccagtgat<br>aatttcttcaaggaattaattcatgtcaatcatttgattggccataatttgaaggatcgtgaaacc<br>atcaggtcagacacattcttcatatacagcaaacgaatcttcaaagatggagcaatcctcagt<br>caagtcctcaaaaattcatctaaattagtgctagtgtcaggtgatctcagtgaaaacaccgtaa<br>tgtcctgtgccaacattgcctctactgtagcacggctatgcgagaacgggcttcccaaagact<br>tctgttactatttaaactatataatgagttgtgtgcagacatactttgactctgagttctccatcacc<br>aacaattcgcaccccgatcttaatcagtcgtggattgaggacatctcttttgtgcactcatatgtt<br>ctgactcctgcccaattagggggactgagtaaccttcaatactcaaggctctacactagaaat<br>atcggtgacccggggactactgcttttgcagagatcaagcgactagaagcagtgggattact<br>gagtcctaacattatgactaatatcttaactaggccgcctgggaatggagattgggccagtct<br>gtgcaacgacccatactctttcaattttgagactgttgcaagcccaaatattgttcttaagaaac<br>atacgcaaagagtcctatttgaaacttgttcaaatcccttattgtctggagtgcacacagaggat<br>aatgaggcagaagagaaggcattggctgaattcttgcttaatcaagaggtgattcatccccgc<br>gttgcgcatgccatcatggaggcaagctctgtaggtaggagaaagcaaattcaagggcttgt<br>tgacacaacaaacaccgtaattaagattgcgcttactaggaggccattaggcatcaagaggc<br>tgatgcggatagtcaattattctagcatgcatgcaatgctgtttagagacgatgtttttcctcca<br>gtagatccaaccaccccttagtctcttctaatatgtgttctctgacactggcagactatgcacgg<br>aatagaagctggtcacctttgacgggaggcaggaaaatactgggtgtatctaatcctgatac<br>gatagaactcgtagagggtgagattcttagtgtaagcggagggtgtacaagatgtgacagc<br>ggagatgaacaatttacttggttccatcttccaagcaatatagaattgaccgatgacaccagca<br>agaatcctccgatgagggtaccatatctcgggtcaaagacacaggagaggagagctgcctc<br>acttgcaaaaatagctcatatgtcgccacatgtaaaggctgccctaagggcatcatccgtgtt<br>gatctgggcttatggggataatgaagtaaattggactgctgctcttacgattgcaaaatctcgg<br>tgtaatgtaaacttagagtatcttcggttactgtcccctttacccacggctgggaatcttcaacat<br>agactagatgatggtataactcagatgacattcaccccctgcatctctctacagggtgtcacctt<br>acattcacatatccaatgattctcaaaggctgttcactgaagaaggagtcaaagaggggaat<br>gtggtttaccaacagatcatgctcttgggtttatctctaatcgaatcgatctttccaatgacaaca<br>accaggacatatgatgagatcacactgcacctacatagtaaatttagttgctgtatcagagaa<br>gcacctgttgcggttcctttcgagctacttggggtggtaccggaactgaggacagtgacctca<br>aataagtttatgtatgatcctagccctgtatcggagggagactttgcgagacttgacttagctat<br>cttcaagagttatgagcttaatctggagtcatatcccacgatagagctaatgaacattctttcaat<br>atccagcgggaagttgattggccagtctgtggtttcttatgatgaagatacctccataaagaat<br>gacgccataatagtgtatgacaatacccgaaattggatcagtgaagctcagaattcagatgtg<br>gtccgcctatttgaatatgcagcacttgaagtgctcctcgactgttcttaccaactctattacctg<br>agagtaagaggcctggacaatattgtcttatatatgggtgatttatacaagaatatgccaggaa<br>ttctactttccaacattgcagctacaatatctcatcccgtcattcattcaaggttacatgcagtgg<br>gcctggtcaaccatgacggatcacaccaacttgcagatacggattttatcgaaatgtctgcaa<br>aactattagtatcttgcacccgacgtgtgatctccggcttatattcaggaaataagtatgatctg<br>ctgttcccatctgtcttagatgataacctgaatgagaagatgcttcagctgatatcccggttatg<br>ctgtctgtacacggtactctttgctacaacaagagaaatcccgaaaataagaggcttaactgc<br>agaagagaaatgttcaatactcactgagtatttactgtcggatgctgtgaaaccattacttagcc<br>ccgatcaagtgagctctatcatgtctcctaacataattacattcccagctaatctgtactacatgt<br>ctcggaagagcctcaatttgatcagggaaagggaggacagggatactatcctggcgttgttg<br>ttcccccaagagccattattagagttcccttctgtgcaagatattggtgctcgagtgaaagatc<br>cattcacccgacaacctgcggcatttttgcaagagttagatttgagtgctccagcaaggtatga<br>cgcattcacacttagtcagattcatcctgaactcacatctccaaatccggaggaagactactta | |

TABLE 10-continued

Exemplary plasmid sequences encoding chimeric NDVs (nucleic acid)

| Name | Sequence | SEQ ID NO. |
|---|---|---|
| | gtacgatacttgttcagagggatagggactgcatcttcctcttggtataaggcatctcatctcct<br>ttctgtacccgaggtaagatgtgcaagacacgggaactccttatacttagctgaagggagcg<br>gagccatcatgagtcttctcgaactgcatgtaccacatgaaactatctattacaatacgctctttt<br>caaatgagatgaacccccccgcaacgacatttcgggccgaccccaactcagtttttgaattcg<br>gttgtttataggaatctacaggcggaggtaacatgcaaagatggatttgtccaagagttccgtc<br>cattatggagagaaaatacagaggaaagcgacctgacctcagataaagtagtggggtatatt<br>acatctgcagtgccctacagatctgtatcattgctgcattgtgacattgaaattcctccagggtc<br>caatcaaagcttactagatcaactagctatcaatttatctctgattgccatgcattctgtaaggga<br>gggcggggtagtaatcatcaaagtgttgtatgcaatgggatactactttcatctactcatgaact<br>tgtttgctccgtgttccacaaaaggatatattctctctaatggttatgcatgtcgaggagatatgg<br>agtgttacctggtatttgtcatgggttacctgggcgggcctacatttgtacatgaggtggtgag<br>gatggcgaaaactctggtgcagcggcacggtacgcttttgtctaaatcagatgagatcacact<br>gaccaggttattcacctcacagcggcagcgtgtgacagacatcctatccagtcctttaccaag<br>attaataaagtacttgaggaagaatattgacactgcgctgattgaagccgggggacagcccg<br>tccgtccattctgtgcggagagtctggtgagcacgctagcgaacataactcagataacccag<br>atcatcgctagtcacattgacacagttatccggtctgtgatatatatggaagctgagggtgatct<br>cgctgacacagtatttctatttaccccttacaatctctctactgacgggaaaaagaggacatca<br>cttaaacagtgcacgagacagatcctagaggttacaatactaggtcttagagtcgaaaatctc<br>aataaaataggcgatataatcagcctagtgcttaaaggcatgatctccatggaggaccttatc<br>ccactaaggacatacttgaagcatagtacctgccctaaatatttgaaggctgtcctaggtatta<br>ccaaactcaaagaaatgtttacagacacttctgtactgtacttgactcgtgctcaacaaaaattc<br>tacatgaaaactataggcaatgcagtcaaaggatattacagtaactgtgactcttaacgaaaat<br>cacatattaataggctcctttttttggccaattgtattcttgttgatttaatcatattatgttagaaaaa<br>agttgaaccctgactccttaggactcgaattcgaactcaaataaatgtcttaaaaaaaggttgc<br>gcacaattattcttgagtgtagtctcgtcattcaccaaatctttgtttggt | |
| Exemplary nucleic acid sequence encoding NDV genome encoding a human IL-12 transgene (Version 3) | accaaacagagaatccgtgagttacgataaaaggcgaaggagcaattgaagtcgcacggg<br>tagaaggtgtgaatctcgagtgcgagcccgaagcacaaactcgagaaagccttctgccaac<br>atgtcttccgtatttgatgagtacgaacagctcctcgcggctcagactcgccccaatggagct<br>catggagggggagaaaaagggagtaccttaaaagtagacgtcccggtattcactcttaaca<br>gtgatgacccagaagatagatggagctttgtggtattctgcctccggattgctgttagcgaag<br>atgccaacaaaccactcaggcaaggtgctctcatatctcttttatgctcccactcacaggtaat<br>gaggaaccatgttgcccttgcagggaaacagaatgaagccacattggccgtgcttgagattg<br>atggctttgccaacggcacgccccagttcaacaataggagtggagtgtctgaagagagagc<br>acagagatttgcgatgatagcaggatctctccctcgggcatgcagcaacggaaccccgttc<br>gtcacagccggggccgaagatgatgcaccagaagacatcaccgataccctggagaggat<br>cctctctatccaggctcaagtatgggtcacagtagcaaaagccatgactgcgtatgagactg<br>cagatgagtcggaaacaaggcgaatcaataagtatatgcagcaaggcagggtccaaaaga<br>aatacatcctctaccccgtatgcaggagcacaatccaactcacgatcagacagtctcttgcag<br>tccgcatctttttggttagcgagctcaagagaggccgcaacacggcaggtggtacctctactt<br>attataacctggtaggggacgtagactcatacatcaggaataccgggcttactgcattcttctt<br>gacactcaagtacggaatcaacaccaagacatcagcccttgcacttagtagcctctcaggcg<br>acatccagaagatgaagcagctcatgcgtttgtatcggatgaaaggagataatgcgccgtac<br>atgacattacttggtgatagtgaccagatgagctttgcgcctgccgagtatgcacaactttact<br>cctttgccatgggtatggcatcagtcctagataaaggtactgggaaataccaatttgccaggg<br>actttatgagcacatcattctggagacttggagtagagtacgctcaggctcagggaagtagc<br>attaacgaggatatggctgccgagctaaagctaaccccagcagcaaggagggggcctggca<br>gctgctgcccaacgggtctccgaggagaccagcagcatagacatgcctactcaacaagtc<br>ggagtcctcactgggcttagcgagggggggtcccaagctctacaaggcggatcgaataga<br>tcgcaagggcaaccagaagccggggatggggagacccaattcctggatctgatgagagc<br>ggtagcaaatagcatgagggaggcgccaaactctgcacagggcactccccaatcggggc<br>ctcccccaactcctgggccatcccaagataacgacaccgactgggggtattgatggacaaa<br>acccagcctgcttccacaaaaacatcccaatgccctcacccgtagtcgacccctcgatttgc<br>ggctctatatgaccacaccctcaaacaaacatcccccctctttcctccctcccccctgctgtacaa<br>ctacgtacgccctagataccacaggcacaatgcggctcactaacaatcaaaacagagccga<br>gggaattagaaaaaagtacgggtagaagagggatattcagagatcagggcaagtctcccg<br>agtctctgctctctcctctacctgatagaccaggacaaacatggccacctttacagatgcaga<br>gatcgacgagctatttgagacaagtggaactgtcattgacaacataattacagcccagggta<br>aaccagcagagactgttggaaggagtgcaatcccacaaggcaagaccaaggtgctgagc<br>gcagcatgggagaagcatgggagcatccagccaccggccagtcaagacaaccccgatcg<br>acaggacagatctgacaaacaaccatccacacccgagcaaacgaccccgcatgacagcc<br>cgccggccacatccgccgaccagcccccccacccaggccacagacgaagccgtcgacac<br>acagctcaggaccggagcaagcaactctctgctgttgatgcttgacaagctcagcaataaat<br>cgtccaatgctaaaaagggcccatggtcgagcccccaagaggggaatcaccaacgtccga<br>ctcaacagcaggggagtcaacccagtcgcggaaacagtcaggaaagaccgcagaaccaa<br>gtcaaggccgcccctggaaaccagggcacagacgtgaacacagcatatcatggacaatgg<br>gaggagtcacaactatcagctggtgcaacccctcatgctctccgatcaaggcagagccaag<br>acaatacccttgtatctgcggatcatgtccagccacctgtagactttgtgcaagcgatgatgtc<br>tatgatggaggcgatatcacagagagtaagtaaggttgactatcagctagatcttgtcttgaaa<br>cagacatcctccatccctatgatgcggtccgaaatccaacagctgaaaacatctgttgcagtc<br>atggaagccaacttgggaatgatgaagattctggatcccggttgtgccaacatttcatctctga<br>gtgatctacgggcagttgcccgatctcacccggttttagtttcaggccctggagacccctctc<br>cctatgtgacacaaggaggcgaaatggcacttaataaactttcgcaaccagtgccacatcca<br>tctgaattgattaaacccgccactgcatgcgggcctgatataggagtggaaaaggacactgt<br>ccgtgcattgatcatgtcacgcccaatgcacccgagttcttcagccaagctcctaagcaagtt | 67 |

TABLE 10-continued

| Exemplary plasmid sequences encoding chimeric NDVs (nucleic acid) | | |
|---|---|---|
| Name | Sequence | SEQ ID NO. |
| | agatgcagccgggtcgatcgaggaaatcaggaaaatcaagcgccttgctctaaatggctaa ttactactgccacacgtagcgggtccctgtccactcggcatcacacggaatctgcaccgagtt cccccCCGCGGTTAGAAAAAATACGGGTAGAACCGCCAC Catgtgtcaccagcagttggtcatctcttggttttccctggtttttctggcatctcccctcgtggc catatgggaactgaagaaagatgtttatgtcgtagaattggattggtatccggatgcccctgg agaaatggtggtcctcacctgtgacacccctgaagaagatggtatcacctggaccttggacc agagcagtgaggtcttaggctctggcaaaaccctgaccatccaagtcaaagagtttggagat gctggccagtacacctgtcacaaaggaggcgaggttctaagccattcgctcctgctgcttca caaaaaggaagatggaatttggtccactgatattttaaaggaccagaaagaacccaaaaata agacctttctaagatgcgaggccaagaattattctggacgtttcacctgctggtggctgacga caatcagtactgatttgacattcagtgtcaaaagcagcagaggctcttctgacccccaaggg gtgacgtgcggagctgctacactctctgcagagagagtcagaggggacaacaaggagtat gagtactcagtggagtgccaggaggacagtgcctgcccagctgctgaggagagtctgccc attgaggtcatggtggatgccgttcacaagctcaagtatgaaaactacaccagcagcttcttc atcagggacatcatcaaacctgacccacccaagaacttgcagctgaagccattaaagaattc tcggcaggtggaggtcagctgggagtaccctgacacctggagtactccacattcctacttctc cctgacattctgcgttcaggtccagggcaagagcaagagagaaaagaaagatagagtcttc acggacaagacctcagccacggtcatctgccgcaaaaatgccagcattagcgtgcgggcc caggaccgctactatagctcatcttggagcgaatgggcatctgtgccctgcagtggtggcgg tggcggcggatctagaaacctccccgtggccactccagacccaggaatgttcccatgccttc accactcccaaaacctgctgagggccgtcagcaacatgctccagaaggccagacaaactct agaattttacccttgcacttctgaagagattgatcatgaagatatcacaaaagataaaaccagc acagtggaggcctgtttaccattggaattaaccaagaatgagagttgcctaaattccagagag acctctttcataactaatgggagttgcctggcctccagaaagacctcttttatgatggccctgtg ccttagtagtatttatgaagacttgaagatgtaccaggtggagttcaagaccatgaatgcaaa gcttctgatggatcctaagaggcagatctttctagatcaaaacatgctggcagttattgatgag ctgatgcaggccctgaatttcaacagtgagactgtgccacaaaaatcctcccttgaagaacc ggatttttataaaactaaaatcaagctctgcatacttcttcatgctttcagaattcgggcagtgac tattgatagagtgatgagctatctgaatgcttcctaaTGATCCGCGGacccaaggtcc aactctccaagcggcaatcctctctcgcttcctcagccccactgaatgatcgcgtaaccgtaa ttaatctagctacatttaagattaagaaaaaatacgggtagaattggagtgccccaattgtgcc aagatggactcatctaggacaattgggctgtactttgattctgcccattcttctagcaacctgtta gcatttccgatcgtcctacaagacacaggagatgggaagaagcaaatcgccccgcaatata ggatccagcgccttgacttgtggactgatagtaaggaggactcagtattcatcaccacctatg gattcatctttcaagttgggaatgaagaagccaccgtcggcatgatcgatgataaacccaag cgcgagttactttccgctgcgatgctctgcctaggaagcgtcccaaataccggagaccttatt gagctggcaagggcctgtctcactatgatagtcacatgcaagaagagtgcaactaatactga gagaatggttttctcagtagtgcaggcaccccaagtgctgcaaagctgtagggttgtggcaa acaaatactcatcagtgaatgcagtcaagcacgtgaaagcgccagagaagattcccggga gtggaaccctagaatacaaggtgaactttgtctccttgactgtggtaccgaagagggatgtct acaagatcccagctgcagtattgaaggtttctggctcgagtctgtacaatcttgcgctcaatgt cactattaatgtggaggtagacccgaggagtccttggttaaatctctgtctaagtctgacagc ggatactatgctaacctcttcttgcatattggacttatgaccactgtagataggaaggggaaga aagtgacatttgacaagctggaaaagaaaataaggagccttgatctatctgtcgggctcagtg atgtgctcgggccttccgtgttggtaaaagcaagaggtgcacggactaagcttttggcacctt tcttctctagcagtgggacagcctgctatcccatagcaaatgcttctcctcaggtggccaagat actctggagtcaaaccgcgtgcctgcggagcgttaaaatcattatccaagcaggtacccaac gcgctgtcgcagtgaccgccgaccacgaggttacctctactaagctggagaaggggcaca cccttgccaaatacaatccttttaagaaataagctgcgtctctgagattgcgctccgcccactc acccagatcatcatgacacaaaaaactaatctgtcttgattatttacagttagtttacctgtctatc aagttagaaaaaacacgggtagaagattctggatcccggttggcgccctccaggtgcaaga tgggctccagaccttctaccaagaacccagcacctatgatgctgactatccgggttgcgctg gtactgagttgcatctgtccggcaaactccattgatggcaggcctcttgcagctgcaggaatt gtggttacaggagacaaagccgtcaacatatacacctcatcccagacaggatcaatcatagt taagctcctcccgaatctgcccaaggataaggaggcatgtgcgaaagccccccttggatgcat acaacaggacattgaccactttgctcaccccccttggtgactctatccgtaggatacaagagt ctgtgactacatctggaggggggagacaggggcgccttataggcgccattattggcggtgt ggctcttggggttgcaactgccgcacaaataacagcggccgcagctctgatacaagccaaa caaaatgctgccaacatcctccgacttaaagagagcattgccgcaaccaatgaggctgtgca tgaggtcactgacggattatcgcaactagcagtggcagttgggaagatgcagcagtttgttaa tgaccaatttaataaaacagctcaggaattagactgcatcaaaattgcacagcaagttggtgta gagctcaacctgtacctaaccgaattgactacagtattcggaccacaaatcacttcacctgctt taaacaagctgactattcaggcactttacaatctagctggtggaaatatggattacttattgact aagttaggtgtagggaacaatcaactcagctcattaatcggtagcggcttaatcaccggtaac cctattctatacgactcacagactcaactcttgggtatacaggtaactGCCccttcagtcgg gaacctaaataatatgcgtgccacctacttggaaaccttatccgtaagcacacaaccaggggatt tgcctcggcacttgtcccaaaagtggtgacacaggtcggttctgtgatagaagaacttgacac ctcatactgtatagaaactgacttagatttatattgtacaagaatagtaacgttccctatgtcccct ggtatttattcctgcttgagcggcaatacgtcggcctgtatgtactcaaagaccgaaggcgca cttactacaccatacatgactatcaaaggttcagtcatcgccaactgcaagatgacaacatgta gatgtgtaaaccccccgggtatcatatcgcaaaactatggagaagccgtgtctctaatagata aacaatcatgcaatgttttatccttaggcgggataactttaaggctcagtggggaattcgatgta acttatcagaagaatatctcaatacaagattctcaagtaataataacaggcaatcttgatatctc aactgagcttgggaatgtcaacaactcgatcagtaatgctttgaataagttagaggaaagcaa cagaaaactagacaaagtcaatgtcaaactgactagcacatctgctctcattacctatatcgttt | |

TABLE 10-continued

Exemplary plasmid sequences encoding chimeric NDVs (nucleic acid)

| Name | Sequence | SEQ ID NO. |
|---|---|---|
| | tgactatcatatctcttgtttttggtatacttagcctgattctagcatgctacctaatgtacaagcaa<br>aaggcgcaacaaaagaccttattatggcttgggaataatactctagatcagatgagagccact<br>acaaaaatgtgaacacagatgaggaacgaaggtttccctaatagtaatttgtgtgaaagttctg<br>gtagtctgtcagttcagagagttaagaaaaaactaccggttgtagatgaccaaaggacgatat<br>acgggtagaacggtaagagaggccgcccctcaattgcgagccaggcttcacaacctccgtt<br>ctaccgcttcaccgacaacagtcctcaatcatggaccgcgccgttagccaagttgcgttaga<br>gaatgatgaaagagaggcaaaaaatacatggcgcttgatattccggattgcaatcttattctta<br>acagtagtgaccttggctatatctgtagcctcccttttatatagcatgggggctagcacaccta<br>gcgatcttgtaggcataccgactaggatttccagggcagaagaaaagattacatctacacttg<br>gttccaatcaagatgtagtagataggatatataagcaagtggcccttgagtctccgttggcatt<br>gttaaatactgagaccacaattatgaacgcaataacatctctctcttatcagattaatggagctg<br>caaacaacagtgggtgggggcacctatccatgacccagattatatagggggggataggca<br>aagaactcattgtagatgatgctagtgatgtcacatcattctatccctctgcatttcaagaacatc<br>tgaattttatcccggcgcctactacaggatcaggttgcactcgaataccctcatttgacatgagt<br>gctacccattactgctacacccataatgtaatattgtctggatgcagagatcactcacattcata<br>tcagtatttagcacttggtgtgctccggacatctgcaacagggagggtattcttttctactctgc<br>gttccatcaacctggacgacacccaaaatcggaagtcttgcagtgtgagtgcaactcccctg<br>ggttgtgatatgctgtgctcgaaagtcacggagacagaggaagaagattataactcagctgt<br>ccctacgcggatggtacatgggaggttagggttcgacggccagtaccacgaaaaggacct<br>agatgtcacaacattattcggggactgggtggccaactacccaggagtagggggtggatctt<br>ttattgacagccgcgtatggttctcagtctacggagggttaaaacccaattcacccagtgaca<br>ctgtacaggaagggaaatatgtgatatacaagcgatacaatgacacatgcccagatgagca<br>agactaccagattcgaatggccaagtcttcgtataagcctggacggtttggtgggaaacgca<br>tacagcaggctatcttatctatcaaggtgtcaacatccttaggcgaagacccggtactgactgt<br>accgcccaacacagtcacactcatgggggccgaaggcagaattctcacagtagggacatct<br>catttcttgtatcaacgagggtcatcatacttctctcccgcgttattatatcctatgacagtcagc<br>aacaaaacagccactcttcatagtccttatacattcaatgccttcactcggccaggtagtatcc<br>cttgccaggcttcagcaagatgccccaactcgtgtgttactggagtctatacagatccatatcc<br>cctaatcttctatagaaaccacaccttgcgaggggtattcgggacaatgcttgatggtgtacaa<br>gcaagacttaaccctgcgtctgcagtattcgatagcacatcccgcagtcgcattactcgagtg<br>agttcaagcagtaccaaagcagcatacacaacatcaacttgttttaaagtggtcaagactaat<br>aagacctattgtctcagcattgctgaaatatctaatactctcttcggagaattcagaatcgtccc<br>gttactagttgagatcctcaaagatgacggggttagagaagccaggtctggctagttgagtca<br>attataaaggagttggaaagatggcattgtatcacctatcttctgcgacatcaagaatcaaacc<br>gaatgccggcgcgtgctcgaattccatgttgccagttgaccacaatcagccagtgctcatgc<br>gatcagattaagccttgtcaatagtctcttgattaagaaaaaatgtaagtggcaatgagataca<br>aggcaaaacagctcatggttaacaatacgggtaggacatggcgagctccggtcctgaaag<br>ggcagagcatcagattatcctaccagagtcacacctgtcttcaccattggtcaagcacaaact<br>actctattactggaaattaactgggctaccgcttcctgatgaatgtgacttcgaccacctcattct<br>cagccgacaatggaaaaaaatacttgaatcggcctctcctgatactgagagaatgataaaac<br>tcggaagggcagtacaccaaactcttaaccacaattccagaataaccggagtgctccaccc<br>caggtgtttagaagaactggctaatattgaggtcccagattcaaccaacaaatttcggaagatt<br>gagaagaagatccaaattcacaacacgagatatggagaactgttcacaaggctgtgtacgc<br>atatagagaagaaactgctggggtcatcttggtctaacaatgtcccccggtcagaggagttca<br>gcagcattcgtacggatccggcattctggtttcactcaaaatggtccacagccaagtttgcatg<br>gctccatataaaacagatccagaggcatctgatggtggcagctaggacaaggtctgcggcc<br>aacaaattggtgatgctaacccataaggtaggccaagtctttgtcactcctgaacttgtcgttgt<br>gacgcatacgaatgagaacaagttcacatgtcttacccaggaacttgtattgatgtatgcagat<br>atgatggagggcagagatatggtcaacataatatcaaccacggcggtgcatctcagaagctt<br>atcagagaaaattgatgacattttgcggttaatagacgctctggcaaaagacttgggtaatcaa<br>gtctacgatgttgtatcactaatggagggatttgcatacggagctgtccagctactcgagccgt<br>caggtacatttgcaggagatttcttcgcattcaacctgcaggagcttaaagacattctaattgg<br>cctcctccccaatgatatagcagaatccgtgactcatgcaatcgctactgtattctctggtttag<br>aacagaatcaagcagctgagatgttgtgtctgttgcgtctgtggggtcacccactgcttgagt<br>cccgtattgcagcaaaggcagtcaggagccaaatgtgcgcaccgaaaatggtagactttga<br>tatgatccttcaggtactgtctttcttcaagggaacaatcatcaacgggtacagaaagaagaat<br>gcaggtgtgtggccgcgagtcaaagtggatacaatatatgggaaggtcattgggcaactac<br>atgcagattcagcagagatttcacacgatatcatgttgagagagtataagagtttatctgcactt<br>gaatttgagccatgtatagaatatgaccctgtcaccaacctgagcatgttcctaaaagacaag<br>gcaatcgcacaccccaacgataattggcttgcctcgtttaggcggaaccttctctccgaagac<br>cagaagaaacatgtaaaagaagcaacttcgactaatcgcctcttgatagagtttttagagtcaa<br>atgattttgatccatataaagagatggaatatctgacgacccttgagtaccttagagatgacaat<br>gtggcagtatcatactcgctcaaggagaaggaagtgaaagttaatggacggatcttcgctaa<br>gctgacaaagaagttaaggaactgtcaggtgatggcggaagggatcctagccgatcagatt<br>gcacctttctttcagggaaatggagtcattcaggatagcatatccttgaccaagagtatgctag<br>cgatgagtcaactgtcttttaacagcaataagaaacgtatcactgactgtaaagaaagagtatc<br>ttcaaaccgcaatcatgatccgaaaagcaagaaccgtcggagagttgcaaccttcataacaa<br>ctgacctgcaaaagtactgtcttaattggagatatcagacaatcaaattgttcgctcatgccatc<br>aatcagttgatgggcctacctcacttcttcgaatggattcacctaagactgatggacactacga<br>tgttcgtaggagaccctttcaatcctccaagtgaccctactgactgtgacctctcaagagtccc<br>taatgatgacatatatattgtcagtgccagagggggtatcgaaggattatgccagaagctatg<br>gacaatgatctcaattgctgcaatccaacttgctgcagctagatcgcattgtcgtgttgcctgta<br>tggtacagggtgataatcaagtaatagcagtaacgagagaggtaagatcagacgactctcc<br>ggagatggtgttgacacagttgcatcaagccagtgataatttcttcaaggaattaattcatgtca<br>atcatttgattggccataatttgaaggatcgtgaaaccatcaggtcagacacattcttcatatac | |

TABLE 10-continued

| Exemplary plasmid sequences encoding chimeric NDVs (nucleic acid) | | |
|---|---|---|
| Name | Sequence | SEQ ID NO. |
| | agcaaacgaatcttcaaagatggagcaatcctcagtcaagtcctcaaaaattcatctaaattag<br>tgctagtgtcaggtgatctcagtgaaaacaccgtaatgtcctgtgccaacattgcctctactgt<br>agcacggctatgcgagaacgggcttcccaaagacttctgttactatttaaactatataatgagtt<br>gtgtgcagacatactttgactctgagttctccatcaccaacaattcgcaccccgatcttaatcag<br>tcgtggattgaggacatctcttttgtgcactcatatgttctgactcctgcccaattagggggact<br>gagtaaccttcaatactcaaggctctacactagaaatatcggtgacccggggactactgctttt<br>gcagagatcaagcgactagaagcagtgggattactgagtcctaacattatgactaatatctta<br>actaggccgcctgggaatggagattgggccagtctgtgcaacgacccatactctttcaatttt<br>gagactgttgcaagcccaaatattgttcttaagaaacatacgcaaagagtcctatttgaaactt<br>gttcaaatcccttattgtctggagtgcacacagaggataatgaggcagaagagaaggcattg<br>gctgaattcttgcttaatcaagaggtgattcatccccgcgttgcgcatgccatcatggaggca<br>agctctgtaggtaggagaaagcaaattcaagggcttgttgacacaacaaacaccgtaattaa<br>gattgcgcttactaggaggccattaggcatcaagaggctgatgcggatagtcaattattctag<br>catgcatgcaatgctgtttagagacgatgtttttcctccagtagatccaaccaccccttagtctc<br>ttctaatatgtgttctctgacactggcagactatgcacggaatagaagctggtcacctttgacg<br>ggaggcaggaaaatactgggtgtatctaatcctgatacgatagaactcgtagagggtgagat<br>tcttagtgtaagcggagggtgtacaagatgtgacagcggagatgaacaatttacttggttcca<br>tcttccaagcaatatagaattgaccgatgacaccagcaagaatcctccgatgagggtaccat<br>atctcgggtcaaagacacaggagaggagagctgcctcacttgcaaaaatagctcatatgtcg<br>ccacatgtaaaggctgccctaagggcatcatccgtgttgatctgggcttatggggataatgaa<br>gtaaattggactgctgctcttacgattgcaaaatctcggtgtaatgtaaacttagagtatcttcg<br>gttactgtccccttacccacggctgggaatcttcaacatagactagatgatggtataactcag<br>atgacattcacccctgcatctctctacagggtgtcaccttacattcacatatccaatgattctcaa<br>aggctgttcactgaagaaggagtcaaagaggggaatgtggtttaccaacagatcatgctctt<br>gggtttatctctaatcgaatcgatctttccaatgacaacaaccaggacatatgatgagatcaca<br>ctgcacctacatagtaaatttagttgctgtatcagagaagcacctgttgcggttcctttcgagct<br>acttggggtggtaccggaactgaggacagtgacctcaaataagtttatgtatgatcctagccc<br>tgtatcggagggagactttgcgagacttgacttagctatcttcaagagttatgagcttaatctgg<br>agtcatatcccacgatagagctaatgaacattctttcaatatccagcgggaagttgattggcca<br>gtctgtggtttcttatgatgaagatacctccataaagaatgacgccataatagtgtatgacaata<br>cccgaaattggatcagtgaagctcagaattcagatgtggtccgcctatttgaatatgcagcact<br>tgaagtgctcctcgactgttcttaccaactctattacctgagagtaagaggcctggacaatatt<br>gtcttatatatgggtgatttatacaagaatatgccaggaattctactttccaacattgcagctaca<br>atatctcatcccgtcattcattcaaggttacatgcagtgggcctggtcaaccatgacggatcac<br>accaacttgcagatacggattttatcgaaatgtctgcaaaactattagtatcttgcacccgacgt<br>gtgatctccggcttatattcaggaaataagtatgatctgctgttcccatctgtcttagatgataac<br>ctgaatgagaagatgcttcagctgatatcccggttatgctgtctgtacacggtactctttgctac<br>aacaagagaaatcccgaaaataagaggcttaactgcagaagagaaatgttcaatactcactg<br>agtatttactgtcggatgctgtgaaaccattacttagccccgatcaagtgagctctatcatgtct<br>cctaacataattacattcccagctaatctgtactacatgtctcggaagagcctcaatttgatcag<br>ggaaagggaggacagggatactatcctggcgttgttgttcccccaagagccattattagagtt<br>cccttctgtgcaagatattggtgctcgagtgaaagatccattcacccgacaacctgcggcattt<br>ttgcaagagttagatttgagtgctccagcaaggtatgacgcattcacacttagtcagattcatc<br>ctgaactcacatctccaaatccggaggaagactacttagtacgatacttgttcagagggatag<br>ggactgcatcttcctcttggtataaggcatctcatctcctttctgtacccgaggtaagatgtgca<br>agacacgggaactccttatacttagctgaagggagcggagccatcatgagtcttctcgaact<br>gcatgtaccacatgaaactatctattacaatacgctcttttcaaatgagatgaaccccccgcaa<br>cgacatttcgggccgaccccaactcagtttttgaattcggttgtttataggaatctacaggcgg<br>aggtaacatgcaaagatggatttgtccaagagttccgtccattatggagagaaaatacagag<br>gaaagcgacctgacctcagataaagtagtggggtatattacatctgcagtgccctacagatct<br>gtatcattgctgcattgtgacattgaaattcctccagggtccaatcaaagcttactagatcaact<br>agctatcaatttatctctgattgccatgcattctgtaagggagggcggggtagtaatcatcaaa<br>gtgttgtatgcaatgggatactactttcatctactcatgaacttgtttgctccgtgttccacaaaa<br>ggatatattctctctaatggttatgcatgtcgaggagatatggagtgttacctggtatttgtcatg<br>ggttacctgggcgggcctacatttgtacatgaggtggtgaggatggcgaaaactctggtgca<br>gcggcacggtacgcttttgtctaaatcagatgagatcacactgaccaggttattcacctcaca<br>gcggcagcgtgtgacagacatcctatccagtcctttaccaagattaataaagtacttgaggaa<br>gaatattgacactgcgctgattgaagccgggggacagcccgtccgtccattctgtgcggag<br>agtctggtgagcacgctagcgaacataactcagataacccagatcatcgctagtcacattga<br>cacagttatccggtctgtgatatatatggaagctgagggtgatctcgctgacacagtatttctat<br>ttaccccttacaatctctctactgacgggaaaaagaggacatcacttaaacagtgcacgagac<br>agatcctagaggttacaatactaggtcttagagtcgaaaatctcaataaaataggcgatataat<br>cagcctagtgcttaaaggcatgatctccatggaggaccttatcccactaaggacatacttgaa<br>gcatagtacctgccctaaatatttgaaggctgtcctaggtattaccaaactcaaagaaatgttta<br>cagacacttctgtactgtacttgactcgtgctcaacaaaaattctacatgaaaactataggcaat<br>gcagtcaaaggatattacagtaactgtgactcttaacgaaaatcacatattaataggctccttttt<br>tggccaattgtattcttgttgatttaatcatattatgttagaaaaaagttgaaccctgactccttag<br>gactcgaattcgaactcaaataaatgtcttaaaaaaaggttgcgcacaattattcttgagtgtag<br>tctcgtcattcaccaaatctttgtttggt | |

TABLE 11

NDV plasmid sequence

| Name | Sequence | SEQ ID NO. |
|---|---|---|
| pT7NDV-LS-L289A plasmid | tcttccgcttcctcgctcactgactcgctgcgctcggtcgttcggctgcggcgagcggtatca<br>gctcactcaaaggcggtaatacggttatccacagaatcaggggataacgcaggaaagaac<br>atgtgagcaaaaggccagcaaaaggccaggaaccgtaaaaaggccgcgttgctggcgttt<br>ttccataggctccgcccccctgacgagcatcacaaaaatcgacgctcaagtcagaggtggc<br>gaaacccgacaggactataaagataccaggcgtttccccctggaagctccctcgtgcgctct<br>cctgttccgaccctgccgcttaccggatacctgtccgcctttctcccttcgggaagcgtggcg<br>ctttctcatagctcacgctgtaggtatctcagttcggtgtaggtcgttcgctccaagctgggctg<br>tgtgcacgaaccccccgttcagcccgaccgctgcgccttatccggtaactatcgtcttgagtc<br>caacccggtaagacacgacttatcgccactggcagcagccactggtaacaggattagcaga<br>gcgaggtatgtaggcggtgctacagagttcttgaagtggtggcctaactacggctacactag<br>aagaacagtatttggtatctgcgctctgctgaagccagttaccttcggaaaaagagttggtag<br>ctcttgatccggcaaacaaaccaccgctggtagcggtggtttttttgtttgcaagcagcagatt<br>acgcgcagaaaaaaaggatctcaagaagatcctttgatcttttctacggggtctgacgctcag<br>tggaacgaaaactcacgttaagggattttggtcatgagattatcaaaaaggatcttcacctaga<br>tccttttaaattaaaaatgaagttttaaatcaatctaaagtatatatgagtaaacttggtctgacag<br>ttaccaatgcttaatcagtgaggcacctatctcagcgatctgtctatttcgttcatccatagttgc<br>ctgactccccgtcgtgtagataactacgatacgggagggcttaccatctggccccagtgctg<br>caatgataccgcgagacccacgctcaccggctccagatttatcagcaataaaccagccagc<br>cggaagggccgagcgcagaagtggtcctgcaactttatccgcctccatccagtctattaattg<br>ttgccgggaagctagagtaagtagttcgccagttaatagtttgcgcaacgttgttgccattgct<br>acaggcatcgtggtgtcacgctcgtcgtttggtatggcttcattcagctccggttcccaacgat<br>caaggcgagttacatgatcccccatgttgtgcaaaaaagcggttagctccttcggtcctccga<br>tcgttgtcagaagtaagttggccgcagtgttatcactcatggttatggcagcactgcataattct<br>cttactgtcatgccatccgtaagatgcttttctgtgactggtgagtactcaaccaagtcattctga<br>gaatagtgtatgcggcgaccgagttgctcttgcccggcgtcaatacgggataataccgcgcc<br>acatagcagaactttaaaagtgctcatcattggaaaacgttcttcggggcgaaaactctcaag<br>gatcttaccgctgttgagatccagttcgatgtaacccactcgtgcacccaactgatcttcagca<br>tcttttactttcaccagcgtttctgggtgagcaaaaacaggaaggcaaaatgccgcaaaaaag<br>ggaataagggcgacacggaaatgttgaatactcatactcttcctttttcaatattattgaagcatt<br>tatcagggttattgtctcatgagcggatacatatttgaatgtatttagaaaaataaacaaatagg<br>ggttccgcgcacatttccccgaaaagtgccacctgacgtctaagaaaccattattatcatgac<br>attaacctataaaaataggcgtatcacgaggccctttcgtctcgcgcgtttcggtgatgacggt<br>gaaaacctctgacacatgcagctcccggagacggtcacagcttgtctgtaagcggatgccg<br>ggagcagacaagcccgtcagggcgcgtcagcgggtgttggcgggtgtcggggctggctt<br>aactatgcggcatcagagcagattgtactgagagtgcaccataaaattgtaaacgttaatatttt<br>gttaaaattcgcgttaaatttttgttaaatcagctcattttttaaccaataggccgaaatcggcaa<br>aatcccttataaatcaaaagaatagcccgagatagggttgagtgttgttccagtttggaacaag<br>agtccactattaaagaacgtggactccaacgtcaaagggcgaaaaaccgtctatcagggcg<br>atggcccactacgtgaaccatcacccaaatcaagttttttggggtcgaggtgccgtaaagca<br>ctaaatcggaaccctaaagggagcccccgatttagagcttgacggggaaagccggcgaac<br>gtggcgagaaaggaagggaagaaagcgaaaggagcgggcgctagggcgctggcaagt<br>gtagcggtcacgctgcgcgtaaccaccacacccgccgcgcttaatgcgccgctacagggc<br>gcgtactatggttgctttgacgtatgcggtgtgaaataccgcacagatgcgtaaggagaaaat<br>accgcatcaggcgccattcgccattcaggctgcgcaactgttgggaagggcgatcggtgcg<br>ggcctcttcgctattacgccagctggcgaaagggggatgtgctgcaaggcgattaagttgg<br>gtaacgccagggttttcccagtcacgacgttgtaaaacgacggccagtgccaagctttaata<br>cgactcactatagggaccaaacagagaatccgtgagttacgataaaaggcgaaggagcaa<br>ttgaagtcgcacgggtagaaggtgtgaatctcgagtgcgagcccgaagcacaaactcgag<br>aaagccttctgccaacatgtcttccgtatttgatgagtacgaacagctcctcgcggctcagact<br>cgcccccaatggagctcatggaggggggagaaaaagggagtaccttaaaagtagacgtcccg<br>gtattcactcttaacagtgatgacccagaagatagatggagctttgtggtattctgcctccggat<br>tgctgttagcgaagatgccaacaaaccactcaggcaaggtgctctcatatctcttttatgctcc<br>cactcacaggtaatgaggaaccatgttgcccttgcagggaaacagaatgaagccacattgg<br>ccgtgcttgagattgatggctttgccaacggcacgccccagttcaacaataggagtggagtg<br>tctgaagagagagcacagagatttgcgatgatagcaggatctctccctcgggcatgcagca<br>acggaaccccgttcgtcacagccggggccgaagatgatgcaccagaagacatcaccgata<br>ccctggagaggatcctctctatccaggctcaagtatgggtcacagtagcaaaagccatgact<br>gcgtatgagactgcagatgagtcggaaacaaggcgaatcaataagtatatgcagcaaggca<br>gggtccaaaagaaatacatcctctaccccgtatgcaggagcacaatccaactcacgatcag<br>acagtctcttgcagtccgcatctttttggttagcgagctcaagagaggccgcaacacggcag<br>gtggtacctctacttattataacctggtaggggacgtagactcatacatcaggaataccgggc<br>ttactgcattcttcttgacactcaagtacggaatcaacaccaagacatcagcccttgcacttagt<br>agcctctcaggcgacatccagaagatgaagcagctcatgcgtttgtatcggatgaaaggag<br>ataatgcgccgtacatgacattacttggtgatagtgaccagatgagctttgcgcctgccgagt<br>atgcacaactttactcctttgccatgggtatggcatcagtcctagataaaggtactgggaaata<br>ccaatttgccagggactttatgagcacatcattctggagacttggagtagagtacgctcaggc<br>tcagggaagtagcattaacgaggatatggctgccgagctaaagctaaccccagcagcaag<br>gaggggcctggcagctgctgcccaacgggtctccgaggagaccagcagcatagacatgc<br>ctactcaacaagtcggagtcctcactgggcttagcgaggggggggtcccaagctctacaagg<br>cggatcgaatagatcgcaagggcaaccagaagccggggatggggagacccaattcctgg<br>atctgatgagagcggtagcaaatagcatgagggaggcgccaaactctgcacagggcactc<br>cccaatcggggcctcccccaactcctgggccatcccaagataacgacaccgactgggggt<br>attgatggacaaaacccagcctgcttccacaaaaacatcccaatgccctcacccgtagtcga<br>cccctcgatttgcggctctatatgaccacaccctcaaacaaacatcccccctctttcctccctcc<br>ccctgctgtacaactacgtacgccctagataccacaggcacaatgcggctcactaacaatca | 21 |

TABLE 11-continued

| NDV plasmid sequence | | |
|---|---|---|
| Name | Sequence | SEQ ID NO. |
| | aaacagagccgagggaattagaaaaaagtacgggtagaagagggatattcagagatcagg<br>gcaagtctcccgagtctctgctctctcctctacctgatagaccaggacaaacatggccaccttt<br>acagatgcagagatcgacgagctatttgagacaagtggaactgtcattgacaacataattaca<br>gcccagggtaaaccagcagagactgttggaaggagtgcaatcccacaaggcaagaccaa<br>ggtgctgagcgcagcatgggagaagcatgggagcatccagccaccggccagtcaagaca<br>accccgatcgacaggacagatctgacaaacaaccatccacacccgagcaaacgaccccg<br>catgacagcccgccggccacatccgccgaccagcccccacccaggccacagacgaag<br>ccgtcgacacacagctcaggaccggagcaagcaactctctgctgttgatgcttgacaagctc<br>agcaataaatcgtccaatgctaaaaagggcccatggtcgagcccccaagaggggaatcac<br>caacgtccgactcaacagcaggggagtcaacccagtcgcggaaacagtcaggaaagacc<br>gcagaaccaagtcaaggccgcccctggaaaccagggcacagacgtgaacacagcatatc<br>atggacaatgggaggagtcacaactatcagctggtgcaacccctcatgctctccgatcaagg<br>cagagccaagacaatacccttgtatctgcggatcatgtccagccacctgtagactttgtgcaa<br>gcgatgatgtctatgatggaggcgatatcacagagagtaagtaaggttgactatcagctagat<br>cttgtcttgaaacagacatcctccatccctatgatgcggtccgaaatccaacagctgaaaaca<br>tctgttgcagtcatggaagccaacttgggaatgatgaagattctggatcccggttgtgccaac<br>atttcatctctgagtgatctacgggcagttgcccgatctcacccggttttagtttcaggccctgg<br>agacccctctccctatgtgacacaaggaggcgaaatggcacttaataaactttcgcaaccag<br>tgccacatccatctgaattgattaaacccgccactgcatgcgggcctgatataggagtggaa<br>aaggacactgtccgtgcattgatcatgtcacgcccaatgcacccgagttcttcagccaagctc<br>ctaagcaagttagatgcagccgggtcgatcgaggaaatcaggaaaatcaagcgccttgctc<br>taaatggctaattactactgccacacgtagcgggtccctgtccactcggcatcacacggaatc<br>tgcaccgagttcccccccgcggacccaaggtccaactctccaagcggcaatcctctctcgct<br>tcctcagccccactgaatgatcgcgtaaccgtaattaatctagctacatttaagattaagaaaa<br>aatacgggtagaattggagtgccccaattgtgccaagatggactcatctaggacaattgggc<br>tgtactttgattctgcccattcttctagcaacctgttagcatttccgatcgtcctacaagacacag<br>gagatgggaagaagcaaatcgccccgcaatataggatccagcgccttgacttgtggactga<br>tagtaaggaggactcagtattcatcaccacctatggattcatctttcaagttgggaatgaagaa<br>gccaccgtcggcatgatcgatgataaacccaagcgcgagttactttccgctgcgatgctctg<br>cctaggaagcgtcccaaataccggagaccttattgagctggcaagggcctgtctcactatga<br>tagtcacatgcaagaagagtgcaactaatactgagagaatggttttctcagtagtgcaggcac<br>cccaagtgctgcaaagctgtagggttgtggcaaacaaatactcatcagtgaatgcagtcaag<br>cacgtgaaagcgccagagaagattcccgggagtggaaccctagaatacaaggtgaactttg<br>tctccttgactgtggtaccgaagagggatgtctacaagatcccagctgcagtattgaaggtttc<br>tggctcgagtctgtacaatcttgcgctcaatgtcactattaatgtggaggtagacccgaggagt<br>cctttggttaaatctctgtctaagtctgacagcggatactatgctaacctcttcttgcatattggac<br>ttatgaccactgtagataggaaggggaagaaagtgacatttgacaagctggaaaagaaaat<br>aaggagccttgatctatctgtcgggctcagtgatgtgctcgggccttccgtgttggtaaaagc<br>aagaggtgcacggactaagcttttggcacctttcttctctagcagtgggacagcctgctatcc<br>catagcaaatgcttctcctcaggtggccaagatactctggagtcaaaccgcgtgcctgcgga<br>gcgttaaaatcattatccaagcaggtacccaacgcgctgtcgcagtgaccgccgaccacga<br>ggttacctctactaagctggagaaggggcacacccttgccaaatacaatccttttaagaaata<br>agctgcgtctctgagattgcgctccgcccactcacccagatcatcatgacacaaaaaactaat<br>ctgtcttgattatttacagttagtttacctgtctatcaagttagaaaaaacacgggtagaagattct<br>ggatcccggttggcgccctccaggtgcaagatgggctccagaccttctaccaagaacccag<br>cacctatgatgctgactatccgggttgcgctggtactgagttgcatctgtccggcaaactccat<br>tgatggcaggcctcttgcagctgcaggaattgtggttacaggagacaaagccgtcaacatat<br>acacctcatcccagacaggatcaatcatagttaagctcctcccgaatctgcccaaggataag<br>gaggcatgtgcgaaagccccccttggatgcatacaacaggacattgaccactttgctcacccc<br>ccttggtgactctatccgtaggatacaagagtctgtgactacatctggagggggagacagg<br>ggcgccttataggcgccattattggcggtgtggctcttggggttgcaactgccgcacaaataa<br>cagcggccgcagctctgatacaagccaaacaaaatgctgccaacatcctccgacttaaaga<br>gagcattgccgcaaccaatgaggctgtgcatgaggtcactgacggattatcgcaactagca<br>gtggcagttgggaagatgcagcagtttgttaatgaccaatttaataaaacagctcaggaatta<br>gactgcatcaaaattgcacagcaagttggtgtagagctcaacctgtacctaaccgaattgact<br>acagtattcggaccacaaatcacttcacctgctttaaacaagctgactattcaggcactttaca<br>atctagctggtggaaatatggattacttattgactaagttaggtgtagggaacaatcaactcag<br>ctcattaatcggtagcggcttaatcaccggtaaccctattctatacgactcacagactcaactct<br>tgggtatacaggtaactgccccttcagtcgggaacctaaataatatgcgtgccacctacttgg<br>aaaccttatccgtaagcacaaccaggggatttgcctcggcacttgtcccaaaagtggtgaca<br>caggtcggttctgtgatagaagaacttgacacctcatactgtatagaaactgacttagatttata<br>ttgtacaagaatagtaacgttccctatgtcccctggtatttattcctgcttgagcggcaatacgtc<br>ggcctgtatgtactcaaagaccgaaggcgcacttactacaccatacatgactatcaaaggttc<br>agtcatcgccaactgcaagatgacaacatgtagatgtgtaaacccccgggtatcatatcgc<br>aaaactatggagaagccgtgtctctaatagataaacaatcatgcaatgttttatccttaggcgg<br>gataactttaaggctcagtggggaattcgatgtaacttatcagaagaatatctcaatacaagatt<br>ctcaagtaataataacaggcaatcttgatatctcaactgagcttgggaatgtcaacaactcgat<br>cagtaatgctttgaataagttagaggaaagcaacagaaaactagacaaagtcaatgtcaaac<br>tgactagcacatctgctctcattacctatatcgttttgactatcatatctcttgtttttggtatacttag<br>cctgattctagcatgctacctaatgtacaagcaaaaggcgcaacaaaagaccttattatggctt<br>gggaataatactctagatcagatgagagccactacaaaaatgtgaacacagatgaggaacg<br>aaggtttccctaatagtaatttgtgtgaaagttctggtagtctgtcagttcagagagttaagaaa<br>aaactaccggttgtagatgaccaaaggacgatatacgggtagaacggtaagagaggccgc<br>ccctcaattgcgagccaggcttcacaacctccgttctaccgcttcaccgacaacagtcctcaa<br>tcatggaccgcgccgttagccaagttgcgttagagaatgatgaaagagaggcaaaaaatac | |

TABLE 11-continued

| NDV plasmid sequence | | |
|---|---|---|
| Name | Sequence | SEQ ID NO. |
| | atggcgcttgatattccggattgcaatcttattcttaacagtagtgaccttggctatatctgtagc<br>ctcccttttatatagcatgggggctagcacacctagcgatcttgtaggcataccgactaggatt<br>tccagggcagaagaaaagattacatctacacttggttccaatcaagatgtagtagataggata<br>tataagcaagtggcccttgagtctccgttggcattgttaaatactgagaccacaattatgaacg<br>caataacatctctctcttatcagattaatggagctgcaaacaacagtgggtgggggcaccta<br>tccatgacccagattatatagggggataggcaaagaactcattgtagatgatgctagtgatg<br>tcacatcattctatccctctgcatttcaagaacatctgaattttatcccggcgcctactacaggat<br>caggttgcactcgaatacccteatttgacatgagtgctacccattactgctacacccataatgta<br>atattgtctggatgcagagatcactcacattcatatcagtatttagcacttggtgtgctccggac<br>atctgcaacagggagggtattcttttctactctgcgttccatcaacctggacgacacccaaaat<br>cggaagtcttgcagtgtgagtgcaactcccctgggttgtgatatgctgtgctcgaaagtcacg<br>gagacagaggaagaagattataactcagctgtccctacgcggatggtacatgggaggttag<br>ggttcgacggccagtaccacgaaaaggacctagatgtcacaacattattcggggactgggt<br>ggccaactacccaggagtagggggtggatcttttattgacagccgcgtatggttctcagtcta<br>cggagggttaaaacccaattcacccagtgacactgtacaggaagggaaatatgtgatataca<br>agcgatacaatgacacatgcccagatgagcaagactaccagattcgaatggccaagtcttc<br>gtataagcctggacggtttggtgggaaacgcatacagcaggctatcttatctatcaaggtgtc<br>aacatccttaggcgaagacccggtactgactgtaccgcccaacacagtcacactcatgggg<br>gccgaaggcagaattctcacagtagggacatctcatttcttgtatcaacgagggtcatcatact<br>tctctcccgcgttattatatcctatgacagtcagcaacaaaacagccactcttcatagtccttata<br>cattcaatgccttcactcggccaggtagtatcccttgccaggcttcagcaagatgccccaact<br>cgtgtgttactggagtctatacagatccatatcccctaatcttctatagaaaccacaccttgcga<br>ggggtattcgggacaatgcttgatggtgtacaagcaagacttaaccctgcgtctgcagtattc<br>gatagcacatcccgcagtcgcattactcgagtgagttcaagcagtaccaaagcagcatacac<br>aacatcaacttgttttaaagtggtcaagactaataagacctattgtctcagcattgctgaaatatc<br>taatactctcttcggagaattcagaatcgtcccgttactagttgagatcctcaaagatgacggg<br>gttagagaagccaggtctggctagttgagtcaattataaaggagttggaaagatggcattgta<br>tcacctatcttctgcgacatcaagaatcaaaccgaatgccggcgcgtgctcgaattccatgtt<br>gccagttgaccacaatcagccagtgctcatgcgatcagattaagccttgtcaatagtctcttga<br>ttaagaaaaaatgtaagtggcaatgagatacaaggcaaaacagctcatggttaacaatacgg<br>gtaggacatggcgagctccggtcctgaaagggcagagcatcagattatcctaccagagtca<br>cacctgtcttcaccattggtcaagcacaaactactctattactggaaattaactgggctaccgct<br>tcctgatgaatgtgacttcgaccacctcattctcagccgacaatggaaaaaaatacttgaatcg<br>gcctctcctgatactgagagaatgataaaactcggaagggcagtacaccaaactcttaacca<br>caattccagaataaccggagtgctccaccccaggtgtttagaagaactggctaatattgaggt<br>cccagattcaaccaacaaatttcggaagattgagaagaagatccaaattcacaacacgagat<br>atggagaactgttcacaaggctgtgtacgcatatagagaagaaactgctggggtcatcttggt<br>ctaacaatgtcccccggtcagaggagttcagcagcattcgtacggatccggcattctggtttc<br>actcaaaatggtccacagccaagtttgcatggctccatataaaacagatccagaggcatctg<br>atggtggcagctaggacaaggtctgcggccaacaaattggtgatgctaacccataaggtag<br>gccaagtctttgtcactcctgaacttgtcgttgtgacgcatacgaatgagaacaagttcacatg<br>tcttacccaggaacttgtattgatgtatgcagatatgatggagggcagagatatggtcaacata<br>atatcaaccacggcggtgcatctcagaagcttatcagagaaaattgatgacattttgcggttaa<br>tagacgctctggcaaaagacttgggtaatcaagtctacgatgttgtatcactaatggagggatt<br>tgcatacggagctgtccagctactcgagccgtcaggtacatttgcaggagatttcttcgcattc<br>aacctgcaggagcttaaagacattctaattggcctcctccccaatgatatagcagaatccgtg<br>actcatgcaatcgctactgtattctctggtttagaacagaatcaagcagctgagatgttgtgtct<br>gttgcgtctgtggggtcacccactgcttgagtcccgtattgcagcaaaggcagtcaggagcc<br>aaatgtgcgcaccgaaaatggtagactttgatatgatccttcaggtactgtctttcttcaaggga<br>acaatcatcaacgggtacagaaagaagaatgcaggtgtgtggccgcgagtcaaagtggat<br>acaatatatgggaaggtcattgggcaactacatgcagattcagcagagatttcacacgatatc<br>atgttgagagagtataagagtttatctgcacttgaatttgagccatgtatagaatatgaccctgt<br>caccaacctgagcatgttcctaaaagacaaggcaatcgcacaccccaacgataattggcttg<br>cctcgtttaggcggaaccttctctccgaagaccagaagaaacatgtaaaagaagcaacttcg<br>actaatcgcctcttgatagagtttttagagtcaaatgattttgatccatataaagagatggaatat<br>ctgacgacccttgagtaccttagagatgacaatgtggcagtatcatactcgctcaaggagaa<br>ggaagtgaaagttaatggacggatcttcgctaagctgacaaagaagttaaggaactgtcagg<br>tgatggcggaagggatcctagccgatcagattgcacctttctttcagggaaatggagtcattc<br>aggatagcatatccttgaccaagagtatgctagcgatgagtcaactgtcttttaacagcaataa<br>gaaacgtatcactgactgtaaagaaagagtatcttcaaaccgcaatcatgatccgaaaagca<br>agaaccgtcggagagttgcaaccttcataacaactgacctgcaaaagtactgtcttaattgga<br>gatatcagacaatcaaattgttcgctcatgccatcaatcagttgatgggcctacctcacttcttc<br>gaatggattcacctaagactgatggacactacgatgttcgtaggagaccctttcaatcctcca<br>agtgaccctactgactgtgacctctcaagagtccctaatgatgacatatatattgtcagtgcca<br>gagggggtatcgaaggattatgccagaagctatggacaatgatctcaattgctgcaatccaa<br>cttgctgcagctagatcgcattgtcgtgttgcctgtatggtacagggtgataatcaagtaatag<br>cagtaacgagagaggtaagatcagacgactctccggagatggtgttgacacagttgcatca<br>agccagtgataatttcttcaaggaattaattcatgtcaatcatttgattggccataatttgaaggat<br>cgtgaaaccatcaggtcagacacattcttcatatacagcaaacgaatcttcaaagatggagca<br>atcctcagtcaagtcctcaaaaattcatctaaattagtgctagtgtcaggtgatctcagtgaaaa<br>caccgtaatgtcctgtgccaacattgcctctactgtagcacggctatgcgagaacgggcttcc<br>caaagacttctgttactatttaaactatataatgagttgtgtgcagacatactttgactctgagttc<br>tccatcaccaacaattcgcaccccgatcttaatcagtcgtggattgaggacatctcttttgtgca<br>ctcatatgttctgactcctgcccaattaggggactgagtaaccttcaatactcaaggctctac<br>actagaaatatcggtgacccggggactactgcttttgcagagatcaagcgactagaagcagt | |

TABLE 11-continued

NDV plasmid sequence

| Name | Sequence | SEQ ID NO. |
| --- | --- | --- |
| | gggattactgagtcctaacattatgactaatatcttaactaggccgcctgggaatggagattgg<br>gccagtctgtgcaacgacccatactctttcaattttgagactgttgcaagcccaaatattgttctt<br>aagaaacatacgcaaagagtcctatttgaaacttgttcaaatcccttattgtctggagtgcaca<br>cagaggataatgaggcagaagagaaggcattggctgaattcttgcttaatcaagaggtgatt<br>catccccgcgttgcgcatgccatcatggaggcaagctctgtaggtaggagaaagcaaattc<br>aagggcttgttgacacaacaaacaccgtaattaagattgcgcttactaggaggccattaggc<br>atcaagaggctgatgcggatagtcaattattctagcatgcatgcaatgctgtttagagacgatg<br>tttttcctccagtagatccaaccaccccttagtctcttctaatatgtgttctctgacactggcaga<br>ctatgcacggaatagaagctggtcacctttgacgggaggcaggaaaatactgggtgtatcta<br>atcctgatacgatagaactcgtagagggtgagattcttagtgtaagcggagggtgtacaagat<br>gtgacagcggagatgaacaatttacttggttccatcttccaagcaatatagaattgaccgatga<br>caccagcaagaatcctccgatgagggtaccatatctcgggtcaaagacacaggagaggag<br>agctgcctcacttgcaaaaatagctcatatgtcgccacatgtaaaggctgccctaagggcatc<br>atccgtgttgatctgggcttatggggataatgaagtaaattggactgctgctcttacgattgcaa<br>aatctcggtgtaatgtaaacttagagtatcttcggttactgtcccctttacccacggctgggaat<br>cttcaacatagactagatgatggtataactcagatgacattcaccccctgcatctctctacaggg<br>tgtcaccttacattcacatatccaatgattctcaaaggctgttcactgaagaaggagtcaaaga<br>ggggaatgtggtttaccaacagatcatgctcttgggtttatctctaatcgaatcgatctttccaat<br>gacaacaaccaggacatatgatgagatcacactgcacctacatagtaaatttagttgctgtatc<br>agagaagcacctgttgcggttcctttcgagctacttggggtggtaccggaactgaggacagt<br>gacctcaaataagtttatgtatgatcctagccctgtatcggagggagactttgcgagacttgac<br>ttagctatcttcaagagttatgagcttaatctggagtcatatcccacgatagagctaatgaacat<br>tctttcaatatccagcgggaagttgattggccagtctgtggtttcttatgatgaagatacctccat<br>aaagaatgacgccataatagtgtatgacaatacccgaaattggatcagtgaagctcagaattc<br>agatgtggtccgcctatttgaatatgcagcacttgaagtgctcctcgactgttcttaccaactct<br>attacctgagagtaagaggcctggacaatattgtcttatatatgggtgatttatacaagaatatg<br>ccaggaattctactttccaacattgcagctacaatatctcatcccgtcattcattcaaggttacat<br>gcagtgggcctggtcaaccatgacggatcacaccaacttgcagatacggattttatcgaaat<br>gtctgcaaaactattagtatcttgcacccgacgtgtgatctccggcttatattcaggaaataagt<br>atgatctgctgttcccatctgtcttagatgataacctgaatgagaagatgcttcagctgatatcc<br>cggttatgctgtctgtacacggtactctttgctacaacaagagaaatcccgaaaataagaggc<br>ttaactgcagaagagaaatgttcaatactcactgagtatttactgtcggatgctgtgaaaccatt<br>acttagccccgatcaagtgagctctatcatgtctcctaacataattacattcccagctaatctgta<br>ctacatgtctcggaagagcctcaatttgatcagggaaagggaggacagggatactatcctgg<br>cgttgttgttcccccaagagccattattagagttcccttctgtgcaagatattggtgctcgagtg<br>aaagatccattcacccgacaacctgcggcatttttgcaagagttagatttgagtgctccagca<br>aggtatgacgcattcacacttagtcagattcatcctgaactcacatctccaaatccggaggaa<br>gactacttagtacgatacttgttcagagggatagggactgcatcttcctcttggtataaggcatc<br>tcatctcctttctgtacccgaggtaagatgtgcaagacacgggaactccttatacttagctgaa<br>gggagcggagccatcatgagtcttctcgaactgcatgtaccacatgaaactatctattacaat<br>acgctcttttcaaatgagatgaacccccccgcaacgacatttcgggccgaccccaactcagttt<br>ttgaattcggttgtttataggaatctacaggcggaggtaacatgcaaagatggatttgtccaag<br>agttccgtccattatggagagaaaatacagaggaaagcgacctgacctcagataaagtagtg<br>gggtatattacatctgcagtgccctacagatctgtatcattgctgcattgtgacattgaaattcct<br>ccagggtccaatcaaagcttactagatcaactagctatcaatttatctctgattgccatgcattct<br>gtaagggagggcggggtagtaatcatcaaagtgttgtatgcaatgggatactactttcatcta<br>ctcatgaacttgtttgctccgtgttccacaaaaggatatattctctctaatggttatgcatgtcga<br>ggagatatggagtgttacctggtatttgtcatgggttacctgggcgggcctacatttgtacatg<br>aggtggtgaggatggcgaaaactctggtgcagcggcacggtacgcttttgtctaaatcagat<br>gagatcacactgaccaggttattcacctcacagcggcagcgtgtgacagacatcctatccag<br>tcctttaccaagattaataaagtacttgaggaagaatattgacactgcgctgattgaagccggg<br>ggacagcccgtccgtccattctgtgcggagagtctggtgagcacgctagcgaacataactc<br>agataacccagatcatcgctagtcacattgacacagttatccggtctgtgatatatatggaagc<br>tgagggtgatctcgctgacacagtatttctatttaccccttacaatctctctactgacgggaaaa<br>agaggacatcacttaaacagtgcacgagacagatcctagaggttacaatactaggtcttaga<br>gtcgaaaatctcaataaaataggcgatataatcagcctagtgcttaaaggcatgatctccatg<br>gaggaccttatcccactaaggacatacttgaagcatagtacctgccctaaatatttgaaggct<br>gtcctaggtattaccaaactcaaagaaatgtttacagacacttctgtactgtacttgactcgtgct<br>caacaaaaattctacatgaaaactataggcaatgcagtcaaaggatattacagtaactgtgac<br>tcttaacgaaaatcacatattaataggctcctttttttggccaattgtattcttgttgatttaatcatatt<br>atgttagaaaaaagttgaaccctgactccttaggactcgaattcgaactcaaataaatgtcttaa<br>aaaaaggttgcgcacaattattcttgagtgtagtctcgtcattcaccaaatctttgtttggtgcgc<br>gcggccggcatggtcccagcctcctcgctggcgccggctgggcaacattccgaggggac<br>cgtcccctcggtaatggcgaatgggacgtcgactgctaacaaagcccgaaaggaagctga<br>gttggctgctgccaccgctgagcaataactagcataaccccttggggcctctaaacgggtctt<br>gaggggttttttgctgaaaggaggaactatatgcgcgcagatctgtcatgatgatcattgcaat<br>tggatccatatatagggcccgggttataattacctcaggtcgacgtcccatggccattcgaatt<br>cgtaatcatggtcatagctgtttcctgtgtgaaattgttatccgctcacaattccacacaacatac<br>gagccggaagcataaagtgtaaagcctggggtgcctaatgagtgagctaactcacattaatt<br>gcgttgcgctcactgcccgctttccagtcgggaaacctgtcgtgccagctgcattaatgaatc<br>ggccaacgcgcggggagaggcggtttgcgtattgggcgc | |

TABLE 12

Exemplary antibody-related sequences

| Name | Sequence | SEQ ID NO. |
|---|---|---|
| Pembrolizumab Light Chain CDR1 | RASKGVSTSGYSYLH | 1 |
| Pembrolizumab Light Chain CDR2 | LASYLES | 2 |
| Pembrolizumab Light Chain CDR3 | QHSRDLPLT | 3 |
| Pembrolizumab Light Chain Variable Region | EIVLTQSPATLSLSPGERATLSCRASKGVSTSGYSYLHWYQ QKPGQAPRLLIYLASYLESGVPARFSGSGSGTDFTLTISSLE PEDFAVYYCQHSRDLPLTFGGGTKVEIK | 4 |
| Pembrolizumab Light Chain | EIVLTQSPATLSLSPGERATLSCRASKGVSTSGYSYLHWYQ QKPGQAPRLLIYLASYLESGVPARFSGSGSGTDFTLTISSLE PEDFAVYYCQHSRDLPLTFGGGTKVEIKRTVAAPSVFIFPP SDEQLKSGTASVVCLLNNFYPREAKVQWKVDNALQSGNS QESVTEQDSKDSTYSLSSTLTLSKADYEKHKVYACEVTHQ GLSSPVTKSFNRGEC | 5 |
| Pembrolizumab Heavy Chain CDR1 | NYYMY | 6 |
| Pembrolizumab Heavy Chain CDR2 | GINPSNGGTNFNEKFKN | 7 |
| Pembrolizumab Heavy Chain CDR3 | RDYRFDMGFDY | 8 |
| Pembrolizumab Heavy Chain Variable Region | QVQLVQSGVEVKKPGASVKVSCKASGYTFTNYYMYWVR QAPGQGLEWMGGINPSNGGTNFNEKFKNRVTLTTDSSTTT AYMELKSLQFDDTAVYYCARRDYRFDMGFDYWGQGTTV TVSS | 9 |
| Pembrolizumab Heavy Chain | QVQLVQSGVEVKKPGASVKVSCKASGYTFTNYYMYWVR QAPGQGLEWMGGINPSNGGTNFNEKFKNRVTLTTDSSTTT AYMELKSLQFDDTAVYYCARRDYRFDMGFDYWGQGTTV TVSSASTKGPSVFPLAPCSRSTSESTAALGCLVKDYFPEPV TVSWNSGALTSGVHTFPAVLQSSGLYSLSSVVTVPSSSLGT KTYTCNVDHKPSNTKVDKRVESKYGPPCPPCPAPEFLGGP SVFLFPPKPKDTLMISRTPEVTCVVVDVSQEDPEVQFNWY VDGVEVHNAKTKPREEQFNSTYRVVSVLTVLHQDWLNG KEYKCKVSNKGLPSSIEKTISKAKGQPREPQVYTLPPSQEE MTKNQVSLTCLVKGFYPSDIAVEWESNGQPENNYKTTPP VLDSDGSFFLYSRLTVDKSRWQEGNVFSCSVMHEALHNH YTQKSLSLSLGK | 10 |
| Nivolumab Light Chain CDR1 | RASQSVSSYLA | 11 |
| Nivolumab Light Chain CDR2 | DASNRAT | 12 |
| Nivolumab Light Chain CDR3 | QQSSNWPRT | 13 |
| Nivolumab Light Chain Variable Region | EIVLTQSPATLSLSPGERATLSCRASQSVSSYLAWYQQKPG QAPRLLIYDASNRATGIPARFSGSGSGTDFTLTISSLEPEDF AVYYCQQSSNWPRTFGQGTKVEIK | 14 |
| Nivolumab Light Chain | EIVLTQSPATLSLSPGERATLSCRASQSVSSYLAWYQQKPG QAPRLLIYDASNRATGIPARFSGSGSGTDFTLTISSLEPEDF AVYYCQQSSNWPRTFGQGTKVEIKRTVAAPSVFIFPPSDE QLKSGTASVVCLLNNFYPREAKVQWKVDNALQSGNSQES VTEQDSKDSTYSLSSTLTLSKADYEKHKVYACEVTHQGLS SPVTKSFNRGEC | 15 |

TABLE 12-continued

Exemplary antibody-related sequences

| Name | Sequence | SEQ ID NO. |
|---|---|---|
| Nivolumab Heavy Chain CDR1 | NSGMH | 16 |
| Nivolumab Heavy Chain CDR2 | VIWYDGSKRYYADSVKG | 17 |
| Nivolumab Heavy Chain CDR3 | NDDY | 18 |
| Nivolumab Heavy Chain Variable Region | QVQLVESGGGVVQPGRSLRLDCKASGITFSNSGMHWVRQ APGKGLEWVAVIWYDGSKRYYADSVKGRFTISRDNSKNT LFLQMNSLRAEDTAVYYCATNDDYWGQGTLVTVSS | 19 |
| Nivolumab Heavy Chain | QVQLVESGGGVVQPGRSLRLDCKASGITFSNSGMHWVRQ APGKGLEWVAVIWYDGSKRYYADSVKGRFTISRDNSKNT LFLQMNSLRAEDTAVYYCATNDDYWGQGTLVTVSSAST KGPSVFPLAPCSRSTSESTAALGCLVKDYFPEPVTVSWNSG ALTSGVHTFPAVLQSSGLYSLSSVVTVPSSSLGTKTYTCNV DHKPSNTKVDKRVESKYGPPCPPCPAPEFLGGPSVFLFPPK PKDTLMISRTPEVTCVVVDVSQEDPEVQFNWYVDGVEVH NAKTKPREEQFNSTYRVVSVLTVLHQDWLNGKEYKCKVS NKGLPSSIEKTISKAKGQPREPQVYTLPPSQEEMTKNQVSL TCLVKGFYPSDIAVEWESNGQPENNYKTTPPVLDSDGSFF LYSRLTVDKSRWQEGNVFSCSVMHEALHNHYTQKSLSLS LGK | 20 |

TABLE 13

Primer sequences

| Name | Sequence | SEQ ID NO. |
|---|---|---|
| Human IL-12 Forward primer | GCACCGAGTTCCCCCCCGCGGTTAGAAA AAATACGGGTAGAACCGCCACCATGGGT CACCAGCAG | 32 |
| Human IL-12 Reverse primer | AGTTGGACCTTGGGTCCGCGGATTAGGA AGCATTCAG | 33 |
| muIL-2 Forward Primer | GCACCGAGTTCCCCCCCGCGGTTAGAAA AAATACGGGTAGAACCGCCACCATGTACA GCATGCAG | 34 |
| muIL-2 Reverse Primer | AGTTGGACCTTGGGTCCGCGGATTATTG AGGGCTTGT | 35 |
| Primer | TCGATCGAGGAAATCAGG | 36 |
| Primer | GTACAGCCCAATTGTCC | 37 |

TABLE 15

Cleavage sequences

| Name | Sequence | SEQ ID NO. |
|---|---|---|
| S116 F protein cleavage site | HNRTKSF | 56 |
| S116K F protein cleavage site | HNKTKSF | 58 |
| S116m F protein cleavage site | HNRMKSF | 69 |

TABLE 15-continued

Cleavage sequences

| Name | Sequence | SEQ ID NO. |
|---|---|---|
| S116KMF protein cleavage site | HNKMSFI | 70 |
| R116 F protein cleavage site | HNRTKRFI | 71 |
| LaSota strain F protein cleavage site | GRQGRL | 72 |

6. EXAMPLES

The working examples of International Patent Application Publication No. WO 2014/158811 (i.e., Sections 6 and 7 of International Patent Application Publication No. WO 2014/158811) and U.S. Patent Application Publication Nos. 2016/0015760 A1 (i.e., Section 6 of U.S. Patent Application Publication No. 2016/0015760 A1) and 2014/0271677 A1 (i.e., Sections 6 and 7 of U.S. Patent Application Publication No. 2014/0271677 A1) are incorporated by reference herein in their entireties.

6.1 Example 1

This example demonstrates the therapeutic efficacy of NDV therapy in combination with immune checkpoint modulators that are immunostimulatory in the treatment of cancer.

6.1.1 Materials & Methods 6.1.1.1 Mice

BALB/c mice (6-8 weeks old), and WT C57BL/6 mice were purchased from Jackson Laboratory. All mice were maintained in microisolator cages and treated in accordance with the NIH and American Association of Laboratory Animal Care regulations. All mouse procedures and experiments for this study were approved by the Memorial Sloan-Kettering Cancer Center Institutional Animal Care and Use Committee.

6.1.1.2 Cell Lines

The murine cancer cell lines for melanoma (B16F10), and colon carcinoma (CT26 and MC38) were maintained in RPMI medium supplemented with 10% fetal calf serum and penicillin with streptomycin. The murine prostate cancer cell line TRAMP-C2 was maintained in DMEM medium supplemented with 5% fetal calf serum (FCS; Mediatech, Inc.), 5% Nu Serum IV (BD Biosciences) HEPES, 2-ME, pen/strep, L-glut, 5 μg/mL insulin (Sigma), and 10 nmol/L DHT (Sigma).

6.1.1.3 Antibodies

Therapeutic anti-PD-1 (clone RMP1-14) and anti-PD-L1 monoclonal antibodies were produced by BioXcell. Antibodies used for flow cytometry were purchased from eBioscience, Biolegend, Invitrogen, and BD Pharmingen.

6.1.1.4 Viruses and Cloning

Recombinant lentogenic NDV LaSota strain was used for all experiments. Viruses were rescued from cDNA using methods described previously and sequenced by reverse transcription PCR for insert fidelity. Virus titers were determined by serial dilution and immunofluorescence in Vero cells.

6.1.1.5 In Vitro Infection Experiments

For evaluation of upregulation of surface MHC-I, MHC-II, and ICAM-1 by NDV, and for evaluation of surface expression of the ICOSL transgene from the NDV-ICOSL virus, B16F10 cells were infected in 6-well dishes at MOI 2 in triplicate. Twenty-four hours later, the cells were harvested by mechanical scraping and processed for surface labeling and quantification by flow cytometry. For virus growth curve experiments, B16F10 cells were incubated at room temperature with the virus in 6-well culture dishes at the indicated MOIs in a total volume of 100 μl. One hour after the incubation, the infection media was aspirated and the cells were incubated at 37° C. in 1 ml of DMEM with 10% chick allantoic fluid. After 24, 48, and 72 hours, the supernatants were collected and virus titers were determined as above. For in vitro cytotoxicity experiments, the infections were carried out in a similar fashion. At 24, 48, 72, and 96 hours post infection the cells were washed and incubated with 1% Triton X-100 at 37° C. for 30 minutes. LDH activity in the lysates was determined using the Promega CytoTox 96 assay kit, according to the manufacturer's instructions.

6.1.1.6 Tumor Challenge Survival Experiments

Bilateral flank tumor models were established to monitor for therapeutic efficacy in both injected and systemic tumors. Treatment schedules and cell doses were established for each tumor model to achieve 10-20% tumor clearance by NDV or anti-PD-1 as single agents. For experiments evaluating combination therapy of wild-type NDV (NDV-WT) with immune checkpoint blockade, B16F10 tumors were implanted by injection of $2\times10^5$ B16F10 cells in the right flank i.d. on day 0 and $5\times10^4$ cells in the left flank on day 4. On days 7, 10, 13, and 16 the mice were treated with 4 intratumoral injections of $2\times10^7$ pfu of NDV in PBS in a total volume of 100 μl. Concurrently, on days 7, 10, 13, and 16 the mice received 4 i.p. injections of anti-PD-1 antibody (250 μg). Control groups received a corresponding dose of isotype antibody i.p. and intratumoral injection of PBS. Tumor size and incidence were monitored over time by measurement with a caliper.

For the TRAMP-C2 model, $5\times10^5$ cells were implanted in right flank on day 0 and $5\times10^5$ cells were implanted in the left flank on day 8. Treatment was performed on days 11, 14, 17, and 20 in the similar fashion to above.

For the CT26 model, tumors were implanted by injection of $1\times10^6$ CT26 cells in the right flank i.d. on day 0 and $1\times10^6$ cells in the left flank on day 2. Treatment was carried out as above on days 6, 9, and 12.

6.1.1.7 Isolation of Tumor-Infiltrating Lymphocytes

B16F10 tumors were implanted by injection of $2\times10^5$ B16F10 cells in the right flank i.d. on day 0 and $2\times10^5$ cells in the left flank on day 4. On days 7, 10, and 13 the mice were treated with 3 intratumoral injections of $2\times10^7$ pfu of NDV, and 250 μg of i.p. anti-PD-1 antibody, where specified. On day 15, mice were sacrificed by $CO_2$ inhalation. Tumors and tumor-draining lymph nodes were removed using forceps and surgical scissors and weighed. Tumors from each group were minced with scissors prior to incubation with 1.67 Wunsch U/mL Liberase and 0.2 mg/mL DNase for 30 minutes at 37° C. Tumors were homogenized by repeated pipetting and filtered through a 70-μm nylon filter. Cell suspensions were washed once with complete RPMI and purified on a Ficoll gradient to eliminate dead cells. Cells from tumor draining lymph nodes were isolated by grinding the lymph nodes through a 70-μm nylon filter.

6.1.1.8 Flow Cytometry

Cells isolated from tumors or tumor-draining lymph nodes were processed for surface labeling with several antibody panels staining CD45, CD3, CD4, CD8, CD44, PD-1, ICOS, CD11c, CD19, NK1.1, CD11b, F4/80, Ly6C and Ly6G. Fixable viability dye eFluor780 (eBioscience) was used to distinguish the live cells. Cells were further permeabilized using FoxP3 fixation and permeabilization kit (eBioscience) and stained for Ki-67, FoxP3, Granzyme B, CTLA-4, and IFN gamma. Data was acquired using the LSRII Flow cytometer (BD Biosciences) and analyzed using FlowJo software (Treestar).

6.1.1.9 DC Purification and Loading

Spleens from naïve mice were isolated and digested with 1.67 Wunsch U/mL Liberase and 0.2 mg/mL DNase for 30 minutes at 37° C. The resulting cell suspensions were filtered through 70 um nylon filter and washed once with complete RPMI. CD11c+ dendritic cells were purified by positive selection using Miltenyi magnetic beads. Isolated dendritic cells were cultured overnight with recombinant GM-CSF and B16F10 tumor lysates and were purified on Ficoll gradient.

6.1.1.10 Analysis of Cytokine Production

Cell suspensions from tumors or tumor-draining lymph nodes were pooled and enriched for T cells using a Miltenyi T-cell purification kit. Isolated T cells were counted and co-cultured for 8 hours with dendritic cells loaded with B16F10 tumor cell lysates in the presence of 20 U/ml IL-2 (R and D) plus Brefeldin A (BD Bioscience). After restimulation, lymphocytes were processed for flow cytometry as above.

6.1.1.11 Statistics

Data were analyzed by 2-tailed Student's t test, and $P<0.05$ was considered statistically significant.

6.1.2 Results

In order to characterize the anti-tumor immune response induced by Newcastle disease virus (NDV) infection, the expression of MHC I and MHC II molecules as well as ICAM-1 on the surface of in vitro infected cells was assessed. As shown in FIG. 1, NDV infection in B16 melanoma cells induces upregulation of MHC class I and II molecules as well as adhesion molecule ICAM-1, all of which are thought to be important for recruitment of tumor-specific lymphocytes and activation of anti-tumor immune response. Next, the anti-tumor immune response induced by NDV infection in vivo was assessed in a murine melanoma model and an established 2-flank model that allowed for monitoring of responses both in the virus-injected tumors as well as distant tumors which do not receive the virus. As shown in FIGS. 2A-2E, the virus-infected tumors show dramatic infiltration with immune cells such as NK cells, macrophages, and CD8 and CD4 cells, but not regulatory T cells. Since part of this immune response could be a response to virus, rather than tumor, the immune response with respect to contralateral tumors was assessed (FIGS. 3A-3C). Interestingly, these tumors demonstrated a similar degree of increased CD8 and CD4 effector, but not T reg infiltrate. Analysis of these cells revealed that they upregulate activation, proliferation, and lytic markers (FIGS. 4A-4C). NDV monotherapy was effective in controlling the treated tumors (FIG. 5A), but only marginally slowed down the growth of the contralateral tumors (FIG. 5B). Mice that cleared the tumors, however, demonstrated some degree of protection against further tumor challenge (FIGS. 5C-5D), suggesting that NDV therapy can induce a lasting immunity.

Next, it was assessed whether additional mechanisms could be targeted to enhance the anti-tumor effect generated by NDV. Characterization of tumor-infiltrating lymphocytes from both NDV-injected and non-injected tumors revealed upregulation of the inhibitory receptor CTLA-4 on lymphocytes (FIG. 5E-F).

To determine whether targeting immune checkpoints in combination with NDV therapy could be beneficial, the effect on the PD-1-PD-L1 pathway following NDV infection was assessed. As shown in FIGS. 6A-6C, NDV infected tumor cells both in vitro and in vivo had upregulated the expression of the inhibitory PD-L1 ligand on the surface of the cells. This effect was not just a result of a direct virus infection, but was also seen when non-infected cells were treated with UV-inactivated supernatants from the virus infected cells (FIG. 6B) and in contralateral, noninfected, tumors (FIG. 6C). This prompted testing combination therapy with NDV and anti-PD-1 antibody. NDV therapy in combination with anti-PD-1 in the aggressive B16 melanoma model resulted in cures in the majority of animals, an effect that was associated with increased tumor infiltration with activated effector lymphocytes (FIGS. 7A-7F).

Throughout the studies conducted, the therapeutic efficacy of a combination therapy decreased when larger tumor challenge was used. Next, activation markers that could predict a better response and could be targeted for further improvement in therapeutic efficacy were assessed. ICOS upregulation has been previously been shown to be associated with more durable therapeutic responses and increased survival in patients treated with anti-CTLA-4 therapy for malignant melanoma.

Overall, these studies demonstrate that combination of NDV with immune checkpoint regulatory antibodies can be used as a strategy to circumvent the limitation of both oncolytic virus therapy and antibody therapy. This finding has clinical application.

6.2 Example 2

This example demonstrates the anti-tumor immune responses induced by oncolytic NDV and the anti-tumor responses induced by NDV in combination with PD-1 blockade.

6.2.1 Materials & Methods 6.2.1.1 Mice

C57BL/6J and Balb/C mice were purchased from Jackson Laboratory. IFNAR−/−mice on C57BL/6J background were a kind gift of Dr. Eric Pamer. Pmel-1 and Trp-1 TCR transgenic mice have been reported (Overwijk et al., 2003, J. Exp. Med, 198:568, Muransky et al., 2008, Blood 112: 362) and were provided by N. Restifo (National Cancer Institute, Bethesda, MD). Trp1 mice were crossed to CD2: luciferase mice provided by Patrick Hwu at M D Anderson Cancer Center (Houston, TX) to create Trp1 Luciferase$^+$ (Trp1-Fluc) mice. All mice were maintained in microisolator cages and treated in accordance with the NIH and American Association of Laboratory Animal Care regulations. All mouse procedures and experiments for this study were approved by the Memorial Sloan-Kettering Cancer Center Institutional Animal Care and Use Committee.

6.2.1.2 Cell Lines

The murine cancer cell lines for melanoma (B16F10), and colon carcinoma (CT26 and MC38) were maintained in RPMI medium supplemented with 10% fetal calf serum and penicillin with streptomycin. The murine prostate cancer cell line TRAMP-C2 was maintained in DMEM medium supplemented with 5% fetal calf serum (FCS; Mediatech, Inc.), 5% Nu Serum IV (BD Biosciences) HEPES, 2-ME, pen/strep, L-glut, 5 μg/mL insulin (Sigma), and 10 nmol/L DHT (Sigma).

6.2.1.3 Antibodies

Therapeutic anti-PD-1 (clone RMP1-14), anti-PD-L1 (clone 9G2), anti-CD8 (clone 2.43), anti-CD4 (clone GK1.5), anti-IFN-gamma (clone XMG1.2), and anti-NK1.1 (clone PK136) monoclonal antibodies were produced by BioXcell. Antibodies used for flow cytometry were purchased from eBioscience, Biolegend, Invitrogen, and BD Pharmingen.

6.2.1.4 Viruses and Cloning

Recombinant lentogenic NDV LaSota strain was used for all experiments. Viruses were rescued from cDNA using methods described previously and sequenced by reverse transcription PCR for insert fidelity. Virus titers were determined by serial dilution and immunofluorescence in Vero cells.

6.2.1.5 In Vitro Infection Experiments

For cell surface labeling, cells were infected in 6-well dishes at MOI 2 (B16F10) or MOI 5 (TRAMP C2) in triplicate. Twenty-four hours later, the cells were harvested by scraping and processed for surface labeling and quantification by flow cytometry. For in vitro cytotoxicity experiments, cells were infected at the indicated MOI's and incubated at 37° C. in serum-free media in presence of 250 ng/ml TPCK trypsin. At 24, 48, 72, and 96 hours post infection the cells were washed and incubated with 1% Triton X-100 at 37° C. for 30 minutes. LDH activity in the lysates was determined using the Promega CytoTox 96 assay kit, according to the manufacturer's instructions.

6.2.1.6 Tumor Challenge Survival Experiments

Bilateral flank tumor models were established to monitor for therapeutic efficacy in both injected and systemic tumors. Treatment schedules and cell doses were established for each tumor model to achieve 10-20% tumor clearance by NDV. For experiments evaluating combination therapy of NDV with anti-PD-1 antibody, B16F10 tumors were implanted by injection of $2\times10^5$ B16F10F10 cells in the right flank intradermally (i.d.) on day 0 and $5\times10^4$ cells in the left flank on day 4. On days 7, 9, 11, and 13 the mice were treated with intratumoral injections of $2\times10^7$ pfu of NDV in PBS in a total volume of 100 μl. Concurrently, on days 7, 9, 11, and 13 the mice received intraperitoneal (i.p.) injections of anti-PD-1 antibody (250 μg) or anti-PD-L1 antibody (250 μg). Control groups received a corresponding dose of isotype antibody i.p. and intratumoral injection of PBS. The animals were euthanized for signs of distress or when the total tumor volume reached 1000 $mm^3$. For depletion of immune cells, mice were injected i.p. with 500 μg of monoclonal antibodies to CD8+, CD4+, NK1.1 or IFNγ one day before and two days after tumor challenge, followed by injection of 250 μg every 5 days throughout the experiment. For the TRAMP-C2 model, $1\times10^6$ cells were implanted in the right flank on day 0 and $5\times10^5$ cells were implanted in the left flank on day 4. Treatment was performed on days 7, 10, 13, and 16 in the similar fashion to above. For the CT26 model, tumors were implanted by injection of $1\times10^6$ CT26 cells in the right flank i.d. on day 0 and $1\times10^6$ cells in the left flank on day 2. Treatment was carried out as above on days 6, 9, and 12. Isolation of Trp1 and Pmel lymphocytes and adoptive transfer Spleens and lymph nodes from transgenic mice were isolated and grinded through 70-um nylon filters. CD4+ and CD8+ cells were purified by positive selection using Miltenyi magnetic beads.

The isolated Trp1 or Pmel cells were injected into recipient animals via the tail vein at the indicated schedule at $2.5\times10^4$ cells per mouse and $1\times10^6$ cells per mouse, respectively.

6.2.1.7 Serum Transfer Experiments

Groups of tumor-bearing mice were treated intratumorally with single injection of NDV or PBS. On day 4, blood was collected by terminal bleeding and serum was isolated by centrifugation. Sera were pooled from each group and UV-treated in Stratalinker 1800 with six pulses of 300 $mJ/cm^2$ UV light to inactivate any virus that could be potentially present. Undiluted 100 μl of serum was injected intratumorally into naïve B16F10 tumor-bearing mice for a total of 3 injections given every other day. Tumors were removed 3 days after the last injection and processed for isolation of tumor-infiltrating lymphocytes as described below.

6.2.1.8 Bioluminescence Imaging

Mice were imaged every 2-3 days starting on day 6. Mice were injected retro-orbitally with 50 μl of 40 mg/ml D-luciferin (Caliper Life Sciences) in PBS and imaged immediately using the IVIS Imaging System (Caliper Life Sciences). Gray-scale photographic images and bioluminescence color images were superimposed using The Living Image, version 4.0 (Caliper Life Sciences) software overlay. A region of interest (ROI) was manually selected over the tumor and the area of the ROI was kept constant.

6.2.1.9 Isolation of Tumor-Infiltrating Lymphocytes

B16F10 tumors were implanted by injection of $2\times10^5$ B16F10 cells in the right flank i.d. on day 0 and $2\times10^5$ cells in the left flank on day 4. On days 7, 9, and 11 the mice were treated with intratumoral injections of $2\times10^7$ pfu of NDV, and i.p. anti-PD-1 antibody where specified. Rare animals that died from tumor burden (always in untreated control groups) or animals that completely cleared the tumors (always in treatment groups) were not used for the analysis. On day 15, mice were sacrificed and tumors and tumor-draining lymph nodes were removed using forceps and surgical scissors and weighed. Tumors from each group were minced with scissors prior to incubation with 1.67 Wunsch U/mL Liberase and 0.2 mg/mL DNase for 30 minutes at 37° C. Tumors were homogenized by repeated pipetting and filtered through a 70-μm nylon filter. Cell suspensions were washed once with complete RPMI and purified on a Ficoll gradient to eliminate dead cells. Cells from tumor draining lymph nodes were isolated by grinding the lymph nodes through a 70-μm nylon filter.

6.2.1.10 Flow Cytometry

Cells isolated from tumors or tumor-draining lymph nodes were processed for surface labeling with several antibody panels staining for CD45, CD3, CD4, CD8, CD44, ICOS, CD11c, CD19, NK1.1, CD11b, F4/80, Ly6C and Ly6G. Fixable viability dye eFluor506 (eBioscience) was used to distinguish the live cells. Cells were further permeabilized using FoxP3 fixation and permeabilization kit (eBioscience) and stained for Ki-67, FoxP3, Granzyme B, CTLA-4, and IFNγ. Data was acquired using the LSRII Flow cytometer (BD Biosciences) and analyzed using FlowJo software (Treestar).

6.2.1.11 DC Purification and Loading

Spleens from naïve mice were isolated and digested with 1.67 Wunsch U/mL Liberase and 0.2 mg/mL DNase for 30 minutes at 37° C. The resulting cell suspensions were filtered through 70 um nylon filter and washed once with complete RPMI. CD11c+DC's were purified by positive selection using Miltenyi magnetic beads. Isolated DC's were cultured overnight with recombinant GM-CSF and B16F10 tumor lysates and were purified on Ficoll gradient.

6.2.1.12 Analysis of Cytokine Production

Cell suspensions from tumors or tumor-draining lymph nodes were pooled and enriched for T cells using a Miltenyi T-cell purification kit. Isolated T cells were counted and co-cultured for 8 hours with DC's loaded with B16F10 tumor cell lysates in the presence of 20 U/ml IL-2 (R and D) plus Brefeldin A (BD Bioscience). After restimulation, lymphocytes were processed for flow cytometry as above.

6.2.1.13 Immunofluorescence and Microscopy

Tumors were dissected from the mice, washed in PBS, fixed in 4% paraformaldehyde, and processed for paraffin embedding according to protocols described previously. Sections were cut using a microtome, mounted on slides, and processed for staining with hematoxylin and eosin (H&E) or with anti-CD3 and anti-FoxP3 antibody. Slides were analyzed on Zeiss Axio 2 wide-field microscope using 10× and 20× objectives.

6.2.1.14 Statistics

Data were analyzed by 2-tailed Student's t test (for comparisons of 2 groups) and ANOVA where appropriate. Data for survival were analyzed by Log-Rank (Mantel-Cox) Test. Two-sided $p<0.05$ was considered statistically significant ($P\leq0.05$ (*), $P\leq0.01$ (), $P<0.001$ (*) $P<0.0001$ (****)).

6.2.2 Results 6.2.2.1 NDV Replication is Restricted to the Injected Tumor Site

The viral distribution kinetics with intratumoral and systemic administration of NDV were characterized. Intratumoral injection of recombinant NDV expressing firefly luciferase reporter (NDV-Fluc) resulted in sustained luciferase signal in the injected flank tumor, while systemic administration of the virus resulted in no detectable luciferase signal in the tumor (FIG. 8A). As limited systemic virus delivery was unlikely to induce sufficient tumor lysis and immune response, the intratumoral NDV injection was explored as a means to elicit an anti-tumor immune response that could potentially overcome the limitations of systemic OV therapy. As such, for further studies modeled metastatic disease was modeled by using the bilateral flank B16F10 tumor model (FIG. 10A). NDV-Fluc administration into the right flank tumor resulted in viral replication within the injected tumor, with the luciferase signal detectable for up to 96 hours (FIGS. 8B-8D). No virus was detected in the contralateral (left flank) tumor by luminescent imaging (FIGS. 8B-8D), by passage in embryonated eggs, or RT-PCR. This system thus allowed for the characterization of the immune responses in both virus-injected and distant tumors, which were not directly affected by NDV.

6.2.2.2 NDV Therapy Increases Local and Distant Tumor Lymphocyte Infiltration and Delays Tumor Growth Analysis of the virus-injected tumors revealed an inflammatory response as evidenced by increased infiltration with cells expressing leukocyte common antigen CD45 (FIGS. 9A-9B). The immune infiltrates were characterized by increase in innate immune compartment, including myeloid cells, NK cells, and NKT cells (FIG. 9C), and the adaptive compartment, including CD8+ and conventional CD4+ FoxP3− (Tconv) T cells, leading to significant increase of CD8 and Tconv to regulatory (Treg) T cell ratios ($p=0.0131$ and $p=0.0006$, respectively) (FIGS. 9D-9F). Remarkably, analysis of the contralateral tumors revealed a similar increase in the inflammatory infiltrates (FIGS. 10B and 10C), characterized by increased numbers of both innate immune cells (FIG. 10D) and effector T cells (FIGS. 10E and 10G). Notably, although there were no major changes in the absolute number of Tregs (FIG. 10G), there was a substantial decrease in their relative percentages (FIGS. 10E, 10F, and 10H), with significant enhancement of the CD8 and Tconv to Treg ratios ($p=0.002$ and $p=0.0021$, respectively) (FIG. 10I). Effector T cells isolated from the distal tumors expressed increased activation, proliferation, and lytic markers ICOS, Ki-67, and Granzyme B, respectively (FIGS. 10J and 10K). As previously, virus or viral RNA was unable to be isolated from the distant tumors, suggesting that the observed changes in the distant tumor microenvironment were not due to direct viral infection. In order to further exclude the possibility of undetectable local viral spread, tumors were implanted at other distant sites, such as bilateral posterior footpads, which generated similar findings (FIGS. 11A-11E).

Consistent with the observed inflammatory effect, intratumoral administration of NDV resulted in growth delay not only of the injected, but also of the contralateral tumors, resulting in prolonged animal survival (FIGS. 10L and 10M). To determine whether this effect was transient and whether durable anti-tumor protection was possible, single-flank B16F10 tumor-bearing mice were intratumorally treated with NDV, and long-term survivors were injected with B16F10 cells on the opposite flank. The majority of the animals demonstrated tumor growth delay, and 30% of the animals completely rejected rechallenged cells, suggesting that intratumoral therapy with NDV can indeed induce protective anti-tumor memory responses (FIG. 13).

6.2.2.3 NDV Induces Tumor Infiltration and Expansion of Tumor-Specific Lymphocytes To determine whether the anti-tumor immune response was dependent on the NDV-injected tumor type or a result of nonspecific inflammation generated by NDV infection, the experiment was performed with heterologous tumors (MC38 colon carcinoma and B16F10 melanoma) implanted at the opposite flanks (FIG. 12A). To track tumor-specific lymphocytes, T cell receptor-transgenic congenically-marked CD8+(Pmel) cells or luciferase-marked CD4+ (Trp1) cells recognizing the melanoma differentiation antigens gp100 (Pmel) and Trp1 (Trp1) were adoptively transferred (Muranski et al., 2008, Blood, 112: 362; Overwijk et al., 2003, J Exp Med, 198: 569). Bioluminescent imaging was used to measure the distribution and expansion kinetics of the adoptively transferred Trp1 cells. Transfer of Trp1 cells into PBS-treated tumor-bearing animals failed to result in Trp1 accumulation in the tumors, highlighting the highly immunosuppressive nature of the tumor microenvironment in this model (FIGS. 12B-12D). NDV injection into B16F10 tumors resulted in significant increase in the luciferase signal within the injected tumors (FIGS. 12B-12D), indicating Trp1 T cell expansion (area under the curve (AUC) p=0.0084). Remarkably, similar expansion was seen in the contralateral tumor, albeit at a delay (p=0.0009) (FIGS. 12B-12D). In contrast, NDV injection into MC38 tumors failed to induce substantial Trp1 infiltration into the injected MC38 tumors or distant B16F10 tumors (FIGS. 12B-12D), suggesting that the distant tumor-specific lymphocyte infiltration is likely dependent on the antigen identity of the injected tumor. Similarly, intratumoral injection of NDV resulted in increased infiltration of Pmel cells in distant tumors, which was more pronounced when the injected tumor was B16F10 rather than MC38 (FIG. 12E).

Interestingly, although infiltration of distant B16F10 tumors with adoptively-transferred lymphocytes was dependent on the injected tumor identity, distant tumors did demonstrate increased immune infiltration even when the primary injected tumor was MC38 (FIG. 12F), suggesting that a nonspecific inflammatory response component may also play a role. Indeed, serum from NDV-treated animals, treated with UV irradiation to inactivate any potential virus, induced tumor leukocyte infiltration when injected intratumorally into naïve B16F10 tumor-bearing mice (FIGS. 12G and 12H), with the majority of the increase seen in the NK and CD8+ compartments (p=0.0089 and p=0.0443, respectively) (FIG. 12I).

6.2.2.4 NDV Upregulates CTLA-4 on Tumor-Infiltrating T Cells

Despite the prominent inflammatory response and growth delay seen in distant tumors, complete contralateral tumor rejection with long-term survival was only seen in approximately 10% of animals (FIG. 10M), suggestive of active immunosuppressive mechanisms in the tumor microenvironment. Characterization of NDV-injected and distant tumors revealed upregulation of CTLA-4 on tumor-infiltrating T cells (FIG. 14).

6.2.2.5 NDV Therapy Leads to Upregulation of PD-L1 on Tumor Cells and on Tumor Infiltrating Leukocytes To determine whether targeting other immune checkpoints in combination with NDV therapy could be beneficial, the effect on the PD-1-PD-L1 pathway following NDV infection was assessed. As shown in FIG. 15, NDV infected tumor cells both in vitro and in vivo had upregulated the expression of the inhibitory PD-L1 ligand on the surface of the cells (FIG. 15A), which was also seen in the distant, noninfected, tumors. The upregulation of PD-L1 was not just restricted to tumor cells, but was also seen on tumor infiltrating leukocytes of both innate and adaptive immune lineages (FIG. 15B).

6.2.2.6 Combination Therapy of NDV with PD-1 and PD-L1-Blocking Antibodies Leads to Improved Anti-Tumor Immunity and Long-Term Animal Survival The combination of NDV with antibody blocking PD-1 and the combination of NDV with antibody blocking PD-L1 were evaluated in the bilateral flank melanoma model described above. NDV therapy in combination with either anti-PD-1 or anti-PD-L1 antibody led to improved animal survival (FIGS. 16A-16D and FIGS. 17A-17D). Distant tumors from animals treated with combination of NDV and anti-PD-1 antibody were characterized. As can be seen from FIGS. 18A-18E, combination of intratumoral NDV with systemic PD-1 blockade led to marked distant tumor infiltration with immune cells, with the increase in tumor-infiltrating CD8 cells being the most pronounced finding. The infiltrating cells upregulated proliferation and lytic markers Ki67 and granzyme B, respectively (FIGS. 19A-19B).

6.2.2.7 NDV Induces Tumor Immune Infiltration Upregulation of ICOS on CD4 and CD8 Cells in the Virus-Injected and Distant Tumors and Tumor Draining Lymph Nodes (TDLN)

The findings above demonstrated that combination of intratumoral NDV with systemic immune checkpoint blockade results in significant synergy between the two therapeutic approaches. To further build on these findings, enhancement of T cell effector function within the tumor microenvironment through a relevant co-stimulatory pathway may drive a better anti-tumor immune response was investigated. Previous studies identified the sustained upregulation of inducible costimulator (ICOS) on T cells as a strong indicator of response to CTLA-4 blockade in patients (Carthon et al., 2010, Clin. Canc. Res., 16:2861). ICOS is a CD28 homologue upregulated on the surface of activated T cells that has been shown to be critical for T cell-dependent B lymphocyte responses and development of all T helper subsets (Simpson et al., 2010 Curr Opin Immunol. 22:326). The role of ICOS in anti-tumor tumor efficacy of CTLA-4 blockade was recently confirmed by mouse studies, where ICOS-deficient mice were severely compromised in development of anti-tumor response with CTLA-4 blockade (Fu et al., 2011, Cancer Res., 71:5445).

The expression of ICOS in bilateral flank tumor models treated with NDV were characterized to determine whether the receptor could serve as a target in this therapeutic approach. To characterize the local and abscopal effects of intratumoral NDV therapy, bilateral flank B16F10 melanoma models were utilized, with the virus administered to a unilateral tumor (FIG. 20A). Activation markers that could predict a better response and could be targeted for further improvement in therapeutic efficacy were assessed. The example focused on ICOS, as sustained ICOS upregulation has been previously been shown to be associated with more durable therapeutic responses and increased survival in patients treated with anti-CTLA-4 therapy for malignant melanoma. Analysis of lymphocytes isolated from the tumors and tumor-draining lymph nodes identified upregulation of the co-stimulatory molecule ICOS as one of the activation markers in the treated animals (FIGS. 20B and 20C).

6.2.3 Conclusion

To trigger immunogenic tumor cell death and an inflammatory response, nonpathogenic NDV was employed, which, despite its relatively weak lytic activity, has been demonstrated to be a potent inducer of type I IFN and DC maturation (Wilden et al., 2009, Int J Oncol 34: 971; Kato et al., 2005, Immunity 23: 19). A bilateral flank melanoma model with staggered implantation of tumors at a schedule that was previously demonstrated not to be affected by concomitant immunity was utilized (Turk et al., 2004, J Exp Med 200: 771). This example demonstrates that intratumoral injection of NDV results in distant tumor immune infiltration in the absence of distant virus spread. Notably, this effect was associated with relative reduction in the number of Tregs and marked enhancement of CD4 and CD8 effector to Treg ratios, which has been previously demonstrated to be a marker of a favorable immunological response to immunotherapy (Quezada et al., 2006, J Clin Invest 116: 1935; Curran et al., 2010, Proc Natl Acad Sci USA 107: 4275).

The data in this example demonstrates that NDV enhances tumor infiltration with tumor-specific lymphocytes, an effect that was dependent on the identity of the virus-injected tumor. The enhanced tumor infiltration and expansion of adoptively-transferred lymphocytes further suggest the synergy between oncolytic virus therapy and therapeutic approaches utilizing adoptive T cell transfer. It is plausible that the tumor-specific lymphocytes undergo activation and expansion at the site of the initial viral infection, followed by their migration to other tumor sites, which is likely dependent on chemokines and lymphocyte homing receptors (Franciszkiewicz et al., 2012, Cancer Res 72: 6325). The data in this example also demonstrates that distant tumor immune infiltration was in part non-specific and could be induced by NDV infection of a heterologous tumor or by transfer of serum from treated animals to naïve tumor-bearing mice. Increased vascular permeability induced by inflammatory cytokines such as IL-6 may strongly contribute to activation of tumor vasculature and lymphocyte recruitment into the tumors (Fisher et al., 2011, The Journal of clinical investigation 121: 3846).

Despite the pronounced increase in TILs, therapeutic effect in distant tumors was rather modest with NDV monotherapy, highlighting the immunosuppressive nature of the microenvironment of these tumors (Spranger et al., 2013, Sci Transl Med 5).

In summary, this example demonstrates localized intratumoral therapy of B16 melanoma with NDV induces inflammatory responses leading to lymphocytic infiltrates and anti-tumor effect in distant (non-virally injected) tumors without distant virus spread. The inflammatory effect coincided with distant tumor infiltration with tumor-specific CD4+ and CD8+ T cells, which was dependent on the identity of the virus-injected tumor. This example demonstrates that localized therapy with oncolytic NDV induces inflammatory immune infiltrates in distant tumors, making them susceptible to systemic therapy with immunomodulatory antibodies.

6.3 Example 3

This example demonstrates that the intratumoral administration of NDV encoding IL-12 in combination with the administration of anti-PD-1 antibody results in robust anti-tumor activity in both NDV-IL-12 injected and non-injected tumors. As shown below, this anti-tumor activity correlates with the induction of immune genes and the infiltration of CD3+ T cells.

6.3.1 Materials and Methods

6.3.1.1 Cloning and Rescue of Viruses

The NDV genome contains six open reading frames which encode the nucleoprotein (NP), phosphoprotein (P), matrix protein (M), fusion protein (F), hemagglutinin-neuraminidase (HN), and large viral polymerase protein (L). A human IL-12 transgene (SEQ ID NO: 26) consisting of nucleic acid sequences encoding the IL-12 p40 subunit, a GGGGGGS (SEQ ID NO: 24) linker, and the IL-12 p35 subunit was inserted into the SacII cloning site between the P and M genes in the pT7NDV-LS-L289A plasmid (FIG. 21; SEQ ID NO: 21). The resulting pT7NDV-LS-L289A plasmid containing the human IL-12 transgene (SEQ ID NO: 31) is referred to as "NDV-huIL-12" or "pT7NDV-LS-L289A-huIL-12" in this example. As shown in FIG. 21, the pT7NDV-LS-L289A plasmid contains the lentogenic NDV LaSota sequence under the transcriptional control of a T7 promoter. The plasmid contains an L289A mutation in the sequence encoding the NDV F protein. The L289A mutation in the NDV F protein has been reported to render the F protein more fusogenic as compared to the wild-type F protein, and promote oncolytic activity. See, e.g., Sergel et al., 2000, J. Virol. 74:5101; Altomonte et al., 2010, Mol. Ther. 18:275.

To generate the human IL-12 transgene for insertion into the pT7NDV-LS-L289A plasmid, forward and reverse primers (SEQ ID NOs: 32 and 33) were designed with the "Rule of Six" in mind and these primers were used to generate a PCR fragment with ends that have 15 base pairs of homology with the SacII cloning site in the pT7NDV-LS-L289A plasmid. Since successful rescue of NDV requires that the genome with the transgene follow the "Rule of Six", the "Rule of Six" was considered during primer design and confirmed and corrected when necessary. The pT7NDV-LS-L289A plasmid was digested with SacII (NEB, Catalogue #R0157S) overnight at 37 degrees Celsius followed by Alkaline phosphatase (NEB, Catalogue #M02895) treatment for 30 minutes at 37 degrees Celsius to prevent plasmid re-circularization. After digestion and alkaline phosphatase treatment, the linearized plasmid was purified using the NucleoSpin clean-up kit (Macherey-Nagel, Catalogue #740609.250). The PCR fragment and the cut plasmid were then infused together using the Infusion HD cloning kit from Takara Clontech. The resulting plasmids were transformed into Max Efficiency Stbl2 Competent Cells (Life Technologies, Catalogue #10268-019). Positives clones were identified by colony PCR and sequence confirmation. For sequence confirmation, primers annealing outside of the cloned region were utilized (TCGATCGAGGAAATCAGG (SEQ ID NO: 36) and GTACAGCCCAATTGTCC (SEQ ID NO: 37). Thereafter, an endotoxin free midi prep was generated using the PureLink HiPure Midi prep kit (Invitrogen, Catalogue #K210004).

A similar strategy as described above with respect to the NDV-huIL-12 construct was utilized for the cloning and rescue of NDV encoding a murine IL-12 transgene (SEQ ID NO: 30). Namely, forward and reverse primers (SEQ ID NOS: 34 and 35) were designed with the "Rule of Six" in mind and the primers were used to generate a PCR fragment with ends that have 15 base pairs of homology with the SacII cloning site in the pT7NDV-LS-L289A plasmid. The PCR fragment was cloned into the pT7NDV-LS-L289A plasmid using the techniques described above and positive clones were selected as described above. The pT7NDV-LS-L289A plasmid containing the murine IL-12 transgene (SEQ ID NO: 31) is referred to as "NDV-muIL-12," or pT7NDV-LS-L289A-muIL-12 in this example.

Baby hamster kidney (BHK)-derived cells expressing T7 RNA polymerase (BSR-T7) were transfected with plasmids encoding L, NP, P and T7 RNA polymerase proteins and the pT7NDV-LS-L289A-huIL-12 plasmid or pT7NDV-LS-L289A-muIL-12 using the TransIT®-LT1 Transfection Reagent (Mirrus, Catalogue #MIR2300). In particular, for the rescue transfection, 30 μL of Trans-IT LT1 reagent and 150 μL of OptiMEM were used per well with the following plasmid concentrations (μg/well in a 6 well plate): 4.0 μg pT7NDV-LS-L289A-huIL-12 or pT7NDV-LS-L289A-muIL-12 plasmid; 2.0 μg of N plasmid, 1.0 μg of P plasmid; 1.0 μg of L plasmid; 2.0 μg of T7opt plasmid (Addgene plasmid #65974, obtained as a gift from Benhur Lee lab). To generate NDV-WT, rescue transfection was performed in a similar manner with pT7NDV-LS-L289A (i.e., the pT7NDV-LS-L289A-huIL-12 plasmid lacking the huIL-12 transgene). See, e.g., Ayllon et al., 2013, J. of Visualized Experiments, 80:e50830 for a description of the process for rescuing recombinant NDV from cDNA. The supernatant along with the cells were collected (using a cell scraper) 48 hours post-transfection and kept on ice until injected into the allantoic cavities of 9-10 day old embryonated chicken eggs. Injected eggs were incubated at 37 degree Celsius for 2 days, followed by overnight incubation at 4 degree Celsius. Allantoic fluid was then harvested. To harvest the allantoic fluid, the eggs' shells were cracked open under sterile conditions, the allantoic fluid was retrieved using a pipette and transferred into sterile falcon tubes kept on ice, and cellular debris were cleared by centrifugation (15×g). To confirm viral growth, a sample of this allantoic fluid was then used in a hemagglutination assay. The viruses were then aliquoted and directly frozen (−80 degrees Celsius) until use.

No observable difference in virus titer was observed with the introduction of the murine or human IL-12 transgene into the NDV. Representative virus titers are listed as follows after culture in eggs: $1.40\times10^8$ for NDV-huIL12; $3\times10^8$ for NDV-wt; and $1.7\times10^8$ for NDV-mIL12.

6.3.1.2 Hemagglutination (HA) Assay

HA assays were done using V-bottomed microtiter plates. 50 μL of 1×PBS was added to every well in the plate except for the first row. The first row received 100 μL of neat (i.e., undiluted) allantoic fluid carrying the virus. Two-fold serial dilutions of the virus suspension was then done across the entire row. Excess 50 μL was discarded after the last row. All wells had a final volume of 50 μL. 50 μL of 0.5% turkey erythrocyte suspension was then added to every well and the plate was tapped gently. The plate was incubated at 4 degrees Celsius for 20-30 minutes for the erythrocytes to settle. Samples showing complete hemagglutination were considered positive for virus. Negative results were observed as clear red pellets at the bottom of the plate.

6.3.1.3 IL-12 Expression huIL-12 and muIL-12 expression was confirmed by commercially available kits from R&D systems—Human IL-12 Quantikine ELISA kits (D2050) and Mouse IL-12 Quantikine ELISA kits (M1270).

6.3.1.4 Analysis of NDV-huIL-12

NDV-huIL-12 was quantified and characterized by flow virometry using techniques described in Vlasak et al., Vaccine 34(2016) 2321-2328, which is incorporated by reference herein in its entirety.

In addition, the expression of the six NDV proteins (F, HN, NP, L, P, and M) were analyzed by SDS-PAGE under reducing conditions. In particular, the SDS-PAGE analysis was executed using Invitrogen NuPAGE 4-12% Bis-Tris gels (ThermoFisher Scientific, Catalog No. NP0321BOX) in a MOPS (3-(N-morpholino)propanesulfonic acid)) buffer matrix. Samples were reduced using lithium dodecyl sulfate (LDS) and dithiothreitol (DTT) and heat treated for 10 minutes at 70° C. The gels were stained using GelCode Blue Stain (ThermoFisher Scientific, Catalog No. 24590) overnight, destained with water before imaged using a Molecular Dynamics Personal Densitometer SI and ImageQuant software.

Further, NDV titers were determined by a plaque assay with Vero cells in the presence of trypsin as described in Newcastle disease virus: propagation, quantification, and storage. Curr. Protoc Microbiol. 2006, June, Chapter 15: Unit 15F.2, which is incorporated by reference herein in its entirety.

6.3.1.5 Mice

WT C57BL/6 mice were purchased from Jackson Laboratory. All mice were maintained in microisolator cages and treated in accordance with the NIH and American Association of Laboratory Animal Care regulations. All mouse procedures and experiments for this study were approved by the Merck Research Laboratories (Boston and Palo Alto) Institutional Animal Care and Use Committee(s).

6.3.1.6 Cell Lines

The murine cancer cell line for melanoma (B16F10), was maintained in DMEM medium supplemented with 10% fetal calf serum.

6.3.1.7 Antibodies

Anti-mouse PD-1 monoclonal antibody (muDX400) and mouse IgG1 isotype control antibody (Mouse×[HEXON_Adenovirus] (TC31.27F11.C2) IgG1) were produced by Merck Research Laboratories.

6.3.1.8 Viruses and Cloning

Recombinant lentogenic NDV LaSota strain was used for all experiments. Viruses were rescued from cDNA using methods described previously and sequenced by reverse transcription PCR for insert fidelity. Virus titers were determined by serial dilution and immunofluorescence in Vero cells.

6.3.1.9 Tumor Challenge Experiments

Bilateral flank tumor models were established to monitor for therapeutic efficacy in both injected and systemic tumors. Treatment schedules and cell doses were established for each tumor model to achieve 10-20% tumor clearance by NDV or anti-PD-1 as single agents. For experiments evaluating combination therapy of either wild-type NDV (NDV-WT) or NDV expressing mouse IL-12 (NDV-muIL-12) with PD-1 blockade, B16F10 tumors were implanted by injection of $2\times10^5$ and $1\times10^5$ B16F10 cells subcutaneously (SC) in the right flank and left flank, respectively. Dosing was initiated 7-9 days following tumor implantation. Day 0 indicates first day of dosing. On Days 0, 2, 4 and 6 the mice were treated with 4 intratumoral injections of $1\times10^7$ pfu of NDV-WT or NDV-muIL-12 in PBS in a total volume of 100 μl in the tumor in right flank (referred to as injected tumors). Tumors in left flanks are referred to as non-injected tumors. Concurrently, on Days 0, 4, and 8 or on Days 0 and 6 (depending on study design), mice received either 3 or 2 i.p. injections of anti-PD-1 antibody (10 mg/kg). Control groups received a corresponding dose of isotype antibody i.p. and intratumoral injection of PBS. Tumor size and incidence were monitored over time by measurement with a caliper. Following euthanasia of animals, tumors were either harvested and snap frozen using liquid nitrogen for RNA isolation and gene expression analysis or fixed in 10% neutral buffered formalin for 48 hour, transferred to 70% ethanol, and embedded in paraffin blocks for immunohistochemistry.

6.3.1.10 Immunohistochemistry

Mouse CD3 staining was performed on 4 μm thick formalin-fixed, paraffin-embedded tissue sections. The sections were deparaffinized and rehydrated in an ethanol series. Slides were subjected to heat-induced epitope retrieval and blocking of endogenous peroxidase before incubation with the primary antibody, anti-mouse CD3 rat mAb clone CD3-12 (AbD Serotec, Catalog No. MCA1477) at working dilution of 1:1000 for 60 mins at room temperature. Sections were then incubated with secondary antibody, Rabbit anti-Rat IgG H&L preadsorbed (Abcam, ab102248) for 15 mins, followed by ImmPRESS™ HRP Anti-Rabbit IgG (Peroxidase) Polymer Detection Kit (Vector Laboratories, Catalog No. MP-7401) for 15 mins. Antigen-antibody binding was visualized with the use of 3,3-diaminobenzidine (Dako, Catalog No. K3468). Sections were counterstained with Mayer's Hematoxylin (Poly Scientific, Catalog No. S216-1GL), dehydrated, and cover-slipped.

6.3.1.11 Human Tumor Histoculture

Human tumor specimens from patients with renal cell carcinoma, colorectal carcinoma, breast carcinoma, non-small cell lung carcinoma, and head and neck squamous cell carcinoma were obtained from commercial sources (BioOptions, Boston BioSource (Tufts), Folio Biosciences, and Tissue Solutions) and academic collaborators (University of Rochester) in accordance with state and federal regulations. Fresh tumor tissues were collected within 1 hour following surgery to remove the tumors from the patients, placed in AQIX transportation medium and transported overnight at 4° C. to Merck Research Laboratories, Palo Alto, CA The tumors were embedded in 1% low-melting gel and cut into 400 μm slices using the McIlwain Tissue Chopper. The tumor slices were set onto Millicell-CM inserts in 6-well dishes containing 1 mL Dulbecco's modified Eagle's medium, 10% FBS, 100 U/mL penicillin, and 100 μg/mL streptomycin.

In the following experiments, 5 samples of renal cell carcinoma (RCC; n=4), 3 samples of colorectal carcinoma (CRC), 2 samples of breast carcinoma, and one sample of head and neck squamous cell carcinoma were evaluated. Alternatively, 6 samples of RCC, 1 sample of CRC, and 2 samples of non-small cell lung carcinoma (NSCLC) were evaluated. The tumor slices were incubated with $3\times10^7$ pfu NDV-WT or NDV-huIL-12 or recombinant IL-12 at 10, 25 and 50 ng/mL and cultured at the air medium interface for 24 or 48 hours at 37° C. in an atmosphere with 5% $CO_2$. For certain experiments, the samples were snap-frozen (i.e., the samples were placed in tubes and dropped into liquid nitrogen until frozen and then transported on dry ice and stored at −80° C.) and RNA from the samples was isolated as described in Section 6.3.1.13, below.

For other experiments, media from the tissue samples was analyzed for cytokines and chemokines using various kits. GM-CSF, IFN-γ, IL-10, IL-12p70, IL-1-0, IL-2, IL-6, IL-8, and TNF-α were analyzed using the Human ProInflammatory 9-Plex Tissue Culture Kit (Meso Scale Discovery, Catalog No. K15007B-2). IFN-α-2a was analyzed using the Human IFN-α Tissue Culture Kit (Meso Scale Discovery, Catalog No. K151ACB-4); and IFN-β was analyzed using the Human IFN-β Tissue Culture Kit (Meso Scale Discovery, Catalog No. K151ADB-4). Eotaxin, Eotaxin-3, IL-8, IP-10, MCP-1, MCP-4, MIP-1a, MIP-1b, MDC, and TARC were analyzed using the V-PLEX Chemokine Panel 1 (human) Kit (Meso Scale Discovery, Catalog No. K15047D-2) and IP-10 was analyzed using IP-10 Tissue Culture Kit (Meso Scale Discovery, Catalog No. K151AVB).

6.3.1.12 Human Whole Blood Assay

Whole blood from patients with solid tumors (n=5) were obtained from Conversant Bio (Huntsville, AL), and whole blood from healthy donors (n=5) were obtained through the Merck Research Laboratories internal blood donor program. The following two experimental conditions were used. (1) 1 mL whole blood was left untreated or treated with $3\times10^7$ pfu NDV-WT or NDV-huIL-12 for 48 hours. Plasma was collected for assessment of protein concentrations of various cytokines and chemokines using kits described above for the human tumor histoculture studies. (2) 4 mL whole blood was left untreated or treated with $3\times10^7$ pfu NDV-WT or NDV-huIL-12 for 24 hours. Whole blood was collected into PAXgene blood RNA tubes (BD Biosciences Catalog No. 762165), and following RNA isolation, gene expression of panel of immune genes was analyzed using the Fluidigm RTqPCR platform (see Section 6.3.1.13).

6.3.1.13 Extraction of RNA and Real-Time Quantitative Polymerase Chain Reaction (RTqPCR)

RNA was isolated from mouse B16F10 tumors (Section 6.3.1.9), human tumor specimens (Section 6.3.1.11), and human whole blood (Section 6.3.1.12). Total RNA was isolated by homogenization into RNA STAT-60 (Tel-Test Inc., Friendswood, TX)) using a polytron homogenizer. The total RNA was extracted according to the manufacturer's protocol. After precipitation with isopropanol, total RNA was re-extracted with phenol:chloroform:isoamyl alcohol (25:24:1) using phase-lock light tubes.

DNase-treated total RNA was reverse-transcribed using QUANTITECT™ Reverse Transcription Kit (Qiagen, Catalog No. 2015310) according to manufacturer's protocol. Primers were obtained from Life Technologies:

| Mouse genes | |
|---|---|
| Molecular Profiling Gene ID | Life Technologies Catalog # |
| Cd3-ε | Mm01179194_m1 |
| Cd8b1-CD8 | Mm00438116_m1 |
| Gzmb | Mm00442834_m1 |
| IL-12a-IL-12p35 | Mm00434165_m1 |
| IL-15 | Mm00434210_m1 |
| Ifn-γ | Mm01168134_m1 |
| Irf7 | Mm00516788_m1 |
| Mx1 | Mm00487795_mH |
| Oas1a | Mm00836412_m1 |
| Pdcd1-PD-1 | Mm00435532_m1 |
| Cd274-Pd-l1, B7h1 | Mm00452054_m1 |
| Ubb | Mm01622233_g1 |

| Human genes | |
|---|---|
| Molecular Profiling Gene ID | Life Technologies Catalog# |
| CXCL9 | Hs00171065_m1 |
| Cxcl10 (Ip-10) | Hs00171042_m1 |
| CXCL11 | Hs00171138_m1 |
| DDX58 | Hs00204833_m1 |
| DHX58 | Hs00225561_m1 |
| GBP4 | Hs00925073_m1 |
| HERC6 | Hs00215555_m1 |
| IFIT1 | Hs00356631_g1 |
| IFIT2-ISG54 | Hs00533665_m1 |
| IFIT3 | Hs01922752_s1 |
| IFN-γ | Hs00989291_m1 |
| IL-12B-Il-12P40 | Hs01011518_m1 |
| IRF7 | Hs01014809_g1 |
| MX2 | Hs01550811_m1 |
| OAS3 | Hs00196324_m1 |
| OASl | Hs00388714_m1 |
| PARP14 | Hs00981511_m1 |
| CD274-PD-L1, B7H1 | Hs00204257_m1 |
| USP18 | Hs00276441_m1 |
| UBB | Hs00430290_m1 |

Real time quantitative polymerase chain reaction (RTqPCR) on 10 ng of cDNA from each sample was conducted using unlabeled primers at 900 nM each with 250 nM of FAM labeled probe in a TAQMAN™ RTqPCR reaction (Thermo Fisher Scientific, Foster City, CA) on the Fluidigm Biomark sequence detection system per manufacturer's protocol (Fluidigm, Foster City, CA). Levels of ubiquitin were measured in a separate reaction and were used to normalize the data by the Δ-Δ Ct method. Using the mean cycle threshold (Ct) value for ubiquitin and the gene of interest for each sample, the following equation was used to obtain the normalized values: 1.8(Ct ubiquitin−Ct gene of interest)$\times 10^4$.

6.3.1.14 Nanostring Gene Expression Analysis

For the analyses performed in Section 6.3.2.6, infra, RNA was quantified using the NanoDrop ND1000 spectrophotometer (Thermo Fisher Scientific). Gene expression analysis was conducted on the NanoString nCounter gene expression platform (NanoString Technologies). A custom code set consisting of a 800-gene panel related to T cell biology, immune regulation, and cellular markers of tumor-infiltrating lymphocytes and tumorassociated macrophages was used. Per sample, 50 ng of total RNA in a final volume of 5 μL was mixed with a 3' biotinylated capture probe and a 5' reporter probe tagged with a fluorescent barcode from the custom gene expression code set. Probes and target transcripts were hybridized overnight at 65° C. for 12-16 hours per the manufacturer's recommendations. Hybridized samples were run on the NanoString nCounter preparation station using the high-sensitivity protocol, in which excess capture and reporter probes were removed and transcript-specific ternary complexes were immobilized on a streptavidin-coated cartridge. The samples were scanned at maximum scan resolution on the nCounter Digital Analyzer. Gene expression data for each individual sample were normalized by HK (housekeeping) normalization. For each tumor sample, raw counts were log 10 transformed and then each gene normalized by subtracting off the arithmetic mean of all housekeeping genes (Table 15). Gene Expression Profiling (GEP) Signature scores were calculated as a weighted sum of the housekeeping normalized values of the 18 gene Up-Down Signature (Table 15). The house keeping normalized value for each gene was multiplied by the coefficient for that gene from the set of scoring weights to generate a weighted RNA value for each of the genes in the 18 gene signature, and adding the weighted RNA values to produce the signature score for the tumor sample. See Ayers et al., 2017, J of Clinical Investigation 127: 2930-2940 and WO2016094377.

TABLE 15

| 18 Gene Up-Down Signature | | |
|---|---|---|
| Gene Symbol | Accession No. | Scoring Weight Set |
| CCL5 | NM_002985.2 | 0.008346 |
| CD27 | NM_001242.4 | 0.072293 |
| CD274 | NM_014143.3 | 0.042853 |
| CD276 | NM_001024736.1 | −0.0239 |
| CD8A | NM_001768.5 | 0.031021 |
| CMKRLR1 | NM_004072.1 | 0.151253 |
| CXCL9 | NM_002416.1 | 0.074135 |
| CXCR6 | NM_006564.1 | 0.004313 |
| HLA.DQA1 | NM_002122.3 | 0.020091 |
| HLA.DRB1 | NM_002124.1 | 0.058806 |
| HLA.E | NM_005516.4 | 0.07175 |
| IDO1 | NM_002164.3 | 0.060679 |
| LAG3 | NM_002286.5 | 0.123895 |
| NKG7 | NM_005601.3 | 0.075524 |
| PDCD1LG2 | NM_025239.3 | 0.003734 |
| PSMB10 | NM_002801.2 | 0.032999 |
| STAT1 | NM_007315.2 | 0.250229 |
| TIGIT | NM_173799.2 | 0.084767 |

| Housekeeping Normalization Genes | |
|---|---|
| Gene Symbol | Accession No. |
| ABCF1 | NM_001090.2 |
| C14ORF102 | NM_017970.3 |
| G6PD | NM_000402.2 |
| OAZ1 | NM_004152.2 |
| POLR2A | NM_000937.2 |
| SDHA | NM_004168.1 |
| STK11IP | NM_052902.2 |
| TBC1D10B | NM_015527.3 |
| TBP | NM_001172085.1 |
| UBB | NM_018955.2 |
| ZBTB34 | NM_001099270.1 |

6.3.1.15 Cell Viability Assay

Cells (10,000/well/200 μL DMEM or RPMI supplemented with 10% FBS) were plated in replicates of 8 to 96-well plates and incubated at 37° C. in an atmosphere with 5% $CO_2$ for 18 hours to allow the cells to attach. Cell culture media was removed from wells prior to infection with NDV-huIL-12. In replicates of 8, cells were infected with NDV-huIL-12 at MOI 2 (20,000 pfu) or 6 (60,000 pfu) in 20 μL serum-free media (DMEM+0.3% BSA+penicillin/streptomycin). Media without virus (mock-infected) or media with 10 μM puromycin (or its vehicle DMSO) were added in parallel wells. Plates were incubated on a flat surface at room temperature for 1 hour, followed by aspiration of the media. Cell culture medium (100 μL) with 10% serum was added to each well, and the plates were incubated at 37° C. in an atmosphere with 5% $CO_2$ for 48 hours. Supernatants were collected and stored at −80° C. for analysis of cytokines and chemokines. The plates were then analyzed using a Cell Titer Glo assay kit (Promega, Catalog No. G7573) according to manufacturer's instructions.

6.3.1.16 Analysis of Cytokines and Chemokines from Human Tumor Cell Lines

The supernatants from the 26 cell lines that were infected with NDV-huIL-12 (MOI 2, replicates of 4) were assayed for various cytokines and chemokines. IL-10, IL-1β, IL-2, MCP-1, IL-6, IL-8, IL-10, IL-12p70, MIP-1b, and TNF-α were analyzed using a Human Custom Biomarker kit (Meso Scale Discovery, Catalog No. K15067L-2). IFN-α2a, IFN-β, IFN-γ, and IL-29/IFN-λ1 were analyzed using the Human Interferon Combo kit (Meso Scale Discovery, Catalog No. K15094K-2).

6.3.1.17 Statistics

Tumor Volumes: Follow-up of individual animals could be terminated early because of excessive tumor burden or other reasons. Depending on the reason and tumor size at the last measurement, the last observed tumor volume was treated as a lower bound on volume at all later days for that animal (right-censored data).

To compare two treatment groups on a given day, a generalization of the nonparametric Mann-Whitney (or Wilcoxon rank sum) test that allows for right-censored data was used: the Peto and Peto version of the Gehan-Breslow test. Two-sided p-values were estimated from 20,000 random reassignments of animals between the two treatments being compared. To control the familywise error rate across all time points for a given pair of treatments, p-values were multiplicity adjusted by Holm's method. A p-value of less than 0.05 was used to define statistical significance.

Gene expression data from tumor challenge studies: To compare two treatment groups on a given day, nonparametric Mann-Whitney test was used. A p-value of less than 0.05 was used to define statistical significance.

Cytokine/chemokine and/or gene expression data from human tumor histoculture and whole blood studies: To compare two treatment groups on a given day, nonparametric Wilcoxon signed rank test was used. A p-value of less than 0.05 was used to define statistical significance.

6.3.1.18 IL-12 Bioassay

To evaluate the functionality of huIL-12 produced from NDV-huIL-12 in NDV-huIL-12-infected cells, Vero cells were seeded in 6-well tissue culture plates at $5\times10^5$ cells/well and incubated at 37° C., 5% $CO_2$ for 24 hours. Test samples of NDV-huIL-12 viruses were diluted to $1\times10^6$ pfu/mL in Opti-MEM (1×) reduced serum medium and various amounts of the diluted samples were transferred to the cell plate to target MOI between 0.03-1. Opti-MEM (1×) reduced serum medium was then added to each well to a final volume of 2 mL. The infected cell plate was incubated at 37° C., 5% $CO_2$ for 24 hours. The function of the produced huIL-12 in the supernatant was assayed using the PathHunter® Bioassay Detection kit (DiscoverX, Cat #93-0933).

PathHunter® U2OS IL12RB1/IL12RB2 cells were engineered to co-express human IL-12 receptor beta 1 and beta 2. One receptor was fused to Enzyme Donor (ED), and the other receptor was fused to Enzyme Acceptor (EA). Upon binding of functional huIL-12, the two receptors dimerize, forcing complementation of ED and EA to form a functional β-galatosidase that hydrolyzes a substrate to generate a chemiluminescent signal. U2OS IL12RB1/IL12RB2 cells were seeded in a 96-well cell plate at $5\times10^3$ cells/well and incubated at 37° C., 5% $CO_2$ for 4-6 hours. A total of 60 μL supernatant fluids from each well of the infected Vero plate were transferred to the second column of a 96-well sample dilution plate and a 3-fold serial dilution in AssayComplete Cell Plating Reagent (DiscoverX, 93-0563R5A) was carried out across rows. A total of 10 μL of each diluted supernatant was transferred to the U2OS cell plate and the plate was incubated at 37° C., 5% $CO_2$ for 16-20 hours. 10 μL of Detection Reagent 1 was then added to each well and the plate was incubated for 15 minutes at room temperature. 40 μL of Detection Reagent 2 was then added to each well and the plate was further incubated for 60 minutes at room temperature. The chemiluminescence signal was detected using SpectraMax M5 plate reader.

6.3.1.19 Quantitation of huIL-12 by ELISA

Vero cells were seeded in 96-well tissue culture plates at $1\times10^4$ cells/well in Opti-PRO serum free medium (Gibco, Cat. No. 12309-019) supplemented with 2% glutamine (Corning, Cat. No. 25-005-CI) and incubated at 37±2° C., 5±2% $CO_2$ for approximately 24 hours. Test samples of NDV-huIL-12 viruses (batches A and B) were pre-diluted in Opti-MEM (1×) reduced serum medium (Gibco, Cat. No. 31985-070) to target $2\times10^4$ pfu/mL. A total of 300 μL of each pre-diluted test sample was added to the first row of a 0.5 mL Assay Block (Costar, Cat. No. 3956) and a 2-fold serial dilution was performed across rows by transferring 150 μL of sample into 150 μL Opti-MEM (1×) reduced serum medium. Two replicates per sample were prepared. The 96-well plates containing Vero cells were removed from the incubator approximately 24 hours post seeding and spent medium is removed from the plate. The cells were inoculated with 100 μL serially diluted test samples and incubated at 37° C., 5% $CO_2$. After approximately 24 hours incubation, 90 μL of supernatant fluid was removed from the infection plates, transferred to an ELISA plate pre-coated with anti-human IL-12 p70 capture antibody (Affymetrix eBioscience, Cat. No. 14-7128-68) and incubated for two hours at room temperature. The captured huIL-12 was detected with anti-human IL-12 p70 detection antibody (Affymetrix eBioscience, Cat. No. 33-8261-68A) and Avidin-HRP and visualized with a HRP substrate TMB following vendor's procedure (Affymetrix eBioscience, Human IL-12 p70 ELISA Ready-SET-Go! ELISA kit, Cat. No. 88-7126-88). The MOI-dependent huIL-12 expression curve was compared to a NDV-huIL-12 reference standard (FIG. 34).

6.3.1.20 Purification

Purification of NDV-huIL-12 from harvested allantoic fluid uses a process consisting of the following unit operations: (1) clarification, (2) tangential flow filtration, and (3) sterile filtration. Harvested allantoic fluid was clarified using 1.2 μm glass fiber dead end filtration to remove cells and other large debris. The membrane that was used for this step contains a net positive charge which results in a measurable reduction in host cell DNA. The clarified bulk (CB) was subsequently processed by tangential flow filtration (TFF) using 750 kD hollow fiber membranes. During this step the batch was concentrated ~5-fold and diafiltered against 4 diavolumes (DVs) of high salt buffer followed by 4 DVs of low salt formulation buffer and then concentrated ~10-fold. This unit operation constitutes the main purification step whereby residual egg proteins, primarily ovalbumin, and residual DNA are reduced to acceptable levels. The step also serves to exchange buffer to one compatible with formulation. The TFF Product (TFFP) was then sterile filtered through a 0.2 μm filter and dispensed into appropriate sterile storage containers. The purified virus bulk (PVB) was then frozen and stored at −70 degrees Celsius.

6.3.2 Results

6.3.2.1 Anti-Tumor Efficacy and Mechanism of Action of NDV-muIL-12 in Combination with Anti-muPD-1 mAb in Syngeneic Mouse B16F10 Bilateral Tumor Model B16F10 tumors are poorly infiltrated with T cells and resistant to anti-PD-1 therapy. B16F10 tumors display very aggressive growth and represent a high-bar model. Therefore, the B16F10 model was selected to evaluate NDV vectors encoding the mouse IL-12 transgene in comparison to unarmed NDV ("NDV wild-type" ("NDV-WT")). The NDV vectors were evaluated in two-tumor bearing C57BL/6 mice to evaluate the abscopal effect (i.e., anti-tumor efficacy in the tumor that was not administered NDV).

Compared to mouse IgG1 isotype control (Group 1), administration of muDX400 alone (Group 2) did not result in significant reduction in tumor volumes of either injected tumors (p=1.0) or non-injected tumors (p=0.475) (FIG. 22). Compared to NDV-WT (Group 3), administration of NDV-muIL-12 alone (Group 5) resulted in significant reduction in tumor volumes of injected tumors (p=0.027) but not of non-injected tumors (p=1.0) (FIG. 22). However, compared to NDV-muIL-12 (Group 5), NDV-muIL-12 in combination with muDX400 (Group 6) resulted in significant reduction in tumor volumes of both injected tumors (p=0.047) and non-injected tumors (p=0.020) (FIGS. 22A-22D). In addition, NDV-muIL-12 in combination with muDX400 resulted in 6 out of 10 complete regressions (CRs) and 5 out of 10 CRs in injected tumors and non-injected tumors, respectively (FIGS. 22A-22D). These results were reproducible in an independent experiment, are consistent with previous findings demonstrating that in mouse pre-clinical models, NDV breaks resistance to immune checkpoint blockade (Zamarin et al., 2014, Sci. Transl. Med. 6:226ra32 (2014)). For injected tumors, the number of complete regressions were as follows: Group 1: 0; Group 2: 0; Group 3: 1; Group 4: 1; Group 5: 2; and Group 6: 6. For non-injected tumors, the number of complete regressions were as follows: Group 1: 0; Group 2: 1; Group 3: 1; Group 4: 3; Group 5: 0; and Group 6: 5.

Figures 23A, 23B, 23C, 23D:
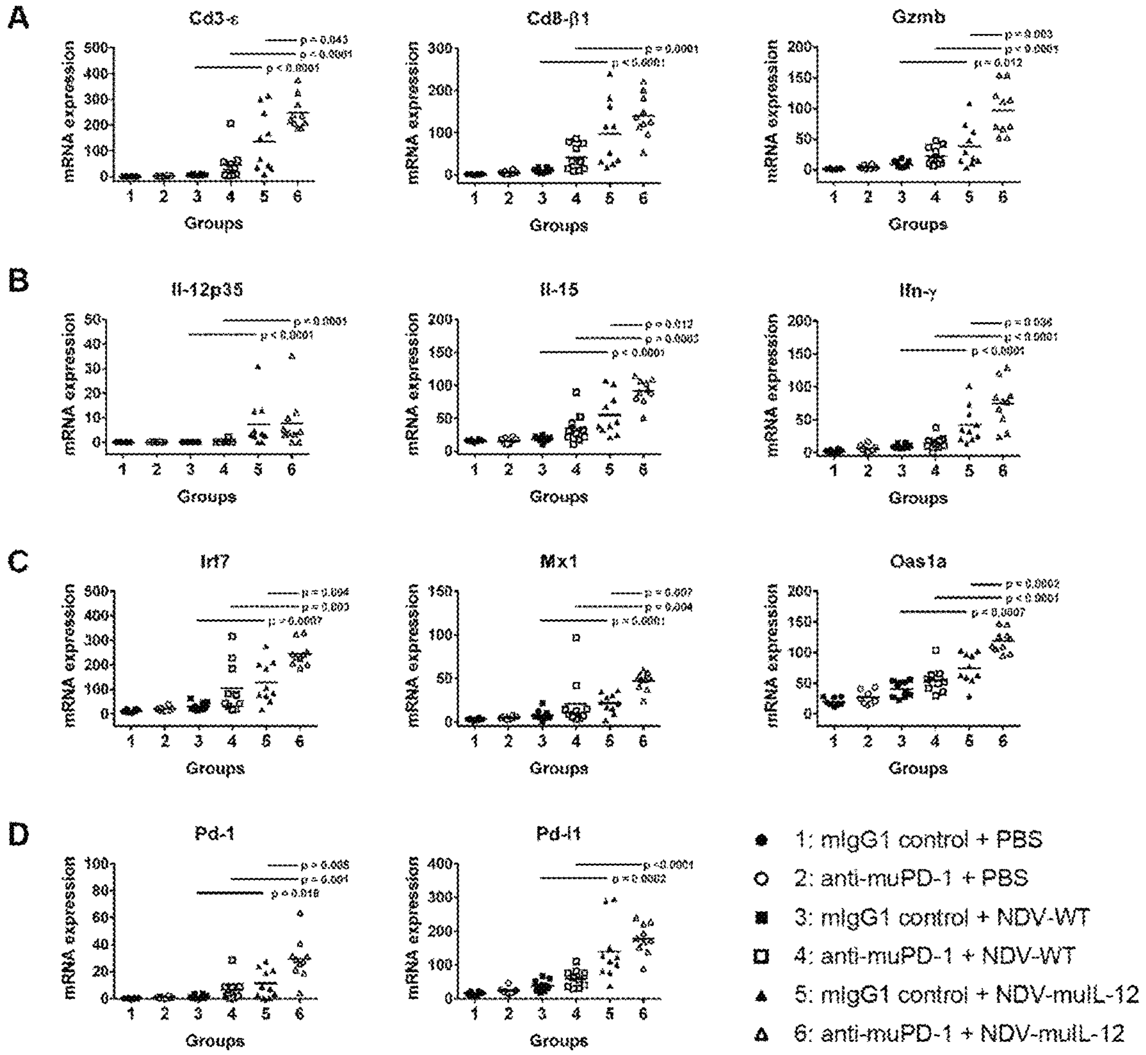
Figures 24A, 24B, 24C, 24D:
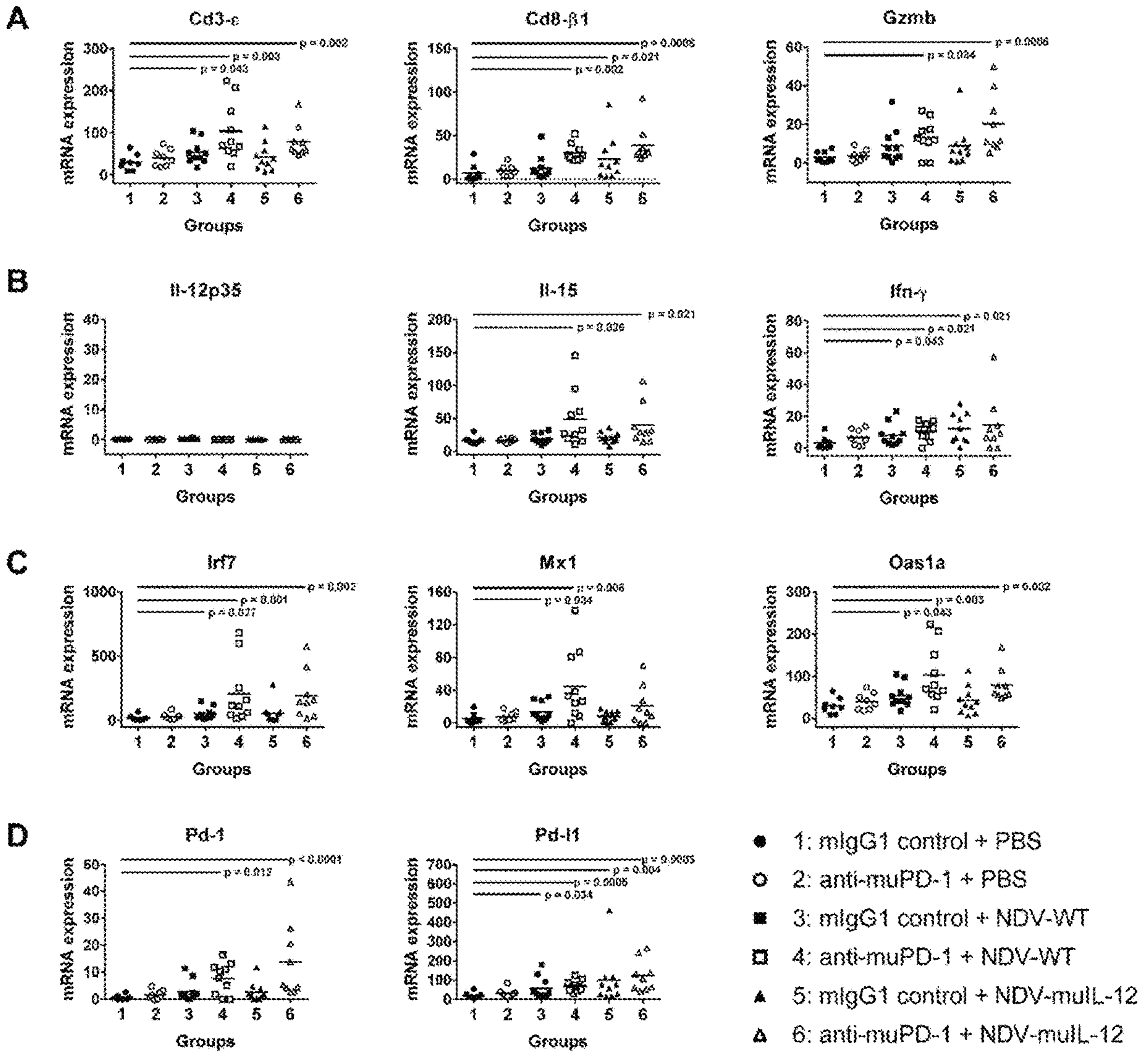

In the same study, tumors were harvested on Day 14 to evaluate expression of various immune genes. FIG. 23 and FIG. 24 show mRNA expression of representative genes for T cell markers (FIG. 23A and FIG. 24A), cytokines (FIG. 23B and FIG. 24B), IFN-inducible genes (FIG. 23C and FIG. 24C), and PD-1 pathway (FIG. 23D and FIG. 24D) in injected tumors and non-injected tumors, respectively. mRNA expression of Il-12p35 is only detected in injected tumors of animals which were administered NDV-muIL-12 (Groups 5 and 6). This result suggests that NDV itself did not induce IL-12. Also the lack of detection of mRNA expression of Il-12p35 in the non-injected tumors of Groups 5 and 6 supports previous findings that NDV is restricted to the NDV injected tumors (Zamarin et al., 2014, Sci. Transl. Med. 6:226ra32 (2014). As shown in FIGS. 23A-23D, mRNA expression of CD3-ε, CD8-β, Gzmb, IL-12p35, IL-15, IFN-γ, Irf7, Mx1, Oas1a, PD-1, and PD-L1 in the injected tumors increased with the following order of treatments: control (Group 1), muDX400 monotherapy (Group 2), NDV-WT monotherapy (Group 3), combination of muDX400 and NDV-WT (Group 4), NDV-muIL-12 monotherapy (Group 5), and combination of muDX400 and NDV-muIL-12 (Group 6), and the increase is statistically significant (p<0.05) between Groups 3 and 5 and Groups 4 and 6. Increases of these genes in the non-injected tumors are stastically significant between control (Group 1) and combination of muDX400 with either NDV-WT (Group 4) or NDV-muIL-12 (Group 6) (FIGS. 24A-24D). Similar results were obtained from an independent experiment.

In another independent bilateral B16F10 study, mouse B16F10 cells were subcutaneously implanted into the right flanks ($2\times10^5$ cells) and left flanks ($1\times10^5$ cells) of immunocompetent C57BL/6J mice. Animals were assigned into 6 groups 7 days after implantation (Day 0) based on tumor volume (TV) in the right flanks (injected tumors) with median TV=56 $mm^3$. The median TV in the left flanks (non-injected tumors) was 38 $mm^3$. Dosing was initiated on Day 0. Mouse IgG1 isotype control and muDX400 at 10 mg/kg were administered intraperitoneally every 4 days for a total of 3 doses. PBS, NDV-WT, and NDV-muIL-12 at $1\times10^7$ pfu were administered into the tumors on the right flanks every 2 days for a total of 4 doses. Animals were followed up to Day 54. Animals were euthanized when the sum of volumes of injected and non-injected tumors was ≥2000 $mm^3$ or body weight loss was ≥20%. There were 10 animals in each group. As shown in FIGS. 25A-25B, treatment with intratumoral NDV-muIL-12 in combination with muDX400 resulted in longest overall survival of the animals.

In another bilateral B16F10 study, mouse B16F10 cells were subcutaneously implanted into the right flanks ($2\times10^5$ cells) and left flanks ($1\times10^5$ cells) of immunocompetent C57BL/6J mice. Animals were assigned into 6 groups 9 days after implantation (Day 0) based on tumor volume (TV) in the right flanks (injected tumors) with median TV=108 $mm^3$. The median TV in the left flanks (non-injected tumors) was 83 $mm^3$. Dosing was initiated on Day 0. Mouse IgG1 isotype control and muDX400 at 10 mg/kg were administered intraperitoneally every 4 days for a total of 2 doses. PBS, NDV-WT, and NDV-muIL-12 at $1\times10^7$ pfu were administered into the tumors on the right flanks every 2 days for a total of 4 doses. Injected and non-injected tumors (n=3/group) were harvested on Day 8, and CD3 expression analyzed by immunohistochemistry. As shown in FIGS. 26A-26B, treatment with intratumoral NDV-muIL-12 in combination with muDX400 resulted in a strikingly high infiltration of CD3+ T cells in both the injected and non-injected tumors. Flow cytometry analysis suggested that the majority of the infiltrating CD3+ cells are activated CD8 or CD4 effector cells (not shown).

In addition, the anti-tumor efficacy of arming NDV with IL-12 versus other cytokines (IL-23, IL-27, and IL-2) in combination with anti-muPD-1 monoclonal antibody (muDX400) in the bilateral B16F10 was assessed. In the study comparing NDV-muIL-12 with NDV-muIL-23 and muIL-27, in combination with muDX400, treatment with NDV-muIL-12+muDX400 resulted in the highest number of regressions (complete and partial) in injected and non-injected tumors (FIGS. 37A-37N) but there was not a significant reduction in tumor volumes for either injected or non-injected tumors (p>0.05). In this study, the combination of NDV-muIL-12 and muDX400 resulted in a higher number of complete regressions in injected tumors and non-injected tumors than the combination of anti-muDX400 and NDV-muIL-23 or NDV-muIL-27 (FIGS. 37G and 37N). Further, in the study comparing NDV-muIL-12 with NDV-mIL-2, in combination with muDX400, the effect on the injected tumors with the two treatments were comparable resulting in comparable number of complete and partials regressions and comparable median TV and 68% confidence interval at Day 18 (see FIGS. 38C, 38D, and 38I). For the non-injected tumors (FIGS. 38G, 38H, and 38J), although the reduction in tumor volume at Day 18 was not significant between the two treatments (p>0.05), NDV-muIL-12+muDX400 resulted in median TV=130 $mm^3$ and tighter 68% confidence interval (102, 244 $mm^3$) compared to NDV-muIL-2+muDX400: median TV=255 with 68% confidence interval (207, 1036 $mm^3$). In this study, the combination of NDV-muIL-12 and muDX400 resulted in a higher number of complete regressions in non-injected tumors than the combination of muDX400 and NDV-muIL-IL-2 (FIG. 38J).

6.3.2.2 Lytic Activity of NDV-huIL-12 in Human Tumor Cell Lines

The lytic activity of NDV-huIL-12 was assessed in a panel of 26 human cancer cell lines at multiplicity of infection (MOI) of 2 and 6, 48 hours following infection (FIG. 27A). The panel included 7 cancer types: melanoma, HNSCC (head and neck squamous cell carcinoma), lung, breast, ovarian, colon, and pancreatic carcinomas. Cell viability was assessed by an ATP-based quantification method 48 hours after virus infection (FIG. 27A). For each cell line, lytic activity of NDV-huIL-12 (MOI 2 and 6) was expressed as a percentage of viability relative to mock-infected cells; lytic activity of 10 μM puromycin (positive control) was expressed as a percentage of viability relative to vehicle (DMSO) treated cells.

With a monobasic F protein cleavage site, NDV-huIL-12 is limited to a single cycle of replication in tumor cells. With this consideration, the criterion for sensitivity to NDV-huIL-12 was set at >20% reduction in cell viability with MOI of 2. By this criterion, 22 out of the 26 cell lines were sensitive to lysis by NDV-huIL-12. At a MOI of 6, all cell lines were sensitive to lysis by NDV-huIL-12 (>20% reduction in cell viability). In conclusion, lytic activity of NDV-huIL-12 was demonstrated in range of human tumor cell lines.

6.3.2.3 Induction of Cytokines and Chemokines in Human Tumor Cell Lines with NDV-huIL-12 Treatment The cell culture supernatants from the 26 human tumor cell lines that were assayed for lytic activity of NDV-huIL-12 (MOI 2) or mock infected were harvested at 48 hours and analyzed for various cytokines and chemokines by immunoassays. Mean concentrations of IL-12p70, IFN-β, and IP-10 are presented in FIG. 27B. NDV-huIL-12 induced secretion of levels of IL-12p70 that were above the upper limit of detection in the immunoassay in all the cell lines except lung carcinoma cell line H322. NDV-huIL-12 did not induce IFN-γ in any of the cell lines (data not shown); this is expected as IL-12 receptor is mainly expressed by activated T cells and NK cells. NDV-huIL 12 induced IFN-α-2a in only 2 cell lines (breast SK BR-3 an HNSCC SCC15; data not shown) but induced IFN-β in a third of the cell lines. In addition, NDV-huIL-12 induced moderate/high levels of IP-10 in 20 cell lines.

6.3.2.4 Induction of Immune Genes in Human Tumor Histoculture and Whole Blood with NDV-huIL-12 Treatment The human tumor histoculture approach allows culturing of intact fresh cancer tissues in the presence of drug for up to 48 hours. The effect of drugs on cancer cells and pre-existing immune cells in the tumor specimens can be assessed. Induction of cytokines and chemokines (protein expression) and immune genes (gene expression) by NDV-WT and NDV-huIL-12 was evaluated in this platform. In these studies, 4 samples of renal cell carcinoma (RCC), 3 samples of colorectal carcinoma (CRC), 2 samples of breast carcinoma, and 1 sample of HNSCC were treated with $3\times10^7$ pfu NDV-WT or NDV-huIL-12 for up to 48 hours. At the 24- and 48-hour time points, supernatants from the histoculture were collected and analyzed for various cytokines and chemokines by immunoassays, and tumors were snap-frozen and RNA was isolated for analysis of immune genes. Mean concentrations of IFN-α-2a, IFN-β, IL-12p70, and IFN-γ, and IP-10 are presented in FIG. 28, and gene expression of IFN-inducible genes IRF7, IFIT2, and MX2, chemokines CXCL9, CXCL10 (IP-10), and CXCL11, IL-12P40, IFN-γ, and PD-L1 are presented in FIGS. 29A-29D. Both NDV-WT and NDV-huIL-12 induced secretion of IFN-α-2a and IP-10; neither induced secretion of IFN-β. Only NDV-huIL 12 induced IL-12p70 and IFN-γ. The analysis of gene expression of various immune genes showed that NDV-huIL-12 induced strong type 1 IFN and IL-12 responses along with induction of chemokines and PD-L1 in multiple tumor types.

Similarly, induction of cytokines and chemokines (protein expression) (FIG. 30) and immune genes (gene expression) (FIGS. 31A-31D) by NDV-WT and NDV-huIL-12 was evaluated in whole blood from both patients with solid tumor malignancies (n=5) and normal donors (n=5). Although cancer cells may be present in the whole blood from the cancer patients, the pattern of immune activation with NDV-WT and NDV-huIL-12 is comparable between blood from both sets of donors. The pattern of induction of IFN-α-2a, IFN-β, IL-12p70, and IFN-γ, and IP-10 and gene expression of IFN inducible genes, chemokines, Il-12p40, IFN-γ, and Pd 11 were similar to that observed in the human tumor histoculture, suggesting that NDV-huIL-12 is in part acting on the immune cells in the intact tumor tissues.

Type I IFN pathway has emerged as an important regulator of anti-tumor immune response, with several studies demonstrating its role in antigen presentation and dendritic cell maturation (see, e.g., Zitvogel et al., Nature reviews. Immunology 15, 405-414 (2015), Fuertes et al., J Exp Med 208, 2005-2016 (2011), Diamond et al., J Exp Med 208, 1989-2003 (2011), Kato et al., Immunity 23, 19-28 (2005)). In the human tumor histoculture platform, treatment of tumors with $3\times10^7$ pfu NDV-huIL-12 resulted in secretion of levels of IL-12 (11189±2877 pg/mL) that is in range with treatment with 25 ng/mL (9636±1405 pg/mL) and 50 ng/mL (15308±1726 pg/mL) of recombinant IL-12 (FIG. 41A-41D). However, only treatment with NDV-huIL-12 but not recombinant IL-12 (10 to 50 ng/mL) induced IFN-α-2a and IFN-β in most of the donors tested (FIG. 41A-41D). In addition, treatment with NDV-huIL-12 induced secretion of significantly higher levels of IP-10 which plays an important role in T cell recruitment to the tumor site (FIG. 41A-41D).

6.3.2.5 Identification of NDV-huIL-12 Response Signature

The human tumor histoculture platform was utilized to identify genes that were modulated at least 2-fold, p<0.01, following treatment with $3\times10^7$ pfu NDV-huIL-12 for up to 48 hours. Gene expression was analyzed by RNA sequencing. The response signature that includes interferon-inducible genes (e.g., GBP4, IFIT1, IFIT2, IFIT3, OAS3, and OASL), chemokines (e.g., CXCL10 and CXCL11), and PD-L1 was confirmed in additional tumor samples (n=14) by RTqPCR analysis (FIG. 39).

6.3.2.6 Induction of NDV-huIL-12 Response-Signature in Both GEP-Negative and GEP-Positive Tumors Using RNA from baseline tumor samples of anti-PD-1 pembrolizumab-treated patients, an immune-related gene-expression profile (GEP) correlating with clinical benefit with pembrolizumab was identified (Ayers et al., 2017, J of Clinical Investigation 127: 2930-2940). The T cell-inflamed GEP contained IFN-γ-responsive genes related to antigen presentation, chemokine expression, cytotoxic activity, and adaptive immune resistance. Patients who are GEP-negative, rarely respond to pembrolizumab. It is demonstrated in the human tumor histoculture platform that the increase in GEP score is higher for NDV-huIL-12 compared to NDV-WT for treatment of tumors (n=19). In addition, treatment with $3\times10^7$ pfu NDV-huIL-12 has a statistically significant increase in GEP score when compared to medium controls ($P<0.0001$), including conversion of a GEP-negative score (GEP score<−0.318) to a GEP-positive score (GEP score>−0.318), (FIGS. 40A-B).

6.3.2.7 Analytical Development and Characterization of NDV-huIL12

NDV-huIL12 was generated according to the methods provided in Section 6.3.1.1. NDV-huIL-12 can be quantified and characterized by flow virometry (FV, the use of a flow cytometer to analyze and quantitate individual particles). See, e.g., Vlasak et al., 2016, Vaccine 34:2321-2328 for a description of flow virometry. FV analysis showed that the majority of particles can be labeled with the mouse anti-NDV HN antibody 7B1 (ISMMS), suggesting that the majority of the particles are NDV-huIL-12 viruses (FIG. 32). NDV-huIL-12 shows pleiomorphic particle size distribution, consistent with the reported paramyxoviruses (Goff et al., 2012, J Virol. 86(19):10852-6).

NDV contains six proteins: F, HN, NP, L, P, and M. SDS-PAGE analysis under reducing condition can separate 6 proteins ($F_1$ (~47 kDa), HN (~63 kDa), NP (~53 kDa), L (~250 kDa), P (~42 kDa), and M (~40 kDa)) and serve as a qualitative purity assay. The purified NDV-huIL-12 was analyzed by SDS-PAGE (FIG. 33). It showed a similar protein banding pattern as other reported NDVs, suggesting that the majority proteins in the vaccine are viral proteins.

The production of human IL-12 by NDV-huIL-12 was confirmed by infecting Vero cells and quantitating IL-12 in the culture medium harvested 24 hours following infection. IL-12 was assayed by ELISA (FIG. 34). FIG. 34 shows the MOI-dependent huIL-12 expression compared to a reference batch of NDV-huIL-12.

The activity of expressed huIL-12 was measured in a cell-based functional assay using PathHunter Dimerization assay from DiscoverX (FIG. 35). This assay detects huIL-12 induced receptor dimerization in engineered cells. Functional huIL-12 was detected in the supernatants of the NDV-huIL-12-infected vero cells at MOI of 0.1-1 (FIG. 35). The cell-based assay is optimized to characterize the purified viruses.

The cell-based assay is optimized to characterize the purified viruses.

6.4 Example 4: Clinical Study

The pre-clinical data described herein support the combination of intratumoral administration of NDV-huIL-12 with systemic intravenous co-administration of a blockade of immune checkpoint inhibitor PD-1 (see, e.g., Section 6.3). Combination of pembrolizumab and NDV-huIL-12 in patients with advanced solid tumors with accessible cutaneous and subcutaneous malignant lesions to permit intratumoral administration of NDV-huIL-12 is evaluated in clinical trials. These solid tumors include relapsed/refractory solid tumor types such as melanoma, squamous cell cancer of the head and neck (SSCHN), breast carcinoma, uterine cancer, gastric cancer, esophageal cancer, liver cancer, brain cancer, sarcoma with dermal metastases as well as other malignancies with accessible dermal/SC/nodal metastases. For indications where anti-PD-1/PD L1 therapy is approved, treatment of patients refractory or relapsed from these therapies as well as patients with no anticipated response to these agents are included in the study. Patients with relapsed, refractory and/or relapsed and refractory tumor types and tumors that are not usually responsive to anti-PD-1/PD-L1 but are amenable to intratumoral injection are also evaluated. Additional tumor types that are accessible by image-guidance, such as those with liver metastases are considered.

6.4.1 Production of NDV-huIL-12 and Purification of Virus

The NDV-huIL-12 may be produced in embryonated eggs or cell culture. In embryonated eggs, the NDV-huIL-12 may be propagated in the allantoic cavity of specific pathogen free embryonated chicken eggs. The NDV-huIL-12 may be purified using methods such as described in Section 6.3.1.20, supra. NDV-huIL-12 clinical drug product (DP) may be provided in a sterile solution for injection.

The NDV-huIL-12 may comprise a packaged genome comprising a nucleotide sequence encoding an IL-12 p40 subunit, said IL-12 p40 subunit comprising the amino acid sequence set forth in SEQ ID NO: 40, optionally wherein said nucleotide sequence comprises the nucleotide sequence set forth in SEQ ID NO: 54 or 64. The NDV-huIL-12 may comprise a packaged genome comprising a nucleotide sequence encoding an IL-12 p40 subunit, said IL-12 p40 subunit comprising an amino acid sequence set forth in SEQ ID NO: 38, optionally wherein said nucleotide sequence comprises the nucleotide sequence set forth in SEQ ID NO: 57 or 59. The NDV-huIL-12 may comprise a packaged genome comprising a nucleotide sequence encoding an IL-12 p40 subunit, said IL-12 p40 subunit comprising the amino acid sequence set forth in SEQ ID NO: 23, optionally wherein said nucleotide sequence comprises the nucleotide sequence set forth in SEQ ID NO: 27.

The NDV-huIL-12 may comprise a packaged genome comprising a nucleotide sequence encoding an IL-12 p35 subunit, said IL-12 p35 subunit comprising the amino acid sequence set forth in SEQ ID NO: 41, optionally wherein said nucleotide sequence comprises the nucleotide sequence set forth in SEQ ID NO:55 or 65. The NDV-huIL-12 may comprise a packaged genome comprising a nucleotide sequence encoding an IL-12 p35 subunit, said IL-12 p35 subunit comprising the amino acid sequence set forth in SEQ ID NO: 25, optionally wherein said nucleotide sequence comprises the nucleotide sequence set forth in SEQ ID NO:29.

The NDV hulL-12 may comprise a packaged genome comprising the nucleotide sequence set forth in SEQ ID NO: 51. Alternatively, the NDV hulL-12 may comprise a packaged genome comprising the nucleotide sequence set forth in SEQ ID NO: 52. Alternatively, NDV hulL-12 may comprise a packaged genome comprising the nucleotide sequence set forth in SEQ ID NO: 60.

The NDV-huIL-12 may comprise a packaged genome comprising a transgene encoding an amino acid sequence, wherein said amino acid sequence comprises the amino acid sequence set forth in SEQ ID NO: 42, optionally wherein said transgene comprises the nucleotide sequence set forth in SEQ ID NO: 53 or 66. The NDV-huIL-12 may comprise a packaged genome comprising a transgene encoding an amino acid sequence, wherein said amino acid sequence comprises the amino acid sequence set forth in SEQ ID NO: 43, optionally wherein said transgene comprises the nucleotide sequence set forth in SEQ ID NO: 63 or 68. The NDV-hulL-12 may comprise a packaged genome comprising a transgene encoding an amino acid sequence, wherein said amino acid sequence comprises the amino acid sequence set forth in SEQ ID NO: 22, optionally wherein said transgene comprises the nucleotide sequence set forth in SEQ ID NO: 26. The NDV-huIL-12 may comprise a packaged genome comprising a transgene encoding an amino acid sequence, wherein said amino acid sequence comprises the amino acid sequence set forth in SEQ ID NO: 39, optionally wherein said transgene comprises the nucleotide sequence set forth in SEQ ID NO: 61.

6.5 Example 5: rNDV-muIL12 Expression in BSRT7 Cells and Allantoic Fluid

The expression of mulL-12 in BSRT7 cells infected with rNDV-muIL-12 was evaluated. rNDV-muIL-12 was generated as described in Section 6.3.1.1. BSRT7 cells were infected with rNDV-muIL-12 (also referred to as "NDV-muIL 12") at a multiplicity of infection ("MOI") of 3 or 10 and supernatants were collected at 24 or 48 hours post-infection. mulL-12 concentration in the collected supernatants was measured using the Mouse IL-12p70 Quantikine ELISA Kit (R&D Systems, Catalog No. M1270). BSRT7 cells infected with rNDV-muIL-12 under the tested conditions yielded detectable levels of muIL-12 (FIG. 36). Without being bound by any particular theory, it is hypothesized that the lower concentration of mulL-12 in cells infected at higher MOI as compared to cells infected at a lower MOI was due to a lower number of viable cells infected at the higher MOI producing mulL-12 as compared to the number of viable cells infected at the lower MOI producing mulL-12 (data not shown).

mulL-12 was also detected in the allantoic fluid of 10 day old embryonated eggs infected with 100 μl of rNDV-muIL-12 from a previous passage at 1:100000 dilution. The eggs were incubated for 2 days at 37 degrees Celsius, after which the allantoic fluid was collected from the eggs according to methods previously described (FIG. 36). muIL-12 concentration in the allantoic fluid was measured using the Mouse IL-12p70 Quantikine ELISA Kit (R&D Systems, Catalog No. M1270).

7. EMBODIMENTS

Provided herein are the following exemplary embodiments:

1. A method for treating cancer, comprising administering to a human subject in need thereof a first composition comprising a chimeric Newcastle disease virus (NDV) and a second composition comprising an antagonist of human PD-1 or a ligand thereof, wherein the chimeric NDV comprises a packaged genome comprising a transgene encoding human interleukin-12 ("IL-12"), wherein the transgene encodes a human IL-12 p40 subunit and a human IL-12 p35 subunit.

2. The method of embodiment 1, wherein the chimeric NDV comprises an NDV backbone which is lentogenic.

3. The method of embodiment 1 or 2, wherein the chimeric NDV comprises an NDV backbone of LaSota strain.

4. The method of embodiment 1 or 2, wherein the chimeric NDV comprises an NDV backbone of Hitchner B1 strain.

5. The method of embodiment 1 or 2, wherein the packaged genome comprises a nucleotide sequence encoding a mutated F protein and the mutated F protein is incorporated into the virion of the chimeric NDV, wherein the mutated F protein comprises a mutated cleavage site.

6. The method of embodiment 5, wherein the mutated cleavage site is $^{111}$H-N-R-T-K-R/F-I$^{118}$(SEQ ID NO: 71).

7. The method of embodiment 1, wherein the chimeric NDV comprises an NDV backbone of a r73T-R116 virus.

8. The method of any one of embodiments 1 to 4, wherein the packaged genome comprises a nucleotide sequence encoding a mutated F protein with the amino acid mutation L289A, wherein the mutated F protein is incorporated into the virion of the chimeric NDV.

9. The method of any one of embodiments 1 to 8, wherein the IL-12 comprises the amino acid sequence set forth in SEQ ID NO:39.

10. The method of embodiment 9, wherein the transgene comprises the nucleotide sequence set forth in SEQ ID NO: 61.

11. The method of any one of embodiments 1 to 8, wherein the IL-12 comprises the amino acid sequence set forth in SEQ ID NO:22.

12. The method of embodiment 11, wherein the transgene comprises the nucleotide sequence set forth in SEQ ID NO: 26.

13. The method of any one of embodiments 1 to 8, wherein the IL-12 comprises the amino acid sequence set forth in SEQ ID NO:43.

14. The method of embodiment 13, wherein the transgene comprises the nucleotide sequence set forth in SEQ ID NO: 63.

15. The method of embodiment 13, wherein the transgene comprises the nucleotide sequence set forth in SEQ ID NO: 68.

16. The method of any one of embodiments 1 to 8, wherein the IL-12 comprises the amino acid sequence set forth in SEQ ID NO:42.

17. The method of embodiment 16, wherein the transgene comprises the nucleotide sequence set forth in SEQ ID NO: 53.

18. The method of embodiment 16, wherein the transgene comprises the nucleotide sequence set forth in SEQ ID NO: 66.

19. The method of any one of embodiments 1 to 8, wherein the IL-12 p40 subunit comprises the amino acid sequence set forth in SEQ ID NO: 38.

20. The method of any one of embodiments 1 to 8, wherein the IL-12 p40 subunit comprises the amino acid sequence set forth in SEQ ID NO: 23.

21. The method of embodiment 19 or 20, wherein the IL-12 p35 subunit comprises the amino acid sequence set forth in SEQ ID NO: 41.

22. The method of embodiment 19 or 20, wherein the IL-12 p35 subunit comprises the amino acid sequence set forth in SEQ ID NO: 25.

23. The method of any one of embodiments 1 to 22, wherein the transgene is inserted between two transcription units of the packaged genome.

24. The method of embodiment 23, wherein the packaged genome comprises a transcription unit for an NDV NP gene, a transcription unit for an NDV P gene, a transcription unit for an NDV M gene, a transcription unit for an NDV F gene, a transcription unit for an NDV HN gene, and a transcription unit for an NDV L gene.

25. The method of embodiment 24, wherein the two transcription units of the packaged genome are the transcription units for the NDV P gene and the NDV M gene.

26. The method of embodiment 1, wherein the packaged genome comprises the nucleotide sequence set forth in SEQ ID NO:51.

27. The method of embodiment 1, wherein the packaged genome comprises the nucleotide sequence set forth in SEQ ID NO:52.

28. The method of embodiment 1, wherein the packaged genome comprises the nucleotide sequence set forth in SEQ ID NO:60.

29. The method of any one of embodiments 1 to 28, wherein the antagonist of human PD-1 or a ligand thereof is an antibody that binds to human PD-1.

30. The method of embodiment 29, wherein the antibody blocks the interaction between human PD-1 and its ligands, PD-L1 and PD-L2.

31. The method of embodiment 29 or 30, wherein the antibody is pembrolizumab.

32. The method of embodiment 29 or 30, wherein the antibody is nivolumab or MEDI0680.

33. The method of embodiment 29 or 30, wherein the antibody comprises a variable light chain region (VLCR) complementarity determining region (CDR)1 comprising the amino acid sequence RASKGVSTSGYSYLH (SEQ ID NO: 1), a VLCR CDR2 comprising the amino acid sequence LASYLES (SEQ ID NO: 2), a VLCR CDR3 comprising the amino acid sequence QHSRDLPLT(SEQ ID NO: 3), a variable heavy chain region (VHCR) CDR 1 comprising the amino acid sequence NYYMY (SEQ ID NO: 6), a VHCR CDR2 comprising the amino acid sequence GINPSNGGTNFNEKFKN (SEQ ID NO: 7), and a VHCR CDR3 comprising the amino acid sequence RDYRFDMGFDY (SEQ ID NO: 8).

34. The method of embodiment 29 or 30, wherein the antibody comprises:

```
(a) a VLCR comprising the amino acid sequence
                                      (SEQ ID NO: 4)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIK;
and

(b) a VHCR comprising the amino acid sequence
                                      (SEQ ID NO: 9)
QVQLVQSGVEVKKPGASVKVSCKASGYTFTNYYMYWVRQAPGQGLEWMG

GINPSNGGTNFNEKFKNRVTLTTDSSTTTAYMELKSLQFDDTAVYYCAR

RDYRFDMGFDYWGQGTTVTVSS.
```

35. The method of embodiment 29 or 30, wherein the antibody comprises:

```
(a) a light chain comprising the amino acid
sequence
                                      (SEQ ID NO: 5)
EIVLTQSPATLSLSPGERATLSCRASKGVSTSGYSYLHWYQQKPGQAPR

LLIYLASYLESGVPARFSGSGSGTDFTLTISSLEPEDFAVYYCQHSRDL

PLTFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC;
and

(b) a heavy chain comprising the amino acid
sequence
                                      (SEQ ID NO: 10)
QVQLVQSGVEVKKPGASVKVSCKASGYTFTNYYMYWVRQAPGQGLEWMG

GINPSNGGTNFNEKFKNRVTLTTDSSTTTAYMELKSLQFDDTAVYYCAR

RDYRFDMGFDYWGQGTTVTVSSASTKGPSVFPLAPCSRSTSESTAALGC

LVKDYFPEPVTVSWNSGALTSGVHTFPAVLQSSGLYSLSSVVTVPSSSL

GTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQP

REPQVYTLPPSQEEMTKNQVSLTCLVKGFYPSDIAVEWESNGQPENNYK

TTPPVLDSDGSFFLYSRLTVDKSRWQEGNVFSCSVMHEALHNHYTQKSL

SLSLGK.
```

36. The method of embodiment 29 or 30, wherein the antibody comprises a VLCR CDR1 comprising the amino acid sequence RASQSVSSYLA (SEQ ID NO: 11), a VLCR CDR2 comprising the amino acid sequence DASNRAT (SEQ ID NO: 12), a VLCR CDR3 comprising the amino acid sequence QQSSNWPRT (SEQ ID NO: 13), a VHCR CDR1 comprising the amino acid sequence NSGMH (SEQ ID NO: 16), a VHCR CDR2 comprising the amino acid sequence VIWYDGSKRYYADSVKG (SEQ ID NO: 17), and a VHCR CDR3 comprising the amino acid sequence NDDY (SEQ ID NO: 18).

37. The method of embodiment 29 or 30, wherein the antibody comprises:

```
(a) a VLCR comprising the amino acid sequence
                                      (SEQ ID NO: 14)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIK;
and

(b) a VHCR comprising the amino acid sequence
                                      (SEQ ID NO: 19)
QVQLVESGGGVVQPGRSLRLDCKASGITFSNSGMHWVRQAPGKGLEWVA

VIWYDGSKRYYADSVKGRFTISRDNSKNTLFLQMNSLRAEDTAVYYCAT

NDDYWGQGTLVTVSS.
```

38. The method of embodiment 29 or 30, wherein the antibody comprises:

```
(a) a light chain comprising the amino acid
sequence
                                    (SEQ ID NO: 15)
EIVLTQSPATLSLSPGERATLSCRASQSVSSYLAWYQQKPGQAPRLLIY

DASNRATGIPARFSGSGSGTDFTLTISSLEPEDFAVYYCQQSSNWPRTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC;
and

(b) a heavy chain comprising the amino acid
sequence
                                    (SEQ ID NO: 20)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK.
```

39. The method of any one of embodiments 1 to 28, wherein the antagonist of human PD-1 or a ligand thereof is an antibody that binds to human PD-L1.

40. The method of embodiment 39, wherein the antibody is durvalumab, avelumab, bms-936559, or atezolizumab.

41. The method of any one of embodiments 1 to 40, wherein the first composition is administered to the subject intratumorally or intra-nodally.

42. The method of embodiment 41, wherein the subject exhibits cutaneous or subcutaneous tumors or tumors within the lymph node.

43. The method of any one of embodiments 1 to 42, wherein the second composition is administered to the subject intravenously.

44. The method of any one of embodiments 1 to 42, wherein the second composition is administered to the subject subcutaneously.

45. The method of any one of embodiments 1 to 44, wherein the cancer is melanoma, kidney cancer, lung cancer, bladder cancer, ovarian cancer, hepatocellular carcinoma, pancreatic cancer, renal cancer, colorectal cancer, breast cancer, or head and neck cancer.

46. The method of any one of embodiments 1 to 44, wherein the cancer is non-small cell lung cancer, classical Hodgkin lymphoma, microsatellite instability-high cancer, melanoma, gastric cancer, urothelial carcinoma, or head and neck squamous cell cancer.

47. The method of any one of embodiments 1 to 44, wherein the cancer is diffuse large B-cell lymphoma or cervical cancer.

48. The method of any one of embodiments 1 to 44, wherein the cancer is melanoma, non-small cell lung cancer, head and neck cancer (HNSCC head and neck squamous cell carcinoma), Urothelial cancer, Triple negative breast cancer, gastric cancer, gastroesophageal junction adenocarcinoma, classical Hodgkin lymphoma, non-Hodgkin lymphoma, primary mediastinal B-cell lymphoma, mesothelioma, ovarian cancer, small cell lung cancer, esophageal cancer, nasopharyngeal cancer, anal cancer, biliary tract cancer, colorectal cancer, ER+/HER2− breast cancer, cervical cancer, thyroid cancer, salivary cancer, endometrial cancer, prostate cancer, glioblastoma, microsatellite instability-high (MSI-H) or mismatch repair deficient cancer (tissue agnostic), or tumors with high tumor mutational burden (tissue agnostic).

49. The method of embodiment 45, wherein the lung cancer is non-small cell lung cancer.

50. The method of embodiment 45, wherein the head and neck cancer is squamous cell carcinoma of the head and neck, the renal cancer is renal cell carcinoma, the colorectal cancer is colorectal carcinoma, or the breast cancer is breast carcinoma, triple negative breast cancer, or ER+/HER2− breast cancer.

51. The method of any one of embodiments 1 to 44, wherein the cancer is a solid tumor selected from the group consisting of melanoma, sarcoma, uterine cancer, gastric cancer, esophageal cancer, liver cancer, brain cancer, head and neck squamous cell carcinoma, and breast carcinoma.

52. The method of any one of embodiments 1 to 44, wherein the cancer is non-Hodgkin lymphoma or Hodgkin lymphoma.

53. The method of any one of embodiments 1 to 52, wherein the cancer is metastatic.

54. The method of any one of embodiments 1 to 51, wherein the cancer is unresectable.

55. The method of any one of embodiments 1 to 52, wherein the cancer comprises a dermal, subcutaneous, or nodal metastasis.

56. The method of any one of embodiments 1 to 55, wherein the cancer is refractory or relapsed, or both.

57. The method of any one of embodiments 1 to 56, wherein a biopsy of the cancer is PD-L1-positive.

58. The method of embodiment 57, wherein the biopsy has a tumor proportion score of at least 1%.

59. The method of embodiment 57, wherein the biopsy has a combined positive score of at least 1.

60. The method of any one of embodiments 1 to 56, wherein a biopsy of the cancer is PD-L1-negative.

61. The method of embodiment 60, wherein the biopsy has a tumor proportion score of less than 1%.

62. The method of embodiment 60, wherein the biopsy has a combined positive score of less than 1.

63. The method of any one of embodiments 1 to 62, wherein the subject is refractory to monotherapy treatment with an antibody that binds to PD-1 and blocks the interaction between PD-1 and its ligands, PD-L1 and PD-L2.

64. The method of embodiment 63, wherein the administration of the chimeric NDV induces IL-12p70 expression, IFN-γ expression or both IL-12p70 and IFN-γ expression.

65. The method of embodiment 63, wherein the administration of the chimeric NDV increases the Gene Expression Profiling (GEP) score of the 18-gene signature of Table 15.

66. The method of any one of embodiments 1 to 62, wherein the subject is refractory or unresponsive to monotherapy treatment with an antagonist of human PD-1 or a ligand thereof.

67. The method of embodiment 66, wherein the antagonist of PD-1 or a ligand thereof is nivolumab, AMP-224, MEDI0680, pembrolizumab, durvalumab, avelumab, bms-936559, or atezolizumab.

68. A chimeric NDV comprising a packaged genome, said packaged genome comprising a transgene encoding a human IL-12, wherein the IL-12 comprises the amino acid sequence set forth in SEQ ID NO:39.

69. The chimeric NDV of embodiment 68, wherein the transgene comprises the nucleotide sequence set forth in SEQ ID NO:61.

70. A chimeric NDV comprising a packaged genome, said packaged genome comprising a transgene encoding a human IL-12, wherein the IL-12 comprises the amino acid sequence set forth in SEQ ID NO:22.

71. The chimeric NDV of embodiment 70, wherein the transgene comprises the nucleotide sequence set forth in SEQ ID NO:26.

72. A chimeric NDV comprising a packaged genome, said packaged genome comprising a transgene encoding a human IL-12, wherein the IL-12 comprises the amino acid sequence set forth in SEQ ID NO:43.

73. The chimeric NDV of embodiment 72, wherein the transgene comprises the nucleotide sequence set forth in SEQ ID NO:63.

74. The chimeric NDV of embodiment 72, wherein the transgene comprises the nucleotide sequence set forth in SEQ ID NO:68.

75. A chimeric NDV comprising a packaged genome, said packaged genome comprising a transgene encoding a human IL-12, wherein the IL-12 comprises the amino acid sequence set forth in SEQ ID NO:42.

76. The chimeric NDV of embodiment 75, wherein the transgene comprises the nucleotide sequence set forth in SEQ ID NO:53.

77. The chimeric NDV of embodiment 75, wherein the transgene comprises the nucleotide sequence set forth in SEQ ID NO:66.

78. The chimeric NDV of any one of embodiments 68 to 77, wherein the chimeric NDV comprises an NDV backbone which is lentogenic.

79. The chimeric NDV of any one of embodiments 68 to 78, wherein the chimeric NDV comprises an NDV backbone of LaSota strain.

80. The chimeric NDV of any one of embodiments 68 to 78, wherein the chimeric NDV comprises an NDV backbone of Hitchner B1 strain.

81. The chimeric NDV of any one of embodiments 68 to 78, wherein the packaged genome comprises a nucleotide sequence encoding a mutated F protein and the mutated F protein is incorporated into the virion of the chimeric NDV, wherein the mutated F protein comprises a mutated cleavage site.

82. The chimeric NDV of embodiment 81, wherein the mutated cleavage site is $^{111}$H-N-R-T-K-R/F-I$^{118}$ (SEQ ID NO: 71).

83. The chimeric NDV of any one of embodiments 68 to 77, wherein the chimeric NDV comprises an NDV backbone of a r73T-R116 virus.

84. The chimeric NDV of any one of embodiments 68 to 80, wherein the packaged genome comprises a nucleotide sequence encoding a mutated F protein with the amino acid mutation L289A, wherein the mutated F protein is incorporated into the virion of the chimeric NDV.

85. The chimeric NDV of any one of embodiments 68 to 71, wherein the packaged genome comprises the nucleotide sequence set forth in SEQ ID NO:51.

86. The chimeric NDV of embodiment 72, 73, 75 or 76, wherein the packaged genome comprises the nucleotide sequence set forth in SEQ ID NO:52.

87. The chimeric NDV of embodiment 72, 74, 75 or 77, wherein the packaged genome comprises the nucleotide sequence set forth in SEQ ID NO:60.

88. The chimeric NDV of any one of embodiments 68 to 84, wherein the transgene is inserted between two transcription units of the packaged genome.

89. The chimeric NDV of embodiment 88, wherein the packaged genome comprises a transcription unit for an NDV NP gene, a transcription unit for an NDV P gene, a transcription unit for an NDV M gene, a transcription unit for an NDV F gene, a transcription unit for an NDV HN gene, and a transcription unit for an NDV L gene.

90. The chimeric NDV of embodiment 89, wherein the two transcription units of the packaged genome are the transcription units for the NDV P gene and the NDV M gene.

91. A chimeric NDV for use in a method for treating cancer in a human subject, wherein the chimeric NDV comprises a packaged genome comprising a transgene encoding human interleukin-12 ("IL-12"), wherein the transgene encodes a human IL-12 p40 subunit and a human IL-12 p35 subunit, and wherein the method further comprises administering an antagonist of human PD-1 or a ligand thereof.

92. The chimeric NDV of embodiment 91, wherein the chimeric NDV comprises an NDV backbone which is lentogenic.

93. The chimeric NDV of embodiment 91 or 92, wherein the chimeric NDV comprises an NDV backbone of Hitchner B1.

94. The chimeric NDV of embodiment 91 or 92, wherein the chimeric NDV comprises an NDV backbone of LaSota strain.

95. The chimeric NDV of embodiment 91 or 92, wherein the packaged genome comprises a nucleotide sequence encoding a mutated F protein and the mutated F protein is incorporated into the virion of the chimeric NDV, wherein the mutated F protein comprises a mutated cleavage site.

96. The chimeric NDV of embodiment 95, wherein the mutated cleavage site is $^{111}$H-N-R-T-K-R/F-I$^{118}$ (SEQ ID NO: 71).

97. The chimeric NDV of embodiment 91, wherein the chimeric NDV comprises an NDV backbone of a r73T-R116 virus.

98. The chimeric NDV of any one of embodiments 91 to 94, wherein the packaged genome comprises a nucleotide sequence encoding a mutated F protein with the amino acid mutation L289A, wherein the mutated F protein is incorporated into the virion of the chimeric NDV.

99. The chimeric NDV of any one of embodiments 91 to 98, wherein the IL-12 comprises the amino acid sequence set forth in SEQ ID NO:39.

100. The chimeric NDV of embodiment 99, wherein the transgene comprises the nucleotide sequence set forth in SEQ ID NO: 61.

101. The chimeric NDV of any one of embodiments 91 to 98, wherein the IL-12 comprises the amino acid sequence set forth in SEQ ID NO:22.

102. The chimeric NDV of embodiment 101, wherein the transgene comprises the nucleotide sequence set forth in SEQ ID NO: 26.

103. The chimeric NDV of any one of embodiments 91 to 98, wherein the IL-12 comprises the amino acid sequence set forth in SEQ ID NO:43.

104. The chimeric NDV of embodiment 103, wherein the transgene comprises the nucleotide sequence set forth in SEQ ID NO: 63.

105. The chimeric NDV of embodiment 103, wherein the transgene comprises the nucleotide sequence set forth in SEQ ID NO: 68.

106. The chimeric NDV of any one of embodiments 91 to 98, wherein the IL-12 comprises the amino acid sequence set forth in SEQ ID NO:42.

107. The chimeric NDV of embodiment 106, wherein the transgene comprises the nucleotide sequence set forth in SEQ ID NO: 53.

108. The chimeric NDV of embodiment 106, wherein the transgene comprises the nucleotide sequence set forth in SEQ ID NO: 66.

109. The chimeric NDV of any one of embodiments 91 to 98, wherein the IL-12 p40 subunit comprises the amino acid sequence set forth in SEQ ID NO: 38.

110. The chimeric NDV of any one of embodiments 91 to 98, wherein the IL-12 p40 subunit comprises the amino acid sequence set forth in SEQ ID NO: 40.

111. The chimeric NDV of embodiment 109 or 110, wherein the IL-12 p35 subunit comprises the amino acid sequence set forth in SEQ ID NO: 41.

112. The chimeric NDV of embodiment 109 or 110, wherein the IL-12 p35 subunit comprises the amino acid sequence set forth in SEQ ID NO: 25.

113. The chimeric NDV of any one of embodiments 91 to 112, wherein the transgene is inserted between two transcription units of the packaged genome.

114. The chimeric NDV of embodiment 113, wherein the packaged genome comprises a transcription unit for an NDV NP gene, a transcription unit for an NDV P gene, a transcription unit for an NDV M gene, a transcription unit for an NDV F gene, a transcription unit for an NDV HN gene, and a transcription unit for an NDV L gene.

115. The chimeric NDV of embodiment 114, wherein the two transcription units of the packaged genome are the transcription units for the NDV P gene and the NDV M gene.

116. The chimeric NDV of embodiment 91, wherein the packaged genome comprises the nucleotide sequence set forth in SEQ ID NO:51.

117. The chimeric NDV of embodiment 91, wherein the packaged genome comprises the nucleotide sequence set forth in SEQ ID NO:52.

118. The chimeric NDV of embodiment 91, wherein the packaged genome comprises the nucleotide sequence set forth in SEQ ID NO:60.

119. The chimeric NDV of any one of embodiments 91 to 118, wherein the antagonist of human PD-1 or a ligand thereof is an antibody that binds to PD-1.

120. The chimeric NDV of embodiment 119, wherein the antibody blocks the interaction between human PD-1 and its ligands, PD-L1 and PD-L2.

121. The chimeric NDV of embodiment 119 or 120, wherein the antibody is pembrolizumab.

122. The chimeric NDV of embodiment 119 or 120, wherein the antibody is nivolumab or MEDI0680.

123. The chimeric NDV of embodiment 119 or 120, wherein the antibody comprises a variable light chain region (VLCR) complementarity determining region (CDR)1 comprising the amino acid sequence RASKGVSTSGYSYLH (SEQ ID NO: 1), a VLCR CDR2 comprising the amino acid sequence LASYLES (SEQ ID NO: 2), a VLCR CDR3 comprising the amino acid sequence QHSRDLPLT(SEQ ID NO: 3), a variable heavy chain region (VHCR) CDR 1 comprising the amino acid sequence NYYMY (SEQ ID NO: 6), a VHCR CDR2 comprising the amino acid sequence GINPSNGGTNFNEKFKN (SEQ ID NO: 7), and a VHCR CDR3 comprising the amino acid sequence RDYRFDMGFDY (SEQ ID NO: 8).

124. The chimeric NDV of embodiment 119 or 120, wherein the antibody comprises:

(a) a VLCR comprising the amino acid sequence
(SEQ ID NO: 4)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIK;
and (b) a VHCR comprising the amino acid sequence
(SEQ ID NO: 9)
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSS.

125. The chimeric NDV of embodiment 119 or 120, wherein the antibody comprises:

(a) a light chain comprising the amino acid sequence
(SEQ ID NO: 5)
EIVLTQSPATLSLSPGERATLSCRASKGVSTSGYSYLHWYQQKPGQAPRL
LIYLASYLESGVPARFSGSGSGTDFTLTISSLEPEDFAVYYCQHSRDLPL
TFGGGTKVEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC;
and (b) a heavy chain comprising the amino acid sequence
(SEQ ID NO: 10)
QVQLVQSGVEVKKPGASVKVSCKASGYTFTNYYMYWVRQAPGQGLEWMGG
INPSNGGTNFNEKFKNRVTLTTDSSTTTAYMELKSLQFDDTAVYYCARRD
YRFDMGFDYWGQGTTVTVSSASTKGPSVFPLAPCSRSTSESTAALGCLVK
DYFPEPVTVSWNSGALTSGVHTFPAVLQSSGLYSLSSVVTVPSSSLGTKT
YTCNVDHKPSNTKVDKRVESKYGPPCPPCPAPEFLGGPSVFLFPPKPKDT
LMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYT
LPPSQEEMTKNQVSLTCLVKGFYPSDIAVEWESNGQPENNYKTTPPVLDS
DGSFFLYSRLTVDKSRWQEGNVFSCSVMHEALHNHYTQKSLSLSLGK.

126. The chimeric NDV of embodiment 119 or 120, wherein the antibody comprises a VLCR CDR1 comprising the amino acid sequence RASQSVSSYLA (SEQ ID NO: 11), a VLCR CDR2 comprising the amino acid sequence DASNRAT (SEQ ID NO: 12), a VLCR CDR3 comprising the amino acid sequence QQSSNWPRT (SEQ ID NO: 13), a VHCR CDR1 comprising the amino acid sequence NSGMH (SEQ ID NO: 16), a VHCR CDR2 comprising the amino acid sequence VIWYDGSKRYYADSVKG (SEQ ID NO: 17), and a VHCR CDR3 comprising the amino acid sequence NDDY (SEQ ID NO: 18).

127. The chimeric NDV of embodiment 119 or 120, wherein the antibody comprises:

```
(a) a VLCR comprising the amino acid sequence
                                        (SEQ ID NO: 14)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIK;
and

(b) a VHCR comprising the amino acid sequence
                                        (SEQ ID NO: 19)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSS.
```

128. The chimeric NDV of embodiment 119 or 120, wherein the antibody comprises:

```
(a) a light chain comprising the amino acid
sequence
                                        (SEQ ID NO: 15)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC;
and

(b) a heavy chain comprising the amino acid
sequence
                                        (SEQ ID NO: 20)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK.
```

129. The chimeric NDV of any one of embodiments 91 to 118, wherein the antagonist of human PD-1 or a ligand thereof is an antibody that binds to human PD-L1.

130. The chimeric NDV of embodiment 129, wherein the antibody is durvalumab, avelumab, bms-936559, or atezolizumab.

131. The chimeric NDV of any one of embodiments 91 to 130, wherein the chimeric NDV is administered to the subject intratumorally or intra-nodally.

132. The chimeric NDV of embodiment 131, wherein the subject exhibits cutaneous or subcutaneous tumors or tumors within the lymph node.

133. The chimeric NDV of any one of embodiments 91 to 131, wherein the antagonist of human PD-1 or a ligand thereof is administered to the subject intravenously.

134. The chimeric NDV of any one of embodiments 91 to 131, wherein the antagonist of human PD-1 or a ligand thereof is administered to the subject subcutaneously.

135. The chimeric NDV of any one of embodiments 91 to 134, wherein the cancer is melanoma, kidney cancer, lung cancer, bladder cancer, ovarian cancer, hepatocellular carcinoma, pancreatic cancer, renal cancer, colorectal cancer, breast cancer, or head and neck cancer.

136. The chimeric NDV of any one of embodiments 91 to 134, wherein the cancer is non-small cell lung cancer, classical Hodgkin lymphoma, microsatellite instability-high cancer, melanoma, gastric cancer, urothelial carcinoma, or head and neck squamous cell cancer.

137. The chimeric NDV of any one of embodiments 91 to 134, wherein the cancer is diffuse large B-cell lymphoma or cervical cancer.

138. The chimeric NDV of any one of embodiments 91 to 134, wherein the cancer is melanoma, non-small cell lung cancer, head and neck cancer (HNSCC head and neck squamous cell carcinoma), Urothelial cancer, Triple negative breast cancer, gastric cancer-gastroesophageal junction adenocarcinoma, classical Hodgkin lymphoma, non-Hodgkin lymphoma, primary mediastinal B-cell lymphoma, mesothelioma, ovarian cancer, small cell lung cancer, esophageal cancer, nasopharyngeal cancer, anal cancer, biliary tract cancer, colorectal cancer, ER+/HER2− breast cancer, cervical cancer, thyroid cancer, salivary cancer, endometrial cancer, prostate cancer, glioblastoma, microsatellite instability-high (MSI-H) or mismatch repair deficient cancer (tissue agnostic), or tumors with high tumor mutational burden (tissue agnostic)

139. The chimeric NDV of embodiment 135, wherein the lung cancer is non-small cell lung cancer.

140. The chimeric NDV of embodiment 135, wherein the head and neck cancer is squamous cell carcinoma of the head and neck, the renal cancer is renal cell carcinoma, the colorectal cancer is colorectal carcinoma, or the breast cancer is breast carcinoma, triple negative breast cancer, or ER+/HER2− breast cancer.

141. The chimeric NDV of any one of embodiments 91 to 134, wherein the cancer is a solid tumor selected from the group consisting of melanoma, sarcoma, uterine cancer, gastric cancer, esophageal cancer, liver cancer, brain cancer, head and neck squamous cell carcinoma, and breast carcinoma.

142. The chimeric NDV of any one of embodiments 91 to 134, wherein the cancer is Non-Hodgkin lymphoma or Hodgkin lymphoma.

143. The chimeric NDV of any one of embodiments 91 to 142, wherein the cancer is metastatic.

144. The chimeric NDV of any one of embodiments 91 to 141, wherein the cancer is unresectable.

145. The chimeric NDV of any one of embodiments 91 to 142, wherein the cancer comprises a dermal, subcutaneous, or nodal metastasis.

146. The chimeric NDV of any one of embodiments 91 to 145, wherein the cancer is refractory, relapsed or both.

147. The chimeric NDV of any one of embodiments 91 to 145, wherein a biopsy of the cancer is PD-L1-positive.

148. The chimeric NDV of embodiment 147, wherein the biopsy has a tumor proportion score of at least 1%.

149. The chimeric NDV of embodiment 147, wherein the biopsy has a combined positive score of at least 1.

150. The chimeric NDV of any one of embodiments 91 to 146, wherein a biopsy of the cancer is PD-L1-negative.

151. The chimeric NDV of embodiment 150, wherein the biopsy has a tumor proportion score of less than 1%.

152. The chimeric NDV of embodiment 150, wherein the biopsy has a combined positive score of less than 1.

153. The chimeric NDV of any one of embodiments 91 to 152, wherein the subject is refractory to montherapy treatment with an antibody that binds to PD-1 and blocks the interaction between PD-1 and its ligands, PD-L1 and PD-L2.

154. The chimeric NDV of embodiment 153, wherein the administration of the chimeric NDV induces IL-12p70 expression, IFN-γ expression, or both IL-12p70 and IFN-γ expression.

155. The chimeric NDV of embodiment 153, wherein the administration of the chimeric NDV increases the GEP score of the 18-gene signature of Table 15.

156. The chimeric NDV of any one of embodiments 91 to 152, wherein the subject is refractory or unresponsive to monotherapy treatment with an antagonist of PD-1 or a ligand thereof.

157. The chimeric NDV of embodiment 156, wherein the antagonist of PD-1 or a ligand thereof is nivolumab, AMP-224, MEDI0680, pembrolizumab, durvalumab, avelumab, bms-936559, or atezolizumab.

The invention is not to be limited in scope by the specific embodiments described herein. Indeed, various modifications of the invention in addition to those described will become apparent to those skilled in the art from the foregoing description and accompanying Figures. Such modifications are intended to fall within the scope of the appended claims.

All references cited herein are incorporated herein by reference in their entirety and for all purposes to the same extent as if each individual publication or patent or patent application was specifically and individually indicated to be incorporated by reference in its entirety for all purposes.

What is claimed:

1. A chimeric NDV comprising a packaged genome, said packaged genome comprising a transgene encoding a human IL-12, wherein the transgene comprises the corresponding negative sense RNA sequence of the nucleotide sequence set forth in SEQ ID NO:61 or 26.

2. A chimeric NDV comprising a packaged genome, said packaged genome comprising a transgene encoding a human IL-12, wherein the IL-12 comprises the amino acid sequence set forth in SEQ ID NO:43 or 42.

3. The chimeric NDV of claim 2, wherein the transgene comprises the corresponding negative sense RNA sequence of the nucleotide sequence set forth in SEQ ID NO:63, 68, 53, or 66.

4. The chimeric NDV of claim 1, wherein the chimeric NDV comprises an NDV backbone of LaSota strain and the packaged genome comprises a nucleotide sequence encoding a mutated F protein with the amino acid mutation L289A, wherein the mutated F protein is incorporated into the virion of the chimeric NDV.

5. The chimeric NDV of claim 1, wherein the packaged genome comprises a transcription unit for an NDV NP gene, a transcription unit for an NDV P gene, a transcription unit for an NDV M gene, a transcription unit for an NDV F gene, a transcription unit for an NDV HN gene, and a transcription unit for an NDV L gene, and wherein the transgene is inserted between the NDV P gene and the NDV M gene of the packaged genome.

6. The chimeric NDV of claim 1, wherein the packaged genome comprises the nucleotide sequence set forth in SEQ ID NO:51.

7. The chimeric NDV of claim 2, wherein the packaged genome comprises the nucleotide sequence set forth in SEQ ID NO:52 or 60.

8. A pharmaceutical composition comprising the chimeric NDV of claim 1, in an admixture with a pharmaceutically acceptable carrier.

9. A pharmaceutical composition comprising the chimeric NDV of claim 2, in an admixture with a pharmaceutically acceptable carrier.

* * * * *

SEQUENCE LISTING

```
<160> NUMBER OF SEQ ID NOS: 72

<210> SEQ ID NO 1
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ala Ser Lys Gly Val Ser Thr Ser Gly Tyr Ser Tyr Leu His
1               5                   10                  15


<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Leu Ala Ser Tyr Leu Glu Ser
1               5


<210> SEQ ID NO 3
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln His Ser Arg Asp Leu Pro Leu Thr
1               5


<210> SEQ ID NO 4
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4
```

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110


<210> SEQ ID NO 5
<211> LENGTH: 218
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215


<210> SEQ ID NO 6
<211> LENGTH: 5
```

-continued

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 6

Asn Tyr Tyr Met Tyr
1 5

<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 7

Gly Ile Asn Pro Ser Asn Gly Gly Thr Asn Phe Asn Glu Lys Phe Lys
1 5 10 15

Asn

<210> SEQ ID NO 8
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 8

Arg Asp Tyr Arg Phe Asp Met Gly Phe Asp Tyr
1 5 10

<210> SEQ ID NO 9
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic polypeptide"

<400> SEQUENCE: 9

Gln Val Gln Leu Val Gln Ser Gly Val Glu Val Lys Lys Pro Gly Ala
1 5 10 15

Ser Val Lys Val Ser Cys Lys Ala Ser Gly Tyr Thr Phe Thr Asn Tyr
20 25 30

Tyr Met Tyr Trp Val Arg Gln Ala Pro Gly Gln Gly Leu Glu Trp Met
35 40 45

Gly Gly Ile Asn Pro Ser Asn Gly Gly Thr Asn Phe Asn Glu Lys Phe
50 55 60

Lys Asn Arg Val Thr Leu Thr Thr Asp Ser Ser Thr Thr Thr Ala Tyr
65 70 75 80

Met Glu Leu Lys Ser Leu Gln Phe Asp Asp Thr Ala Val Tyr Tyr Cys
85 90 95

Ala Arg Arg Asp Tyr Arg Phe Asp Met Gly Phe Asp Tyr Trp Gly Gln
100 105 110

Gly Thr Thr Val Thr Val Ser Ser
115 120

<210> SEQ ID NO 10
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 10

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350
```

-continued

```
Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445


<210> SEQ ID NO 11
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ala Ser Gln Ser Val Ser Ser Tyr Leu Ala
1               5                   10


<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ala Ser Asn Arg Ala Thr
1               5


<210> SEQ ID NO 13
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gln Gln Ser Ser Asn Trp Pro Arg Thr
1               5


<210> SEQ ID NO 14
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
```

```
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys
            100                 105


<210> SEQ ID NO 15
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Ser Asn Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 16
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic peptide"

<400> SEQUENCE: 16

Asn Ser Gly Met His
1 5

<210> SEQ ID NO 17
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 17

Val Ile Trp Tyr Asp Gly Ser Lys Arg Tyr Tyr Ala Asp Ser Val Lys
1 5 10 15

Gly

<210> SEQ ID NO 18
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 18

Asn Asp Asp Tyr
1

<210> SEQ ID NO 19
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

Gln Val Gln Leu Val Glu Ser Gly Gly Gly Val Val Gln Pro Gly Arg
1 5 10 15

Ser Leu Arg Leu Asp Cys Lys Ala Ser Gly Ile Thr Phe Ser Asn Ser
20 25 30

Gly Met His Trp Val Arg Gln Ala Pro Gly Lys Gly Leu Glu Trp Val
35 40 45

Ala Val Ile Trp Tyr Asp Gly Ser Lys Arg Tyr Tyr Ala Asp Ser Val
50 55 60

Lys Gly Arg Phe Thr Ile Ser Arg Asp Asn Ser Lys Asn Thr Leu Phe
65 70 75 80

Leu Gln Met Asn Ser Leu Arg Ala Glu Asp Thr Ala Val Tyr Tyr Cys
85 90 95

Ala Thr Asn Asp Asp Tyr Trp Gly Gln Gly Thr Leu Val Thr Val Ser
100 105 110

Ser

<210> SEQ ID NO 20
<211> LENGTH: 440
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 20

```
Gln Val Gln Leu Val Glu Ser Gly Gly Gly Val Val Gln Pro Gly Arg
1               5                   10                  15

Ser Leu Arg Leu Asp Cys Lys Ala Ser Gly Ile Thr Phe Ser Asn Ser
            20                  25                  30

Gly Met His Trp Val Arg Gln Ala Pro Gly Lys Gly Leu Glu Trp Val
        35                  40                  45

Ala Val Ile Trp Tyr Asp Gly Ser Lys Arg Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Thr Asn Asp Asp Tyr Trp Gly Gln Gly Thr Leu Val Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp
    130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Pro Cys Pro Ala
    210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380
```

```
Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440


<210> SEQ ID NO 21
<211> LENGTH: 18632
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21

tcttccgctt cctcgctcac tgactcgctg cgctcggtcg ttcggctgcg gcgagcggta     60

tcagctcact caaaggcggt aatacggtta tccacagaat caggggataa cgcaggaaag    120

aacatgtgag caaaaggcca gcaaaaggcc aggaaccgta aaaaggccgc gttgctggcg    180

tttttccata ggctccgccc ccctgacgag catcacaaaa atcgacgctc aagtcagagg    240

tggcgaaacc cgacaggact ataaagatac caggcgtttc cccctggaag ctccctcgtg    300

cgctctcctg ttccgaccct gccgcttacc ggatacctgt ccgcctttct cccttcggga    360

agcgtggcgc tttctcatag ctcacgctgt aggtatctca gttcggtgta ggtcgttcgc    420

tccaagctgg gctgtgtgca cgaacccccc gttcagcccg accgctgcgc cttatccggt    480

aactatcgtc ttgagtccaa cccggtaaga cacgacttat cgccactggc agcagccact    540

ggtaacagga ttagcagagc gaggtatgta ggcggtgcta cagagttctt gaagtggtgg    600

cctaactacg gctacactag aagaacagta tttggtatct gcgctctgct gaagccagtt    660

accttcggaa aaagagttgg tagctcttga tccggcaaac aaaccaccgc tggtagcggt    720

ggtttttttg tttgcaagca gcagattacg cgcagaaaaa aaggatctca agaagatcct    780

ttgatctttt ctacggggtc tgacgctcag tggaacgaaa actcacgtta agggattttg    840

gtcatgagat tatcaaaaag gatcttcacc tagatccttt taaattaaaa atgaagtttt    900

aaatcaatct aaagtatata tgagtaaact tggtctgaca gttaccaatg cttaatcagt    960

gaggcaccta tctcagcgat ctgtctattt cgttcatcca tagttgcctg actccccgtc   1020

gtgtagataa ctacgatacg ggagggctta ccatctggcc ccagtgctgc aatgataccg   1080

cgagacccac gctcaccggc tccagattta tcagcaataa accagccagc cggaagggcc   1140

gagcgcagaa gtggtcctgc aactttatcc gcctccatcc agtctattaa ttgttgccgg   1200

gaagctagag taagtagttc gccagttaat agtttgcgca acgttgttgc cattgctaca   1260

ggcatcgtgg tgtcacgctc gtcgtttggt atggcttcat tcagctccgg ttcccaacga   1320

tcaaggcgag ttacatgatc ccccatgttg tgcaaaaaag cggttagctc cttcggtcct   1380

ccgatcgttg tcagaagtaa gttggccgca gtgttatcac tcatggttat ggcagcactg   1440

cataattctc ttactgtcat gccatccgta agatgctttt ctgtgactgg tgagtactca   1500

accaagtcat tctgagaata gtgtatgcgg cgaccgagtt gctcttgccc ggcgtcaata   1560

cgggataata ccgcgccaca tagcagaact ttaaaagtgc tcatcattgg aaaacgttct   1620

tcggggcgaa aactctcaag gatcttaccg ctgttgagat ccagttcgat gtaacccact   1680
```

-continued

```
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
aaagtgccac ctgacgtcta agaaaccatt attatcatga cattaaccta taaaaatagg   1980
cgtatcacga ggccctttcg tctcgcgcgt ttcggtgatg acggtgaaaa cctctgacac   2040
atgcagctcc cggagacggt cacagcttgt ctgtaagcgg atgccgggag cagacaagcc   2100
cgtcagggcg cgtcagcggg tgttggcggg tgtcggggct ggcttaacta tgcggcatca   2160
gagcagattg tactgagagt gcaccataaa attgtaaacg ttaatatttt gttaaaattc   2220
gcgttaaatt tttgttaaat cagctcattt tttaaccaat aggccgaaat cggcaaaatc   2280
ccttataaat caaaagaata gcccgagata gggttgagtg ttgttccagt ttggaacaag   2340
agtccactat taaagaacgt ggactccaac gtcaaagggc gaaaaaccgt ctatcagggc   2400
gatggcccac tacgtgaacc atcacccaaa tcaagttttt tggggtcgag gtgccgtaaa   2460
gcactaaatc ggaaccctaa agggagcccc cgatttagag cttgacgggg aaagccggcg   2520
aacgtggcga gaaaggaagg gaagaaagcg aaaggagcgg gcgctagggc gctggcaagt   2580
gtagcggtca cgctgcgcgt aaccaccaca cccgccgcgc ttaatgcgcc gctacagggc   2640
gcgtactatg gttgctttga cgtatgcggt gtgaaatacc gcacagatgc gtaaggagaa   2700
aataccgcat caggcgccat tcgccattca ggctgcgcaa ctgttgggaa gggcgatcgg   2760
tgcgggcctc ttcgctatta cgccagctgg cgaaaggggg atgtgctgca aggcgattaa   2820
gttgggtaac gccagggttt tcccagtcac gacgttgtaa aacgacggcc agtgccaagc   2880
tttaatacga ctcactatag ggaccaaaca gagaatccgt gagttacgat aaaaggcgaa   2940
ggagcaattg aagtcgcacg ggtagaaggt gtgaatctcg agtgcgagcc cgaagcacaa   3000
actcgagaaa gccttctgcc aacatgtctt ccgtatttga tgagtacgaa cagctcctcg   3060
cggctcagac tcgccccaat ggagctcatg gagggggaga aaaagggagt accttaaaag   3120
tagacgtccc ggtattcact cttaacagtg atgacccaga agatagatgg agctttgtgg   3180
tattctgcct ccggattgct gttagcgaag atgccaacaa accactcagg caaggtgctc   3240
tcatatctct tttatgctcc cactcacagg taatgaggaa ccatgttgcc cttgcaggga   3300
aacagaatga agccacattg gccgtgcttg agattgatgg ctttgccaac ggcacgcccc   3360
agttcaacaa taggagtgga gtgtctgaag agagagcaca gagatttgcg atgatagcag   3420
gatctctccc tcgggcatgc agcaacggaa ccccgttcgt cacagccggg gccgaagatg   3480
atgcaccaga agacatcacc gataccctgg agaggatcct ctctatccag gctcaagtat   3540
gggtcacagt agcaaaagcc atgactgcgt atgagactgc agatgagtcg gaaacaaggc   3600
gaatcaataa gtatatgcag caaggcaggg tccaaaagaa atacatcctc taccccgtat   3660
gcaggagcac aatccaactc acgatcagac agtctcttgc agtccgcatc tttttggtta   3720
gcgagctcaa gagaggccgc aacacggcag gtggtacctc tacttattat aacctggtag   3780
gggacgtaga ctcatacatc aggaataccg ggcttactgc attcttcttg acactcaagt   3840
acggaatcaa caccaagaca tcagcccttg cacttagtag cctctcaggc gacatccaga   3900
agatgaagca gctcatgcgt ttgtatcgga tgaaaggaga taatgcgccg tacatgacat   3960
tacttggtga tagtgaccag atgagctttg cgcctgccga gtatgcacaa ctttactcct   4020
```

-continued

```
ttgccatggg tatggcatca gtcctagata aaggtactgg gaaataccaa tttgccaggg   4080
actttatgag cacatcattc tggagacttg gagtagagta cgctcaggct cagggaagta   4140
gcattaacga ggatatggct gccgagctaa agctaacccc agcagcaagg aggggcctgg   4200
cagctgctgc ccaacgggtc tccgaggaga ccagcagcat agacatgcct actcaacaag   4260
tcggagtcct cactgggctt agcgaggggg ggtcccaagc tctacaaggc ggatcgaata   4320
gatcgcaagg gcaaccagaa gccggggatg gggagaccca attcctggat ctgatgagag   4380
cggtagcaaa tagcatgagg gaggcgccaa actctgcaca gggcactccc caatcggggc   4440
ctcccccaac tcctgggcca tcccaagata acgacaccga ctgggggtat tgatggacaa   4500
aacccagcct gcttccacaa aaacatccca atgccctcac ccgtagtcga cccctcgatt   4560
tgcggctcta tatgaccaca ccctcaaaca aacatccccc tctttcctcc ctccccctgc   4620
tgtacaacta cgtacgccct agataccaca ggcacaatgc ggctcactaa caatcaaaac   4680
agagccgagg gaattagaaa aaagtacggg tagaagaggg atattcagag atcagggcaa   4740
gtctcccgag tctctgctct ctcctctacc tgatagacca ggacaaacat ggccaccttt   4800
acagatgcag agatcgacga gctatttgag acaagtggaa ctgtcattga caacataatt   4860
acagcccagg gtaaaccagc agagactgtt ggaaggagtg caatcccaca aggcaagacc   4920
aaggtgctga gcgcagcatg ggagaagcat gggagcatcc agccaccggc cagtcaagac   4980
aaccccgatc gacaggacag atctgacaaa caaccatcca cacccgagca aacgaccccg   5040
catgacagcc cgccggccac atccgccgac cagcccccca cccaggccac agacgaagcc   5100
gtcgacacac agctcaggac cggagcaagc aactctctgc tgttgatgct tgacaagctc   5160
agcaataaat cgtccaatgc taaaaagggc ccatggtcga gcccccaaga ggggaatcac   5220
caacgtccga ctcaacagca ggggagtcaa cccagtcgcg gaaacagtca ggaaagaccg   5280
cagaaccaag tcaaggccgc ccctggaaac cagggcacag acgtgaacac agcatatcat   5340
ggacaatggg aggagtcaca actatcagct ggtgcaaccc ctcatgctct ccgatcaagg   5400
cagagccaag acaataccct tgtatctgcg gatcatgtcc agccacctgt agactttgtg   5460
caagcgatga tgtctatgat ggaggcgata tcacagagag taagtaaggt tgactatcag   5520
ctagatcttg tcttgaaaca gacatcctcc atccctatga tgcggtccga aatccaacag   5580
ctgaaaacat ctgttgcagt catggaagcc aacttgggaa tgatgaagat tctggatccc   5640
ggttgtgcca acatttcatc tctgagtgat ctacgggcag ttgcccgatc tcacccggtt   5700
ttagtttcag gccctggaga cccctctccc tatgtgacac aaggaggcga aatggcactt   5760
aataaacttt cgcaaccagt gccacatcca tctgaattga ttaaacccgc cactgcatgc   5820
gggcctgata taggagtgga aaaggacact gtccgtgcat tgatcatgtc acgcccaatg   5880
cacccgagtt cttcagccaa gctcctaagc aagttagatg cagccgggtc gatcgaggaa   5940
atcaggaaaa tcaagcgcct tgctctaaat ggctaattac tactgccaca cgtagcgggt   6000
ccctgtccac tcggcatcac acggaatctg caccgagttc ccccccgcgg acccaaggtc   6060
caactctcca agcggcaatc ctctctcgct tcctcagccc cactgaatga tcgcgtaacc   6120
gtaattaatc tagctacatt taagattaag aaaaaatacg ggtagaattg gagtgcccca   6180
attgtgccaa gatggactca tctaggacaa ttgggctgta ctttgattct gcccattctt   6240
ctagcaacct gttagcattt ccgatcgtcc tacaagacac aggagatggg aagaagcaaa   6300
tcgccccgca atataggatc cagcgccttg acttgtggac tgatagtaag gaggactcag   6360
tattcatcac cacctatgga ttcatctttc aagttgggaa tgaagaagcc accgtcggca   6420
```

tgatcgatga taaacccaag cgcgagttac tttccgctgc gatgctctgc ctaggaagcg 6480
tcccaaatac cggagacctt attgagctgg caagggcctg tctcactatg atagtcacat 6540
gcaagaagag tgcaactaat actgagagaa tggttttctc agtagtgcag gcaccccaag 6600
tgctgcaaag ctgtagggtt gtggcaaaca aatactcatc agtgaatgca gtcaagcacg 6660
tgaaagcgcc agagaagatt cccgggagtg gaaccctaga atacaaggtg aactttgtct 6720
ccttgactgt ggtaccgaag agggatgtct acaagatccc agctgcagta ttgaaggttt 6780
ctggctcgag tctgtacaat cttgcgctca atgtcactat taatgtggag gtagacccga 6840
ggagtccttt ggttaaatct ctgtctaagt ctgacagcgg atactatgct aacctcttct 6900
tgcatattgg acttatgacc actgtagata ggaaggggaa gaaagtgaca tttgacaagc 6960
tggaaaagaa aataaggagc cttgatctat ctgtcgggct cagtgatgtg ctcgggcctt 7020
ccgtgttggt aaaagcaaga ggtgcacgga ctaagctttt ggcacctttc ttctctagca 7080
gtgggacagc ctgctatccc atagcaaatg cttctcctca ggtggccaag atactctgga 7140
gtcaaaccgc gtgcctgcgg agcgttaaaa tcattatcca agcaggtacc caacgcgctg 7200
tcgcagtgac cgccgaccac gaggttacct ctactaagct ggagaagggg cacacccttg 7260
ccaaatacaa tccttttaag aaataagctg cgtctctgag attgcgctcc gcccactcac 7320
ccagatcatc atgacacaaa aaactaatct gtcttgatta tttacagtta gtttacctgt 7380
ctatcaagtt agaaaaaaca cgggtagaag attctggatc ccggttggcg ccctccaggt 7440
gcaagatggg ctccagacct tctaccaaga acccagcacc tatgatgctg actatccggg 7500
ttgcgctggt actgagttgc atctgtccgg caaactccat tgatggcagg cctcttgcag 7560
ctgcaggaat tgtggttaca ggagacaaag ccgtcaacat atacacctca tcccagacag 7620
gatcaatcat agttaagctc ctcccgaatc tgcccaagga taaggaggca tgtgcgaaag 7680 ccccttgga tgcatacaac aggacattga ccactttgct caccccccctt ggtgactcta 7740 tccgtaggat acaagagtct gtgactacat ctggaggggg gagacagggg cgccttatag 7800
gcgccattat tggcggtgtg gctcttgggg ttgcaactgc cgcacaaata acagcggccg 7860
cagctctgat acaagccaaa caaaatgctg ccaacatcct ccgacttaaa gagagcattg 7920
ccgcaaccaa tgaggctgtg catgaggtca ctgacggatt atcgcaacta gcagtggcag 7980
ttgggaagat gcagcagttt gttaatgacc aatttaataa aacagctcag gaattagact 8040
gcatcaaaat tgcacagcaa gttggtgtag agctcaacct gtacctaacc gaattgacta 8100
cagtattcgg accacaaatc acttcacctg ctttaaacaa gctgactatt caggcacttt 8160
acaatctagc tggtggaaat atggattact tattgactaa gttaggtgta gggaacaatc 8220
aactcagctc attaatcggt agcggcttaa tcaccggtaa ccctattcta tacgactcac 8280
agactcaact cttgggtata caggtaactg ccccttcagt cgggaaccta aataatatgc 8340
gtgccaccta cttggaaacc ttatccgtaa gcacaaccag gggatttgcc tcggcacttg 8400
tcccaaaagt ggtgacacag gtcggttctg tgatagaaga acttgacacc tcatactgta 8460
tagaaactga cttagattta tattgtacaa gaatagtaac gttccctatg tcccctggta 8520
tttattcctg cttgagcggc aatacgtcgg cctgtatgta ctcaaagacc gaaggcgcac 8580
ttactacacc atacatgact atcaaaggtt cagtcatcgc caactgcaag atgacaacat 8640
gtagatgtgt aaaccccccg ggtatcatat cgcaaaacta tggagaagcc gtgtctctaa 8700
tagataaaca atcatgcaat gttttatcct taggcgggat aactttaagg ctcagtgggg 8760

-continued

```
aattcgatgt aacttatcag aagaatatct caatacaaga ttctcaagta ataataacag   8820
gcaatcttga tatctcaact gagcttggga atgtcaacaa ctcgatcagt aatgctttga   8880
ataagttaga ggaaagcaac agaaaactag acaaagtcaa tgtcaaactg actagcacat   8940
ctgctctcat tacctatatc gttttgacta tcatatctct tgtttttggt atacttagcc   9000
tgattctagc atgctaccta atgtacaagc aaaaggcgca acaaaagacc ttattatggc   9060
ttgggaataa tactctagat cagatgagag ccactacaaa aatgtgaaca cagatgagga   9120
acgaaggttt ccctaatagt aatttgtgtg aaagttctgg tagtctgtca gttcagagag   9180
ttaagaaaaa actaccggtt gtagatgacc aaaggacgat atacgggtag aacggtaaga   9240
gaggccgccc ctcaattgcg agccaggctt cacaacctcc gttctaccgc ttcaccgaca   9300
acagtcctca atcatggacc gcgccgttag ccaagttgcg ttagagaatg atgaaagaga   9360
ggcaaaaaat acatggcgct tgatattccg gattgcaatc ttattcttaa cagtagtgac   9420
cttggctata tctgtagcct ccctttata tagcatgggg gctagcacac ctagcgatct   9480
tgtaggcata ccgactagga tttccagggc agaagaaaag attacatcta cacttggttc   9540
caatcaagat gtagtagata ggatatataa gcaagtggcc cttgagtctc cgttggcatt   9600
gttaaatact gagaccacaa ttatgaacgc aataacatct ctctcttatc agattaatgg   9660
agctgcaaac aacagtgggt gggggcacc tatccatgac ccagattata tagggggat   9720
aggcaaagaa ctcattgtag atgatgctag tgatgtcaca tcattctatc cctctgcatt   9780
tcaagaacat ctgaatttta tcccggcgcc tactacagga tcaggttgca ctcgaatacc   9840
ctcatttgac atgagtgcta cccattactg ctacacccat aatgtaatat tgtctggatg   9900
cagagatcac tcacattcat atcagtattt agcacttggt gtgctccgga catctgcaac   9960
agggagggta ttcttttcta ctctgcgttc catcaacctg gacgacaccc aaaatcggaa  10020
gtcttgcagt gtgagtgcaa ctcccctggg ttgtgatatg ctgtgctcga aagtcacgga  10080
gacagaggaa gaagattata actcagctgt ccctacgcgg atggtacatg ggaggttagg  10140
gttcgacggc cagtaccacg aaaaggacct agatgtcaca acattattcg ggactgggt  10200
ggccaactac ccaggagtag gggtggatc ttttattgac agccgcgtat ggttctcagt  10260
ctacggaggg ttaaaaccca attcacccag tgacactgta caggaaggga aatatgtgat  10320
atacaagcga tacaatgaca catgcccaga tgagcaagac taccagattc gaatggccaa  10380
gtcttcgtat aagcctggac ggtttggtgg gaaacgcata cagcaggcta tcttatctat  10440
caaggtgtca acatccttag gcgaagaccc ggtactgact gtaccgccca acacagtcac  10500
actcatgggg gccgaaggca gaattctcac agtagggaca tctcatttct tgtatcaacg  10560
agggtcatca tacttctctc ccgcgttatt atatcctatg acagtcagca acaaaacagc  10620
cactcttcat agtccttata cattcaatgc cttcactcgg ccaggtagta tcccttgcca  10680
ggcttcagca agatgcccca actcgtgtgt tactggagtc tatacagatc catatcccct  10740
aatcttctat agaaaccaca ccttgcgagg ggtattcggg acaatgcttg atggtgtaca  10800
agcaagactt aaccctgcgt ctgcagtatt cgatagcaca tcccgcagtc gcattactcg  10860
agtgagttca agcagtacca aagcagcata cacaacatca acttgtttta aagtggtcaa  10920
gactaataag acctattgtc tcagcattgc tgaaatatct aatactctct tcggagaatt  10980
cagaatcgtc ccgttactag ttgagatcct caaagatgac ggggttagag aagccaggtc  11040
tggctagttg agtcaattat aaaggagttg gaaagatggc attgtatcac ctatcttctg  11100
cgacatcaag aatcaaaccg aatgccggcg cgtgctcgaa ttccatgttg ccagttgacc  11160
```

acaatcagcc agtgctcatg cgatcagatt aagccttgtc aatagtctct tgattaagaa 11220
aaaatgtaag tggcaatgag atacaaggca aaacagctca tggttaacaa tacgggtagg 11280
acatggcgag ctccggtcct gaaagggcag agcatcagat tatcctacca gagtcacacc 11340
tgtcttcacc attggtcaag cacaaactac tctattactg gaaattaact gggctaccgc 11400
ttcctgatga atgtgacttc gaccacctca ttctcagccg acaatggaaa aaaatacttg 11460
aatcggcctc tcctgatact gagagaatga taaaactcgg aagggcagta caccaaactc 11520
ttaaccacaa ttccagaata accggagtgc tccaccccag gtgtttagaa gaactggcta 11580
atattgaggt cccagattca accaacaaat ttcggaagat tgagaagaag atccaaattc 11640
acaacacgag atatggagaa ctgttcacaa ggctgtgtac gcatatagag aagaaactgc 11700
tggggtcatc ttggtctaac aatgtccccc ggtcagagga gttcagcagc attcgtacgg 11760
atccggcatt ctggtttcac tcaaaatggt ccacagccaa gtttgcatgg ctccatataa 11820
aacagatcca gaggcatctg atggtggcag ctaggacaag gtctgcggcc aacaaattgg 11880
tgatgctaac ccataaggta ggccaagtct ttgtcactcc tgaacttgtc gttgtgacgc 11940
atacgaatga gaacaagttc acatgtctta cccaggaact tgtattgatg tatgcagata 12000
tgatggaggg cagagatatg gtcaacataa tatcaaccac ggcggtgcat ctcagaagct 12060
tatcagagaa aattgatgac attttgcggt taatagacgc tctggcaaaa gacttgggta 12120
atcaagtcta cgatgttgta tcactaatgg agggatttgc atacggagct gtccagctac 12180
tcgagccgtc aggtacattt gcaggagatt tcttcgcatt caacctgcag gagcttaaag 12240
acattctaat tggcctcctc cccaatgata tagcagaatc cgtgactcat gcaatcgcta 12300
ctgtattctc tggtttagaa cagaatcaag cagctgagat gttgtgtctg ttgcgtctgt 12360
ggggtcaccc actgcttgag tcccgtattg cagcaaaggc agtcaggagc caaatgtgcg 12420
caccgaaaat ggtagacttt gatatgatcc ttcaggtact gtctttcttc aagggaacaa 12480
tcatcaacgg gtacagaaag aagaatgcag gtgtgtggcc gcgagtcaaa gtggatacaa 12540
tatatgggaa ggtcattggg caactacatg cagattcagc agagatttca cacgatatca 12600
tgttgagaga gtataagagt ttatctgcac ttgaatttga gccatgtata gaatatgacc 12660
ctgtcaccaa cctgagcatg ttcctaaaag acaaggcaat cgcacacccc aacgataatt 12720
ggcttgcctc gtttaggcgg aaccttctct ccgaagacca gaagaaacat gtaaaagaag 12780
caacttcgac taatcgcctc ttgatagagt ttttagagtc aaatgatttt gatccatata 12840
aagagatgga atatctgacg acccttgagt accttagaga tgacaatgtg gcagtatcat 12900
actcgctcaa ggagaaggaa gtgaaagtta atggacggat cttcgctaag ctgacaaaga 12960
agttaaggaa ctgtcaggtg atggcggaag ggatcctagc cgatcagatt gcacctttct 13020
ttcagggaaa tggagtcatt caggatagca tatccttgac caagagtatg ctagcgatga 13080
gtcaactgtc ttttaacagc aataagaaac gtatcactga ctgtaaagaa agagtatctt 13140
caaaccgcaa tcatgatccg aaaagcaaga accgtcggag agttgcaacc ttcataacaa 13200
ctgacctgca aaagtactgt cttaattgga gatatcagac aatcaaattg ttcgctcatg 13260
ccatcaatca gttgatgggc ctacctcact tcttcgaatg gattcaccta agactgatgg 13320
acactacgat gttcgtagga gaccctttca atcctccaag tgaccctact gactgtgacc 13380
tctcaagagt ccctaatgat gacatatata ttgtcagtgc cagagggggt atcgaaggat 13440
tatgccagaa gctatggaca atgatctcaa ttgctgcaat ccaacttgct gcagctagat 13500

-continued

```
cgcattgtcg tgttgcctgt atggtacagg gtgataatca agtaatagca gtaacgagag  13560
aggtaagatc agacgactct ccggagatgg tgttgacaca gttgcatcaa gccagtgata  13620
atttcttcaa ggaattaatt catgtcaatc atttgattgg ccataatttg aaggatcgtg  13680
aaaccatcag gtcagacaca ttcttcatat acagcaaacg aatcttcaaa gatggagcaa  13740
tcctcagtca agtcctcaaa aattcatcta aattagtgct agtgtcaggt gatctcagtg  13800
aaaacaccgt aatgtcctgt gccaacattg cctctactgt agcacggcta tgcgagaacg  13860
ggcttcccaa agacttctgt tactatttaa actatataat gagttgtgtg cagacatact  13920
ttgactctga gttctccatc accaacaatt cgcaccccga tcttaatcag tcgtggattg  13980
aggacatctc ttttgtgcac tcatatgttc tgactcctgc ccaattaggg ggactgagta  14040
accttcaata ctcaaggctc tacactagaa atatcggtga cccggggact actgcttttg  14100
cagagatcaa gcgactagaa gcagtgggat tactgagtcc taacattatg actaatatct  14160
taactaggcc gcctgggaat ggagattggg ccagtctgtg caacgaccca tactctttca  14220
attttgagac tgttgcaagc ccaaatattg ttcttaagaa acatacgcaa agagtcctat  14280
ttgaaacttg ttcaaatccc ttattgtctg gagtgcacac agaggataat gaggcagaag  14340
agaaggcatt ggctgaattc ttgcttaatc aagaggtgat tcatccccgc gttgcgcatg  14400
ccatcatgga ggcaagctct gtaggtagga gaaagcaaat tcaagggctt gttgacacaa  14460
caaacaccgt aattaagatt gcgcttacta ggaggccatt aggcatcaag aggctgatgc  14520
ggatagtcaa ttattctagc atgcatgcaa tgctgtttag agacgatgtt ttttcctcca  14580
gtagatccaa ccacccctta gtctcttcta atatgtgttc tctgacactg gcagactatg  14640
cacggaatag aagctggtca cctttgacgg gaggcaggaa aatactgggt gtatctaatc  14700
ctgatacgat agaactcgta gagggtgaga ttcttagtgt aagcggaggg tgtacaagat  14760
gtgacagcgg agatgaacaa tttacttggt tccatcttcc aagcaatata gaattgaccg  14820
atgacaccag caagaatcct ccgatgaggg taccatatct cgggtcaaag acacaggaga  14880
ggagagctgc ctcacttgca aaaatagctc atatgtcgcc acatgtaaag gctgccctaa  14940
gggcatcatc cgtgttgatc tgggcttatg gggataatga agtaaattgg actgctgctc  15000
ttacgattgc aaaatctcgg tgtaatgtaa acttagagta tcttcggtta ctgtcccctt  15060
tacccacggc tgggaatctt caacatagac tagatgatgg tataactcag atgacattca  15120
cccctgcatc tctctacagg gtgtcacctt acattcacat atccaatgat tctcaaaggc  15180
tgttcactga agaaggagtc aaagagggga atgtggttta ccaacagatc atgctcttgg  15240
gtttatctct aatcgaatcg atctttccaa tgacaacaac caggacatat gatgagatca  15300
cactgcacct acatagtaaa tttagttgct gtatcagaga agcacctgtt gcggttcctt  15360
tcgagctact tggggtggta ccggaactga ggacagtgac ctcaaataag tttatgtatg  15420
atcctagccc tgtatcggag ggagactttg cgagacttga cttagctatc ttcaagagtt  15480
atgagcttaa tctggagtca tatcccacga tagagctaat gaacattctt tcaatatcca  15540
gcgggaagtt gattggccag tctgtggttt cttatgatga agatacctcc ataaagaatg  15600
acgccataat agtgtatgac aatacccgaa attggatcag tgaagctcag aattcagatg  15660
tggtccgcct atttgaatat gcagcacttg aagtgctcct cgactgttct taccaactct  15720
attacctgag agtaagaggc ctggacaata ttgtcttata tatgggtgat ttatacaaga  15780
atatgccagg aattctactt tccaacattg cagctacaat atctcatccc gtcattcatt  15840
caaggttaca tgcagtgggc ctggtcaacc atgacggatc acaccaactt gcagatacgg  15900
```

```
attttatcga aatgtctgca aaactattag tatcttgcac ccgacgtgtg atctccggct  15960
tatattcagg aaataagtat gatctgctgt tcccatctgt cttagatgat aacctgaatg  16020
agaagatgct tcagctgata tcccggttat gctgtctgta cacggtactc tttgctacaa  16080
caagagaaat cccgaaaata agaggcttaa ctgcagaaga gaaatgttca atactcactg  16140
agtatttact gtcggatgct gtgaaaccat tacttagccc cgatcaagtg agctctatca  16200
tgtctcctaa cataattaca ttcccagcta atctgtacta catgtctcgg aagagcctca  16260
atttgatcag ggaaagggag gacagggata ctatcctggc gttgttgttc cccaagagc   16320
cattattaga gttcccttct gtgcaagata ttggtgctcg agtgaaagat ccattcaccc  16380
gacaacctgc ggcatttttg caagagttag atttgagtgc tccagcaagg tatgacgcat  16440
tcacacttag tcagattcat cctgaactca catctccaaa tccggaggaa gactacttag  16500
tacgatactt gttcagaggg atagggactg catcttcctc ttggtataag gcatctcatc  16560
tcctttctgt acccgaggta agatgtgcaa gacacgggaa ctccttatac ttagctgaag  16620
ggagcggagc catcatgagt cttctcgaac tgcatgtacc acatgaaact atctattaca  16680
atacgctctt ttcaaatgag atgaaccccc cgcaacgaca tttcgggccg accccaactc  16740
agtttttgaa ttcggttgtt tataggaatc tacaggcgga ggtaacatgc aaagatggat  16800
ttgtccaaga gttccgtcca ttatggagag aaaatacaga ggaaagcgac ctgacctcag  16860
ataaagtagt ggggtatatt acatctgcag tgccctacag atctgtatca ttgctgcatt  16920
gtgacattga aattcctcca gggtccaatc aaagcttact agatcaacta gctatcaatt  16980
tatctctgat tgccatgcat tctgtaaggg agggcggggt agtaatcatc aaagtgttgt  17040
atgcaatggg atactacttt catctactca tgaacttgtt tgctccgtgt tccacaaaag  17100
gatatattct ctctaatggt tatgcatgtc gaggagatat ggagtgttac ctggtatttg  17160
tcatgggtta cctgggcggg cctacatttg tacatgaggt ggtgaggatg gcgaaaactc  17220
tggtgcagcg gcacggtacg cttttgtcta aatcagatga gatcacactg accaggttat  17280
tcacctcaca gcggcagcgt gtgacagaca tcctatccag tcctttacca agattaataa  17340
agtacttgag gaagaatatt gacactgcgc tgattgaagc cgggggacag cccgtccgtc  17400
cattctgtgc ggagagtctg gtgagcacgc tagcgaacat aactcagata acccagatca  17460
tcgctagtca cattgacaca gttatccggt ctgtgatata tatggaagct gagggtgatc  17520
tcgctgacac agtatttcta tttacccctt acaatctctc tactgacggg aaaaagagga  17580
catcacttaa acagtgcacg agacagatcc tagaggttac aatactaggt cttagagtcg  17640
aaaatctcaa taaaataggc gatataatca gcctagtgct taaaggcatg atctccatgg  17700
aggaccttat cccactaagg acatacttga agcatagtac ctgccctaaa tatttgaagg  17760
ctgtcctagg tattaccaaa ctcaaagaaa tgtttacaga cacttctgta ctgtacttga  17820
ctcgtgctca acaaaaattc tacatgaaaa ctataggcaa tgcagtcaaa ggatattaca  17880
gtaactgtga ctcttaacga aaatcacata ttaataggct cctttttttgg ccaattgtat  17940
tcttgttgat ttaatcatat tatgttagaa aaaagttgaa ccctgactcc ttaggactcg  18000
aattcgaact caaataaatg tcttaaaaaa aggttgcgca caattattct tgagtgtagt  18060
ctcgtcattc accaaatctt tgtttggtgc gcgcggccgg catggtccca gcctcctcgc  18120
tggcgccggc tgggcaacat tccgagggga ccgtcccctc ggtaatggcg aatgggacgt  18180
cgactgctaa caaagcccga aaggaagctg agttggctgc tgccaccgct gagcaataac  18240
```

```
tagcataacc ccttggggcc tctaaacggg tcttgagggg ttttttgctg aaaggaggaa  18300

ctatatgcgc gcagatctgt catgatgatc attgcaattg gatccatata tagggcccgg  18360

gttataatta cctcaggtcg acgtcccatg gccattcgaa ttcgtaatca tggtcatagc  18420

tgtttcctgt gtgaaattgt tatccgctca caattccaca caacatacga gccggaagca  18480

taaagtgtaa agcctggggt gcctaatgag tgagctaact cacattaatt gcgttgcgct  18540

cactgcccgc tttccagtcg ggaaacctgt cgtgccagct gcattaatga atcggccaac  18600

gcgcggggag aggcggtttg cgtattgggc gc                                18632


<210> SEQ ID NO 22
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285
```

```
Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Gly Gly Ser Arg
                325                 330                 335

Asn Leu Pro Val Ala Thr Pro Asp Pro Gly Met Phe Pro Cys Leu His
            340                 345                 350

His Ser Gln Asn Leu Leu Arg Ala Val Ser Asn Met Leu Gln Lys Ala
        355                 360                 365

Arg Gln Thr Leu Glu Phe Tyr Pro Cys Thr Ser Glu Glu Ile Asp His
    370                 375                 380

Glu Asp Ile Thr Lys Asp Lys Thr Ser Thr Val Glu Ala Cys Leu Pro
385                 390                 395                 400

Leu Glu Leu Thr Lys Asn Glu Ser Cys Leu Asn Ser Arg Glu Thr Ser
                405                 410                 415

Phe Ile Thr Asn Gly Ser Cys Leu Ala Ser Arg Lys Thr Ser Phe Met
            420                 425                 430

Met Ala Leu Cys Leu Ser Ser Ile Tyr Glu Asp Ser Lys Met Tyr Gln
        435                 440                 445

Val Glu Phe Lys Thr Met Asn Ala Lys Leu Leu Met Asp Pro Lys Arg
    450                 455                 460

Gln Ile Phe Leu Asp Gln Asn Met Leu Ala Val Ile Asp Glu Leu Met
465                 470                 475                 480

Gln Ala Leu Asn Phe Asn Ser Glu Thr Val Pro Gln Lys Ser Ser Leu
                485                 490                 495

Glu Glu Pro Asp Phe Tyr Lys Thr Lys Ile Lys Leu Cys Ile Leu Leu
            500                 505                 510

His Ala Phe Arg Ile Arg Ala Val Thr Ile Asp Arg Val Met Ser Tyr
        515                 520                 525

Leu Asn Ala Ser
    530


<210> SEQ ID NO 23
<211> LENGTH: 328
<212> TYPE: PRT
<213> ORGANISM: Homo sapiens

<400> SEQUENCE: 23

Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
```

```
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325


<210> SEQ ID NO 24
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gly Gly Gly Gly Gly Gly Ser
1               5


<210> SEQ ID NO 25
<211> LENGTH: 197
<212> TYPE: PRT
<213> ORGANISM: Homo sapiens

<400> SEQUENCE: 25

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80
```

```
Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Ser Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 26
<211> LENGTH: 1599
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
atgggtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagtggtggc ggtggcggcg gatctagaaa cctccccgtg   1020

gccactccag acccaggaat gttcccatgc cttcaccact cccaaaacct gctgagggcc   1080

gtcagcaaca tgctccagaa ggccagacaa actctagaat tttacccttg cacttctgaa   1140

gagattgatc atgaagatat cacaaaagat aaaaccagca cagtggaggc ctgtttacca   1200

ttggaattaa ccaagaatga gagttgccta aattccagag agacctcttt cataactaat   1260

gggagttgcc tggcctccag aaagacctct tttatgatgg ccctgtgcct tagtagtatt   1320
```

tatgaagact cgaagatgta ccaggtggag ttcaagacca tgaatgcaaa gcttctgatg 1380
gatcctaaga ggcagatctt tctagatcaa aacatgctgg cagttattga tgagctgatg 1440
caggccctga atttcaacag tgagactgtg ccacaaaaat cctcccttga agaaccggat 1500
ttttataaaa ctaaaatcaa gctctgcata cttcttcatg ctttcagaat tcgggcagtg 1560
actattgata gagtgatgag ctatctgaat gcttcctaa 1599

<210> SEQ ID NO 27
<211> LENGTH: 984
<212> TYPE: DNA
<213> ORGANISM: Homo sapiens

<400> SEQUENCE: 27
atgggtcacc agcagttggt catctcttgg ttttccctgg tttttctggc atctcccctc 60
gtggccatat gggaactgaa gaaagatgtt tatgtcgtag aattggattg gtatccggat 120
gcccctggag aaatggtggt cctcacctgt gacacccctg aagaagatgg tatcacctgg 180
accttggacc agagcagtga ggtcttaggc tctggcaaaa ccctgaccat ccaagtcaaa 240
gagtttggag atgctggcca gtacacctgt cacaaaggag gcgaggttct aagccattcg 300
ctcctgctgc ttcacaaaaa ggaagatgga atttggtcca ctgatatttt aaaggaccag 360
aaagaaccca aaaataagac ctttctaaga tgcgaggcca agaattattc tggacgtttc 420
acctgctggt ggctgacgac aatcagtact gatttgacat tcagtgtcaa aagcagcaga 480
ggctcttctg acccccaagg ggtgacgtgc ggagctgcta cactctctgc agagagagtc 540
agaggggaca acaaggagta tgagtactca gtggagtgcc aggaggacag tgcctgccca 600
gctgctgagg agagtctgcc cattgaggtc atggtggatg ccgttcacaa gctcaagtat 660
gaaaactaca ccagcagctt cttcatcagg gacatcatca aacctgaccc acccaagaac 720
ttgcagctga agccattaaa gaattctcgg caggtggagg tcagctggga gtaccctgac 780
acctggagta ctccacattc ctacttctcc ctgacattct gcgttcaggt ccagggcaag 840
agcaagagag aaaagaaaga tagagtcttc acggacaaga cctcagccac ggtcatctgc 900
cgcaaaaatg ccagcattag cgtgcgggcc caggaccgct actatagctc atcttggagc 960
gaatgggcat ctgtgccctg cagt 984

<210> SEQ ID NO 28
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 28
ggtggcggtg gcggcggatc t 21

<210> SEQ ID NO 29
<211> LENGTH: 594
<212> TYPE: DNA
<213> ORGANISM: Homo sapiens

<400> SEQUENCE: 29
agaaacctcc ccgtggccac tccagaccca ggaatgttcc catgccttca ccactcccaa 60
aacctgctga gggccgtcag caacatgctc cagaaggcca gacaaactct agaattttac 120
ccttgcactt ctgaagagat tgatcatgaa gatatcacaa aagataaaac cagcacagtg 180
gaggcctgtt taccattgga attaaccaag aatgagagtt gcctaaattc cagagagacc 240
tctttcataa ctaatgggag ttgcctggcc tccagaaaga cctcttttat gatggccctg 300
tgccttagta gtatttatga agactcgaag atgtaccagg tggagttcaa gaccatgaat 360
gcaaagcttc tgatggatcc taagaggcag atctttctag atcaaaacat gctggcagtt 420
attgatgagc tgatgcaggc cctgaatttc aacagtgaga ctgtgccaca aaaatcctcc 480
cttgaagaac cggattttta taaaactaaa atcaagctct gcatacttct tcatgctttc 540
agaattcggg cagtgactat tgatagagtg atgagctatc tgaatgcttc ctaa 594

<210> SEQ ID NO 30
<211> LENGTH: 1641
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30
atgtctgcac ttctgatcct agctcttgtt ggagctgcag ttgctgacta caaagacgat 60
gacgacaagc tttgggagct ggagaaagac gtttatgttg tagaggtgga ctggactccc 120
gatgcccctg gagaaacagt gaacctcacc tgtgacacgc ctgaagaaga tgacatcacc 180
tggacctcag accagagaca tggagtcata ggctctggaa agaccctgac catcactgtc 240
aaagagtttc tggatgctgg ccagtacacc tgccacaaag gaggcgagac tctgagccac 300
tcacatctgc tgctccacaa gaaggaaaat ggaatttggt ccactgaaat tttaaaaaat 360
ttcaaaaaca agactttcct gaagtgtgaa gcaccaaatt actccggacg gttcacgtgc 420
tcatggctgg tgcaaagaaa catggacttg aagttcaaca tcaagagcag tagcagttcc 480
cctgactctc gggcagtgac atgtggaatg gcgtctctgt ctgcagagaa ggtcacactg 540
gaccaaaggg actatgagaa gtattcagtg tcctgccagg aggatgtcac ctgcccaact 600
gctgaggaga ccctgcccat tgaactggcg ttggaagcac ggcagcagaa taaatatgag 660
aactacagca ccagcttctt catcagggac atcatcaaac cagacccgcc caagaacttg 720
cagatgaagc ctttgaagaa ctcacaggtg gaggtcagct gggagtaccc tgactcctgg 780
agcactcccc attcctactt ctccctcaag ttctttgttc gaatccagcg caagaaagaa 840
aagatgaagg agacagagga ggggtgtaac cagaaaggtg cgttcctcgt agagaagaca 900
tctaccgaag tccaatgcaa aggcgggaat gtctgcgtgc aagctcagga tcgctattac 960
aattcctcgt gcagcaagtg ggcatgtgtt ccctgcaggg tccgatcctc tagaggtagt 1020
ggatccggtg gcagtggagg ttctggatct ggtaagctta gggtcattcc agtctctgga 1080
cctgccaggt gtcttagcca gtcccgaaac ctgctgaaga ccacagatga catggtgaag 1140
acggccagag aaaaactgaa acattattcc tgcactgctg aagacatcga tcatgaagac 1200
atcacacggg accaaaccag cacattgaag acctgtttac cactggaact acacaagaac 1260
gagagttgcc tggctactag agagacttct tccacaacaa gagggagctg cctgccccca 1320
cagaagacgt ctttgatgat gaccctgtgc cttggtagca tctatgagga cttgaagatg 1380
taccagacag agttccaggc catcaacgca gcacttcaga atcacaacca tcagcagatc 1440
attctagaca agggcatgct ggtggccatc gatgagctga tgcagtctct gaatcataat 1500
ggcgagactc tgcgccagaa acctcctgtg ggagaagcag acccttacag agtgaaaatg 1560
aagctctgca tcctgcttca cgccttcagc acccgcgtcg tgaccatcaa cagggtgatg 1620
ggctatctga gctccgccta a 1641

<210> SEQ ID NO 31
<211> LENGTH: 20210
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31
tcagctcact caaaggcggt aatacggtta tccacagaat caggggataa cgcaggaaag 60
aacatgtgag caaaaggcca gcaaaaggcc aggaaccgta aaaaggccgc gttgctggcg 120
tttttccata ggctccgccc ccctgacgag catcacaaaa atcgacgctc aagtcagagg 180
tggcgaaacc cgacaggact ataaagatac caggcgtttc cccctggaag ctccctcgtg 240
cgctctcctg ttccgaccct gccgcttacc ggatacctgt ccgcctttct cccttcggga 300
agcgtggcgc tttctcatag ctcacgctgt aggtatctca gttcggtgta ggtcgttcgc 360
tccaagctgg gctgtgtgca cgaacccccc gttcagcccg accgctgcgc cttatccggt 420
aactatcgtc ttgagtccaa cccggtaaga cacgacttat cgccactggc agcagccact 480
ggtaacagga ttagcagagc gaggtatgta ggcggtgcta cagagttctt gaagtggtgg 540
cctaactacg gctacactag aagaacagta tttggtatct gcgctctgct gaagccagtt 600
accttcggaa aaagagttgg tagctcttga tccggcaaac aaaccaccgc tggtagcggt 660
ggtttttttg tttgcaagca gcagattacg cgcagaaaaa aaggatctca agaagatcct 720
ttgatctttt ctacggggtc tgacgctcag tggaacgaaa actcacgtta agggattttg 780
gtcatgagat tatcaaaaag gatcttcacc tagatccttt taaattaaaa atgaagtttt 840
aaatcaatct aaagtatata tgagtaaact tggtctgaca gttaccaatg cttaatcagt 900
gaggcaccta tctcagcgat ctgtctattt cgttcatcca tagttgcctg actccccgtc 960
gtgtagataa ctacgatacg ggagggctta ccatctggcc ccagtgctgc aatgataccg 1020
cgagacccac gctcaccggc tccagattta tcagcaataa accagccagc cggaagggcc 1080
gagcgcagaa gtggtcctgc aactttatcc gcctccatcc agtctattaa ttgttgccgg 1140
gaagctagag taagtagttc gccagttaat agtttgcgca acgttgttgc cattgctaca 1200
ggcatcgtgg tgtcacgctc gtcgtttggt atggcttcat tcagctccgg ttcccaacga 1260
tcaaggcgag ttacatgatc ccccatgttg tgcaaaaaag cggttagctc cttcggtcct 1320
ccgatcgttg tcagaagtaa gttggccgca gtgttatcac tcatggttat ggcagcactg 1380
cataattctc ttactgtcat gccatccgta agatgctttt ctgtgactgg tgagtactca 1440
accaagtcat tctgagaata gtgtatgcgg cgaccgagtt gctcttgccc ggcgtcaata 1500
cgggataata ccgcgccaca tagcagaact ttaaaagtgc tcatcattgg aaaacgttct 1560
tcggggcgaa aactctcaag gatcttaccg ctgttgagat ccagttcgat gtaacccact 1620
cgtgcaccca actgatcttc agcatctttt actttcacca gcgtttctgg gtgagcaaaa 1680
acaggaaggc aaaatgccgc aaaaaaggga ataagggcga cacggaaatg ttgaatactc 1740
atactcttcc tttttcaata ttattgaagc atttatcagg gttattgtct catgagcgga 1800
tacatatttg aatgtattta gaaaaataaa caaatagggg ttccgcgcac atttccccga 1860

-continued

```
aaagtgccac ctgacgtcta agaaaccatt attatcatga cattaaccta taaaaatagg   1920
cgtatcacga ggccctttcg tctcgcgcgt ttcggtgatg acggtgaaaa cctctgacac   1980
atgcagctcc cggagacggt cacagcttgt ctgtaagcgg atgccgggag cagacaagcc   2040
cgtcagggcg cgtcagcggg tgttggcggg tgtcggggct ggcttaacta tgcggcatca   2100
gagcagattg tactgagagt gcaccataaa attgtaaacg ttaatatttt gttaaaattc   2160
gcgttaaatt tttgttaaat cagctcattt tttaaccaat aggccgaaat cggcaaaatc   2220
ccttataaat caaaagaata gcccgagata gggttgagtg ttgttccagt ttggaacaag   2280
agtccactat taaagaacgt ggactccaac gtcaaagggc gaaaaaccgt ctatcagggc   2340
gatggcccac tacgtgaacc atcacccaaa tcaagttttt tggggtcgag gtgccgtaaa   2400
gcactaaatc ggaaccctaa agggagcccc cgatttagag cttgacgggg aaagccggcg   2460
aacgtggcga gaaaggaagg gaagaaagcg aaaggagcgg gcgctagggc gctggcaagt   2520
gtagcggtca cgctgcgcgt aaccaccaca cccgccgcgc ttaatgcgcc gctacagggc   2580
gcgtactatg gttgctttga cgtatgcggt gtgaaatacc gcacagatgc gtaaggagaa   2640
aataccgcat caggcgccat tcgccattca ggctgcgcaa ctgttgggaa gggcgatcgg   2700
tgcgggcctc ttcgctatta cgccagctgg cgaaaggggg atgtgctgca aggcgattaa   2760
gttgggtaac gccagggttt tcccagtcac gacgttgtaa aacgacggcc agtgccaagc   2820
tttaatacga ctcactatag ggaccaaaca gagaatccgt gagttacgat aaaaggcgaa   2880
ggagcaattg aagtcgcacg ggtagaaggt gtgaatctcg agtgcgagcc cgaagcacaa   2940
actcgagaaa gccttctgcc aacatgtctt ccgtatttga tgagtacgaa cagctcctcg   3000
cggctcagac tcgccccaat ggagctcatg gagggggaga aaaagggagt accttaaaag   3060
tagacgtccc ggtattcact cttaacagtg atgacccaga agatagatgg agctttgtgg   3120
tattctgcct ccggattgct gttagcgaag atgccaacaa accactcagg caaggtgctc   3180
tcatatctct tttatgctcc cactcacagg taatgaggaa ccatgttgcc cttgcaggga   3240
aacagaatga agccacattg gccgtgcttg agattgatgg ctttgccaac ggcacgcccc   3300
agttcaacaa taggagtgga gtgtctgaag agagagcaca gagatttgcg atgatagcag   3360
gatctctccc tcgggcatgc agcaacggaa ccccgttcgt cacagccggg gccgaagatg   3420
atgcaccaga agacatcacc gataccctgg agaggatcct ctctatccag gctcaagtat   3480
gggtcacagt agcaaaagcc atgactgcgt atgagactgc agatgagtcg gaaacaaggc   3540
gaatcaataa gtatatgcag caaggcaggg tccaaaagaa atacatcctc taccccgtat   3600
gcaggagcac aatccaactc acgatcagac agtctcttgc agtccgcatc tttttggtta   3660
gcgagctcaa gagaggccgc aacacggcag gtggtacctc tacttattat aacctggtag   3720
gggacgtaga ctcatacatc aggaataccg ggcttactgc attcttcttg acactcaagt   3780
acggaatcaa caccaagaca tcagcccttg cacttagtag cctctcaggc gacatccaga   3840
agatgaagca gctcatgcgt ttgtatcgga tgaaaggaga taatgcgccg tacatgacat   3900
tacttggtga tagtgaccag atgagctttg cgcctgccga gtatgcacaa ctttactcct   3960
ttgccatggg tatggcatca gtcctagata aaggtactgg gaaataccaa tttgccaggg   4020
actttatgag cacatcattc tggagacttg gagtagagta cgctcaggct cagggaagta   4080
gcattaacga ggatatggct gccgagctaa agctaacccc agcagcaagg aggggcctgg   4140
cagctgctgc ccaacgggtc tccgaggaga ccagcagcat agacatgcct actcaacaag   4200
tcggagtcct cactgggctt agcgaggggg ggtcccaagc tctacaaggc ggatcgaata   4260
```

-continued gatcgcaagg gcaaccagaa gccggggatg gggagaccca attcctggat ctgatgagag 4320
cggtagcaaa tagcatgagg gaggcgccaa actctgcaca gggcactccc caatcggggc 4380
ctcccccaac tcctgggcca tcccaagata acgacaccga ctgggggtat tgatggacaa 4440
aacccagcct gcttccacaa aaacatccca atgccctcac ccgtagtcga cccctcgatt 4500
tgcggctcta tatgaccaca ccctcaaaca aacatccccc tctttcctcc ctccccctgc 4560
tgtacaacta cgtacgccct agataccaca ggcacaatgc ggctcactaa caatcaaaac 4620
agagccgagg gaattagaaa aaagtacggg tagaagaggg atattcagag atcagggcaa 4680
gtctcccgag tctctgctct ctcctctacc tgatagacca ggacaaacat ggccaccttt 4740
acagatgcag agatcgacga gctatttgag acaagtggaa ctgtcattga caacataatt 4800
acagcccagg gtaaaccagc agagactgtt ggaaggagtg caatcccaca aggcaagacc 4860
aaggtgctga gcgcagcatg ggagaagcat gggagcatcc agccaccggc cagtcaagac 4920
aaccccgatc gacaggacag atctgacaaa caaccatcca cacccgagca aacgaccccg 4980
catgacagcc cgccggccac atccgccgac cagcccccca cccaggccac agacgaagcc 5040
gtcgacacac agctcaggac cggagcaagc aactctctgc tgttgatgct tgacaagctc 5100
agcaataaat cgtccaatgc taaaaagggc ccatggtcga gcccccaaga ggggaatcac 5160
caacgtccga ctcaacagca ggggagtcaa cccagtcgcg gaaacagtca ggaaagaccg 5220
cagaaccaag tcaaggccgc ccctggaaac cagggcacag acgtgaacac agcatatcat 5280
ggacaatggg aggagtcaca actatcagct ggtgcaaccc ctcatgctct ccgatcaagg 5340
cagagccaag acaataccct tgtatctgcg gatcatgtcc agccacctgt agactttgtg 5400
caagcgatga tgtctatgat ggaggcgata tcacagagag taagtaaggt tgactatcag 5460
ctagatcttg tcttgaaaca gacatcctcc atccctatga tgcggtccga aatccaacag 5520
ctgaaaacat ctgttgcagt catggaagcc aacttgggaa tgatgaagat tctggatccc 5580
ggttgtgcca acatttcatc tctgagtgat ctacgggcag ttgcccgatc tcacccggtt 5640
ttagtttcag gccctggaga cccctctccc tatgtgacac aaggaggcga aatggcactt 5700
aataaacttt cgcaaccagt gccacatcca tctgaattga ttaaacccgc cactgcatgc 5760
gggcctgata taggagtgga aaaggacact gtccgtgcat tgatcatgtc acgcccaatg 5820
cacccgagtt cttcagccaa gctcctaagc aagttagatg cagccgggtc gatcgaggaa 5880
atcaggaaaa tcaagcgcct tgctctaaat ggctaattac tactgccaca cgtagcgggt 5940
ccctgtccac tcggcatcac acggaatctg caccgagttc ccccccgcgg ttagaaaaaa 6000
tacgggtaga accgccacca tgggtcacca gcagttggtc atctcttggt tttccctggt 6060
ttttctggca tctcccctcg tggccatatg ggaactgaag aaagatgttt atgtcgtaga 6120
attggattgg tatccggatg cccctggaga aatggtggtc ctcacctgtg acacccctga 6180
agaagatggt atcacctgga ccttggacca gagcagtgag gtcttaggct ctggcaaaac 6240
cctgaccatc caagtcaaag agtttggaga tgctggccag tacacctgtc acaaaggagg 6300
cgaggttcta agccattcgc tcctgctgct tcacaaaaag gaagatggaa tttggtccac 6360
tgatatttta aaggaccaga aagaacccaa aaataagacc tttctaagat gcgaggccaa 6420
gaattattct ggacgtttca cctgctggtg gctgacgaca atcagtactg atttgacatt 6480
cagtgtcaaa agcagcagag gctcttctga cccccaaggg gtgacgtgcg gagctgctac 6540
actctctgca gagagagtca gaggggacaa caaggagtat gagtactcag tggagtgcca 6600

```
ggaggacagt gcctgcccag ctgctgagga gagtctgccc attgaggtca tggtggatgc   6660
cgttcacaag ctcaagtatg aaaactacac cagcagcttc ttcatcaggg acatcatcaa   6720
acctgaccca cccaagaact tgcagctgaa gccattaaag aattctcggc aggtggaggt   6780
cagctgggag taccctgaca cctggagtac tccacattcc tacttctccc tgacattctg   6840
cgttcaggtc cagggcaaga gcaagagaga aaagaaagat agagtcttca cggacaagac   6900
ctcagccacg gtcatctgcc gcaaaaatgc cagcattagc gtgcgggccc aggaccgcta   6960
ctatagctca tcttggagcg aatgggcatc tgtgccctgc agtggtggcg gtggcggcgg   7020
atctagaaac ctccccgtgg ccactccaga cccaggaatg ttcccatgcc ttcaccactc   7080
ccaaaacctg ctgagggccg tcagcaacat gctccagaag gccagacaaa ctctagaatt   7140
ttacccttgc acttctgaag agattgatca tgaagatatc acaaaagata aaaccagcac   7200
agtggaggcc tgtttaccat tggaattaac caagaatgag agttgcctaa attccagaga   7260
gacctctttc ataactaatg ggagttgcct ggcctccaga aagacctctt ttatgatggc   7320
cctgtgcctt agtagtattt atgaagactc gaagatgtac caggtggagt tcaagaccat   7380
gaatgcaaag cttctgatgg atcctaagag gcagatcttt ctagatcaaa acatgctggc   7440
agttattgat gagctgatgc aggccctgaa tttcaacagt gagactgtgc cacaaaaatc   7500
ctcccttgaa gaaccggatt tttataaaac taaaatcaag ctctgcatac ttcttcatgc   7560
tttcagaatt cgggcagtga ctattgatag agtgatgagc tatctgaatg cttcctaatg   7620
atccgcggac ccaaggtcca actctccaag cggcaatcct ctctcgcttc ctcagcccca   7680
ctgaatgatc gcgtaaccgt aattaatcta gctacattta agattaagaa aaaatacggg   7740
tagaattgga gtgccccaat tgtgccaaga tggactcatc taggacaatt gggctgtact   7800
ttgattctgc ccattcttct agcaacctgt tagcatttcc gatcgtccta caagacacag   7860
gagatgggaa gaagcaaatc gccccgcaat ataggatcca gcgccttgac ttgtggactg   7920
atagtaagga ggactcagta ttcatcacca cctatggatt catctttcaa gttgggaatg   7980
aagaagccac cgtcggcatg atcgatgata aacccaagcg cgagttactt tccgctgcga   8040
tgctctgcct aggaagcgtc ccaaataccg gagaccttat tgagctggca agggcctgtc   8100
tcactatgat agtcacatgc aagaagagtg caactaatac tgagagaatg gttttctcag   8160
tagtgcaggc accccaagtg ctgcaaagct gtagggttgt ggcaaacaaa tactcatcag   8220
tgaatgcagt caagcacgtg aaagcgccag agaagattcc cgggagtgga accctagaat   8280
acaaggtgaa ctttgtctcc ttgactgtgg taccgaagag ggatgtctac aagatcccag   8340
ctgcagtatt gaaggtttct ggctcgagtc tgtacaatct tgcgctcaat gtcactatta   8400
atgtggaggt agacccgagg agtcctttgg ttaaatctct gtctaagtct gacagcggat   8460
actatgctaa cctcttcttg catattggac ttatgaccac tgtagatagg aaggggaaga   8520
aagtgacatt tgacaagctg gaaaagaaaa taaggagcct tgatctatct gtcgggctca   8580
gtgatgtgct cgggccttcc gtgttggtaa aagcaagagg tgcacggact aagcttttgg   8640
cacctttctt ctctagcagt gggacagcct gctatcccat agcaaatgct tctcctcagg   8700
tggccaagat actctggagt caaaccgcgt gcctgcggag cgttaaaatc attatccaag   8760
caggtaccca acgcgctgtc gcagtgaccg ccgaccacga ggttacctct actaagctgg   8820
agaaggggca cacccttgcc aaatacaatc cttttaagaa ataagctgcg tctctgagat   8880
tgcgctccgc ccactcaccc agatcatcat gacacaaaaa actaatctgt cttgattatt   8940
tacagttagt ttacctgtct atcaagttag aaaaaacacg ggtagaagat tctggatccc   9000
```

-continued

```
ggttggcgcc ctccaggtgc aagatgggct ccagaccttc taccaagaac ccagcaccta   9060
tgatgctgac tatccgggtt gcgctggtac tgagttgcat ctgtccggca aactccattg   9120
atggcaggcc tcttgcagct gcaggaattg tggttacagg agacaaagcc gtcaacatat   9180
acacctcatc ccagacagga tcaatcatag ttaagctcct cccgaatctg cccaaggata   9240
aggaggcatg tgcgaaagcc cccttggatg catacaacag gacattgacc actttgctca   9300
ccccccttgg tgactctatc cgtaggatac aagagtctgt gactacatct ggaggggga   9360
gacaggggcg ccttataggc gccattattg gcggtgtggc tcttggggtt gcaactgccg   9420
cacaaataac agcggccgca gctctgatac aagccaaaca aaatgctgcc aacatcctcc   9480
gacttaaaga gagcattgcc gcaaccaatg aggctgtgca tgaggtcact gacggattat   9540
cgcaactagc agtggcagtt gggaagatgc agcagtttgt taatgaccaa tttaataaaa   9600
cagctcagga attagactgc atcaaaattg cacagcaagt tggtgtagag ctcaacctgt   9660
acctaaccga attgactaca gtattcggac cacaaatcac ttcacctgct ttaaacaagc   9720
tgactattca ggcactttac aatctagctg gtggaaatat ggattactta ttgactaagt   9780
taggtgtagg gaacaatcaa ctcagctcat taatcggtag cggcttaatc accggtaacc   9840
ctattctata cgactcacag actcaactct tgggtataca ggtaactgcc ccttcagtcg   9900
ggaacctaaa taatatgcgt gccacctact tggaaacctt atccgtaagc acaaccaggg   9960
gatttgcctc ggcacttgtc ccaaaagtgg tgacacaggt cggttctgtg atagaagaac  10020
ttgacacctc atactgtata gaaactgact tagatttata ttgtacaaga atagtaacgt  10080
tccctatgtc ccctggtatt tattcctgct tgagcggcaa tacgtcggcc tgtatgtact  10140
caaagaccga aggcgcactt actacaccat acatgactat caaaggttca gtcatcgcca  10200
actgcaagat gacaacatgt agatgtgtaa acccccggg tatcatatcg caaaactatg  10260
gagaagccgt gtctctaata gataaacaat catgcaatgt tttatcctta ggcgggataa  10320
ctttaaggct cagtggggaa ttcgatgtaa cttatcagaa gaatatctca atacaagatt  10380
ctcaagtaat aataacaggc aatcttgata tctcaactga gcttgggaat gtcaacaact  10440
cgatcagtaa tgctttgaat aagttagagg aaagcaacag aaaactagac aaagtcaatg  10500
tcaaactgac tagcacatct gctctcatta cctatatcgt tttgactatc atatctcttg  10560
tttttggtat acttagcctg attctagcat gctacctaat gtacaagcaa aaggcgcaac  10620
aaaagacctt attatggctt gggaataata ctctagatca gatgagagcc actacaaaaa  10680
tgtgaacaca gatgaggaac gaaggtttcc ctaatagtaa tttgtgtgaa agttctggta  10740
gtctgtcagt tcagagagtt aagaaaaaac taccggttgt agatgaccaa aggacgatat  10800
acgggtagaa cggtaagaga ggccgcccct caattgcgag ccaggcttca caacctccgt  10860
tctaccgctt caccgacaac agtcctcaat catggaccgc gccgttagcc aagttgcgtt  10920
agagaatgat gaaagagagg caaaaaatac atggcgcttg atattccgga ttgcaatctt  10980
attcttaaca gtagtgacct tggctatatc tgtagcctcc cttttatata gcatgggggc  11040
tagcacacct agcgatcttg taggcatacc gactaggatt tccagggcag aagaaaagat  11100
tacatctaca cttggttcca atcaagatgt agtagatagg atatataagc aagtggccct  11160
tgagtctccg ttggcattgt taaatactga gaccacaatt atgaacgcaa taacatctct  11220
ctcttatcag attaatggag ctgcaaacaa cagtgggtgg ggggcaccta tccatgaccc  11280
agattatata ggggggatag gcaaagaact cattgtagat gatgctagtg atgtcacatc  11340
```

-continued

```
attctatccc tctgcatttc aagaacatct gaattttatc ccggcgccta ctacaggatc  11400
aggttgcact cgaataccct catttgacat gagtgctacc cattactgct acacccataa  11460
tgtaatattg tctggatgca gagatcactc acattcatat cagtatttag cacttggtgt  11520
gctccggaca tctgcaacag ggagggtatt cttttctact ctgcgttcca tcaacctgga  11580
cgacacccaa aatcggaagt cttgcagtgt gagtgcaact cccctgggtt gtgatatgct  11640
gtgctcgaaa gtcacggaga cagaggaaga agattataac tcagctgtcc ctacgcggat  11700
ggtacatggg aggttagggt tcgacggcca gtaccacgaa aaggacctag atgtcacaac  11760
attattcggg gactgggtgg ccaactaccc aggagtaggg ggtggatctt ttattgacag  11820
ccgcgtatgg ttctcagtct acggagggtt aaaacccaat tcacccagtg acactgtaca  11880
ggaagggaaa tatgtgatat acaagcgata caatgacaca tgcccagatg agcaagacta  11940
ccagattcga atggccaagt cttcgtataa gcctggacgg tttggtggga aacgcataca  12000
gcaggctatc ttatctatca aggtgtcaac atccttaggc gaagacccgg tactgactgt  12060
accgcccaac acagtcacac tcatgggggc cgaaggcaga attctcacag tagggacatc  12120
tcatttcttg tatcaacgag ggtcatcata cttctctccc gcgttattat atcctatgac  12180
agtcagcaac aaaacagcca ctcttcatag tccttataca ttcaatgcct tcactcggcc  12240
aggtagtatc ccttgccagg cttcagcaag atgccccaac tcgtgtgtta ctggagtcta  12300
tacagatcca tatcccctaa tcttctatag aaaccacacc ttgcgagggg tattcgggac  12360
aatgcttgat ggtgtacaag caagacttaa ccctgcgtct gcagtattcg atagcacatc  12420
ccgcagtcgc attactcgag tgagttcaag cagtaccaaa gcagcataca caacatcaac  12480
ttgttttaaa gtggtcaaga ctaataagac ctattgtctc agcattgctg aaatatctaa  12540
tactctcttc ggagaattca gaatcgtccc gttactagtt gagatcctca aagatgacgg  12600
ggttagagaa gccaggtctg gctagttgag tcaattataa aggagttgga aagatggcat  12660
tgtatcacct atcttctgcg acatcaagaa tcaaaccgaa tgccggcgcg tgctcgaatt  12720
ccatgttgcc agttgaccac aatcagccag tgctcatgcg atcagattaa gccttgtcaa  12780
tagtctcttg attaagaaaa aatgtaagtg gcaatgagat acaaggcaaa acagctcatg  12840
gttaacaata cgggtaggac atggcgagct ccggtcctga aagggcagag catcagatta  12900
tcctaccaga gtcacacctg tcttcaccat tggtcaagca caaactactc tattactgga  12960
aattaactgg gctaccgctt cctgatgaat gtgacttcga ccacctcatt ctcagccgac  13020
aatggaaaaa aatacttgaa tcggcctctc ctgatactga gagaatgata aaactcggaa  13080
gggcagtaca ccaaactctt aaccacaatt ccagaataac cggagtgctc caccccaggt  13140
gtttagaaga actggctaat attgaggtcc cagattcaac caacaaattt cggaagattg  13200
agaagaagat ccaaattcac aacacgagat atggagaact gttcacaagg ctgtgtacgc  13260
atatagagaa gaaactgctg gggtcatctt ggtctaacaa tgtcccccgg tcagaggagt  13320
tcagcagcat tcgtacggat ccggcattct ggtttcactc aaaatggtcc acagccaagt  13380
ttgcatggct ccatataaaa cagatccaga ggcatctgat ggtggcagct aggacaaggt  13440
ctgcggccaa caaattggtg atgctaaccc ataaggtagg ccaagtcttt gtcactcctg  13500
aacttgtcgt tgtgacgcat acgaatgaga acaagttcac atgtcttacc caggaacttg  13560
tattgatgta tgcagatatg atggagggca gagatatggt caacataata tcaaccacgg  13620
cggtgcatct cagaagctta tcagagaaaa ttgatgacat tttgcggtta atagacgctc  13680
tggcaaaaga cttgggtaat caagtctacg atgttgtatc actaatggag ggatttgcat  13740
```

```
acggagctgt ccagctactc gagccgtcag gtacatttgc aggagatttc ttcgcattca  13800
acctgcagga gcttaaagac attctaattg gcctcctccc caatgatata gcagaatccg  13860
tgactcatgc aatcgctact gtattctctg gtttagaaca gaatcaagca gctgagatgt  13920
tgtgtctgtt gcgtctgtgg ggtcacccac tgcttgagtc ccgtattgca gcaaaggcag  13980
tcaggagcca aatgtgcgca ccgaaaatgg tagactttga tatgatcctt caggtactgt  14040
ctttcttcaa gggaacaatc atcaacgggt acagaaagaa gaatgcaggt gtgtggccgc  14100
gagtcaaagt ggatacaata tatgggaagg tcattgggca actacatgca gattcagcag  14160
agatttcaca cgatatcatg ttgagagagt ataagagttt atctgcactt gaatttgagc  14220
catgtataga atatgaccct gtcaccaacc tgagcatgtt cctaaaagac aaggcaatcg  14280
cacaccccaa cgataattgg cttgcctcgt ttaggcggaa ccttctctcc gaagaccaga  14340
agaaacatgt aaaagaagca acttcgacta atcgcctctt gatagagttt ttagagtcaa  14400
atgattttga tccatataaa gagatggaat atctgacgac ccttgagtac cttagagatg  14460
acaatgtggc agtatcatac tcgctcaagg agaaggaagt gaaagttaat ggacggatct  14520
tcgctaagct gacaaagaag ttaaggaact gtcaggtgat ggcggaaggg atcctagccg  14580
atcagattgc acctttcttt cagggaaatg gagtcattca ggatagcata tccttgacca  14640
agagtatgct agcgatgagt caactgtctt ttaacagcaa taagaaacgt atcactgact  14700
gtaaagaaag agtatcttca aaccgcaatc atgatccgaa aagcaagaac cgtcggagag  14760
ttgcaacctt cataacaact gacctgcaaa agtactgtct taattggaga tatcagacaa  14820
tcaaattgtt cgctcatgcc atcaatcagt tgatgggcct acctcacttc ttcgaatgga  14880
ttcacctaag actgatggac actacgatgt tcgtaggaga ccctttcaat cctccaagtg  14940
accctactga ctgtgacctc tcaagagtcc ctaatgatga catatatatt gtcagtgcca  15000
gagggggtat cgaaggatta tgccagaagc tatggacaat gatctcaatt gctgcaatcc  15060
aacttgctgc agctagatcg cattgtcgtg ttgcctgtat ggtacagggt gataatcaag  15120
taatagcagt aacgagagag gtaagatcag acgactctcc ggagatggtg ttgacacagt  15180
tgcatcaagc cagtgataat ttcttcaagg aattaattca tgtcaatcat ttgattggcc  15240
ataatttgaa ggatcgtgaa accatcaggt cagacacatt cttcatatac agcaaacgaa  15300
tcttcaaaga tggagcaatc ctcagtcaag tcctcaaaaa ttcatctaaa ttagtgctag  15360
tgtcaggtga tctcagtgaa aacaccgtaa tgtcctgtgc caacattgcc tctactgtag  15420
cacggctatg cgagaacggg cttcccaaag acttctgtta ctatttaaac tatataatga  15480
gttgtgtgca gacatacttt gactctgagt tctccatcac caacaattcg caccccgatc  15540
ttaatcagtc gtggattgag gacatctctt ttgtgcactc atatgttctg actcctgccc  15600
aattaggggg actgagtaac cttcaatact caaggctcta cactagaaat atcggtgacc  15660
cggggactac tgcttttgca gagatcaagc gactagaagc agtgggatta ctgagtccta  15720
acattatgac taatatctta actaggccgc ctgggaatgg agattgggcc agtctgtgca  15780
acgacccata ctctttcaat tttgagactg ttgcaagccc aaatattgtt cttaagaaac  15840
atacgcaaag agtcctattt gaaacttgtt caaatccctt attgtctgga gtgcacacag  15900
aggataatga ggcagaagag aaggcattgg ctgaattctt gcttaatcaa gaggtgattc  15960
atccccgcgt tgcgcatgcc atcatggagg caagctctgt aggtaggaga aagcaaattc  16020
aagggcttgt tgacacaaca aacaccgtaa ttaagattgc gcttactagg aggccattag  16080
```

-continued

```
gcatcaagag gctgatgcgg atagtcaatt attctagcat gcatgcaatg ctgtttagag  16140
acgatgtttt ttcctccagt agatccaacc accccttagt ctcttctaat atgtgttctc  16200
tgacactggc agactatgca cggaatagaa gctggtcacc tttgacggga ggcaggaaaa  16260
tactgggtgt atctaatcct gatacgatag aactcgtaga gggtgagatt cttagtgtaa  16320
gcggagggtg tacaagatgt gacagcggag atgaacaatt tacttggttc catcttccaa  16380
gcaatataga attgaccgat gacaccagca agaatcctcc gatgagggta ccatatctcg  16440
ggtcaaagac acaggagagg agagctgcct cacttgcaaa aatagctcat atgtcgccac  16500
atgtaaaggc tgccctaagg gcatcatccg tgttgatctg ggcttatggg gataatgaag  16560
taaattggac tgctgctctt acgattgcaa aatctcggtg taatgtaaac ttagagtatc  16620
ttcggttact gtccccttta cccacggctg ggaatcttca acatagacta gatgatggta  16680
taactcagat gacattcacc cctgcatctc tctacagggt gtcaccttac attcacatat  16740
ccaatgattc tcaaaggctg ttcactgaag aaggagtcaa agaggggaat gtggtttacc  16800
aacagatcat gctcttgggt ttatctctaa tcgaatcgat ctttccaatg acaacaacca  16860
ggacatatga tgagatcaca ctgcacctac atagtaaatt tagttgctgt atcagagaag  16920
cacctgttgc ggttcctttc gagctacttg ggtggtaccc ggaactgagg acagtgacct  16980
caaataagtt tatgtatgat cctagccctg tatcggaggg agactttgcg agacttgact  17040
tagctatctt caagagttat gagcttaatc tggagtcata tcccacgata gagctaatga  17100
acattctttc aatatccagc gggaagttga ttggccagtc tgtggtttct tatgatgaag  17160
atacctccat aaagaatgac gccataatag tgtatgacaa tacccgaaat tggatcagtg  17220
aagctcagaa ttcagatgtg gtccgcctat ttgaatatgc agcacttgaa gtgctcctcg  17280
actgttctta ccaactctat tacctgagag taagaggcct ggacaatatt gtcttatata  17340
tgggtgattt atacaagaat atgccaggaa ttctactttc caacattgca gctacaatat  17400
ctcatcccgt cattcattca aggttacatg cagtgggcct ggtcaaccat gacggatcac  17460
accaacttgc agatacggat tttatcgaaa tgtctgcaaa actattagta tcttgcaccc  17520
gacgtgtgat ctccggctta tattcaggaa ataagtatga tctgctgttc ccatctgtct  17580
tagatgataa cctgaatgag aagatgcttc agctgatatc ccggttatgc tgtctgtaca  17640
cggtactctt tgctacaaca agagaaatcc cgaaaataag aggcttaact gcagaagaga  17700
aatgttcaat actcactgag tatttactgt cggatgctgt gaaaccatta cttagccccg  17760
atcaagtgag ctctatcatg tctcctaaca taattacatt cccagctaat ctgtactaca  17820
tgtctcggaa gagcctcaat ttgatcaggg aaagggagga cagggatact atcctggcgt  17880
tgttgttccc ccaagagcca ttattagagt tcccttctgt gcaagatatt ggtgctcgag  17940
tgaaagatcc attcacccga caacctgcgg catttttgca agagttagat ttgagtgctc  18000
cagcaaggta tgacgcattc acacttagtc agattcatcc tgaactcaca tctccaaatc  18060
cggaggaaga ctacttagta cgatacttgt tcagagggat agggactgca tcttcctctt  18120
ggtataaggc atctcatctc ctttctgtac ccgaggtaag atgtgcaaga cacgggaact  18180
ccttatactt agctgaaggg agcggagcca tcatgagtct tctcgaactg catgtaccac  18240
atgaaactat ctattacaat acgctctttt caaatgagat gaaccccccg caacgacatt  18300
tcgggccgac cccaactcag tttttgaatt cggttgttta taggaatcta caggcggagg  18360
taacatgcaa agatggattt gtccaagagt tccgtccatt atggagagaa aatacagagg  18420
aaagcgacct gacctcagat aaagtagtgg ggtatattac atctgcagtg ccctacagat  18480
```

ctgtatcatt gctgcattgt gacattgaaa ttcctccagg gtccaatcaa agcttactag 18540
atcaactagc tatcaattta tctctgattg ccatgcattc tgtaagggag ggcggggtag 18600
taatcatcaa agtgttgtat gcaatgggat actactttca tctactcatg aacttgtttg 18660
ctccgtgttc cacaaaagga tatattctct ctaatggtta tgcatgtcga ggagatatgg 18720
agtgttacct ggtatttgtc atgggttacc tgggcgggcc tacatttgta catgaggtgg 18780
tgaggatggc gaaaactctg gtgcagcggc acggtacgct tttgtctaaa tcagatgaga 18840
tcacactgac caggttattc acctcacagc ggcagcgtgt gacagacatc ctatccagtc 18900
ctttaccaag attaataaag tacttgagga agaatattga cactgcgctg attgaagccg 18960
ggggacagcc cgtccgtcca ttctgtgcgg agagtctggt gagcacgcta gcgaacataa 19020
ctcagataac ccagatcatc gctagtcaca ttgacacagt tatccggtct gtgatatata 19080
tggaagctga gggtgatctc gctgacacag tatttctatt taccccttac aatctctcta 19140
ctgacgggaa aaagaggaca tcacttaaac agtgcacgag acagatccta gaggttacaa 19200
tactaggtct tagagtcgaa aatctcaata aaataggcga tataatcagc ctagtgctta 19260
aaggcatgat ctccatggag gaccttatcc cactaaggac atacttgaag catagtacct 19320
gccctaaata tttgaaggct gtcctaggta ttaccaaact caaagaaatg tttacagaca 19380
cttctgtact gtacttgact cgtgctcaac aaaaattcta catgaaaact ataggcaatg 19440
cagtcaaagg atattacagt aactgtgact cttaacgaaa atcacatatt aataggctcc 19500
ttttttggcc aattgtattc ttgttgattt aatcatatta tgttagaaaa aagttgaacc 19560
ctgactcctt aggactcgaa ttcgaactca aataaatgtc ttaaaaaaag gttgcgcaca 19620
attattcttg agtgtagtct cgtcattcac caaatctttg tttggtgcgc gcggccggca 19680
tggtcccagc ctcctcgctg gcgccggctg ggcaacattc cgaggggacc gtcccctcgg 19740
taatggcgaa tgggacgtcg actgctaaca aagcccgaaa ggaagctgag ttggctgctg 19800
ccaccgctga gcaataacta gcataacccc ttggggcctc taaacgggtc ttgaggggtt 19860
ttttgctgaa aggaggaact atatgcgcgc agatctgtca tgatgatcat tgcaattgga 19920
tccatatata gggcccgggt tataattacc tcaggtcgac gtcccatggc cattcgaatt 19980
cgtaatcatg gtcatagctg tttcctgtgt gaaattgtta tccgctcaca attccacaca 20040
acatacgagc cggaagcata aagtgtaaag cctggggtgc ctaatgagtg agctaactca 20100
cattaattgc gttgcgctca ctgcccgctt tccagtcggg aaacctgtcg tgccagctgc 20160
attaatgaat cggccaacgc gcggggagag gcggtttgcg tattgggcgc 20210

<210> SEQ ID NO 32
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 32
gcaccgagtt cccccccgcg gttagaaaaa atacgggtag aaccgccacc atgggtcacc 60
agcag 65

<210> SEQ ID NO 33
<211> LENGTH: 37
<212> TYPE: DNA

<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 33
agttggacct tgggtccgcg gattaggaag cattcag 37

<210> SEQ ID NO 34
<211> LENGTH: 65
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 34
gcaccgagtt cccccccgcg gttagaaaaa atacgggtag aaccgccacc atgtacagca 60
tgcag 65

<210> SEQ ID NO 35
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 35
agttggacct tgggtccgcg gattattgag ggcttgt 37

<210> SEQ ID NO 36
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
tcgatcgagg aaatcagg 18

<210> SEQ ID NO 37
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 37
gtacagccca attgtcc 17

<210> SEQ ID NO 38
<211> LENGTH: 306
<212> TYPE: PRT
<213> ORGANISM: Homo sapiens

<400> SEQUENCE: 38

Ile Trp Glu Leu Lys Lys Asp Val Tyr Val Val Glu Leu Asp Trp Tyr
1 5 10 15

```
Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

<210> SEQ ID NO 39
<211> LENGTH: 510
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 39

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
```

-continued

```
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser Gly Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
            340                 345                 350

Tyr Pro Cys Thr Ser Glu Glu Ile Asp His Glu Asp Ile Thr Lys Asp
        355                 360                 365

Lys Thr Ser Thr Val Glu Ala Cys Leu Pro Leu Glu Leu Thr Lys Asn
    370                 375                 380

Glu Ser Cys Leu Asn Ser Arg Glu Thr Ser Phe Ile Thr Asn Gly Ser
385                 390                 395                 400

Cys Leu Ala Ser Arg Lys Thr Ser Phe Met Met Ala Leu Cys Leu Ser
                405                 410                 415

Ser Ile Tyr Glu Asp Ser Lys Met Tyr Gln Val Glu Phe Lys Thr Met
            420                 425                 430

Asn Ala Lys Leu Leu Met Asp Pro Lys Arg Gln Ile Phe Leu Asp Gln
        435                 440                 445

Asn Met Leu Ala Val Ile Asp Glu Leu Met Gln Ala Leu Asn Phe Asn
    450                 455                 460

Ser Glu Thr Val Pro Gln Lys Ser Ser Leu Glu Glu Pro Asp Phe Tyr
465                 470                 475                 480
```

```
Lys Thr Lys Ile Lys Leu Cys Ile Leu Leu His Ala Phe Arg Ile Arg
                485                 490                 495

Ala Val Thr Ile Asp Arg Val Met Ser Tyr Leu Asn Ala Ser
            500                 505                 510


<210> SEQ ID NO 40
<211> LENGTH: 328
<212> TYPE: PRT
<213> ORGANISM: Homo sapiens

<400> SEQUENCE: 40

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325
```

<210> SEQ ID NO 41
<211> LENGTH: 197
<212> TYPE: PRT
<213> ORGANISM: Homo sapiens

<400> SEQUENCE: 41

```
Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
            20                  25                  30

Ala Arg Gln Thr Leu Glu Phe Tyr Pro Cys Thr Ser Glu Glu Ile Asp
        35                  40                  45

His Glu Asp Ile Thr Lys Asp Lys Thr Ser Thr Val Glu Ala Cys Leu
    50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser
        195
```

<210> SEQ ID NO 42
<211> LENGTH: 532
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110
```

-continued

```
Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Gly Gly Ser Arg
                325                 330                 335

Asn Leu Pro Val Ala Thr Pro Asp Pro Gly Met Phe Pro Cys Leu His
            340                 345                 350

His Ser Gln Asn Leu Leu Arg Ala Val Ser Asn Met Leu Gln Lys Ala
        355                 360                 365

Arg Gln Thr Leu Glu Phe Tyr Pro Cys Thr Ser Glu Glu Ile Asp His
    370                 375                 380

Glu Asp Ile Thr Lys Asp Lys Thr Ser Thr Val Glu Ala Cys Leu Pro
385                 390                 395                 400

Leu Glu Leu Thr Lys Asn Glu Ser Cys Leu Asn Ser Arg Glu Thr Ser
                405                 410                 415

Phe Ile Thr Asn Gly Ser Cys Leu Ala Ser Arg Lys Thr Ser Phe Met
            420                 425                 430

Met Ala Leu Cys Leu Ser Ser Ile Tyr Glu Asp Leu Lys Met Tyr Gln
        435                 440                 445

Val Glu Phe Lys Thr Met Asn Ala Lys Leu Leu Met Asp Pro Lys Arg
    450                 455                 460

Gln Ile Phe Leu Asp Gln Asn Met Leu Ala Val Ile Asp Glu Leu Met
465                 470                 475                 480

Gln Ala Leu Asn Phe Asn Ser Glu Thr Val Pro Gln Lys Ser Ser Leu
                485                 490                 495

Glu Glu Pro Asp Phe Tyr Lys Thr Lys Ile Lys Leu Cys Ile Leu Leu
            500                 505                 510

His Ala Phe Arg Ile Arg Ala Val Thr Ile Asp Arg Val Met Ser Tyr
        515                 520                 525

Leu Asn Ala Ser
```

530

<210> SEQ ID NO 43
<211> LENGTH: 510
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Ile Trp Glu Leu Lys Lys Asp Val Tyr Val Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
        35                  40                  45

Ser Gly Lys Thr Leu Thr Ile Gln Val Lys Glu Phe Gly Asp Ala Gly
    50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Trp Ser Glu Trp Ala Ser Val Pro
    290                 295                 300

Cys Ser Gly Gly Gly Gly Gly Gly Ser Arg Asn Leu Pro Val Ala Thr
305                 310                 315                 320

Pro Asp Pro Gly Met Phe Pro Cys Leu His His Ser Gln Asn Leu Leu
                325                 330                 335

Arg Ala Val Ser Asn Met Leu Gln Lys Ala Arg Gln Thr Leu Glu Phe
            340                 345                 350
```

Tyr Pro Cys Thr Ser Glu Glu Ile Asp His Glu Asp Ile Thr Lys Asp
355 360 365

Lys Thr Ser Thr Val Glu Ala Cys Leu Pro Leu Glu Leu Thr Lys Asn
370 375 380

Glu Ser Cys Leu Asn Ser Arg Glu Thr Ser Phe Ile Thr Asn Gly Ser
385 390 395 400

Cys Leu Ala Ser Arg Lys Thr Ser Phe Met Met Ala Leu Cys Leu Ser
405 410 415

Ser Ile Tyr Glu Asp Leu Lys Met Tyr Gln Val Glu Phe Lys Thr Met
420 425 430

Asn Ala Lys Leu Leu Met Asp Pro Lys Arg Gln Ile Phe Leu Asp Gln
435 440 445

Asn Met Leu Ala Val Ile Asp Glu Leu Met Gln Ala Leu Asn Phe Asn
450 455 460

Ser Glu Thr Val Pro Gln Lys Ser Ser Leu Glu Glu Pro Asp Phe Tyr
465 470 475 480

Lys Thr Lys Ile Lys Leu Cys Ile Leu Leu His Ala Phe Arg Ile Arg
485 490 495

Ala Val Thr Ile Asp Arg Val Met Ser Tyr Leu Asn Ala Ser
500 505 510

<210> SEQ ID NO 44
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Arg" or "Asp" or "Cys" or "Glu" or "Gly" or "Gln" or "Ser" or "Tyr" or "Asn" or "His" or "Ile" or "Leu" or "Lys" or "Met" or "Phe" or "Thr" or "Trp" or "Val"
<220> FEATURE:
<221> NAME/KEY: MISC_FEATURE
<222> LOCATION: (1)..(5)
<223> OTHER INFORMATION: /note="Variant residues given in the sequence have no preference with respect to those in the annotations for variant positions"

<400> SEQUENCE: 44

Val Pro Gly Ala Gly
1 5

<210> SEQ ID NO 45
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (4)..(4)
<223> OTHER INFORMATION: /replace="Arg" or "Asp" or "Cys" or "Glu" or "Gly" or "Gln" or "Ser" or "Tyr" or "Asn" or "His" or "Ile" or "Leu" or "Lys" or "Met" or "Phe" or "Thr" or "Trp" or "Val"
<220> FEATURE:
<221> NAME/KEY: VARIANT
<222> LOCATION: (9)..(9)
<223> OTHER INFORMATION: /replace="Arg" or "Asp" or "Cys" or "Glu" or "Gly" or "Gln" or "Ser" or "Tyr" or "Asn" or "His" or "Ile" or "Leu" or "Lys" or "Met" or "Phe" or "Thr" or "Trp" or "Val"

<220> FEATURE:
<221> NAME/KEY: MISC_FEATURE
<222> LOCATION: (1)..(10)
<223> OTHER INFORMATION: /note="Variant residues given in the sequence have no preference with respect to those in the annotations for variant positions"

<400> SEQUENCE: 45

Val Pro Gly Ala Gly Val Pro Gly Ala Gly
1               5                   10

<210> SEQ ID NO 46
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Gly Gly Gly Gly Ser
1               5

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Gly Gly Gly Gly Ser Gly Gly Gly Gly Ser
1               5                   10

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

Gly Gly Gly Gly Ser Gly Gly Gly Gly Ser Gly Gly Gly Gly Ser
1               5                   10                  15

<210> SEQ ID NO 49
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 15186
<212> TYPE: RNA

-continued

<213> ORGANISM: Newcastle disease virus

<400> SEQUENCE: 50
accaaacaaa gauuugguga augacgagac uacacucaag aauaauugug cgcaaccuuu 60
uuuuaagaca uuuauuugag uucgaauucg aguccuaagg agucaggguu caacuuuuuu 120
cuaacauaau augauuaaau caacaagaau acaauuggcc aaaaaaggag ccuauuaaua 180
ugugauuuuc guuaagaguc acaguuacug uaauauccuu ugacugcauu gccuauaguu 240
uucauguaga auuuuuguug agcacgaguc aaguacagua cagaaguguc uguaaacauu 300
ucuuugaguu ugguaauacc uaggacagcc uucaaauauu uagggcaggu acuaugcuuc 360
aaguaugucc uuaguggau aagguccucc auggagauca ugccuuuaag cacuaggcug 420
auuauaucgc cuauuuuauu gagauuuucg acucuaagac cuaguauugu aaccucuagg 480
aucugucucg ugcacuguuu aagugauguc cucuuuuucc cgucaguaga gagauuguaa 540
gggguaaaua gaaauacugu gucagcgaga ucacccucag cuuccauaua uaucacagac 600
cggauaacug ugucaaugug acuagcgaug aucuggguua ucugaguuau guucgcuagc 660
gugcucacca gacucuccgc acagaaugga cggacgggcu guccccggc uucaaucagc 720 gcagugucaa uauucuuccu caaguacuuu auuaaucuug guaaaggacu ggauaggaug 780
ucugucacac gcugccgcug ugaggugaau aaccugguca gugugaucuc aucugauuua 840
gacaaaagcg uaccgugccg cugcaccaga guuuucgcca uccucaccac cucauguaca 900
aauguaggcc cgcccaggua acccaugaca aauaccaggu aacacuccau aucuccucga 960
caugcauaac cauuagagag aauauauccu uuuguggaac acggagcaaa caaguucaug 1020
aguagaugaa aguaguaucc cauugcauac aacacuuuga ugauuacuac cccgcccucc 1080
cuuacagaau gcauggcaau cagagauaaa uugauagcua guugaucuag uaagcuuuga 1140
uuggacccug gaggaauuuc aaugucacaa ugcagcaaug auacagaucu guagggcacu 1200
gcagauguaa uauaccccac uacuuuaucu gaggucaggu cgcuuuccuc uguauuuucu 1260
cuccauaaug gacggaacuc uuggacaaau ccaucuuugc auguuaccuc cgccuguaga 1320
uuccuauaaa caaccgaauu caaaaacuga guuggggucg gcccgaaaug ucguugcggg 1380 gguucaucu cauuugaaaa gagcguauug uaauagauag uuucaugugg uacaugcagu 1440
ucgagaagac ucaugauggc uccgcucccu ucagcuaagu auaaggaguu cccgugucuu 1500
gcacaucuua ccucggguac agaaaggaga ugagaugccu uauaccaaga ggaagaugca 1560
gucccuaucc cucugaacaa guaucguacu aaguagucuu ccuccggauu uggagaugug 1620
aguucaggau gaaucugacu aagugugaau gcgucauacc uugcuggagc acucaaaucu 1680
aacucuugca aaaaugccgc agguugucgg gugaauggau cuuucacucg agcaccaaua 1740
ucuugcacag aagggaacuc uaauaauggc ucuuggggga acaacaacgc caggauagua 1800
ucccuguccu cccuuucccu gaucaaauug aggcucuucc gagacaugua guacagauua 1860
gcugggaaug uaauuauguu aggagacaug auagagcuca cuugaucggg gcuaaguaau 1920
gguuucacag cauccgacag uaaauacuca gugaguauug aacauuucuc uucugcaguu 1980
aagccucuua uuuucgggau uucucuuguu guagcaaaga guaccgugua cagacagcau 2040
aaccgggaua ucagcugaag caucuucuca uucagguuau caucuaagac agaugggaac 2100
agcagaucau acuuauuucc ugaauauaag ccggagauca cacgucgggu gcaagauacu 2160
aauaguuuug cagacauuuc gauaaaaucc guaucugcaa guugguguga uccgucaugg 2220
uugaccaggc ccacugcaug uaaccuugaa ugaaugacgg gaugagauau uguagcugca 2280

-continued auguuggaaa guagaauucc uggcauauuc uuguauaaau cacccauaua uaagacaaua 2340
uuguccaggc cucuuacucu cagguaauag aguugguaag aacagucgag gagcacuuca 2400
agugcugcau auucaaauag gcggaccaca ucugaauucu gagcuucacu gauccaauuu 2460
cggguauugu cauacacuau uauggcguca uucuuuaugg agguaucuuc aucauaagaa 2520
accacagacu ggccaaucaa cuucccgcug gauauugaaa gaauguucau uagcucuauc 2580
gugggauaug acuccagauu aagcucauaa cucuugaaga uagcuaaguc aagucucgca 2640
aagucucccu ccgauacagg gcuaggauca uacauaaacu uauuugaggu cacuguccuc 2700
aguuccggua ccaccccaag uagcucgaaa ggaaccgcaa caggugcuuc ucugauacag 2760
caacuaaauu uacuauguag gugcagugug aucucaucau auguccuggu uguugucauu 2820
ggaaagaucg auucgauuag agauaaaccc aagagcauga ucuguuggua aaccacauuc 2880
cccucuuuga cuccuucuuc agugaacagc cuuugagaau cauuggauau gugaauguaa 2940
ggugacaccc uguagagaga ugcaggggug aaugucaucu gaguuauacc aucaucuagu 3000
cuauguugaa gauucccagc cgugggu aaa ggggacagua accgaagaua cucuaaguuu 3060
acauuacacc gagauuuugc aaucguaaga gcagcagucc aauuuacuuc auuaucccca 3120
uaagcccaga ucaacacgga ugaugcccuu agggcagccu uuacaugugg cgacauauga 3180
gcuauuuuug caagugaggc agcucuccuc uccugugucu uugacccgag auaugguacc 3240
cucaucggag gauucuugcu ggugucaucg gucaauucua uauugcuugg aagauggaac 3300
caaguaaauu guucaucucc gcugucacau cuuguacacc cuccgcuuac acuaagaauc 3360
ucacccucua cgaguucuau cguaucagga uuagauacac ccaguauuuu ccugccuccc 3420
gucaaaggug accagcuucu auuccgugca uagucugcca gugucagaga acacauauua 3480
gaagagacua aggggugguu ggaucuacug gaggaaaaaa caucgucucu aaacagcauu 3540
gcaugcaugc uagaauaauu gacuauccgc aucagccucu ugaugccuaa uggccuccua 3600
guaagcgcaa ucuuaauuac gguguuuguu gugucaacaa gcccuugaau uugcuuucuc 3660
cuaccuacag agcuugccuc caugauggca ugcgcaacgc ggggaugaau caccucuuga 3720
uuaagcaaga auucagccaa ugccuucucu ucugccucau uauccucugu gugcacucca 3780
gacaauaagg gauuugaaca aguuucaaau aggacucuuu gcguauguuu cuuaagaaca 3840
auauuugggc uugcaacagu cucaaaauug aaagaguaug ggucguugca cagacuggcc 3900
caaucuccau ucccaggcgg ccuaguuaag auauuaguca uaauguuagg acucaguaau 3960
cccacugcuu cuagucgcuu gaucucugca aaagcaguag uccccggguc accgauauuu 4020
cuaguguaga gccuugagua uugaagguua cucagucccc cuaauugggc aggagucaga 4080
acauaugagu gcacaaaaga gauguccuca auccacgacu gauuaagauc ggggugcgaa 4140
uuguuggug a uggagaacuc agagucaaag uaugucugca cacaacucau uauauaguuu 4200
aaauaguaac agaagucuuu gggaagcccg uucucgcaua gccgugcuac aguagaggca 4260
auguuggcac aggacauuac gguguuuuca cugagaucac cugacacuag cacuaauuua 4320
gaugaauuuu ugaggacuug acugaggauu gcuccaucuu ugaagauucg uuugcuguau 4380
augaagaaug ugucugaccu gaugguuuca cgauccuuca aauuauggcc aaucaaauga 4440
uugacaugaa uuaauuccuu gaagaaauua ucacuggcuu gaugcaacug ugucaacacc 4500
aucuccggag agucgucuga ucuuaccucu cucguuacug cuauuacuug auuaucaccc 4560
uguaccauac aggcaacacg acaaugcgau cuagcugcag caaguuggau ugcagcaauu 4620

-continued gagaucauug uccauagcuu cuggcauaau ccuucgauac ccccucuggc acugacaaua 4680
uauaugucau cauuagggac ucuugagagg ucacagucag uagggucacu uggaggauug 4740
aaagggucuc cuacgaacau cguagugucc aucagucuua ggugaaucca uucgaagaag 4800
ugagguaggc ccaucaacug auugauggca ugagcgaaca auuugauugu cugauaucuc 4860
caauuaagac aguacuuuug caggucaguu guuaugaagg uugcaacucu ccgacgguuc 4920
uugcuuuucg gaucaugauu gcgguuugaa gauacucuuu cuuuacaguc agugauacgu 4980
uucuuauugc uguuaaaaga caguugacuc aucgcuagca uacucuuggu caaggauaug 5040
cuauccugaa ugacuccauu ucccugaaag aaaggugcaa ucugaucggc uaggaucccu 5100
uccgccauca ccugacaguu ccuuaacuuc uuugucagcu uagcgaagau ccguccauua 5160
acuuucacuu ccuucuccuu gagcgaguau gauacugcca cauugucauc ucuaagguac 5220
ucaagggucg ucagauauuc caucucuuua uauggaucaa aaucauuuga cucuaaaaac 5280
ucuaucaaga ggcgauuagu cgaaguugcu ucuuuuacau guuucuucug gucuucggag 5340
agaagguucc gccuaaacga ggcaagccaa uuaucguugg ggugugcgau ugccuugucu 5400
uuuaggaaca ugcucagguu ggugacaggg ucauauucua uacauggcuc aaauucaagu 5460
gcagauaaac ucuuauacuc ucucaacaug auaucgugug aaaucucugc ugaaucugca 5520
uguaguugcc caaugaccuu cccauauauu guauccacuu ugacucgcgg ccacacaccu 5580
gcauucuucu uucuguaccc guugaugauu guucccuuga agaaagacag uaccugaagg 5640
aucauaucaa agucuaccau uuucggugcg cacauuuggc uccugacugc cuuugcugca 5700
auacgggacu caagcagugg gugaccccac agacgcaaca gacacaacau cucagcugcu 5760
ugauucuguu cuaaaccaga gaauacagua gcgauugcau gagucacgga uucugcuaua 5820
ucauugggga ggaggccaau uagaaugucu uuaagcuccu gcagguugaa ugcgaagaaa 5880
ucuccugcaa auguaccuga cggcucgagu agcuggacag cuccguaugc aaaucccucc 5940
auuagugaua caacaucgua gacuugauua cccaagucuu uugccagagc gucuauuaac 6000
cgcaaaaugu caucaauuuu cucugauaag cuucugagau gcaccgccgu gguugauauu 6060
auguugacca uaucucugcc cuccaucaua ucugcauaca ucaauacaag uuccugggua 6120
agacauguga acuuguucuc auucguaugc gucacaacga caaguucagg agugacaaag 6180
acuuggccua ccuuaugggu uagcaucacc aauuuguugg ccgcagaccu uguccuagcu 6240
gccaccauca gaugccucug gaucuguuuu auauggagcc augcaaacuu ggcuguggac 6300
cauuuugagu gaaaccagaa ugccggaucc guacgaaugc ugcugaacuc cucugaccgg 6360
gggacauugu uagaccaaga ugaccccagc aguuucuucu cuauaugcgu acacagccuu 6420
gugaacaguu cuccauaucu cguguuguga auuuggaucu ucuucucaau cuuccgaaau 6480
uuguugguug aaucugggac cucaauauua gccaguucuu cuaaacaccu ggggguggagc 6540
acuccgguua uucuggaauu gugguuaaga guuuggugua cugcccuucc gaguuuuauc 6600
auucucucag uaucaggaga ggccgauuca aguauuuuuu uccauugucg gcugagaaug 6660
agguggucga agucacauuc aucaggaagc gguagcccag uuaauuucca guaauagagu 6720
aguuugugcu ugaccaaugg ugaagacagg ugugacucug guaggauaau cugaugcucu 6780
gcccuuucag gaccggagcu cgccaugucc uacccguauu guuaaccaug agcuguuuug 6840
ccuuguaucu cauugccacu uacauuuuuu cuuaaucaag agacuauuga caaggcuuaa 6900
ucugaucgca ugagcacugg cugauugugg ucaacuggca acauggaauu cgagcacgcg 6960
ccggcauucg guuugauucu ugaugucgca gaagauaggu gauacaaugc caucuuucca 7020

-continued

```
acuccuuuau aauugacuca acuagccaga ccuggcuucu cuaaccccgu caucuuugag   7080
gaucucaacu aguaacggga cgauucugaa uucuccgaag agaguauuag auauuucagc   7140
aaugcugaga caauaggucu uauuagucuu gaccacuuua aaacaaguug auguugugua   7200
ugcugcuuug guacugcuug aacucacucg aguaaugcga cugcgggaug ugcuaucgaa   7260
uacugcagac gcaggguuaa gucuugcuug uacaccauca agcauugucc cgaauacccc   7320
ucgcaaggug ugguuucuau agaagauuag gggauaugga ucuguauaga cuccaguaac   7380
acacgaguug gggcaucuug cugaagccug gcaagggaua cuaccuggcc gagugaaggc   7440
auugaaugua uaaggacuau gaagaguggc uguuuuguug cugacuguca uaggauauaa   7500
uaacgcggga gagaaguaug augacccucg uugauacaag aaaugagaug ucccuacugu   7560
gagaauucug ccuucggccc ccaugagugu gacuguguug ggcgguacag ucaguaccgg   7620
gucuucgccu aaggauguug acaccuugau agauaagaua gccugcugua ugcguuuccc   7680
accaaaccgu ccaggcuuau acgaagacuu ggccauucga aucugguagu cuugcucauc   7740
ugggcaugug ucauuguauc gcuuguauau cacauauuuc ccuuccugua cagugucacu   7800
gggugaauug gguuuuaacc cuccguagac ugagaaccau acgcggcugu caauaaaaga   7860
uccacccccu acuccugggu aguuggccac ccaguccccg aauaauguug ugacaucuag   7920
guccuuuucg ugguacuggc cgucgaaccc uaaccuccca uguaccaucc gcguagggac   7980
agcugaguua uaaucuucuu ccucugucuc cgugacuuuc gagcacagca uaucacaacc   8040
caggggaguu gcacucacac ugcaagacuu ccgauuuugg gugucgucca gguugaugga   8100
acgcagagua gaaaagaaua cccucccugu ugcagauguc cggagcacac caagugcuaa   8160
auacugauau gaaugugagu gaucucugca uccagacaau auuacauuau ggguguagca   8220
guaaugggua gcacucaugu caaaugaggg uauucgagug caaccugauc cuguaguagg   8280
cgccgggaua aaauucagau guucuugaaa ugcagaggga uagaaugaug ugacaucacu   8340
agcaucaucu acaaugaguu cuuugccuau ccccccuaua uaaucugggu cauggauagg   8400
ugccccccac ccacuguugu uugcagcucc auuaaucuga uaagagagag auguuauugc   8460
guucauaauu guggucucag uauuuaacaa ugccaacgga gacucaaggg ccacuugcuu   8520
auauauccua ucuacuacau cuugauugga accaagugua gauguaaucu uuucuucugc   8580
ccuggaaauc cuagucggua ugccuacaag aucgcuaggu gugcuagccc ccaugcuaua   8640
uaaaagggag gcuacagaua uagccaaggu cacuacuguu aagaauaaga uugcaauccg   8700
gaauaucaag cgccauguau uuuuugccuc ucuuucauca uucucuaacg caacuuggcu   8760
aacggcgcgg uccaugauug aggacuguug ucggugaagc gguagaacgg agguugugaa   8820
gccuggcucg caauugaggg gcggccucuc uuaccguucu acccguauau cguccuuugg   8880
ucaucuacaa ccgguaguuu uuucuuaacu cucugaacug acagacuacc agaacuuuca   8940
cacaaauuac uauuagggaa accuucguuc cucaucugug uucacauuuu uguaguggcu   9000
cucaucugau cuagaguauu auucccaagc cauaauaagg ucuuuuguug cgccuuuugc   9060
uuguacauua gguagcaugc uagaaucagg cuaaguauac caaaaacaag agauaugaua   9120
gucaaaacga uauagguaau gagagcagau gugcuaguca guuugacauu gacuuugucu   9180
aguuucugu ugcuuuccuc uaacuuauuc aaagcauuac ugaucgaguu guugacauuc   9240
ccaagcucag uugagauauc aagauugccu guuauuauua cuugagaauc uuguauugag   9300
auauucuucu gauaaguuac aucgaauucc ccacugagcc uuaaaguuau cccgccuaag   9360
```

-continued gauaaaacau ugcaugauug uuuaucuauu agagacacgg cuucuccaua guuuugcgau 9420
augauacccg gggguuuac acaucuacau guugucaucu ugcaguuggc gaugacugaa 9480
ccuuugauag ucauguaugg uguaguaagu gcgccuucgg ucuuugagua cauacaggcc 9540
gacguauugc cgcucaagca ggaauaaaua ccaggggaca uagggaacgu uacuauucuu 9600
guacaauaua aaucuaaguc aguuucuaua caguaugagg ugucaaguuc uucuaucaca 9660
gaaccgaccu gugucaccac uuuugggaca agugccgagg caaauccccu gguugugcuu 9720
acggauaagg uuuccaagua gguggcacgc auauuauuua gguucccgac ugaaggugca 9780
guuaccugua uacccaagag uugagucugu gagucguaua gaauaggguu accggugauu 9840
aagccgcuac cgauuaauga gcugaguuga uuguucccua caccuaacuu agucaauaag 9900
uaauccauau uuccaccagc uagauuguaa agugccugaa uagucagcuu guuuaaagca 9960
ggugaaguga uuuguggucc gaauacugua gucaauucgg uuagguacag guugagcucu 10020
acaccaacuu gcugugcaau uuugaugcag ucuaauuccu gagcuguuuu auuaaauugg 10080
ucauuaacaa acugcugcau cuucccaacu gccacugcua guugcgauaa uccgucagug 10140
accucaugca cagccucauu gguugcggca augcucucuu uaagucggag gauguuggca 10200
gcauuuuguu uggcuuguau cagagcugcg gccgcuguua uuugugcggc aguugcaacc 10260
ccaagagcca caccgccaau aauggcgccu auaaggcgcc ccugucuccc cccuccagau 10320
guagucacag acucuuguau ccuacggaua gagucaccaa gggggggugag caaagugguc 10380 aauguccugu uguaugcauc caagggggcu uucgcacaug ccuccuuauc cuugggcaga 10440
uucgggagga gcuuaacuau gauugauccu gucugggaug agguguauau guugacggcu 10500
uugucuccug uaaccacaau uccugcagcu gcaagaggcc ugccaucaau ggaguuugcc 10560
ggacagaugc aacucaguac cagcgcaacc cggauaguca gcaucauagg ugcuggguuc 10620
uugguagaag gucuggagcc caucuugcac cuggagggcg ccaaccggga uccagaaucu 10680
ucuacccgug uuuuuucuaa cuugauagac agguaaacua acuguaaaua aucaagacag 10740
auuaguuuuu ugugucauga ugaucugggu gagugggcgg agcgcaaucu cagagacgca 10800
gcuuauuucu uaaaaggauu guauuuggca agggugugcc ccuucuccag cuuaguagag 10860
guaaccucgu ggucggcggu cacugcgaca gcgcguuggg uaccugcuug gauaaugauu 10920
uuaacgcucc gcaggcacgc gguuugacuc cagaguaucu uggccaccug aggagaagca 10980
uuugcuaugg gauagcaggc ugucccacug cuagagaaga aaggugccaa aagcuuaguc 11040
cgugcaccuc uugcuuuuac caacacggaa ggcccgagca caucacugag cccgacagau 11100
agaucaaggc uccuuauuuu cuuuuccagc uugucaaaug ucacuuucuu ccccuuccua 11160
ucuacagugg ucauaagucc aauaugcaag aagagguuag cauaguaucc gcugucagac 11220
uuagacagag auuuaaccaa aggacuccuc gggucuaccu ccacauuaau agugacauug 11280
agcgcaagau uguacagacu cgagccagaa accuucaaua cugcagcugg gaucuuguag 11340
acaucccucu ucgguaccac agucaaggag acaaaguuca ccuuguauuc uaggguucca 11400
cucccgggaa ucuucucugg cgcuuucacg ugcuugacug cauucacuga ugaguauuug 11460
uuugccacaa cccuacagcu uugcagcacu uggggugccu gcacuacuga gaaaaccauu 11520
cucucaguau uaguugcacu cuucuugcau gugacuauca uagugagaca ggcccuugcc 11580
agcucaauaa ggucuccggu auuugggacg cuuccuaggc agagcaucgc agcggaaagu 11640
aacucgcgcu uggguuuauc aucgaucaug ccgacggugg cuucuucauu cccaacuuga 11700
aagaugaauc cauagguggu gaugaauacu gaguccuccu uacuaucagu ccacaaguca 11760

```
aggcgcugga uccuauauug cggggcgauu ugcuucuucc caucuccugu gucuuguagg  11820
acgaucggaa augcuaacag guugcuagaa gaaugggcag aaucaaagua cagcccaauu  11880
guccuagaug aguccaucuu ggcacaauug gggcacucca auucuacccg uauuuuuucu  11940
uaaucuuaaa uguagcuaga uuaauuacgg uuacgcgauc auucaguggg gcugaggaag  12000
cgagagagga uugccgcuug gagaguugga ccuugggucc gcgggggga acucggugca  12060
gauuccgugu gaugccgagu ggacagggac ccgcuacgug uggcaguagu aauuagccau  12120
uuagagcaag gcgcuugauu uuccugauuu ccucgaucga cccggcugca ucuaacuugc  12180
uuaggagcuu ggcugaagaa cucgggugca uugggcguga caugaucaau gcacggacag  12240
uguccuuuuc cacuccuaua ucaggcccgc augcaguggc ggguuuaauc aauucagaug  12300
gauguggcac ugguugcgaa aguuuauuaa gugccauuuc gccuccuugu gucacauagg  12360
gagaggggguc uccagggccu gaaacuaaaa ccgggugaga ucgggcaacu gcccguagau  12420
cacucagaga ugaaauguug gcacaaccgg gauccagaau cuucaucauu cccaaguugg  12480
cuuccaugac ugcaacagau guuuucagcu guuggauuuc ggaccgcauc auagggaugg  12540
aggaugucug uuucaagaca agaucuagcu gauagucaac cuuacuuacu cucugugaua  12600
ucgccuccau cauagacauc aucgcuugca caaagucuac agguggcugg acaugauccg  12660
cagauacaag gguauugucu uggcucugcc uugaucggag agcaugaggg guugcaccag  12720
cugauaguug ugacuccucc cauuguccau gauaugcugu guucacgucu gugcccuggu  12780
uuccaggggc ggccuugacu ugguucugcg gucuuuccug acuguuuccg cgacuggguu  12840
gacuccccug cuguugaguc ggacguuggu gauuccccuc uugggggcuc gaccaugggc  12900
ccuuuuuagc auuggacgau uuauugcuga gcuugucaag caucaacagc agagaguugc  12960
uugcuccggu ccugagcugu gugucgacgg cuucgucugu ggccugggug gggggcuggu  13020
cggcggaugu ggccggcggg cugucaugcg gggucguuug cucgggugug gaugguuguu  13080
ugucagaucu guccugucga ucgggguugu cuugacuggc cgguggcugg augcucccau  13140
gcuucuccca ugcugcgcuc agcaccuugg ucuugccuug ugggauugca cuccuuccaa  13200
cagucucugc ugguuuaccc ugggcuguaa uuauguuguc aaugacaguu ccacuugucu  13260
caaauagcuc gucgaucucu gcaucuguaa agguggccau guuuguccug gucuaucagg  13320
uagaggagag agcagagacu cgggagacuu gcccugaucu cugaauaucc cucuucuacc  13380
cguacuuuuu ucuaauuccc ucggcucugu uuugauuguu agugagccgc auugugccug  13440
ugguaucuag ggcguacgua guuguacagc agggggaggg aggaaagagg gggauguuug  13500
uuugagggug uggucauaua gagccgcaaa ucgaggggguc gacuacgggu gagggcauug  13560
ggauguuuuu guggaagcag gcuggguuuu guccaucaau acccccaguc ggugucguua  13620
ucuugggaug gcccaggagu ugggggaggc cccgauuggg gagugcccug ugcagaguuu  13680
ggcgccuccc ucaugcuauu ugcuaccgcu cucaucagau ccaggaauug ggucuccccca  13740
uccccggcuu cugguugccc uugcgaucua uucgauccgc cuuguagagc uugggacccc  13800
cccucgcuaa gcccagugag gacuccgacu uguugaguag gcaugucuau gcugcugguc  13860
uccucggaga cccguugggc agcagcugcc aggccccucc uugcugcugg gguuagcuuu  13920
agcucggcag ccauauccuc guuaaugcua cuucccugag ccugagcgua cucuacucca  13980
agucuccaga augaugugcu cauaaagucc cuggcaaauu gguauuuccc aguaccuuua  14040
ucuaggacug augccauacc cauggcaaag gaguaaaguu gugcauacuc ggcaggcgca  14100
```

-continued aagcucaucu ggucacuauc accaaguaau gucauguacg gcgcauuauc uccuuucauc 14160
cgauacaaac gcaugagcug cuucaucuuc uggaugucgc cugagaggcu acuaagugca 14220
agggcugaug ucuuggugu u gauuccguac uugaguguca agaagaaugc aguaagcccg 14280
guauuccuga uguaugaguc uacguccccu accagguuau aauaaguaga gguaccaccu 14340
gccguguugc ggccucucuu gagcucgcua accaaaaaga ugcggacugc aagagacugu 14400
cugaucguga guuggauugu gcuccugcau acgggguaga ggauguauuu cuuuuggacc 14460
cugccuugcu gcauauacuu auugauucgc cuuguuuccg acucaucugc agucucauac 14520
gcagucaugg cuuuugcuac ugugacccau acuugagccu ggauagagag gauccucucc 14580
aggguaucgg ugaugucuuc uggugcauca ucuucggccc cggcugugac gaacgggguu 14640
ccguugcugc augcccgagg gagagauccu gcuaucaucg caaaucucug ugcucucucu 14700
ucagacacuc cacuccuauu guugaacugg ggcgugccgu uggcaaagcc aucaaucuca 14760
agcacggcca auguggcuuc auucuguuuc ccugcaaggg caacaugguu ccucauuacc 14820
ugugaguggg agcauaaaag agauaugaga gcaccuugcc ugagugguuu guuggcaucu 14880
ucgcuaacag caauccggag gcagaauacc acaaagcucc aucuaucuuc ugggucauca 14940
cuguuaagag ugaauaccgg gacgucuacu uuuaagguac ucccuuuuuc ucccccucca 15000
ugagcuccau uggggcgagu cugagccgcg aggagcuguu cguacucauc aaauacggaa 15060
gacauguugg cagaaggcuu ucucgaguuu gugcuucggg cucgcacucg agauucacac 15120
cuucuacccg ugcgacuuca auugcuccuu cgccuuuuau cguaacucac ggauucucug 15180
uuuggu 15186

<210> SEQ ID NO 51
<211> LENGTH: 16824
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 51
accaaacaaa gauuugguga augacgagac uacacucaag aauaauugug cgcaaccuuu 60
uuuuaagaca uuuauuugag uucgaauucg aguccuaagg agucaggguu caacuuuuuu 120
cuaacauaau augauuaaau caacaagaau acaauuggcc aaaaaaggag ccuauuaaua 180
ugugauuuuc guuaagaguc acaguuacug uaauauccuu ugacugcauu gccuauaguu 240
uucauguaga auuuuuguug agcacgaguc aaguacagua cagaaguguc uguaaacauu 300
ucuuugaguu ugguaauacc uaggacagcc uucaaauauu uagggcaggu acuaugcuuc 360
aaguaugucc uuagugggau aagguccucc auggagauca ugccuuuaag cacuaggcug 420
auuauaucgc cuauuuuauu gagauuuucg acucuaagac cuaguauugu aaccucuagg 480
aucugucucg ugcacuguuu aagugauguc cuuuuuuucc cgucaguaga gagauuguaa 540
gggguaaaua gaaauacugu gucagcgaga ucacccucag cuuccauaua uaucacagac 600
cggauaacug ugucaaugug acuagcgaug aucuggguua ucugaguuau guucgcuagc 660
gugcucacca gacucuccgc acagaaugga cggacgggcu guccccggc uucaaucagc 720 gcagugucaa uauucuuccu caaguacuuu auuaaucuug guaaaggacu ggauaggaug 780
ucugucacac gcugccgcug ugaggugaau aaccugguca gugugaucuc aucugauuua 840
gacaaaagcg uaccgugccg cugcaccaga guuuucgcca uccucaccac cucauguaca 900

-continued

```
aauguaggcc cgcccaggua acccaugaca aauaccaggu aacacuccau aucuccucga    960
caugcauaac cauuagagag aauauauccu uuuguggaac acggagcaaa caaguucaug   1020
aguagaugaa aguaguaucc cauugcauac aacacuuuga ugauuacuac cccgcccucc   1080
cuuacagaau gcauggcaau cagagauaaa uugauagcua guugaucuag uaagcuuuga   1140
uuggacccug gaggaauuuc aaugucacaa ugcagcaaug auacagaucu guagggcacu   1200
gcagauguaa uauaccccac uacuuuaucu gaggucaggu cgcuuuccuc uguauuuucu   1260
cuccauaaug gacggaacuc uuggacaaau ccaucuuugc auguuaccuc cgccuguaga   1320
uuccuauaaa caaccgaauu caaaaacuga guuggggucg gcccgaaaug ucguugcggg   1380
gguucaucu cauuugaaaa gagcguauug uaauagauag uuucaugugg uacaugcagu   1440
ucgagaagac ucaugauggc uccgcucccu ucagcuaagu auaaggaguu cccgugucuu   1500
gcacaucuua ccucggguac agaaaggaga ugagaugccu uauaccaaga ggaagaugca   1560
gucccuaucc cucugaacaa guaucguacu aaguagucuu ccuccggauu uggagaugug   1620
aguucaggau gaaucugacu aagugugaau gcgucauacc uugcuggagc acucaaaucu   1680
aacucuugca aaaaugccgc agguugucgg gugaauggau cuuucacucg agcaccaaua   1740
ucuugcacag aagggaacuc uaauaauggc ucuuggggga acaacaacgc caggauagua   1800
ucccuguccu cccuuucccu gaucaaauug aggcucuucc gagacaugua guacagauua   1860
gcugggaaug uaauuauguu aggagacaug auagagcuca cuugaucggg gcuaaguaau   1920
gguuucacag cauccgacag uaaauacuca gugaguauug aacauuucuc uucugcaguu   1980
aagccucuua uuuucgggau uucucuuguu guagcaaaga guaccgugua cagacagcau   2040
aaccgggaua ucagcugaag caucuucuca uucagguuau caucuaagac agaugggaac   2100
agcagaucau acuuauuucc ugaauauaag ccggagauca cacgucgggu gcaagauacu   2160
aauaguuuug cagacauuuc gauaaaaucc guaucugcaa guugguguga uccgucaugg   2220
uugaccaggc ccacugcaug uaaccuugaa ugaaugacgg gaugagauau uguagcugca   2280
auguuggaaa guagaauucc uggcauauuc uuguauaaau cacccauaua uaagacaaua   2340
uuguccaggc cucuuacucu cagguaauag aguugguaag aacagucgag gagcacuuca   2400
agugcugcau auucaaauag gcggaccaca ucugaauucu gagcuucacu gauccaauuu   2460
cggguauugu cauacacuau uauggcguca uucuuuaugg agguaucuuc aucauaagaa   2520
accacagacu ggccaaucaa cuucccgcug gauauugaaa gaauguucau uagcucuauc   2580
gugggauaug acuccagauu aagcucauaa cucuugaaga uagcuaaguc aagucucgca   2640
aagucucccu ccgauacagg gcuaggauca uacauaaacu uauuugaggu cacuguccuc   2700
aguuccggua ccaccccaag uagcucgaaa ggaaccgcaa caggugcuuc ucugauacag   2760
caacuaaauu uacuauguag gugcagugug aucucaucau auguccuggu uguugucauu   2820
ggaaagaucg auucgauuag agauaaaccc aagagcauga ucuguuggua aaccacauuc   2880
cccucuuuga cuccuucuuc agugaacagc cuuugagaau cauuggauau gugaauguaa   2940
ggugacaccc uguagagaga ugcaggggug aaugucaucu gaguuauacc aucaucuagu   3000
cuauguugaa gauucccagc cguggguaaa ggggacagua accgaagaua cucuaaguuu   3060
acauuacacc gagauuuugc aaucguaaga gcagcagucc aauuuacuuc auuaucccca   3120
uaagcccaga ucaacacgga ugaugcccuu agggcagccu uuacaugugg cgacauauga   3180
gcuauuuuug caagugaggc agcucuccuc uccugugucu uugacccgag auaugguacc   3240
```

-continued cucaucggag gauucuugcu ggugucaucg gucaauucua uauugcuugg aagauggaac 3300
caaguaaauu guucaucucc gcugucacau cuuguacacc cuccgcuuac acuaagaauc 3360
ucacccucua cgaguucuau cguaucagga uuagauacac ccaguauuuu ccugccuccc 3420
gucaaaggug accagcuucu auuccgugca uagucugcca gugucagaga acacauauua 3480
gaagagacua aggggugguu ggaucuacug gaggaaaaaa caucgucucu aaacagcauu 3540
gcaugcaugc uagaauaauu gacuauccgc aucagccucu ugaugccuaa uggccuccua 3600
guaagcgcaa ucuuaauuac gguguuuguu gugucaacaa gcccuugaau uugcuuucuc 3660
cuaccuacag agcuugccuc caugauggca ugcgcaacgc ggggaugaau caccucuuga 3720
uuaagcaaga auucagccaa ugccuucucu ucugccucau uauccucugu gugcacucca 3780
gacaauaagg gauuugaaca aguuucaaau aggacucuuu gcguauguuu cuuaagaaca 3840
auauuugggc uugcaacagu cucaaaauug aaagaguaug ggucguugca cagacuggcc 3900
caaucuccau ucccaggcgg ccuaguuaag auauuaguca uaauguuagg acucaguaau 3960
cccacugcuu cuagucgcuu gaucucugca aaagcaguag uccccggguc accgauauuu 4020
cuaguguaga gccuugagua uugaagguua cucagucccc cuaauugggc aggagucaga 4080
acauaugagu gcacaaaaga gauguccuca auccacgacu gauuaagauc ggggugcgaa 4140
uuguugguga uggagaacuc agagucaaag uaugucugca cacaacucau uauauaguuu 4200
aaauaguaac agaagucuuu gggaagcccg uucucgcaua gccgugcuac aguagaggca 4260
auguuggcac aggacauuac ggguguuuca cugagaucac cugacacuag cacuaauuua 4320
gaugaauuuu ugaggacuug acugaggauu gcuccaucuu ugaagauucg uuugcuguau 4380
augaagaaug ugucugaccu gaugguuuca cgauccuuca aauuauggcc aaucaaauga 4440
uugacaugaa uuaauuccuu gaagaaauua ucacuggcuu gaugcaacug ugucaacacc 4500
aucuccggag agucgucuga ucuuaccucu cucguuacug cuauuacuug auuaucaccc 4560
uguaccauac aggcaacacg acaaugcgau cuagcugcag caaguuggau ugcagcaauu 4620
gagaucauug uccauagcuu cuggcauaau ccuucgauac cccucuggc acugacaaua 4680
uauaugucau cauuagggac ucuugagagg ucacagucag uagggucacu uggaggauug 4740
aaagggucuc cuacgaacau cguagugucc aucagucuua ggugaaucca uucgaagaag 4800
ugagguaggc ccaucaacug auugauggca ugagcgaaca auuugauugu cugauaucuc 4860
caauuaagac aguacuuuug caggucaguu guuaugaagg uugcaacucu ccgacgguuc 4920
uugcuuuucg gaucaugauu gcgguuugaa gauacucuuu cuuuacaguc agugauacgu 4980
uucuuauugc uguuaaaaga caguugacuc aucgcuagca uacucuuggu caaggauaug 5040
cuauccugaa ugacuccauu ucccugaaag aaaggugcaa ucugaucggc uaggaucccu 5100
uccgccauca ccugacaguu ccuuaacuuc uuugucagcu uagcgaagau ccguccauua 5160
acuuucacuu ccuucuccuu gagcgaguau gauacugcca cauugucauc ucuaagguac 5220
ucaagggucg ucagauauuc caucucuuua uauggaucaa aaucauuuga cucuaaaaac 5280
ucuaucaaga ggcgauuagu cgaaguugcu ucuuuuacau guuucuucug gucuucggag 5340
agaagguucc gccuaaacga ggcaagccaa uuaucguugg ggugugcgau ugccuugucu 5400
uuuaggaaca ugcucagguu ggugacaggg ucauauucua uacauggcuc aaauucaagu 5460
gcagauaaac ucuuauacuc ucucaacaug auaucgugug aaaucucugc ugaaucugca 5520
uguaguugcc caaugaccuu cccauauauu guauccacuu ugacucgcgg ccacacaccu 5580
gcauucuucu uucuguaccc guugaugauu guucccuuga agaaagacag uaccugaagg 5640

-continued aucauaucaa agucuaccau uuucggugcg cacauuuggc uccugacugc cuuugcugca 5700
auacgggacu caagcagugg gugaccccac agacgcaaca gacacaacau cucagcugcu 5760
ugauucuguu cuaaaccaga gaauacagua gcgauugcau gagucacgga uucugcuaua 5820
ucauugggga ggaggccaau uagaaugucu uuaagcuccu gcagguugaa ugcgaagaaa 5880
ucuccugcaa auguaccuga cggcucgagu agcuggacag cuccguaugc aaaucccucc 5940
auuagugaua caacaucgua gacuugauua cccaagucuu uugccagagc gucuauuaac 6000
cgcaaaaugu caucaauuuu cucugauaag cuucugagau gcaccgccgu gguugauauu 6060
auguugacca uaucucugcc cuccaucaua ucugcauaca ucaauacaag uuccugggua 6120
agacauguga acuuguucuc auucguaugc gucacaacga caaguucagg agugacaaag 6180
acuuggccua ccuuaugggu uagcaucacc aauuuguugg ccgcagaccu uguccuagcu 6240
gccaccauca gaugccucug gaucuguuuu auauggagcc augcaaacuu ggcuguggac 6300
cauuuugagu gaaaccagaa ugccggaucc guacgaaugc ugcugaacuc cucugaccgg 6360
gggacauugu uagaccaaga ugaccccagc aguuucuucu cuauaugcgu acacagccuu 6420
gugaacaguu cuccauaucu cguguuguga auuuggaucu ucuucucaau cuuccgaaau 6480
uuguugguug aaucugggac cucaauauua gccaguucuu cuaaacaccu gggguggagc 6540
acuccgguua uucuggaauu gugguuaaga guuuggugua cugcccuucc gaguuuuauc 6600
auucucucag uaucaggaga ggccgauuca aguauuuuuu uccauugucg gcugagaaug 6660
agguggucga agucacauuc aucaggaagc gguagcccag uuaauuucca guaauagagu 6720
aguuugugcu ugaccaaugg ugaagacagg ugugacucug guaggauaau cugaugcucu 6780
gcccuuucag gaccggagcu cgccaugucc uacccguauu guuaaccaug agcuguuuug 6840
ccuuguaucu cauugccacu uacauuuuuu cuuaaucaag agacuauuga caaggcuuga 6900
ucugaucgca ugagcacugg cugauugugg ucaacuggca acauggaauu cgagcacgcg 6960
ccggcauucg guuugauucu ugaugucgca gaagauaggu gauacaaugc caucuuucca 7020
acuccuuuau aauugacuca acuagccaga ccuggcuucu cuaaccccgu caucuuugag 7080
gaucucaacu aguaacggga cgauucugaa uucuccgaag agaguauuag auauuucagc 7140
aaugcugaga caauaggucu uauuagucuu gaccacuuua aaacaaguug auguugugua 7200
ugcugcuuug guacugcuug aacucacucg aguaaugcga cugcgggaug ugcuaucgaa 7260
uacugcagac gcaggguuaa gucuugcuug uacaccauca agcauugucc cgaauacccc 7320
ucgcaaggug ugguuucuau agaagauuag gggauaugga ucuguauaga cuccaguaac 7380
acacgaguug gggcaucuug cugaagccug gcaagggaua cuaccuggcc gagugaaggc 7440
auugaaugua uaaggacuau gaagaguggc uguuuuguug cugacuguca uaggauauaa 7500
uaacgcggga gagaaguaug augacccucg uugauacaag aaaugagaug ucccuacugu 7560
gagaauucug ccuucggccc ccaugagugu gacuguguug ggcgguacag ucaguaccgg 7620
gucuucgccu aaggauguug acaccuugau agauaagaua gccugcugua ugcguuuccc 7680
accaaaccgu ccaggcuuau acgaagacuu ggccauucga aucugguagu cuugcucauc 7740
ugggcaugug ucauuguauc gcuuguauau cacauauuuc ccuuccugua cagugucacu 7800
gggugaauug gguuuuaacc cuccguagac ugagaaccau acgcggcugu caauaaaaga 7860
uccacccccu acuccugggu aguuggccac ccaguccccg aauaauguug ugacaucuag 7920
guccuuuucg ugguacuggc cgucgaaccc uaaccuccca uguaccaucc gcguagggac 7980

-continued

```
agcugaguua uaaucuucuu ccucugucuc cgugacuuuc gagcacagca uaucacaacc   8040
caggggaguu gcacucacac ugcaagacuu ccgauuuugg gugucgucca gguugaugga   8100
acgcagagua gaaaagaaua cccucccugu ugcagauguc cggagcacac caagugcuaa   8160
auacugauau gaaugugagu gaucucugca uccagacaau auuacauuau ggguguagca   8220
guaaugggua gcacucaugu caaaugaggg uauucgagug caaccugauc cuguaguagg   8280
cgccgggaua aaauucagau guucuugaaa ugcagaggga uagaaugaug ugacaucacu   8340
agcaucaucu acaaugaguu cuuugccuau cccccccuaua uaaucugggu cauggauagg   8400
ugcccccac ccacuguugu uugcagcucc auuaaucuga uaagagagag auguuauugc   8460
guucauaauu gugggucucag uauuuaacaa ugccaacgga gacucaaggg ccacuugcuu   8520
auauauccua ucuacuacau cuugauugga accaagugua gauguaaucu uuucuucugc   8580
ccuggaaauc cuagucggua ugccuacaag aucgcuaggu gugcuagccc ccaugcuaua   8640
uaaaagggag gcuacagaua uagccaaggu cacuacuguu aagaauaaga uugcaauccg   8700
gaauaucaag cgccauguau uuuuugccuc ucuuucauca uucucuaacg caacuuggcu   8760
aacggcgcgg uccaugauug aggacuguug ucggugaagc gguagaacgg agguugugaa   8820
gccuggcucg caauugaggg gcggccucuc uuaccguucu acccguauau cguccuuugg   8880
ucaucuacaa ccgguaguuu uuucuuaacu cucugaacug acagacuacc agaacuuuca   8940
cacaaauuac uauuagggaa accuucguuc cucaucugug uucacauuuu uguaguggcu   9000
cucaucugau cuagaguauu auucccaagc cauaauaagg ucuuuuguug cgccuuuugc   9060
uuguacauua gguagcaugc uagaaucagg cuaaguauac caaaaacaag agauaugaua   9120
gucaaaacga uauagguaau gagagcagau gugcuaguca guuugacauu gacuuugucu   9180
aguuucugu ugcuuucccuc uaacuuauuc aaagcauuac ugaucgaguu guugacauuc   9240
ccaagcucag uugagauauc aagauugccu guuauuauua cuugagaauc uuguauugag   9300
auauucuucu gauaaguuac aucgaauucc ccacugagcc uuaaaguuau cccgccuaag   9360
gauaaaacau ugcaugauug uuuaucuauu agagacacgg cuucuccaua guuuugcgau   9420
augauacccg gggggguuuac acaucuacau guugucaucu ugcaguuggc gaugacugaa   9480
ccuuugauag ucauguaugg uguaguaagu gcgccuucgg ucuuugagua cauacaggcc   9540
gacguauugc cgcucaagca ggaauaaaua ccaggggaca uagggaacgu uacuauucuu   9600
guacaauaua aaucuaaguc aguuucuaua caguaugagg ugucaaguuc uucuaucaca   9660
gaaccgaccu gugucaccac uuuugggaca agugccgagg caaaucccccu gguugugcuu   9720
acggauaagg uuuccaagua ggugggcacgc auauuauuua gguucccgac ugaaggggca   9780
guuaccugua uacccaagag uugagucugu gagucguaua gaauaggguu accggugauu   9840
aagccgcuac cgauuaauga gcugaguuga uuguucccua caccuaacuu agucaauaag   9900
uaauccauau uuccaccagc uagauuguaa agugccugaa uagucagcuu guuuaaagca   9960
ggugaaguga uuuguggucc gaauacugua gucaauucgg uuagguacag guugagcucu  10020
acaccaacuu gcugugcaau uuugaugcag ucuaauuccu gagcuguuuu auuaaauugg  10080
ucauuaacaa acugcugcau cuucccaacu gccacugcua guugcgauaa uccgucagug  10140
accucaugca cagccucauu gguugcggca augcucucuu uaagucggag gauguuggca  10200
gcauuuuguu uggcuuguau cagagcugcg gccgcuguua uuugugcggc aguugcaacc  10260
ccaagagcca caccgccaau aauggcgccu auaaggcgcc ccugucuccc cccuccagau  10320
guagucacag acucuuguau ccuacggaua gagucaccaa ggggggugag caaagugguc  10380
```

-continued aauguccugu uguaugcauc caagggggcu uucgcacaug ccuccuuauc cuugggcaga 10440
uucgggagga gcuuaacuau gauugauccu gucugggaug agguguauau guugacggcu 10500
uugucuccug uaaccacaau uccugcagcu gcaagaggcc ugccaucaau ggaguuugcc 10560
ggacagaugc aacucaguac cagcgcaacc cggauaguca gcaucauagg ugcuggguuc 10620
uugguagaag gucuggagcc caucuugcac cuggagggcg ccaaccggga uccagaaucu 10680
ucuacccgug uuuuuucuaa cuugauagac agguaaacua acuguaaaua aucaagacag 10740
auuaguuuuu ugugucauga ugaucugggu gagugggcgg agcgcaaucu cagagacgca 10800
gcuuauuucu uaaaaggauu guauuuggca agggugugcc ccuucuccag cuuaguagag 10860
guaaccucgu ggucggcggu cacugcgaca gcgcguuggg uaccugcuug gauaaugauu 10920
uuaacgcucc gcaggcacgc gguuugacuc cagaguaucu uggccaccug aggagaagca 10980
uuugcuaugg gauagcaggc ugucccacug cuagagaaga aaggugccaa aagcuuaguc 11040
cgugcaccuc uugcuuuuac caacacggaa ggcccgagca caucacugag cccgacagau 11100
agaucaaggc uccuuauuuu cuuuuccagc uugucaaaug ucacuuucuu ccccuuccua 11160
ucuacagugg ucauaagucc aauaugcaag aagagguuag cauaguaucc gcugucagac 11220
uuagacagag auuuaaccaa aggacuccuc gggucuaccu ccacauuaau agugacauug 11280
agcgcaagau uguacagacu cgagccagaa accuucaaua cugcagcugg gaucuuguag 11340
acaucccucu ucgguaccac agucaaggag acaaaguuca ccuuguauuc uaggguucca 11400
cucccgggaa ucuucucugg cgcuuucacg ugcuugacug cauucacuga ugaguauuug 11460
uuugccacaa cccuacagcu uugcagcacu uggggugccu gcacuacuga gaaaaccauu 11520
cucucaguau uaguugcacu cuucuugcau gugacuauca uagugagaca ggcccuugcc 11580
agcucaauaa ggucuccggu auuugggacg cuuccuaggc agagcaucgc agcggaaagu 11640
aacucgcgcu uggguuuauc aucgaucaug ccgacggugg cuucuucauu cccaacuuga 11700
aagaugaauc cauaggugguu gaugaauacu gaguccuccu uacuaucagu ccacaaguca 11760
aggcgcugga uccuauauug cggggcgauu ugcuucuucc caucuccugu gucuuguagg 11820
acgaucggaa augcuaacag guugcuagaa gaaugggcag aaucaaagua cagcccaauu 11880
guccuagaug aguccaucuu ggcacaauug gggcacucca auucuacccg uauuuuuucu 11940
uaaucuuaaa uguagcuaga uuaauuacgg uuacgcgauc auucaguggg gcugaggaag 12000
cgagagagga uugccgcuug gagaguugga ccuugggucc gcggaucauu aggaagcauu 12060
cagauagcuc aucacucuau caauagucac ugcccgaauu cugaaagcau gaagaaguau 12120
gcagagcuug auuuuaguuu uauaaaaauc cgguucuuca agggaggauu uuuguggcac 12180
agucucacug uugaaauuca gggccugcau cagcucauca auaacugcca gcauguuuug 12240
aucuagaaag aucugccucu uaggauccau cagaagcuuu gcauucaugg ucuugaacuc 12300
caccugguac aucuucgagu cuucauaaau acuacuaagg cacagggcca ucauaaaaga 12360
ggucuuucug gaggccaggc aacucccauu aguuaugaaa gaggucucuc uggaauuuag 12420
gcaacucuca uucuugguua auuccaaugg uaaacaggcc uccacugugc ugguuuuauc 12480
uuuugugaua ucuucaugau caaucucuuc agaagugcaa ggguaaaauu cuagaguuug 12540
ucuggccuuc uggagcaugu ugcugacggc ccucagcagg uuuugggagu ggugaaggca 12600
ugggaacauu ccugggucug gaguggccac ggggagguuu cuagauccgc cgccaccgcc 12660
accacugcag ggcacagaug cccauucgcu ccaagaugag cuauaguagc gguccugggc 12720

-continued ccgcacgcua augcuggcau uuuugcggca gaugaccgug gcugaggucu uguccgugaa 12780
gacucuaucu uucuuuucuc ucuugcucuu gcccuggacc ugaacgcaga augucaggga 12840
gaaguaggaa uguggaguac uccaggugug aggguacucc cagcugaccu ccaccugccg 12900
agaauucuuu aauggcuuca gcugcaaguu cuugggguggg ucagguuuga ugaugucccu 12960
gaugaagaag cugcuggugu aguuuucaua cuugagcuug ugaacggcau ccaccaugac 13020
cucaaugggc agacucuccu cagcagcugg gcaggcacug uccuccuggc acuccacuga 13080
guacucauac uccuuguugu ccccucugac ucucucugca gagaguguag cagcuccgca 13140
cgucaccccu ugggggucag aagagccucu gcugcuuuug acacugaaug ucaaaucagu 13200
acugauuguc gucagccacc agcaggugaa acguccagaa uaauucuugg ccucgcaucu 13260
uagaaagguc uuauuuuugg guucuuucug guccuuuaaa auaucagugg accaaauucc 13320
aucuuccuuu uugugaagca gcaggagcga auggcuuaga accucgccuc cuuugugaca 13380 ggguacugg ccagcaucuc caaacucuuu gacuuggaug gucaggguuu ugccagagcc 13440
uaagaccuca cugcucuggu ccaaggucca ggugauacca ucuucuucag gggugucaca 13500
ggugaggacc accauuucuc caggggcauc cggauaccaa uccaauucua cgacauaaac 13560
aucuuucuuc aguucccaua uggccacgag gggagaugcc agaaaaacca gggaaaacca 13620
agagaugacc aacugcuggu gacccauggu ggcgguucua cccguauuuu uucuaaccgc 13680 ggggggaac ucggugcaga uuccguguga ugccgagugg acagggaccc gcuacgugug 13740
gcaguaguaa uuagccauuu agagcaaggc gcuugauuuu ccugauuucc ucgaucgacc 13800
cggcugcauc uaacuugcuu aggagcuugg cugaagaacu cgggugcauu gggcgugaca 13860
ugaucaaugc acggacagug uccuuuucca cuccuauauc aggcccgcau gcaguggcgg 13920
guuuaaucaa uucagaugga uguggcacug guugcgaaag uuuauuaagu gccauuucgc 13980
cuccuugugu cacauaggga gaggggucuc cagggccuga aacuaaaacc gggugagauc 14040
gggcaacugc ccguagauca cucagagaug aaauguuggc acaaccggga uccagaaucu 14100
ucaucauucc caaguuggcu uccaugacug caacagaugu uuucagcugu uggauuucgg 14160
accgcaucau agggauggag gaugucuguu ucaagacaag aucuagcuga uagucaaccu 14220
uacuuacucu cugugauauc gccuccauca uagacaucau cgcuugcaca aagucuacag 14280
guggcuggac augauccgca gauacaaggg uauugucuug gcucugccuu gaucggagag 14340
caugaggggu ugcaccagcu gauaguugug acuccuccca uuguccauga uaugcugugu 14400
ucacgucugu gcccugguuu ccaggggcgg ccuugacuug guucugcggu cuuuccugac 14460
uguuuccgcg acuggguuga cuccccugcu guugagucgg acguuggauga uuccccucuu 14520 gggggcucga ccaugggccc uuuuuagcau uggacgauuu auugcugagc uugucaagca 14580
ucaacagcag agaguugcuu gcuccggucc ugagcugugu gucgacggcu ucgucugugg 14640 ccugggguggg gggcuggucg gcggaugugg ccggcgggcu gucaugcggg gucguuugcu 14700
cgggugugga ugguuguuug ucagaucugu ccugucgauc gggguugucu ugacuggccg 14760
guggcuggau gcucccaugc uucucccaug cugcgcucag caccuugguc uugccuugug 14820
ggauugcacu ccuuccaaca gucucugcug guuuacccug ggcuguaauu auguugucaa 14880
ugacaguucc acuugucuca aauagcucgu cgaucucugc aucuguaaag guggccaugu 14940
uuguccuggu cuaucaggua gaggagagag cagagacucg ggagacuugc ccugaucucu 15000
gaauaucccu cuucuacccg uacuuuuuuc uaauucccuc ggcucuguuu ugauuguuag 15060
ugagccgcau ugugccugug guaucuaggg cguacguagu uguacagcag ggggagggag 15120
gaaagagggg gauguuuguu ugagggugug gucauauaga gccgcaaauc gaggggucga 15180
cuacggguga gggcauuggg auguuuuugu ggaagcaggc uggguuuugu ccaucaauac 15240
ccccagucgg ugucguuauc uugggauggc ccaggaguug ggggaggccc cgauugggga 15300
gugcccugug cagaguuggg cgccucccuc augcuauuug cuaccgcucu caucagaucc 15360
aggaauuggg ucuccccauc cccggcuucu gguugcccuu gcgaucuauu cgauccgccu 15420
uguagagcuu gggacccccc cucgcuaagc ccagugagga cuccgacuug uugaguaggc 15480
augucuaugc ugcuggucuc cucggagacc cguugggcag cagcugccag gccccuccuu 15540
gcugcugggg uuagcuuuag cucggcagcc auauccucgu uaaugcuacu ucccugagcc 15600
ugagcguacu cuacuccaag ucuccagaau gaugugcuca uaaagucccu ggcaaauugg 15660
uauuucccag uaccuuuauc uaggacugau gccauaccca uggcaaagga guaaaguugu 15720
gcauacucgg caggcgcaaa gcucaucugg ucacuaucac caaguaaugu cauguacggc 15780
gcauuaucuc cuuucauccg auacaaacgc augagcugcu ucaucuucug gaugucgccu 15840
gagaggcuac uaagugcaag ggcugauguc uugguguuga uuccguacuu gagugucaag 15900
aagaaugcag uaagcccggu auuccugaug uaugagucua cguccccuac cagguuauaa 15960
uaaguagagg uaccaccugc cguguugcgg ccucucuuga gcucgcuaac caaaaagaug 16020
cggacugcaa gagacugucu gaucgugagu uggauugugc uccugcauac gggguagagg 16080
auguauuucu uuuggacccu gccuugcugc auauacuuau ugauucgccu uguuuccgac 16140
ucaucugcag ucucauacgc agucauggcu uuugcuacug ugacccauac uugagccugg 16200
auagagagga uccucuccag gguaucggug augucuucug gugcaucauc uucggccccg 16260
gcugugacga acgggguucc guugcugcau gcccgaggga gagauccugc uaucaucgca 16320
aaucucugug cucucucuuc agacacucca cuccuauugu ugaacugggg cgugccguug 16380
gcaaagccau caaucucaag cacggccaau guggcuucau ucuguuuccc ugcaagggca 16440
acaugguucc ucauuaccug ugagugggag cauaaaagag auaugagagc accuugccug 16500
aguggauugu uggcaucuuc gcuaacagca auccggaggc agaauaccac aaagcuccau 16560
cuaucuucug ggucaucacu guuaagagug aauaccggga cgucuacuuu uaagguacuc 16620
ccuuuuucuc ccccuccaug agcuccauug gggcgagucu gagccgcgag gagcuguucg 16680
uacucaucaa auacggaaga cauguuggca gaaggcuuuc ucgaguuugu gcuucgggcu 16740
cgcacucgag auucacaccu ucuacccgug cgacuucaau ugcuccuucg ccuuuuaucg 16800
uaacucacgg auucucuguu uggu 16824

<210> SEQ ID NO 52
<211> LENGTH: 16824
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 52
accaaacaaa gauuugguga augacgagac uacacucaag aauaauugug cgcaaccuuu 60
uuuuaagaca uuuauuugag uucgaauucg aguccuaagg agucaggguu caacuuuuuu 120
cuaacauaau augauuaaau caacaagaau acaauuggcc aaaaaaggag ccuauuaaua 180
ugugauuuuc guuaagaguc acaguuacug uaauauccuu ugacugcauu gccuauaguu 240

-continued

```
uucauguaga auuuuuguug agcacgaguc aaguacagua cagaaguguc uguaaacauu    300
ucuuugaguu ugguaauacc uaggacagcc uucaaauauu uagggcaggu acuaugcuuc    360
aaguaugucc uuagugggau aagguccucc auggagauca ugccuuuaag cacuaggcug    420
auuauaucgc cuauuuuauu gagauuuucg acucuaagac cuaguauugu aaccucuagg    480
aucugucucg ugcacuguuu aagugauguc cucuuuuucc cgucaguaga gagauuguaa    540
gggguaaaua gaaauacugu gucagcgaga ucacccucag cuuccauaua uaucacagac    600
cggauaacug ugucaaugug acuagcgaug aucuggguua ucugaguuau guucgcuagc    660
gugcucacca gacucuccgc acagaaugga cggacgggcu guccccccggc uucaaucagc   720
gcagugucaa uauucuuccu caaguacuuu auuaaucuug guaaaggacu ggauaggaug    780
ucugucacac gcugccgcug ugaggugaau aaccugguca gugugaucuc aucugauuua    840
gacaaaagcg uaccgugccg cugcaccaga guuuucgcca uccucaccac cucauguaca    900
aauguaggcc cgcccaggua acccaugaca aauaccaggu aacacuccau aucuccucga    960
caugcauaac cauuagagag aauauauccu uuuguggaac acggagcaaa caaguucaug   1020
aguagaugaa aguaguaucc cauugcauac aacacuuuga ugauuacuac cccgcccucc   1080
cuuacagaau gcauggcaau cagagauaaa uugauagcua guugaucuag uaagcuuuga   1140
uuggacccug gaggaauuuc aaugucacaa ugcagcaaug auacagaucu guagggcacu   1200
gcagauguaa uauaccccac uacuuuaucu gaggucaggu cgcuuuccuc uguauuuucu   1260
cuccauaaug gacggaacuc uuggacaaau ccaucuuugc auguuaccuc cgccuguaga   1320
uuccuauaaa caaccgaauu caaaaacuga guuggggucg gcccgaaaug ucguugcggg   1380
ggguucaucu cauuugaaaa gagcguauug uaauagauag uuucaugugg uacaugcagu   1440
ucgagaagac ucaugauggc uccgcucccu ucagcuaagu auaaggaguu cccgugucuu   1500
gcacaucuua ccucggguac agaaaggaga ugagaugccu uauaccaaga ggaagaugca   1560
gucccuaucc cucugaacaa guaucguacu aaguagucuu ccuccggauu uggagaugug   1620
aguucaggau gaaucugacu aagugugaau gcgucauacc uugcuggagc acucaaaucu   1680
aacucuugca aaaaugccgc agguugucgg gugaauggau cuuucacucg agcaccaaua   1740
ucuugcacag aagggaacuc uaauaauggc ucuuggggga acaacaacgc caggauagua   1800
ucccuguccu cccuuucccu gaucaaauug aggcucuucc gagacaugua guacagauua   1860
gcugggaaug uaauuauguu aggagacaug auagagcuca cuugaucggg gcuaaguaau   1920
gguuucacag cauccgacag uaaauacuca gugaguauug aacauuucuc uucugcaguu   1980
aagccucuua uuuucgggau uucucuuguu guagcaaaga guaccgugua cagacagcau   2040
aaccgggaua ucagcugaag caucuucuca uucagguuau caucuaagac agaugggaac   2100
agcagaucau acuuauuucc ugaauauaag ccggagauca cacgucgggu gcaagauacu   2160
aauaguuuug cagacauuuc gauaaaaucc guaucugcaa guugguguga uccgucaugg   2220
uugaccaggc ccacugcaug uaaccuugaa ugaaugacgg gaugagauau uguagcugca   2280
auguuggaaa guagaauucc uggcauauuc uuguauaaau cacccauaua uaagacaaua   2340
uuguccaggc cucuuacucu cagguaauag aguugguaag aacagucgag gagcacuuca   2400
agugcugcau auucaaauag gcggaccaca ucugaauucu gagcuucacu gauccaauuu   2460
cggguauugu cauacacuau uauggcguca uucuuuaugg agguaucuuc aucauaagaa   2520
accacagacu ggccaaucaa cuucccgcug gauauugaaa gaauguucau uagcucuauc   2580
gugggauaug acuccagauu aagcucauaa cucuugaaga uagcuaaguc aagucucgca   2640
```

-continued

```
aagucucccu ccgauacagg gcuaggauca uacauaaacu uauuugaggu cacuguccuc   2700
aguuccggua ccaccccaag uagcucgaaa ggaaccgcaa caggugcuuc ucugauacag   2760
caacuaaauu uacuauguag gugcagugug aucucaucau auguccuggu uguugucauu   2820
ggaaagaucg auucgauuag agauaaaccc aagagcauga ucuguuggua aaccacauuc   2880
cccucuuuga cuccuucuuc agugaacagc cuuugagaau cauuggauau gugaauguaa   2940
ggugacaccc uguagagaga ugcaggggug aaugucaucu gaguuauacc aucaucuagu   3000
cuauguugaa gauucccagc cguggguaaa ggggacagua accgaagaua cucuaaguuu   3060
acauuacacc gagauuuugc aaucguaaga gcagcagucc aauuuacuuc auuaucccca   3120
uaagcccaga ucaacacgga ugaugcccuu agggcagccu uuacaugugg cgacauauga   3180
gcuauuuuug caagugaggc agcucuccuc uccugugucu uugacccgag auaugguacc   3240
cucaucggag gauucuugcu ggugucaucg gucaauucua uauugcuugg aagauggaac   3300
caaguaaauu guucaucucc gcugucacau cuuguacacc cuccgcuuac acuaagaauc   3360
ucacccucua cgaguucuau cguaucagga uuagauacac ccaguauuuu ccugccuccc   3420
gucaaaggug accagcuucu auuccgugca uagucugcca gugucagaga acacauauua   3480
gaagagacua aggggugguu ggaucuacug gaggaaaaaa caucgucucu aaacagcauu   3540
gcaugcaugc uagaauaauu gacuauccgc aucagccucu ugaugccuaa uggccuccua   3600
guaagcgcaa ucuuaauuac gguguuuguu gugucaacaa gcccuugaau uugcuuucuc   3660
cuaccuacag agcuugccuc caugauggca ugcgcaacgc ggggaugaau caccucuuga   3720
uuaagcaaga auucagccaa ugccuucucu ucugccucau uauccucugu gugcacucca   3780
gacaauaagg gauuugaaca aguuucaaau aggacucuuu gcguauguuu cuuaagaaca   3840
auauuugggc uugcaacagu cucaaaauug aaagaguaug ggucguugca cagacuggcc   3900
caaucuccau ucccaggcgg ccuaguuaag auauuaguca uaauguuagg acucaguaau   3960
cccacugcuu cuagucgcuu gaucucugca aaagcaguag uccccggguc accgauauuu   4020
cuaguguaga gccuugagua uugaagguua cucagucccc cuaauugggc aggagucaga   4080
acauaugagu gcacaaaaga gauguccuca auccacgacu gauuaagauc ggggugcgaa   4140
uuguugguga uggagaacuc agagucaaag uaugucugca cacaacucau uauauaguuu   4200
aaauaguaac agaagucuuu gggaagcccg uucucgcaua gccgugcuac aguagaggca   4260
auguuggcac aggacauuac gguguuuuca cugagaucac cugacacuag cacuaauuua   4320
gaugaauuuu ugaggacuug acugaggauu gcuccaucuu ugaagauucg uuugcuguau   4380
augaagaaug ugucugaccu gaugguuuca cgauccuuca aauuauggcc aaucaaauga   4440
uugacaugaa uuaauuccuu gaagaaauua ucacuggcuu gaugcaacug ugucaacacc   4500
aucuccggag agucgucuga ucuuaccucu cucguuacug cuauuacuug auuaucaccc   4560
uguaccauac aggcaacacg acaaugcgau cuagcugcag caaguuggau ugcagcaauu   4620
gagaucauug uccauagcuu cuggcauaau ccuucgauac ccccucuggc acugacaaua   4680
uauaugucau cauuagggac ucuugagagg ucacagucag uagggucacu uggaggauug   4740
aaagggucuc cuacgaacau cguaguguccc aucagucuua ggugaaucca uucgaagaag   4800
ugagguaggc ccaucaacug auugauggca ugagcgaaca auuugauugu cugauaucuc   4860
caauuaagac aguacuuuug caggucaguu guuaugaagg uugcaacucu ccgacgguuc   4920
uugcuuuucg gaucaugauu gcgguuugaa gauacucuuu cuuuacaguc agugauacgu   4980
```

-continued

```
uucuuauugc uguuaaaaga caguugacuc aucgcuagca uacucuuggu caaggauaug   5040
cuauccugaa ugacuccauu ucccugaaag aaaggugcaa ucugaucggc uaggaucccu   5100
uccgccauca ccugacaguu ccuuaacuuc uuugucagcu uagcgaagau ccguccauua   5160
acuuucacuu ccuucuccuu gagcgaguau gauacugcca cauugucauc ucuaagguac   5220
ucaagggucg ucagauauuc caucucuuua uauggaucaa aaucauuuga cucuaaaaac   5280
ucuaucaaga ggcgauuagu cgaaguugcu ucuuuuacau guuucuucug gucuucggag   5340
agaagguucc gccuaaacga ggcaagccaa uuaucguugg ggugugcgau ugccuugucu   5400
uuuaggaaca ugcucagguu ggugacaggg ucauauucua uacauggcuc aaauucaagu   5460
gcagauaaac ucuuauacuc ucucaacaug auaucgugug aaaucucugc ugaaucugca   5520
uguaguugcc caaugaccuu cccauauauu guauccacuu ugacucgcgg ccacacaccu   5580
gcauucuucu uucuguaccc guugaugauu guucccuuga agaaagacag uaccugaagg   5640
aucauaucaa agucuaccau uuucggugcg cacauuuggc uccugacugc cuuugcugca   5700
auacgggacu caagcagugg gugaccccac agacgcaaca gacacaacau cucagcugcu   5760
ugauucuguu cuaaaccaga gaauacagua gcgauugcau gagucacgga uucugcuaua   5820
ucauugggga ggaggccaau uagaaugucu uuaagcuccu gcagguugaa ugcgaagaaa   5880
ucuccugcaa auguaccuga cggcucgagu agcuggacag cuccguaugc aaaucccucc   5940
auuagugaua caacaucgua gacuugauua cccaagucuu uugccagagc gucuauuaac   6000
cgcaaaaugu caucaauuuu cucugauaag cuucugagau gcaccgccgu gguugauauu   6060
auguugacca uaucucugcc cuccaucaua ucugcauaca ucaauacaag uuccugggua   6120
agacauguga acuuguucuc auucguaugc gucacaacga caaguucagg agugacaaag   6180
acuuggccua ccuuaugggu uagcaucacc aauuuguugg ccgcagaccu uguccuagcu   6240
gccaccauca gaugccucug gaucuguuuu auauggagcc augcaaacuu ggcuguggac   6300
cauuuugagu gaaaccagaa ugccggaucc guacgaaugc ugcugaacuc cucugaccgg   6360
gggacauugu uagaccaaga ugaccccagc aguuucuucu cuauaugcgu acacagccuu   6420
gugaacaguu cuccauaucu cguguuguga auuuggaucu ucuucucaau cuuccgaaau   6480
uuguugguug aaucugggac cucaauauua gccaguucuu cuaaacaccu ggggguggagc   6540
acuccgguua uucuggaauu gugguuaaga guuuggugua cugcccuucc gaguuuuauc   6600
auucucucag uaucaggaga ggccgauuca aguauuuuuu uccauugucg gcugagaaug   6660
agguggucga agucacauuc aucaggaagc gguagcccag uuaauuucca guaauagagu   6720
aguuugugcu ugaccaaugg ugaagacagg ugugacucug guaggauaau cugaugcucu   6780
gcccuuucag gaccggagcu cgccaugucc uacccguauu guuaaccaug agcuguuuug   6840
ccuuguaucu cauugccacu uacauuuuuu cuuaaucaag agacuauuga caaggcuuaa   6900
ucugaucgca ugagcacugg cugauugugg ucaacuggca acauggaauu cgagcacgcg   6960
ccggcauucg guuugauucu ugaugucgca gaagauaggu gauacaaugc caucuuucca   7020
acuccuuuau aauugacuca acuagccaga ccuggcuucu cuaaccccgu caucuuugag   7080
gaucucaacu aguaacggga cgauucugaa uucuccgaag agaguauuag auauuucagc   7140
aaugcugaga caauaggucu uauuagucuu gaccacuuua aaacaaguug auguugugua   7200
ugcugcuuug guacugcuug aacucacucg aguaaugcga cugcgggaug ugcuaucgaa   7260
uacugcagac gcaggguuaa gucuugcuug uacaccauca agcauugucc cgaauacccc   7320
ucgcaaggug ugguuucuau agaagauuag gggauaugga ucuguauaga cuccaguaac   7380
```

-continued

```
acacgaguug gggcaucuug cugaagccug gcaagggaua cuaccuggcc gagugaaggc   7440
auugaaugua uaaggacuau gaagaguggc uguuuuguug cugacuguca uaggauauaa   7500
uaacgcggga gagaaguaug augacccucg uugauacaag aaaugagaug ucccuacugu   7560
gagaauucug ccuucggccc ccaugagugu gacuguguug ggcgguacag ucaguaccgg   7620
gucuucgccu aaggauguug acaccuugau agauaagaua gccugcugua ugcguuuccc   7680
accaaaccgu ccaggcuuau acgaagacuu ggccauucga aucugguagu cuugcucauc   7740
ugggcaugug ucauuguauc gcuuguauau cacauauuuc ccuuccugua cagugucacu   7800
gggugaauug gguuuuaacc cuccguagac ugagaaccau acgcggcugu caauaaaaga   7860
uccacccccu acuccugggu aguuggccac ccaguccccg aauaauguug ugacaucuag   7920
guccuuuucg ugguacuggc cgucgaaccc uaaccuccca uguaccaucc gcguagggac   7980
agcugaguua uaaucuucuu ccucugucuc cgugacuuuc gagcacagca uaucacaacc   8040
caggggaguu gcacucacac ugcaagacuu ccgauuuugg gugucgucca gguugaugga   8100
acgcagagua gaaaagaaua cccucccugu ugcagauguc cggagcacac caagugcuaa   8160
auacugauau gaaugugagu gaucucugca uccagacaau auuacauuau ggguguagca   8220
guaaugggua gcacucaugu caaaugaggg uauucgagug caaccugauc cuguaguagg   8280
cgccgggaua aaauucagau guucuugaaa ugcagaggga uagaaugaug ugacaucacu   8340
agcaucaucu acaaugaguu cuuugccuau ccccccuaua uaaucugggu cauggauagg   8400
ugcccccac ccacuguugu uugcagcucc auuaaucuga uaagagagag auguuauugc   8460
guucauaauu guggucucag uauuuaacaa ugccaacgga gacucaaggg ccacuugcuu   8520
auauauccua ucuacuacau cuugauugga accaagugua gauguaaucu uuucuucugc   8580
ccuggaaauc cuagucggua ugccuacaag aucgcuaggu gugcuagccc ccaugcuaua   8640
uaaaagggag gcuacagaua uagccaaggu cacuacuguu aagaauaaga uugcaauccg   8700
gaauaucaag cgccauguau uuuugccuc ucuuucauca uucucuaacg caacuuggcu   8760
aacggcgcgg uccaugauug aggacuguug ucggugaagc gguagaacgg agguugugaa   8820
gccuggcucg caauugaggg gcggccucuc uuaccguucu acccguauau cguccuuugg   8880
ucaucuacaa ccgguaguuu uuucuuaacu cucugaacug acagacuacc agaacuuuca   8940
cacaaauuac uauuagggaa accuucguuc cucaucugug uucacauuuu uguaguggcu   9000
cucaucugau cuagaguauu auucccaagc cauaauaagg ucuuuuguug cgccuuuugc   9060
uuguacauua gguagcaugc uagaaucagg cuaaguauac caaaaacaag agauaugaua   9120
gucaaaacga uauagguaau gagagcagau gugcuaguca guuugacauu gacuuugucu   9180
aguuucugu ugcuuuccuc uaacuuauuc aaagcauuac ugaucgaguu guugacauuc   9240
ccaagcucag uugagauauc aagauugccu guuauuauua cuugagaauc uuguauugag   9300
auauucuucu gauaaguuac aucgaauucc ccacugagcc uuaaaguuau cccgccuaag   9360
gauaaaacau ugcaugauug uuuaucuauu agagacacgg cuucuccaua guuuugcgau   9420
augauacccg gggggguuuac acaucuacau guugucaucu ugcaguuggc gaugacugaa   9480
ccuuugauag ucauguaugg uguaguaagu gcgccuucgg ucuuugagua cauacaggcc   9540
gacguauugc cgcucaagca ggaauaaaua ccaggggaca uagggaacgu uacuauucuu   9600
guacaauaua aaucuaaguc aguuucuaua caguaugagg ugucaaguuc uucuaucaca   9660
gaaccgaccu gugucaccac uuuugggaca agugccgagg caaaucccu gguugugcuu   9720
```

-continued acggauaagg uuuccaagua gguggcacgc auauuauuua gguucccgac ugaaggggca 9780
guuaccugua uacccaagag uugagucugu gagucguaua gaauaggguu accggugauu 9840
aagccgcuac cgauuaauga gcugaguuga uuguucccua caccuaacuu agucaauaag 9900
uaauccauau uuccaccagc uagauuguaa agugccugaa uagucagcuu guuuaaagca 9960
ggugaaguga uuuguggucc gaauacugua gucaauucgg uuagguacag guugagcucu 10020
acaccaacuu gcugugcaau uuugaugcag ucuaauuccu gagcuguuuu auuaaauugg 10080
ucauuaacaa acugcugcau cuucccaacu gccacugcua guugcgauaa uccgucagug 10140
accucaugca cagccucauu gguugcggca augcucucuu uaagucggag gauguuggca 10200
gcauuuuguu uggcuuguau cagagcugcg gccgcuguua uuugugcggc aguugcaacc 10260
ccaagagcca caccgccaau aauggcgccu auaaggcgcc ccugucuccc cccuccagau 10320
guagucacag acucuuguau ccuacggaua gagucaccaa gggggugag caaagugguc 10380
aauguccugu uguaugcauc caagggggcu uucgcacaug ccuccuuauc cuugggcaga 10440
uucgggagga gcuuaacuau gauugauccu gucugggaug agguguauau guugacggcu 10500
uugucuccug uaaccacaau uccugcagcu gcaagaggcc ugccaucaau ggaguuugcc 10560
ggacagaugc aacucaguac cagcgcaacc cggauaguca gcaucauagg ugcuggguuc 10620
uugguagaag gucuggagcc caucuugcac cuggagggcg ccaaccggga uccagaaucu 10680
ucuacccgug uuuuuucuaa cuugauagac agguaaacua acuguaaaua aucaagacag 10740
auuaguuuuu ugugucauga ugaucugggu gagugggcgg agcgcaaucu cagagacgca 10800
gcuuauuucu uaaaaggauu guauuuggca agggugugcc ccuucuccag cuuaguagag 10860
guaaccucgu ggucggcggu cacugcgaca gcgcguuggg uaccugcuug gauaaugauu 10920
uuaacgcucc gcaggcacgc gguuugacuc cagaguaucu uggccaccug aggagaagca 10980
uuugcuaugg gauagcaggc ugucccacug cuagagaaga aaggugccaa aagcuuaguc 11040
cgugcaccuc uugcuuuuac caacacggaa ggcccgagca caucacugag cccgacagau 11100
agaucaaggc uccuuauuuu cuuuuccagc uugucaaaug ucacuuucuu ccccuuccua 11160
ucuacagugg ucauaagucc aauaugcaag aagagguuag cauaguaucc gcugucagac 11220
uuagacagag auuuaaccaa aggacuccuc gggucuaccu ccacauuaau agugacauug 11280
agcgcaagau uguacagacu cgagccagaa accuucaaua cugcagcugg gaucuuguag 11340
acaucccucu ucgguaccac agucaaggag acaaaguuca ccuuguauuc uaggguucca 11400
cucccgggaa ucuucucugg cgcuuucacg ugcuugacug cauucacuga ugaguauuug 11460
uuugccacaa cccuacagcu uugcagcacu uggggugccu gcacuacuga gaaaaccauu 11520
cucucaguau uaguugcacu cuucuugcau gugacuauca uagugagaca ggcccuugcc 11580
agcucaauaa ggucuccggu auuugggacg cuuccuaggc agagcaucgc agcggaaagu 11640
aacucgcgcu uggguuuauc aucgaucaug ccgacggugg cuucuucauu cccaacuuga 11700
aagaugaauc cauaggugu gaugaauacu gaguccuccu uacuaucagu ccacaaguca 11760
aggcgcugga uccuauauug cggggcgauu ugcuucuucc caucuccugu gucuuguagg 11820
acgaucggaa augcuaacag guugcuagaa gaaugggcag aaucaaagua cagcccaauu 11880
guccuagaug aguccaucuu ggcacaauug gggcacucca auucuacccg uauuuuuucu 11940
uaaucuuaaa uguagcuaga uuaauuacgg uuacgcgauc auucaguggg gcugaggaag 12000
cgagagagga uugccgcuug gagaguugga ccuugggucc gcggaucauu aggaagcauu 12060
cagauaggac aucacgcggu cgauugucac ggcucugauc cgaaaggcgu gcagcaggau 12120
gcacagcuug aucuuggucu uguagaaauc uggcuccucc agagaggacu ucugaggcac 12180
ugucucgcua uugaaguuca gggccugcau cagcucgucg aucacggcca gcauauucug 12240
auccagaaag aucugccucu uggggguccau cagcagcuug gcguucaugg ucuugaacuc 12300
caccugauac aucuucaggu ccucguagau gcuagacagg cacagggcca ucauaaagcu 12360
ugucuuucua gaggccaggc aggagccguu ggugaugaag cuugucuccc ggcuguucag 12420
acaggacucg uucuugguca gcuccagugg caggcaggcc uccacugugg aggucuuauc 12480
cuuugugaug uccucguggu cgaucuccuc gcugguacaa ggguaaaacu ccagugucug 12540
gcgggccuuc ugcagcauau uggacacggc ccucagcagg uucuggcugu ggugcaggca 12600
ggggaacaug ccugggucag ggguugccac uggcagauuc cuagauccuc cuccuccucc 12660
gccgcugcaa ggcacagagg cccacucgga ccaggagcua gaauaguagc gguccugggc 12720
ccucacgcug auagaggcgu ucuuucuaca gaucacggug gcagaugucu uaucggugaa 12780
cacucugucc uucuucuccc gcuuggacuu gcccugcacc ugcacgcaaa aggucagaga 12840
gaaauaggag ugugguguge uccaggugtuc aggguacucc caggacaccu ccaccugucu 12900
gcuauucuuc agaggcuuca gcugcagguu cuuaggggga ucgggcuuga ugaugucccg 12960
gauaaagaag gagcugguau aauucucgua cuucagcuug ugcacggcau ccaccaucac 13020
uucgauaggc agggacuccu cugcugcugg acaggcagag uccuccuggc acuccacgga 13080
auacucguac uccuuguuau cgccgcgcac ccucucggcg cucagggugg cugcuccgca 13140
ugucacuccc ugugggucag aggaucccu gcuagacuuc acagaaaaug ucagaucggu 13200
ggagauugug gucagccacc aacaggugaa ccggccgcua uaauucuugg ccucgcaccg 13260
caggaagguc uuguucuuug gcuccuucug auccuucagg augucugugg accagaugcc 13320
auccuccuuc uugugcagca gcagcaggga guggcucagc accucuccuc ccuugugaca 13380
gguguacugg ccggcgucgc cgaacuccuu caccuggauu gucagggucu ugccgcuucc 13440
cagcaccucg gagcucugau ccaguguccaa ggugaugcca uccuccucgg gugugucgca 13500
ggucagcacc accaucucgc caggggcauc gggauaccag uccagcucca ccacguacac 13560
auccuuuuuc aguucccaga uugcgaccag aggugaggcc agaaacacca gggagaacca 13620
ugagaugacc agcugcugau ggcacauggu ggcgguucua cccguauuuu uucuaaccgc 13680
ggggggggaac ucggugcaga uuccguguga ugccgagugg acagggaccc gcuacgugug 13740
gcaguaguaa uuagccauuu agagcaaggc gcuugauuuu ccugauuucc ucgaucgacc 13800
cggcugcauc uaacuugcuu aggagcuugg cugaagaacu cgggugcauu gggcgugaca 13860
ugaucaaugc acggacagug uccuuuucca cuccuauauc aggcccgcau gcaguggcgg 13920
guuuaaucaa uucagaugga uguggcacug guugcgaaag uuuauuaagu gccauuucgc 13980
cuccuugugu cacauaggga gaggggucuc cagggccuga aacuaaaacc gggugagauc 14040
gggcaacugc ccguagauca cucagagaug aaauguuggc acaaccggga uccagaaucu 14100
ucaucauucc caaguuggcu uccaugacug caacagaugu uuucagcugu uggauuucgg 14160
accgcaucau agggauggag gaugucuguu ucaagacaag aucuagcuga uagucaaccu 14220
uacuuacucu cugugauauc gccuccauca uagacaucau cgcuugcaca aagucuacag 14280
guggcuggac augauccgca gauacaaggg uauugucuug gcucugccuu gaucggagag 14340
caugaggggu ugcaccagcu gauaguugug acuccuccca uuguccauga uaugcugugu 14400
ucacgucugu gcccugguuu ccaggggcgg ccuugacuug guucugcggu cuuuccugac 14460

-continued

```
uguuuccgcg acuggguuga cuccccugcu guugagucgg acguugguga uuccccucuu  14520
gggggcucga ccaugggccc uuuuuagcau uggacgauuu auugcugagc uugucaagca  14580
ucaacagcag agaguugcuu gcuccggucc ugagcugugu gucgacggcu ucgucugugg  14640
ccuggguggg gggcuggucg gcggaugugg ccggcgggcu gucaugcggg gucguuugcu  14700
cgggugugga ugguuguuug ucagaucugu ccugucgauc gggguugucu ugacuggccg  14760
guggcuggau gcucccaugc uucucccaug cugcgcucag caccuugguc uugccuugug  14820
ggauugcacu ccuuccaaca gucucugcug guuuacccug ggcuguaauu auguugucaa  14880
ugacaguucc acuugucuca aauagcucgu cgaucucugc aucuguaaag guggccaugu  14940
uuguccuggu cuaucaggua gaggagagag cagagacucg ggagacuugc ccugaucucu  15000
gaauaucccu cuucuacccg uacuuuuuuc uaauucccuc ggcucuguuu ugauuguuag  15060
ugagccgcau ugugccugug guaucuaggg cguacguagu uguacagcag ggggagggag  15120
gaaagagggg gauguuuguu ugagggugug gucauauaga gccgcaaauc gaggggucga  15180
cuacggguga gggcauuggg auguuuuugu ggaagcaggc uggguuuugu ccaucaauac  15240
ccccagucgg ugucguuauc uugggauggc ccaggaguug ggggaggccc cgauuggga  15300
gugcccugug cagaguuugg cgccucccuc augcuauuug cuaccgcucu caucagaucc  15360
aggaauuggg ucuccccauc cccggcuucu gguugcccuu gcgaucuauu cgauccgccu  15420
uguagagcuu gggaccccc cucgcuaagc ccagugagga cuccgacuug uugaguaggc  15480
augucuaugc ugcuggucuc cucggagacc cguugggcag cagcugccag gccccuccuu  15540
gcugcugggg uuagcuuuag cucggcagcc auauccucgu uaaugcuacu ucccugagcc  15600
ugagcguacu cuacuccaag ucuccagaau gaugugcuca uaaagucccu ggcaaauugg  15660
uauuucccag uaccuuuauc uaggacugau gccauaccca uggcaaagga guaaaguugu  15720
gcauacucgg caggcgcaaa gcucaucugg ucacuaucac caaguaaugu cauguacggc  15780
gcauuaucuc cuuucauccg auacaaacgc augagcugcu ucaucuucug gaugucgccu  15840
gagaggcuac uaagugcaag ggcugauguc uugguguuga uuccguacuu gagugucaag  15900
aagaaugcag uaagcccggu auuccugaug uaugagucua cguccccuac cagguuauaa  15960
uaaguagagg uaccaccugc cguguugcgg ccucucuuga gcucgcuaac caaaaagaug  16020
cggacugcaa gagacugucu gaucgugagu uggauugugc uccugcauac gggguagagg  16080
auguauuucu uuuggacccu gccuugcugc auauacuuau ugauucgccu uguuuccgac  16140
ucaucugcag ucucauacgc agucauggcu uuugcuacug ugacccauac uugagccugg  16200
auagagagga uccucuccag gguaucggug augucuucug gugcaucauc uucggccccg  16260
gcugugacga acgggguucc guugcugcau gcccgaggga gagauccugc uaucaucgca  16320
aaucucugug cucucucuuc agacacucca cuccuauugu ugaacugggg cgugccguug  16380
gcaaagccau caaucucaag cacggccaau guggcuucau ucuguuuccc ugcaagggca  16440
acaugguucc ucauuaccug ugagugggag cauaaaagag auaugagagc accuugccug  16500
agugguuugu uggcaucuuc gcuaacagca auccggaggc agaauaccac aaagcuccau  16560
cuaucuucug ggucaucacu guuaagagug aauaccggga cgucuacuuu uaagguacuc  16620
ccuuuuucuc ccccuccaug agcuccauug gggcgagucu gagccgcgag gagcuguucg  16680
uacucaucaa auacggaaga cauguuggca gaaggcuuuc ucgaguuugu gcuucgggcu  16740
cgcacucgag auucacaccu ucuacccgug cgacuucaau ugcuccuucg ccuuuuaucg  16800
uaacucacgg auucucuguu uggu                                          16824
```

<210> SEQ ID NO 53
<211> LENGTH: 1599
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 53
atgtgccatc agcagctggt catctcatgg ttctccctgg tgtttctggc ctcacctctg 60
gtcgcaatct gggaactgaa aaaggatgtg tacgtggtgg agctggactg gtatcccgat 120
gcccctggcg agatggtggt gctgacctgc gacacacccg aggaggatgg catcacctgg 180
acactggatc agagctccga ggtgctggga agcggcaaga ccctgacaat ccaggtgaag 240
gagttcggcg acgccggcca gtacacctgt cacaagggag gagaggtgct gagccactcc 300
ctgctgctgc tgcacaagaa ggaggatggc atctggtcca cagacatcct gaaggatcag 360
aaggagccaa agaacaagac cttcctgcgg tgcgaggcca agaattatag cggccggttc 420
acctgttggt ggctgaccac aatctccacc gatctgacat tttctgtgaa gtctagcagg 480
ggatcctctg acccacaggg agtgacatgc ggagcagcca ccctgagcgc cgagagggtg 540
cgcggcgata acaaggagta cgagtattcc gtggagtgcc aggaggactc tgcctgtcca 600
gcagcagagg agtccctgcc tatcgaagtg atggtggatg ccgtgcacaa gctgaagtac 660
gagaattata ccagctcctt ctttatccgg gacatcatca agcccgatcc ccctaagaac 720
ctgcagctga agcctctgaa gaatagcaga caggtggagg tgtcctggga gtaccctgac 780
acctggagca caccacactc ctatttctct ctgacctttt gcgtgcaggt gcagggcaag 840
tccaagcggg agaagaagga cagagtgttc accgataaga catctgccac cgtgatctgt 900
agaaagaacg cctctatcag cgtgagggcc caggaccgct actattctag ctcctggtcc 960
gagtgggcct ctgtgccttg cagcggcgga ggaggaggag gatctaggaa tctgccagtg 1020
gcaacccctg acccaggcat gttcccctgc ctgcaccaca gccagaacct gctgagggcc 1080
gtgtccaata tgctgcagaa ggcccgccag acactggagt tttacccttg taccagcgag 1140
gagatcgacc acgaggacat cacaaaggat aagacctcca cagtggaggc ctgcctgcca 1200
ctggagctga ccaagaacga gtcctgtctg aacagccggg agacaagctt catcaccaac 1260
ggctcctgcc tggcctctag aaagacaagc tttatgatgg ccctgtgcct gtctagcatc 1320
tacgaggacc tgaagatgta tcaggtggag ttcaagacca tgaacgccaa gctgctgatg 1380
gaccccaaga ggcagatctt tctggatcag aatatgctgg ccgtgatcga cgagctgatg 1440
caggccctga acttcaatag cgagacagtg cctcagaagt cctctctgga ggagccagat 1500
ttctacaaga ccaagatcaa gctgtgcatc ctgctgcacg cctttcggat cagagccgtg 1560
acaatcgacc gcgtgatgtc ctatctgaat gcttcctaa 1599

<210> SEQ ID NO 54
<211> LENGTH: 984
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 54

-continued

```
atgtgccatc agcagctggt catctcatgg ttctccctgg tgtttctggc ctcacctctg     60

gtcgcaatct gggaactgaa aaaggatgtg tacgtggtgg agctggactg gtatcccgat    120

gcccctggcg agatggtggt gctgacctgc gacacacccg aggaggatgg catcacctgg    180

acactggatc agagctccga ggtgctggga agcggcaaga ccctgacaat ccaggtgaag    240

gagttcggcg acgccggcca gtacacctgt cacaagggag gagaggtgct gagccactcc    300

ctgctgctgc tgcacaagaa ggaggatggc atctggtcca cagacatcct gaaggatcag    360

aaggagccaa agaacaagac cttcctgcgg tgcgaggcca agaattatag cggccggttc    420

acctgttggt ggctgaccac aatctccacc gatctgacat tttctgtgaa gtctagcagg    480

ggatcctctg acccacaggg agtgacatgc ggagcagcca ccctgagcgc cgagagggtg    540

cgcggcgata acaaggagta cgagtattcc gtggagtgcc aggaggactc tgcctgtcca    600

gcagcagagg agtccctgcc tatcgaagtg atggtggatg ccgtgcacaa gctgaagtac    660

gagaattata ccagctcctt ctttatccgg gacatcatca agcccgatcc ccctaagaac    720

ctgcagctga agcctctgaa gaatagcaga caggtggagg tgtcctggga gtaccctgac    780

acctggagca caccacactc ctatttctct ctgacctttt gcgtgcaggt gcagggcaag    840

tccaagcggg agaagaagga cagagtgttc accgataaga catctgccac cgtgatctgt    900

agaaagaacg cctctatcag cgtgagggcc caggaccgct actattctag ctcctggtcc    960

gagtgggcct ctgtgccttg cagc                                           984
```

<210> SEQ ID NO 55
<211> LENGTH: 594
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 55

```
aggaatctgc cagtggcaac ccctgaccca ggcatgttcc cctgcctgca ccacagccag     60

aacctgctga gggccgtgtc caatatgctg cagaaggccc gccagacact ggagttttac    120

ccttgtacca gcgaggagat cgaccacgag gacatcacaa aggataagac ctccacagtg    180

gaggcctgcc tgccactgga gctgaccaag aacgagtcct gtctgaacag ccgggagaca    240

agcttcatca ccaacggctc ctgcctggcc tctagaaaga caagctttat gatggccctg    300

tgcctgtcta gcatctacga ggacctgaag atgtatcagg tggagttcaa gaccatgaac    360

gccaagctgc tgatggaccc caagaggcag atctttctgg atcagaatat gctggccgtg    420

atcgacgagc tgatgcaggc cctgaacttc aatagcgaga cagtgcctca gaagtcctct    480

ctggaggagc cagatttcta caagaccaag atcaagctgt gcatcctgct gcacgccttt    540

cggatcagag ccgtgacaat cgaccgcgtg atgtcctatc tgaatgcttc ctaa          594
```

<210> SEQ ID NO 56
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

His Asn Arg Thr Lys Ser Phe 1 5

<210> SEQ ID NO 57
<211> LENGTH: 918
<212> TYPE: DNA
<213> ORGANISM: Homo sapiens

<400> SEQUENCE: 57
atatgggaac tgaagaaaga tgtttatgtc gtagaattgg attggtatcc ggatgcccct 60
ggagaaatgg tggtcctcac ctgtgacacc cctgaagaag atggtatcac ctggaccttg 120
gaccagagca gtgaggtctt aggctctggc aaaaccctga ccatccaagt caaagagttt 180
ggagatgctg gccagtacac ctgtcacaaa ggaggcgagg ttctaagcca ttcgctcctg 240
ctgcttcaca aaaaggaaga tggaatttgg tccactgata ttttaaagga ccagaaagaa 300
cccaaaaata agacctttct aagatgcgag gccaagaatt attctggacg tttcacctgc 360
tggtggctga cgacaatcag tactgatttg acattcagtg tcaaaagcag cagaggctct 420
tctgaccccc aaggggtgac gtgcggagct gctacactct ctgcagagag agtcagaggg 480
gacaacaagg agtatgagta ctcagtggag tgccaggagg acagtgcctg cccagctgct 540
gaggagagtc tgcccattga ggtcatggtg gatgccgttc acaagctcaa gtatgaaaac 600
tacaccagca gcttcttcat cagggacatc atcaaacctg acccacccaa gaacttgcag 660
ctgaagccat taaagaattc tcggcaggtg gaggtcagct gggagtaccc tgacacctgg 720
agtactccac attcctactt ctccctgaca ttctgcgttc aggtccaggg caagagcaag 780
agagaaaaga aagatagagt cttcacggac aagacctcag ccacggtcat ctgccgcaaa 840
aatgccagca ttagcgtgcg ggcccaggac cgctactata gctcatcttg gagcgaatgg 900
gcatctgtgc cctgcagt 918

<210> SEQ ID NO 58
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

His Asn Lys Thr Lys Ser Phe
1 5

<210> SEQ ID NO 59
<211> LENGTH: 918
<212> TYPE: DNA
<213> ORGANISM: Homo sapiens

<400> SEQUENCE: 59
atctgggaac tgaaaaagga tgtgtacgtg gtggagctgg actggtatcc cgatgcccct 60
ggcgagatgg tggtgctgac ctgcgacaca cccgaggagg atggcatcac ctggacactg 120
gatcagagct ccgaggtgct gggaagcggc aagaccctga caatccaggt gaaggagttc 180
ggcgacgccg gccagtacac ctgtcacaag ggaggagagg tgctgagcca ctccctgctg 240
ctgctgcaca agaaggagga tggcatctgg tccacagaca tcctgaagga tcagaaggag 300
ccaaagaaca agaccttcct gcggtgcgag gccaagaatt atagcggccg gttcacctgt 360
tggtggctga ccacaatctc caccgatctg acattttctg tgaagtctag caggggatcc 420
tctgacccac agggagtgac atgcggagca gccaccctga gcgccgagag ggtgcgcggc 480
gataacaagg agtacgagta ttccgtggag tgccaggagg actctgcctg tccagcagca 540
gaggagtccc tgcctatcga agtgatggtg gatgccgtgc acaagctgaa gtacgagaat 600
tataccagct ccttctttat ccgggacatc atcaagcccg atccccctaa gaacctgcag 660
ctgaagcctc tgaagaatag cagacaggtg gaggtgtcct gggagtaccc tgacacctgg 720
agcacaccac actcctattt ctctctgacc ttttgcgtgc aggtgcaggg caagtccaag 780
cgggagaaga aggacagagt gttcaccgat aagacatctg ccaccgtgat ctgtagaaag 840
aacgcctcta tcagcgtgag ggcccaggac cgctactatt ctagctcctg gtccgagtgg 900
gcctctgtgc cttgcagc 918

<210> SEQ ID NO 60
<211> LENGTH: 16824
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 60
accaaacaaa gauuugguga augacgagac uacacucaag aauaauugug cgcaaccuuu 60
uuuuaagaca uuuauuugag uucgaauucg aguccuaagg agucaggguu caacuuuuuu 120
cuaacauaau augauuaaau caacaagaau acaauuggcc aaaaaaggag ccuauuaaua 180
ugugauuuuc guuaagaguc acaguuacug uaauauccuu ugacugcauu gccuauaguu 240
uucauguaga auuuuuguug agcacgaguc aaguacagua cagaaguguc uguaaacauu 300
ucuuugaguu ugguaauacc uaggacagcc uucaaauauu uagggcaggu acuaugcuuc 360
aaguaugucc uuagugggau aagguccucc auggagauca ugccuuuaag cacuaggcug 420
auuauaucgc cuauuuuauu gagauuuucg acucuaagac cuaguauugu aaccucuagg 480
aucugucucg ugcacuguuu aagugauguc cucuuuuucc cgucaguaga gagauuguaa 540
gggguaaaua gaaauacugu gucagcgaga ucacccucag cuuccauaua uaucacagac 600
cggauaacug ugucaaugug acuagcgaug aucuggguua ucugaguuau guucgcuagc 660
gugcucacca gacucuccgc acagaaugga cggacgggcu guccccggc uucaaucagc 720 gcagugucaa uauucuuccu caaguacuuu auuaaucuug guaaaggacu ggauaggaug 780
ucugucacac gcugccgcug ugaggugaau aaccugguca gugugaucuc aucugauuua 840
gacaaaagcg uaccgugccg cugcaccaga guuuucgcca uccucaccac cucauguaca 900
aauguaggcc cgcccaggua acccaugaca aauaccaggu aacacuccau aucuccucga 960
caugcauaac cauuagagag aauauauccu uuuguggaac acggagcaaa caaguucaug 1020
aguagaugaa aguaguaucc cauugcauac aacacuuuga ugauuacuac cccgcccucc 1080
cuuacagaau gcauggcaau cagagauaaa uugauagcua guugaucuag uaagcuuuga 1140
uuggacccug gaggaauuuc aaugucacaa ugcagcaaug auacagaucu guagggcacu 1200
gcagauguaa uauaccccac uacuuuaucu gaggucaggu cgcuuuccuc uguauuuucu 1260
cuccauaaug gacggaacuc uuggacaaau ccaucuuugc auguuaccuc cgccuguaga 1320
uuccuauaaa caaccgaauu caaaaacuga guuggggucg gcccgaaaug ucguugcggg 1380 gguucaucu cauuugaaaa gagcguauug uaauagauag uuucaugugg uacaugcagu 1440
ucgagaagac ucaugauggc uccgcucccu ucagcuaagu auaaggaguu cccgugucuu 1500
gcacaucuua ccucggguac agaaaggaga ugagaugccu uauaccaaga ggaagaugca 1560
gucccuaucc cucugaacaa guaucguacu aaguagucuu ccuccggauu uggagaugug 1620
aguucaggau gaaucugacu aagugugaau gcgucauacc uugcuggagc acucaaaucu 1680
aacucuugca aaaaugccgc agguugucgg gugaauggau cuuucacucg agcaccaaua 1740
ucuugcacag aagggaacuc uaauaauggc ucuuggggga acaacaacgc caggauagua 1800
ucccuguccu cccuuucccu gaucaaauug aggcucuucc gagacaugua guacagauua 1860
gcugggaaug uaauuauguu aggagacaug auagagcuca cuugaucggg gcuaaguaau 1920
gguuucacag cauccgacag uaaauacuca gugaguauug aacauuucuc uucugcaguu 1980
aagccucuua uuuucgggau uucucuuguu guagcaaaga guaccgugua cagacagcau 2040
aaccgggaua ucagcugaag caucuucuca uucagguuau caucuaagac agaugggaac 2100
agcagaucau acuuauuucc ugaauauaag ccggagauca cacgucgggu gcaagauacu 2160
aauaguuuug cagacauuuc gauaaaaucc guaucugcaa guuggugauga uccgucaugg 2220
uugaccaggc ccacugcaug uaaccuugaa ugaaugacgg gaugagauau uguagcugca 2280
auguuggaaa guagaauucc uggcauauuc uuguauaaau cacccauaua uaagacaaua 2340
uuguccaggc cucuuacucu cagguaauag aguugguaag aacagucgag gagcacuuca 2400
agugcugcau auucaaauag gcggaccaca ucugaauucu gagcuucacu gauccaauuu 2460
cggguauugu cauacacuau uauggcguca uucuuuaugg agguaucuuc aucauaagaa 2520
accacagacu ggccaaucaa cuucccgcug gauauugaaa gaauguucau uagcucuauc 2580
gugggauaug acuccagauu aagcucauaa cucuugaaga uagcuaaguc aagucucgca 2640
aagucucccu ccgauacagg gcuaggauca uacauaaacu uauuugaggu cacuguccuc 2700
aguuccggua ccaccccaag uagcucgaaa ggaaccgcaa caggugcuuc ucugauacag 2760
caacuaaauu uacuauguag gugcagugug aucucaucau auguccuggu uguugucauu 2820
ggaaagaucg auucgauuag agauaaaccc aagagcauga ucuguuggua aaccacauuc 2880
cccucuuuga cuccuucuuc agugaacagc cuuugagaau cauuggauau gugaauguaa 2940
ggugacaccc uguagagaga ugcaggggug aaugucaucu gaguuauacc aucaucuagu 3000
cuauguugaa gauucccagc cguggguaaa ggggacagua accgaagaua cucuaaguuu 3060
acauuacacc gagauuuugc aaucguaaga gcagcagucc aauuuacuuc auuaucccca 3120
uaagcccaga ucaacacgga ugaugcccuu agggcagccu uuacaugugg cgacauauga 3180
gcuauuuuug caagugaggc agcucuccuc uccugugucu uugacccgag auaugguacc 3240
cucaucggag gauucuugcu ggugucaucg gucaauucua uauugcuugg aagauggaac 3300
caaguaaauu guucaucucc gcugucacau cuuguacacc cuccgcuuac acuaagaauc 3360
ucacccucua cgaguucuau cguaucagga uuagauacac ccaguauuuu ccugccuccc 3420
gucaaaggug accagcuucu auuccgugca uagucugcca gugucagaga acacauauua 3480
gaagagacua aggggugguu ggaucuacug gaggaaaaaa caucgucucu aaacagcauu 3540
gcaugcaugc uagaauaauu gacuauccgc aucagccucu ugaugccuaa uggccuccua 3600
guaagcgcaa ucuuaauuac gguguuuguu gugucaacaa gcccuugaau uugcuuucuc 3660
cuaccuacag agcuugccuc caugauggca ugcgcaacgc ggggaugaau caccucuuga 3720
uuaagcaaga auucagccaa ugccuucucu ucugccucau uauccucugu gugcacucca 3780
gacaauaagg gauuugaaca aguuucaaau aggacucuuu gcguauguuu cuuaagaaca 3840

-continued

```
auauuugggc uugcaacagu cucaaaauug aaagaguaug ggucguugca cagacuggcc   3900
caaucuccau ucccaggcgg ccuaguuaag auauuaguca uaauguuagg acucaguaau   3960
cccacugcuu cuagucgcuu gaucucugca aaagcaguag uccccggguc accgauauuu   4020
cuaguguaga gccuugagua uugaagguua cucagucccc cuaauugggc aggagucaga   4080
acauaugagu gcacaaaaga gauguccuca auccacgacu gauuaagauc ggggugcgaa   4140
uuguugguga uggagaacuc agagucaaag uaugucugca cacaacucau uauauaguuu   4200
aaauaguaac agaagucuuu gggaagcccg uucucgcaua gccgugcuac aguagaggca   4260
auguuggcac aggacauuac gguguuuuca cugagaucac cugacacuag cacuaauuua   4320
gaugaauuuu ugaggacuug acugaggauu gcuccaucuu ugaagauucg uuugcuguau   4380
augaagaaug ugucugaccu gaugguuuca cgauccuuca aauuauggcc aaucaaauga   4440
uugacaugaa uuaauuccuu gaagaaauua ucacuggcuu gaugcaacug ugucaacacc   4500
aucuccggag agucgucuga ucuuaccucu cucguuacug cuauuacuug auuaucaccc   4560
uguaccauac aggcaacacg acaaugcgau cuagcugcag caaguuggau ugcagcaauu   4620
gagaucauug uccauagcuu cuggcauaau ccuucgauac ccccucuggc acugacaaua   4680
uauaugucau cauuagggac ucuugagagg ucacagucag uagggucacu uggaggauug   4740
aaagggucuc cuacgaacau cguagugucc aucagucuua ggugaaucca uucgaagaag   4800
ugagguaggc ccaucaacug auugauggca ugagcgaaca auuugauugu cugauaucuc   4860
caauuaagac aguacuuuug caggucaguu guuaugaagg uugcaacucu ccgacgguuc   4920
uugcuuuucg gaucaugauu gcgguuugaa gauacucuuu cuuuacaguc agugauacgu   4980
uucuuauugc uguuaaaaga caguugacuc aucgcuagca uacucuuggu caaggauaug   5040
cuauccugaa ugacuccauu ucccugaaag aaaggugcaa ucugaucggc uaggaucccu   5100
uccgccauca ccugacaguu ccuuaacuuc uuugucagcu uagcgaagau ccguccauua   5160
acuuucacuu ccuucuccuu gagcgaguau gauacugcca cauugucauc ucuaagguac   5220
ucaagggucg ucagauauuc caucucuuua uauggaucaa aaucauuuga cucuaaaaac   5280
ucuaucaaga ggcgauuagu cgaaguugcu ucuuuuacau guuucuucug gucuucggag   5340
agaagguucc gccuaaacga ggcaagccaa uuaucguugg ggugugcgau ugccuugucu   5400
uuuaggaaca ugcucagguu ggugacaggg ucauauucua uacauggcuc aaauucaagu   5460
gcagauaaac ucuuauacuc ucucaacaug auaucgugug aaaucucugc ugaaucugca   5520
uguaguugcc caaugaccuu cccauauauu guauccacuu ugacucgcgg ccacacaccu   5580
gcauucuucu uucuguaccc guugaugauu guucccuuga agaaagacag uaccugaagg   5640
aucauaucaa agucuaccau uuucggugcg cacauuuggc uccugacugc cuuugcugca   5700
auacgggacu caagcagugg gugaccccac agacgcaaca gacacaacau cucagcugcu   5760
ugauucuguu cuaaaccaga gaauacagua gcgauugcau gagucacgga uucugcuaua   5820
ucauugggga ggaggccaau uagaaugucu uuaagcuccu gcagguugaa ugcgaagaaa   5880
ucuccugcaa auguaccuga cggcucgagu agcuggacag cuccguaugc aaaucccucc   5940
auuagugaua caacaucgua gacuugauua cccaagucuu uugccagagc gucuauuaac   6000
cgcaaaaugu caucaauuuu cucugauaag cuucugagau gcaccgccgu gguugauauu   6060
auguugacca uaucucugcc cuccaucaua ucugcauaca ucaauacaag uuccugggua   6120
agacauguga acuuguucuc auucguaugc gucacaacga caaguucagg agugacaaag   6180
acuuggccua ccuuaugggu uagcaucacc aauuuguugg ccgcagaccu uguccuagcu   6240
```

-continued

```
gccaccauca gaugccucug gaucuguuuu auauggagcc augcaaacuu ggcuguggac   6300
cauuuugagu gaaaccagaa ugccggaucc guacgaaugc ugcugaacuc cucugaccgg   6360
gggacauugu uagaccaaga ugaccccagc aguuucuucu cuauaugcgu acacagccuu   6420
gugaacaguu cuccauaucu cguguuguga auuuggaucu ucuucucaau cuuccgaaau   6480
uuguugguug aaucugggac cucaauauua gccaguucuu cuaaacaccu gggguggagc   6540
acuccgguua uucuggaauu gugguuaaga guuuggugua cugcccuucc gaguuuuauc   6600
auucucucag uaucaggaga ggccgauuca aguauuuuuu uccauugucg gcugagaaug   6660
agguggucga agucacauuc aucaggaagc gguagcccag uuaauuucca guaauagagu   6720
aguuugugcu ugaccaaugg ugaagacagg ugugacucug guaggauaau cugaugcucu   6780
gcccuuucag gaccggagcu cgccaugucc uacccguauu guuaaccaug agcuguuuug   6840
ccuuguaucu cauugccacu uacauuuuuu cuuaaucaag agacuauuga caaggcuuaa   6900
ucugaucgca ugagcacugg cugauugugg ucaacuggca acauggaauu cgagcacgcg   6960
ccggcauucg guuugauucu ugaugucgca gaagauaggu gauacaaugc caucuuucca   7020
acuccuuuau aauugacuca acuagccaga ccuggcuucu cuaaccccgu caucuuugag   7080
gaucucaacu aguaacggga cgauucugaa uucuccgaag agaguauuag auauuucagc   7140
aaugcugaga caauaggucu uauuagucuu gaccacuuua aaacaaguug auguugugua   7200
ugcugcuuug guacugcuug aacucacucg aguaaugcga cugcgggaug ugcuaucgaa   7260
uacugcagac gcaggguuaa gucuugcuug uacaccauca agcauugucc cgaauacccc   7320
ucgcaaggug ugguuucuau agaagauuag gggauaugga ucuguauaga cuccaguaac   7380
acacgaguug gggcaucuug cugaagccug gcaagggaua cuaccuggcc gagugaaggc   7440
auugaaugua uaaggacuau gaagaguggc uguuuuguug cugacuguca uaggauauaa   7500
uaacgcggga gagaaguaug augacccucg uugauacaag aaaugagaug ucccuacugu   7560
gagaauucug ccuucggccc ccaugagugu gacuguguug ggcgguacag ucaguaccgg   7620
gucuucgccu aaggauguug acaccuugau agauaagaua gccugcugua ugcguuuccc   7680
accaaaccgu ccaggcuuau acgaagacuu ggccauucga aucugguagu cuugcucauc   7740
ugggcaugug ucauuguauc gcuuguauau cacauauuuc ccuuccugua cagugucacu   7800
gggugaauug gguuuuaacc cuccguagac ugagaaccau acgcggcugu caauaaaaga   7860
uccaccccu acuccugggu aguuggccac ccaguccccg aauaauguug ugacaucuag   7920
guccuuuucg ugguacuggc cgucgaaccc uaaccuccca uguaccaucc gcguagggac   7980
agcugaguua uaaucuucuu ccucugucuc cgugacuuuc gagcacagca uaucacaacc   8040
caggggaguu gcacucacac ugcaagacuu ccgauuuugg gugucgucca gguugaugga   8100
acgcagagua gaaaagaaua cccucccugu ugcagauguc cggagcacac caagugcuaa   8160
auacugauau gaaugugagu gaucucugca uccagacaau auuacauuau ggguguagca   8220
guaaugggua gcacucaugu caaaugaggg uauucgagug caaccugauc cuguaguagg   8280
cgccgggaua aaauucagau guucuugaaa ugcagaggga uagaaugaug ugacaucacu   8340
agcaucaucu acaaugaguu cuuugccuau ccccccuaua uaaucugggu cauggauagg   8400
ugcccccac ccacuguugu uugcagcucc auuaaucuga uaagagagag auguuauugc   8460
guucauaauu guggucucag uauuuaacaa ugccaacgga gacucaaggg ccacuugcuu   8520
auauauccua ucuacuacau cuugauugga accaagugua gauguaaucu uuucuucugc   8580
```

-continued

```
ccuggaaauc cuagucggua ugccuacaag aucgcuaggu gugcuagccc ccaugcuaua   8640
uaaaagggag gcuacagaua uagccaaggu cacuacuguu aagaauaaga uugcaauccg   8700
gaauaucaag cgccauguau uuuuugccuc ucuuucauca uucucuaacg caacuuggcu   8760
aacggcgcgg uccaugauug aggacuguug ucggugaagc gguagaacgg agguugugaa   8820
gccuggcucg caauugaggg gcggccucuc uuaccguucu acccguauau cguccuuugg   8880
ucaucuacaa ccgguaguuu uuucuuaacu cucugaacug acagacuacc agaacuuuca   8940
cacaaauuac uauuagggaa accuucguuc cucaucugug uucacauuuu uguaguggcu   9000
cucaucugau cuagaguauu auucccaagc cauaauaagg ucuuuuguug cgccuuuugc   9060
uuguacauua gguagcaugc uagaaucagg cuaaguauac caaaaacaag agauaugaua   9120
gucaaaacga uauagguaau gagagcagau gugcuaguca guuugacauu gacuuugucu   9180
aguuuucugu ugcuuuccuc uaacuuauuc aaagcauuac ugaucgaguu guugacauuc   9240
ccaagcucag uugagauauc aagauugccu guuauuauua cuugagaauc uuguauugag   9300
auauucuucu gauaaguuac aucgaauucc ccacugagcc uuaaaguuau cccgccuaag   9360
gauaaaacau ugcaugauug uuuaucuauu agagacacgg cuucuccaua guuuugcgau   9420
augauacccg gggggguuac acaucuacau guugucaucu ugcaguuggc gaugacugaa   9480
ccuuugauag ucauguaugg uguaguaagu gcgccuucgg ucuuugagua cauacaggcc   9540
gacguauugc cgcucaagca ggaauaaaua ccaggggaca uagggaacgu uacuauucuu   9600
guacaauaua aaucuaaguc aguuucuaua caguaugagg ugucaaguuc uucuaucaca   9660
gaaccgaccu gugucaccac uuuugggaca agugccgagg caaaucccccu gguugugcuu   9720
acggauaagg uuuccaagua gguggcacgc auauuauuua gguucccgac ugaaggggca   9780
guuaccugua uacccaagag uugagucugu gagucguaua gaauaggguu accggugauu   9840
aagccgcuac cgauuaauga gcugaguuga uuguucccua caccuaacuu agucaauaag   9900
uaauccauau uuccaccagc uagauuguaa agugccugaa uagucagcuu guuuaaagca   9960
ggugaaguga uuuguggucc gaauacugua gucaauucgg uuagguacag guugagcucu  10020
acaccaacuu gcugugcaau uuugaugcag ucuaauuccu gagcuguuuu auuaaauugg  10080
ucauuaacaa acugcugcau cuucccaacu gccacugcua guugcgauaa uccgucagug  10140
accucaugca cagccucauu gguugcggca augcucucuu uaagucggag gauguuggca  10200
gcauuuuguu uggcuuguau cagagcugcg gccgcuguua uuugugcggc aguugcaacc  10260
ccaagagcca caccgccaau aauggcgccu auaaggcgcc ccugucuccc cccuccagau  10320
guagucacag acucuuguau ccuacggaua gagucaccaa ggggggugag caaagugguc  10380
aauguccugu uguaugcauc caagggggcu uucgcacaug ccuccuuauc cuugggcaga  10440
uucgggagga gcuuaacuau gauugauccu gucugggaug agguguauau guugacggcu  10500
uugucuccug uaaccacaau uccugcagcu gcaagaggcc ugccaucaau ggaguuugcc  10560
ggacagaugc aacucaguac cagcgcaacc cggauaguca gcaucauagg ugcuggguuc  10620
uugguagaag gucuggagcc caucuugcac cuggagggcg ccaaccggga uccagaaucu  10680
ucuacccgug uuuuuucuaa cuugauagac agguaaacua acuguaaaua aucaagacag  10740
auuaguuuuu ugugucauga ugaucugggu gagugggcgg agcgcaaucu cagagacgca  10800
gcuuauuucu uaaaaggauu guauuuggca agggugugcc ccuucuccag cuuaguagag  10860
guaaccucgu ggucggcggu cacugcgaca gcgcguuggg uaccugcuug gauaaugauu  10920
uuaacgcucc gcaggcacgc gguuugacuc cagaguaucu uggccaccug aggagaagca  10980
```

uuugcuaugg gauagcaggc ugucccacug cuagagaaga aaggugccaa aagcuuaguc 11040
cgugcaccuc uugcuuuuac caacacggaa ggcccgagca caucacugag cccgacagau 11100
agaucaaggc uccuuauuuu cuuuuccagc uugucaaaug ucacuuucuu ccccuuccua 11160
ucuacagugg ucauaagucc aauaugcaag aagagguuag cauaguaucc gcugucagac 11220
uuagacagag auuuaaccaa aggacuccuc gggucuaccu ccacauuaau agugacauug 11280
agcgcaagau uguacagacu cgagccagaa accuucaaua cugcagcugg gaucuuguag 11340
acaucccucu ucgguaccac agucaaggag acaaaguuca ccuuguauuc uaggguucca 11400
cucccgggaa ucuucucugg cgcuuucacg ugcuugacug cauucacuga ugaguauuug 11460
uuugccacaa cccuacagcu uugcagcacu uggggugccu gcacuacuga gaaaaccauu 11520
cucucaguau uaguugcacu cuucuugcau gugacuauca uagugagaca ggcccuugcc 11580
agcucaauaa ggucuccggu auuugggacg cuuccuaggc agagcaucgc agcggaaagu 11640
aacucgcgcu uggguuuauc aucgaucaug ccgacggugg cuucuucauu cccaacuuga 11700
aagaugaauc cauagguggu gaugaauacu gaguccuccu uacuaucagu ccacaaguca 11760
aggcgcugga uccuauauug cggggcgauu ugcuucuucc caucuccugu gucuuguagg 11820
acgaucggaa augcuaacag guugcuagaa gaaugggcag aaucaaagua cagcccaauu 11880
guccuagaug aguccaucuu ggcacaauug gggcacucca auucuacccg uauuuuuucu 11940
uaaucuuaaa uguagcuaga uuaauuacgg uuacgcgauc auucaguggg gcugaggaag 12000
cgagagagga uugccgcuug gagaguugga ccuugggucc gcggaucauu aggaagcauu 12060
cagauagcuc aucacucuau caauagucac ugcccgaauu cugaaagcau gaagaaguau 12120
gcagagcuug auuuuaguuu uauaaaaauc cgguucuuca agggaggauu uuuguggcac 12180
agucucacug uugaaauuca gggccugcau cagcucauca auaacugcca gcauguuuug 12240
aucuagaaag aucugccucu uaggauccau cagaagcuuu gcauucaugg ucuugaacuc 12300
caccugguac aucuucaagu cuucauaaau acuacuaagg cacagggcca ucauaaaaga 12360
ggucuuucug gaggccaggc aacucccauu aguuaugaaa gaggucucuc uggaauuuag 12420
gcaacucuca uucuugguua auuccaaugg uaaacaggcc uccacugugc ugguuuuauc 12480
uuuugugaua ucuucaugau caaucucuuc agaagugcaa ggguaaaauu cuagaguuug 12540
ucuggccuuc uggagcaugu ugcugacggc ccucagcagg uuuugggagu ggugaaggca 12600
ugggaacauu ccugggucug gaguggccac ggggagguuu cuagauccgc cgccaccgcc 12660
accacugcag ggcacagaug cccauucgcu ccaagaugag cuauaguagc gguccugggc 12720
ccgcacgcua augcuggcau uuuugcggca gaugaccgug gcugaggucu uguccgugaa 12780
gacucuaucu uucuuuucuc ucuugcucuu gcccuggacc ugaacgcaga augucaggga 12840
gaaguaggaa uguggaguac uccaggugug agggguacucc cagcugaccu ccaccugccg 12900
agaauucuuu aauggcuuca gcugcaaguu cuugggguggg ucagguuuga ugaugucccu 12960
gaugaagaag cugcuggugu aguuuucaua cuugagcuug ugaacggcau ccaccaugac 13020
cucaaugggc agacucuccu cagcagcugg gcaggcacug uccuccuggc acuccacuga 13080
guacucauac uccuuguugu ccccucugac ucucucugca gagaguguag cagcuccgca 13140
cgucaccccu ugggggucag aagagccucu gcugcuuuug acacugaaug ucaaaucagu 13200
acugauuguc gucagccacc agcaggugaa acguccagaa uaauucuugg ccucgcaucu 13260
uagaaagguc uuauuuuugg guucuuucug guccuuuaaa auaucagugg accaaauucc 13320

-continued aucuuccuuu uugugaagca gcaggagcga auggcuuaga accucgccuc cuuugugaca 13380
gguguacugg ccagcaucuc caaacucuuu gacuuggaug gucaggguuu ugccagagcc 13440
uaagaccuca cugcucuggu ccaaggucca ggugauacca ucuucuucag gggugucaca 13500
ggugaggacc accauuucuc caggggcauc cggauaccaa uccaauucua cgacauaaac 13560
aucuuucuuc aguucccaua uggccacgag gggagaugcc agaaaaacca gggaaaacca 13620
agagaugacc aacugcuggu gacacauggu ggcgguucua cccguauuuu uucuaaccgc 13680
gggggggaac ucggugcaga uuccguguga ugccgagugg acagggaccc gcuacgugug 13740
gcaguaguaa uuagccauuu agagcaaggc gcuugauuuu ccugauuucc ucgaucgacc 13800
cggcugcauc uaacuugcuu aggagcuugg cugaagaacu cgggugcauu gggcgugaca 13860
ugaucaaugc acggacagug uccuuuucca cuccuauauc aggcccgcau gcaguggcgg 13920
guuuaaucaa uucagaugga uguggcacug guugcgaaag uuuauuaagu gccauuucgc 13980
cuccuugugu cacauaggga gaggggucuc cagggccuga aacuaaaacc gggugagauc 14040
gggcaacugc ccguagauca cucagagaug aaauguuggc acaaccggga uccagaaucu 14100
ucaucauucc caaguuggcu uccaugacug caacagaugu uuucagcugu uggauuucgg 14160
accgcaucau agggauggag gaugucuguu ucaagacaag aucuagcuga uagucaaccu 14220
uacuuacucu cugugauauc gccuccauca uagacaucau cgcuugcaca aagucuacag 14280
guggcuggac augauccgca gauacaaggg uauugucuug gcucugccuu gaucggagag 14340
caugaggggu ugcaccagcu gauaguugug acuccuccca uuguccauga uaugcugugu 14400
ucacgucugu gcccugguuu ccaggggcgg ccuugacuug guucugcggu cuuuccugac 14460
uguuuccgcg acuggguuga cuccccugcu guugagucgg acguugguga uuccccucuu 14520
gggggcucga ccaugggccc uuuuuagcau uggacgauuu auugcugagc uugucaagca 14580
ucaacagcag agaguugcuu gcuccggucc ugagcugugu gucgacggcu ucgucugugg 14640 ccugggugggg gggcuggucg gcggaugugg ccggcgggcu gucaugcggg gucguuugcu 14700
cgggugugga ugguuguuug ucagaucugu ccugucgauc gggguugucu ugacuggccg 14760
guggcuggau gcucccaugc uucucccaug cugcgcucag caccuugguc uugccuugug 14820
ggauugcacu ccuuccaaca gucucugcug guuuacccug ggcuguaauu auguugucaa 14880
ugacaguucc acuugucuca aauagcucgu cgaucucugc aucuguaaag guggccaugu 14940
uuguccuggu cuaucaggua gaggagagag cagagacucg ggagacuugc ccugaucucu 15000
gaauaucccu cuucuacccg uacuuuuuuc uaauucccuc ggcucuguuu ugauuguuag 15060
ugagccgcau ugugccugug guaucuaggg cguacguagu uguacagcag ggggagggag 15120
gaaagagggg gauguuuguu ugagggugug gucauauaga gccgcaaauc gaggggucga 15180
cuacggguga gggcauuggg auguuuuugu ggaagcaggc uggguuuugu ccaucaauac 15240
ccccagucgg ugucguuauc uugggauggc ccaggaguug ggggaggccc cgauugggga 15300
gugcccugug cagaguuugg cgccucccuc augcuauuug cuaccgcucu caucagaucc 15360
aggaauuggg ucuccccauc cccggcuucu gguugcccuu gcgaucuauu cgauccgccu 15420
uguagagcuu gggacccccc cucgcuaagc ccagugagga cuccgacuug uugaguaggc 15480
augucuaugc ugcuggucuc cucggagacc cguugggcag cagcugccag gccccuccuu 15540
gcugcugggg uuagcuuuag cucggcagcc auauccucgu uaaugcuacu ucccugagcc 15600
ugagcguacu cuacuccaag ucuccagaau gaugugcuca uaaagucccu ggcaaauugg 15660
uauuucccag uaccuuuauc uaggacugau gccauaccca uggcaaagga guaaaguugu 15720
gcauacucgg caggcgcaaa gcucaucugg ucacuaucac caaguaaugu cauguacggc 15780
gcauuaucuc cuuucauccg auacaaacgc augagcugcu ucaucuucug gaugucgccu 15840
gagaggcuac uaagugcaag ggcugauguc uugguguuga uuccguacuu gagugucaag 15900
aagaaugcag uaagcccggu auuccugaug uaugagucua cguccccuac cagguuauaa 15960
uaaguagagg uaccaccugc cguguugcgg ccucucuuga gcucgcuaac caaaaagaug 16020
cggacugcaa gagacugucu gaucgugagu uggauugugc uccugcauac gggguagagg 16080
auguauuucu uuuggacccu gccuugcugc auauacuuau ugauucgccu uguuuccgac 16140
ucaucugcag ucucauacgc agucauggcu uuugcuacug ugacccauac uugagccugg 16200
auagagagga uccucuccag gguaucggug augucuucug gugcaucauc uucggccccg 16260
gcugugacga acgggguucc guugcugcau gcccgaggga gagauccugc uaucaucgca 16320
aaucucugug cucucucuuc agacacucca cuccuauugu ugaacugggg cgugccguug 16380
gcaaagccau caaucucaag cacggccaau guggcuucau ucuguuuccc ugcaagggca 16440
acaugguucc ucauuaccug ugagugggag cauaaaaagag auaugagagc accuugccug 16500
agugguuugu uggcaucuuc gcuaacagca auccggaggc agaauaccac aaagcuccau 16560
cuaucuucug ggucaucacu guuaagagug aauaccggga cgucuacuuu uaagguacuc 16620
ccuuuuucuc ccccuccaug agcuccauug gggcgagucu gagccgcgag gagcuguucg 16680
uacucaucaa auacggaaga cauguuggca gaaggcuuuc ucgaguuugu gcuucgggcu 16740
cgcacucgag auucacaccu ucuacccgug cgacuucaau ugcuccuucg ccuuuuaucg 16800
uaacucacgg auucucuguu uggu 16824

<210> SEQ ID NO 61
<211> LENGTH: 1533
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 61
atatgggaac tgaagaaaga tgtttatgtc gtagaattgg attggtatcc ggatgcccct 60
ggagaaatgg tggtcctcac ctgtgacacc cctgaagaag atggtatcac ctggaccttg 120
gaccagagca gtgaggtctt aggctctggc aaaaccctga ccatccaagt caaagagttt 180
ggagatgctg gccagtacac ctgtcacaaa ggaggcgagg ttctaagcca ttcgctcctg 240
ctgcttcaca aaaaggaaga tggaatttgg tccactgata ttttaaagga ccagaaagaa 300
cccaaaaata agacctttct aagatgcgag gccaagaatt attctggacg tttcacctgc 360
tggtggctga cgacaatcag tactgatttg acattcagtg tcaaaagcag cagaggctct 420
tctgaccccc aaggggtgac gtgcggagct gctacactct ctgcagagag agtcagaggg 480
gacaacaagg agtatgagta ctcagtggag tgccaggagg acagtgcctg cccagctgct 540
gaggagagtc tgcccattga ggtcatggtg gatgccgttc acaagctcaa gtatgaaaac 600
tacaccagca gcttcttcat cagggacatc atcaaacctg acccacccaa gaacttgcag 660
ctgaagccat taaagaattc tcggcaggtg gaggtcagct gggagtaccc tgacacctgg 720
agtactccac attcctactt ctccctgaca ttctgcgttc aggtccaggg caagagcaag 780
agagaaaaga aagatagagt cttcacggac aagacctcag ccacggtcat ctgccgcaaa 840

```
aatgccagca ttagcgtgcg ggcccaggac cgctactata gctcatcttg gagcgaatgg    900

gcatctgtgc cctgcagtgg tggcggtggc ggcggatcta gaaacctccc cgtggccact    960

ccagacccag gaatgttccc atgccttcac cactcccaaa acctgctgag ggccgtcagc   1020

aacatgctcc agaaggccag acaaactcta gaattttacc cttgcacttc tgaagagatt   1080

gatcatgaag atatcacaaa agataaaacc agcacagtgg aggcctgttt accattggaa   1140

ttaaccaaga atgagagttg cctaaattcc agagagacct ctttcataac taatgggagt   1200

tgcctggcct ccagaaagac ctcttttatg atggccctgt gccttagtag tatttatgaa   1260

gactcgaaga tgtaccaggt ggagttcaag accatgaatg caaagcttct gatggatcct   1320

aagaggcaga tctttctaga tcaaaacatg ctggcagtta ttgatgagct gatgcaggcc   1380

ctgaatttca acagtgagac tgtgccacaa aaatcctccc ttgaagaacc ggatttttat   1440

aaaactaaaa tcaagctctg catacttctt catgctttca gaattcgggc agtgactatt   1500

gatagagtga tgagctatct gaatgcttcc taa                                1533
```

```
<210> SEQ ID NO 62
<211> LENGTH: 16824
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 62
```

```
accaaacaga gaatccgtga gttacgataa aaggcgaagg agcaattgaa gtcgcacggg     60

tagaaggtgt gaatctcgag tgcgagcccg aagcacaaac tcgagaaagc cttctgccaa    120

catgtcttcc gtatttgatg agtacgaaca gctcctcgcg gctcagactc gccccaatgg    180

agctcatgga gggggagaaa aagggagtac cttaaaagta gacgtcccgg tattcactct    240

taacagtgat gacccagaag atagatggag ctttgtggta ttctgcctcc ggattgctgt    300

tagcgaagat gccaacaaac cactcaggca aggtgctctc atatctcttt tatgctccca    360

ctcacaggta atgaggaacc atgttgccct tgcagggaaa cagaatgaag ccacattggc    420

cgtgcttgag attgatggct ttgccaacgg cacgccccag ttcaacaata ggagtggagt    480

gtctgaagag agagcacaga gatttgcgat gatagcagga tctctccctc gggcatgcag    540

caacggaacc ccgttcgtca cagccggggc cgaagatgat gcaccagaag acatcaccga    600

taccctggag aggatcctct ctatccaggc tcaagtatgg gtcacagtag caaaagccat    660

gactgcgtat gagactgcag atgagtcgga aacaaggcga atcaataagt atatgcagca    720

aggcagggtc caaaagaaat acatcctcta ccccgtatgc aggagcacaa tccaactcac    780

gatcagacag tctcttgcag tccgcatctt tttggttagc gagctcaaga gaggccgcaa    840

cacggcaggt ggtacctcta cttattataa cctggtaggg gacgtagact catacatcag    900

gaataccggg cttactgcat tcttcttgac actcaagtac ggaatcaaca ccaagacatc    960

agcccttgca cttagtagcc tctcaggcga catccagaag atgaagcagc tcatgcgttt   1020

gtatcggatg aaaggagata atgcgccgta catgacatta cttggtgata gtgaccagat   1080

gagctttgcg cctgccgagt atgcacaact ttactccttt gccatgggta tggcatcagt   1140

cctagataaa ggtactggga aataccaatt tgccagggac tttatgagca catcattctg   1200

gagacttgga gtagagtacg ctcaggctca gggaagtagc attaacgagg atatggctgc   1260

cgagctaaag ctaaccccag cagcaaggag ggcctggca gctgctgccc aacgggtctc   1320
```

-continued

```
cgaggagacc agcagcatag acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catcccccctc tttcctccct ccccctgctg tacaactacg tacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc cccgcggtt agaaaaaata cgggtagaac cgccaccatg   3180
tgccatcagc agctggtcat ctcatggttc tccctggtgt ttctggcctc acctctggtc   3240
gcaatctggg aactgaaaaa ggatgtgtac gtggtggagc tggactggta tcccgatgcc   3300
cctggcgaga tggtggtgct gacctgcgac acacccgagg aggatggcat cacctggaca   3360
ctggatcaga gctccgaggt gctgggaagc ggcaagaccc tgacaatcca ggtgaaggag   3420
ttcggcgacg ccggccagta cacctgtcac aagggaggag aggtgctgag ccactccctg   3480
ctgctgctgc acaagaagga ggatggcatc tggtccacag acatcctgaa ggatcagaag   3540
gagccaaaga acaagacctt cctgcggtgc gaggccaaga attatagcgg ccggttcacc   3600
tgttggtggc tgaccacaat ctccaccgat ctgacatttt ctgtgaagtc tagcagggga   3660
```

-continued

```
tcctctgacc cacagggagt gacatgcgga gcagccaccc tgagcgccga gagggtgcgc   3720
ggcgataaca aggagtacga gtattccgtg gagtgccagg aggactctgc ctgtccagca   3780
gcagaggagt ccctgcctat cgaagtgatg gtggatgccg tgcacaagct gaagtacgag   3840
aattatacca gctccttctt tatccgggac atcatcaagc ccgatccccc taagaacctg   3900
cagctgaagc ctctgaagaa tagcagacag gtggaggtgt cctgggagta ccctgacacc   3960
tggagcacac cacactccta tttctctctg accttttgcg tgcaggtgca gggcaagtcc   4020
aagcgggaga agaaggacag agtgttcacc gataagacat ctgccaccgt gatctgtaga   4080
aagaacgcct ctatcagcgt gagggcccag gaccgctact attctagctc ctggtccgag   4140
tgggcctctg tgccttgcag cggcggagga ggaggaggat ctaggaatct gccagtggca   4200
acccctgacc caggcatgtt cccctgcctg caccacagcc agaacctgct gagggccgtg   4260
tccaatatgc tgcagaaggc ccgccagaca ctggagtttt acccttgtac cagcgaggag   4320
atcgaccacg aggacatcac aaaggataag acctccacag tggaggcctg cctgccactg   4380
gagctgacca agaacgagtc ctgtctgaac agccgggaga caagcttcat caccaacggc   4440
tcctgcctgg cctctagaaa gacaagcttt atgatggccc tgtgcctgtc tagcatctac   4500
gaggacctga agatgtatca ggtggagttc aagaccatga acgccaagct gctgatggac   4560
cccaagaggc agatctttct ggatcagaat atgctggccg tgatcgacga gctgatgcag   4620
gccctgaact tcaatagcga gacagtgcct cagaagtcct ctctggagga gccagatttc   4680
tacaagacca agatcaagct gtgcatcctg ctgcacgcct ttcggatcag agccgtgaca   4740
atcgaccgcg tgatgtccta tctgaatgct tcctaatgat ccgcggaccc aaggtccaac   4800
tctccaagcg gcaatcctct ctcgcttcct cagccccact gaatgatcgc gtaaccgtaa   4860
ttaatctagc tacatttaag attaagaaaa aatacgggta gaattggagt gccccaattg   4920
tgccaagatg gactcatcta ggacaattgg gctgtacttt gattctgccc attcttctag   4980
caacctgtta gcatttccga tcgtcctaca agacacagga gatgggaaga agcaaatcgc   5040
cccgcaatat aggatccagc gccttgactt gtggactgat agtaaggagg actcagtatt   5100
catcaccacc tatggattca tctttcaagt tgggaatgaa gaagccaccg tcggcatgat   5160
cgatgataaa cccaagcgcg agttactttc cgctgcgatg ctctgcctag gaagcgtccc   5220
aaataccgga gaccttattg agctggcaag ggcctgtctc actatgatag tcacatgcaa   5280
gaagagtgca actaatactg agagaatggt tttctcagta gtgcaggcac cccaagtgct   5340
gcaaagctgt agggttgtgg caaacaaata ctcatcagtg aatgcagtca agcacgtgaa   5400
agcgccagag aagattcccg ggagtggaac cctagaatac aaggtgaact ttgtctcctt   5460
gactgtggta ccgaagaggg atgtctacaa gatcccagct gcagtattga aggtttctgg   5520
ctcgagtctg tacaatcttg cgctcaatgt cactattaat gtggaggtag acccgaggag   5580
tcctttggtt aaatctctgt ctaagtctga cagcggatac tatgctaacc tcttcttgca   5640
tattggactt atgaccactg tagataggaa ggggaagaaa gtgacatttg acaagctgga   5700
aaagaaaata aggagccttg atctatctgt cgggctcagt gatgtgctcg ggccttccgt   5760
gttggtaaaa gcaagaggtg cacggactaa gcttttggca cctttcttct ctagcagtgg   5820
gacagcctgc tatcccatag caaatgcttc tcctcaggtg gccaagatac tctggagtca   5880
aaccgcgtgc ctgcggagcg ttaaaatcat tatccaagca ggtacccaac gcgctgtcgc   5940
agtgaccgcc gaccacgagg ttacctctac taagctggag aaggggcaca cccttgccaa   6000
atacaatcct tttaagaaat aagctgcgtc tctgagattg cgctccgccc actcacccag   6060
```

-continued atcatcatga cacaaaaaac taatctgtct tgattattta cagttagttt acctgtctat 6120
caagttagaa aaaacacggg tagaagattc tggatcccgg ttggcgccct ccaggtgcaa 6180
gatgggctcc agaccttcta ccaagaaccc agcacctatg atgctgacta tccgggttgc 6240
gctggtactg agttgcatct gtccggcaaa ctccattgat ggcaggcctc ttgcagctgc 6300
aggaattgtg gttacaggag acaaagccgt caacatatac acctcatccc agacaggatc 6360
aatcatagtt aagctcctcc cgaatctgcc caaggataag gaggcatgtg cgaaagcccc 6420
cttggatgca tacaacagga cattgaccac tttgctcacc cccttggtg actctatccg 6480 taggatacaa gagtctgtga ctacatctgg aggggggaga caggggcgcc ttataggcgc 6540
cattattggc ggtgtggctc ttggggttgc aactgccgca caaataacag cggccgcagc 6600
tctgatacaa gccaaacaaa atgctgccaa catcctccga cttaaagaga gcattgccgc 6660
aaccaatgag gctgtgcatg aggtcactga cggattatcg caactagcag tggcagttgg 6720
gaagatgcag cagtttgtta atgaccaatt taataaaaca gctcaggaat tagactgcat 6780
caaaattgca cagcaagttg gtgtagagct caacctgtac ctaaccgaat tgactacagt 6840
attcggacca caaatcactt cacctgcttt aaacaagctg actattcagg cactttacaa 6900
tctagctggt ggaaatatgg attacttatt gactaagtta ggtgtaggga acaatcaact 6960
cagctcatta atcggtagcg gcttaatcac cggtaaccct attctatacg actcacagac 7020
tcaactcttg ggtatacagg taactgcccc ttcagtcggg aacctaaata atatgcgtgc 7080
cacctacttg gaaaccttat ccgtaagcac aaccagggga tttgcctcgg cacttgtccc 7140
aaaagtggtg acacaggtcg gttctgtgat agaagaactt gacacctcat actgtataga 7200
aactgactta gatttatatt gtacaagaat agtaacgttc cctatgtccc ctggtattta 7260
ttcctgcttg agcggcaata cgtcggcctg tatgtactca aagaccgaag gcgcacttac 7320
tacaccatac atgactatca aaggttcagt catcgccaac tgcaagatga caacatgtag 7380
atgtgtaaac cccccgggta tcatatcgca aaactatgga gaagccgtgt ctctaataga 7440
taaacaatca tgcaatgttt tatccttagg cgggataact ttaaggctca gtggggaatt 7500
cgatgtaact tatcagaaga atatctcaat acaagattct caagtaataa taacaggcaa 7560
tcttgatatc tcaactgagc ttgggaatgt caacaactcg atcagtaatg ctttgaataa 7620
gttagaggaa agcaacagaa aactagacaa agtcaatgtc aaactgacta gcacatctgc 7680
tctcattacc tatatcgttt tgactatcat atctcttgtt tttggtatac ttagcctgat 7740
tctagcatgc tacctaatgt acaagcaaaa ggcgcaacaa aagaccttat tatggcttgg 7800
gaataatact ctagatcaga tgagagccac tacaaaaatg tgaacacaga tgaggaacga 7860
aggtttccct aatagtaatt tgtgtgaaag ttctggtagt ctgtcagttc agagagttaa 7920
gaaaaaacta ccggttgtag atgaccaaag gacgatatac gggtagaacg gtaagagagg 7980
ccgcccctca attgcgagcc aggcttcaca acctccgttc taccgcttca ccgacaacag 8040
tcctcaatca tggaccgcgc cgttagccaa gttgcgttag agaatgatga aagagaggca 8100
aaaaatacat ggcgcttgat attccggatt gcaatcttat tcttaacagt agtgaccttg 8160
gctatatctg tagcctccct tttatatagc atgggggcta gcacacctag cgatcttgta 8220
ggcataccga ctaggatttc cagggcagaa gaaaagatta catctacact tggttccaat 8280
caagatgtag tagataggat atataagcaa gtggcccttg agtctccgtt ggcattgtta 8340
aatactgaga ccacaattat gaacgcaata acatctctct cttatcagat taatggagct 8400

-continued

```
gcaaacaaca gtgggtgggg ggcacctatc catgacccag attatatagg ggggataggc   8460
aaagaactca ttgtagatga tgctagtgat gtcacatcat tctatccctc tgcatttcaa   8520
gaacatctga attttatccc ggcgcctact acaggatcag gttgcactcg aataccctca   8580
tttgacatga gtgctaccca ttactgctac acccataatg taatattgtc tggatgcaga   8640
gatcactcac attcatatca gtatttagca cttggtgtgc tccggacatc tgcaacaggg   8700
agggtattct tttctactct gcgttccatc aacctggacg acacccaaaa tcggaagtct   8760
tgcagtgtga gtgcaactcc cctgggttgt gatatgctgt gctcgaaagt cacggagaca   8820
gaggaagaag attataactc agctgtccct acgcggatgg tacatgggag gttagggttc   8880
gacggccagt accacgaaaa ggacctagat gtcacaacat tattcgggga ctgggtggcc   8940
aactacccag gagtaggggg tggatctttt attgacagcc gcgtatggtt ctcagtctac   9000
ggagggttaa aacccaattc acccagtgac actgtacagg aagggaaata tgtgatatac   9060
aagcgataca atgacacatg cccagatgag caagactacc agattcgaat ggccaagtct   9120
tcgtataagc ctggacggtt tggtgggaaa cgcatacagc aggctatctt atctatcaag   9180
gtgtcaacat ccttaggcga agacccggta ctgactgtac cgcccaacac agtcacactc   9240
atgggggccg aaggcagaat tctcacagta gggacatctc atttcttgta tcaacgaggg   9300
tcatcatact tctctcccgc gttattatat cctatgacag tcagcaacaa aacagccact   9360
cttcatagtc cttatacatt caatgccttc actcggccag gtagtatccc ttgccaggct   9420
tcagcaagat gccccaactc gtgtgttact ggagtctata cagatccata tcccctaatc   9480
ttctatagaa accacacctt gcgaggggta ttcgggacaa tgcttgatgg tgtacaagca   9540
agacttaacc ctgcgtctgc agtattcgat agcacatccc gcagtcgcat tactcgagtg   9600
agttcaagca gtaccaaagc agcatacaca acatcaactt gttttaaagt ggtcaagact   9660
aataagacct attgtctcag cattgctgaa atatctaata ctctcttcgg agaattcaga   9720
atcgtcccgt tactagttga gatcctcaaa gatgacgggg ttagagaagc caggtctggc   9780
tagttgagtc aattataaag gagttggaaa gatggcattg tatcacctat cttctgcgac   9840
atcaagaatc aaaccgaatg ccggcgcgtg ctcgaattcc atgttgccag ttgaccacaa   9900
tcagccagtg ctcatgcgat cagattaagc cttgtcaata gtctcttgat taagaaaaaa   9960
tgtaagtggc aatgagatac aaggcaaaac agctcatggt taacaatacg ggtaggacat  10020
ggcgagctcc ggtcctgaaa gggcagagca tcagattatc ctaccagagt cacacctgtc  10080
ttcaccattg gtcaagcaca aactactcta ttactggaaa ttaactgggc taccgcttcc  10140
tgatgaatgt gacttcgacc acctcattct cagccgacaa tggaaaaaaa tacttgaatc  10200
ggcctctcct gatactgaga gaatgataaa actcggaagg gcagtacacc aaactcttaa  10260
ccacaattcc agaataaccg gagtgctcca ccccaggtgt ttagaagaac tggctaatat  10320
tgaggtccca gattcaacca acaaatttcg gaagattgag aagaagatcc aaattcacaa  10380
cacgagatat ggagaactgt tcacaaggct gtgtacgcat atagagaaga aactgctggg  10440
gtcatcttgg tctaacaatg tcccccggtc agaggagttc agcagcattc gtacggatcc  10500
ggcattctgg tttcactcaa aatggtccac agccaagttt gcatggctcc atataaaaca  10560
gatccagagg catctgatgg tggcagctag gacaaggtct gcggccaaca aattggtgat  10620
gctaacccat aaggtaggcc aagtctttgt cactcctgaa cttgtcgttg tgacgcatac  10680
gaatgagaac aagttcacat gtcttaccca ggaacttgta ttgatgtatg cagatatgat  10740
ggagggcaga gatatggtca acataatatc aaccacggcg gtgcatctca gaagcttatc  10800
```

```
agagaaaatt gatgacattt tgcggttaat agacgctctg gcaaaagact tgggtaatca  10860
agtctacgat gttgtatcac taatggaggg atttgcatac ggagctgtcc agctactcga  10920
gccgtcaggt acatttgcag gagatttctt cgcattcaac ctgcaggagc ttaaagacat  10980
tctaattggc ctcctcccca atgatatagc agaatccgtg actcatgcaa tcgctactgt  11040
attctctggt ttagaacaga atcaagcagc tgagatgttg tgtctgttgc gtctgtgggg  11100
tcacccactg cttgagtccc gtattgcagc aaaggcagtc aggagccaaa tgtgcgcacc  11160
gaaaatggta gactttgata tgatccttca ggtactgtct ttcttcaagg gaacaatcat  11220
caacgggtac agaaagaaga atgcaggtgt gtggccgcga gtcaaagtgg atacaatata  11280
tgggaaggtc attgggcaac tacatgcaga ttcagcagag atttcacacg atatcatgtt  11340
gagagagtat aagagtttat ctgcacttga atttgagcca tgtatagaat atgaccctgt  11400
caccaacctg agcatgttcc taaaagacaa ggcaatcgca caccccaacg ataattggct  11460
tgcctcgttt aggcggaacc ttctctccga agaccagaag aaacatgtaa aagaagcaac  11520
ttcgactaat cgcctcttga tagagttttt agagtcaaat gattttgatc catataaaga  11580
gatggaatat ctgacgaccc ttgagtacct tagagatgac aatgtggcag tatcatactc  11640
gctcaaggag aaggaagtga aagttaatgg acggatcttc gctaagctga caaagaagtt  11700
aaggaactgt caggtgatgg cggaagggat cctagccgat cagattgcac ctttctttca  11760
gggaaatgga gtcattcagg atagcatatc cttgaccaag agtatgctag cgatgagtca  11820
actgtctttt aacagcaata agaaacgtat cactgactgt aaagaaagag tatcttcaaa  11880
ccgcaatcat gatccgaaaa gcaagaaccg tcggagagtt gcaaccttca taacaactga  11940
cctgcaaaag tactgtctta attggagata tcagacaatc aaattgttcg ctcatgccat  12000
caatcagttg atgggcctac ctcacttctt cgaatggatt cacctaagac tgatggacac  12060
tacgatgttc gtaggagacc ctttcaatcc tccaagtgac cctactgact gtgacctctc  12120
aagagtccct aatgatgaca tatatattgt cagtgccaga gggggtatcg aaggattatg  12180
ccagaagcta tggacaatga tctcaattgc tgcaatccaa cttgctgcag ctagatcgca  12240
ttgtcgtgtt gcctgtatgg tacagggtga taatcaagta atagcagtaa cgagagaggt  12300
aagatcagac gactctccgg agatggtgtt gacacagttg catcaagcca gtgataattt  12360
cttcaaggaa ttaattcatg tcaatcattt gattggccat aatttgaagg atcgtgaaac  12420
catcaggtca gacacattct tcatatacag caaacgaatc ttcaaagatg gagcaatcct  12480
cagtcaagtc ctcaaaaatt catctaaatt agtgctagtg tcaggtgatc tcagtgaaaa  12540
caccgtaatg tcctgtgcca acattgcctc tactgtagca cggctatgcg agaacgggct  12600
tcccaaagac ttctgttact atttaaacta tataatgagt tgtgtgcaga catactttga  12660
ctctgagttc tccatcacca acaattcgca ccccgatctt aatcagtcgt ggattgagga  12720
catctctttt gtgcactcat atgttctgac tcctgcccaa ttagggggac tgagtaacct  12780
tcaatactca aggctctaca ctagaaatat cggtgacccg gggactactg cttttgcaga  12840
gatcaagcga ctagaagcag tgggattact gagtcctaac attatgacta atatcttaac  12900
taggccgcct gggaatggag attgggccag tctgtgcaac gacccatact ctttcaattt  12960
tgagactgtt gcaagcccaa atattgttct taagaaacat acgcaaagag tcctatttga  13020
aacttgttca aatcccttat tgtctggagt gcacacagag gataatgagg cagaagagaa  13080
ggcattggct gaattcttgc ttaatcaaga ggtgattcat ccccgcgttg cgcatgccat  13140
```

-continued

```
catggaggca agctctgtag gtaggagaaa gcaaattcaa gggcttgttg acacaacaaa  13200
caccgtaatt aagattgcgc ttactaggag gccattaggc atcaagaggc tgatgcggat  13260
agtcaattat tctagcatgc atgcaatgct gtttagagac gatgtttttt cctccagtag  13320
atccaaccac cccttagtct cttctaatat gtgttctctg acactggcag actatgcacg  13380
gaatagaagc tggtcacctt tgacgggagg caggaaaata ctgggtgtat ctaatcctga  13440
tacgatagaa ctcgtagagg gtgagattct tagtgtaagc ggagggtgta caagatgtga  13500
cagcggagat gaacaattta cttggttcca tcttccaagc aatatagaat tgaccgatga  13560
caccagcaag aatcctccga tgagggtacc atatctcggg tcaaagacac aggagaggag  13620
agctgcctca cttgcaaaaa tagctcatat gtcgccacat gtaaaggctg ccctaagggc  13680
atcatccgtg ttgatctggg cttatgggga taatgaagta aattggactg ctgctcttac  13740
gattgcaaaa tctcggtgta atgtaaactt agagtatctt cggttactgt cccctttacc  13800
cacggctggg aatcttcaac atagactaga tgatggtata actcagatga cattcacccc  13860
tgcatctctc tacagggtgt caccttacat tcacatatcc aatgattctc aaaggctgtt  13920
cactgaagaa ggagtcaaag aggggaatgt ggtttaccaa cagatcatgc tcttgggttt  13980
atctctaatc gaatcgatct ttccaatgac aacaaccagg acatatgatg agatcacact  14040
gcacctacat agtaaattta gttgctgtat cagagaagca cctgttgcgg ttcctttcga  14100
gctacttggg gtggtaccgg aactgaggac agtgacctca aataagttta tgtatgatcc  14160
tagccctgta tcggagggag actttgcgag acttgactta gctatcttca agagttatga  14220
gcttaatctg gagtcatatc ccacgataga gctaatgaac attctttcaa tatccagcgg  14280
gaagttgatt ggccagtctg tggtttctta tgatgaagat acctccataa agaatgacgc  14340
cataatagtg tatgacaata cccgaaattg gatcagtgaa gctcagaatt cagatgtggt  14400
ccgcctattt gaatatgcag cacttgaagt gctcctcgac tgttcttacc aactctatta  14460
cctgagagta agaggcctgg acaatattgt cttatatatg ggtgatttat acaagaatat  14520
gccaggaatt ctactttcca acattgcagc tacaatatct catcccgtca ttcattcaag  14580
gttacatgca gtgggcctgg tcaaccatga cggatcacac caacttgcag atacggattt  14640
tatcgaaatg tctgcaaaac tattagtatc ttgcacccga cgtgtgatct ccggcttata  14700
ttcaggaaat aagtatgatc tgctgttccc atctgtctta gatgataacc tgaatgagaa  14760
gatgcttcag ctgatatccc ggttatgctg tctgtacacg gtactctttg ctacaacaag  14820
agaaatcccg aaaataagag gcttaactgc agaagagaaa tgttcaatac tcactgagta  14880
tttactgtcg gatgctgtga aaccattact tagccccgat caagtgagct ctatcatgtc  14940
tcctaacata attacattcc cagctaatct gtactacatg tctcggaaga gcctcaattt  15000
gatcagggaa agggaggaca gggatactat cctggcgttg ttgttccccc aagagccatt  15060
attagagttc ccttctgtgc aagatattgg tgctcgagtg aaagatccat tcacccgaca  15120
acctgcggca tttttgcaag agttagattt gagtgctcca gcaaggtatg acgcattcac  15180
acttagtcag attcatcctg aactcacatc tccaaatccg gaggaagact acttagtacg  15240
atacttgttc agagggatag ggactgcatc ttcctcttgg tataaggcat ctcatctcct  15300
ttctgtaccc gaggtaagat gtgcaagaca cgggaactcc ttatacttag ctgaagggag  15360
cggagccatc atgagtcttc tcgaactgca tgtaccacat gaaactatct attacaatac  15420
gctcttttca aatgagatga acccccCgca acgacatttc gggccgaccc caactcagtt  15480
tttgaattcg gttgtttata ggaatctaca ggcggaggta acatgcaaag atggatttgt  15540
```

```
ccaagagttc cgtccattat ggagagaaaa tacagaggaa agcgacctga cctcagataa  15600

agtagtgggg tatattacat ctgcagtgcc ctacagatct gtatcattgc tgcattgtga  15660

cattgaaatt cctccagggt ccaatcaaag cttactagat caactagcta tcaatttatc  15720

tctgattgcc atgcattctg taagggaggg cggggtagta atcatcaaag tgttgtatgc  15780

aatgggatac tactttcatc tactcatgaa cttgtttgct ccgtgttcca caaaaggata  15840

tattctctct aatggttatg catgtcgagg agatatggag tgttacctgg tatttgtcat  15900

gggttacctg ggcgggccta catttgtaca tgaggtggtg aggatggcga aaactctggt  15960

gcagcggcac ggtacgcttt tgtctaaatc agatgagatc acactgacca ggttattcac  16020

ctcacagcgg cagcgtgtga cagacatcct atccagtcct ttaccaagat taataaagta  16080

cttgaggaag aatattgaca ctgcgctgat tgaagccggg ggacagcccg tccgtccatt  16140

ctgtgcggag agtctggtga gcacgctagc gaacataact cagataaccc agatcatcgc  16200

tagtcacatt gacacagtta tccggtctgt gatatatatg gaagctgagg gtgatctcgc  16260

tgacacagta tttctattta ccccttacaa tctctctact gacgggaaaa agaggacatc  16320

acttaaacag tgcacgagac agatcctaga ggttacaata ctaggtctta gagtcgaaaa  16380

tctcaataaa ataggcgata taatcagcct agtgcttaaa ggcatgatct ccatggagga  16440

ccttatccca ctaaggacat acttgaagca tagtacctgc cctaaatatt tgaaggctgt  16500

cctaggtatt accaaactca aagaaatgtt tacagacact tctgtactgt acttgactcg  16560

tgctcaacaa aaattctaca tgaaaactat aggcaatgca gtcaaaggat attacagtaa  16620

ctgtgactct taacgaaaat cacatattaa taggctcctt ttttggccaa ttgtattctt  16680

gttgatttaa tcatattatg ttagaaaaaa gttgaaccct gactccttag gactcgaatt  16740

cgaactcaaa taaatgtctt aaaaaaaggt tgcgcacaat tattcttgag tgtagtctcg  16800

tcattcacca aatctttgtt tggt                                         16824
```

<210> SEQ ID NO 63
<211> LENGTH: 1533
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 63

```
atctgggaac tgaaaaagga tgtgtacgtg gtggagctgg actggtatcc cgatgcccct     60

ggcgagatgg tggtgctgac ctgcgacaca cccgaggagg atggcatcac ctggacactg    120

gatcagagct ccgaggtgct gggaagcggc aagaccctga caatccaggt gaaggagttc    180

ggcgacgccg gccagtacac ctgtcacaag ggaggagagg tgctgagcca ctccctgctg    240

ctgctgcaca agaaggagga tggcatctgg tccacagaca tcctgaagga tcagaaggag    300

ccaaagaaca agaccttcct gcggtgcgag gccaagaatt atagcggccg gttcacctgt    360

tggtggctga ccacaatctc caccgatctg acattttctg tgaagtctag caggggatcc    420

tctgacccac agggagtgac atgcggagca gccaccctga gcgccgagag ggtgcgcggc    480

gataacaagg agtacgagta ttccgtggag tgccaggagg actctgcctg tccagcagca    540

gaggagtccc tgcctatcga agtgatggtg gatgccgtgc acaagctgaa gtacgagaat    600

tataccagct ccttctttat ccgggacatc atcaagcccg atccccctaa gaacctgcag    660
```

```
ctgaagcctc tgaagaatag cagacaggtg gaggtgtcct gggagtaccc tgacacctgg    720

agcacaccac actcctattt ctctctgacc ttttgcgtgc aggtgcaggg caagtccaag    780

cgggagaaga aggacagagt gttcaccgat aagacatctg ccaccgtgat ctgtagaaag    840

aacgcctcta tcagcgtgag ggcccaggac cgctactatt ctagctcctg gtccgagtgg    900

gcctctgtgc cttgcagcgg cggaggagga ggaggatcta ggaatctgcc agtggcaacc    960

cctgacccag gcatgttccc ctgcctgcac cacagccaga acctgctgag ggccgtgtcc   1020

aatatgctgc agaaggcccg ccagacactg gagttttacc cttgtaccag cgaggagatc   1080

gaccacgagg acatcacaaa ggataagacc tccacagtgg aggcctgcct gccactggag   1140

ctgaccaaga acgagtcctg tctgaacagc cgggagacaa gcttcatcac caacggctcc   1200

tgcctggcct ctagaaagac aagctttatg atggccctgt gcctgtctag catctacgag   1260

gacctgaaga tgtatcaggt ggagttcaag accatgaacg ccaagctgct gatggacccc   1320

aagaggcaga tctttctgga tcagaatatg ctggccgtga tcgacgagct gatgcaggcc   1380

ctgaacttca atagcgagac agtgcctcag aagtcctctc tggaggagcc agatttctac   1440

aagaccaaga tcaagctgtg catcctgctg cacgcctttc ggatcagagc cgtgacaatc   1500

gaccgcgtga tgtcctatct gaatgcttcc taa                                1533
```

<210> SEQ ID NO 64
<211> LENGTH: 984
<212> TYPE: DNA
<213> ORGANISM: Homo sapiens

<400> SEQUENCE: 64

```
atgtgtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagt                                           984
```

<210> SEQ ID NO 65
<211> LENGTH: 594
<212> TYPE: DNA
<213> ORGANISM: Homo sapiens

<400> SEQUENCE: 65

```
agaaacctcc ccgtggccac tccagaccca ggaatgttcc catgccttca ccactcccaa     60

aacctgctga gggccgtcag caacatgctc cagaaggcca gacaaactct agaattttac    120

ccttgcactt ctgaagagat tgatcatgaa gatatcacaa aagataaaac cagcacagtg    180

gaggcctgtt taccattgga attaaccaag aatgagagtt gcctaaattc cagagagacc    240

tctttcataa ctaatgggag ttgcctggcc tccagaaaga cctcttttat gatggccctg    300

tgccttagta gtatttatga agacttgaag atgtaccagg tggagttcaa gaccatgaat    360

gcaaagcttc tgatggatcc taagaggcag atctttctag atcaaaacat gctggcagtt    420

attgatgagc tgatgcaggc cctgaatttc aacagtgaga ctgtgccaca aaaatcctcc    480

cttgaagaac cggattttta taaaactaaa atcaagctct gcatacttct tcatgctttc    540

agaattcggg cagtgactat tgatagagtg atgagctatc tgaatgcttc ctaa          594
```

```
<210> SEQ ID NO 66
<211> LENGTH: 1599
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66

atgtgtcacc agcagttggt catctcttgg ttttccctgg tttttctggc atctcccctc     60

gtggccatat gggaactgaa gaaagatgtt tatgtcgtag aattggattg gtatccggat    120

gcccctggag aaatggtggt cctcacctgt gacacccctg aagaagatgg tatcacctgg    180

accttggacc agagcagtga ggtcttaggc tctggcaaaa ccctgaccat ccaagtcaaa    240

gagtttggag atgctggcca gtacacctgt cacaaaggag gcgaggttct aagccattcg    300

ctcctgctgc ttcacaaaaa ggaagatgga atttggtcca ctgatatttt aaaggaccag    360

aaagaaccca aaaataagac ctttctaaga tgcgaggcca agaattattc tggacgtttc    420

acctgctggt ggctgacgac aatcagtact gatttgacat tcagtgtcaa aagcagcaga    480

ggctcttctg acccccaagg ggtgacgtgc ggagctgcta cactctctgc agagagagtc    540

agaggggaca acaaggagta tgagtactca gtggagtgcc aggaggacag tgcctgccca    600

gctgctgagg agagtctgcc cattgaggtc atggtggatg ccgttcacaa gctcaagtat    660

gaaaactaca ccagcagctt cttcatcagg gacatcatca aacctgaccc acccaagaac    720

ttgcagctga agccattaaa gaattctcgg caggtggagg tcagctggga gtaccctgac    780

acctggagta ctccacattc ctacttctcc ctgacattct gcgttcaggt ccagggcaag    840

agcaagagag aaaagaaaga tagagtcttc acggacaaga cctcagccac ggtcatctgc    900

cgcaaaaatg ccagcattag cgtgcgggcc caggaccgct actatagctc atcttggagc    960

gaatgggcat ctgtgccctg cagtggtggc ggtggcggcg gatctagaaa cctccccgtg   1020

gccactccag acccaggaat gttcccatgc cttcaccact cccaaaacct gctgagggcc   1080

gtcagcaaca tgctccagaa ggccagacaa actctagaat tttacccttg cacttctgaa   1140

gagattgatc atgaagatat cacaaaagat aaaaccagca cagtggaggc ctgtttacca   1200

ttggaattaa ccaagaatga gagttgccta aattccagag agacctcttt cataactaat   1260

gggagttgcc tggcctccag aaagacctct tttatgatgg ccctgtgcct tagtagtatt   1320

tatgaagact tgaagatgta ccaggtggag ttcaagacca tgaatgcaaa gcttctgatg   1380
```

gatcctaaga ggcagatctt tctagatcaa aacatgctgg cagttattga tgagctgatg 1440
caggccctga atttcaacag tgagactgtg ccacaaaaat cctcccttga agaaccggat 1500
ttttataaaa ctaaaatcaa gctctgcata cttcttcatg ctttcagaat tcgggcagtg 1560
actattgata gagtgatgag ctatctgaat gcttcctaa 1599

<210> SEQ ID NO 67
<211> LENGTH: 16824
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 67
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccct tgcagggaaa cagaatgaag ccacattggc 420
cgtgcttgag attgatggct ttgccaacgg cacgccccag ttcaacaata ggagtggagt 480
gtctgaagag agagcacaga gatttgcgat gatagcagga tctctccctc gggcatgcag 540
caacggaacc ccgttcgtca cagccggggc cgaagatgat gcaccagaag acatcaccga 600
taccctggag aggatcctct ctatccaggc tcaagtatgg gtcacagtag caaaagccat 660
gactgcgtat gagactgcag atgagtcgga aacaaggcga atcaataagt atatgcagca 720
aggcagggtc caaaagaaat acatcctcta ccccgtatgc aggagcacaa tccaactcac 780
gatcagacag tctcttgcag tccgcatctt tttggttagc gagctcaaga gaggccgcaa 840
cacggcaggt ggtacctcta cttattataa cctggtaggg gacgtagact catacatcag 900
gaataccggg cttactgcat tcttcttgac actcaagtac ggaatcaaca ccaagacatc 960
agcccttgca cttagtagcc tctcaggcga catccagaag atgaagcagc tcatgcgttt 1020
gtatcggatg aaaggagata atgcgccgta catgacatta cttggtgata gtgaccagat 1080
gagctttgcg cctgccgagt atgcacaact ttactccttt gccatgggta tggcatcagt 1140
cctagataaa ggtactggga aataccaatt tgccagggac tttatgagca catcattctg 1200
gagacttgga gtagagtacg ctcaggctca gggaagtagc attaacgagg atatggctgc 1260
cgagctaaag ctaaccccag cagcaaggag gggcctggca gctgctgccc aacgggtctc 1320
cgaggagacc agcagcatag acatgcctac tcaacaagtc ggagtcctca ctgggcttag 1380
cgaggggggg tcccaagctc tacaaggcgg atcgaataga tcgcaagggc aaccagaagc 1440
cggggatggg gagacccaat tcctggatct gatgagagcg gtagcaaata gcatgaggga 1500
ggcgccaaac tctgcacagg gcactcccca atcggggcct cccccaactc ctgggccatc 1560
ccaagataac gacaccgact gggggtattg atggacaaaa cccagcctgc ttccacaaaa 1620
acatcccaat gccctcaccc gtagtcgacc cctcgatttg cggctctata tgaccacacc 1680
ctcaaacaaa catcccccctc tttcctccct ccccctgctg tacaactacg tacgccctag 1740
ataccacagg cacaatgcgg ctcactaaca atcaaaacag agccgaggga attagaaaaa 1800

```
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ctcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcggtt agaaaaaata cgggtagaac cgccaccatg   3180
tgtcaccagc agttggtcat ctcttggttt tccctggttt ttctggcatc tcccctcgtg   3240
gccatatggg aactgaagaa agatgtttat gtcgtagaat tggattggta tccggatgcc   3300
cctggagaaa tggtggtcct cacctgtgac acccctgaag aagatggtat cacctggacc   3360
ttggaccaga gcagtgaggt cttaggctct ggcaaaaccc tgaccatcca agtcaaagag   3420
tttggagatg ctggccagta cacctgtcac aaaggaggcg aggttctaag ccattcgctc   3480
ctgctgcttc acaaaaagga agatggaatt tggtccactg atattttaaa ggaccagaaa   3540
gaacccaaaa ataagacctt tctaagatgc gaggccaaga attattctgg acgtttcacc   3600
tgctggtggc tgacgacaat cagtactgat ttgacattca gtgtcaaaag cagcagaggc   3660
tcttctgacc cccaaggggt gacgtgcgga gctgctacac tctctgcaga gagagtcaga   3720
ggggacaaca aggagtatga gtactcagtg gagtgccagg aggacagtgc ctgcccagct   3780
gctgaggaga gtctgcccat tgaggtcatg gtggatgccg ttcacaagct caagtatgaa   3840
aactacacca gcagcttctt catcagggac atcatcaaac ctgacccacc caagaacttg   3900
cagctgaagc cattaaagaa ttctcggcag gtggaggtca gctgggagta ccctgacacc   3960
tggagtactc cacattccta cttctccctg acattctgcg ttcaggtcca gggcaagagc   4020
aagagagaaa agaaagatag agtcttcacg gacaagacct cagccacggt catctgccgc   4080
aaaaatgcca gcattagcgt gcgggcccag gaccgctact atagctcatc ttggagcgaa   4140
```

-continued tgggcatctg tgccctgcag tggtggcggt ggcggcggat ctagaaacct ccccgtggcc 4200
actccagacc caggaatgtt cccatgcctt caccactccc aaaacctgct gagggccgtc 4260
agcaacatgc tccagaaggc cagacaaact ctagaatttt acccttgcac ttctgaagag 4320
attgatcatg aagatatcac aaaagataaa accagcacag tggaggcctg tttaccattg 4380
gaattaacca agaatgagag ttgcctaaat tccagagaga cctctttcat aactaatggg 4440
agttgcctgg cctccagaaa gacctctttt atgatggccc tgtgccttag tagtatttat 4500
gaagacttga agatgtacca ggtggagttc aagaccatga atgcaaagct tctgatggat 4560
cctaagaggc agatcttct agatcaaaac atgctggcag ttattgatga gctgatgcag 4620
gccctgaatt tcaacagtga gactgtgcca caaaaatcct cccttgaaga accggatttt 4680
tataaaacta aaatcaagct ctgcatactt cttcatgctt tcagaattcg ggcagtgact 4740
attgatagag tgatgagcta tctgaatgct tcctaatgat ccgcggaccc aaggtccaac 4800
tctccaagcg gcaatcctct ctcgcttcct cagccccact gaatgatcgc gtaaccgtaa 4860
ttaatctagc tacatttaag attaagaaaa aatacgggta gaattggagt gccccaattg 4920
tgccaagatg gactcatcta ggacaattgg gctgtacttt gattctgccc attcttctag 4980
caacctgtta gcatttccga tcgtcctaca agacacagga gatgggaaga agcaaatcgc 5040
cccgcaatat aggatccagc gccttgactt gtggactgat agtaaggagg actcagtatt 5100
catcaccacc tatggattca tctttcaagt tgggaatgaa gaagccaccg tcggcatgat 5160
cgatgataaa cccaagcgcg agttactttc cgctgcgatg ctctgcctag gaagcgtccc 5220
aaataccgga gaccttattg agctggcaag ggcctgtctc actatgatag tcacatgcaa 5280
gaagagtgca actaatactg agagaatggt tttctcagta gtgcaggcac cccaagtgct 5340
gcaaagctgt agggttgtgg caaacaaata ctcatcagtg aatgcagtca agcacgtgaa 5400
agcgccagag aagattcccg ggagtggaac cctagaatac aaggtgaact ttgtctcctt 5460
gactgtggta ccgaagaggg atgtctacaa gatcccagct gcagtattga aggtttctgg 5520
ctcgagtctg tacaatcttg cgctcaatgt cactattaat gtggaggtag acccgaggag 5580
tcctttggtt aaatctctgt ctaagtctga cagcggatac tatgctaacc tcttcttgca 5640
tattggactt atgaccactg tagataggaa ggggaagaaa gtgacatttg acaagctgga 5700
aaagaaaata aggagccttg atctatctgt cgggctcagt gatgtgctcg ggccttccgt 5760
gttggtaaaa gcaagaggtg cacggactaa gcttttggca cctttcttct ctagcagtgg 5820
gacagcctgc tatcccatag caaatgcttc tcctcaggtg gccaagatac tctggagtca 5880
aaccgcgtgc ctgcggagcg ttaaaatcat tatccaagca ggtacccaac gcgctgtcgc 5940
agtgaccgcc gaccacgagg ttacctctac taagctggag aaggggcaca cccttgccaa 6000
atacaatcct tttaagaaat aagctgcgtc tctgagattg cgctccgccc actcacccag 6060
atcatcatga cacaaaaaac taatctgtct tgattattta cagttagttt acctgtctat 6120
caagttagaa aaaacacggg tagaagattc tggatcccgg ttggcgccct ccaggtgcaa 6180
gatgggctcc agaccttcta ccaagaaccc agcacctatg atgctgacta tccgggttgc 6240
gctggtactg agttgcatct gtccggcaaa ctccattgat ggcaggcctc ttgcagctgc 6300
aggaattgtg gttacaggag acaaagccgt caacatatac acctcatccc agacaggatc 6360
aatcatagtt aagctcctcc cgaatctgcc caaggataag gaggcatgtg cgaaagcccc 6420
cttggatgca tacaacagga cattgaccac tttgctcacc ccccttggtg actctatccg 6480
taggatacaa gagtctgtga ctacatctgg aggggggaga caggggcgcc ttataggcgc 6540
cattattggc ggtgtggctc ttggggttgc aactgccgca caaataacag cggccgcagc 6600
tctgatacaa gccaaacaaa atgctgccaa catcctccga cttaaagaga gcattgccgc 6660
aaccaatgag gctgtgcatg aggtcactga cggattatcg caactagcag tggcagttgg 6720
gaagatgcag cagtttgtta atgaccaatt taataaaaca gctcaggaat tagactgcat 6780
caaaattgca cagcaagttg gtgtagagct caacctgtac ctaaccgaat tgactacagt 6840
attcggacca caaatcactt cacctgcttt aaacaagctg actattcagg cactttacaa 6900
tctagctggt ggaaatatgg attacttatt gactaagtta ggtgtaggga acaatcaact 6960
cagctcatta atcggtagcg gcttaatcac cggtaaccct attctatacg actcacagac 7020
tcaactcttg ggtatacagg taactgcccc ttcagtcggg aacctaaata atatgcgtgc 7080
cacctacttg gaaaccttat ccgtaagcac aaccaggga tttgcctcgg cacttgtccc 7140
aaaagtggtg acacaggtcg gttctgtgat agaagaactt gacacctcat actgtataga 7200
aactgactta gatttatatt gtacaagaat agtaacgttc cctatgtccc ctggtattta 7260
ttcctgcttg agcggcaata cgtcggcctg tatgtactca aagaccgaag gcgcacttac 7320
tacaccatac atgactatca aaggttcagt catcgccaac tgcaagatga caacatgtag 7380
atgtgtaaac cccccgggta tcatatcgca aaactatgga gaagccgtgt ctctaataga 7440
taaacaatca tgcaatgttt tatccttagg cgggataact ttaaggctca gtggggaatt 7500
cgatgtaact tatcagaaga atatctcaat acaagattct caagtaataa taacaggcaa 7560
tcttgatatc tcaactgagc ttgggaatgt caacaactcg atcagtaatg ctttgaataa 7620
gttagaggaa agcaacagaa aactagacaa agtcaatgtc aaactgacta gcacatctgc 7680
tctcattacc tatatcgttt tgactatcat atctcttgtt tttggtatac ttagcctgat 7740
tctagcatgc tacctaatgt acaagcaaaa ggcgcaacaa aagaccttat tatggcttgg 7800
gaataatact ctagatcaga tgagagccac tacaaaaatg tgaacacaga tgaggaacga 7860
aggtttccct aatagtaatt tgtgtgaaag ttctggtagt ctgtcagttc agagagttaa 7920
gaaaaaacta ccggttgtag atgaccaaag gacgatatac gggtagaacg gtaagagagg 7980
ccgcccctca attgcgagcc aggcttcaca acctccgttc taccgcttca ccgacaacag 8040
tcctcaatca tggaccgcgc cgttagccaa gttgcgttag agaatgatga aagagaggca 8100
aaaaatacat ggcgcttgat attccggatt gcaatcttat tcttaacagt agtgaccttg 8160
gctatatctg tagcctccct tttatatagc atgggggcta gcacacctag cgatcttgta 8220
ggcataccga ctaggatttc cagggcagaa gaaaagatta catctacact tggttccaat 8280
caagatgtag tagataggat atataagcaa gtggcccttg agtctccgtt ggcattgtta 8340
aatactgaga ccacaattat gaacgcaata acatctctct cttatcagat taatggagct 8400
gcaaacaaca gtgggtgggg ggcacctatc catgacccag attatatagg ggggataggc 8460
aaagaactca ttgtagatga tgctagtgat gtcacatcat tctatccctc tgcatttcaa 8520
gaacatctga attttatccc ggcgcctact acaggatcag gttgcactcg aataccctca 8580
tttgacatga gtgctaccca ttactgctac acccataatg taatattgtc tggatgcaga 8640
gatcactcac attcatatca gtatttagca cttggtgtgc tccggacatc tgcaacaggg 8700
agggtattct tttctactct gcgttccatc aacctggacg acacccaaaa tcggaagtct 8760
tgcagtgtga gtgcaactcc cctgggttgt gatatgctgt gctcgaaagt cacggagaca 8820
gaggaagaag attataactc agctgtccct acgcggatgg tacatgggag gttagggttc 8880

-continued

```
gacggccagt accacgaaaa ggacctagat gtcacaacat tattcgggga ctgggtggcc   8940
aactacccag gagtaggggg tggatctttt attgacagcc gcgtatggtt ctcagtctac   9000
ggagggttaa aacccaattc acccagtgac actgtacagg aagggaaata tgtgatatac   9060
aagcgataca atgacacatg cccagatgag caagactacc agattcgaat ggccaagtct   9120
tcgtataagc ctggacggtt tggtgggaaa cgcatacagc aggctatctt atctatcaag   9180
gtgtcaacat ccttaggcga agacccggta ctgactgtac cgcccaacac agtcacactc   9240
atgggggccg aaggcagaat tctcacagta gggacatctc atttcttgta tcaacgaggg   9300
tcatcatact tctctcccgc gttattatat cctatgacag tcagcaacaa aacagccact   9360
cttcatagtc cttatacatt caatgccttc actcggccag gtagtatccc ttgccaggct   9420
tcagcaagat gccccaactc gtgtgttact ggagtctata cagatccata tcccctaatc   9480
ttctatagaa accacacctt gcgaggggta ttcgggacaa tgcttgatgg tgtacaagca   9540
agacttaacc ctgcgtctgc agtattcgat agcacatccc gcagtcgcat tactcgagtg   9600
agttcaagca gtaccaaagc agcatacaca acatcaactt gttttaaagt ggtcaagact   9660
aataagacct attgtctcag cattgctgaa atatctaata ctctcttcgg agaattcaga   9720
atcgtcccgt tactagttga gatcctcaaa gatgacgggg ttagagaagc caggtctggc   9780
tagttgagtc aattataaag gagttggaaa gatggcattg tatcacctat cttctgcgac   9840
atcaagaatc aaaccgaatg ccggcgcgtg ctcgaattcc atgttgccag ttgaccacaa   9900
tcagccagtg ctcatgcgat cagattaagc cttgtcaata gtctcttgat taagaaaaaa   9960
tgtaagtggc aatgagatac aaggcaaaac agctcatggt taacaatacg ggtaggacat  10020
ggcgagctcc ggtcctgaaa gggcagagca tcagattatc ctaccagagt cacacctgtc  10080
ttcaccattg gtcaagcaca aactactcta ttactggaaa ttaactgggc taccgcttcc  10140
tgatgaatgt gacttcgacc acctcattct cagccgacaa tggaaaaaaa tacttgaatc  10200
ggcctctcct gatactgaga gaatgataaa actcggaagg gcagtacacc aaactcttaa  10260
ccacaattcc agaataaccg gagtgctcca ccccaggtgt ttagaagaac tggctaatat  10320
tgaggtccca gattcaacca acaaatttcg gaagattgag aagaagatcc aaattcacaa  10380
cacgagatat ggagaactgt tcacaaggct gtgtacgcat atagagaaga aactgctggg  10440
gtcatcttgg tctaacaatg tcccccggtc agaggagttc agcagcattc gtacggatcc  10500
ggcattctgg tttcactcaa aatggtccac agccaagttt gcatggctcc atataaaaca  10560
gatccagagg catctgatgg tggcagctag gacaaggtct gcggccaaca aattggtgat  10620
gctaacccat aaggtaggcc aagtctttgt cactcctgaa cttgtcgttg tgacgcatac  10680
gaatgagaac aagttcacat gtcttaccca ggaacttgta ttgatgtatg cagatatgat  10740
ggagggcaga gatatggtca acataatatc aaccacggcg gtgcatctca gaagcttatc  10800
agagaaaatt gatgacattt tgcggttaat agacgctctg gcaaaagact tgggtaatca  10860
agtctacgat gttgtatcac taatggaggg atttgcatac ggagctgtcc agctactcga  10920
gccgtcaggt acatttgcag gagatttctt cgcattcaac ctgcaggagc ttaaagacat  10980
tctaattggc ctcctcccca atgatatagc agaatccgtg actcatgcaa tcgctactgt  11040
attctctggt ttagaacaga atcaagcagc tgagatgttg tgtctgttgc gtctgtgggg  11100
tcacccactg cttgagtccc gtattgcagc aaaggcagtc aggagccaaa tgtgcgcacc  11160
gaaaatggta gactttgata tgatccttca ggtactgtct ttcttcaagg gaacaatcat  11220
caacgggtac agaaagaaga atgcaggtgt gtggccgcga gtcaaagtgg atacaatata  11280
```

-continued

```
tgggaaggtc attgggcaac tacatgcaga ttcagcagag atttcacacg atatcatgtt  11340
gagagagtat aagagtttat ctgcacttga atttgagcca tgtatagaat atgaccctgt  11400
caccaacctg agcatgttcc taaaagacaa ggcaatcgca caccccaacg ataattggct  11460
tgcctcgttt aggcggaacc ttctctccga agaccagaag aaacatgtaa aagaagcaac  11520
ttcgactaat cgcctcttga tagagttttt agagtcaaat gattttgatc catataaaga  11580
gatggaatat ctgacgaccc ttgagtacct tagagatgac aatgtggcag tatcatactc  11640
gctcaaggag aaggaagtga aagttaatgg acggatcttc gctaagctga caaagaagtt  11700
aaggaactgt caggtgatgg cggaagggat cctagccgat cagattgcac ctttctttca  11760
gggaaatgga gtcattcagg atagcatatc cttgaccaag agtatgctag cgatgagtca  11820
actgtctttt aacagcaata agaaacgtat cactgactgt aaagaaagag tatcttcaaa  11880
ccgcaatcat gatccgaaaa gcaagaaccg tcggagagtt gcaaccttca taacaactga  11940
cctgcaaaag tactgtctta attggagata tcagacaatc aaattgttcg ctcatgccat  12000
caatcagttg atgggcctac ctcacttctt cgaatggatt cacctaagac tgatggacac  12060
tacgatgttc gtaggagacc ctttcaatcc tccaagtgac cctactgact gtgacctctc  12120
aagagtccct aatgatgaca tatatattgt cagtgccaga gggggtatcg aaggattatg  12180
ccagaagcta tggacaatga tctcaattgc tgcaatccaa cttgctgcag ctagatcgca  12240
ttgtcgtgtt gcctgtatgg tacagggtga taatcaagta atagcagtaa cgagagaggt  12300
aagatcagac gactctccgg agatggtgtt gacacagttg catcaagcca gtgataattt  12360
cttcaaggaa ttaattcatg tcaatcattt gattggccat aatttgaagg atcgtgaaac  12420
catcaggtca gacacattct tcatatacag caaacgaatc ttcaaagatg gagcaatcct  12480
cagtcaagtc ctcaaaaatt catctaaatt agtgctagtg tcaggtgatc tcagtgaaaa  12540
caccgtaatg tcctgtgcca acattgcctc tactgtagca cggctatgcg agaacgggct  12600
tcccaaagac ttctgttact atttaaacta tataatgagt tgtgtgcaga catactttga  12660
ctctgagttc tccatcacca acaattcgca ccccgatctt aatcagtcgt ggattgagga  12720
catctctttt gtgcactcat atgttctgac tcctgcccaa ttagggggac tgagtaacct  12780
tcaatactca aggctctaca ctagaaatat cggtgacccg gggactactg cttttgcaga  12840
gatcaagcga ctagaagcag tgggattact gagtcctaac attatgacta atatcttaac  12900
taggccgcct gggaatggag attgggccag tctgtgcaac gacccatact ctttcaattt  12960
tgagactgtt gcaagcccaa atattgttct taagaaacat acgcaaagag tcctatttga  13020
aacttgttca aatcccttat tgtctggagt gcacacagag gataatgagg cagaagagaa  13080
ggcattggct gaattcttgc ttaatcaaga ggtgattcat ccccgcgttg cgcatgccat  13140
catggaggca agctctgtag gtaggagaaa gcaaattcaa gggcttgttg acacaacaaa  13200
caccgtaatt aagattgcgc ttactaggag gccattaggc atcaagaggc tgatgcggat  13260
agtcaattat tctagcatgc atgcaatgct gtttagagac gatgtttttt cctccagtag  13320
atccaaccac cccttagtct cttctaatat gtgttctctg acactggcag actatgcacg  13380
gaatagaagc tggtcacctt tgacgggagg caggaaaata ctgggtgtat ctaatcctga  13440
tacgatagaa ctcgtagagg gtgagattct tagtgtaagc ggagggtgta caagatgtga  13500
cagcggagat gaacaattta cttggttcca tcttccaagc aatatagaat tgaccgatga  13560
caccagcaag aatcctccga tgagggtacc atatctcggg tcaaagacac aggagaggag  13620
```

```
agctgcctca cttgcaaaaa tagctcatat gtcgccacat gtaaaggctg ccctaagggc  13680
atcatccgtg ttgatctggg cttatgggga taatgaagta aattggactg ctgctcttac  13740
gattgcaaaa tctcggtgta atgtaaactt agagtatctt cggttactgt cccctttacc  13800
cacggctggg aatcttcaac atagactaga tgatggtata actcagatga cattcacccc  13860
tgcatctctc tacagggtgt caccttacat tcacatatcc aatgattctc aaaggctgtt  13920
cactgaagaa ggagtcaaag aggggaatgt ggtttaccaa cagatcatgc tcttgggttt  13980
atctctaatc gaatcgatct ttccaatgac aacaaccagg acatatgatg agatcacact  14040
gcacctacat agtaaattta gttgctgtat cagagaagca cctgttgcgg ttcctttcga  14100
gctacttggg gtggtaccgg aactgaggac agtgacctca aataagttta tgtatgatcc  14160
tagccctgta tcggagggag actttgcgag acttgactta gctatcttca agagttatga  14220
gcttaatctg gagtcatatc ccacgataga gctaatgaac attctttcaa tatccagcgg  14280
gaagttgatt ggccagtctg tggtttctta tgatgaagat acctccataa agaatgacgc  14340
cataatagtg tatgacaata cccgaaattg gatcagtgaa gctcagaatt cagatgtggt  14400
ccgcctattt gaatatgcag cacttgaagt gctcctcgac tgttcttacc aactctatta  14460
cctgagagta agaggcctgg acaatattgt cttatatatg ggtgatttat acaagaatat  14520
gccaggaatt ctactttcca acattgcagc tacaatatct catcccgtca ttcattcaag  14580
gttacatgca gtgggcctgg tcaaccatga cggatcacac caacttgcag atacggattt  14640
tatcgaaatg tctgcaaaac tattagtatc ttgcacccga cgtgtgatct ccggcttata  14700
ttcaggaaat aagtatgatc tgctgttccc atctgtctta gatgataacc tgaatgagaa  14760
gatgcttcag ctgatatccc ggttatgctg tctgtacacg gtactctttg ctacaacaag  14820
agaaatcccg aaaataagag gcttaactgc agaagagaaa tgttcaatac tcactgagta  14880
tttactgtcg gatgctgtga aaccattact tagccccgat caagtgagct ctatcatgtc  14940
tcctaacata attacattcc cagctaatct gtactacatg tctcggaaga gcctcaattt  15000
gatcagggaa agggaggaca gggatactat cctggcgttg ttgttccccc aagagccatt  15060
attagagttc ccttctgtgc aagatattgg tgctcgagtg aaagatccat tcacccgaca  15120
acctgcggca tttttgcaag agttagattt gagtgctcca gcaaggtatg acgcattcac  15180
acttagtcag attcatcctg aactcacatc tccaaatccg gaggaagact acttagtacg  15240
atacttgttc agagggatag ggactgcatc ttcctcttgg tataaggcat ctcatctcct  15300
ttctgtaccc gaggtaagat gtgcaagaca cgggaactcc ttatacttag ctgaagggag  15360
cggagccatc atgagtcttc tcgaactgca tgtaccacat gaaactatct attacaatac  15420
gctcttttca aatgagatga accccccgca acgacatttc gggccgaccc caactcagtt  15480
tttgaattcg gttgtttata ggaatctaca ggcggaggta acatgcaaag atggatttgt  15540
ccaagagttc cgtccattat ggagagaaaa tacagaggaa agcgacctga cctcagataa  15600
agtagtgggg tatattacat ctgcagtgcc ctacagatct gtatcattgc tgcattgtga  15660
cattgaaatt cctccagggt ccaatcaaag cttactagat caactagcta tcaatttatc  15720
tctgattgcc atgcattctg taagggaggg cggggtagta atcatcaaag tgttgtatgc  15780
aatgggatac tactttcatc tactcatgaa cttgtttgct ccgtgttcca caaaaggata  15840
tattctctct aatggttatg catgtcgagg agatatggag tgttacctgg tatttgtcat  15900
gggttacctg ggcgggccta catttgtaca tgaggtggtg aggatggcga aaactctggt  15960
gcagcggcac ggtacgcttt tgtctaaatc agatgagatc acactgacca ggttattcac  16020
```

ctcacagcgg cagcgtgtga cagacatcct atccagtcct ttaccaagat taataaagta 16080
cttgaggaag aatattgaca ctgcgctgat tgaagccggg ggacagcccg tccgtccatt 16140
ctgtgcggag agtctggtga gcacgctagc gaacataact cagataaccc agatcatcgc 16200
tagtcacatt gacacagtta tccggtctgt gatatatatg gaagctgagg gtgatctcgc 16260
tgacacagta tttctattta ccccttacaa tctctctact gacgggaaaa agaggacatc 16320
acttaaacag tgcacgagac agatcctaga ggttacaata ctaggtctta gagtcgaaaa 16380
tctcaataaa ataggcgata taatcagcct agtgcttaaa ggcatgatct ccatggagga 16440
ccttatccca ctaaggacat acttgaagca tagtacctgc cctaaatatt tgaaggctgt 16500
cctaggtatt accaaactca aagaaatgtt tacagacact tctgtactgt acttgactcg 16560
tgctcaacaa aaattctaca tgaaaactat aggcaatgca gtcaaaggat attacagtaa 16620
ctgtgactct taacgaaaat cacatattaa taggctcctt ttttggccaa ttgtattctt 16680
gttgatttaa tcatattatg ttagaaaaaa gttgaaccct gactccttag gactcgaatt 16740
cgaactcaaa taaatgtctt aaaaaaaggt tgcgcacaat tattcttgag tgtagtctcg 16800
tcattcacca aatctttgtt tggt 16824

<210> SEQ ID NO 68
<211> LENGTH: 1533
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 68
atatgggaac tgaagaaaga tgtttatgtc gtagaattgg attggtatcc ggatgcccct 60
ggagaaatgg tggtcctcac ctgtgacacc cctgaagaag atggtatcac ctggaccttg 120
gaccagagca gtgaggtctt aggctctggc aaaaccctga ccatccaagt caaagagttt 180
ggagatgctg gccagtacac ctgtcacaaa ggaggcgagg ttctaagcca ttcgctcctg 240
ctgcttcaca aaaaggaaga tggaatttgg tccactgata ttttaaagga ccagaaagaa 300
cccaaaaata agacctttct aagatgcgag gccaagaatt attctggacg tttcacctgc 360
tggtggctga cgacaatcag tactgatttg acattcagtg tcaaaagcag cagaggctct 420
tctgaccccc aaggggtgac gtgcggagct gctacactct ctgcagagag agtcagaggg 480
gacaacaagg agtatgagta ctcagtggag tgccaggagg acagtgcctg cccagctgct 540
gaggagagtc tgcccattga ggtcatggtg gatgccgttc acaagctcaa gtatgaaaac 600
tacaccagca gcttcttcat cagggacatc atcaaacctg acccacccaa gaacttgcag 660
ctgaagccat taaagaattc tcggcaggtg gaggtcagct gggagtaccc tgacacctgg 720
agtactccac attcctactt ctccctgaca ttctgcgttc aggtccaggg caagagcaag 780
agagaaaaga aagatagagt cttcacggac aagacctcag ccacggtcat ctgccgcaaa 840
aatgccagca ttagcgtgcg ggcccaggac cgctactata gctcatcttg gagcgaatgg 900
gcatctgtgc cctgcagtgg tggcggtggc ggcggatcta gaaacctccc cgtggccact 960
ccagacccag gaatgttccc atgccttcac cactcccaaa acctgctgag ggccgtcagc 1020
aacatgctcc agaaggccag acaaactcta gaattttacc cttgcacttc tgaagagatt 1080
gatcatgaag atatcacaaa agataaaacc agcacagtgg aggcctgttt accattggaa 1140

```
ttaaccaaga atgagagttg cctaaattcc agagagacct ctttcataac taatgggagt   1200

tgcctggcct ccagaaagac ctcttttatg atggccctgt gccttagtag tatttatgaa   1260

gacttgaaga tgtaccaggt ggagttcaag accatgaatg caaagcttct gatggatcct   1320

aagaggcaga tctttctaga tcaaaacatg ctggcagtta ttgatgagct gatgcaggcc   1380

ctgaatttca acagtgagac tgtgccacaa aaatcctccc ttgaagaacc ggatttttat   1440

aaaactaaaa tcaagctctg catacttctt catgctttca gaattcgggc agtgactatt   1500

gatagagtga tgagctatct gaatgcttcc taa                                1533
```

<210> SEQ ID NO 69
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 69

```
His Asn Arg Met Lys Ser Phe
1               5
```

<210> SEQ ID NO 70
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 70

```
His Asn Lys Met Ser Phe Ile
1               5
```

<210> SEQ ID NO 71
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 71

```
His Asn Arg Thr Lys Arg Phe Ile
1               5
```

<210> SEQ ID NO 72
<211> LENGTH: 6
<212> TYPE: PRT
<213> ORGANISM: Newcastle disease virus

<400> SEQUENCE: 72

```
Gly Arg Gln Gly Arg Leu
1               5
```